(12) United States Patent
Jung et al.

(10) Patent No.: US 11,991,928 B2
(45) Date of Patent: May 21, 2024

(54) HETEROCYCLIC COMPOUND AND ORGANIC LIGHT-EMITTING DEVICE INCLUDING THE SAME

(71) Applicant: Samsung Electronics Co., Ltd., Suwon-si (KR)

(72) Inventors: Yongsik Jung, Seoul (KR); Eunsuk Kwon, Suwon-si (KR); Hwangsuk Kim, Suwon-si (KR); Yeonsook Chung, Seoul (KR); Hosuk Kang, Suwon-si (KR); Joonghyuk Kim, Seoul (KR); Sungho Nam, Daegu (KR); Youngmok Son, Hwaseong-si (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 568 days.

(21) Appl. No.: 17/199,635

(22) Filed: Mar. 12, 2021

(65) Prior Publication Data
US 2023/0034532 A1 Feb. 2, 2023

(30) Foreign Application Priority Data
Jul. 6, 2020 (KR) .................. 10-2020-0083120

(51) Int. Cl.
*H01L 51/00* (2006.01)
*C07D 209/86* (2006.01)
(Continued)

(52) U.S. Cl.
CPC ....... *H10K 85/6572* (2023.02); *C07D 209/86* (2013.01); *C09K 11/06* (2013.01);
(Continued)

(58) Field of Classification Search
None
See application file for complete search history.

(56) References Cited

U.S. PATENT DOCUMENTS

| 10,407,384 B2 | 9/2019 | Stoessel et al. |
| 2014/0183467 A1 | 7/2014 | Choi et al. |

FOREIGN PATENT DOCUMENTS

| JP | 2002008860 A | 1/2002 |
| WO | 2014088347 A1 | 6/2014 |
| WO | 2014146750 A1 | 9/2014 |

OTHER PUBLICATIONS

Ryota Ieuji et al., "Triplet-triplet upconversion enhanced by spin-orbit coupling in organic light-emitting diodes," Nature Communications, 2019, pp. 1-10.

*Primary Examiner* — Jay Yang
(74) *Attorney, Agent, or Firm* — CANTOR COLBURN LLP

(57) ABSTRACT

A heterocyclic compound represented by Formula 1:

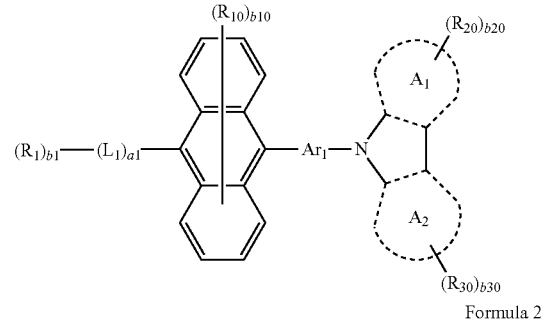

Formula 1

Formula 2

$$*\!\!-\!\!Ar_{11}\!\!-\!\!\!\left(\!Ar_{13}\!\right)_{\overline{m1}}\!\!-\!\!Ar_{12}\!\!-\!\!*'$$

wherein,
$Ar_1$ is a group represented by Formula 2,
$Ar_1$ includes at least one cyano group,
(Continued)

$A_1$, $A_2$, $L_1$, a1, $Ar_{11}$, $Ar_{12}$, $Ar_{13}$, m1, $R_1$, $R_{10}$, $R_{20}$, $R_{30}$, $b_1$, $b_{10}$, $b_{20}$, and $b_{30}$ are the same as described in the present disclosure, and \* and \*' each indicate a binding site to a neighboring atom.

20 Claims, 1 Drawing Sheet

(51) Int. Cl.
    *C09K 11/06*     (2006.01)
    *H10K 85/60*     (2023.01)
    *H10K 50/11*     (2023.01)
    *H10K 50/15*     (2023.01)
    *H10K 50/16*     (2023.01)
    *H10K 50/17*     (2023.01)
    *H10K 50/18*     (2023.01)
    *H10K 101/10*     (2023.01)

(52) U.S. Cl.
    CPC .... *H10K 85/626* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02); *H10K 2101/10* (2023.02)

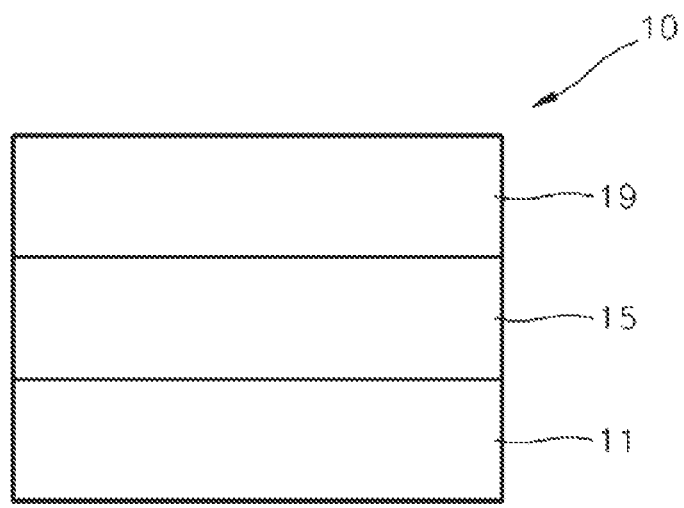

HETEROCYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2020-0083120, filed on Jul. 6, 2020, in the Korean Intellectual Property Office, and all the benefits accruing under 35 U.S.C. § 119, the content of which is incorporated by reference herein in its entirety.

BACKGROUND

1. Field

The present disclosure relates to heterocyclic compounds and organic light-emitting devices including the same.

2. Description of Related Art

Organic light-emitting devices are self-emission devices, which have improved characteristics in terms of a viewing angle, a response time, a brightness, a driving voltage, and a response speed, and produce full-color images.

In an example, an organic light-emitting device includes an anode, a cathode, and an organic layer between the anode and the cathode, wherein the organic layer includes an emission layer. A hole transport region may be located between the anode and the emission layer, and an electron transport region may be located between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state, thereby generating light.

SUMMARY

Provided are novel heterocyclic compounds and organic light-emitting devices including the same.

Additional aspects will be set forth in part in the description which follows and, in part, will be apparent from the description, or may be learned by practice of the presented embodiments of the disclosure.

According to an aspect of an embodiment, a heterocyclic compound represented by Formula 1 is provided:

Formula 1

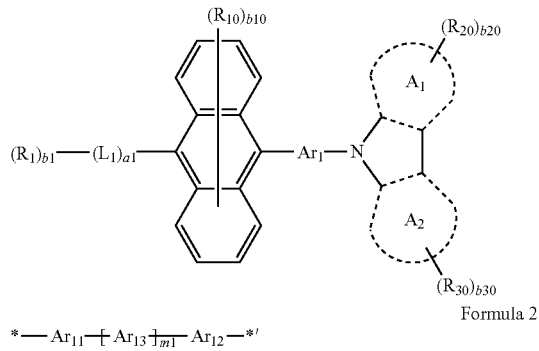

$$*\!-\!Ar_{11}\!\!-\!\!\!\left(Ar_{13}\right)_{\overline{m1}}\!\!-\!\!Ar_{12}\!-\!*'$$
Formula 2 wherein, in Formula 1, $Ar_1$ is a group represented by Formula 2, $Ar_1$ includes at least one cyano group, $A_1$ and $A_2$ are each independently a $C_5$-$C_{30}$ carbocyclic group or a $C_1$-$C_{30}$ heterocyclic group, each $L_1$ is independently an unsubstituted or substituted $C_5$-$C_{30}$ carbocyclic group or an unsubstituted or substituted $C_1$-$C_{30}$ heterocyclic group, and a1 is 0, 1, 2, or 3, where, when a1 is 2 or more, two or more $L_1$(s) are identical to or different from each other, wherein, in Formula 2, $Ar_{11}$ is a group represented by Formula 4, $Ar_{12}$ is a group represented by Formula 5, and $Ar_{13}$ is a group represented by Formula 6, and m1 is 0, 1, 2, or 3,

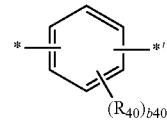
Formula 4

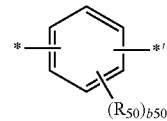
Formula 5

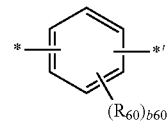
Formula 6 wherein, in Formulae 1, 2, 4, 5, and 6, $R_1$, $R_{10}$, $R_{20}$, $R_{30}$, $R_{40}$, $R_{50}$, and $R_{60}$ are each independently hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), or —P(=O)($Q_8$)($Q_9$), b1 is an integer from 1 to 5, wherein, when b1 is 2 or more, two or more $R_1$(s) are identical to or different from each other, b10 is an integer from 1 to 8, wherein, when b10 is 2 or more, two or more $R_{10}$(s) are identical to or different from each other, b20 and b30 are each independently an integer from 1 to 4, wherein, when b20 is 2 or more, two or more $R_{20}$(s) are identical to or different from each other, and when b30 is 2 or more, two or more $R_{30}$(s) are identical to or different from each other, b40, b50, and b60 are each independently an integer from 1 to 4, wherein, when b40 is 2 or more, two or more $R_{40}$(s) are identical to or different from each other, when b50 is 2 or more, two or more $R_{50}$(s) are identical to or different from each other, and when b60 is 2 or more, two or more $R_{60}$(s) are identical to or different from each other, and *' each indicate a binding site to a neighboring atom, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_1$-$C_{60}$ heteroaryloxy group, the substituted $C_1$-$C_{60}$ heteroarylthio group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_6$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), or —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_6$-$C_{60}$ heteroaryl group, a $C_1$-$C_{60}$ heteroaryloxy group, a $C_6$-$C_{60}$ heteroarylthio group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_6$-$C_{60}$ heteroaryl group, a $C_6$-$C_{60}$ heteroaryloxy group, a $C_6$-$C_{60}$ heteroarylthio group, a monovalent non-aromatic condensed polycyclic group, or a monovalent non-aromatic condensed heteropolycyclic group, each substituted with at least one of deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), or —B($Q_{26}$)($Q_{27}$); or —Si($Q_{31}$)($Q_{32}$)($Q_{33}$), —N($Q_{34}$)($Q_{35}$), and —B($Q_{36}$)($Q_{37}$), wherein $Q_1$ to $Q_7$, $Q_{11}$ to $Q_{17}$, to $Q_{27}$, and $Q_{31}$ to $Q_{37}$ are each independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_6$-$C_{60}$ heteroaryloxy group, a substituted or unsubstituted $C_6$-$C_{60}$ heteroarylthio group, a substituted or unsubstituted monovalent non-aromatic condensed polycyclic group, or a substituted or unsubstituted monovalent non-aromatic condensed heteropolycyclic group.

According to an aspect of another embodiment, an organic light-emitting device comprises a first electrode; a second electrode; and an organic layer located between the first electrode and the second electrode and including an emission layer, wherein the organic layer includes at least one of the heterocyclic compound.

BRIEF DESCRIPTION OF THE DRAWING

The above and other aspects, features, and advantages of certain embodiments of the disclosure will be more apparent from the following description taken in conjunction with the FIGURE, which shows a schematic cross-sectional view of an organic light-emitting device according to one or more embodiments.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms These terms are only used to distinguish one element, component, region, layer or section from another element, component, region, layer or section Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures It will be understood that relative terms are intended to encompass different orientations of the device in addition to the orientation depicted in the Figures For example, if the device in one of the figures is turned over, elements described as being on the "lower" side of other elements would then be oriented on "upper" sides of the other elements The exemplary term "lower," can therefore, encompasses both an orientation of "lower" and "upper," depending on the particular orientation of the FIGURE Similarly, if the device in one of the figures is turned over, elements described as "below" or "beneath" other elements would then be oriented "above" the other elements The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments As such, variations from the shapes of the illustrations as a result, for example, of manufacturing techniques and/or tolerances, are to be expected Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features Moreover, sharp angles that are illustrated may be rounded Thus, the regions illustrated in the figures are schematic in nature and their shapes are not intended to illustrate the precise shape of a region and are not intended to limit the scope of the present claims.

According to one or more embodiments, a heterocyclic compound is represented by Formula 1:

Formula 1

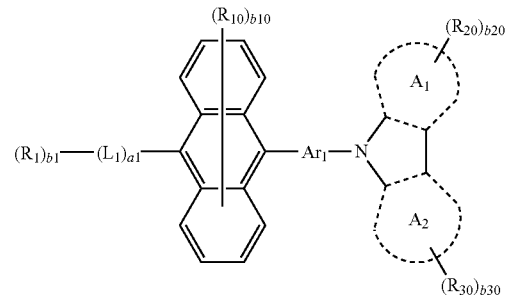

wherein $Ar_1$ in Formula 1 may be a group represented by Formula 2 and include at least one cyano group:

Formula 2

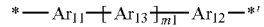

wherein m1 in Formula 2 may be 0, 1, 2, or 3.
In an embodiment, m1 may be 0, 1, or 2.
In one or more embodiments, m1 may be 0 or 1.

In Formula 2, $Ar_{11}$ may be a group represented by Formula 4, $Ar_{12}$ may be a group represented by Formula 5, and $Ar_{13}$ may be a group represented by Formula 6:

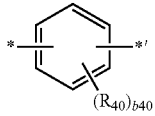

Formula 4

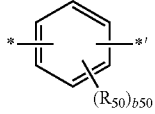

Formula 5

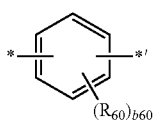

Formula 6 wherein $R_{40}$, $R_{50}$, $R_{60}$, $b_{40}$, $b_{50}$, and $b_{60}$ in Formulae 4 to 6 may each be the same as described in the present specification.

In an embodiment, $Ar_{11}$ may be represented by one of Formulae 4-1 to 4-3:

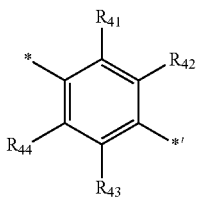

4-1

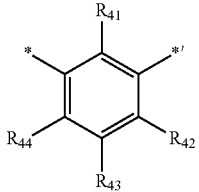

4-2

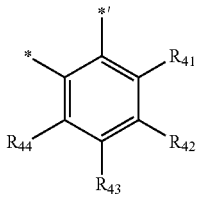

4-3 wherein, in Formulae 4-1 to 4-3,
$R_{41}$ to $R_{44}$ may each be the same as described in the present specification, and
and *' each indicate a binding site to a neighboring atom.

In an embodiment, $Ar_{12}$ may be represented by one of Formulae 5-1 to 5-3:

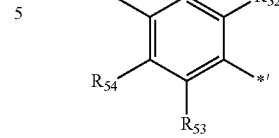

5-1

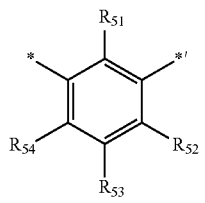

5-2

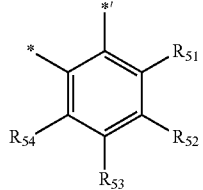

5-3 wherein, in Formulae 5-1 to 5-3,
$R_{51}$ to $R_{54}$ may each be the same as described in the present specification, and
and *' each indicate a binding site to a neighboring atom.

In an embodiment, $Ar_{13}$ may be represented by one of Formulae 6-1 to 6-3:

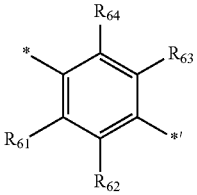

6-1

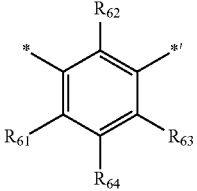

6-2

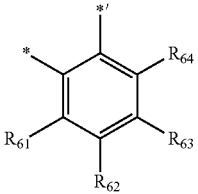

6-3 wherein, in Formulae 6-1 to 6-3,
$R_{61}$ to $R_{64}$ may each be the same as described in the present specification, and
and *' each indicate a binding site to a neighboring atom.

When m1 is 2 or more, two or more $Ar_{13}$(s) may be identical to or different from each other. That is, $Ar_{13}$(s) in the number of m1 may each independently be a group represented by one of Formulae 6-1 to 6-3.

In an embodiment, a moiety represented by *—[Ar₁₃]_{m1}—*' may be a group represented by one of Formulae 6-11 to 6-16:

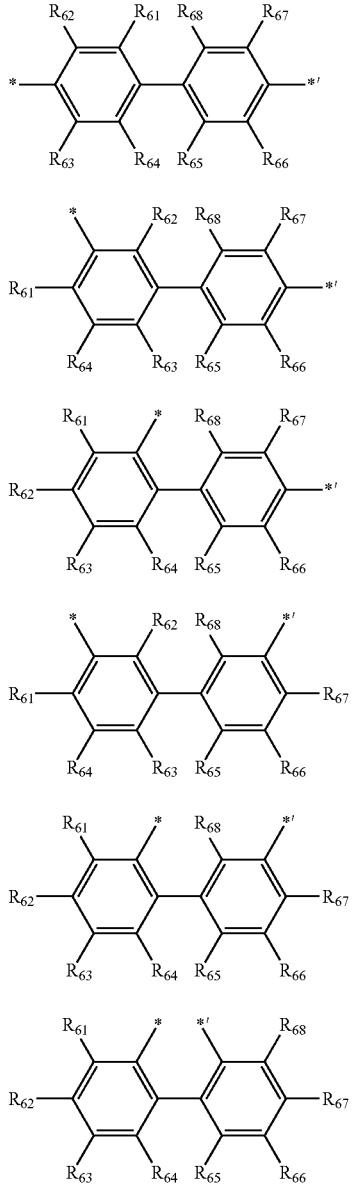

wherein, in Formulae 6-11 to 6-16, $R_{61}$ to $R_{68}$ may each be the same as described in the present specification, and

* and *' each indicate a binding site to a neighboring atom.

In an embodiment, m1 may be 0, 1, or 2.

In one or more embodiments, m1 may be 0 or 1.

In an embodiment, $Ar_1$ in Formula 1 may be represented by Formula 2A:

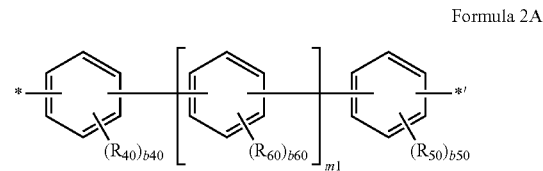

Formula 2A wherein $R_{40}$, $R_{50}$, $R_{60}$, $b_{40}$, $b_{50}$, $b_{60}$, and m1 in Formula 2A may each be the same as described in the present specification.

In one or more embodiments, $Ar_1$ in Formula 1 may be represented by one of Formulae 2-1 to 2-25:

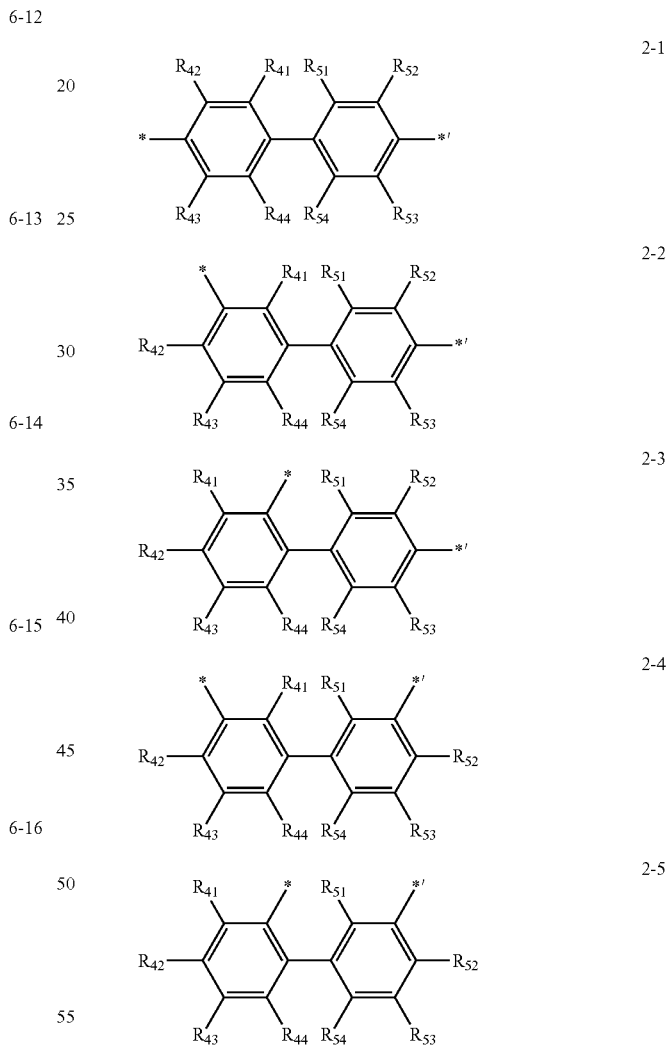

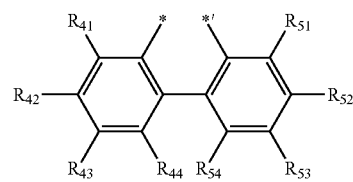

2-7
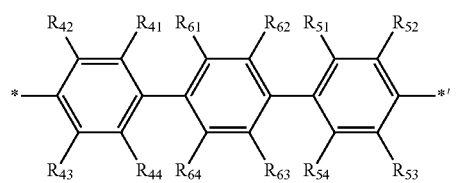
2-8
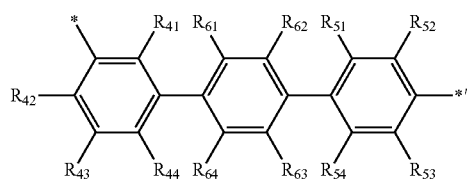
2-9
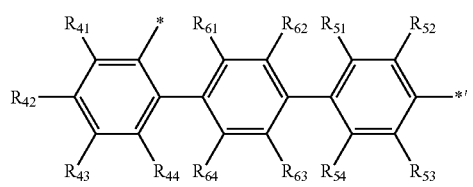
2-10
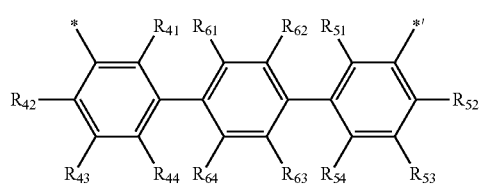
2-11
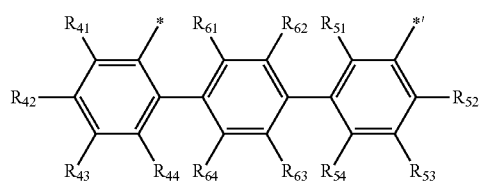
2-12
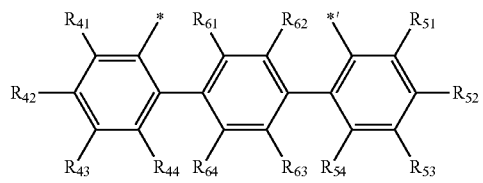
2-13
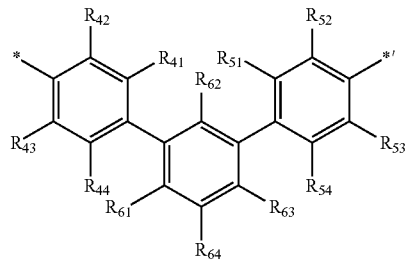
2-14
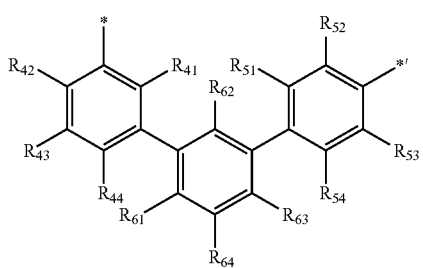
2-15
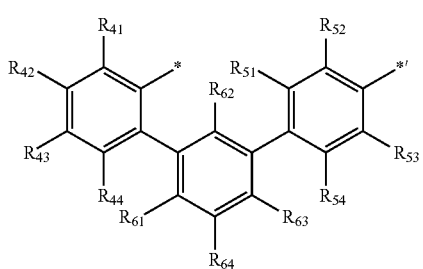
2-16
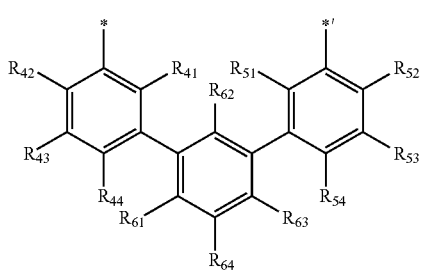
2-17
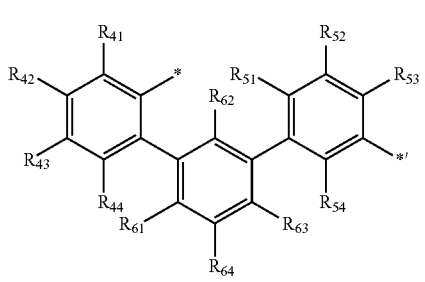
2-18
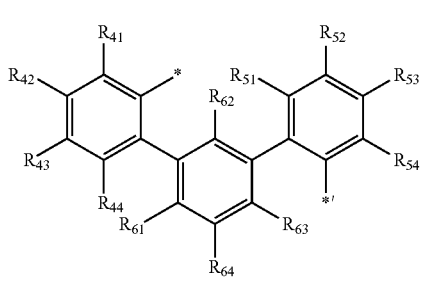

-continued 2-19 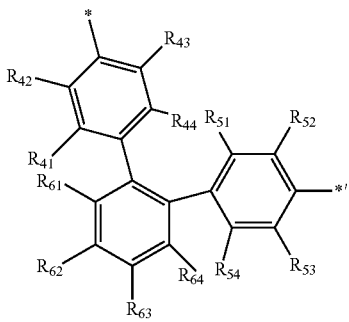

2-20 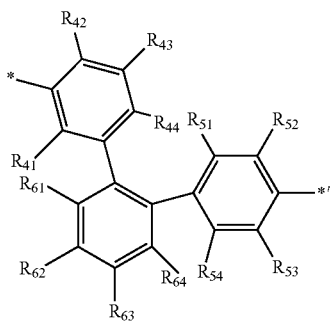

2-21 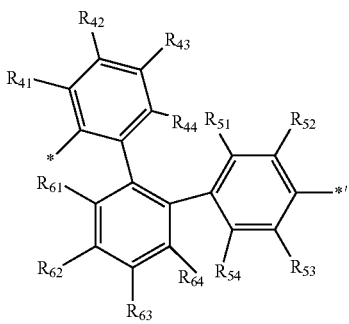

2-22 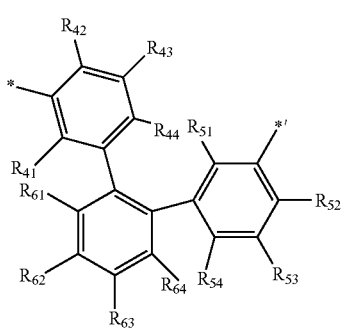

2-23 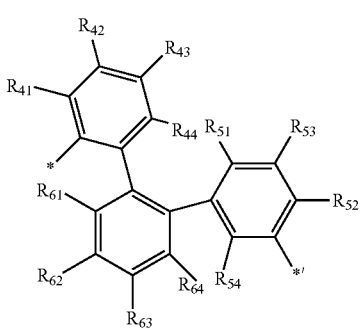

2-24 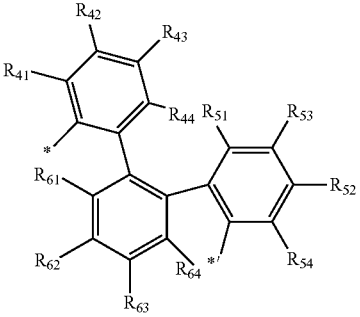

2-25 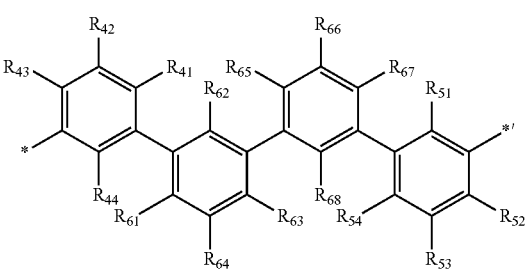

wherein, in Formulae 2-1 to 2-25,
$R_{41}$ to $R_{44}$ may each independently be the same as described in connection with $R_{40}$,
$R_{51}$ to $R_{54}$ may each independently be the same as described in connection with $R_{50}$,
$R_{61}$ to $R_{68}$ may each independently be the same as described in connection with $R_{60}$,
at least one of $R_{41}$ to $R_{44}$, $R_{51}$ to $R_{54}$, and $R_{61}$ to $R_{68}$ may be a cyano group, and
and *' each indicate a binding site to a neighboring atom.

In the formulae above, * and *' are not limited to a binding site to a particular atom. In an embodiment, * in Formula 2 may be a binding site to an anthracene moiety in Formula 1, and *' in Formula 2 may be a binding site to an N atom in Formula 1. In one or more embodiments, * in Formula 2 may be a binding site to an N atom in Formula 1, and *' in Formula 2 may be a binding site to an anthracene moiety in Formula 1. In formulae other than Formula 2, * and *' also indicate a position at which a group represented by each formula binds to any other atom, and do not indicate a site at which a group represented by each formula binds to any particular atom.

In addition, the atom(s) to which * that is shown in different formulae binds may be identical to or different from each other, and atoms to which *' shown in different formulae binds may be identical to or different from each other.

In an embodiment, $Ar_1$ may include 1 to 4 cyano groups. For example, in Formulae 2-1 to 2-25, one to four of $R_{41}$ to $R_{44}$, $R_{51}$ to $R_{54}$, or $R_{61}$ to $R_{64}$ may be cyano groups.

In Formula 1, $A_1$ and $A_2$ may each independently be a $C_5$-$C_{30}$ carbocyclic group or a $C_1$-$C_{30}$ heterocyclic group.

In an embodiment, $A_1$ and $A_2$ may each independently be a benzene group, a naphthalene group, an anthracene group, a phenanthrene group, a triphenylene group, a pyrene group, a 1,2,3,4-tetrahydronaphthalene group, a fluorene group, a carbazole group, a benzofuran group, a dibenzofuran group, a benzothiophene group, a dibenzothiophene group, a benzosilole group, a dibenzosilole group, an azafluorene group, an azacarbazole group, an azadibenzofuran group, an azadibenzothiophene group, an azadibenzosilole group, a pyridine group, a pyrimidine group, a pyrazine group, a pyridazine group, a triazine group, a quinoline group, an isoquinoline group, a quinoxaline group, a quinazoline group, or a phenanthroline group.

In one or more embodiments, $A_1$ and $A_2$ may each independently be a benzene group, a naphthalene group, an anthracene group, a phenanthrene group, a pyridine group, a pyrimidine group, or a pyrazine group.

In one or more embodiments, $A_1$ and $A_2$ may each independently be a benzene group, a naphthalene group, a pyridine group, or a pyrimidine group.

In one or more embodiments, $A_1$ and $A_2$ may each independently be a benzene group or a naphthalene group.

In Formula 1, $L_1$ may be a substituted or unsubstituted $C_5$-$C_{30}$ carbocyclic group and a substituted or unsubstituted $C_1$-$C_{30}$ heterocyclic group.

In an embodiment, $L_1$ may be:
a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group; or
a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_6$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, or a monovalent non-aromatic condensed heteropolycyclic group.

In Formula 1, a1 may be 0, 1, 2, or 3. When a1 is 2 or more, two or more $L_1$(s) may be identical to or different from each other.

In Formulae 1, 2, 4, 5, and 6, $R_{10}$, $R_{20}$, $R_{30}$, $R_{40}$, $R_{50}$, and $R_{60}$ may each independently be hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), or —P(=O)($Q_8$)($Q_9$).

In an embodiment, $R_1$, $R_{10}$, $R_{20}$, $R_{30}$, $R_{40}$, $R_{50}$, and $R_{60}$ may each independently be:
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, or a $C_1$-$C_{20}$ alkoxy group;
a $C_1$-$C_{20}$ alkyl group or a $C_1$-$C_{20}$ alkoxy group, each substituted with at least one of deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, or a pyrimidinyl group;
a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;
a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one of deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group; or —N(Q$_1$)(Q$_2$), —Si(Q$_3$)(Q$_4$)(Q$_5$), —B(Q$_6$)(Q$_7$), and —P(=O)(Q$_8$)(Q$_9$), and Q$_1$ to Q$_9$ may each independently be:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CH$_3$, —CD$_2$CD$_3$, —CD$_2$CD$_2$H, or —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group, each substituted with at least one of deuterium, a $C_1$ to $C_{10}$ alkyl group, and a phenyl group.

In Formula 1, b1 may be an integer from 1 to 5. When b1 is 2 or more, two or more R$_1$(s) may be identical to or different from each other.

In Formula 1, b10 may be an integer from 1 to 8. When b10 is 2 or more, two or more R$_{10}$(s) may be identical to or different from each other.

In Formula 1, b20 and b30 may each independently be an integer from 1 to 4. When b20 is 2 or more, two or more R$_{20}$(s) may be identical to or different from each other. When b30 is 2 or more, two or more R$_{30}$(s) may be identical to or different from each other.

In Formula 1, b40, b50, and b60 may each independently be an integer from 1 to 4. When b40 is 2 or more, two or more R$_{40}$(s) may be identical to or different from each other. When b50 is 2 or more, two or more R$_{50}$(s) may be identical to or different from each other. When b60 is 2 or more, two or more R$_{60}$(s) may be identical to or different from each other.

In an embodiment, R$_1$ may be deuterium, —F, —Cl, —Br, —I, —SF$_5$, a hydroxyl group, a cyano group, a nitro group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_6$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —B(Q$_6$)(Q$_7$), or —P(=O)(Q$_8$)(Q$_9$).

In an embodiment, R$_1$ may be deuterium, —F, a cyano group, a group represented by one Formulae 9-1 to 9-19, or a group represented by one of Formulae 10-1 to 10-194:

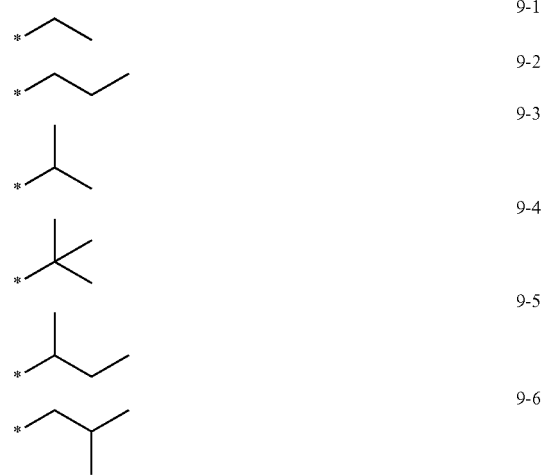

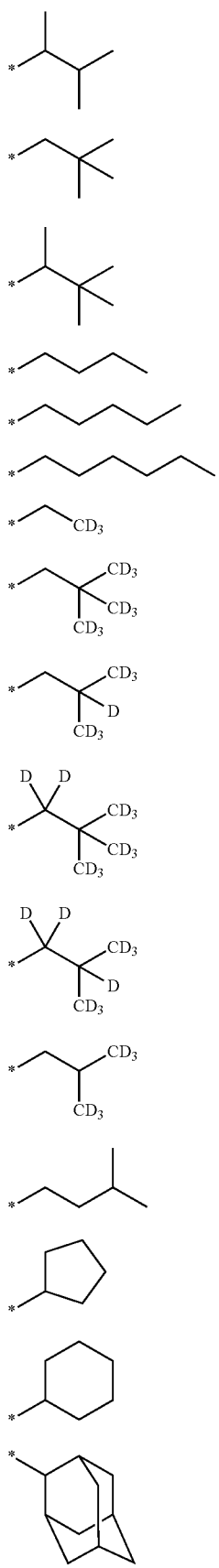
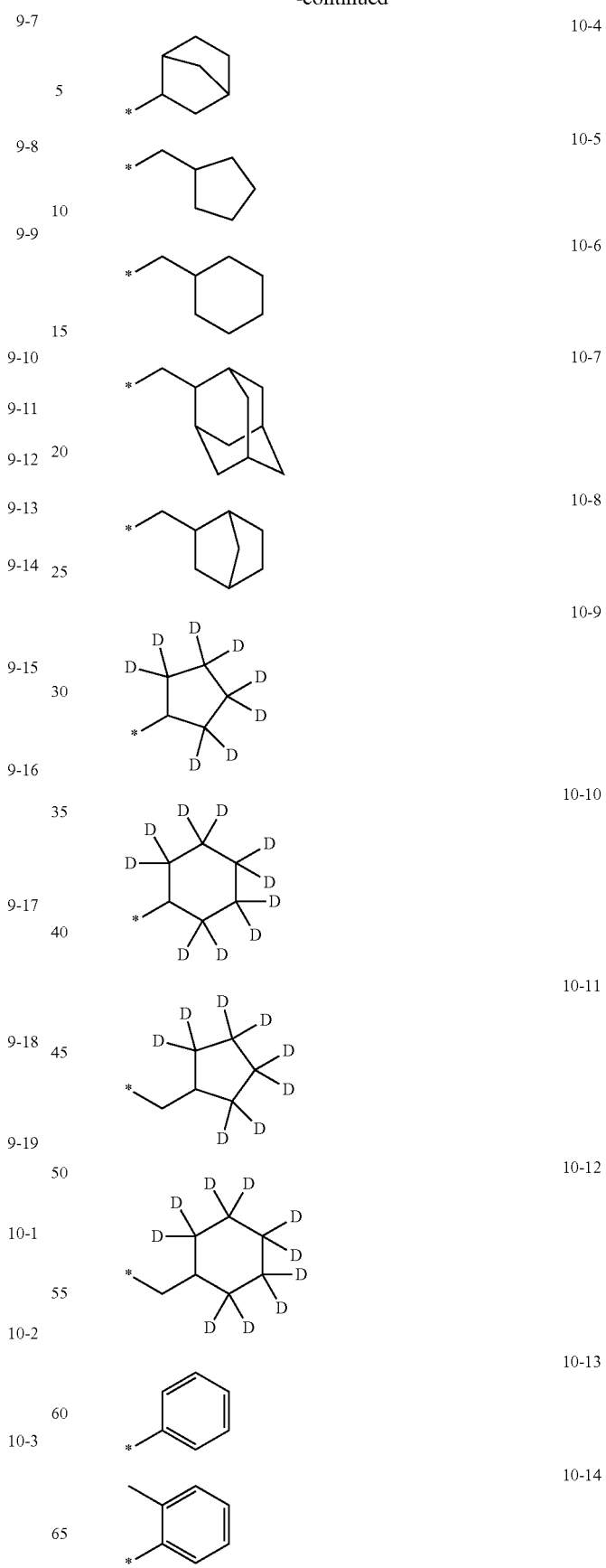

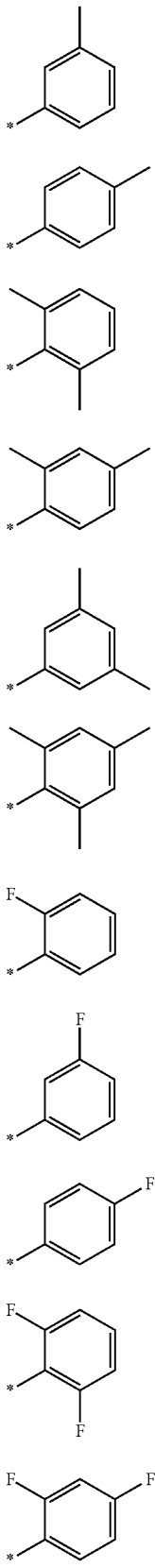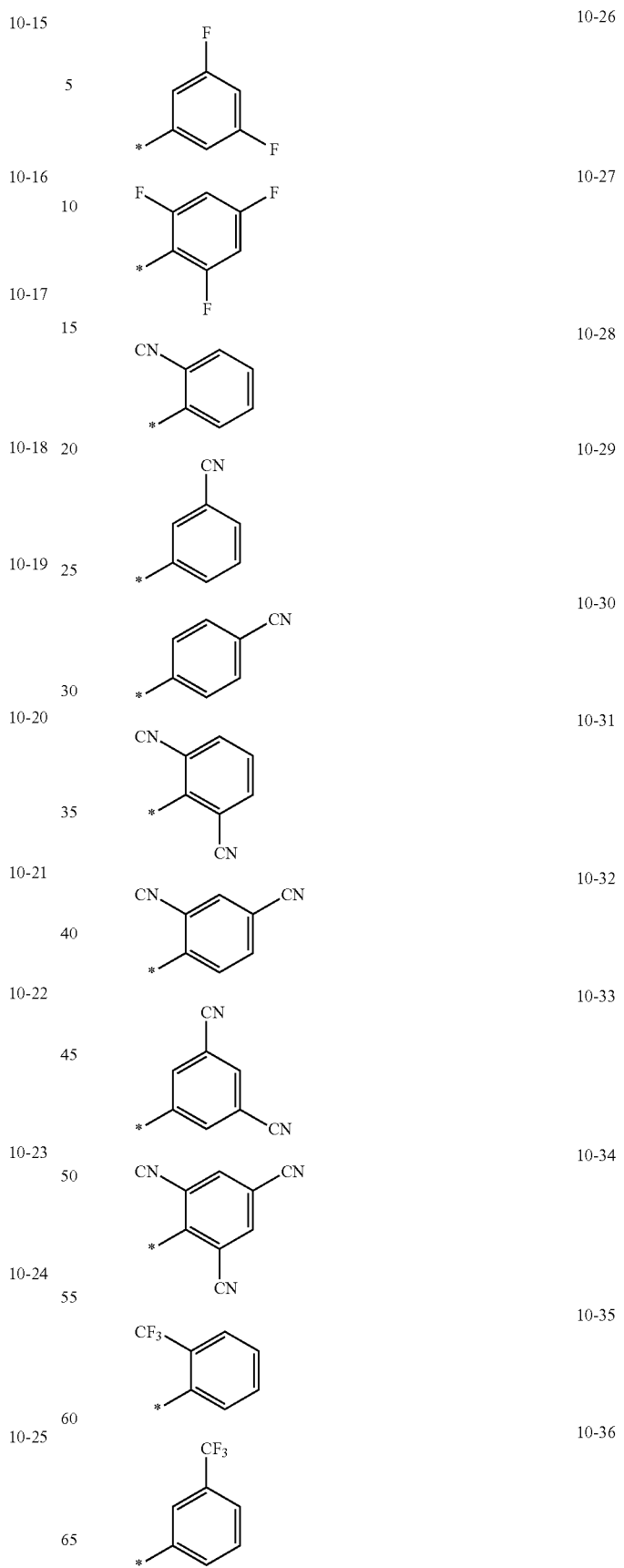

10-37 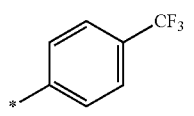
10-38 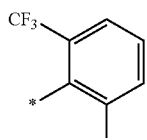
10-39 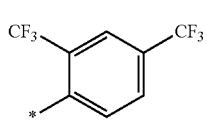
10-40 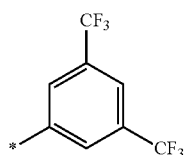
10-41 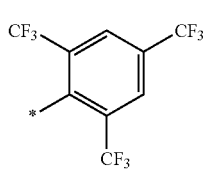
10-42 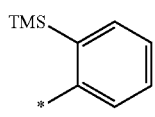
10-43 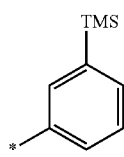
10-44 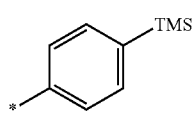
10-45 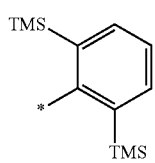
10-46 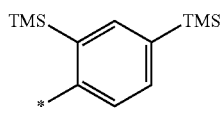
10-47 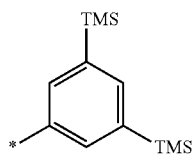
10-48 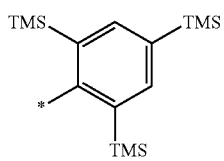
10-49 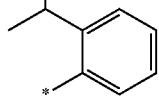
10-50
10-51
10-52 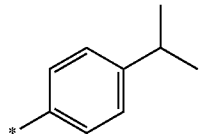
10-53
10-54
10-55
10-56

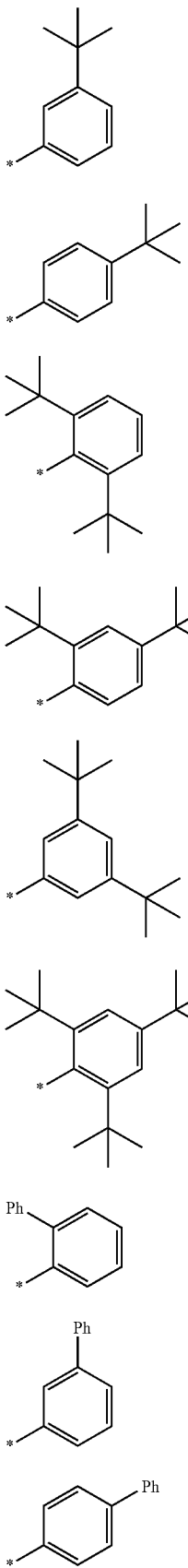
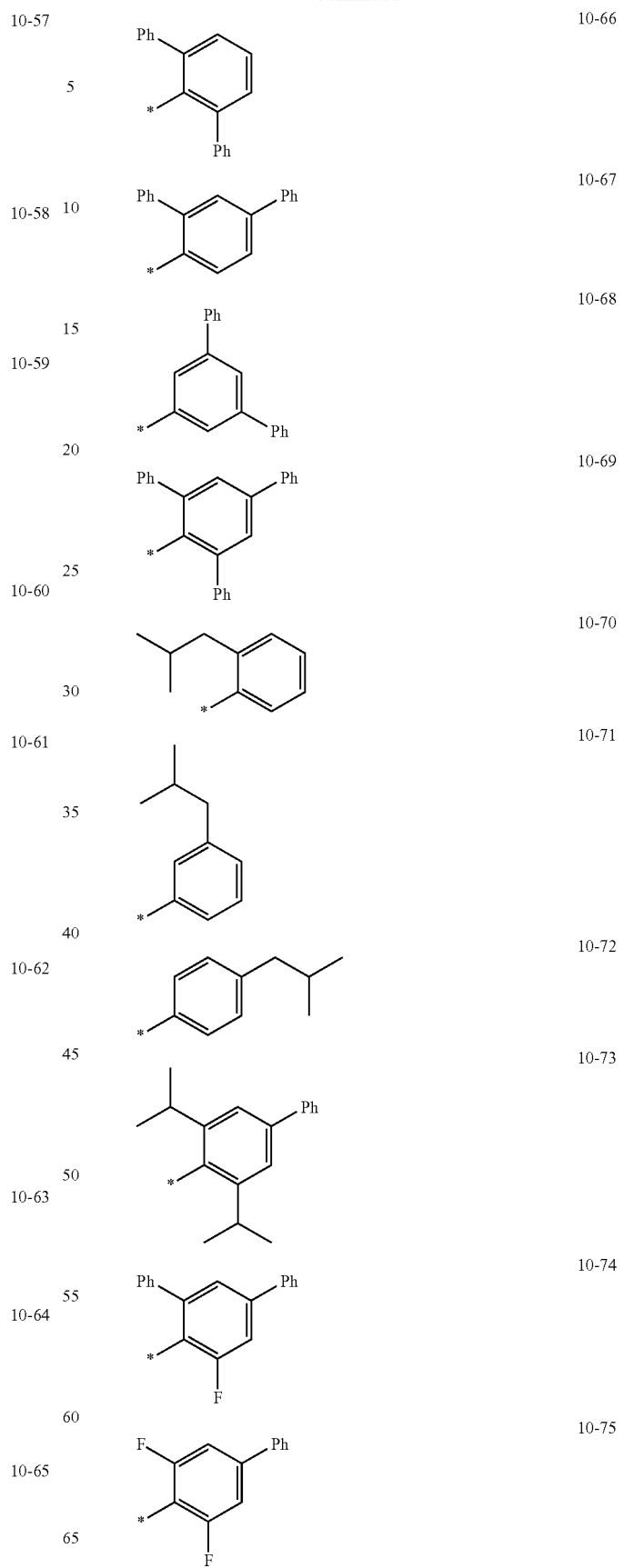

-continued
10-76 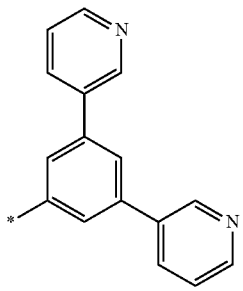
10-77 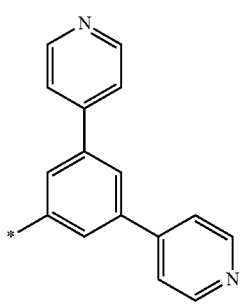
10-78 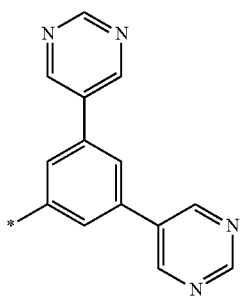
10-79 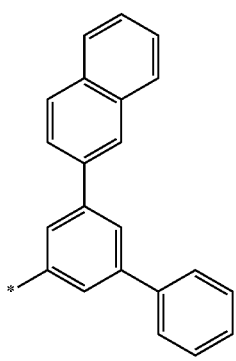
10-80 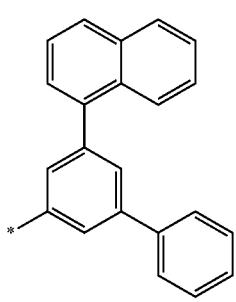
-continued
10-81 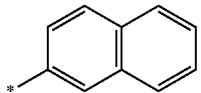
10-82 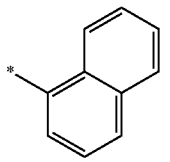
10-83 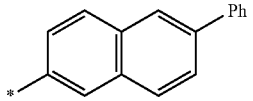
10-84 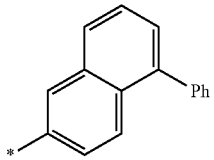
10-85 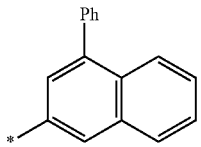
10-86 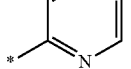
10-87 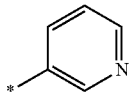
10-88 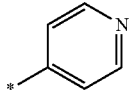
10-89 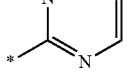
10-90 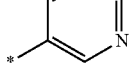
10-91 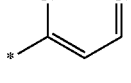
10-92 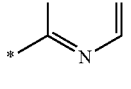

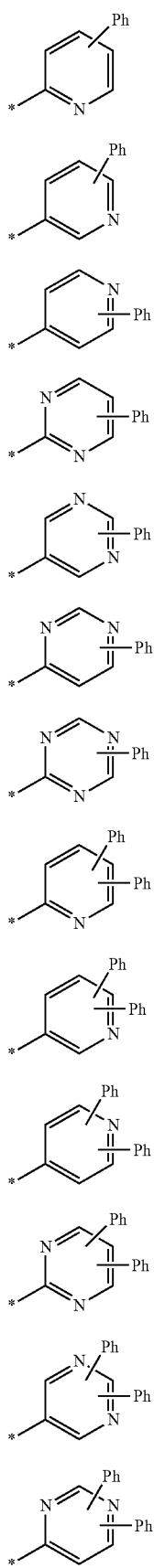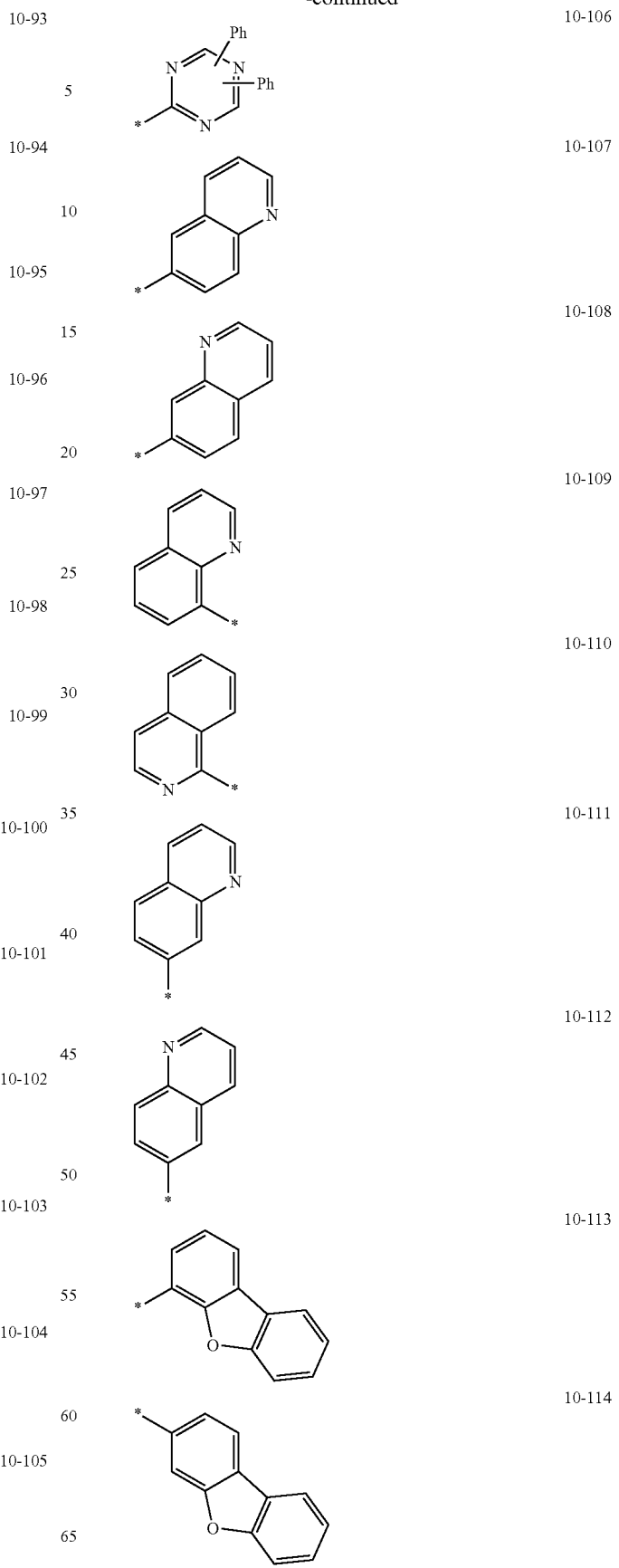

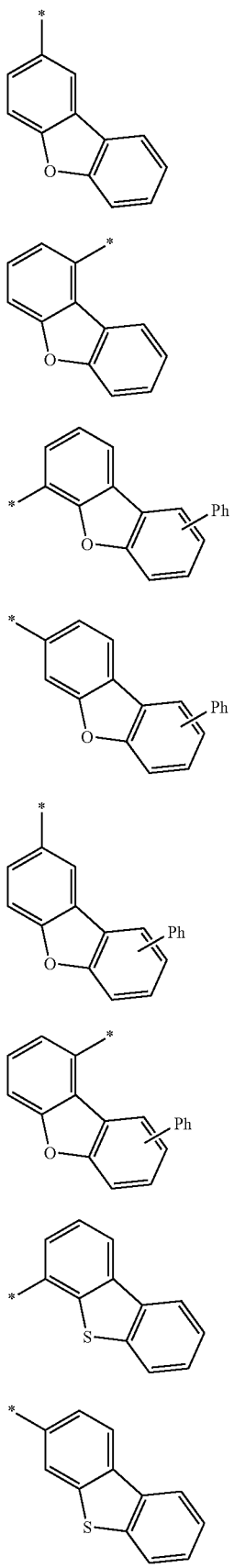
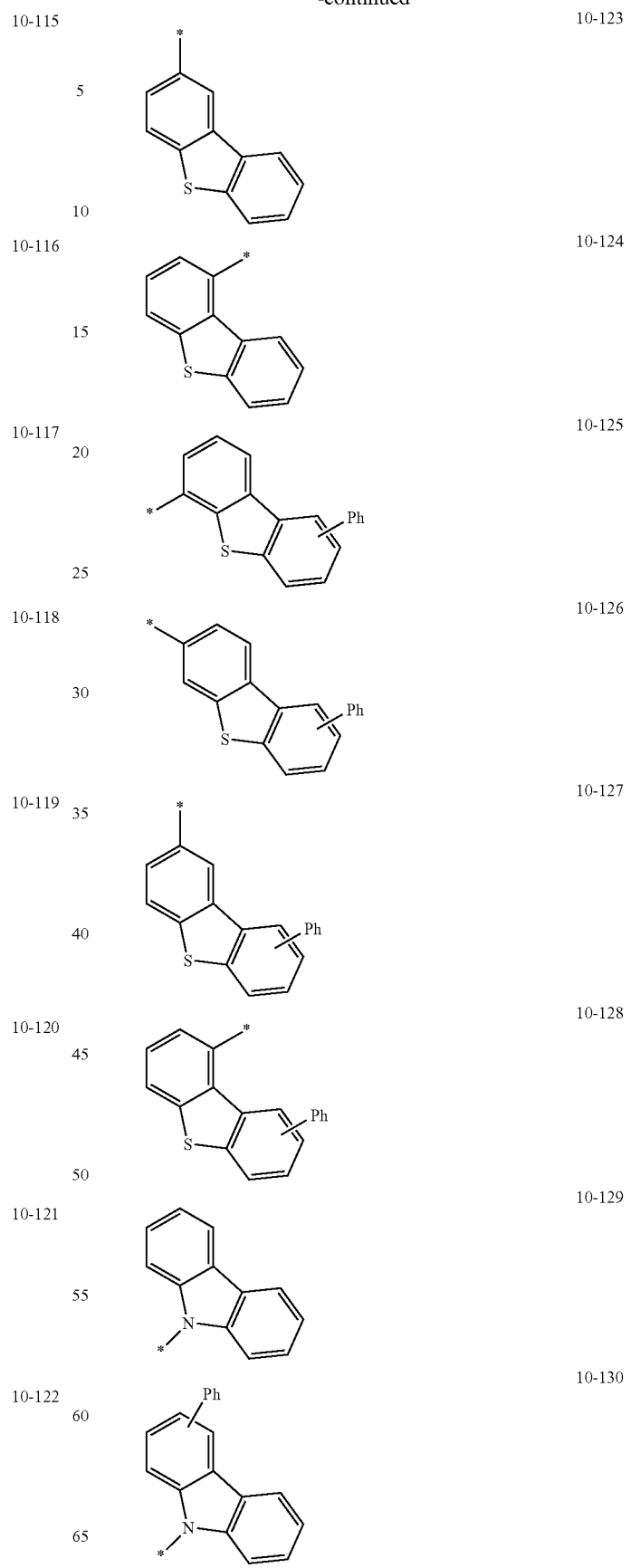

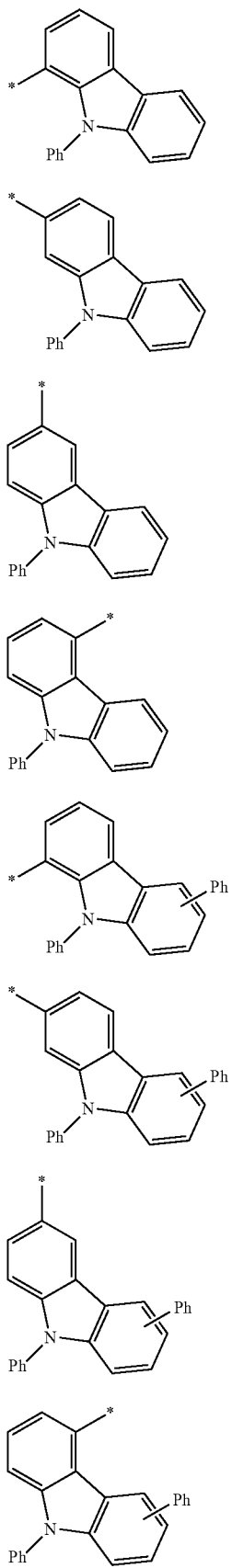

-continued
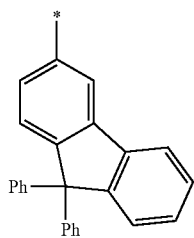
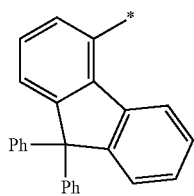
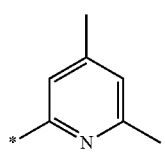
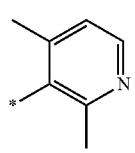
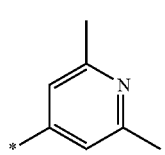
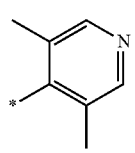
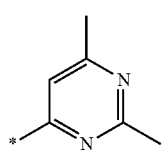
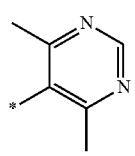
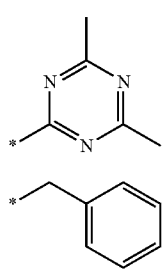
-continued
10-146
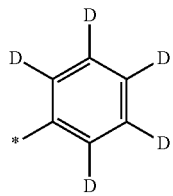
10-147
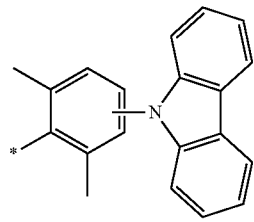
10-148
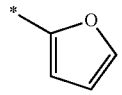
10-149
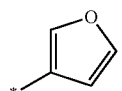
10-150
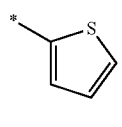
10-151
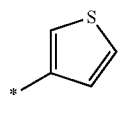
10-152
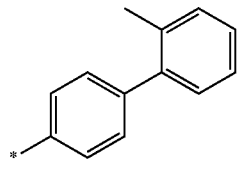
10-153
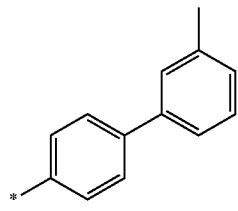
10-154
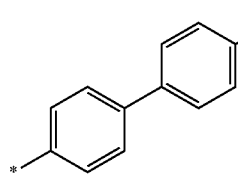
10-155
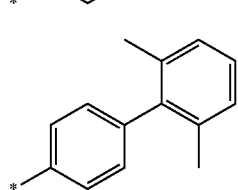

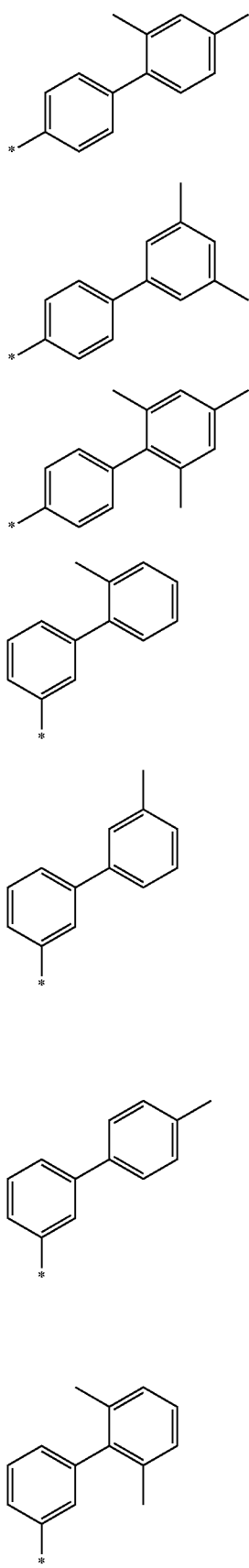
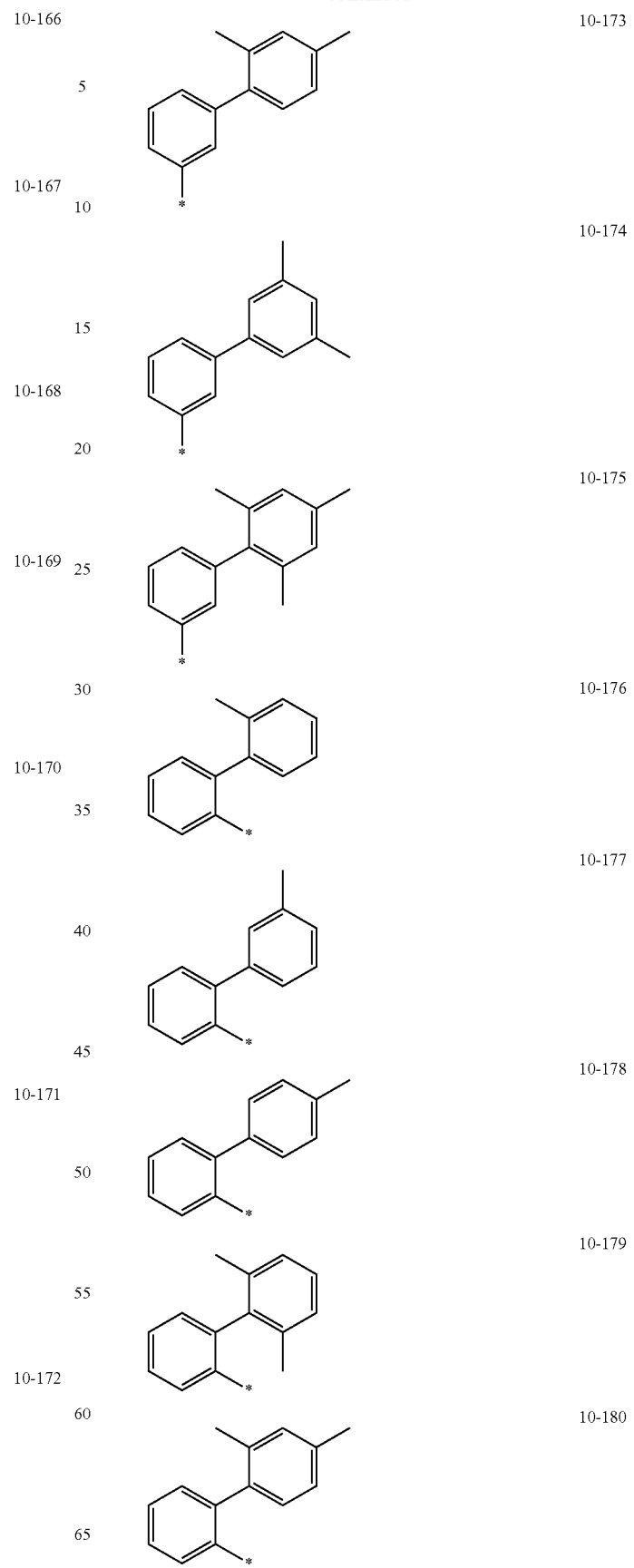

10-181 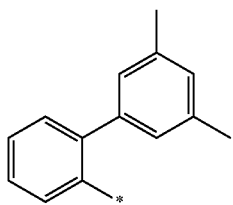

10-182 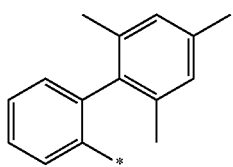

10-183 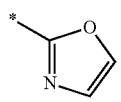

10-184 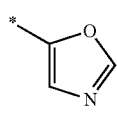

10-185 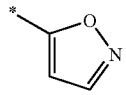

10-186 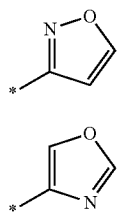

10-187 

10-188 

10-189 

10-190 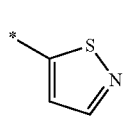

10-191 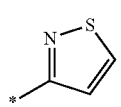

10-192 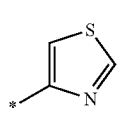

10-193

10-194 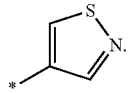

wherein, in Formulae 9-1 to 9-19 and 10-1 to 10-194, * indicates a binding site to a neighboring atom, Ph is a phenyl group, and TMS is a trimethylsilyl group.

In one or more embodiments, $R_1$ may be one of the groups represented by Formulae 9-1 to 9-19, or one of the groups represented by Formulae 10-1 to 10-194.

In an embodiment, $R_{10}$, $R_{20}$, $R_{30}$, $R_{40}$, $R_{50}$, and $R_{60}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a pyridinyl group, a pyrimidinyl group, a pyrazinyl group, a pyridazinyl group, or a triazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, or an imidazopyridinyl group; or a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, or an imidazopyridinyl group, each substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, or a quinazolinyl group.

In one or more embodiments, $R_{10}$, $R_{20}$, $R_{30}$, $R_{40}$, $R_{50}$, and $R_{60}$ may each independently be hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, a group represented by one of Formulae 9-1 to 9-19, or a group represented by one of Formulae 10-1 to 10-194:

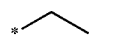
9-1

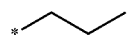
9-2

9-3

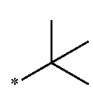
9-4

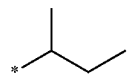
9-5

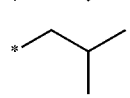
9-6

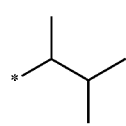
9-7

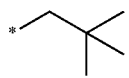
9-8

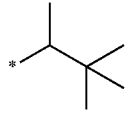
9-9

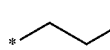
9-10

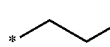
9-11

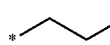
9-12

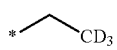
9-13

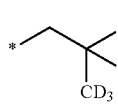
9-14

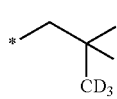
9-15

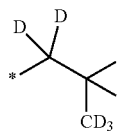
9-16

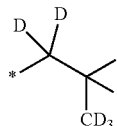
9-17

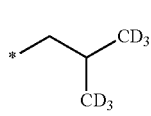
9-18

9-19

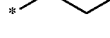
10-1

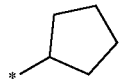
10-2

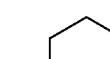
10-3

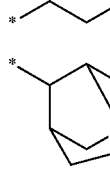
10-4

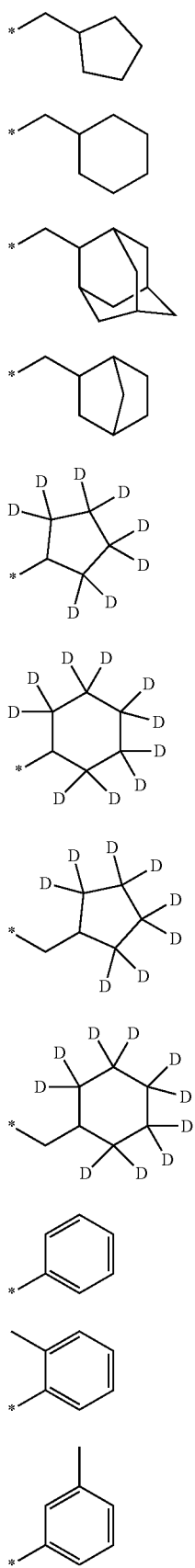
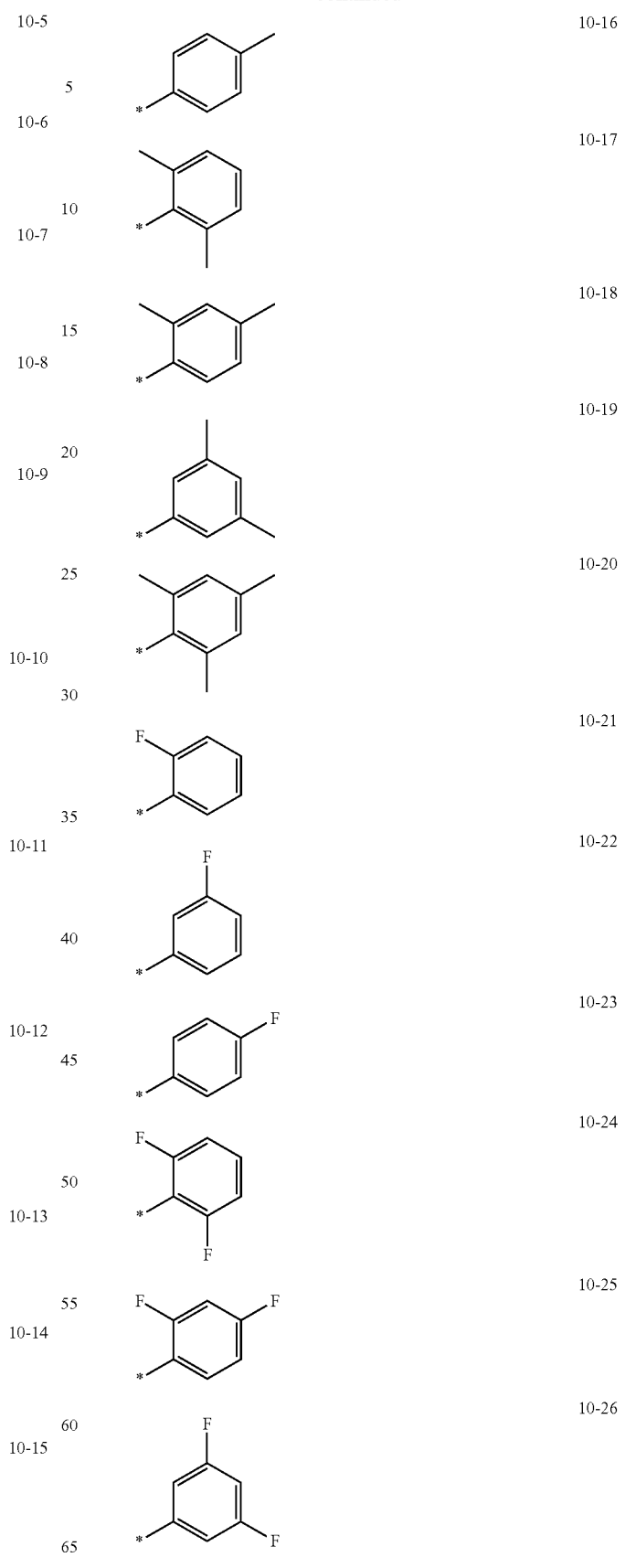

-continued
10-27 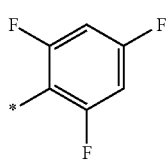
10-28 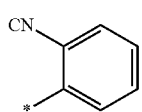
10-29 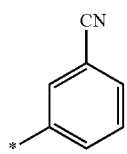
10-30 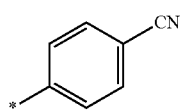
10-31 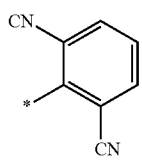
10-32 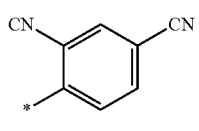
10-33 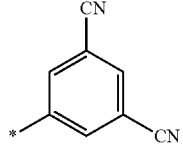
10-34 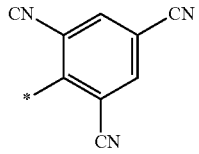
10-35 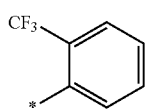
10-36 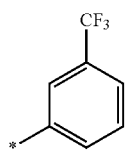
10-37 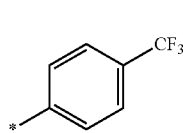
-continued
10-38 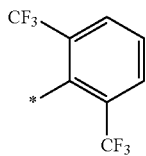
10-39 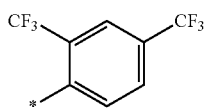
10-40 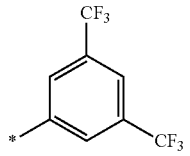
10-41 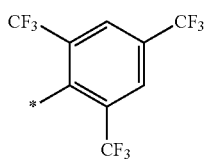
10-42 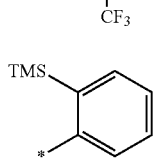
10-43 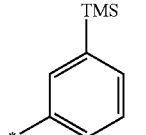
10-44 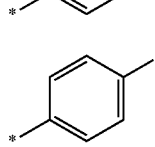
10-45 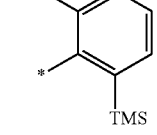
10-46 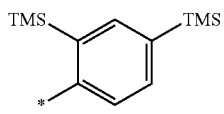
10-47 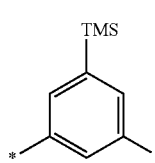
10-48 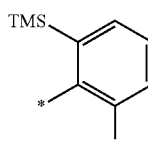

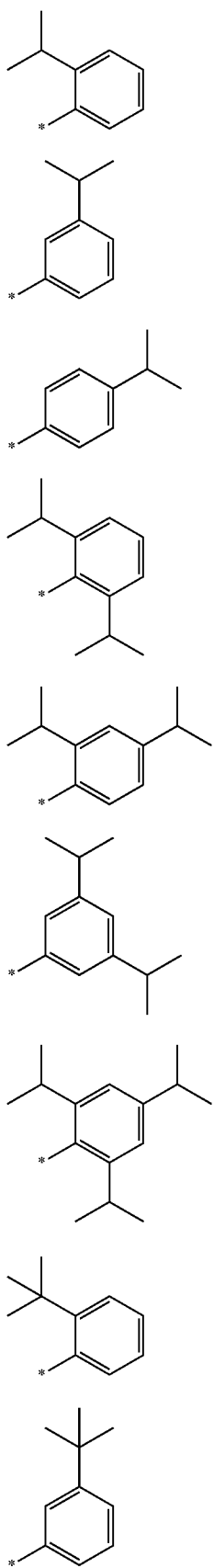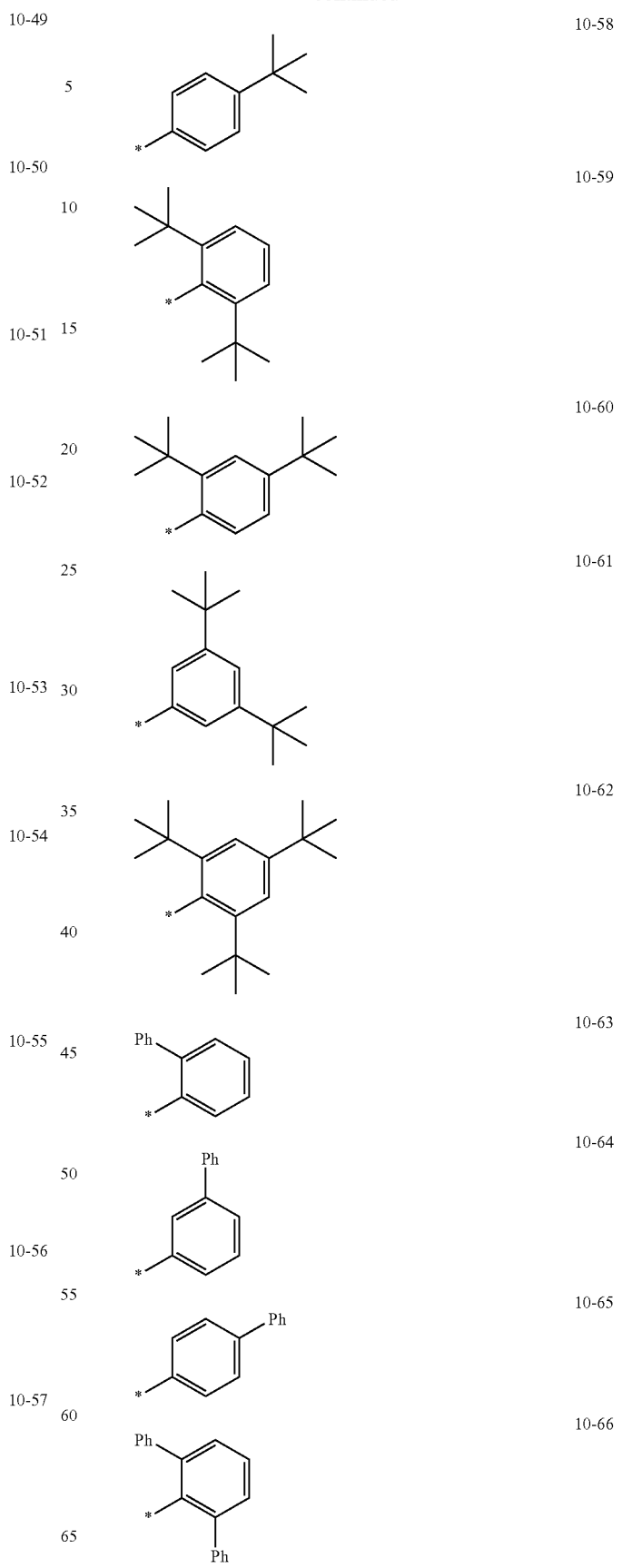

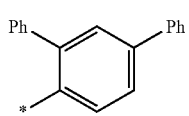
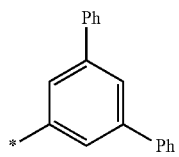
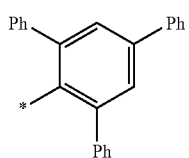
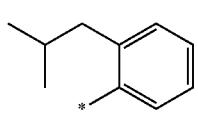
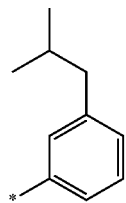
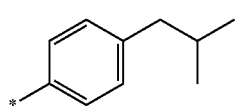
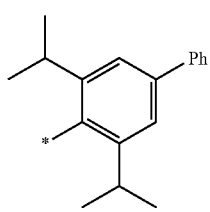
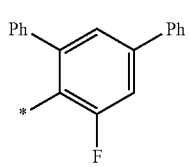
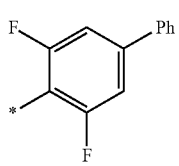
10-67
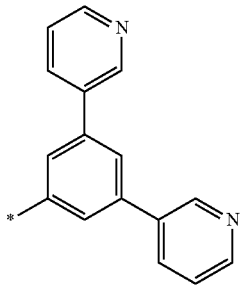
10-68
10-69
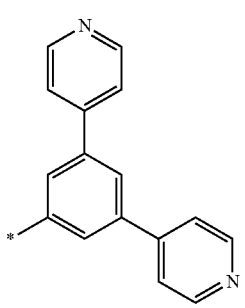
10-70
10-71
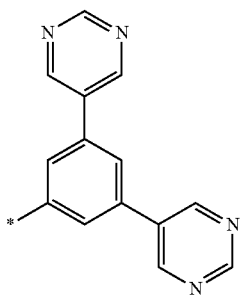
10-72
10-73
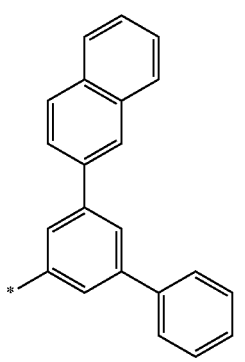
10-74
10-75
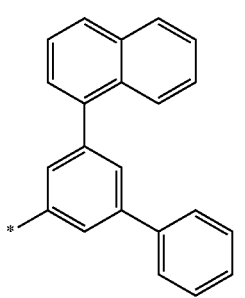
10-76
10-77
10-78
10-79
10-80

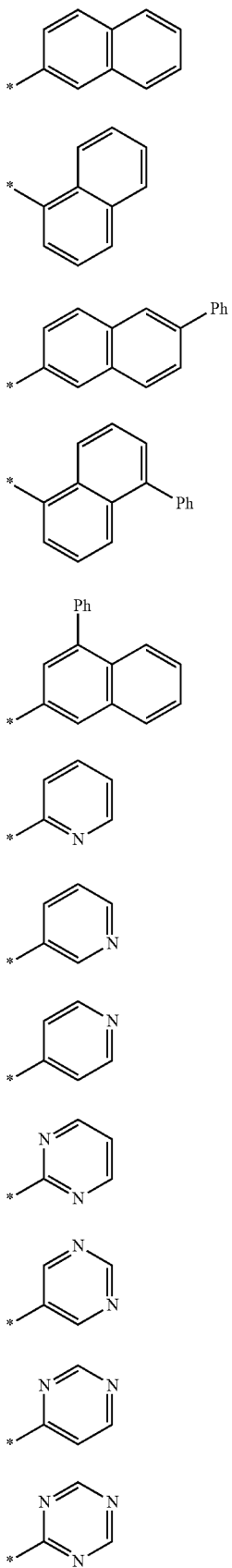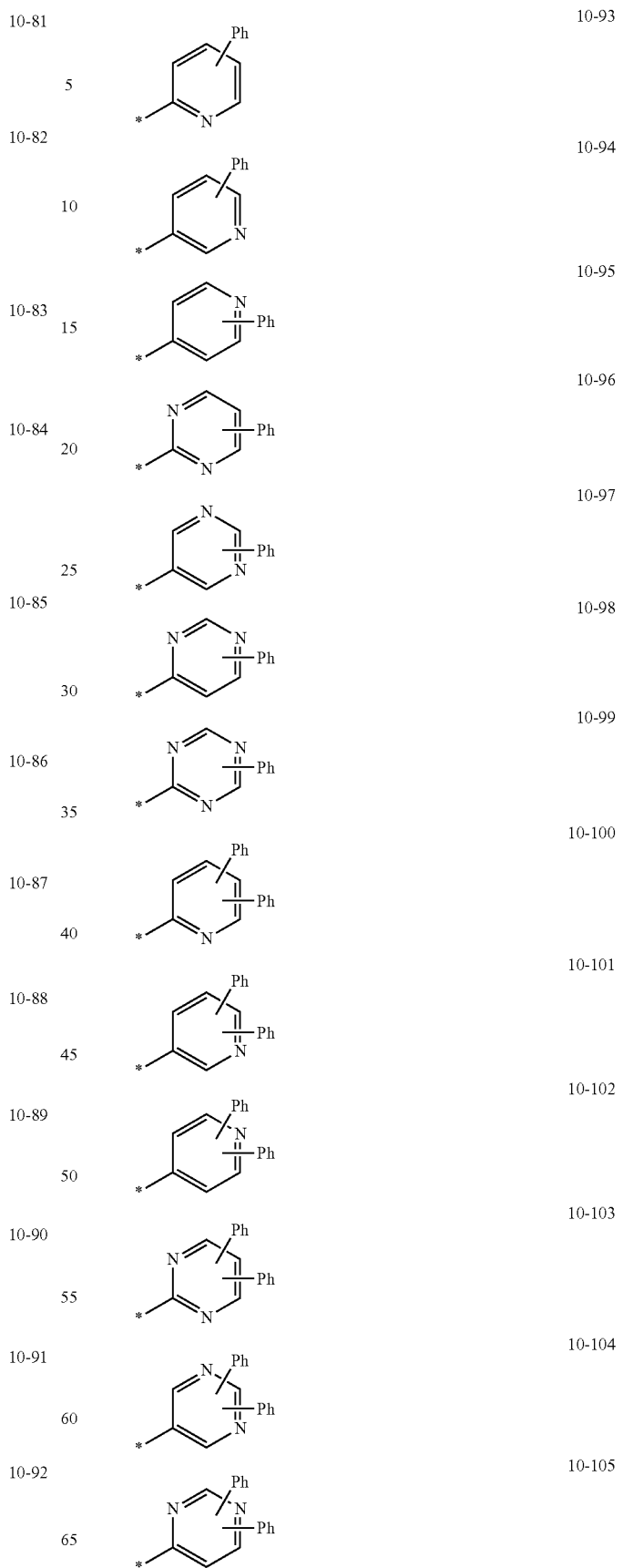

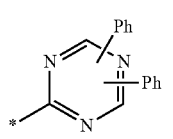
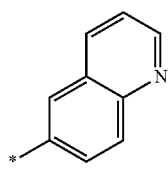
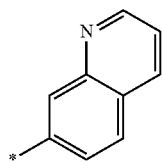
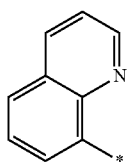
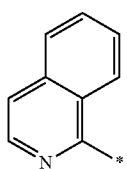
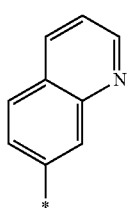
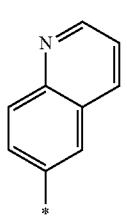
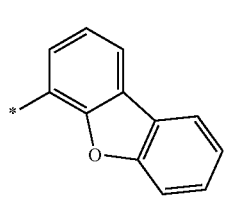
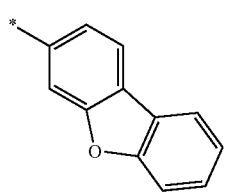
10-106
10-107
10-108
10-109
10-110
10-111
10-112
10-113
10-114
10-115
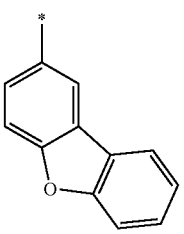
10-116
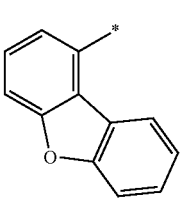
10-117
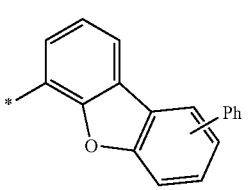
10-118
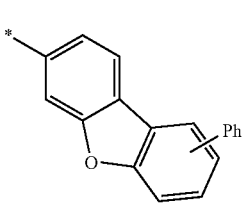
10-119
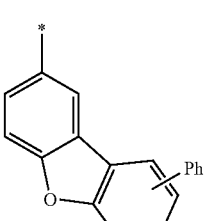
10-120
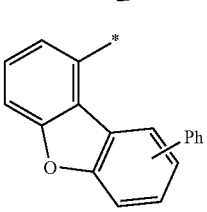
10-121
10-122

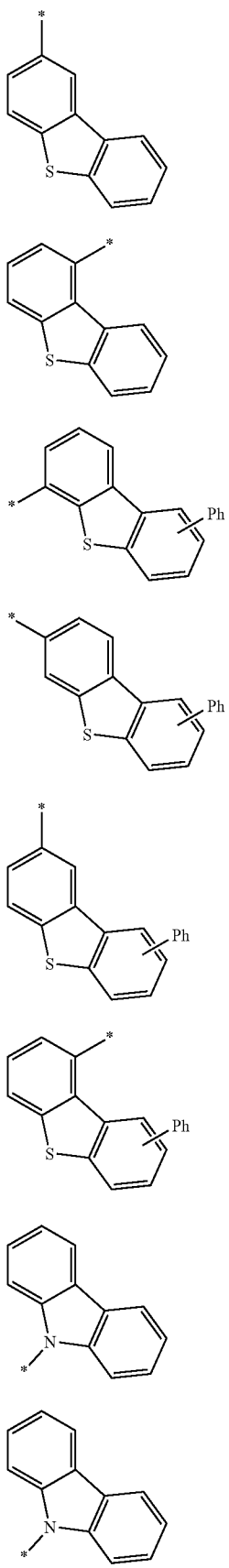
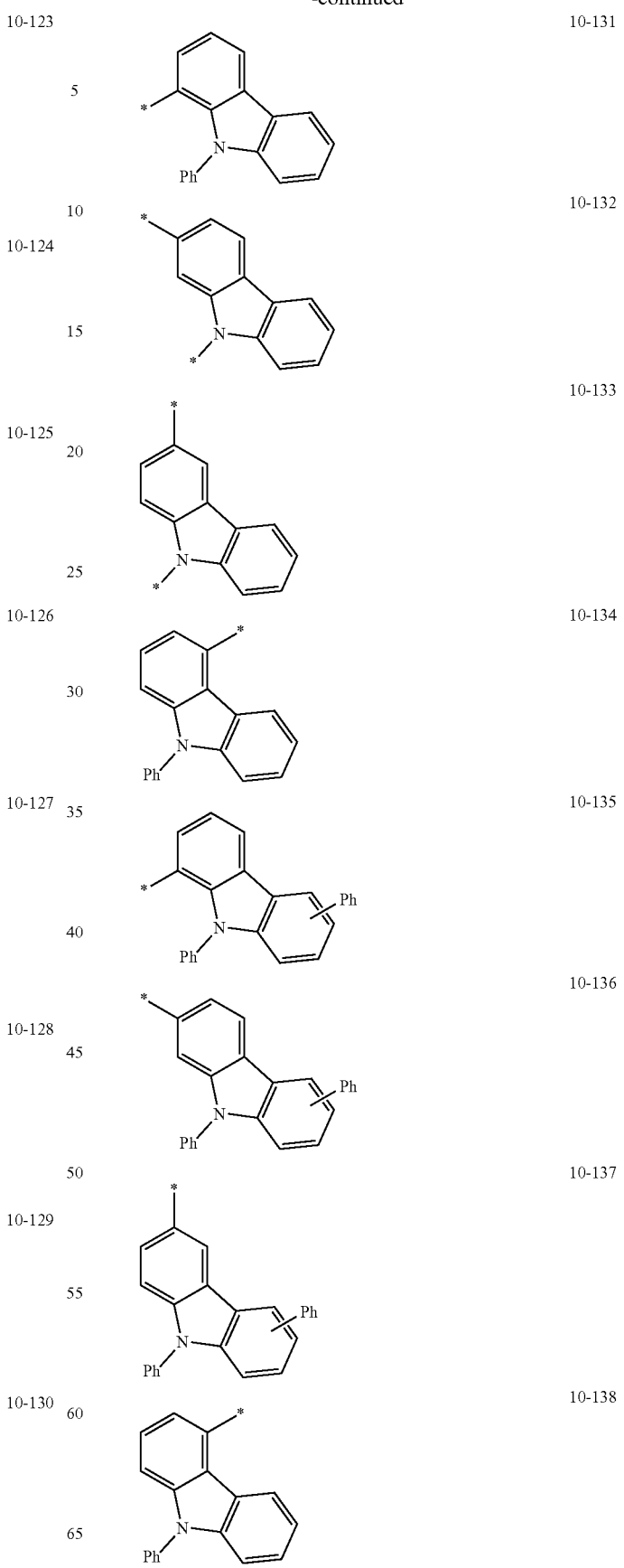

10-139 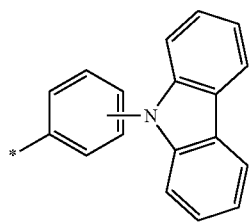
10-140 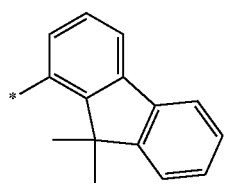
10-141 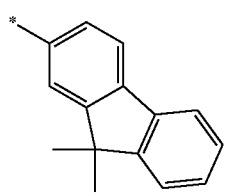
10-142 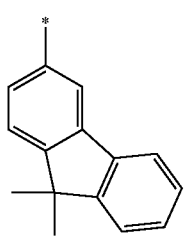
10-143 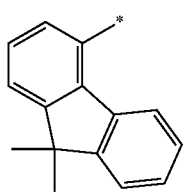
10-144 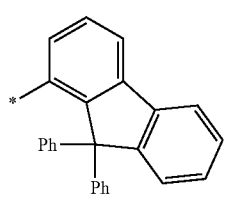
10-145 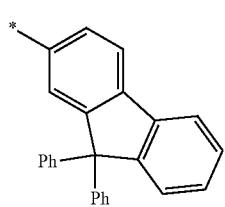
10-146 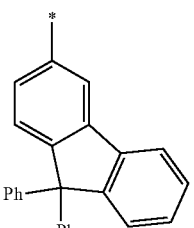
10-147 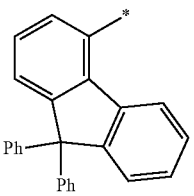
10-148 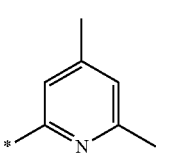
10-149 
10-150 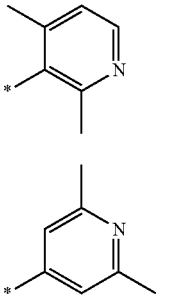
10-151 
10-152 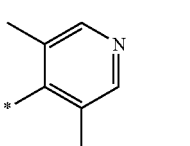
10-153 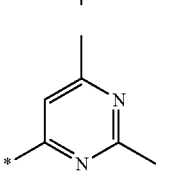
10-154 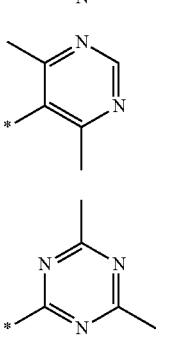
10-155

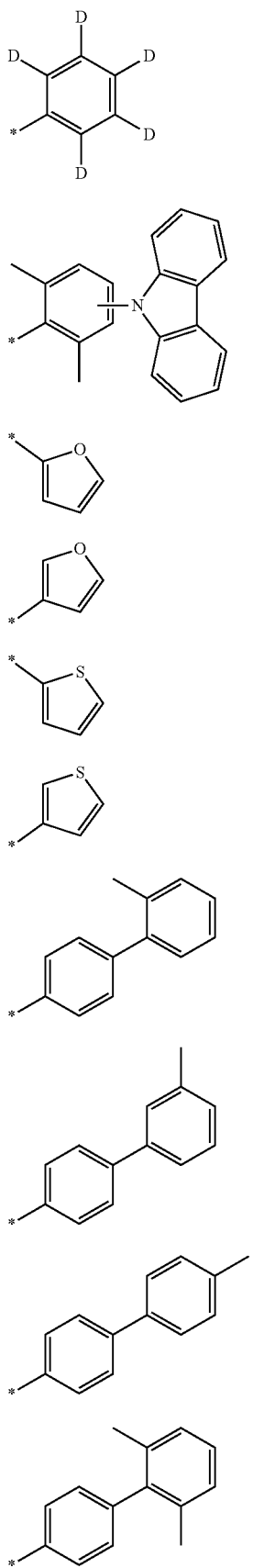
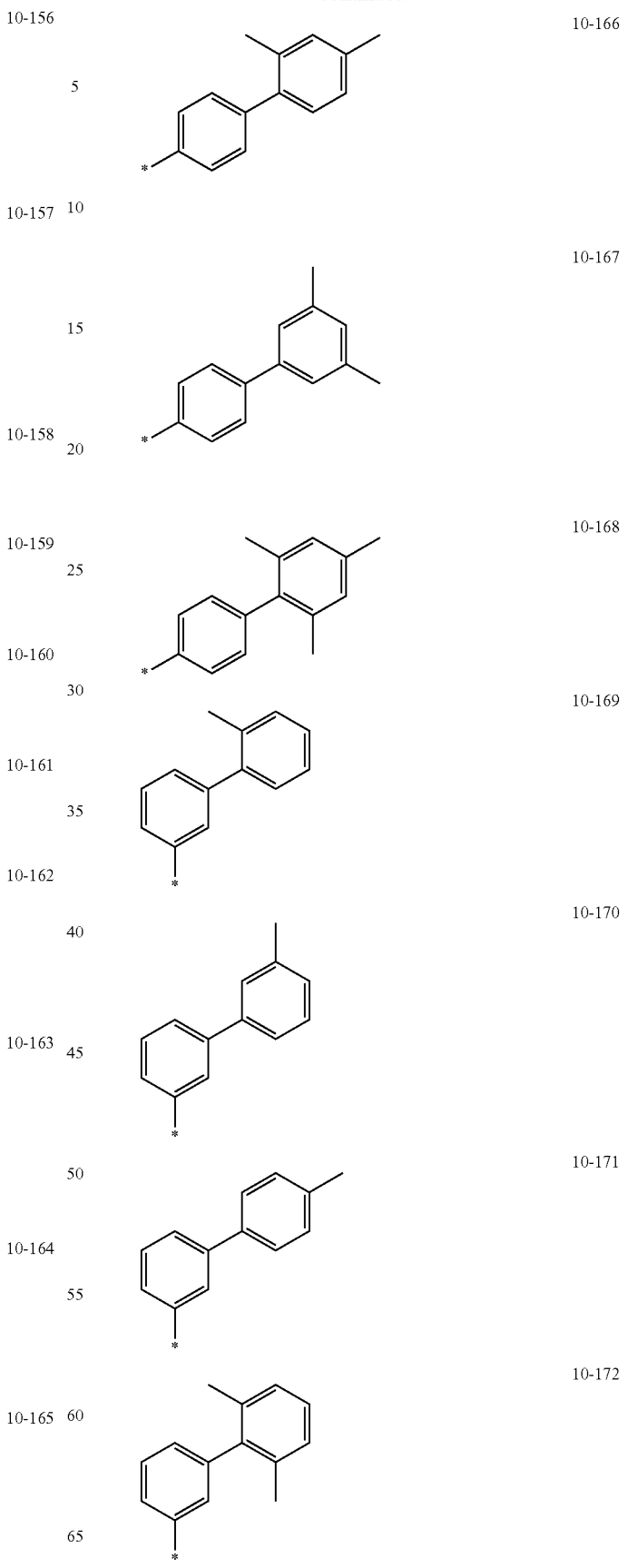

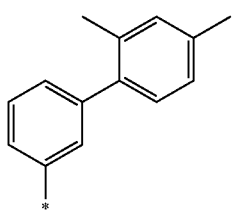
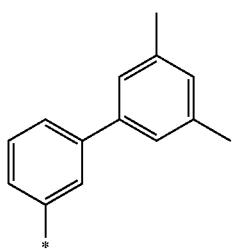
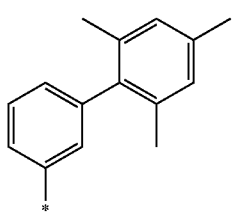
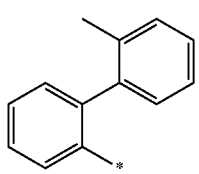
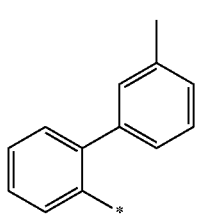
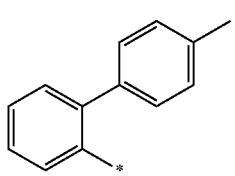
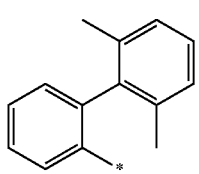
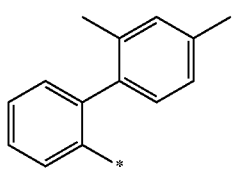
10-173
10-174
10-175
10-176
10-177
10-178
10-179
10-180
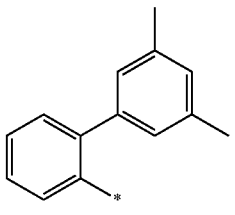
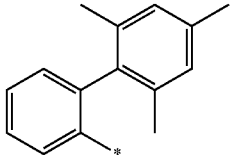
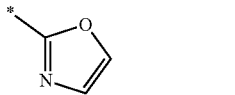
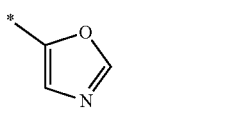
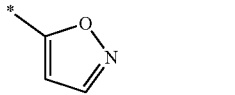
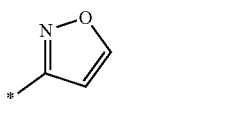
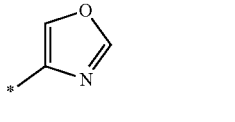
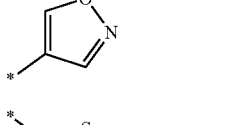
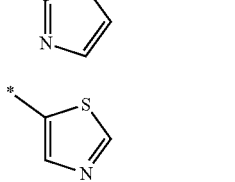

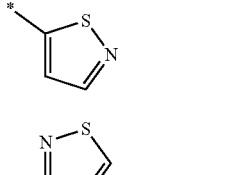
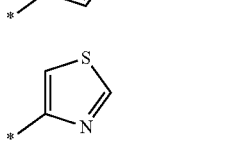
10-181
10-182
10-183
10-184
10-185
10-186
10-187
10-188
10-189
10-190
10-191
10-192
10-193

10-194

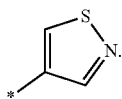

wherein, in Formulae 9-1 to 9-19 and 10-1 to 10-194, * indicates a binding site to a neighboring atom, Ph may be a phenyl group, and TMS may be a trimethylsilyl group.

In an embodiment, $R_{10}$, $R_{20}$, and $R_{30}$ may each independently be hydrogen or a cyano group.

In an embodiment, $R_{40}$, $R_{50}$, and $R_{60}$ may each independently be hydrogen or a cyano group.

In an embodiment, the heterocyclic compound represented by Formula 1 may be a compound represented by Formula 10:

Formula 10

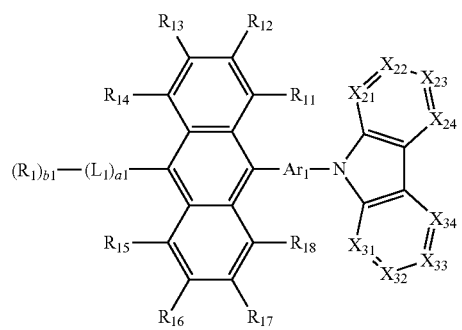

wherein, in Formula 10,
$Ar_1$, $L_1$, a1, $R_1$, and b1 may each be the same as described in the present specification,
$X_{21}$ may be $C(R_{21})$ or N, $X_{22}$ may be $C(R_{22})$ or N, $X_{23}$ may be $C(R_{23})$ or N, and $X_{24}$ may be $C(R_{24})$ or N,
$X_{31}$ may be $C(R_{31})$ or N, $X_{32}$ may be $C(R_{32})$ or N, $X_{33}$ may be $C(R_{33})$ or N, and $X_{34}$ may be $C(R_{34})$ or N,
$R_{11}$ to $R_{18}$ may each independently be the same as described in connection with $R_{10}$,
$R_{21}$ to $R_{24}$ may each independently be the same as described in connection with $R_{20}$, and
$R_{31}$ to $R_{34}$ may each independently be the same as described in connection with $R_{30}$.

In an embodiment, the heterocyclic compound may be one of Compounds 1 to 560:

1

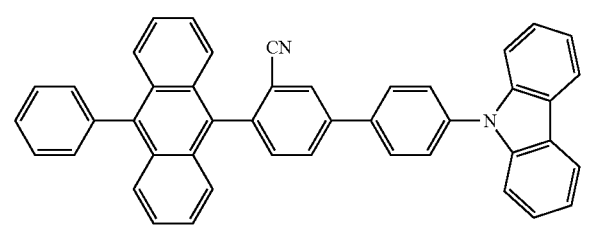

2

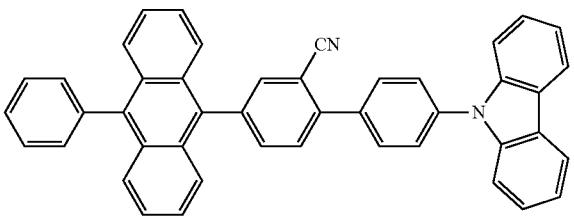

3

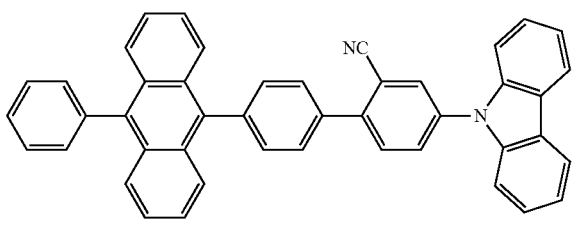

4

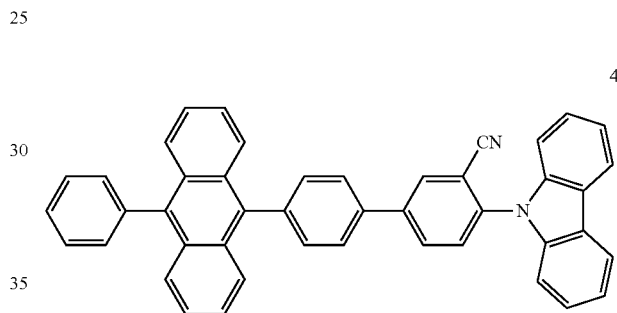

5

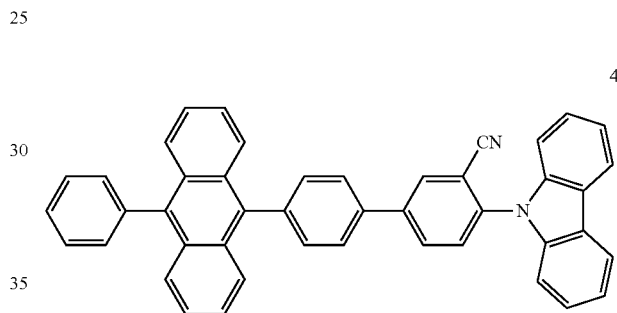

6

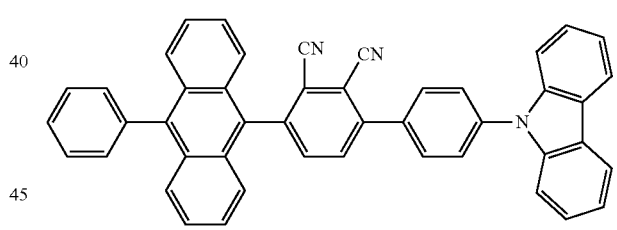

7

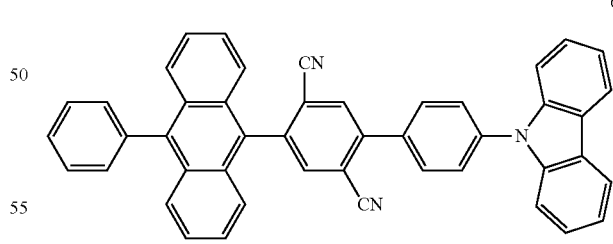

-continued
8
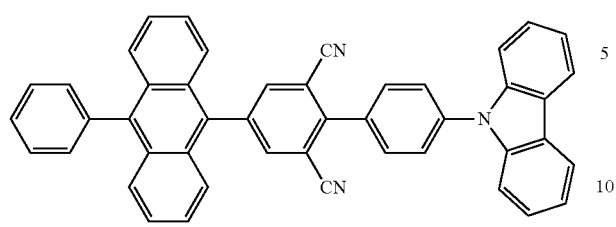
14
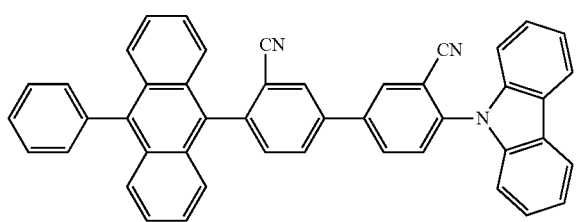
9
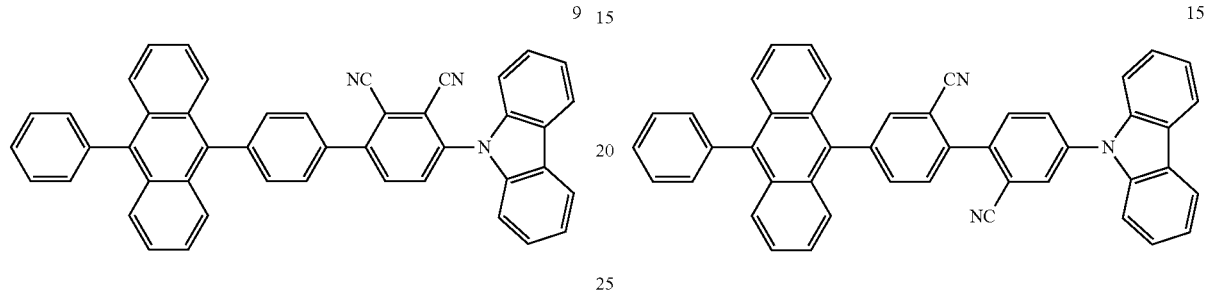
15
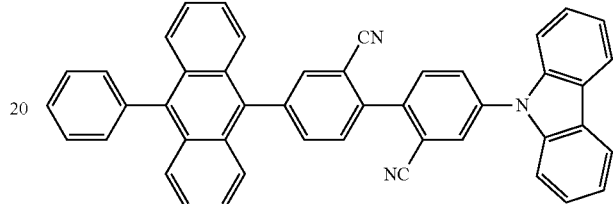
10
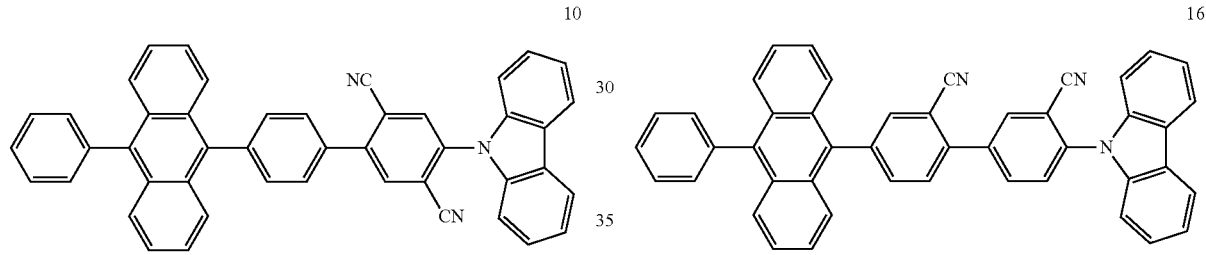
16
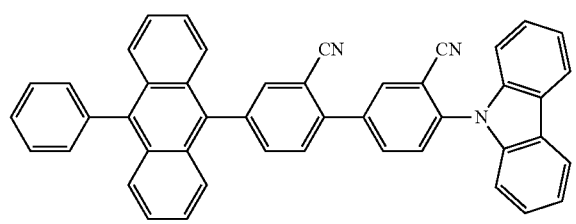
11
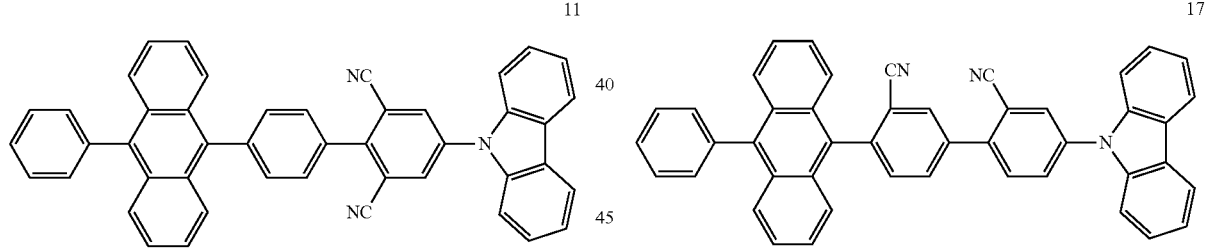
17
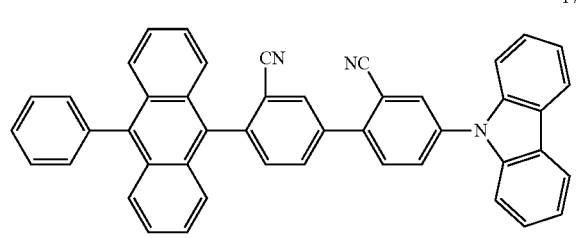
12
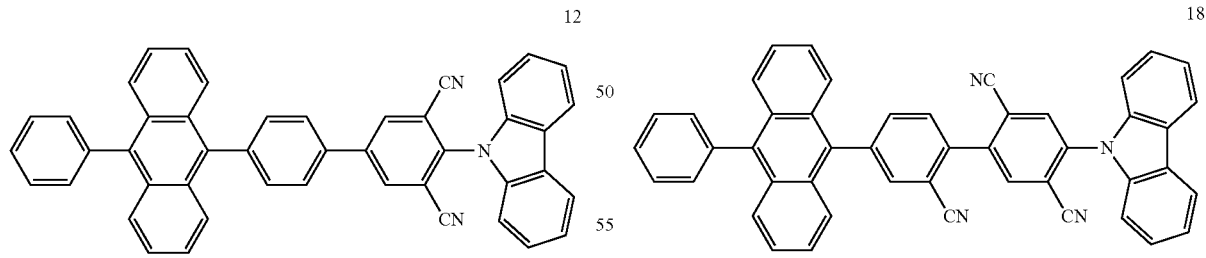
18
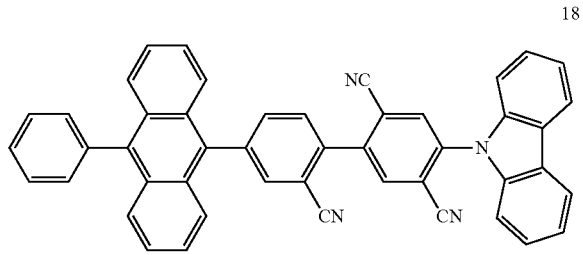
13
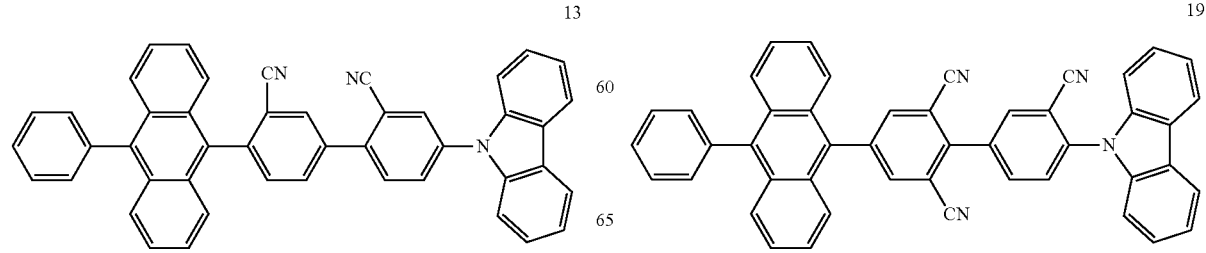
19
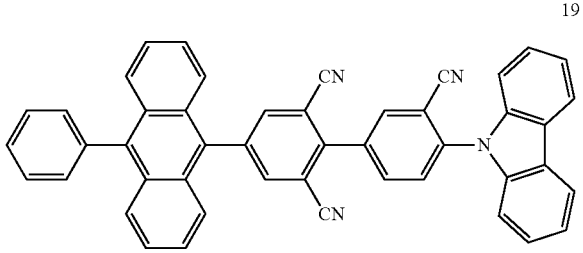

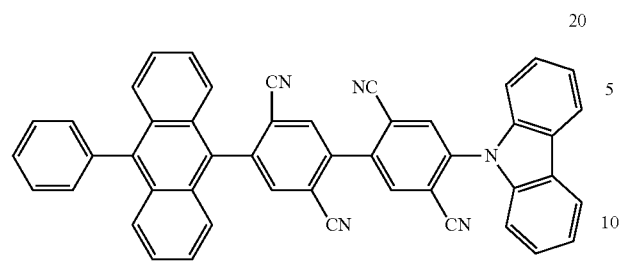
20
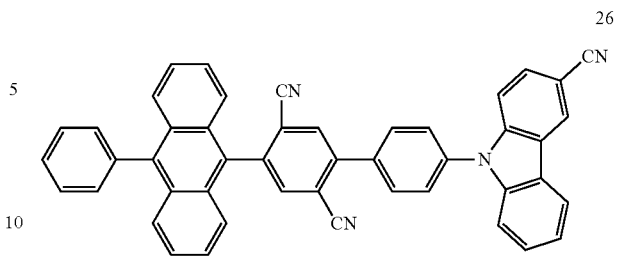
26
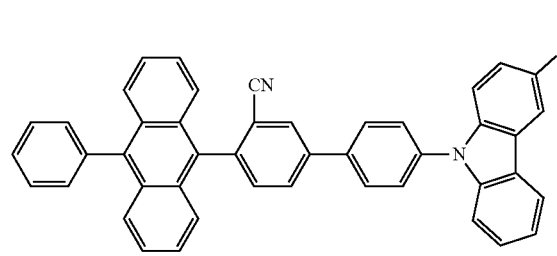
21
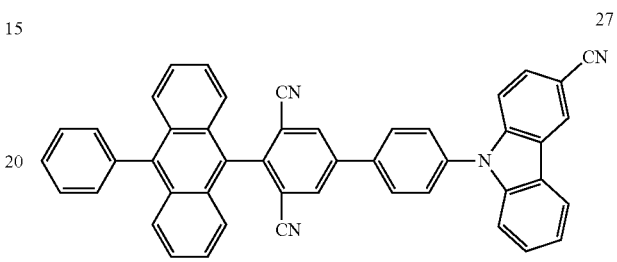
27
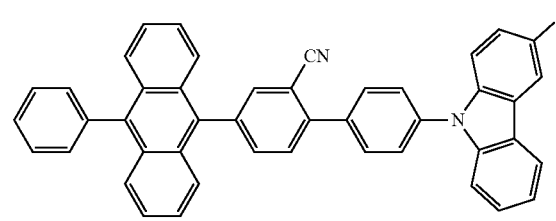
22
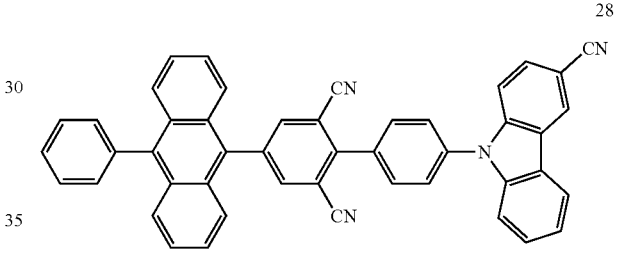
28
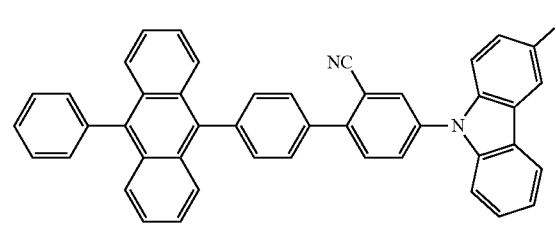
23
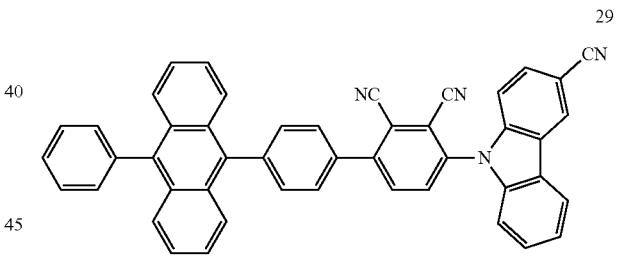
29
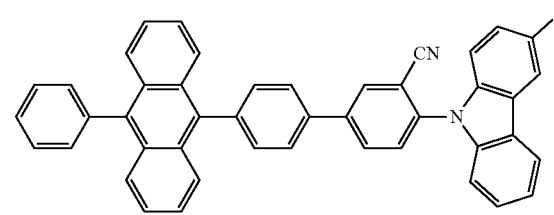
24
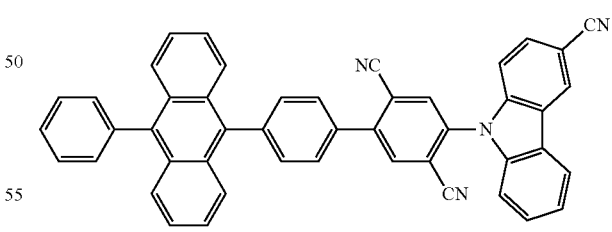
30
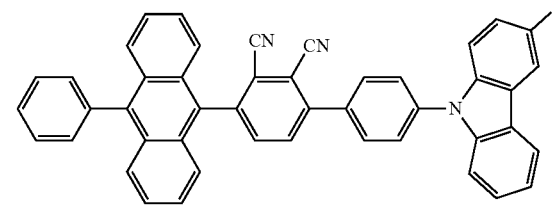
25
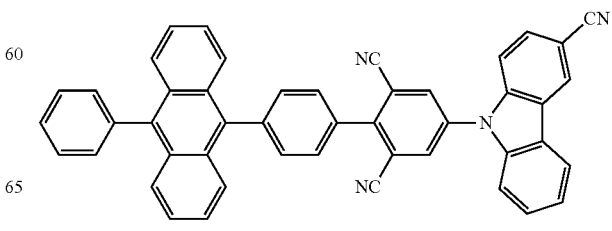
31

-continued
32
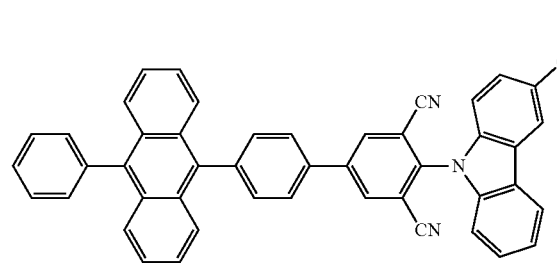
33
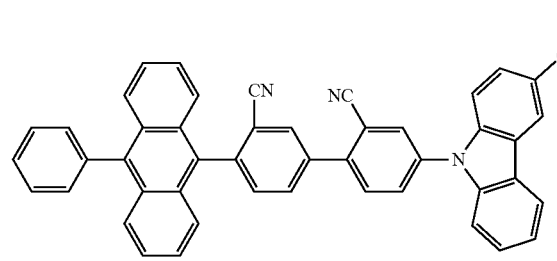
34
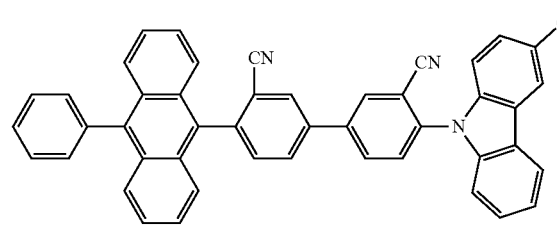
35
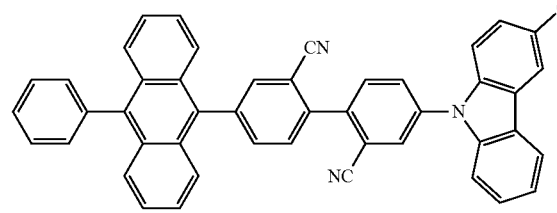
36
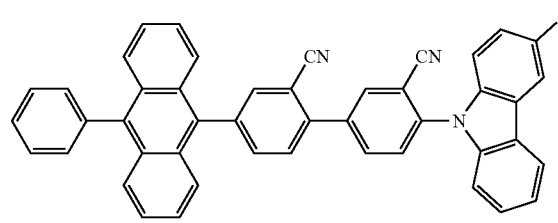
37
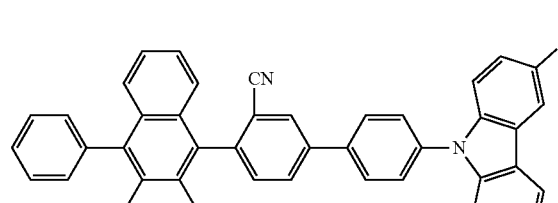
-continued
38
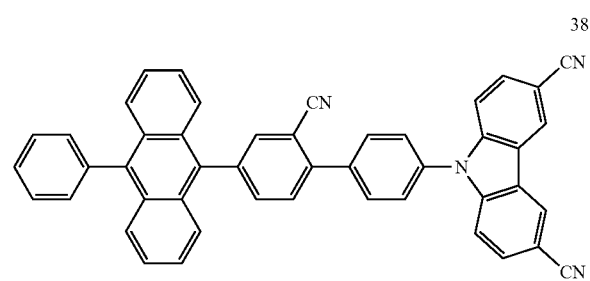
39
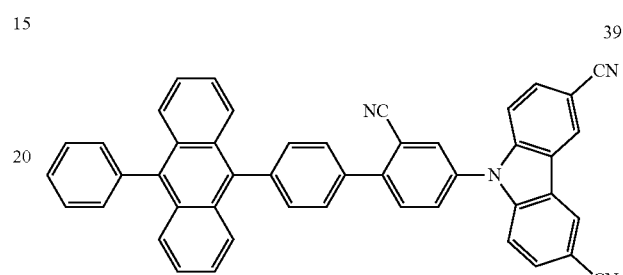
40
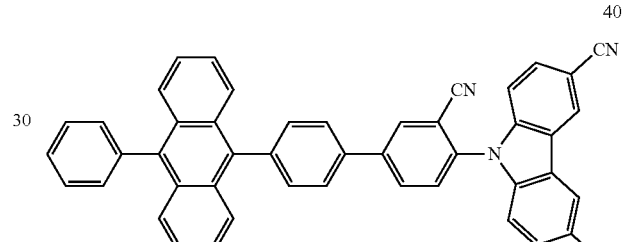
41
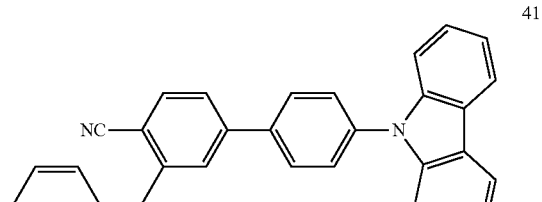
42
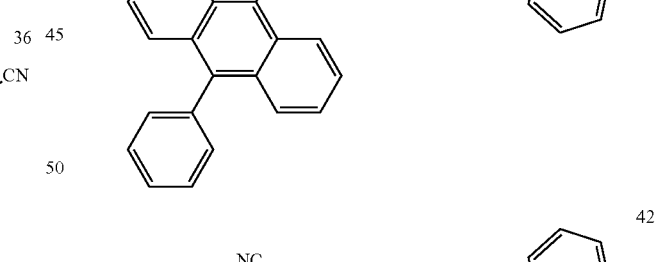

-continued
43
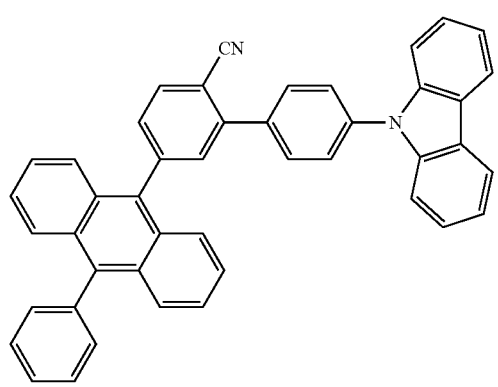
44
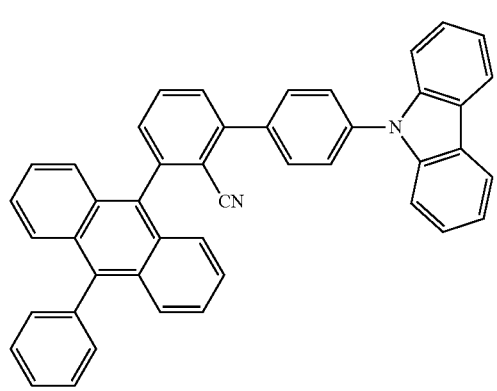
45
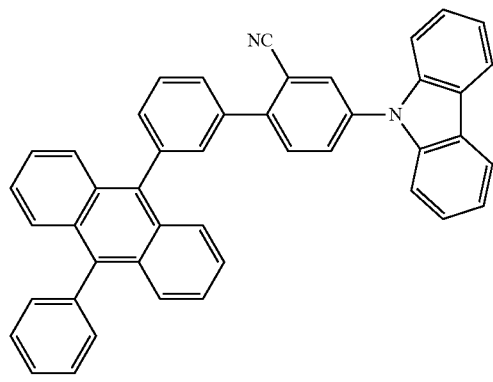
46
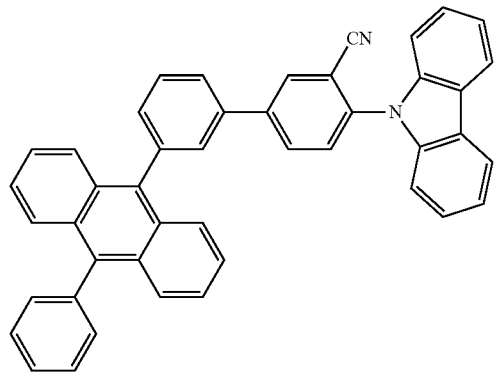
-continued
47
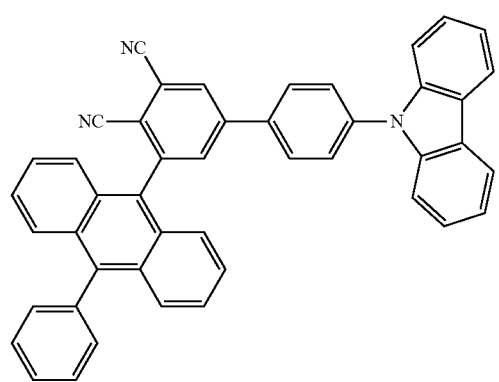
48
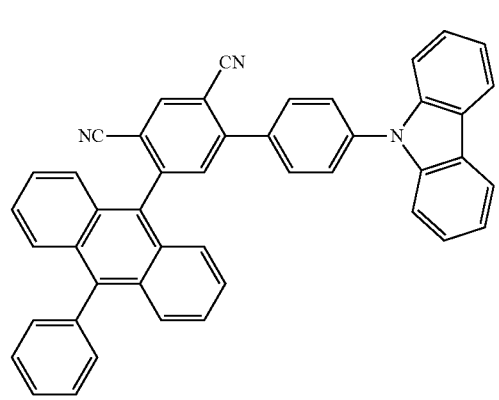
49
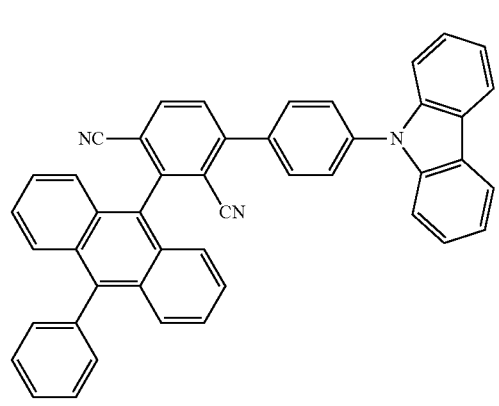
50
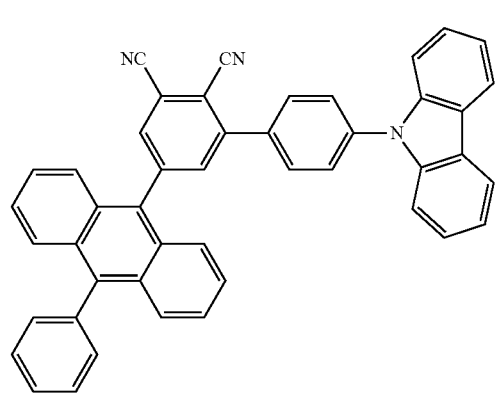

51
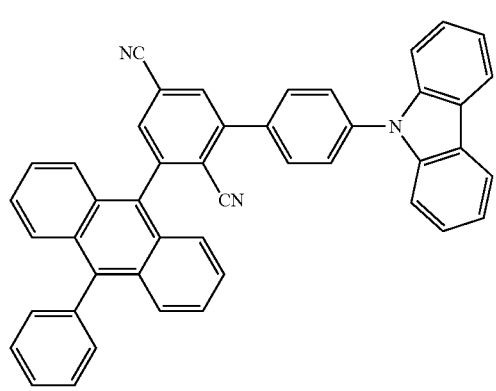
52
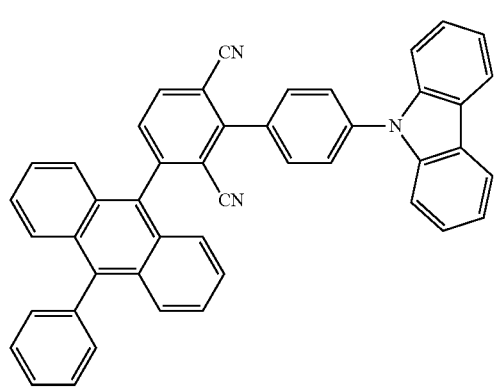
53
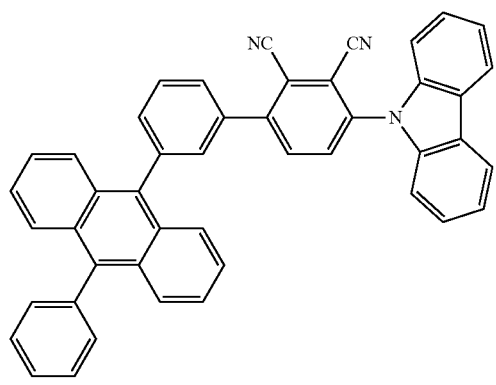
54
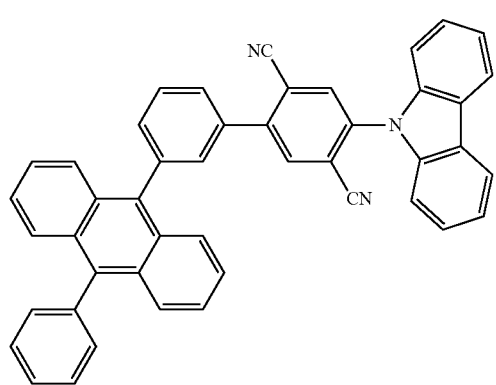
55
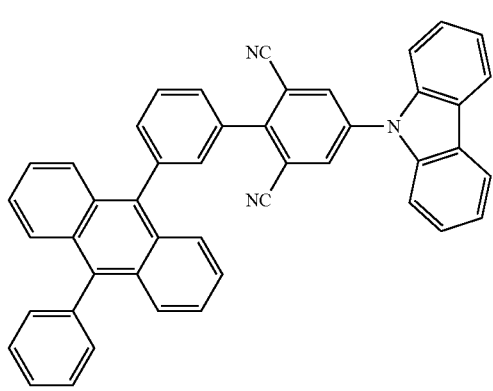
56
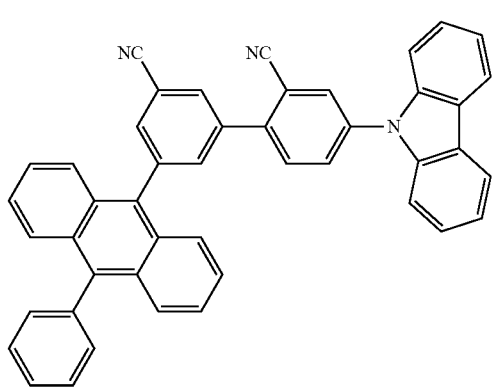
57
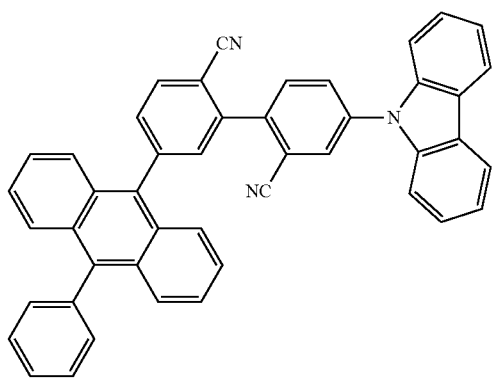
58
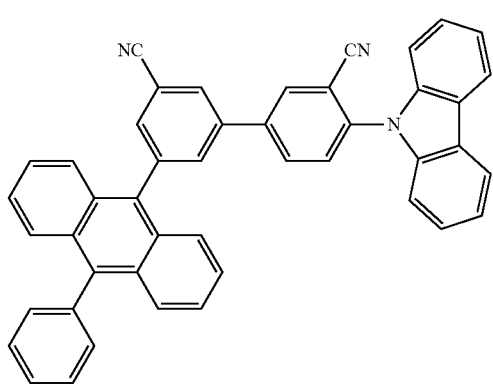

-continued
59
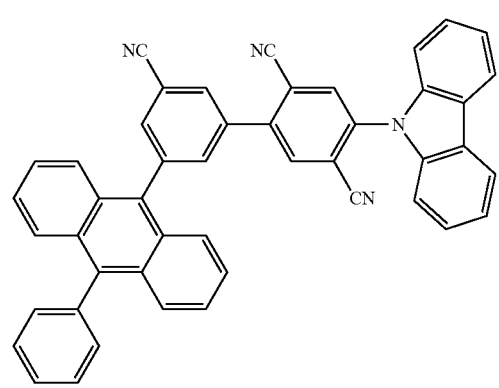
60
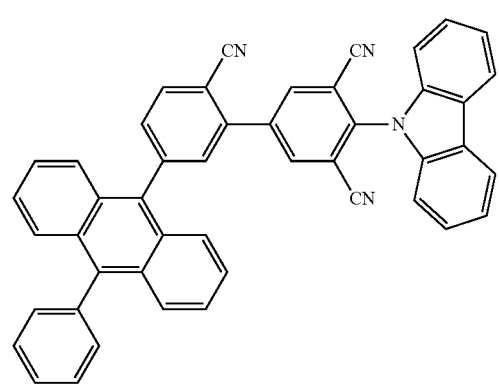
61
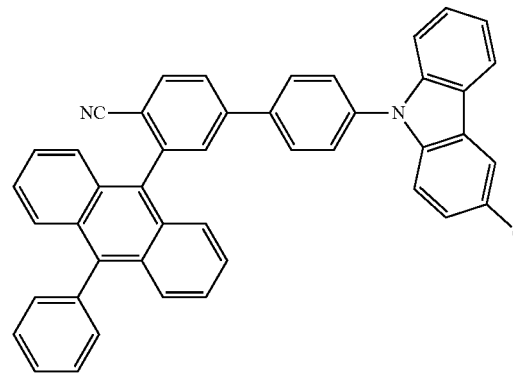
62
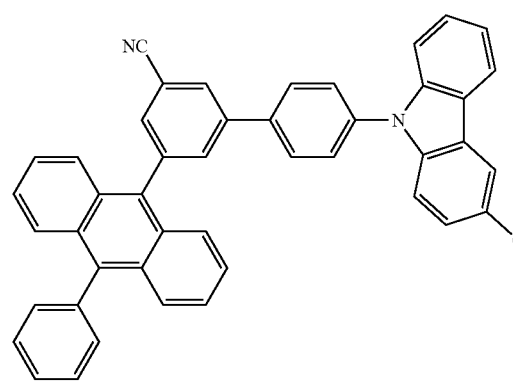
-continued
63
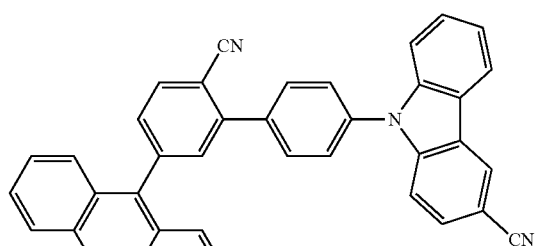
64
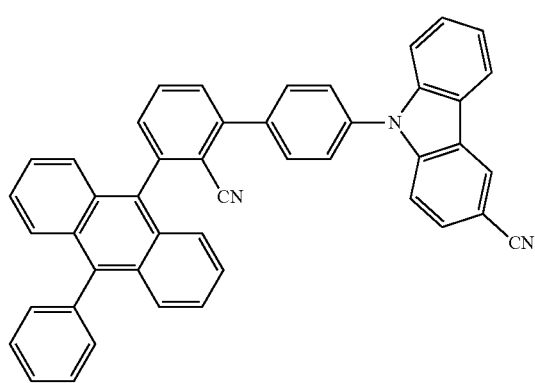
65
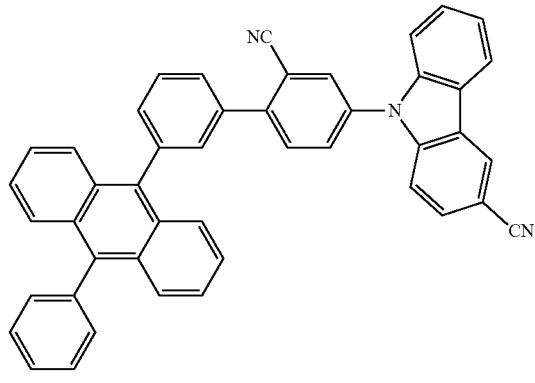
66
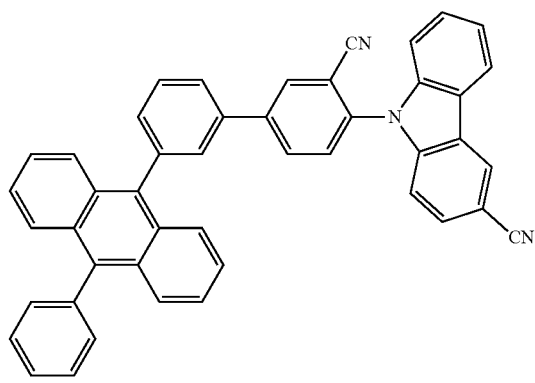

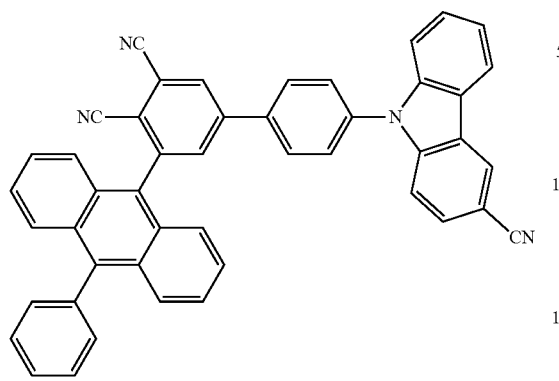
67
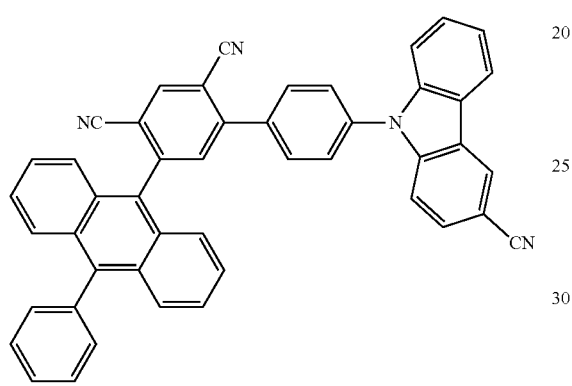
68
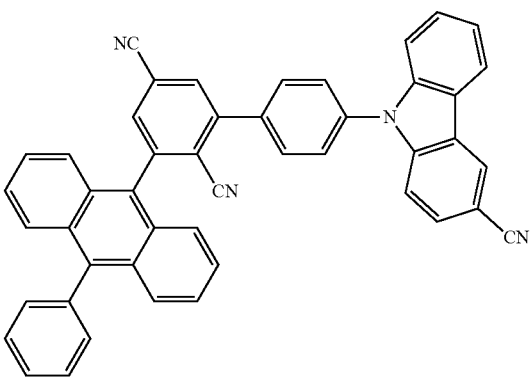
71
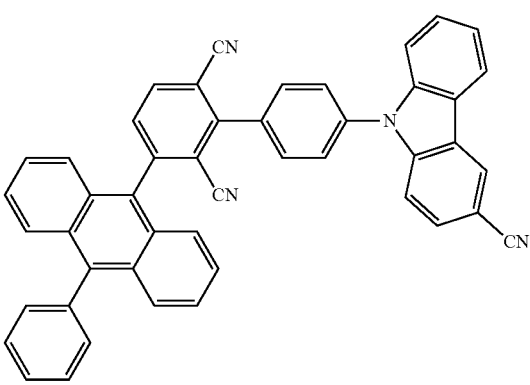
72
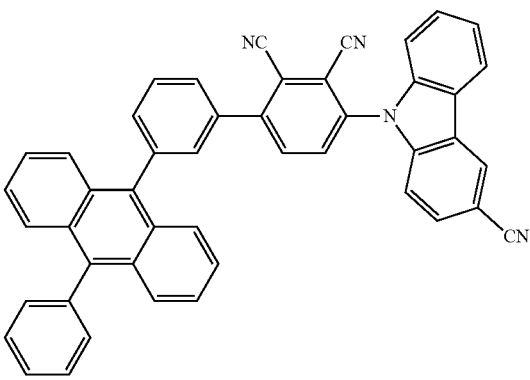
73
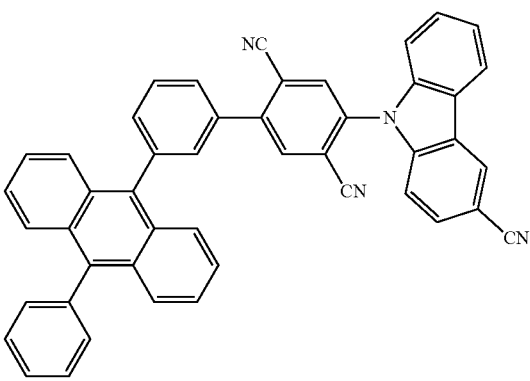
74

75
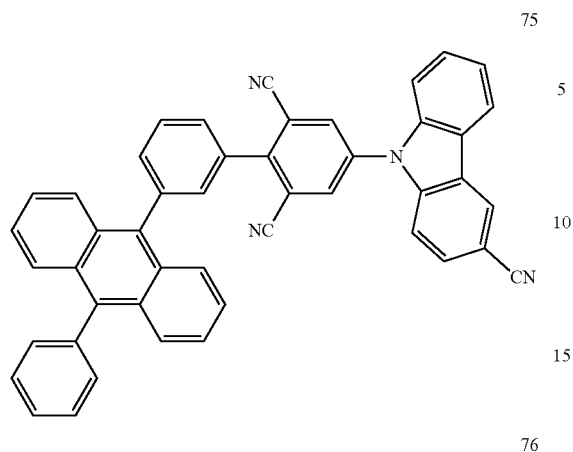
76
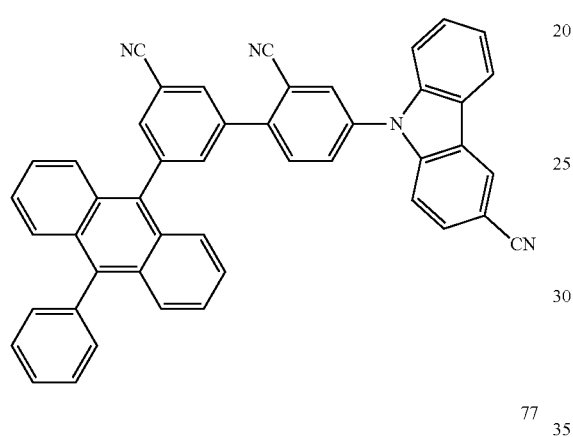
77
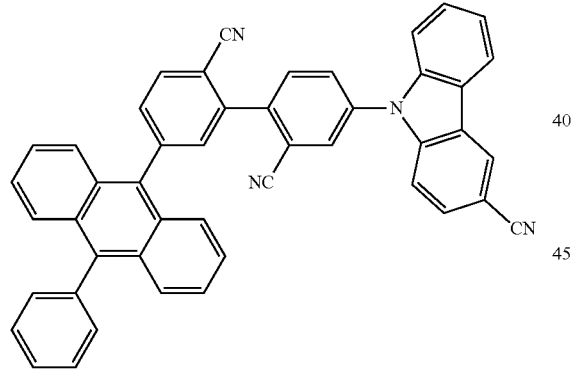
78
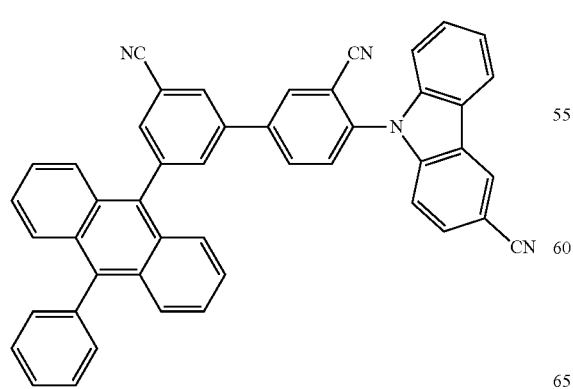
79
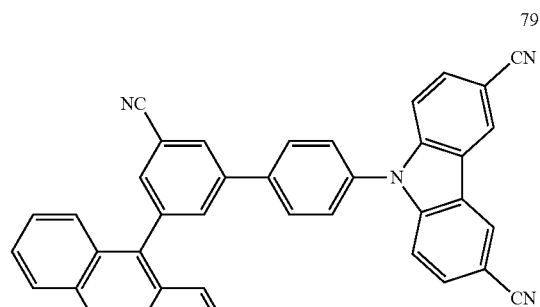
80
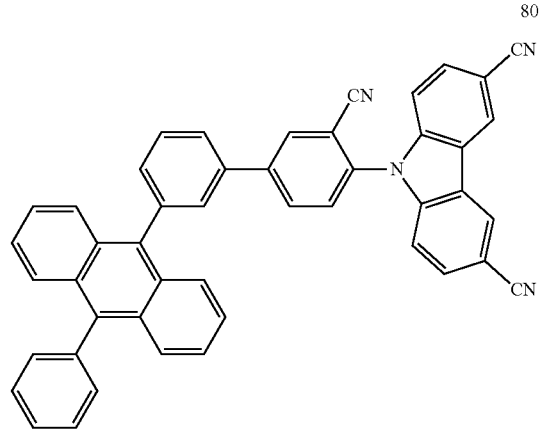
81
82
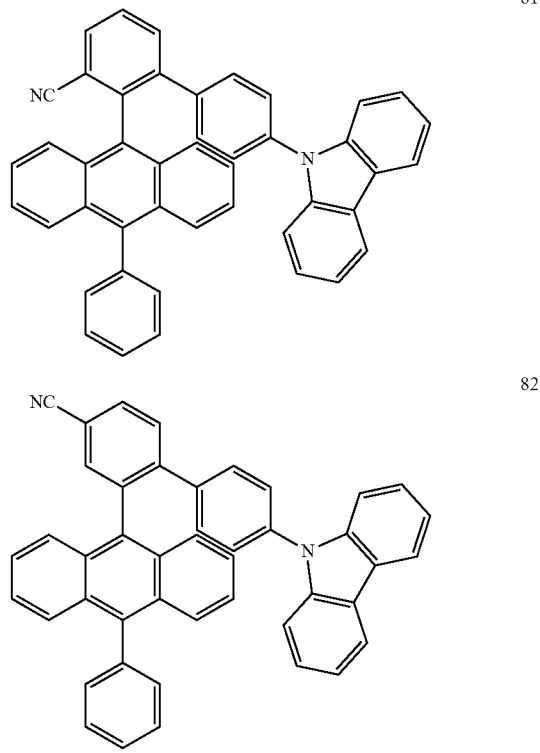

83
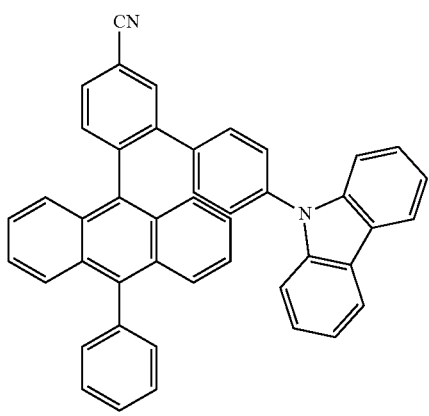
84
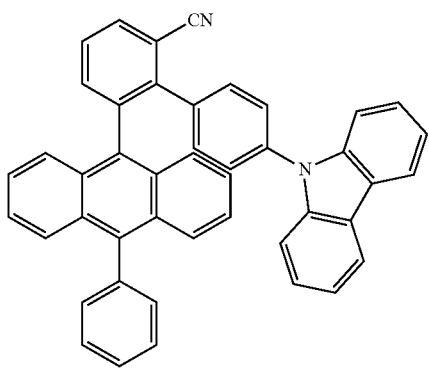
85
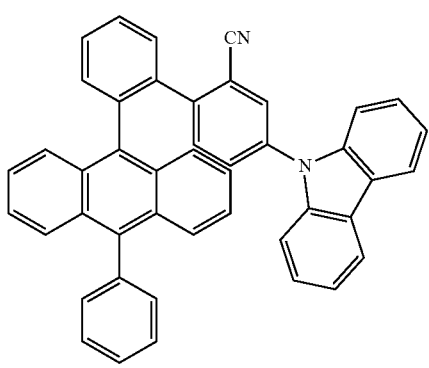
86
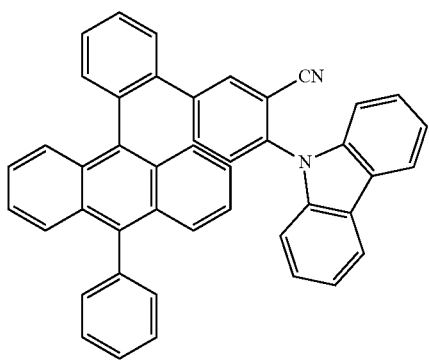
87
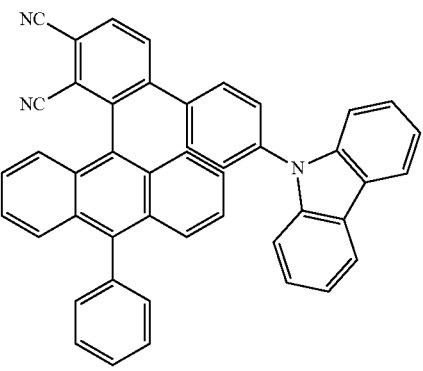
88
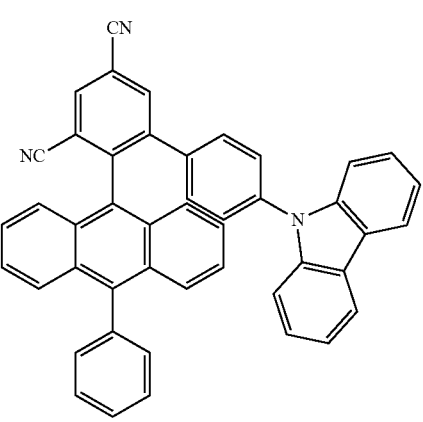
89
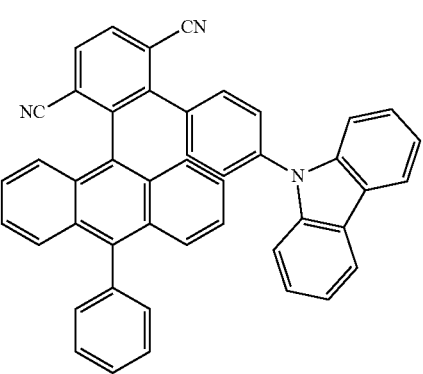
90
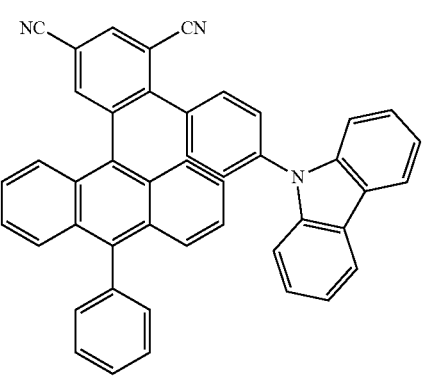

91
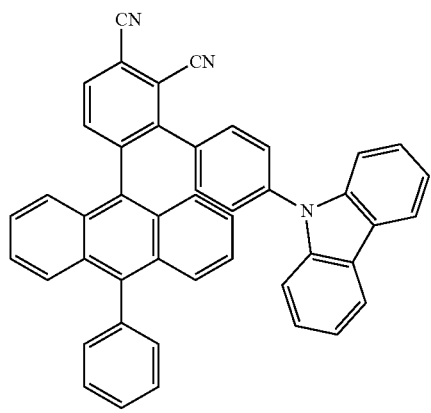
92
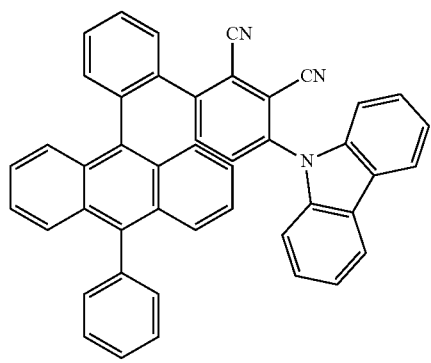
93
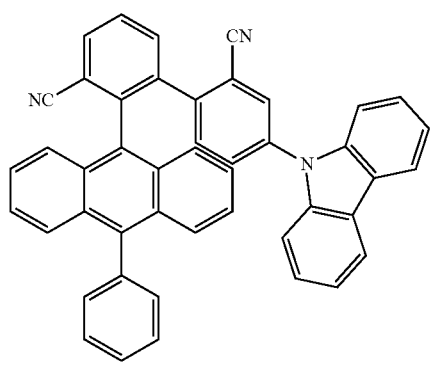
94
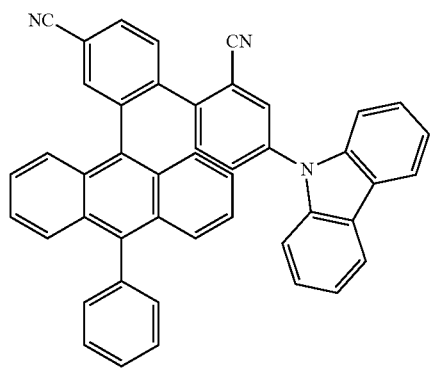
95
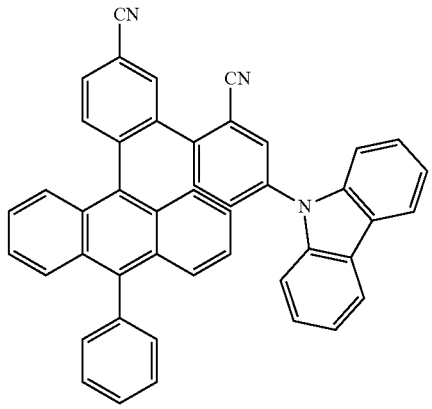
96
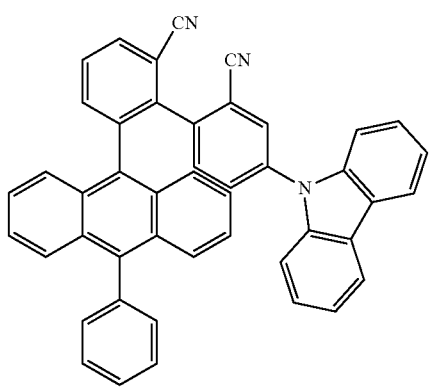
97
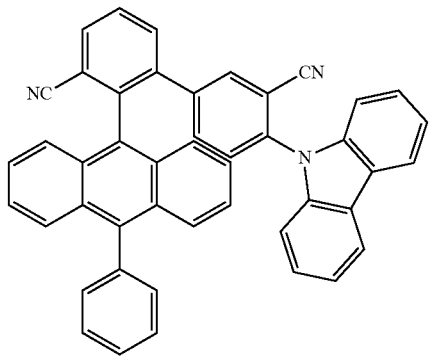
98
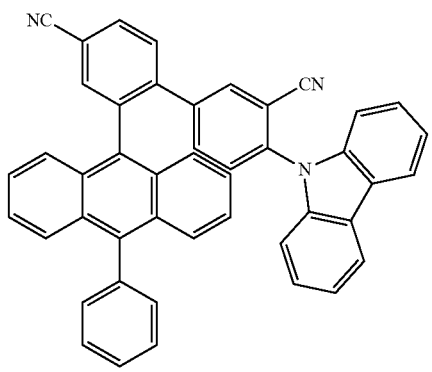

-continued
99
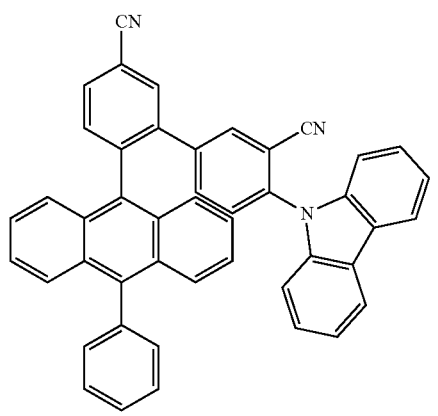
100
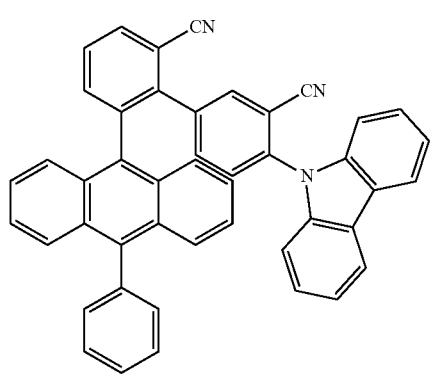
101
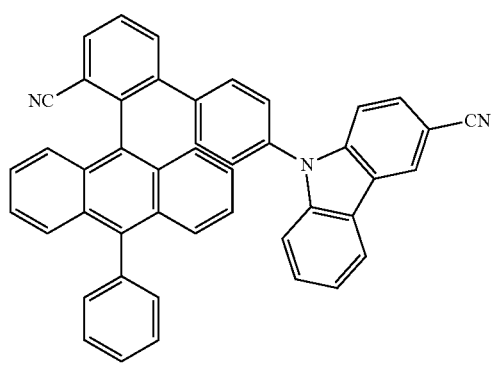
102
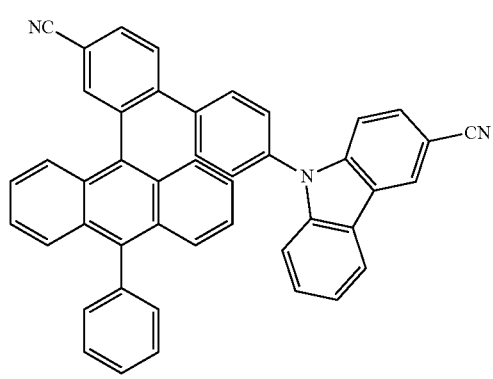
-continued
103
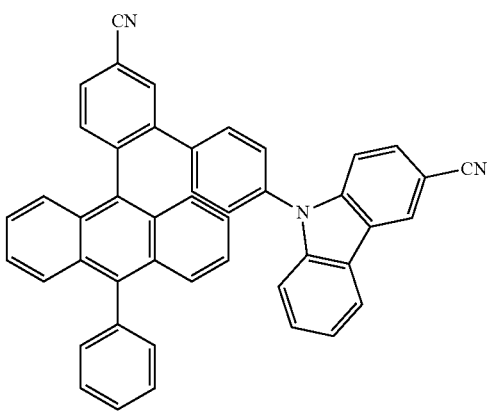
104
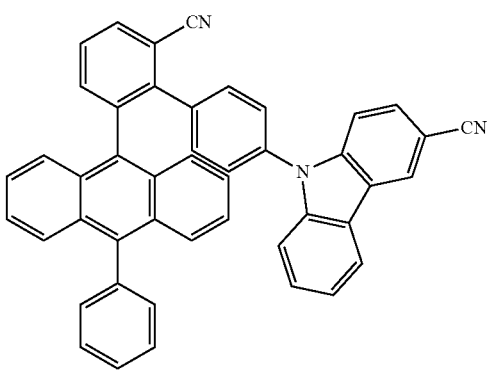
105
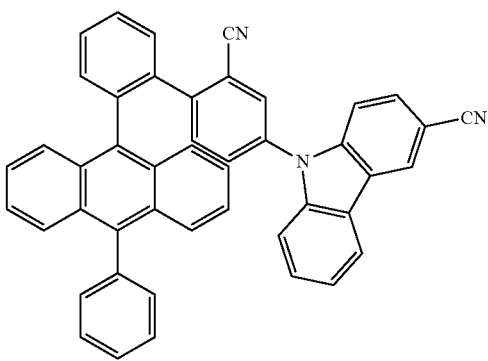
106
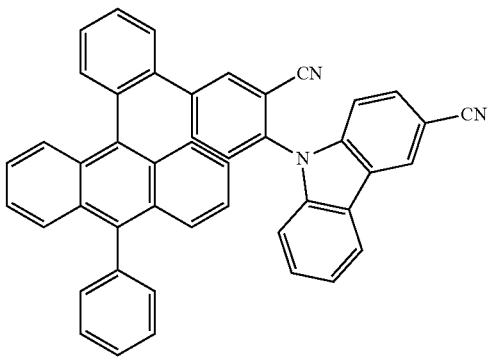

107
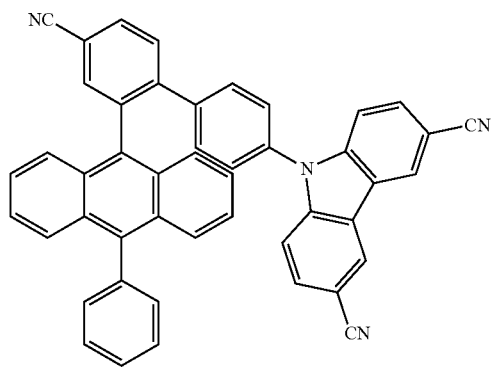
108
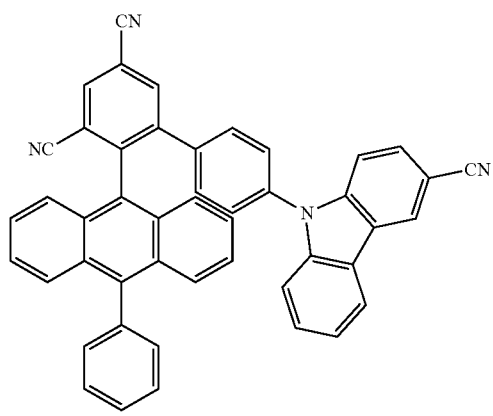
109
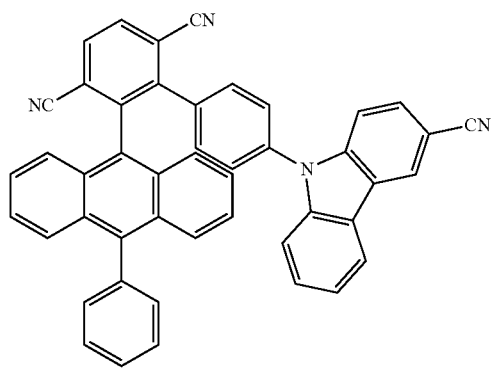
110
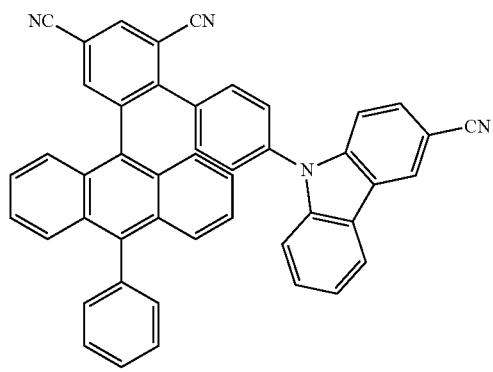
111
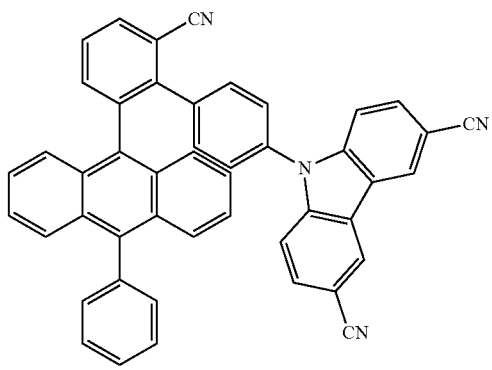
112
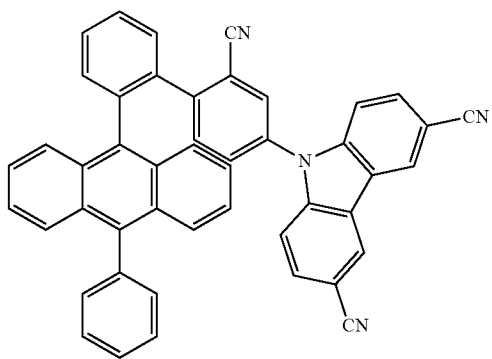
113
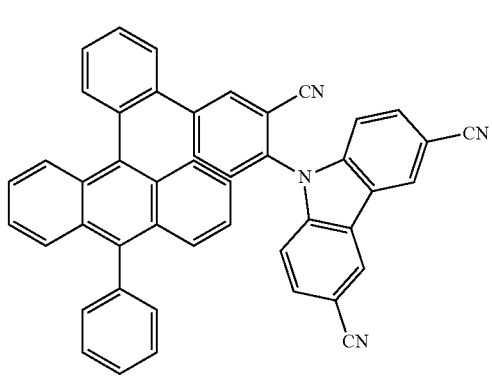
114
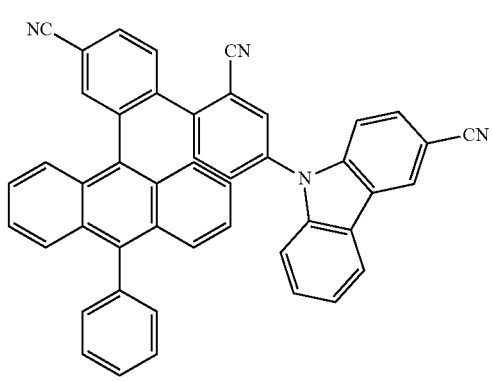

115
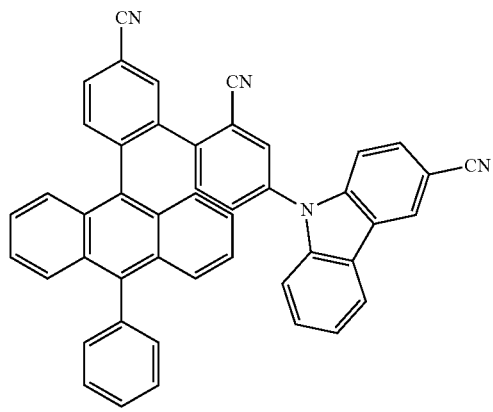
116
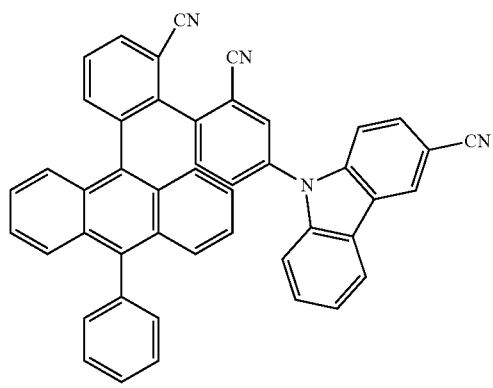
117
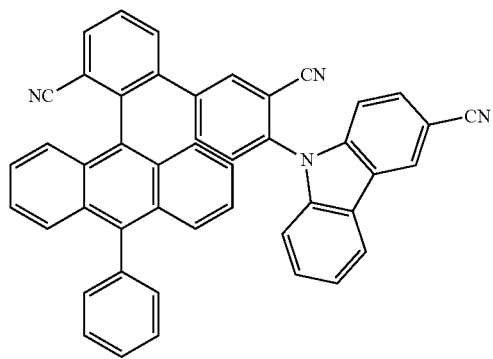
118
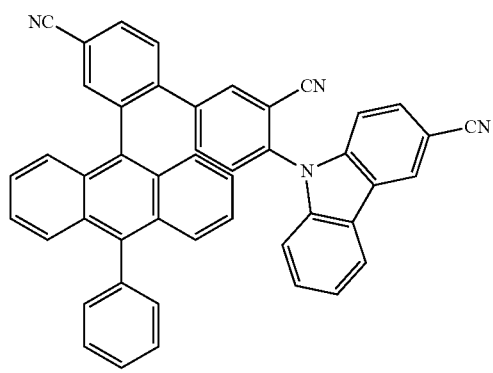
119
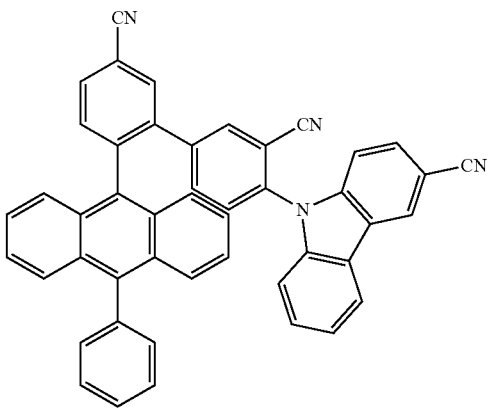
120
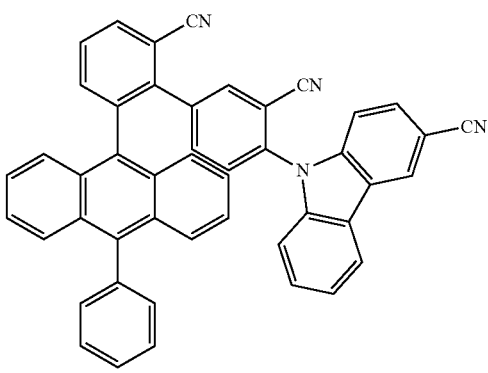
121
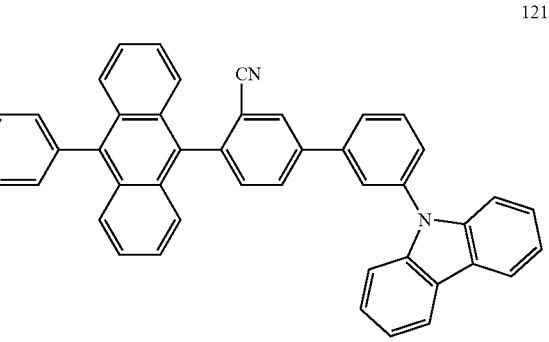
122
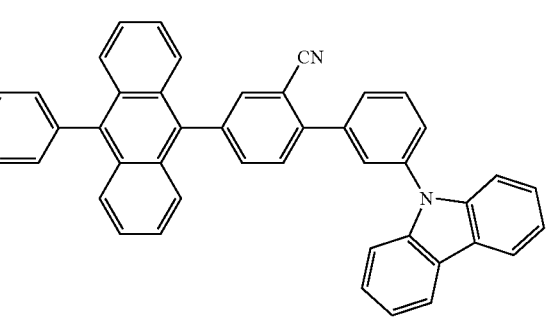

123
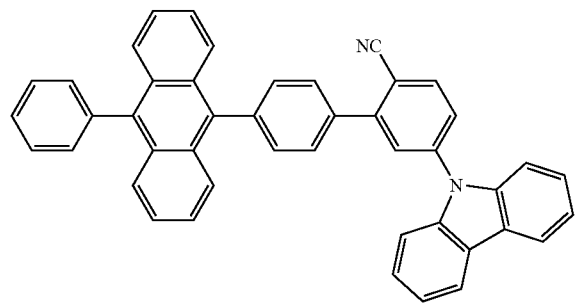
124
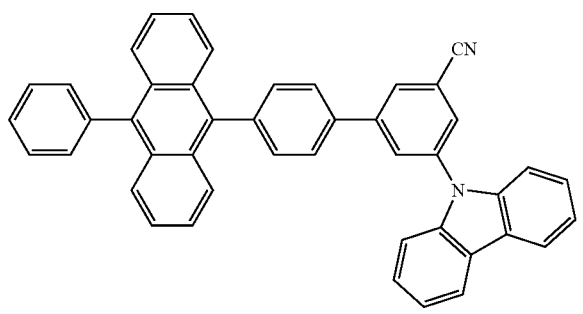
125
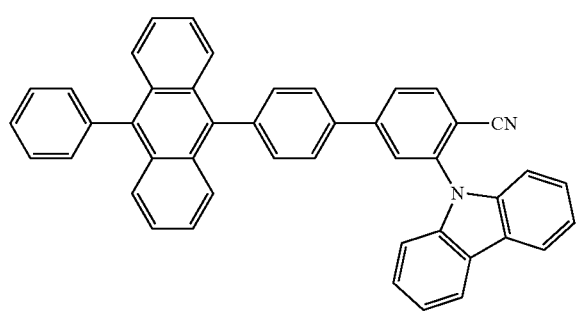
126
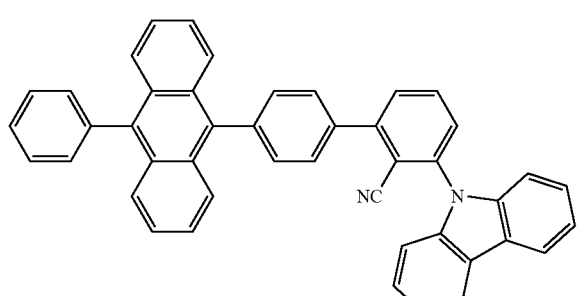
127
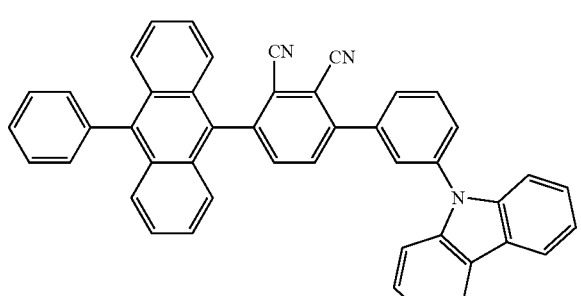
128
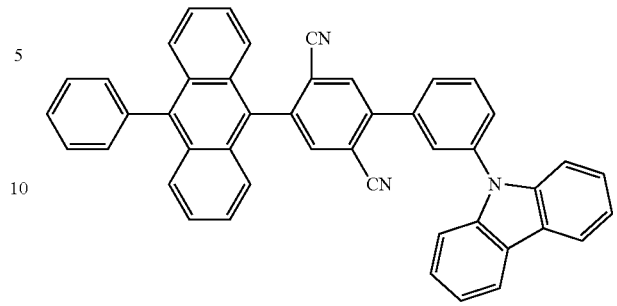
129
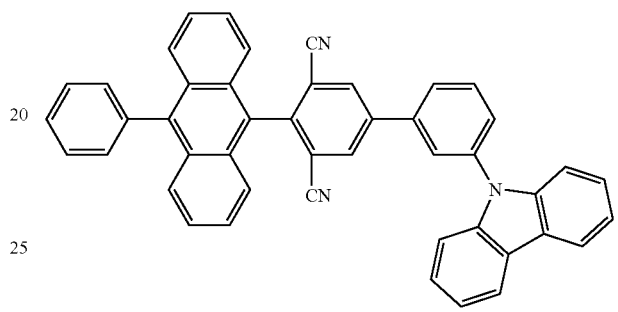
130
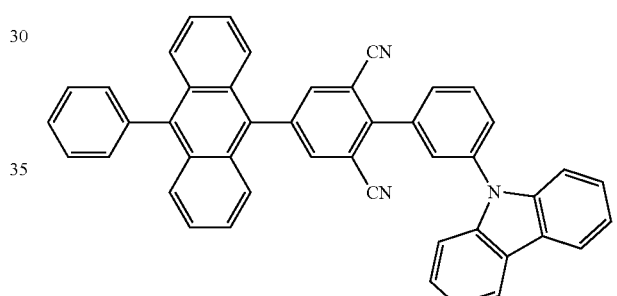
131
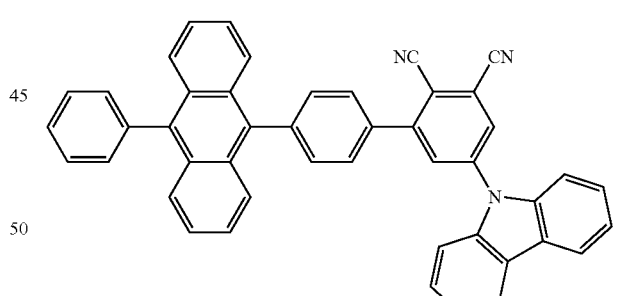
132
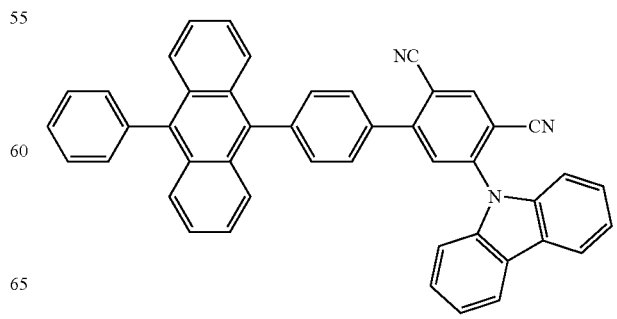

133
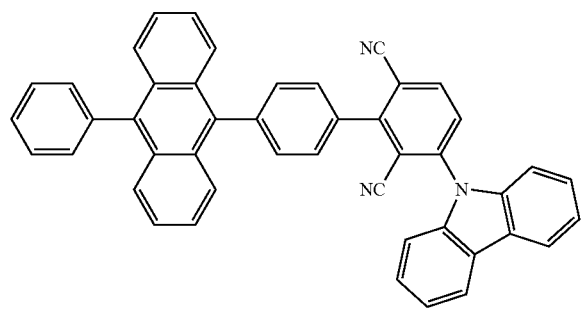
138
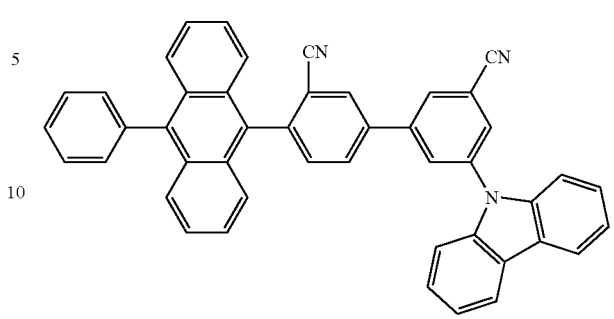
134
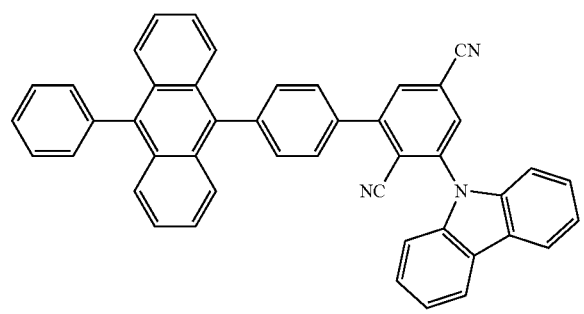
139
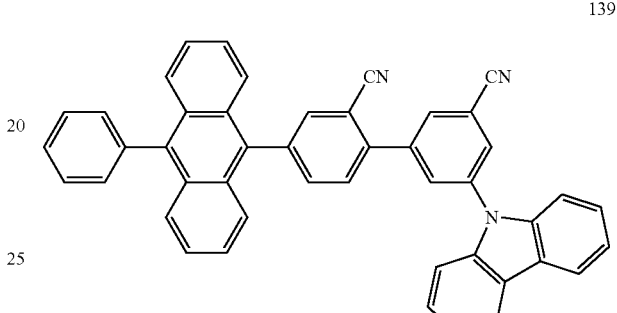
135
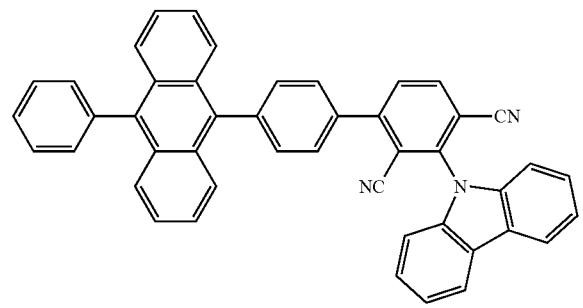
140
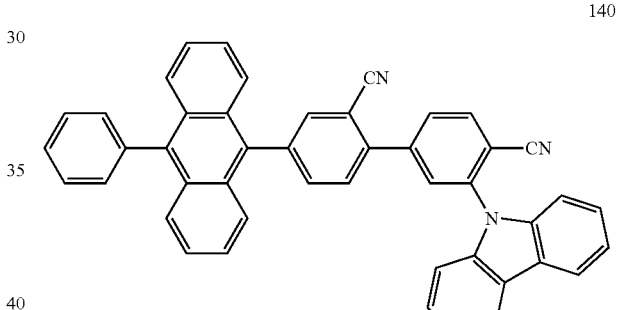
136
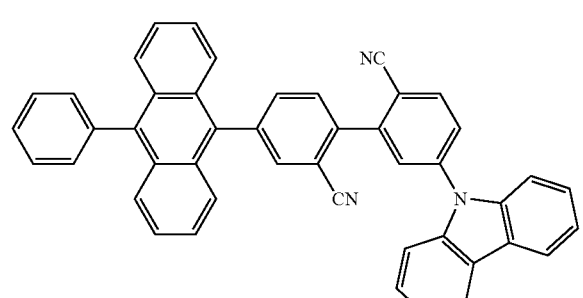
141
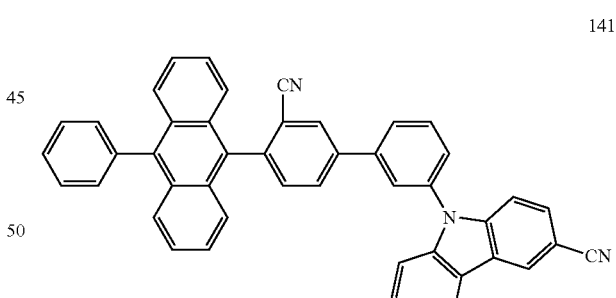
137
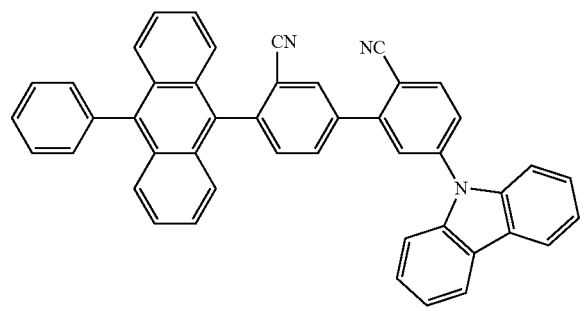
142
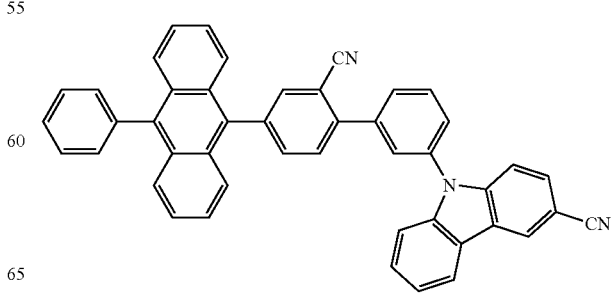

143
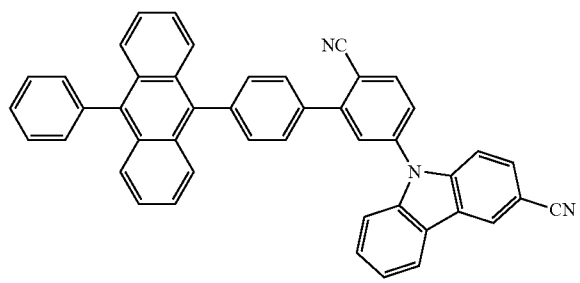
144
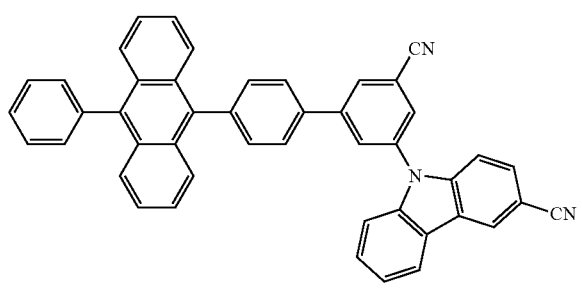
145
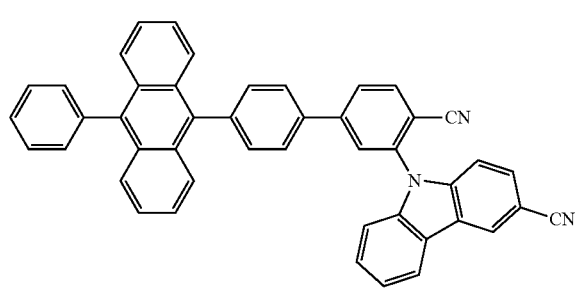
146
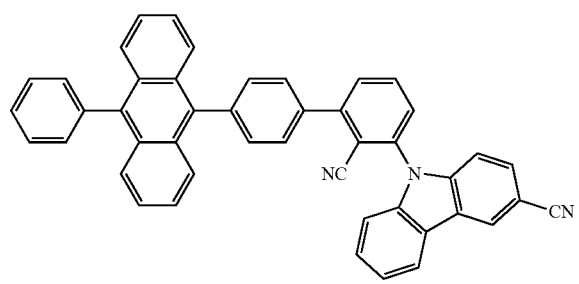
147
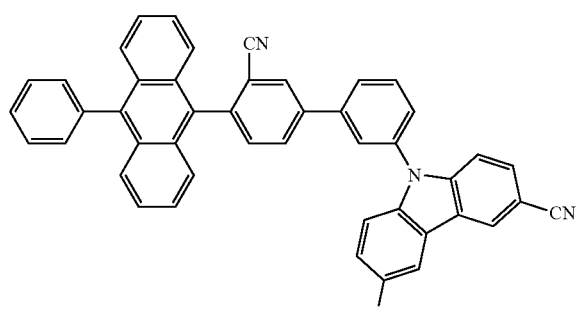
148
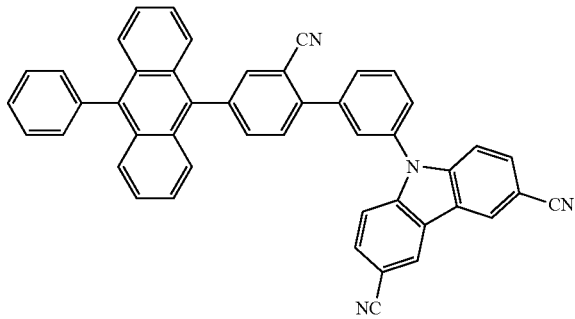
149
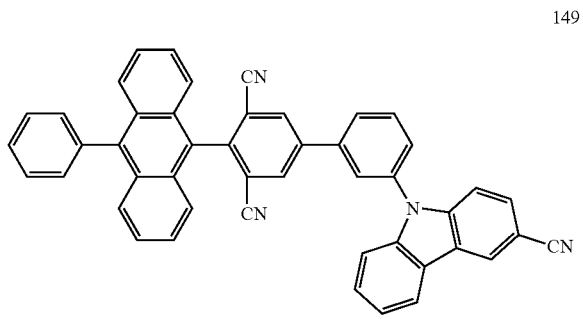
150
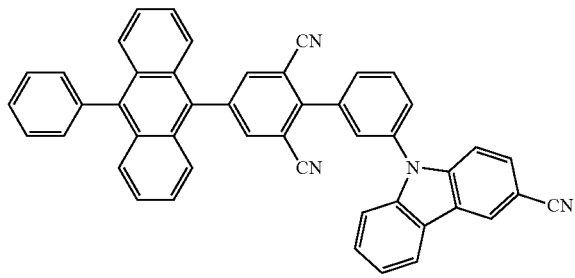
151
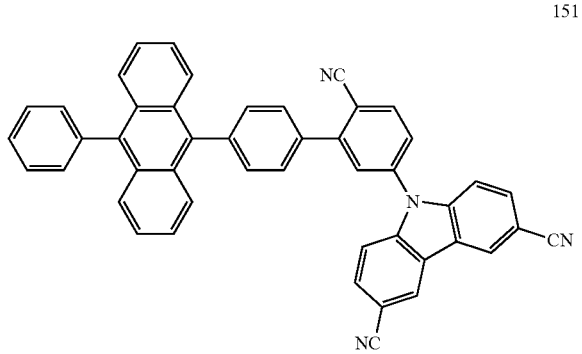
152
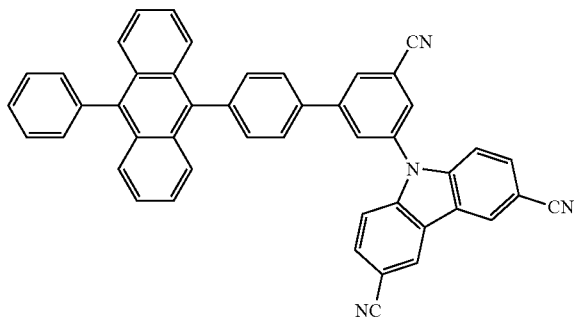

153
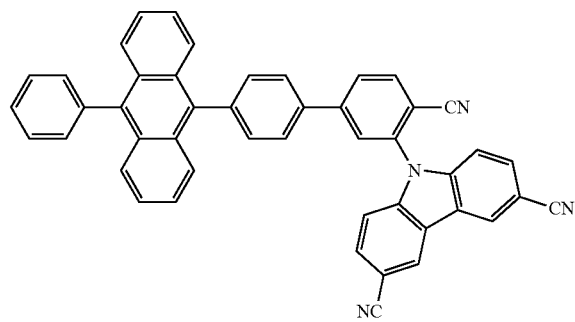
154
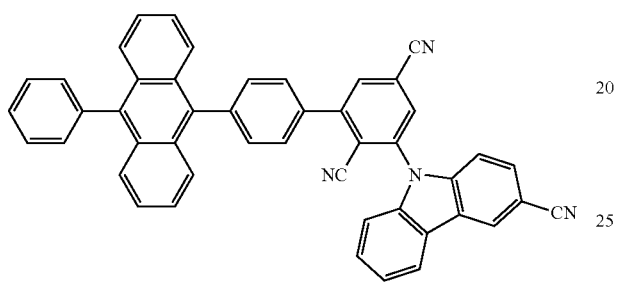
155
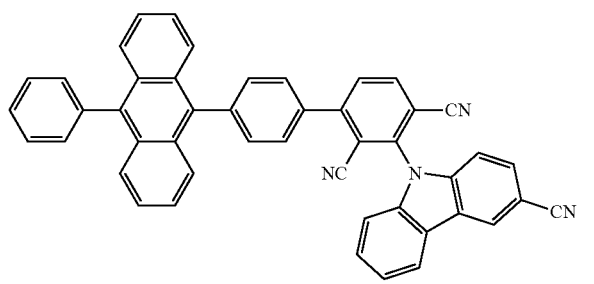
156
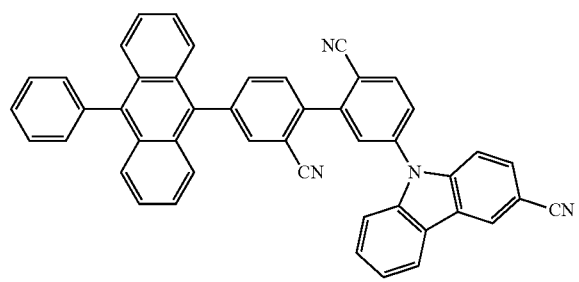
157
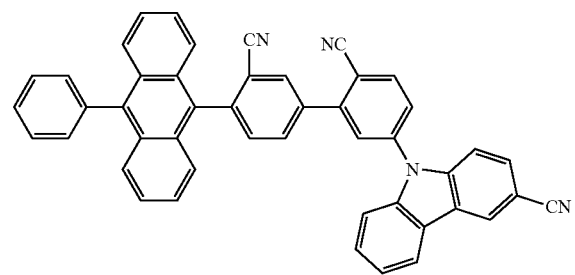
158
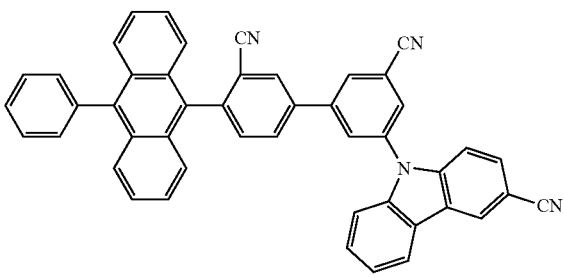
159
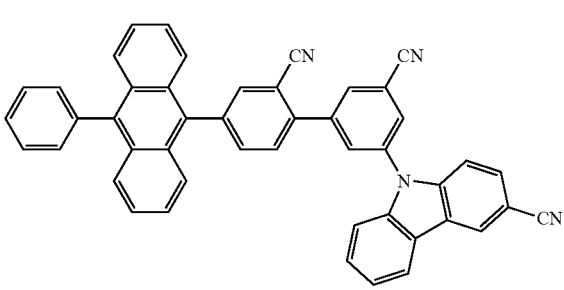
160
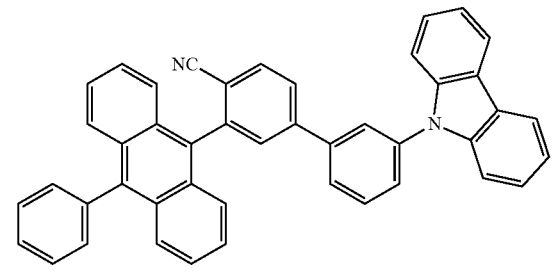
161
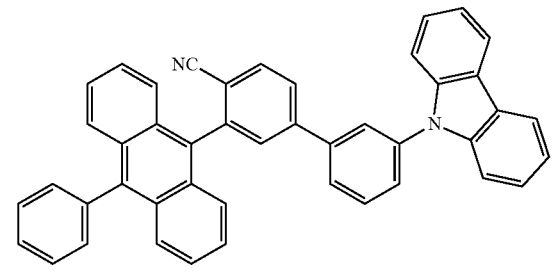
162
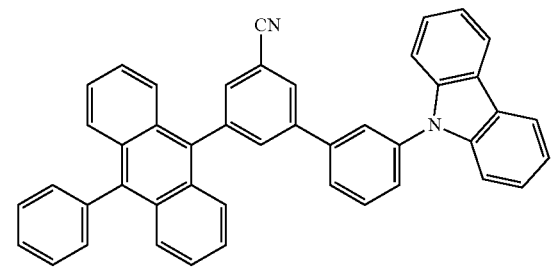

163
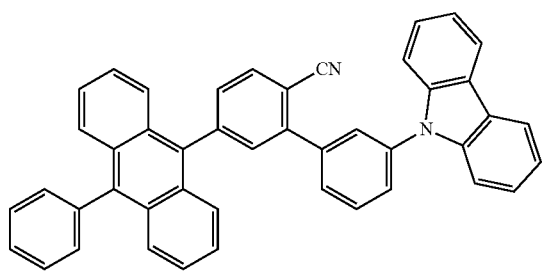
164
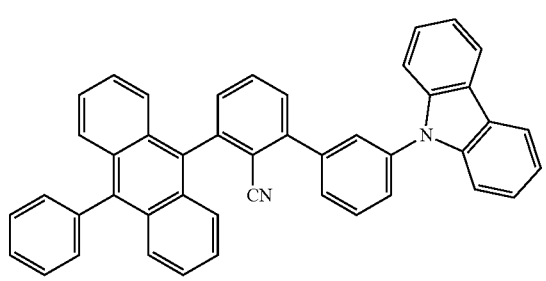
165
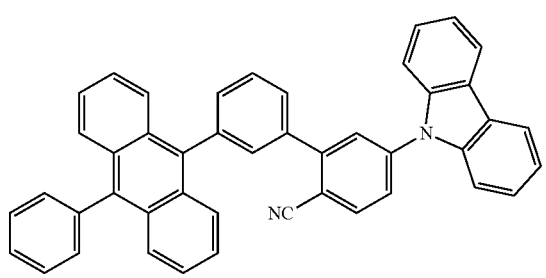
166
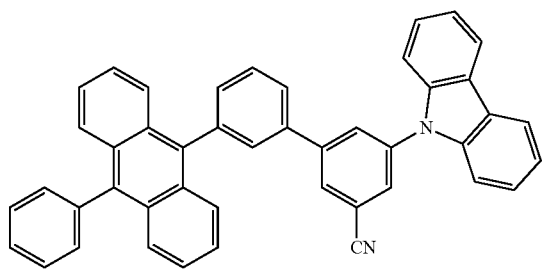
167
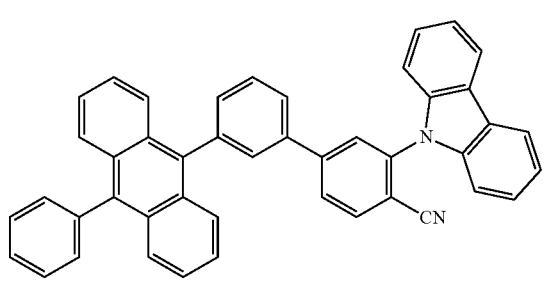
168
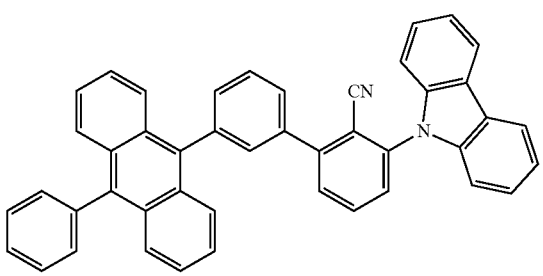
169
170
171
172
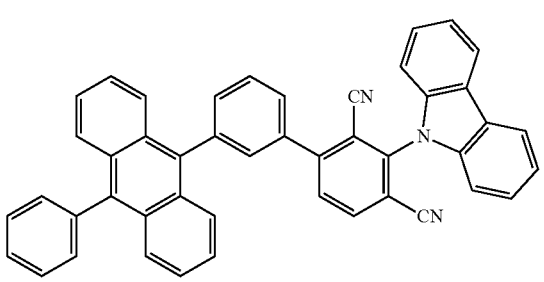

| 173 | 178 |
|---|---|
| 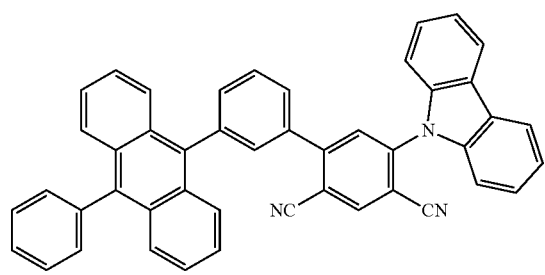 | 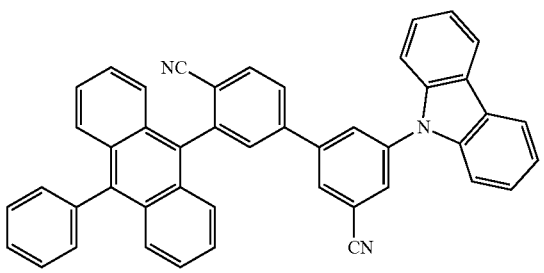 |
| 174 | 179 |
|---|---|
| 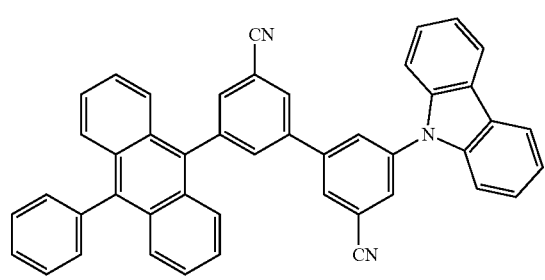 | 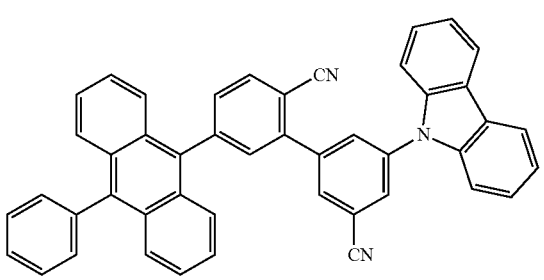 |
| 175 | 180 |
|---|---|
| 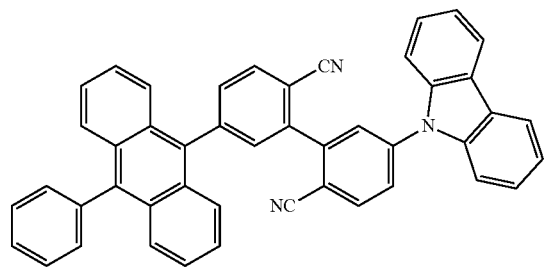 | 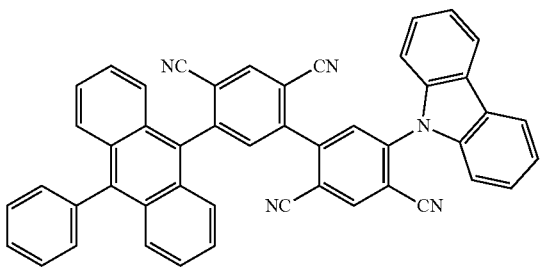 |
| 176 | 181 |
|---|---|
| 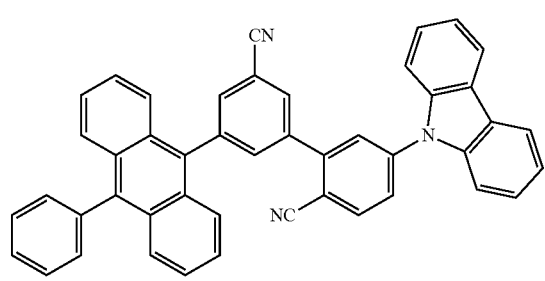 | 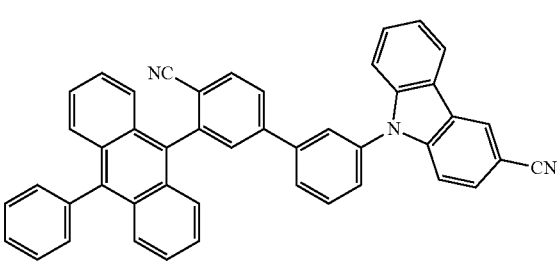 |
| 177 | 182 |
|---|---|
| 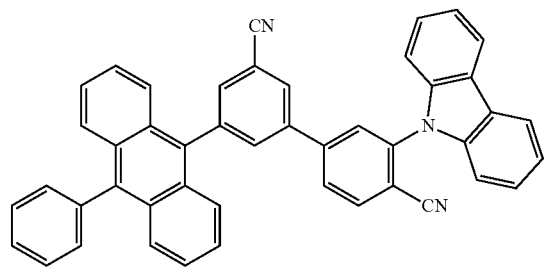 | 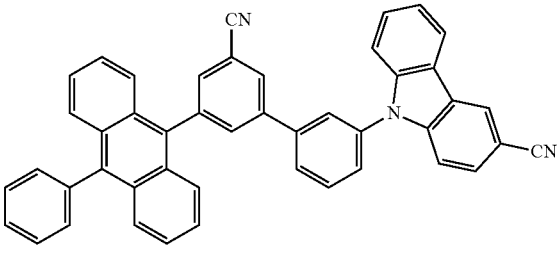 |

103
-continued
183
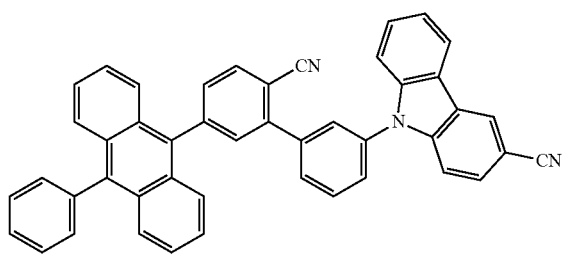
184
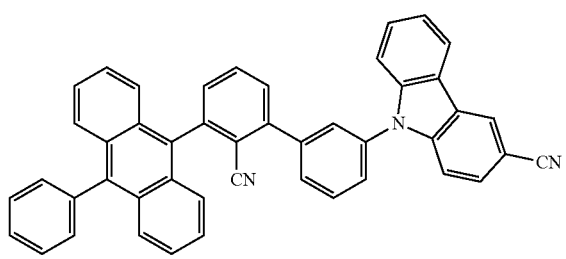
185
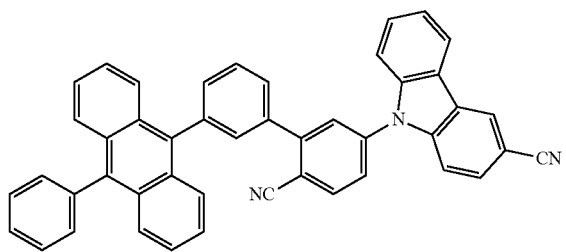
186
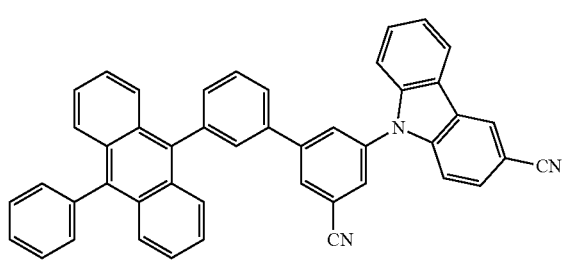
187
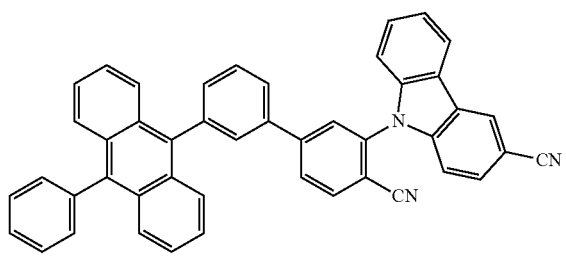
104
-continued
188
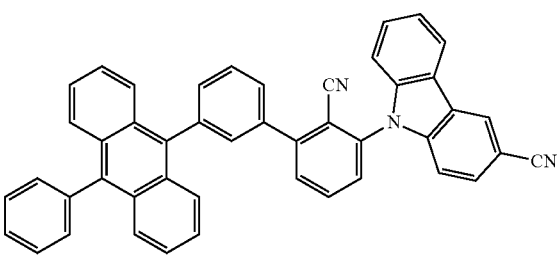
189
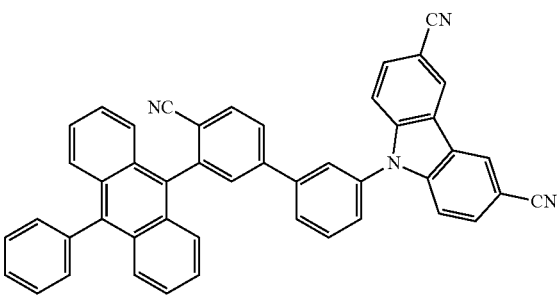
190
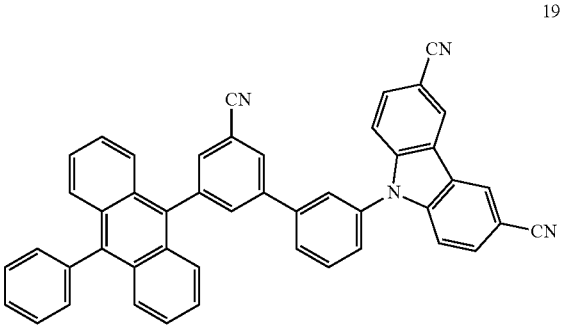
191
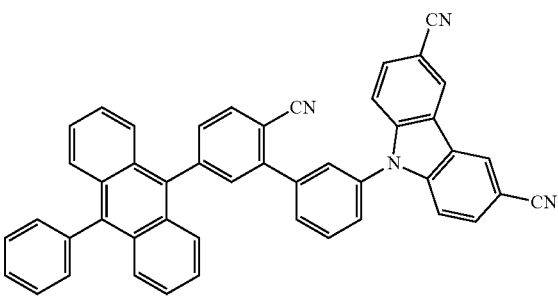
192
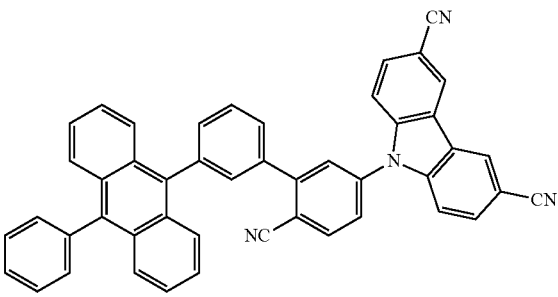

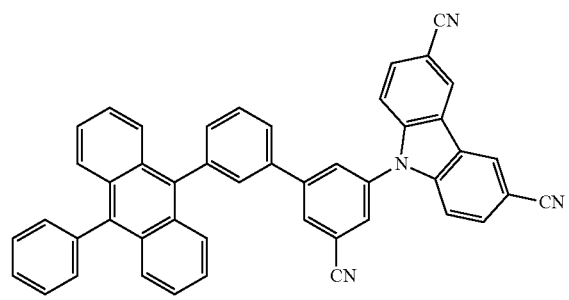
193
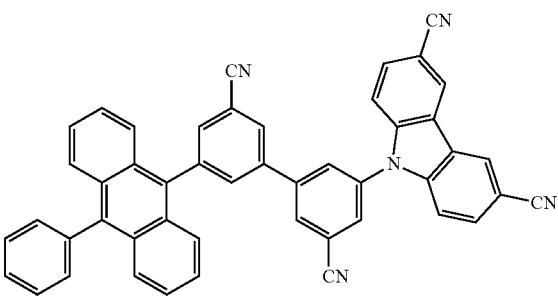
198
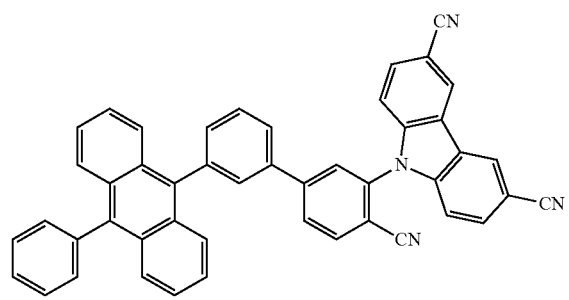
194
199
195
200
196
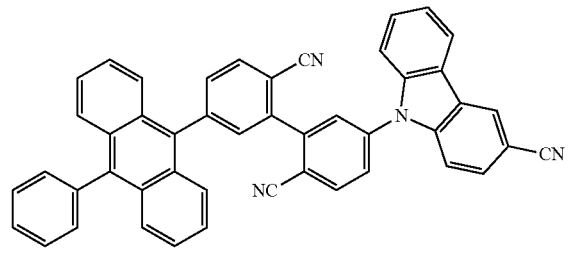
197
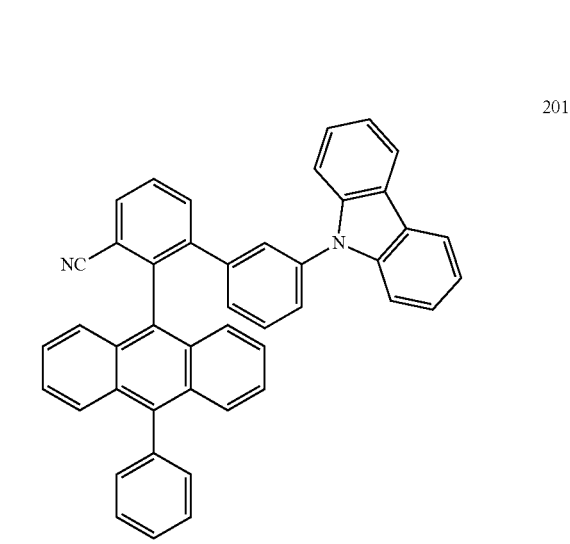
201

202
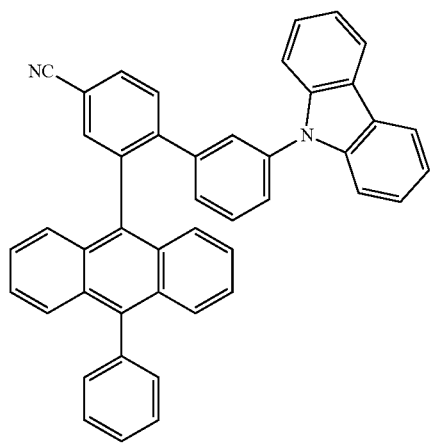
203
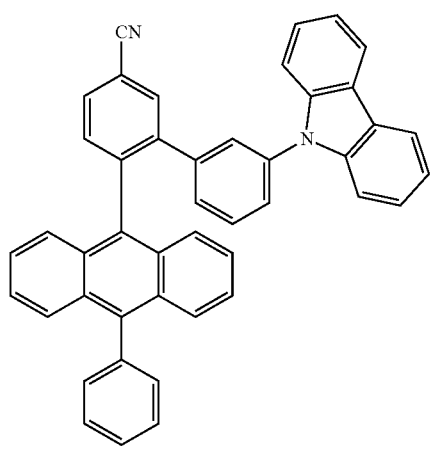
204
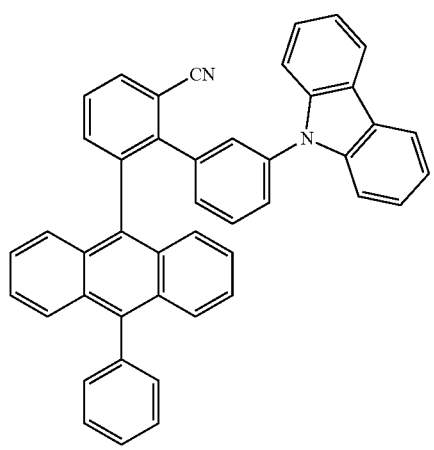
205
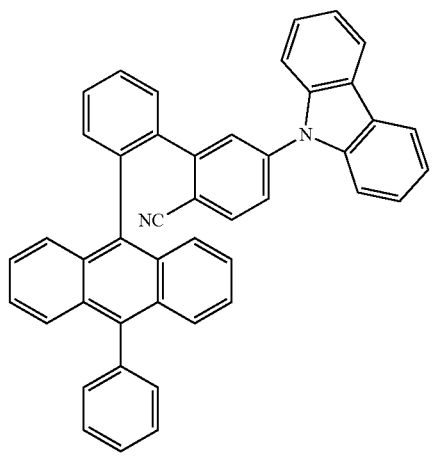
206
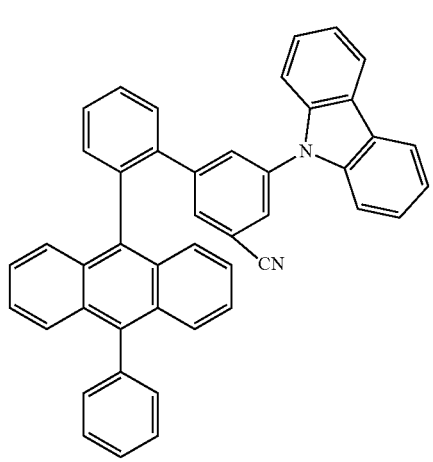
207
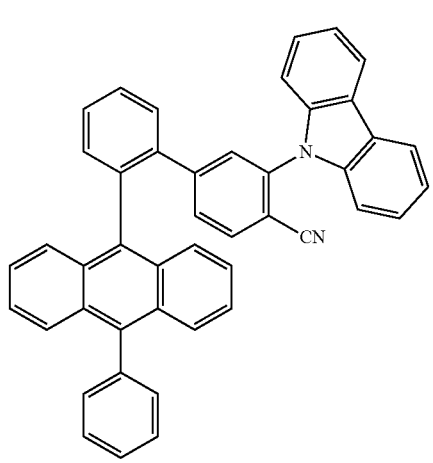

208
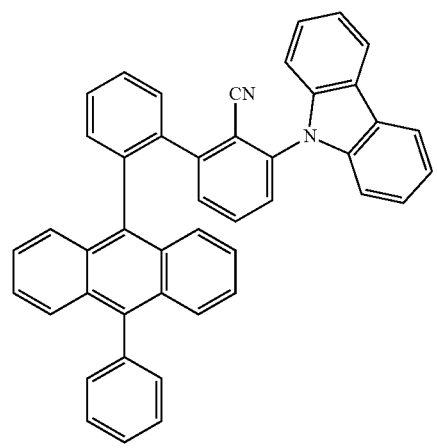
209
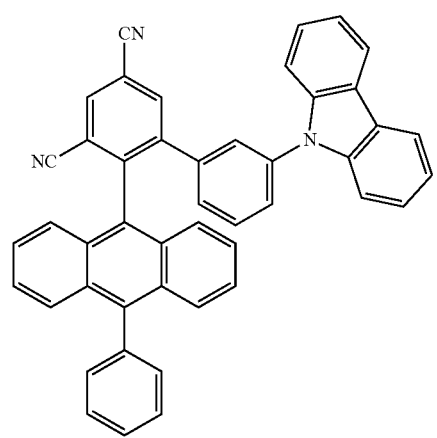
210
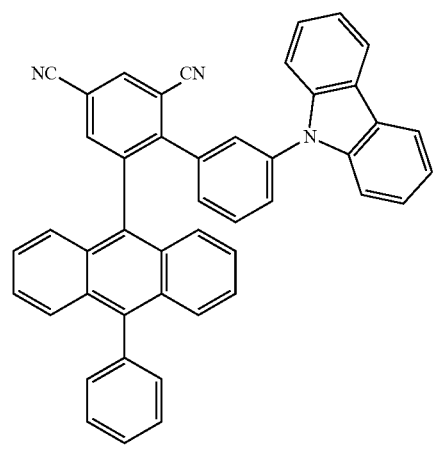
211
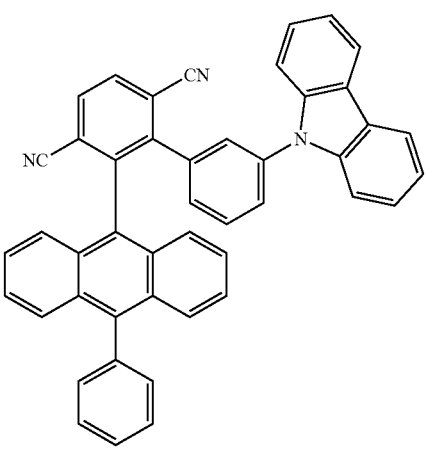
212
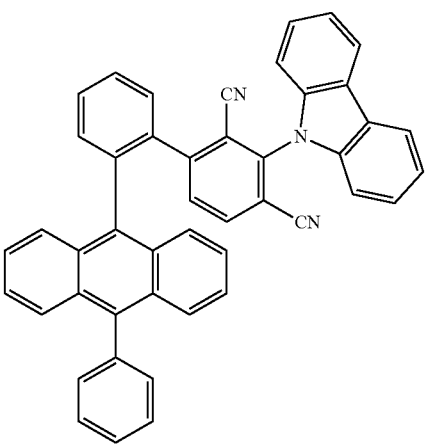
213
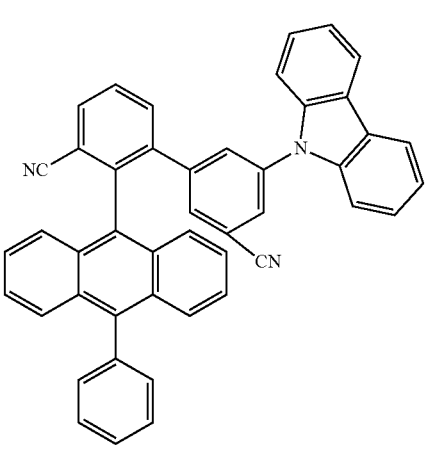

214
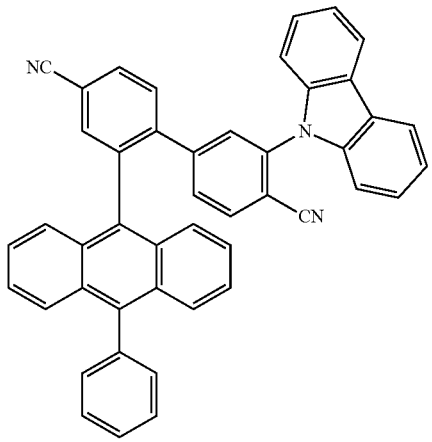
215
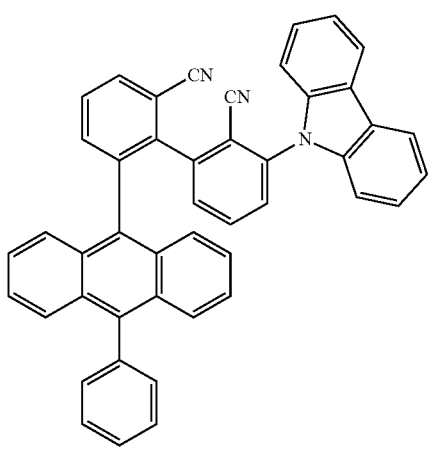
216
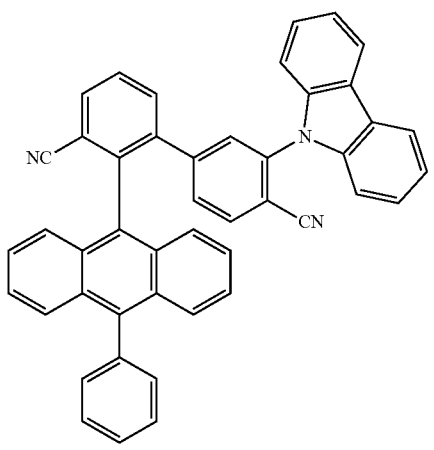
217
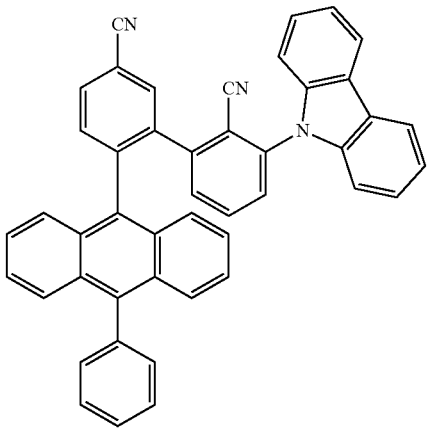
218
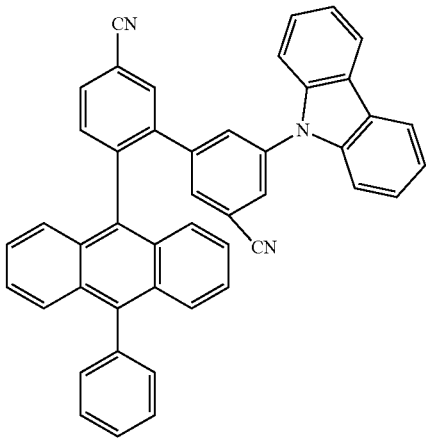
219
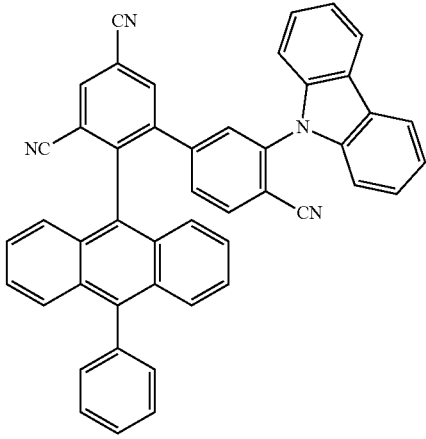

220
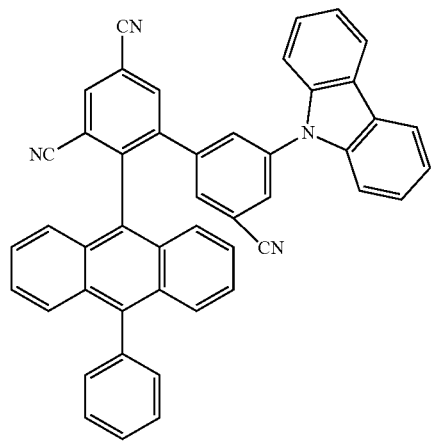
223
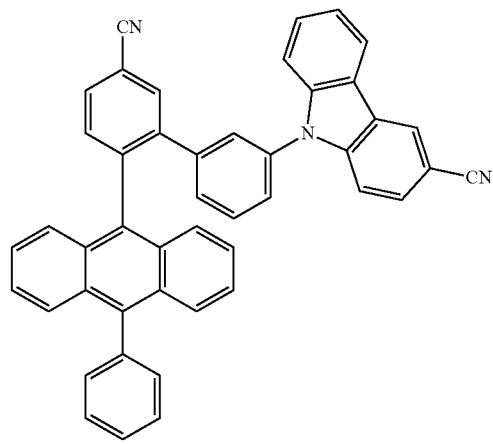
221
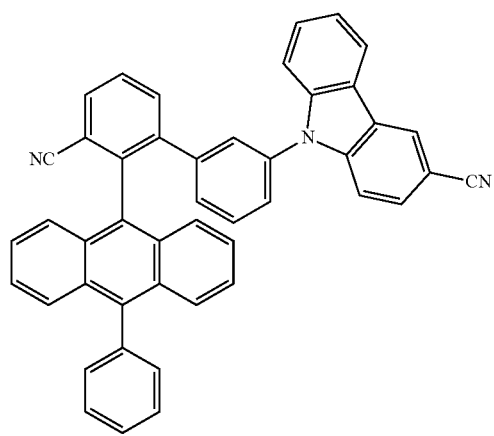
224
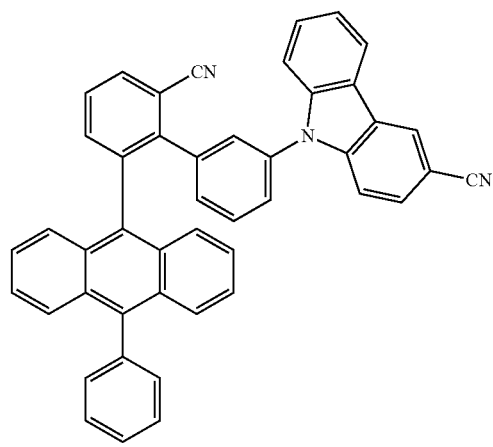
222
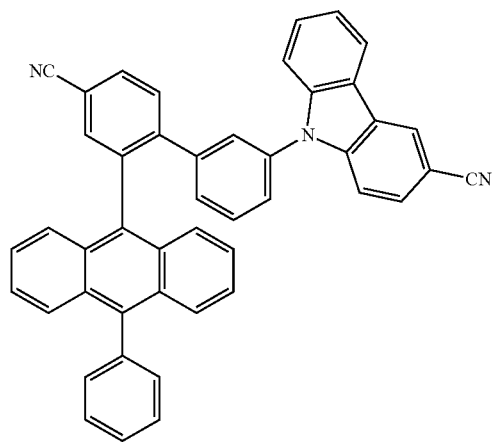
225
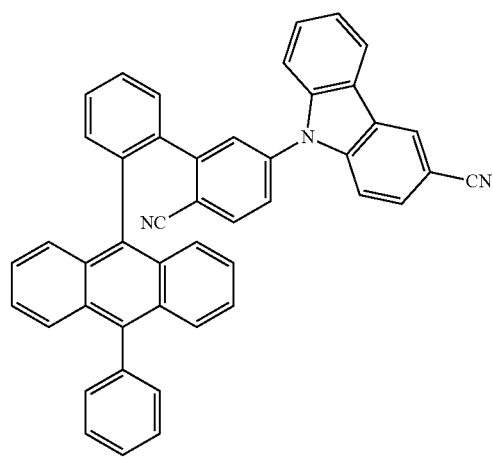

226
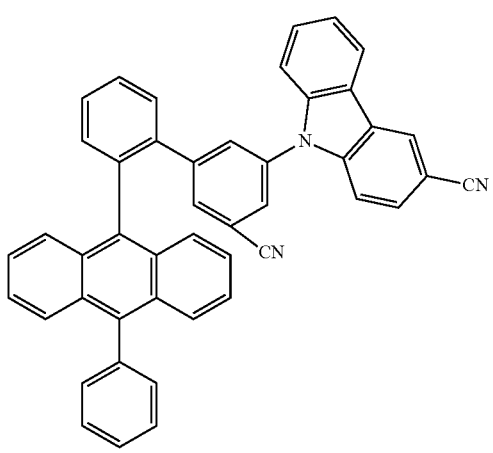
227
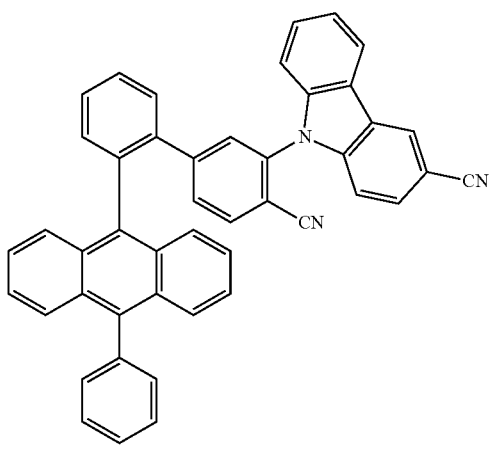
228
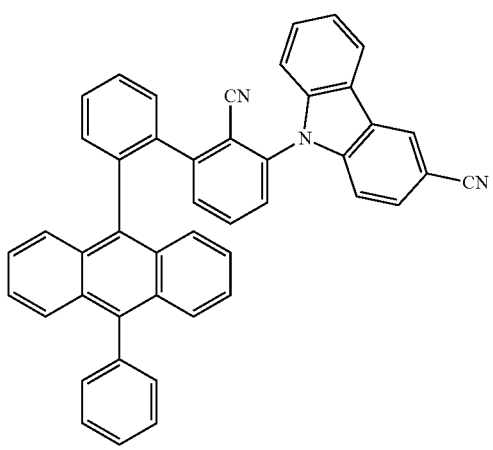
229
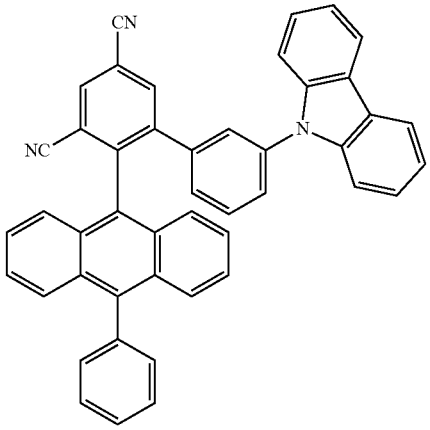
230
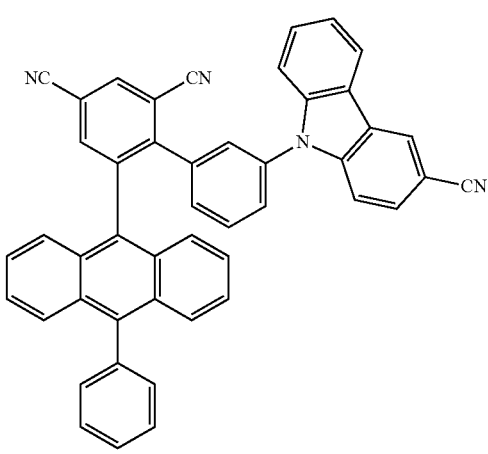
231
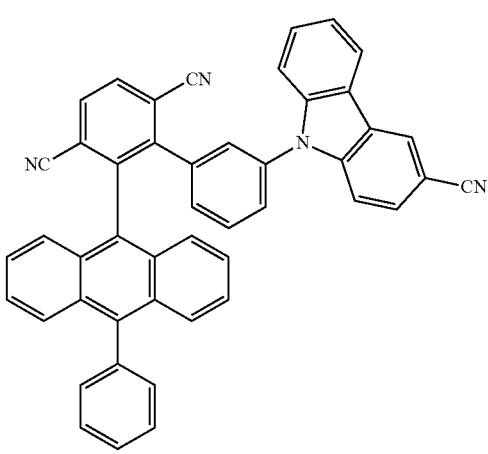

232
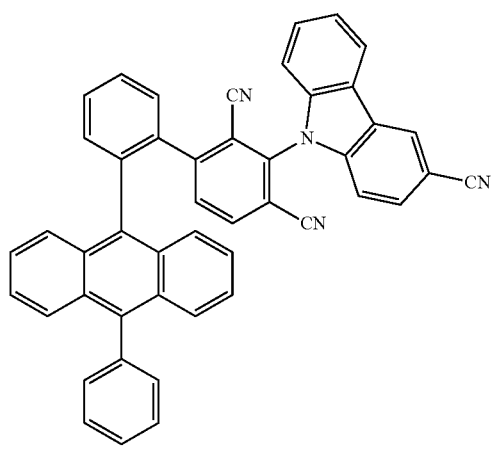
233
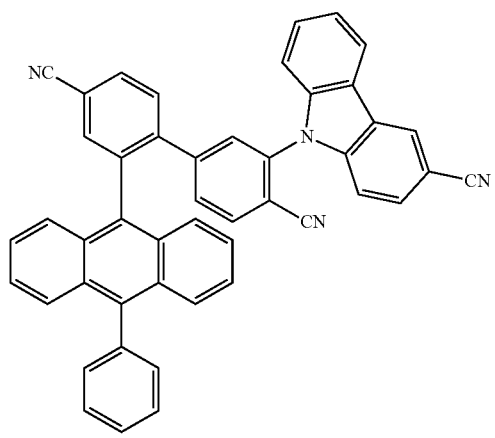
234
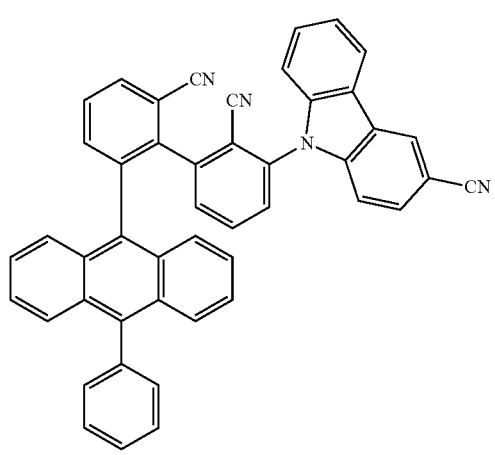
235
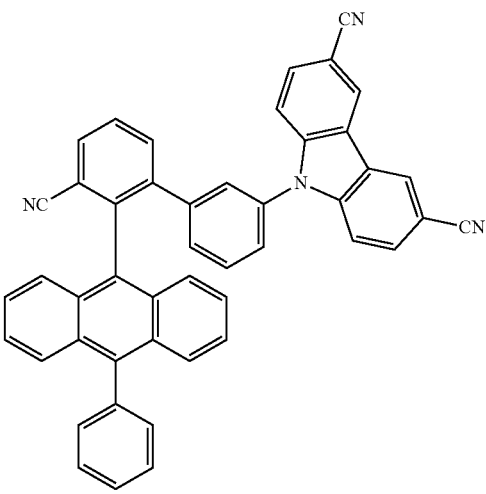
236
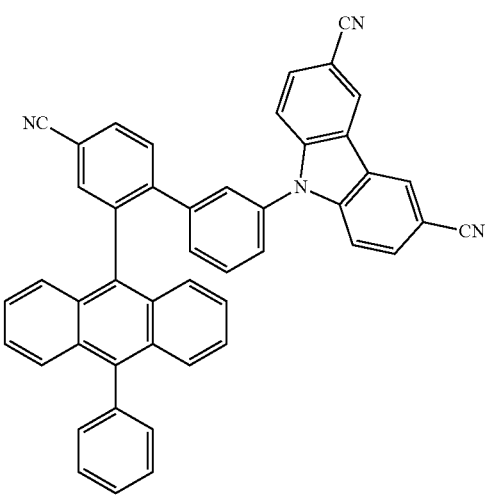
237
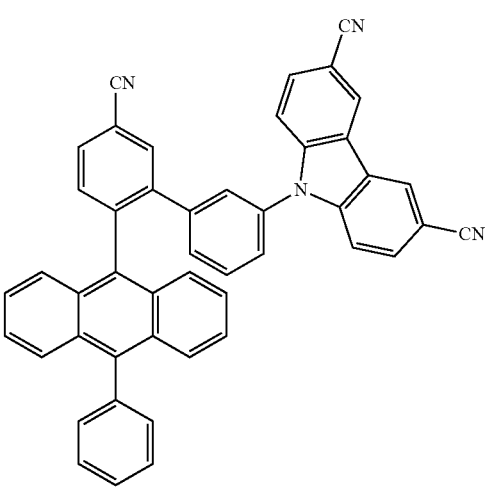

119
-continued
238
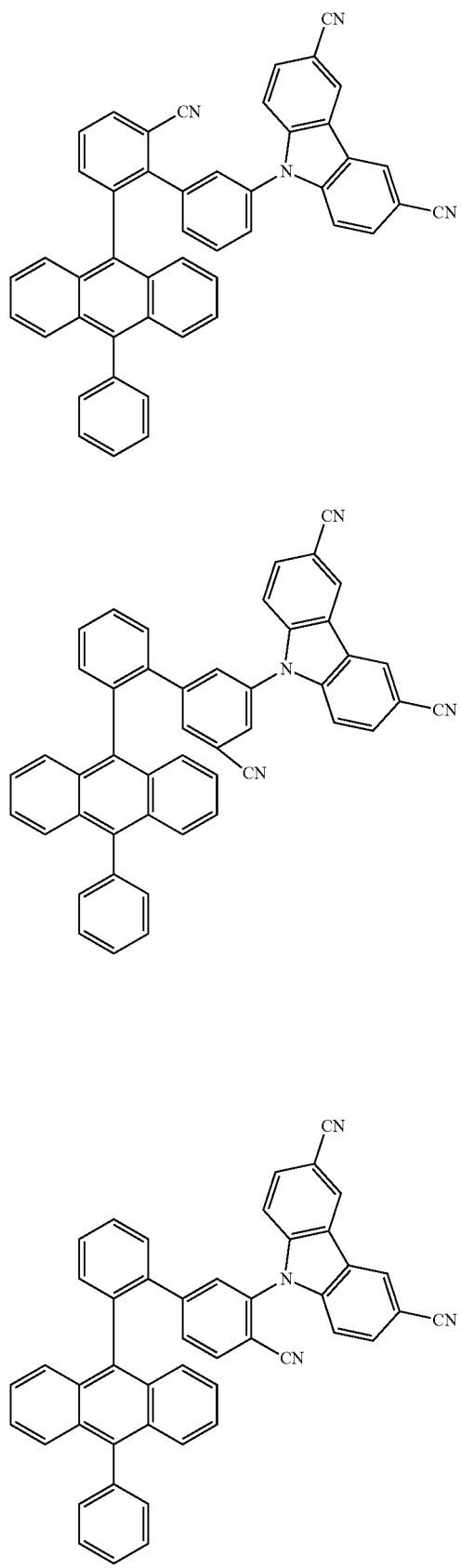
239
240
120
-continued
241
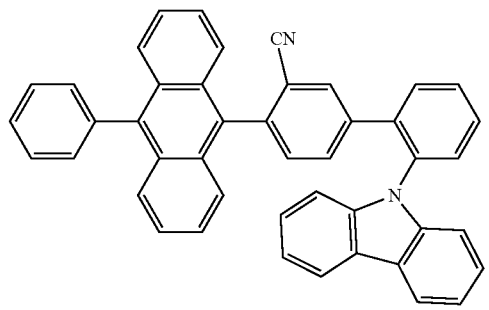
242
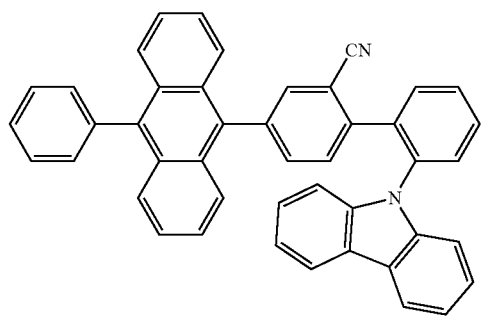
243
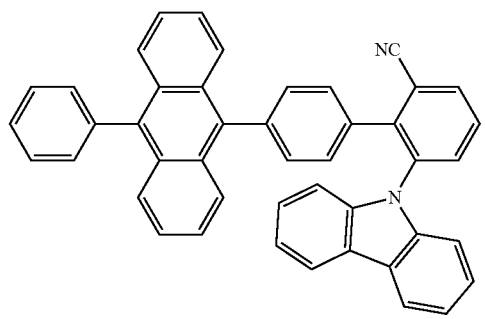
244
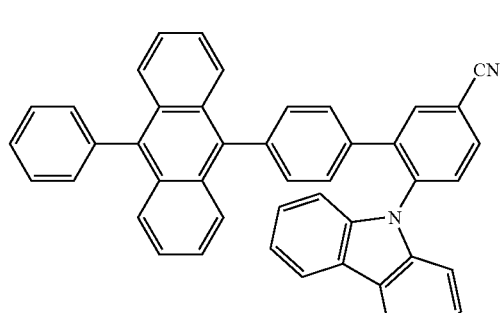
245
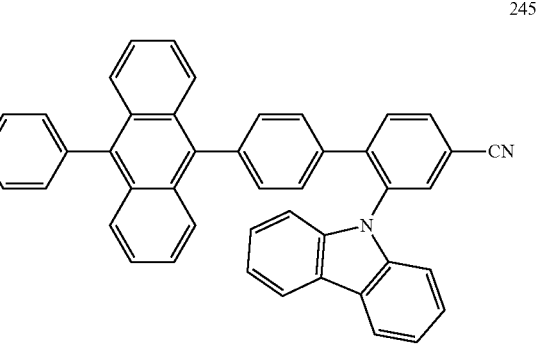

246
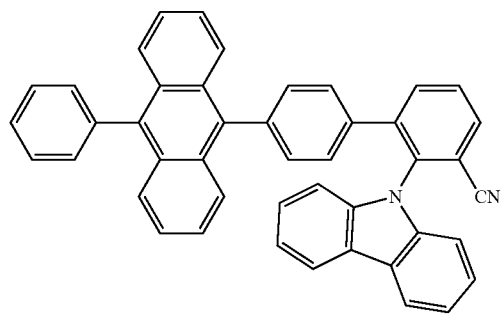
247
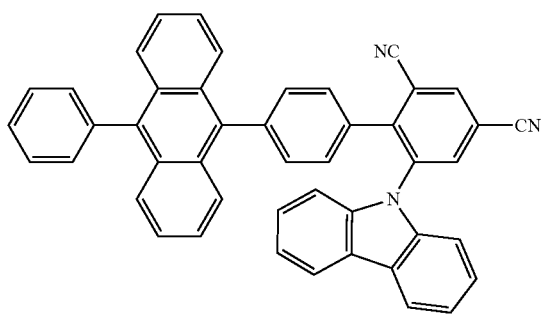
248
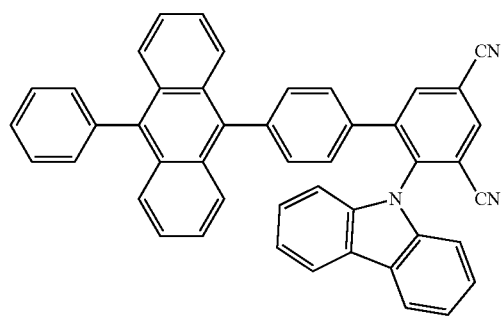
249
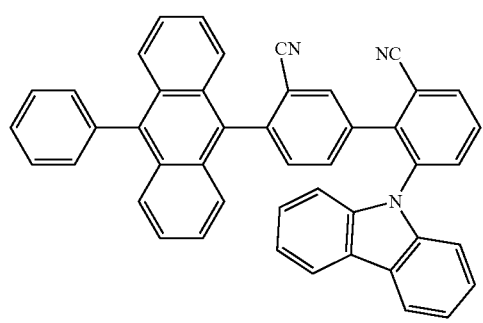
250
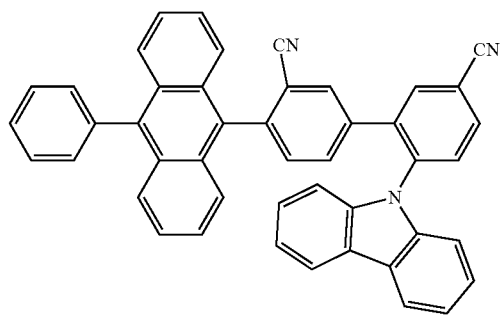
251
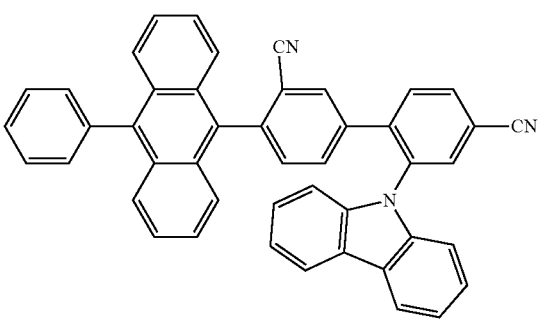
252
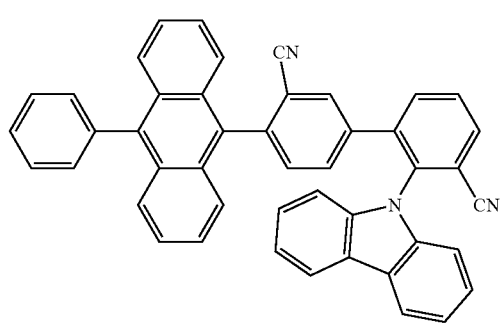
253
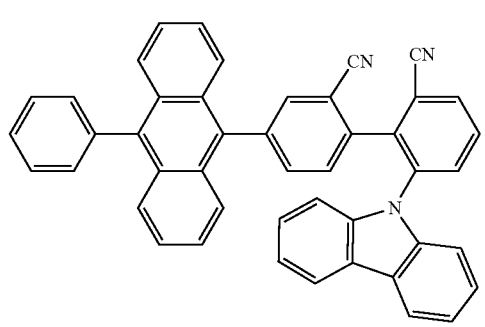

254
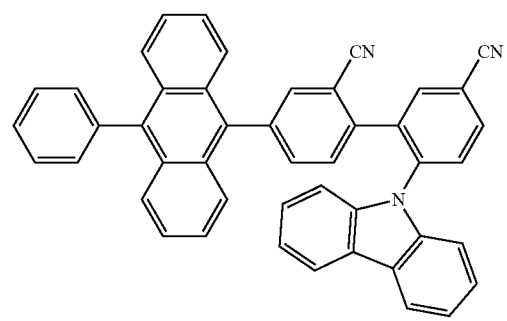
259
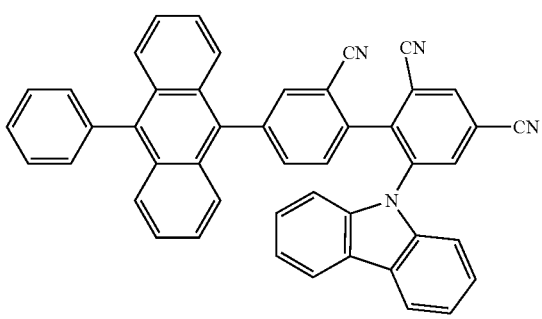
255
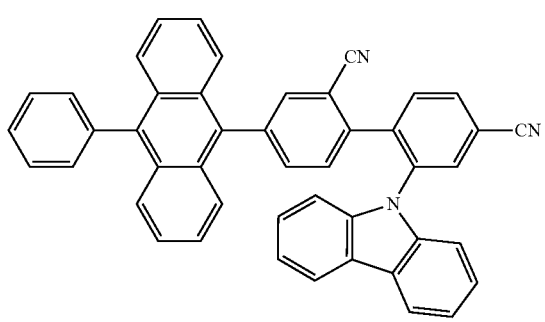
260
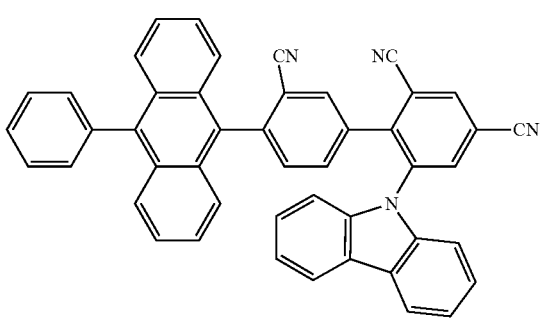
256
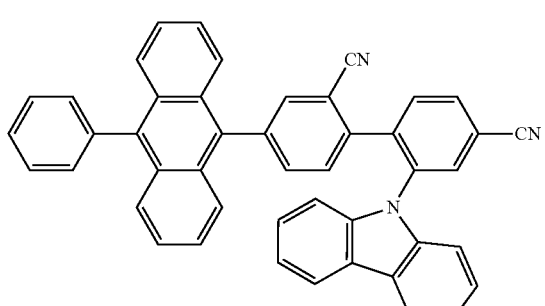
261
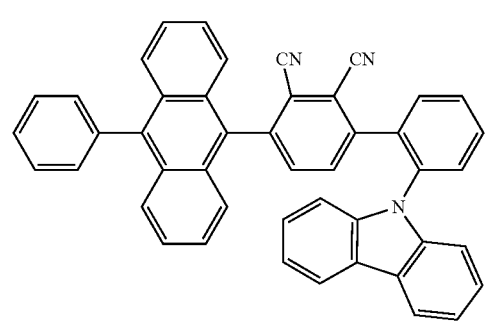
257
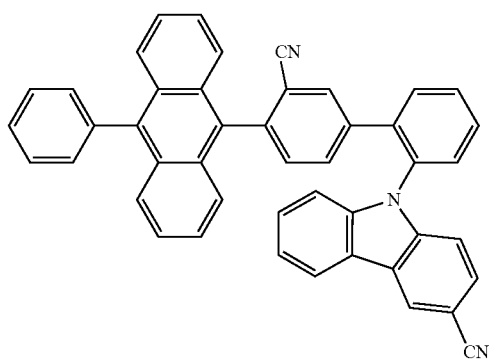
258
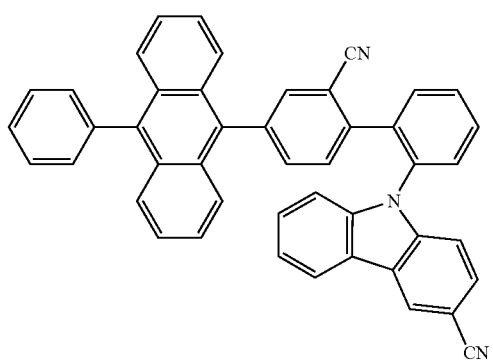
262

263
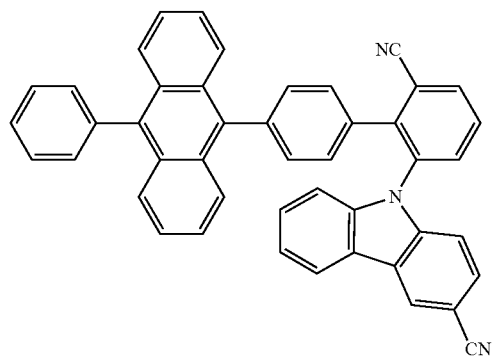
264
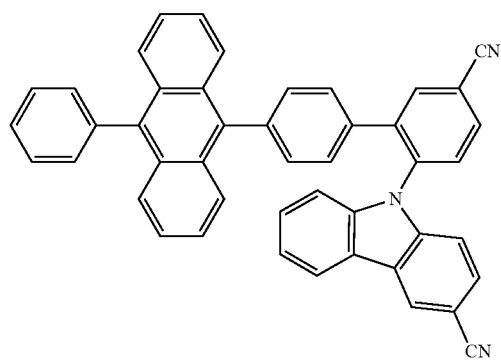
265
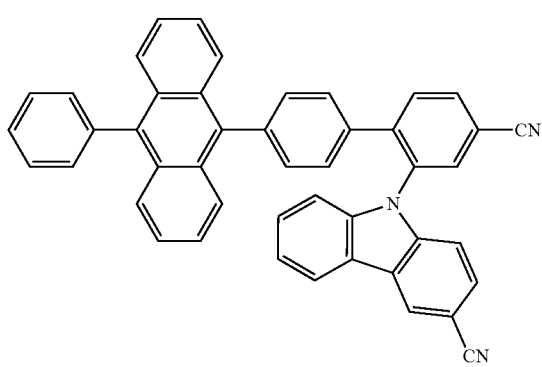
266
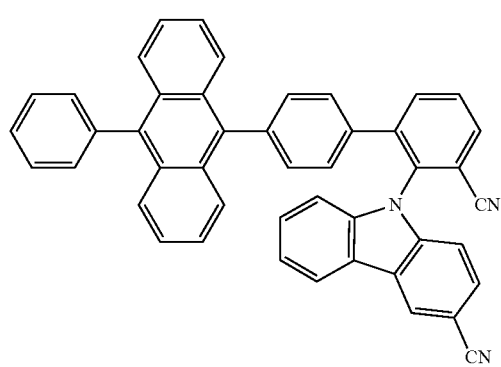
267
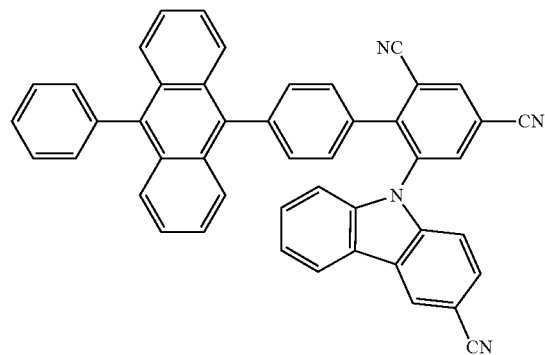
268
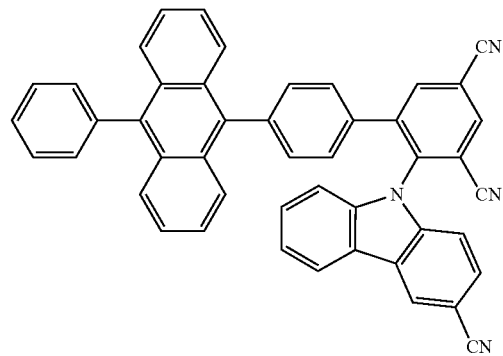
269
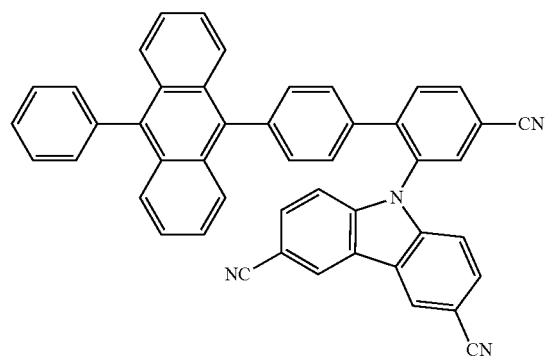
270
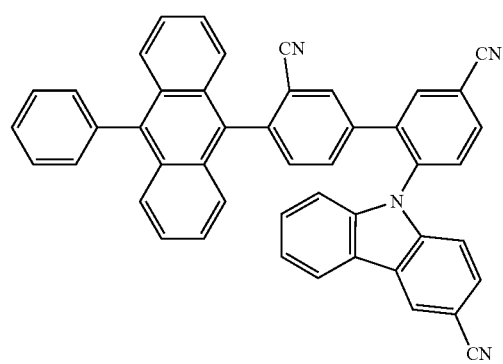

-continued

271

272

273

275

-continued

276

277

278

279

280
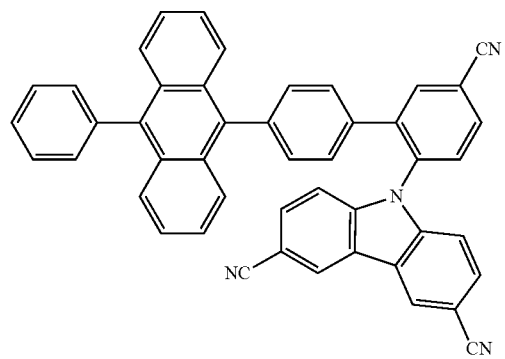
281
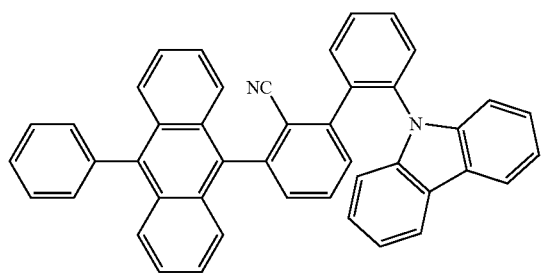
282
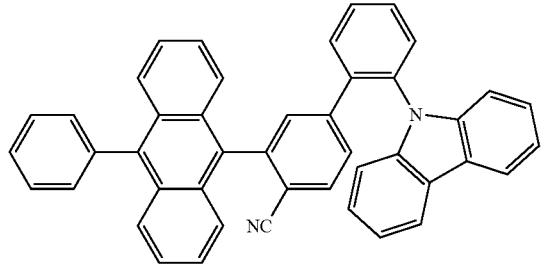
283
284
285
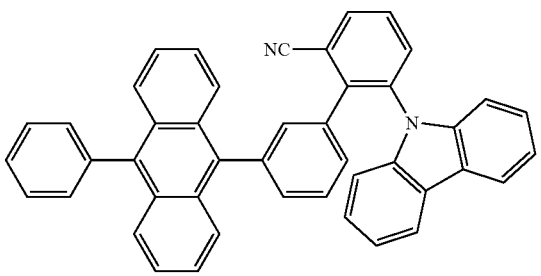
286
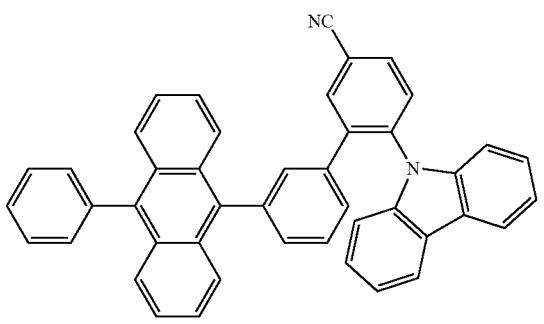
287
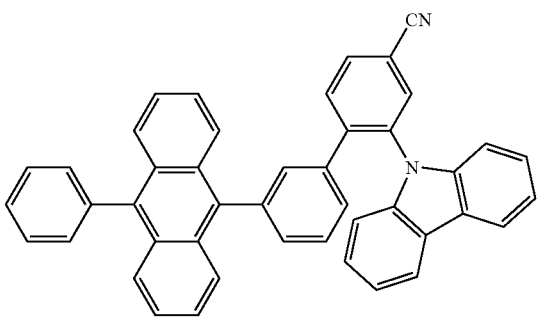
288
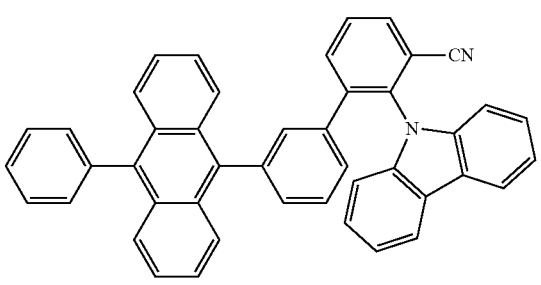
289
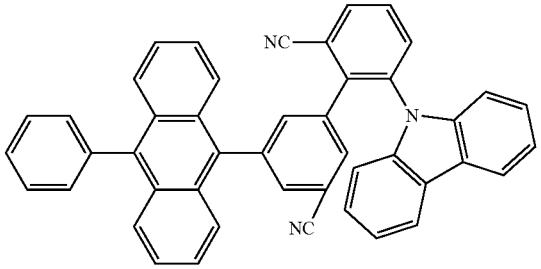

290
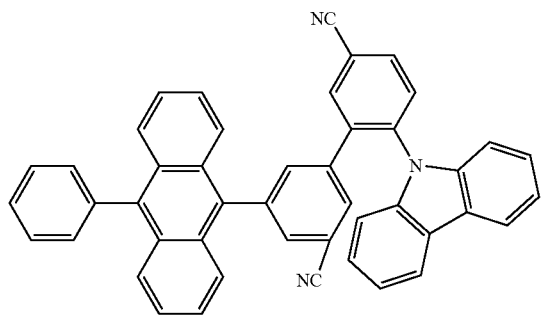
291
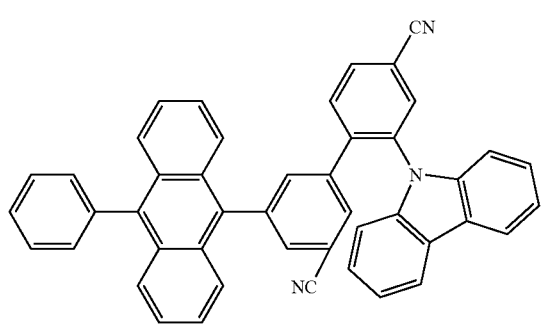
292
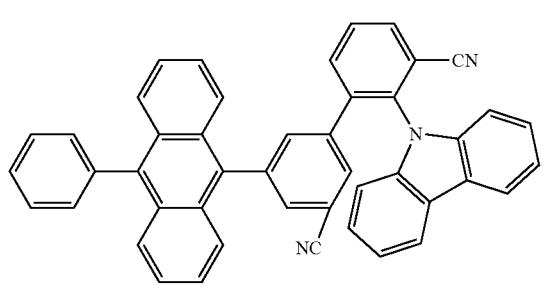
293
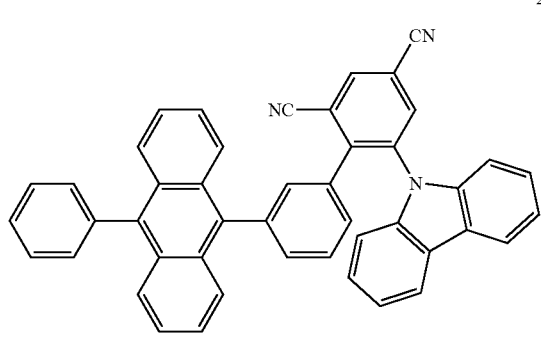
294
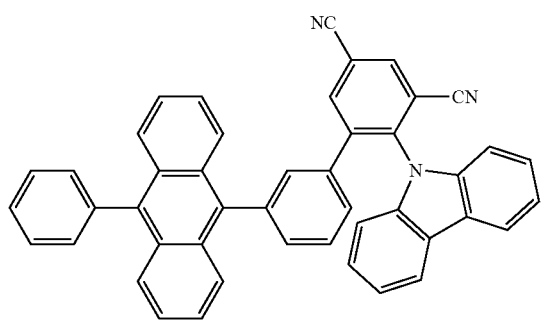
295
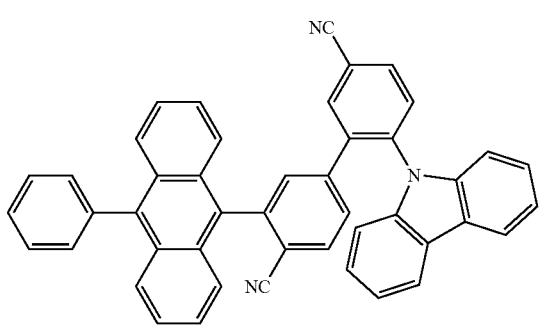
296
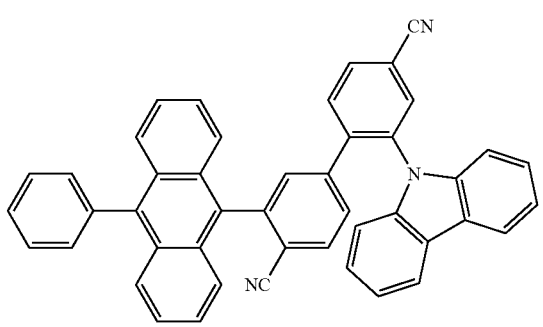
297
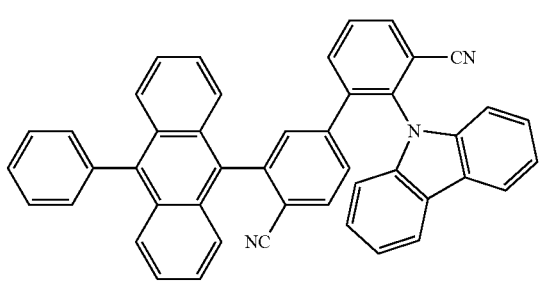
298
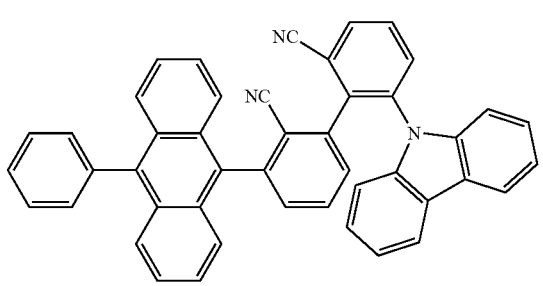
299
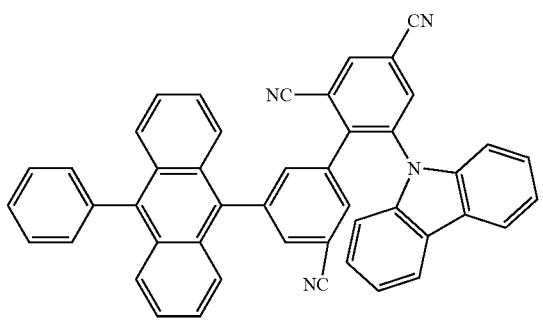

-continued
300
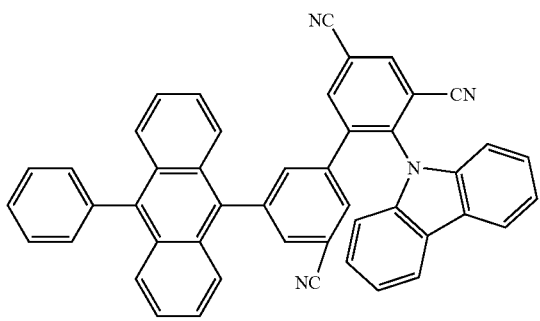
301
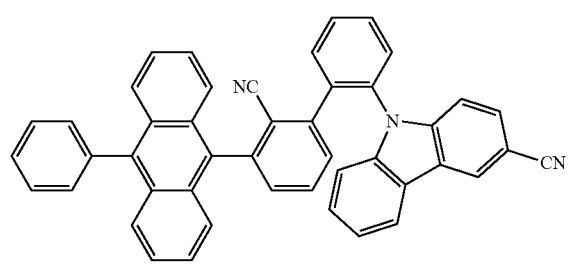
302
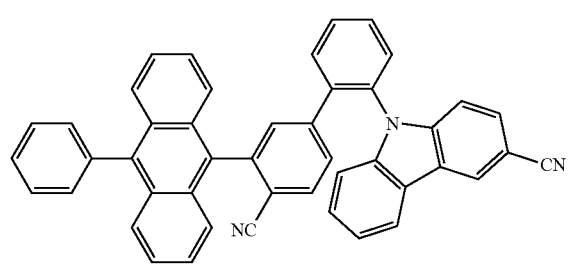
303
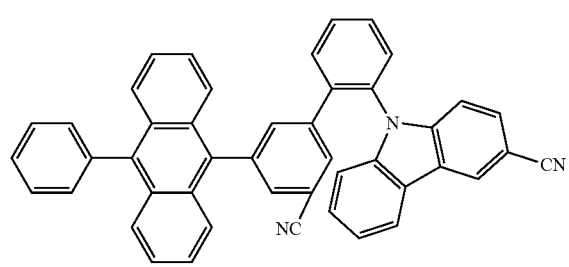
304
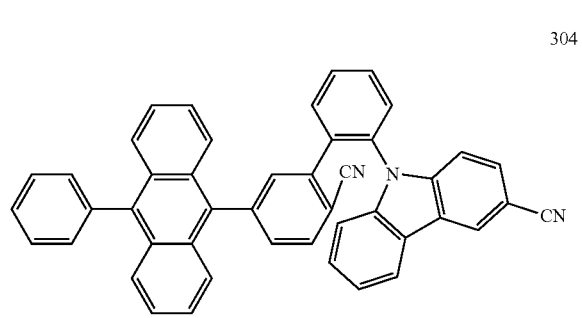
-continued
305
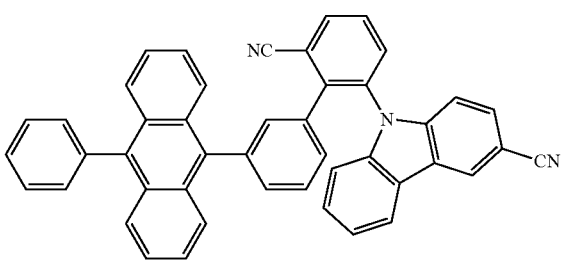
306
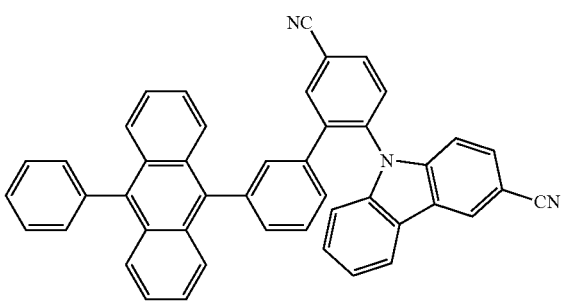
307
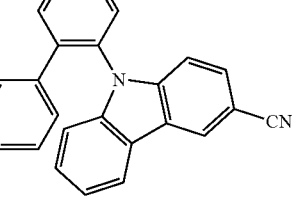
308
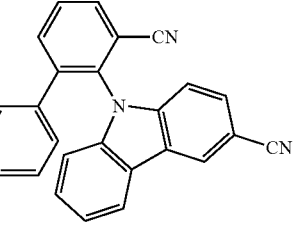
309
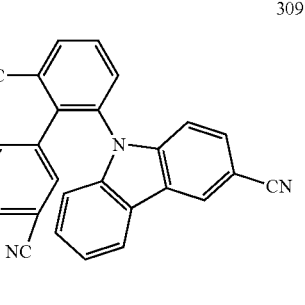

310
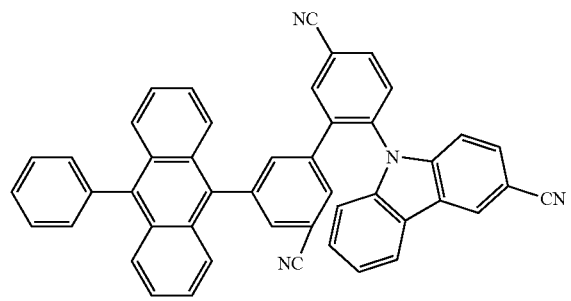
311
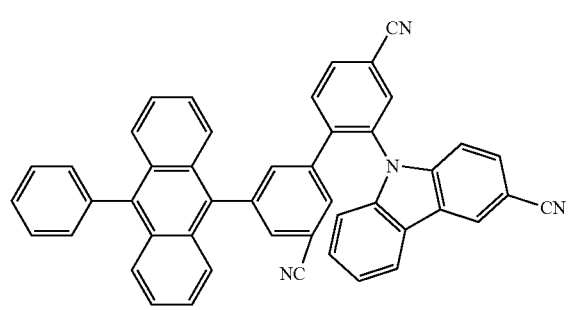
312
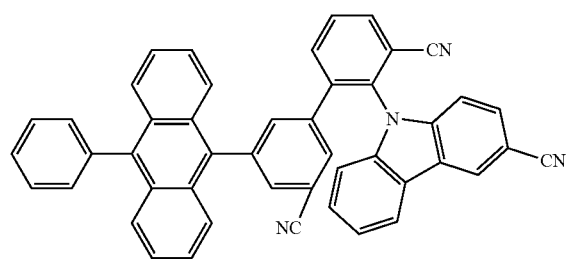
313
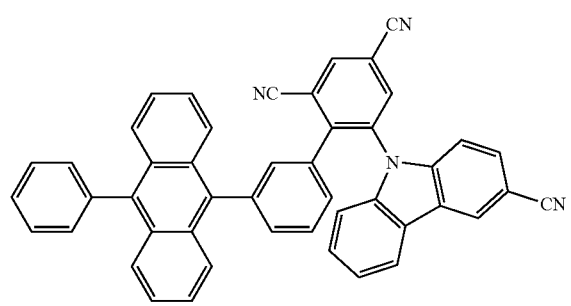
314
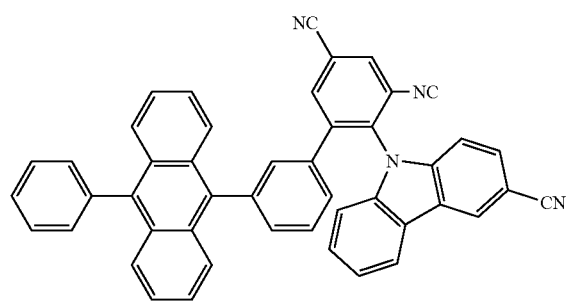
315
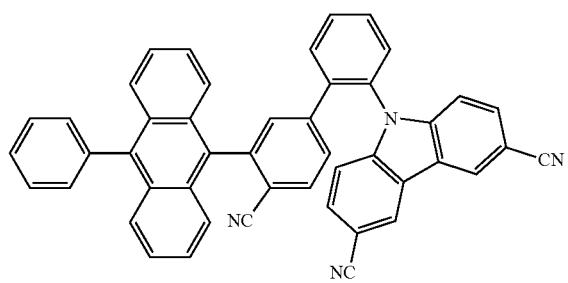
316
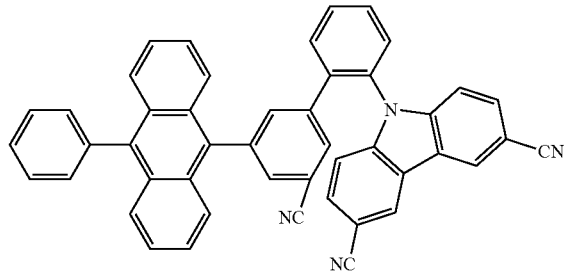
317
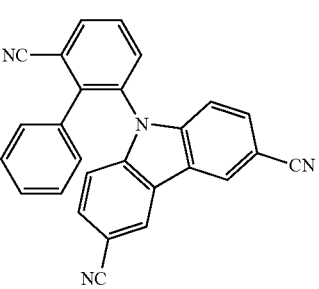
318
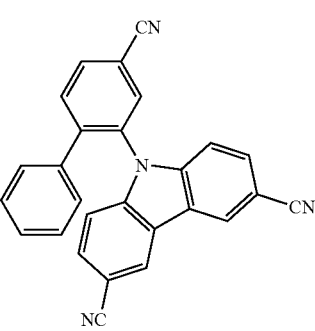
319

-continued
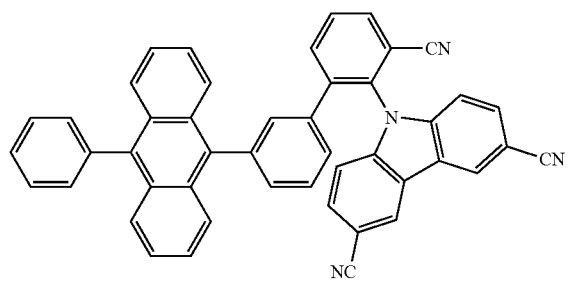
320
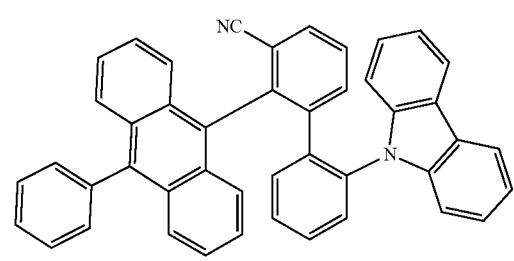
321
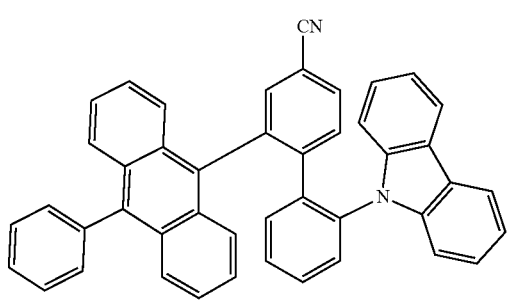
322
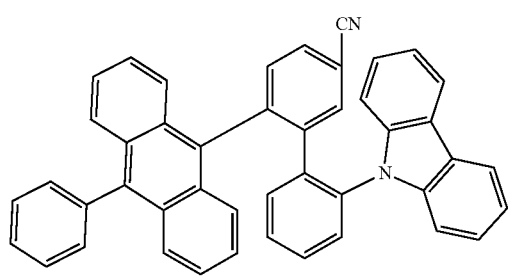
323
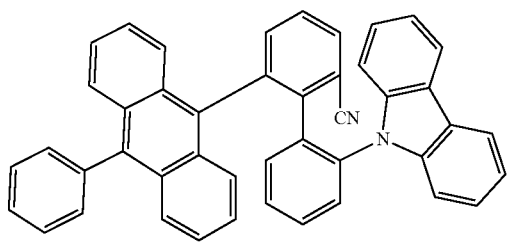
324
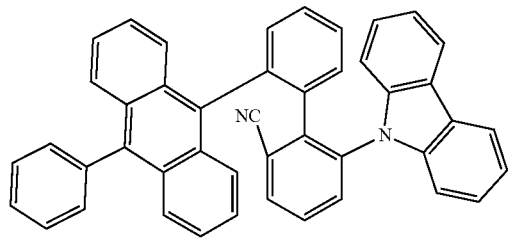
325
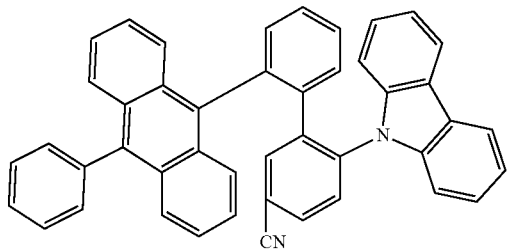
326
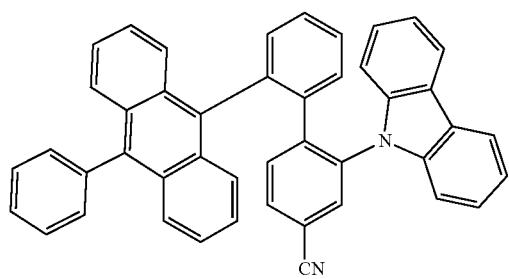
327
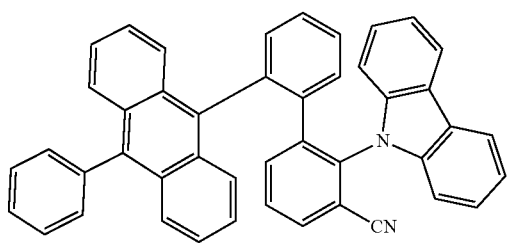
328

-continued
329 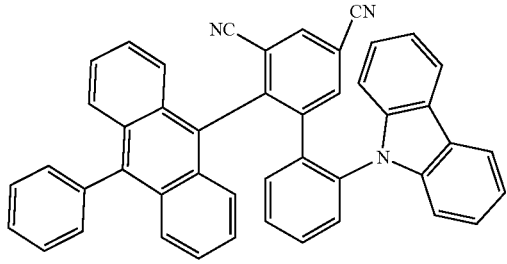
330 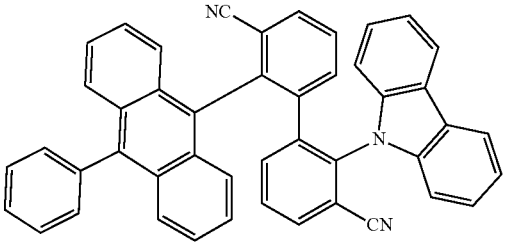
331 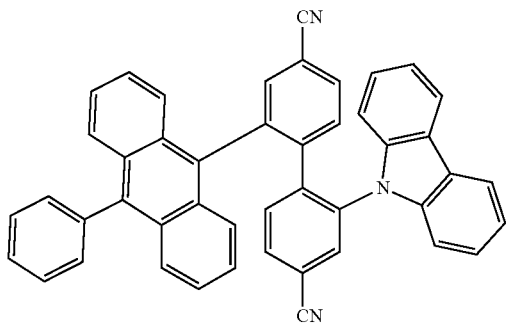
332 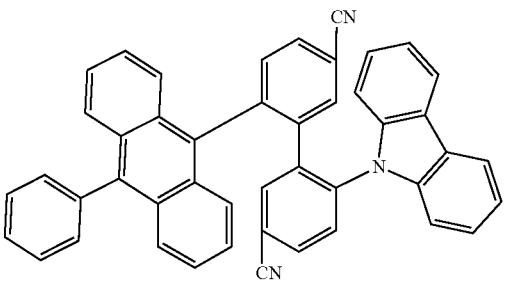
333 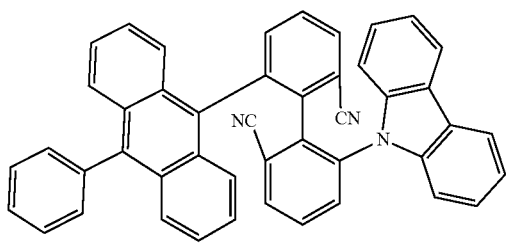
334 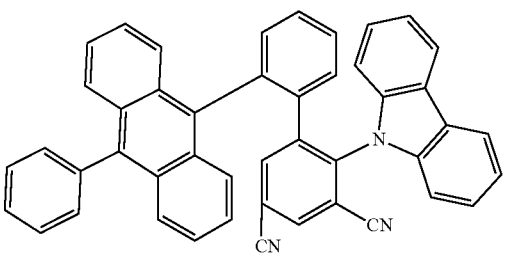
335 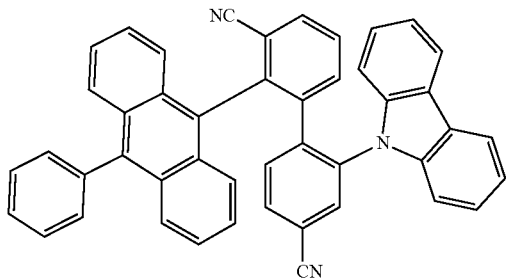
336 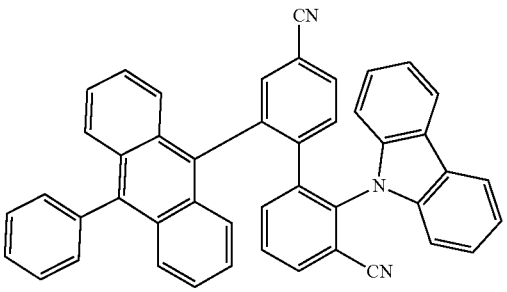
337 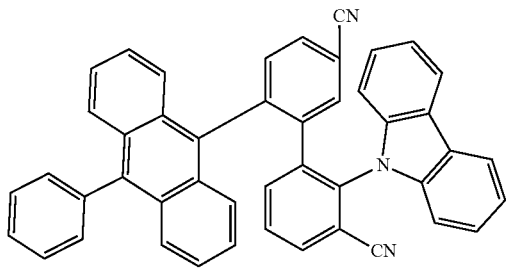
338 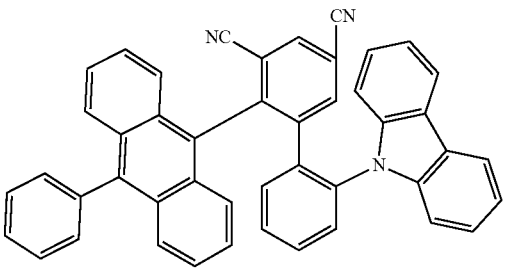

-continued
339 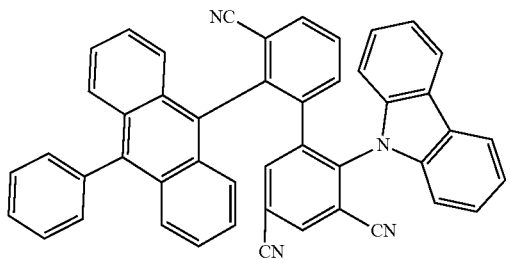
340 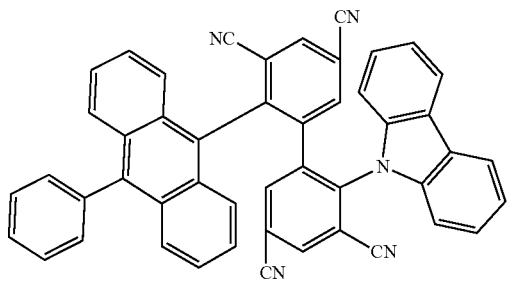
341 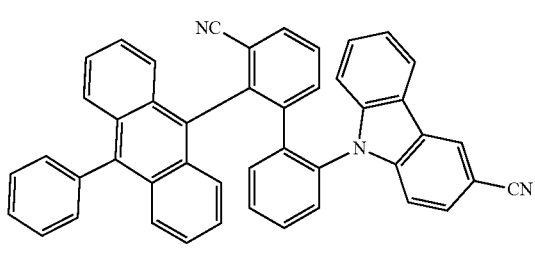
342 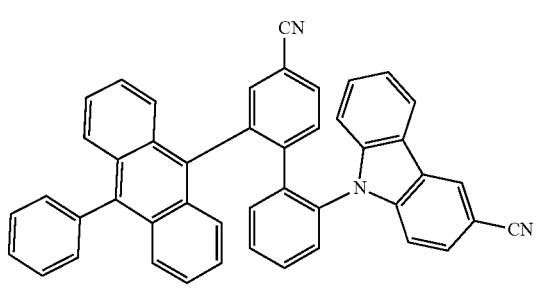
343 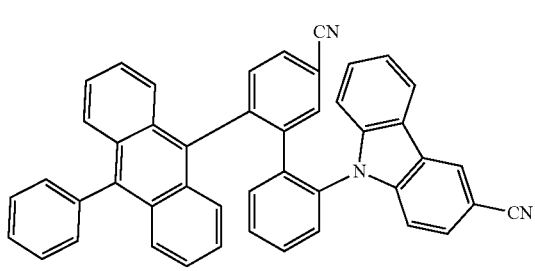
344 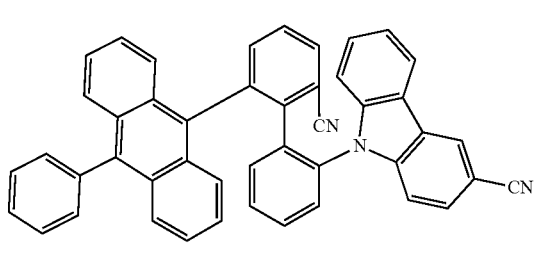
345 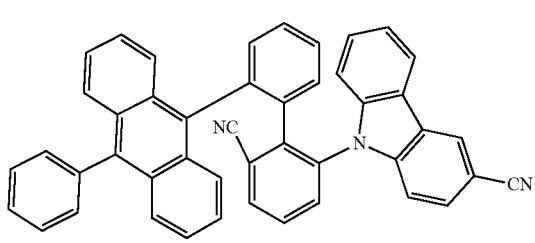
346 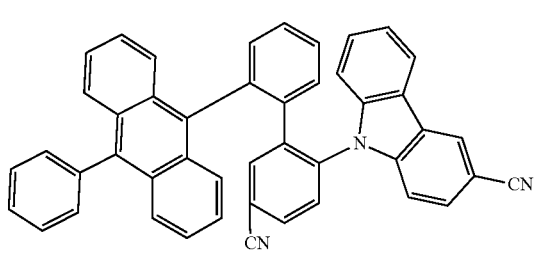
347 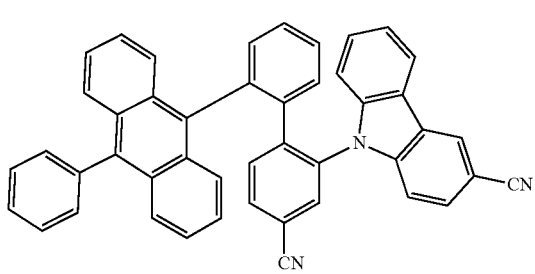
348 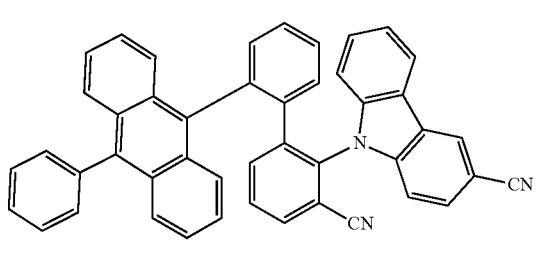

-continued
349 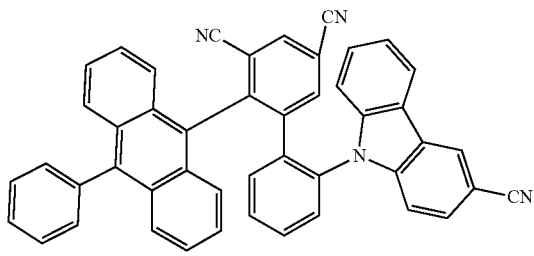
350 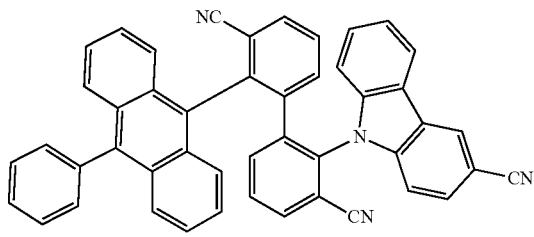
351 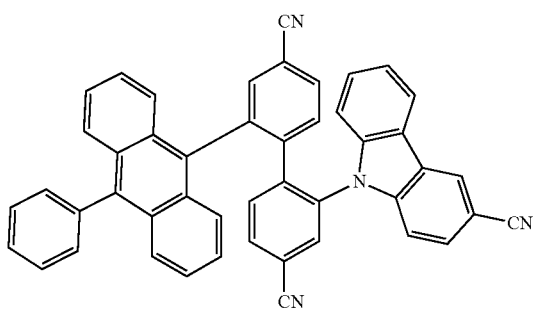
352 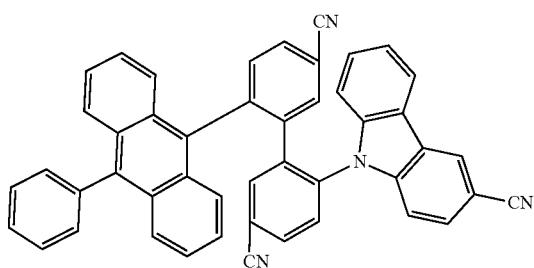
353 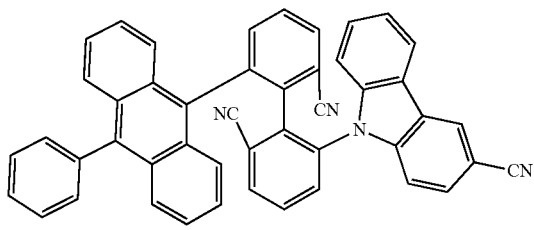
354 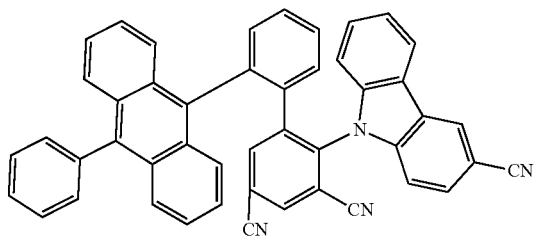
355 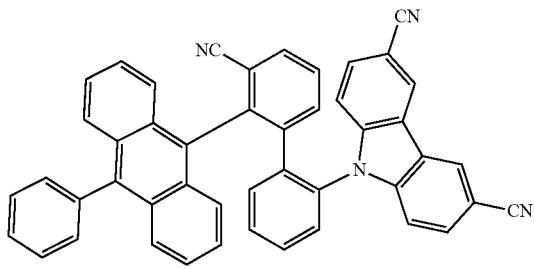
356 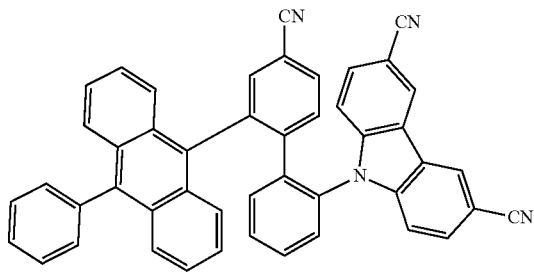
357 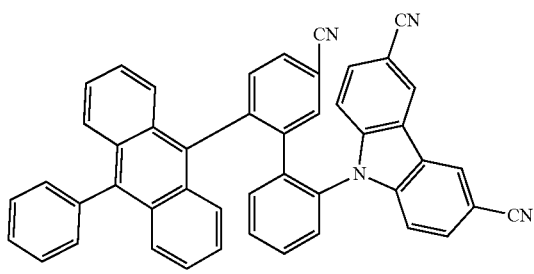
358 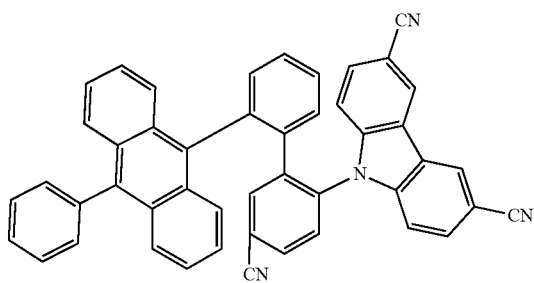

359
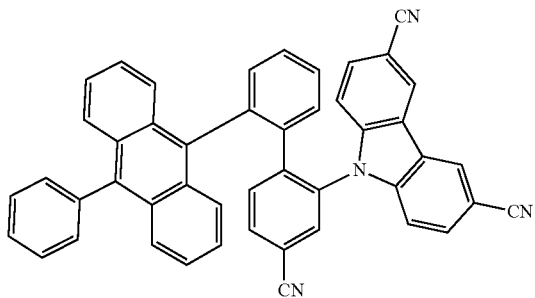
360
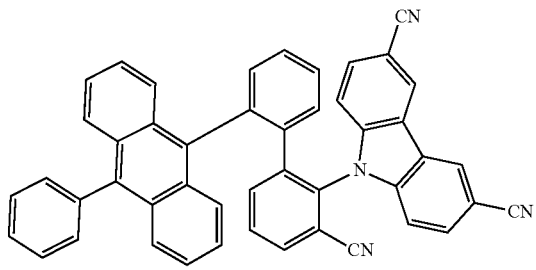
361
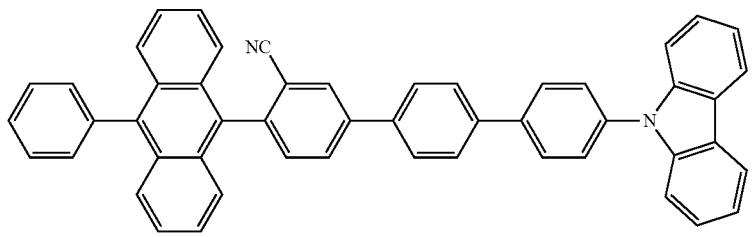
362
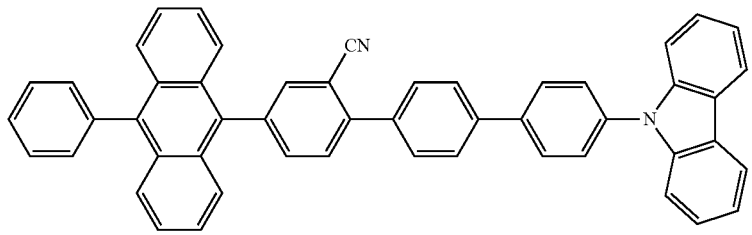
363
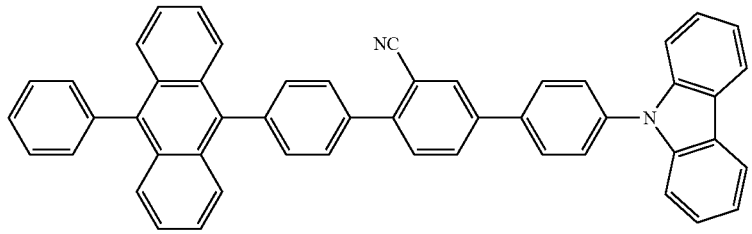
364
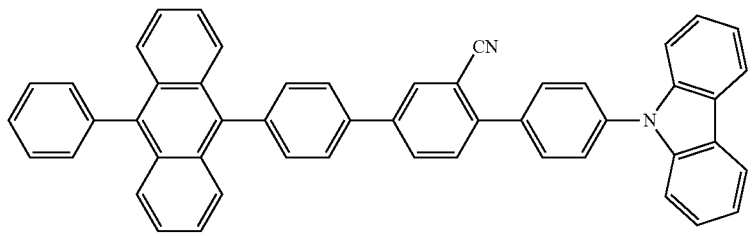
365
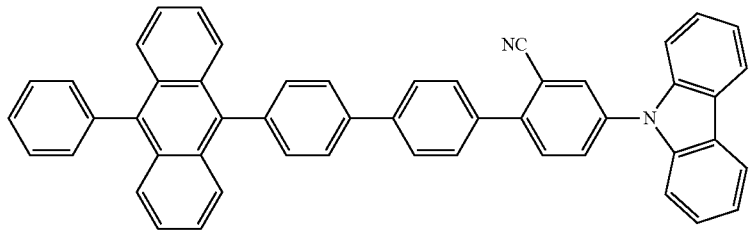

-continued
366
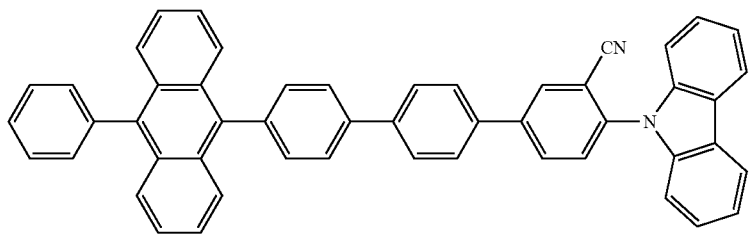
367
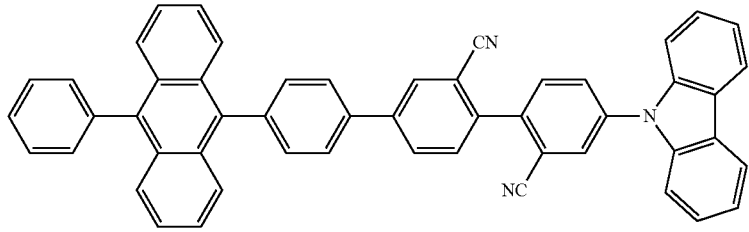
368
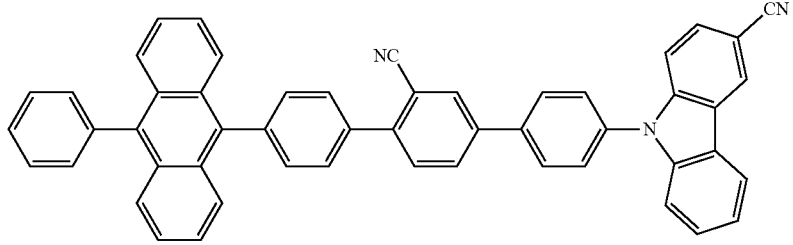
369
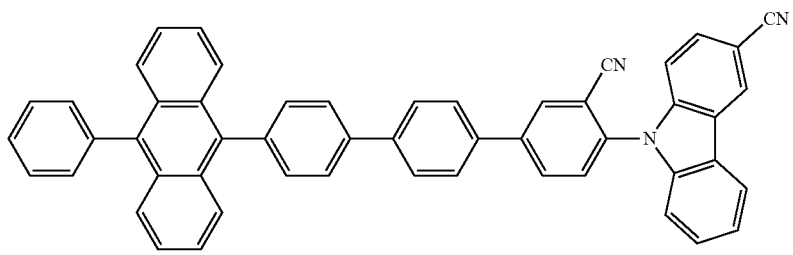
370
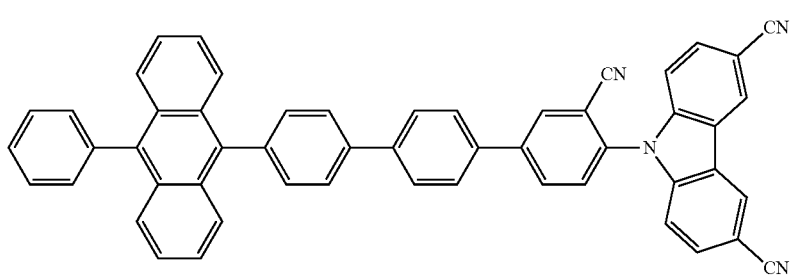
371
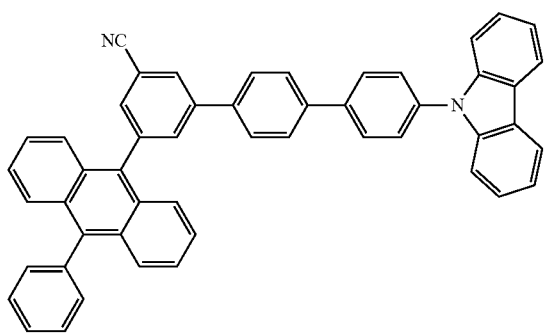
372
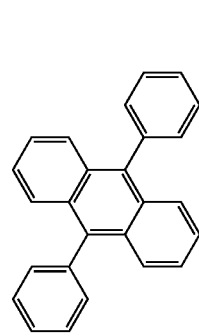

-continued
373
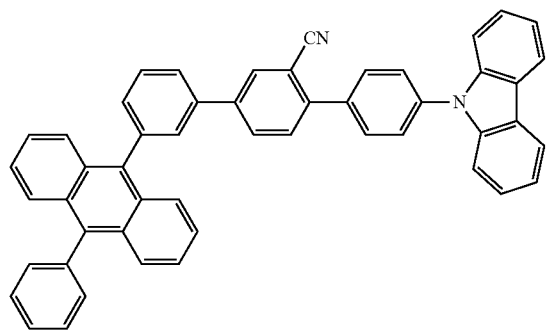
374
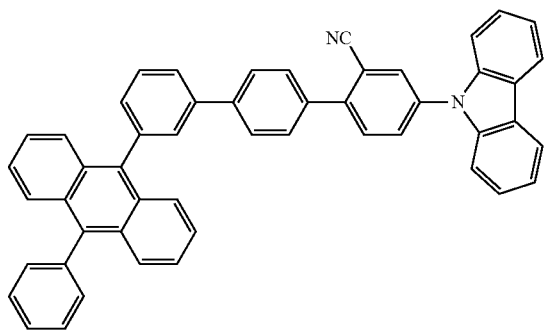
375
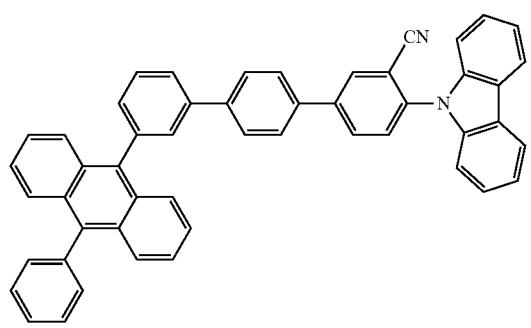
376
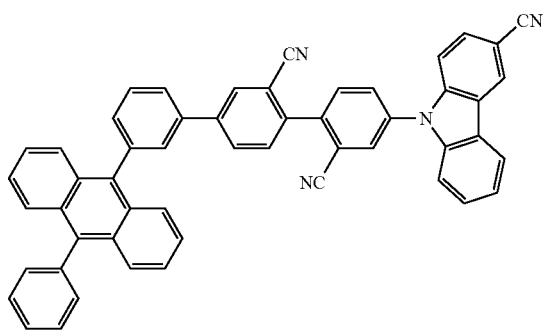
377
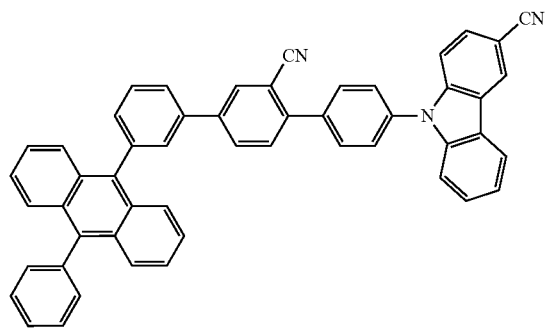
378
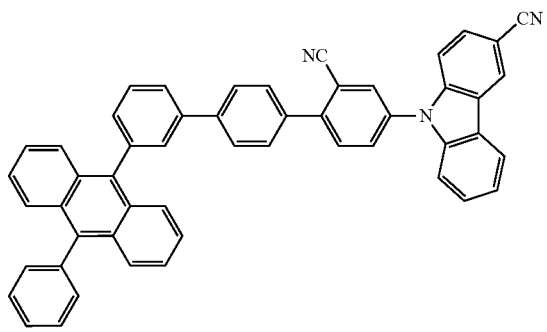
379
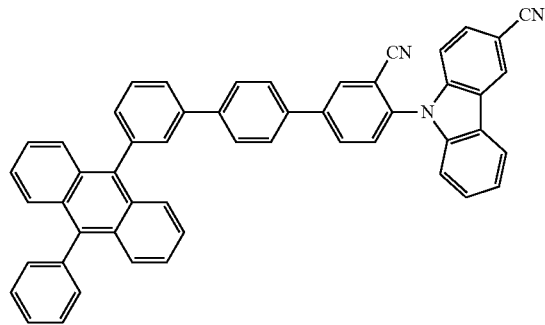
380
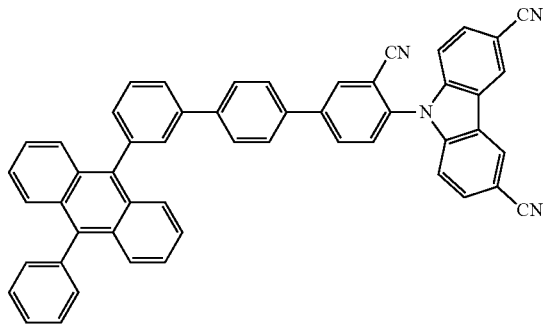

-continued
381
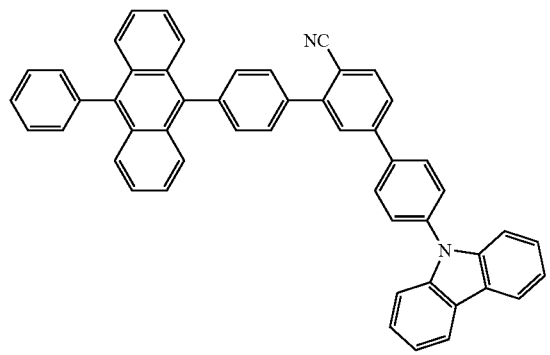
382
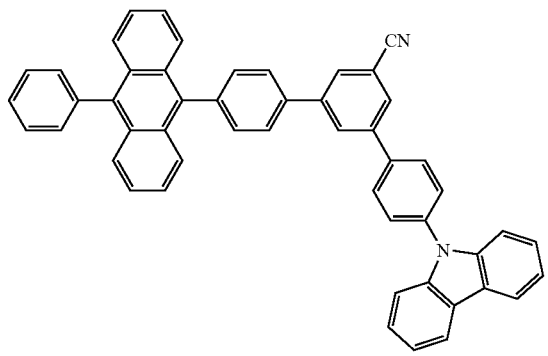
383
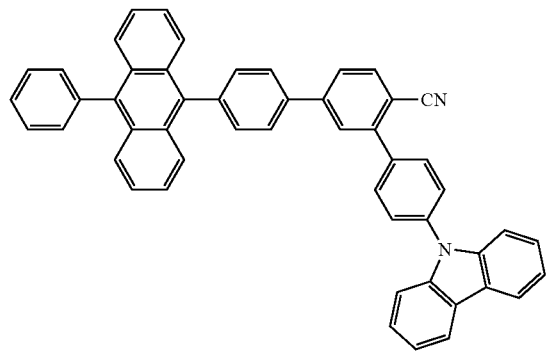
384
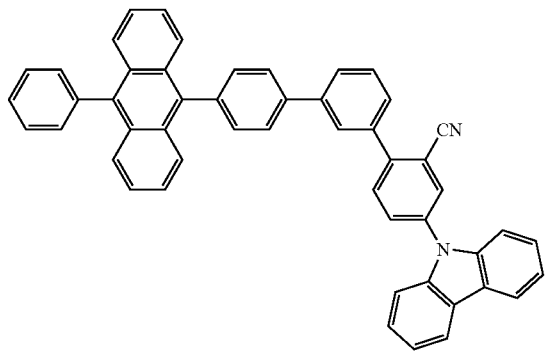
385
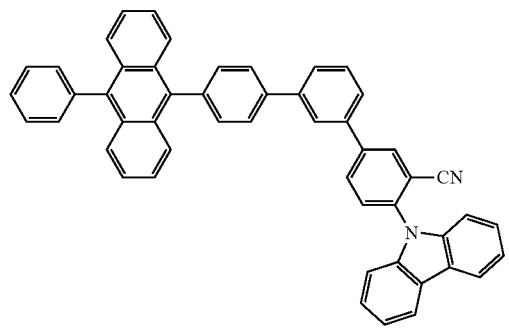
389
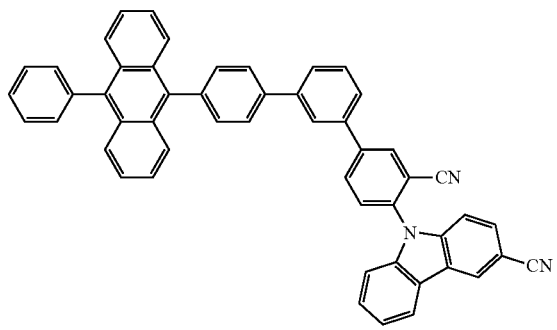
386
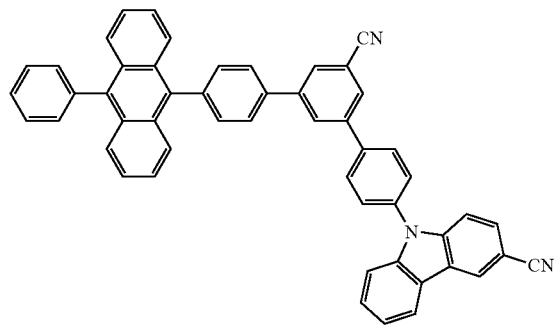
387
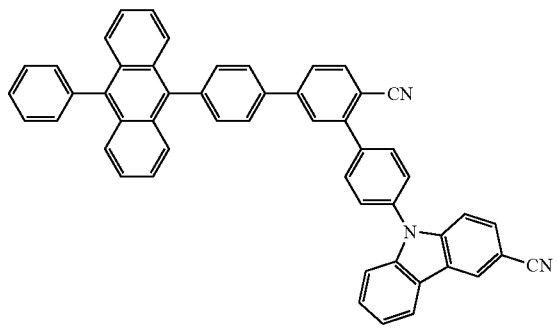

388
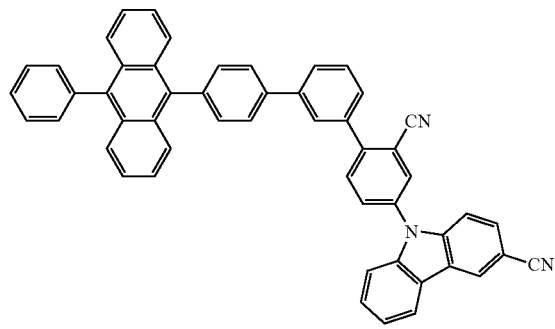
390
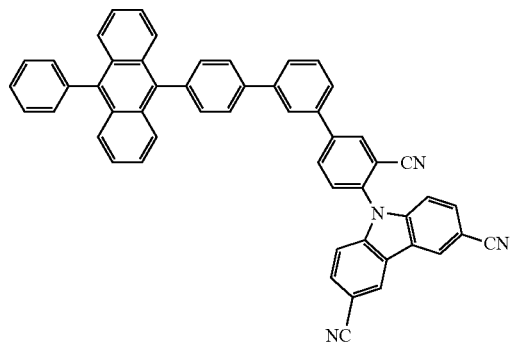
391
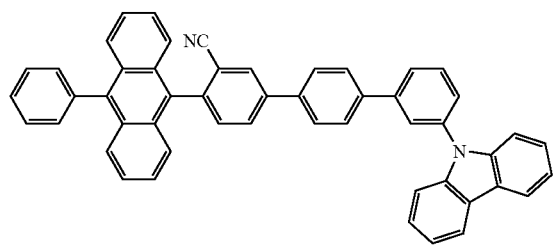
392
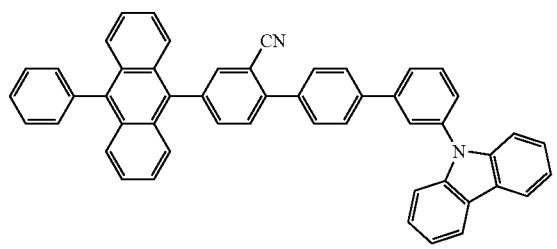
393
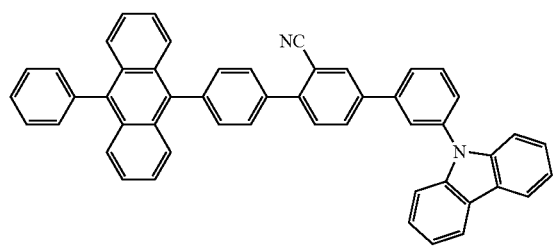
394
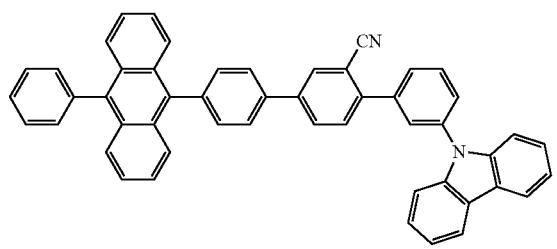
395
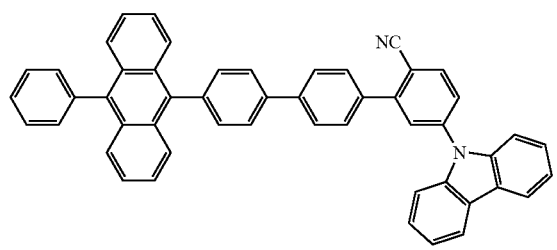
396
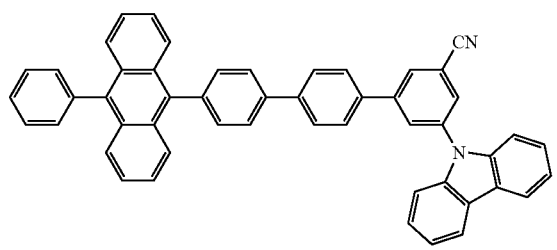
397
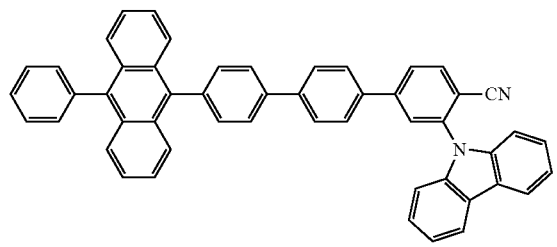
398
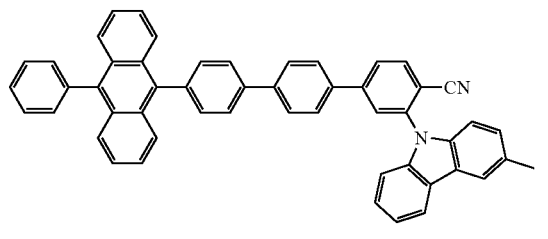

-continued
399
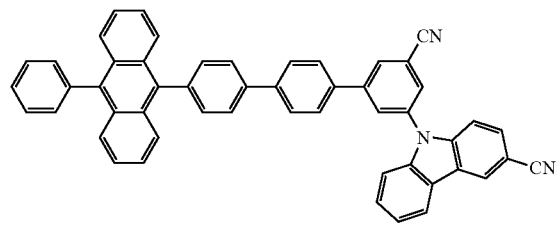
400
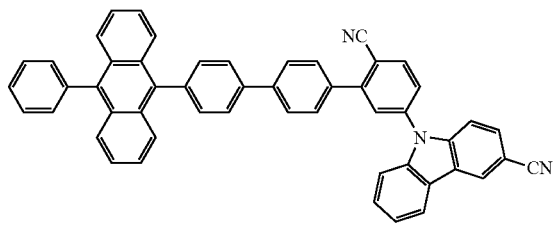
401
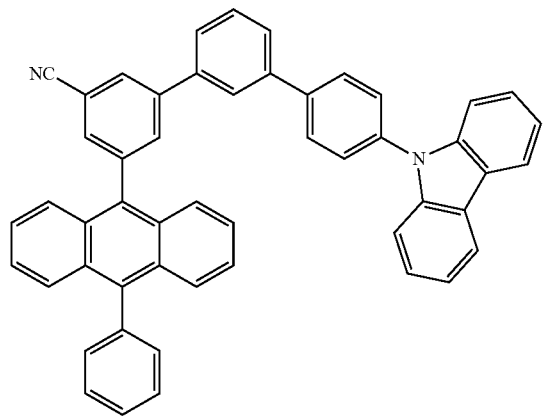
402
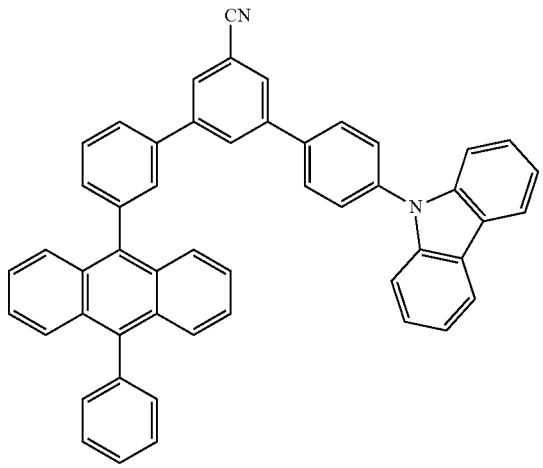
403
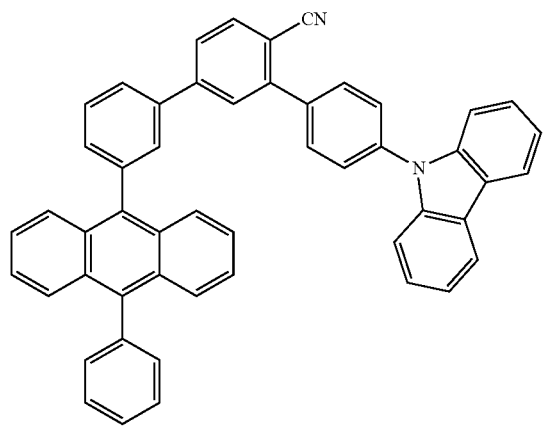
404
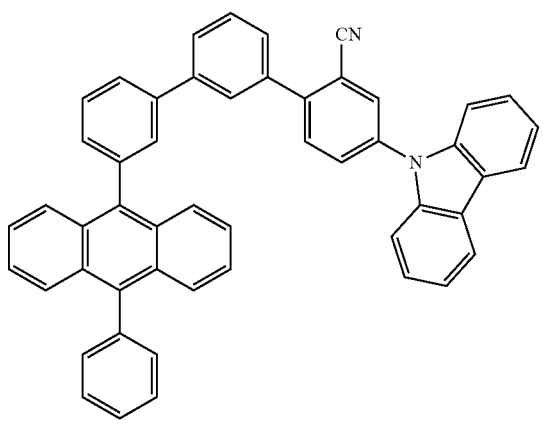

-continued
405
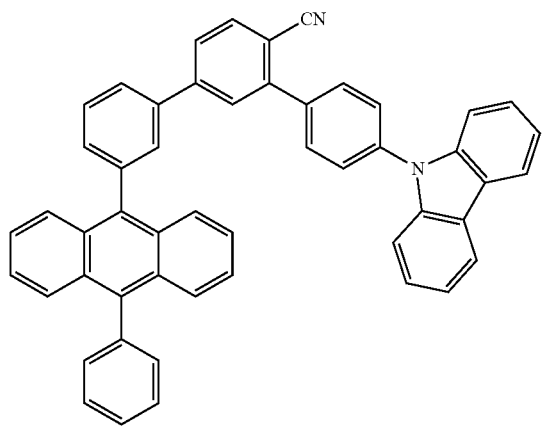
406
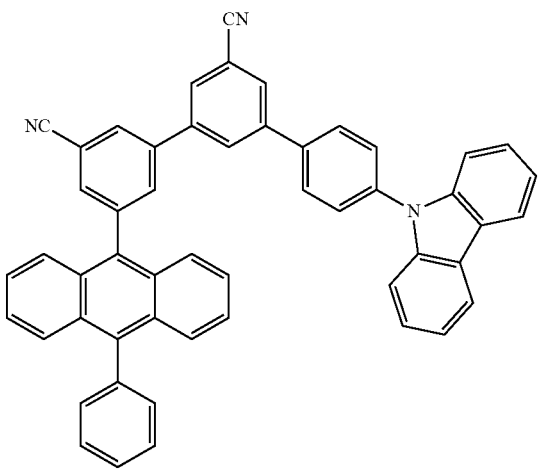
407
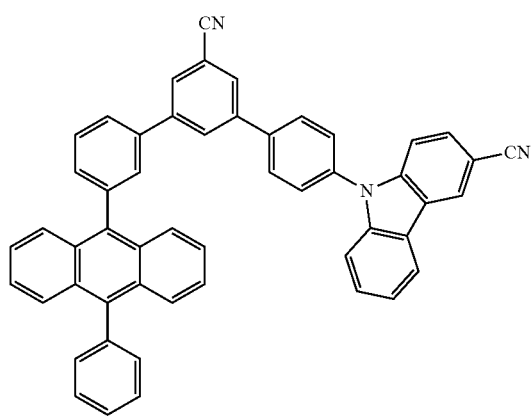
408
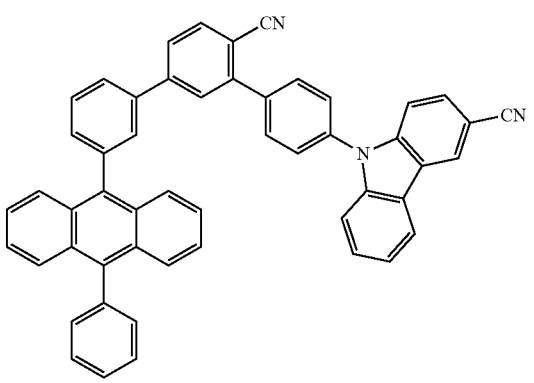
409
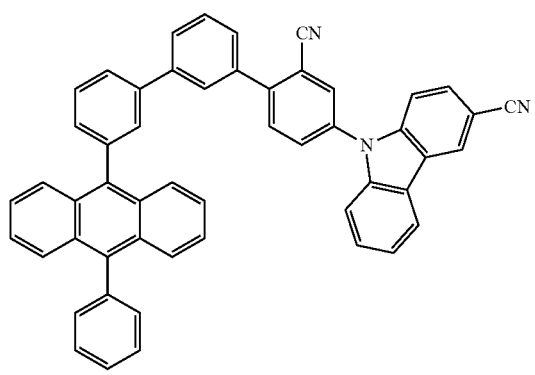
410
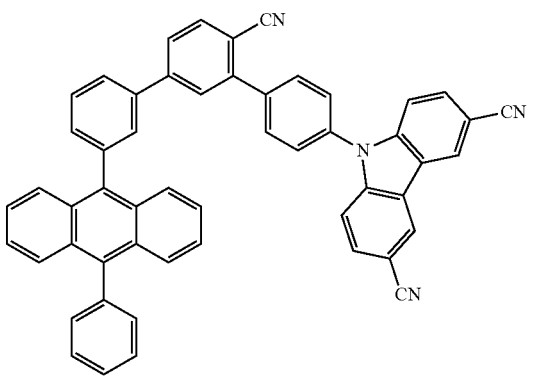

-continued
411
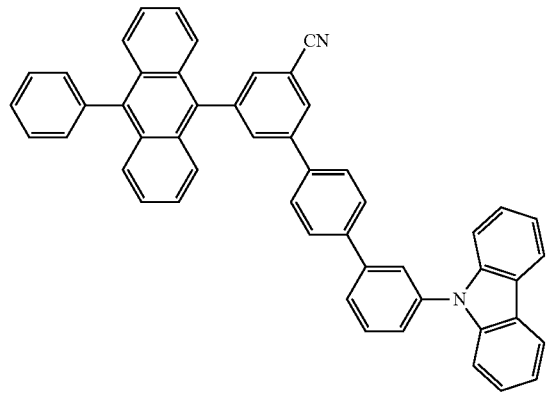
412
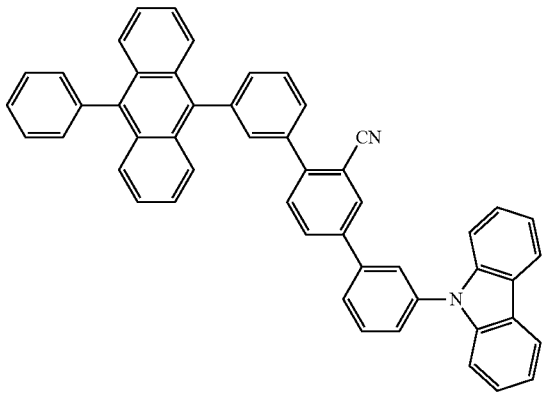
413
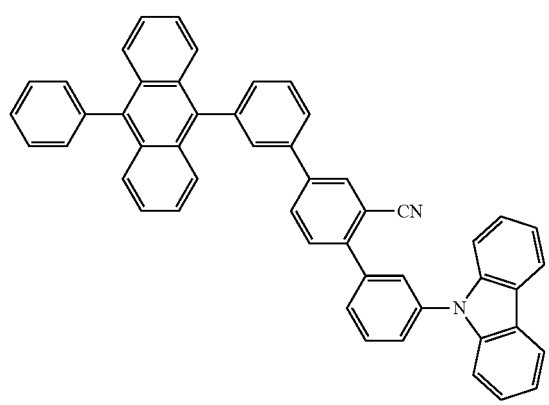
414
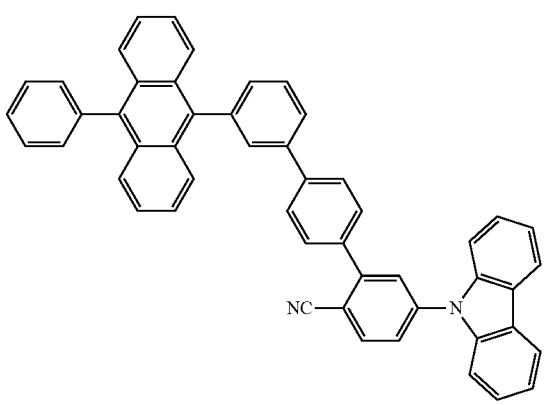
415
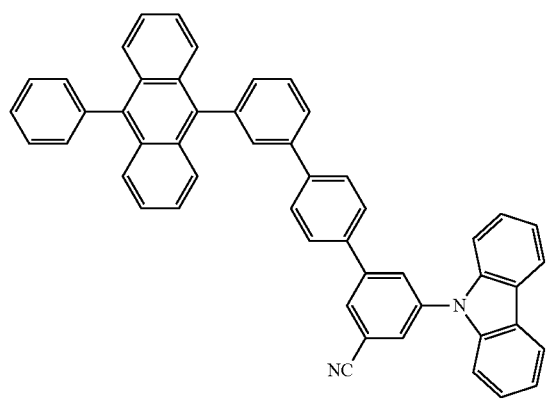
416
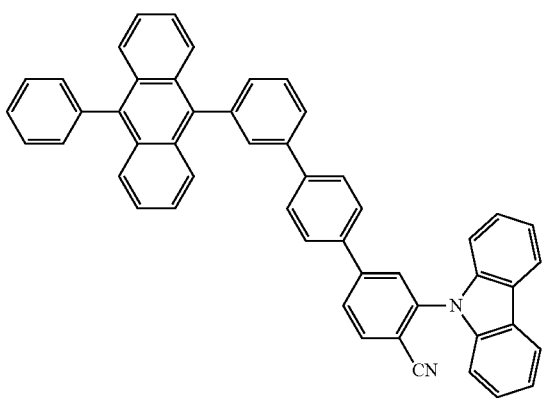
417
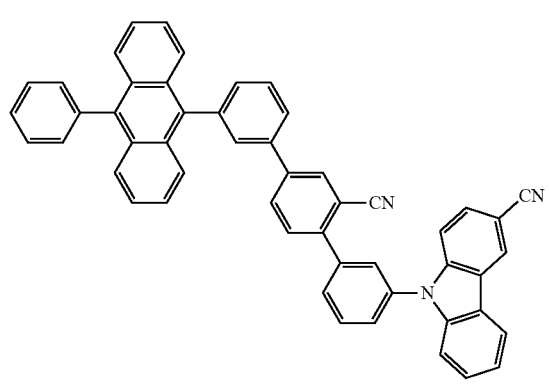
418
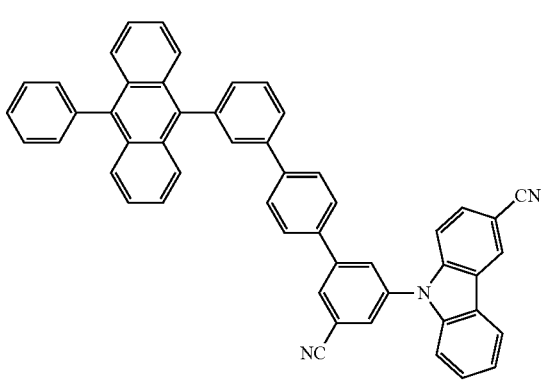

-continued
419
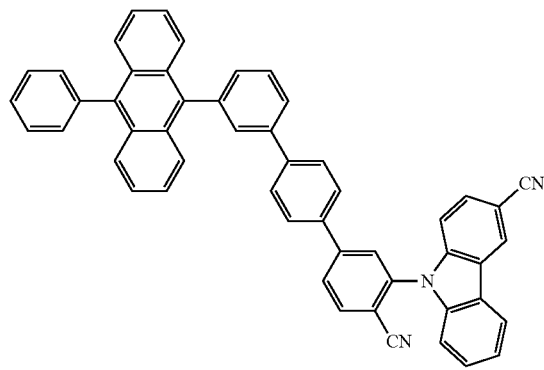
420
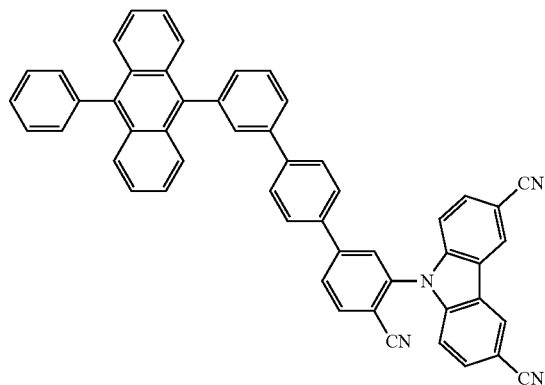
421
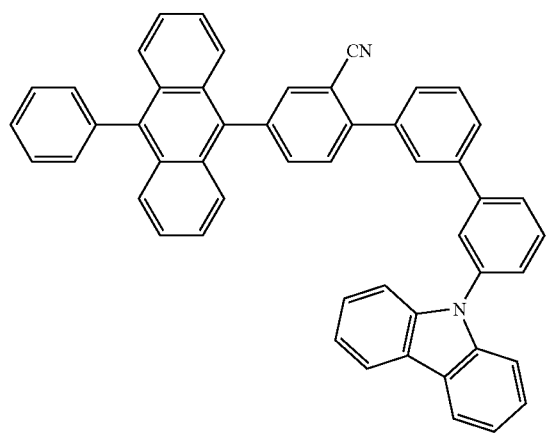
422
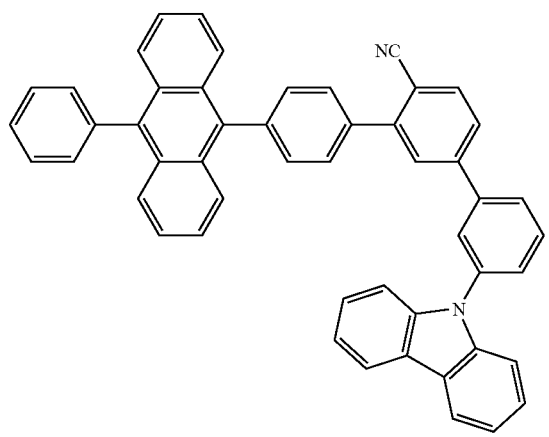
423
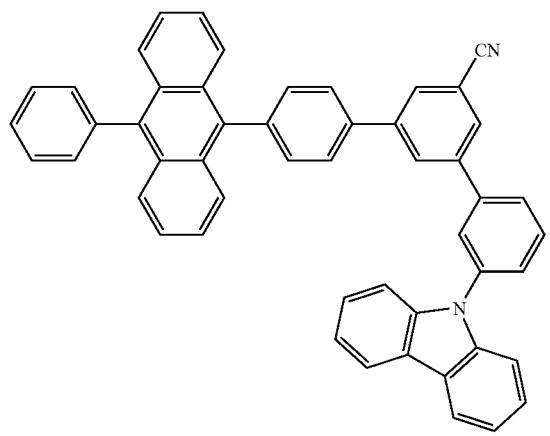
424
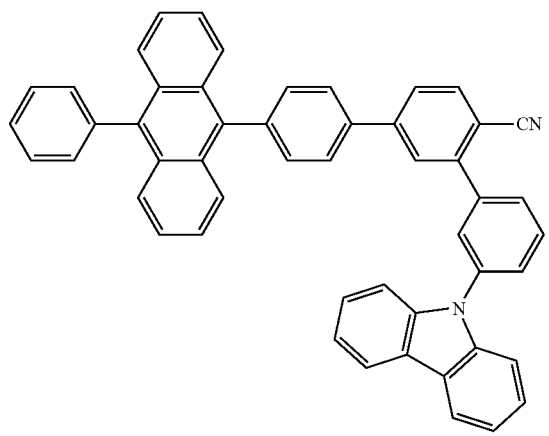

425
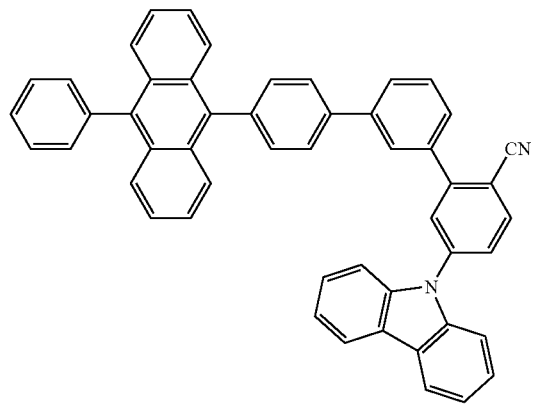
426
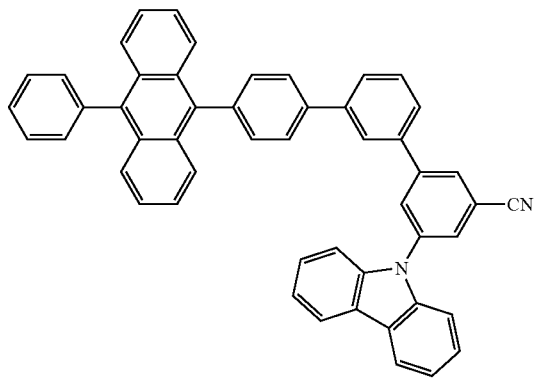
427
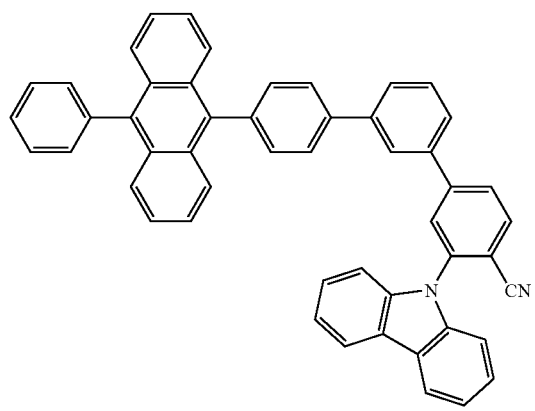
428
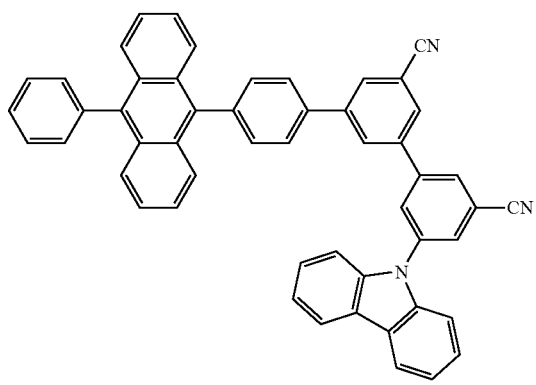
429
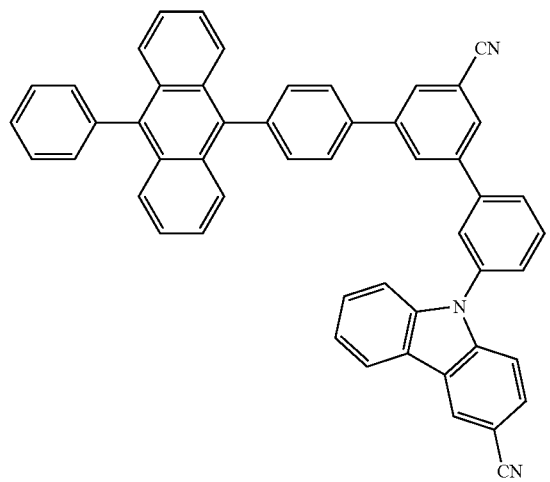
430
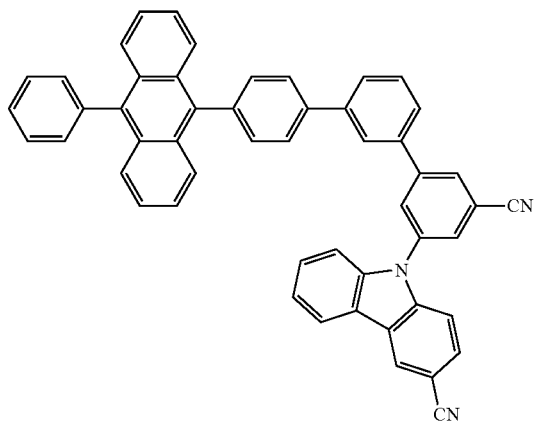
431
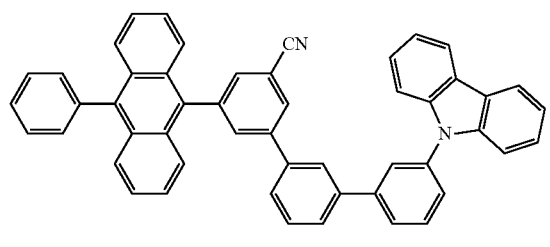
432
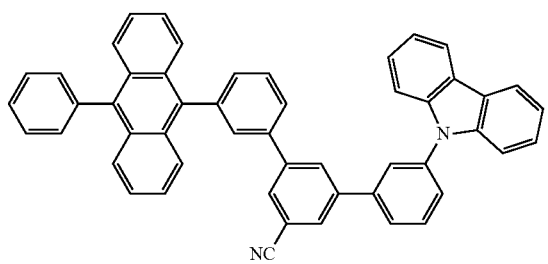

-continued
433
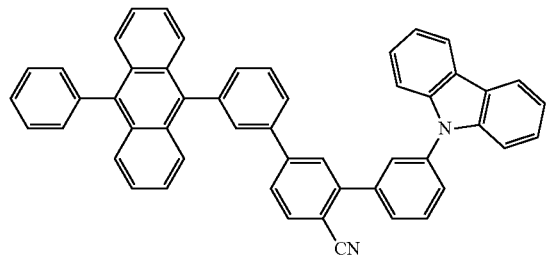
434
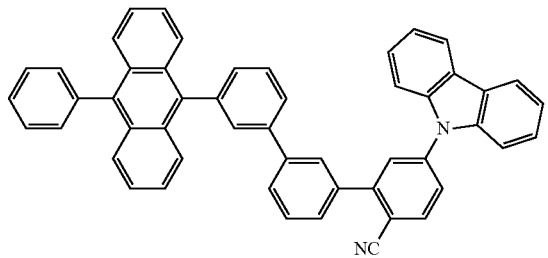
435
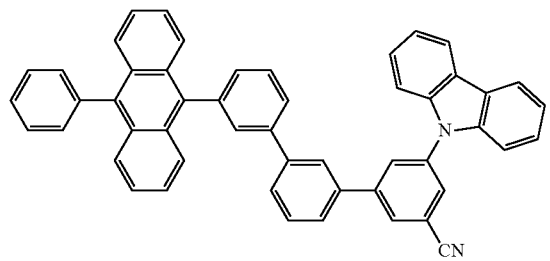
436
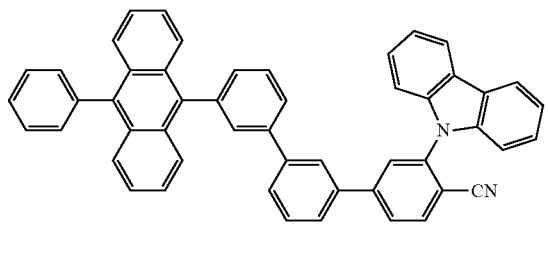
437
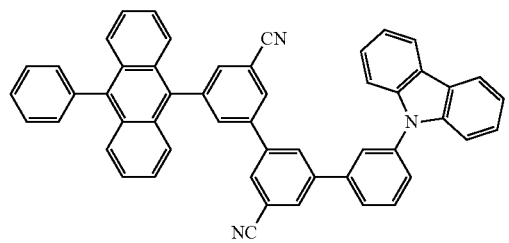
438
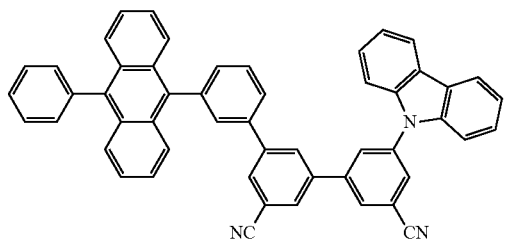
439
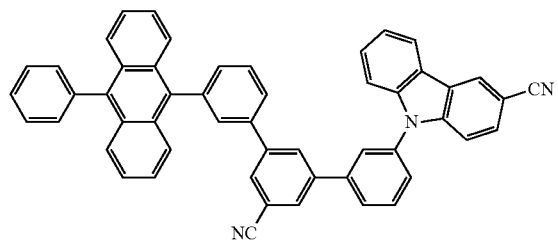
440
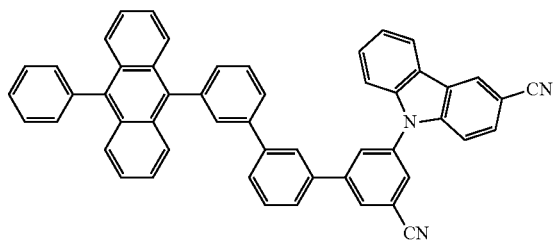
441
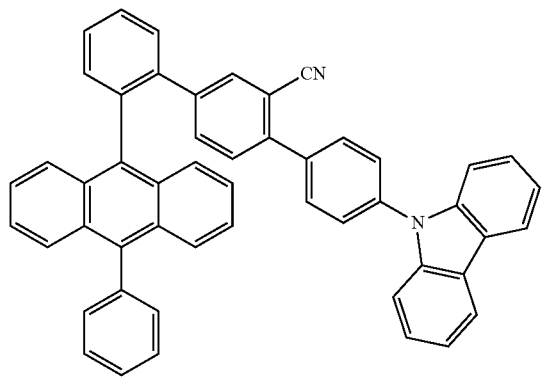
442
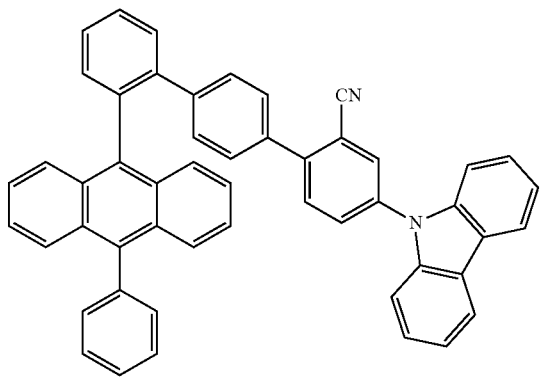

-continued
443
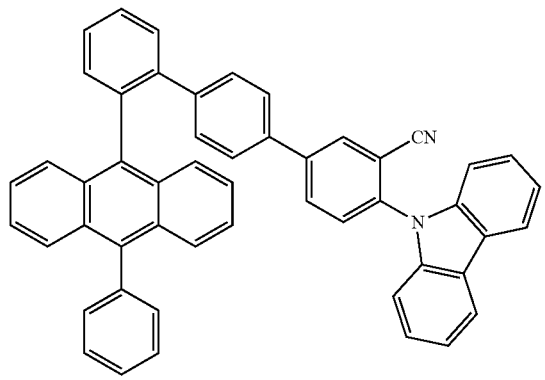
444
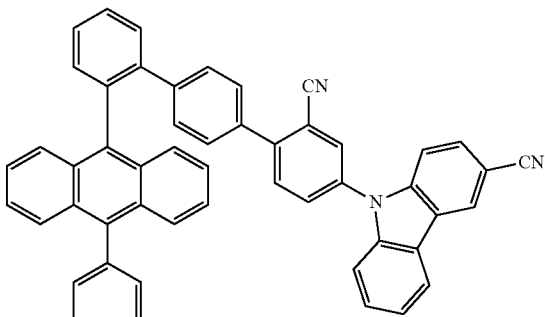
445
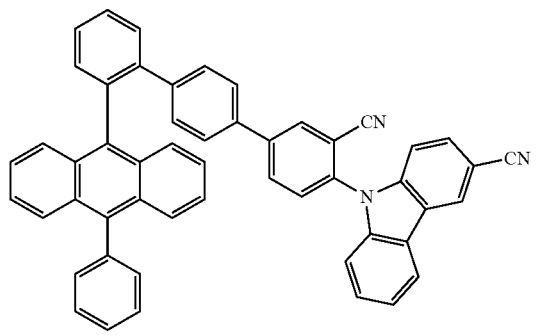
446
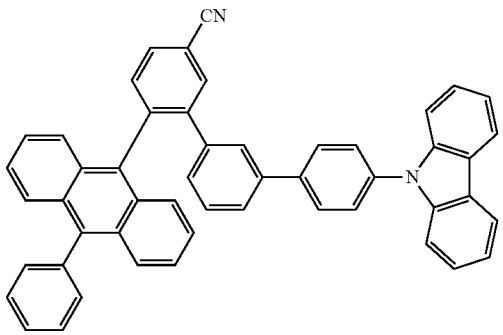
447
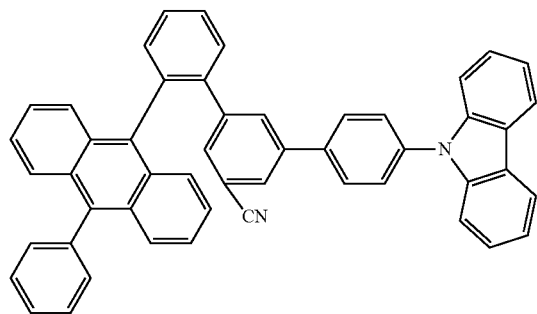
448
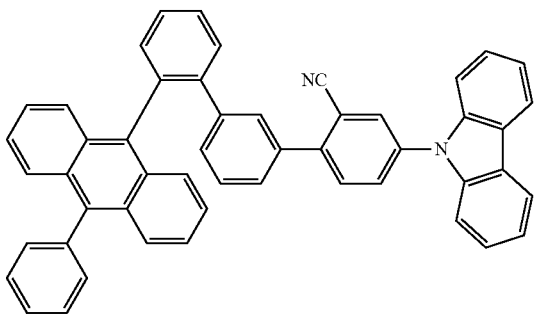
449
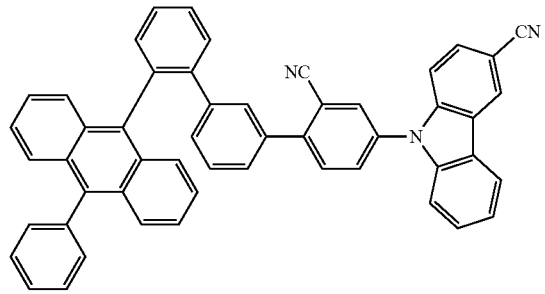
450
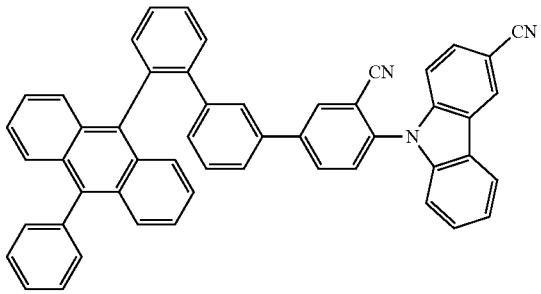

-continued
451
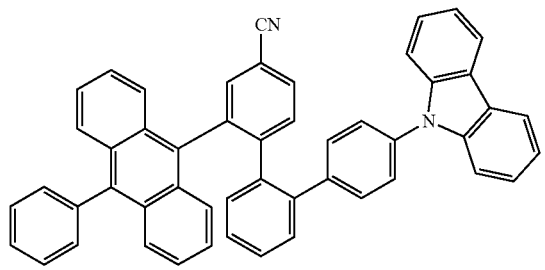
452
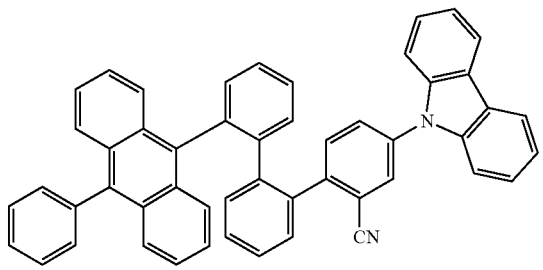
452
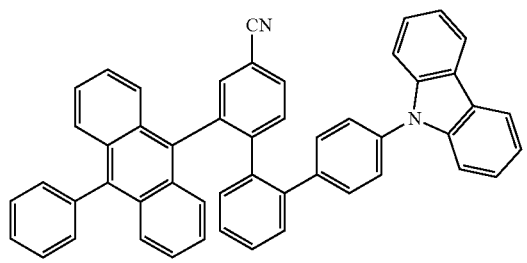
453
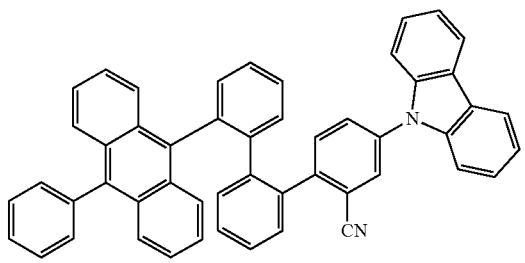
454
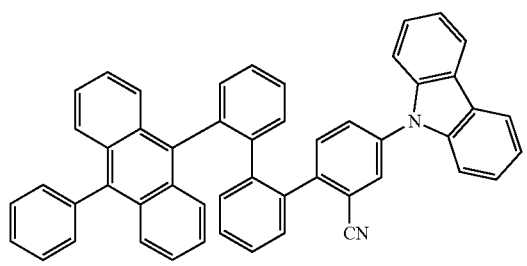
455
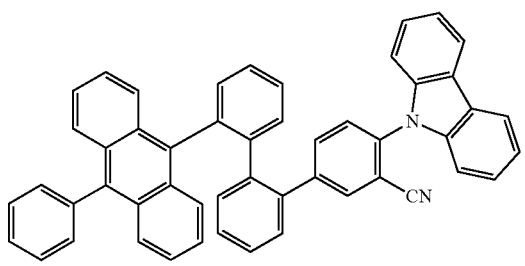
456
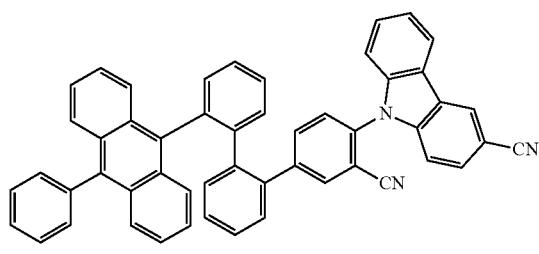
457
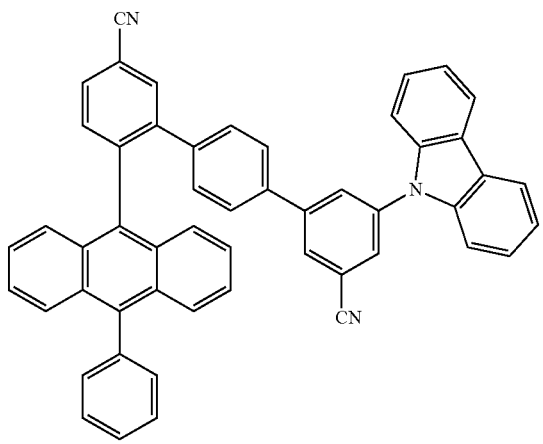

-continued
458
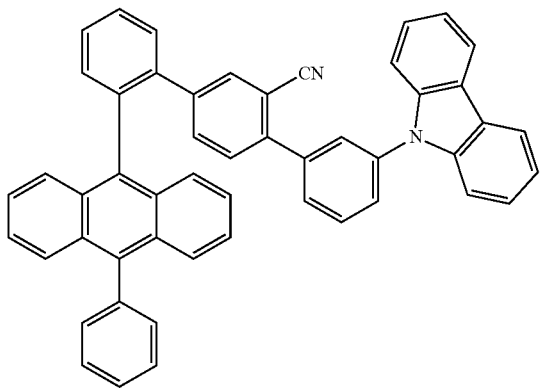
459
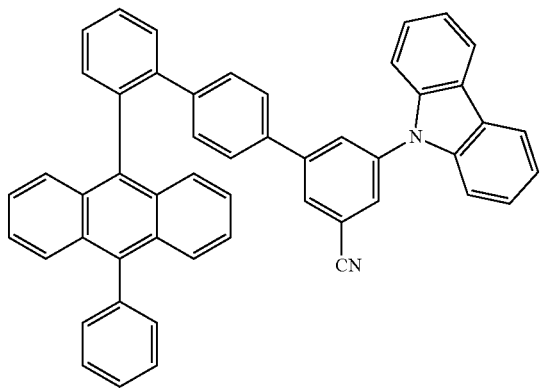
460
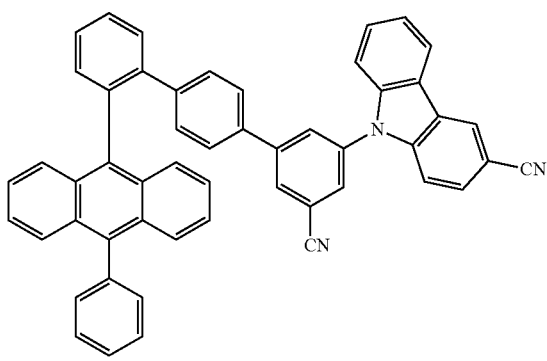
461
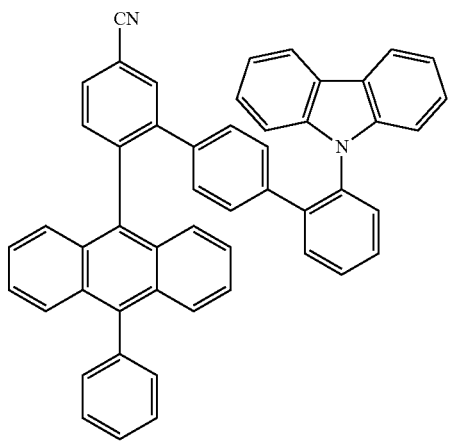
462
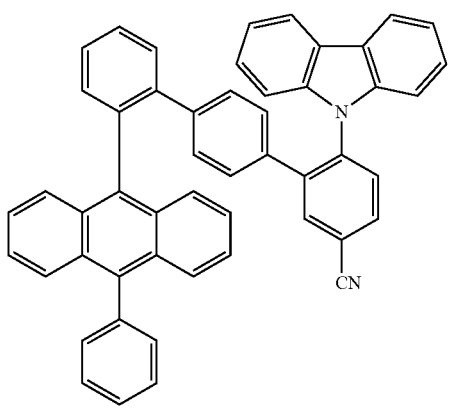
463
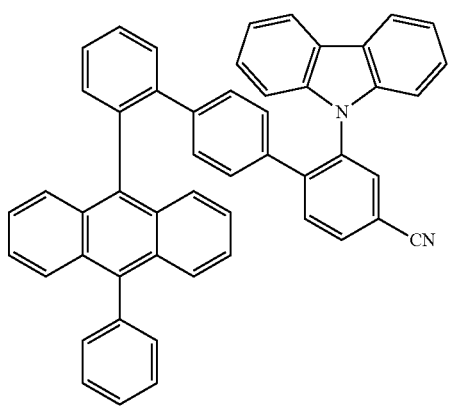

-continued
464
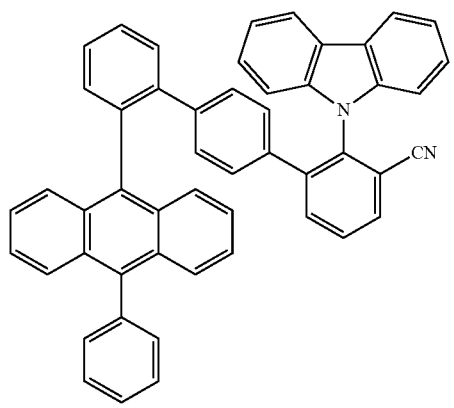
465
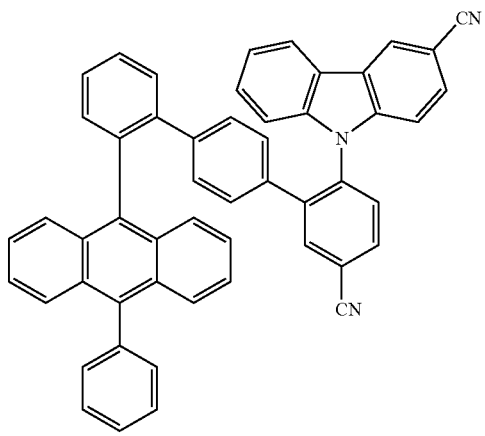
466
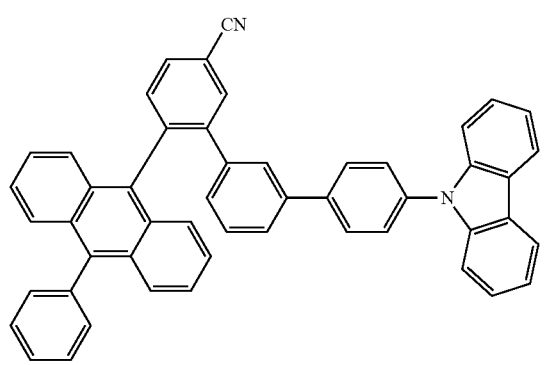
467
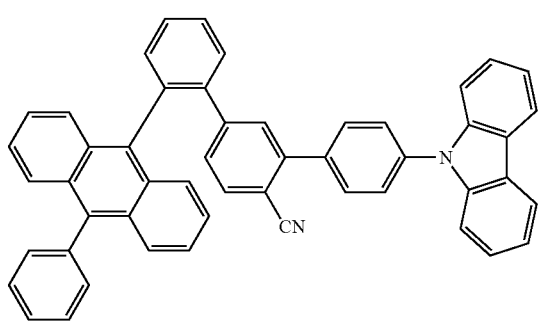
468
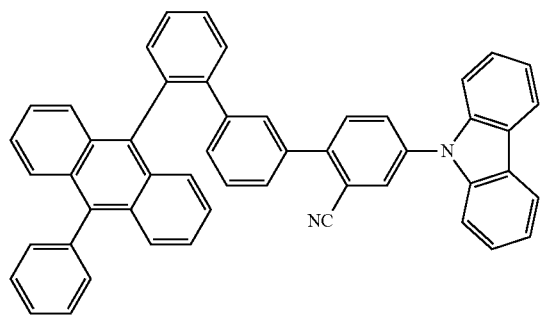
469
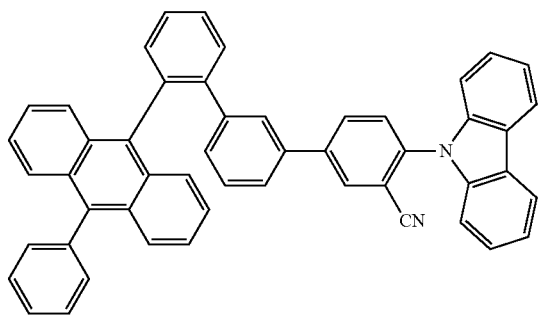
470
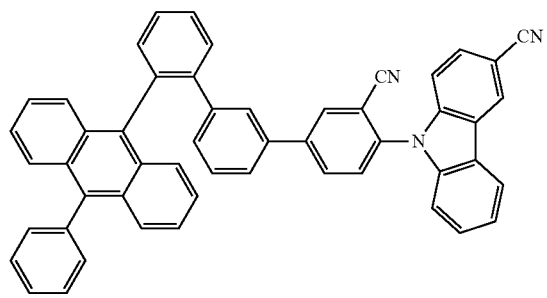
471
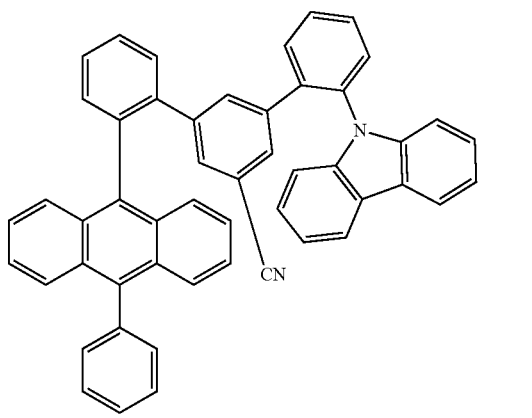

-continued
472
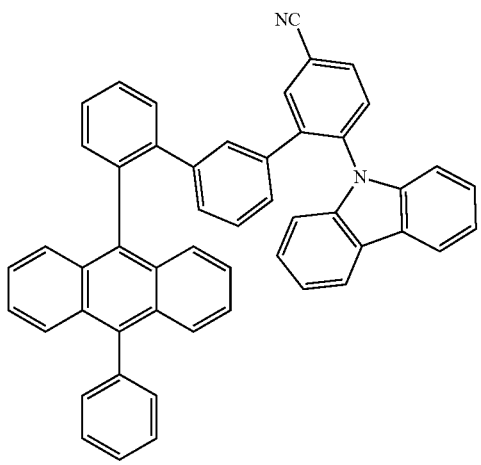
473
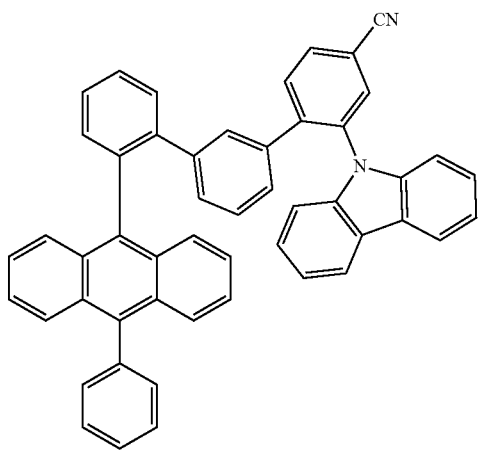
474
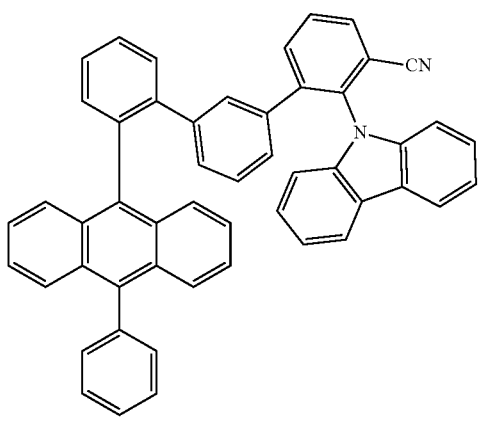
475
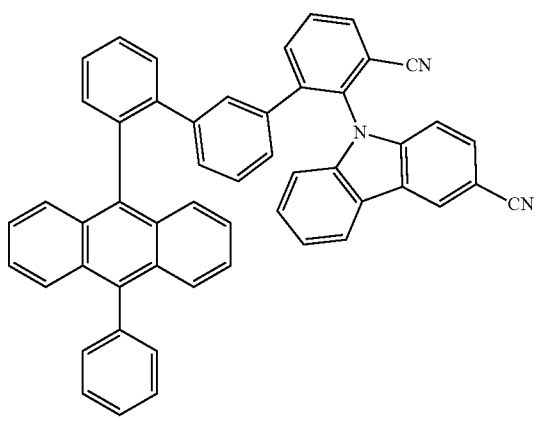
476
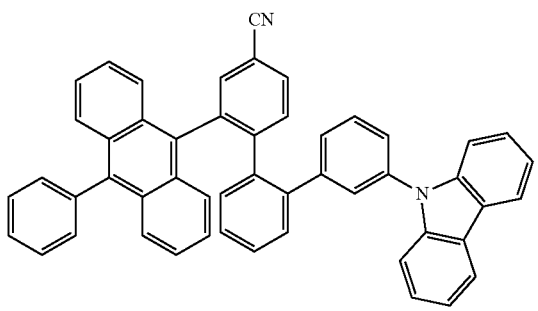
477
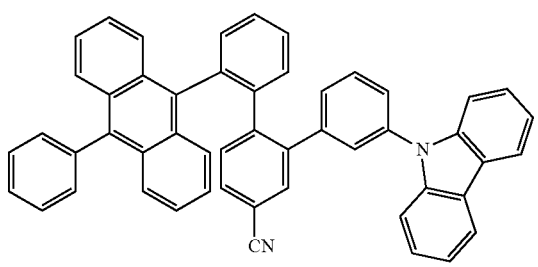
478
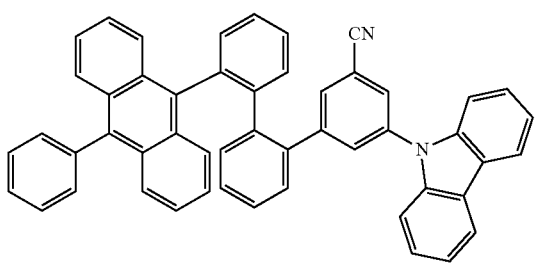
479
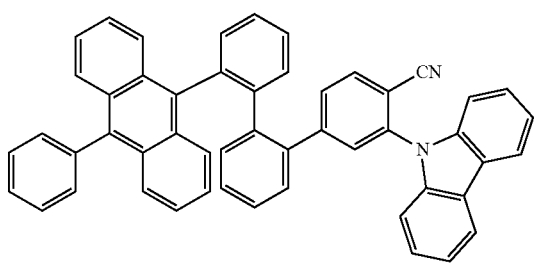

-continued
480
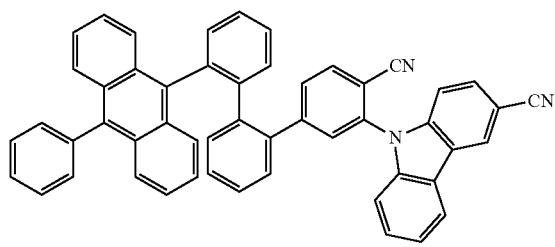
481
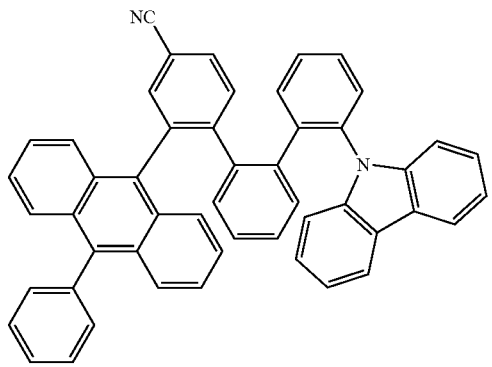
482
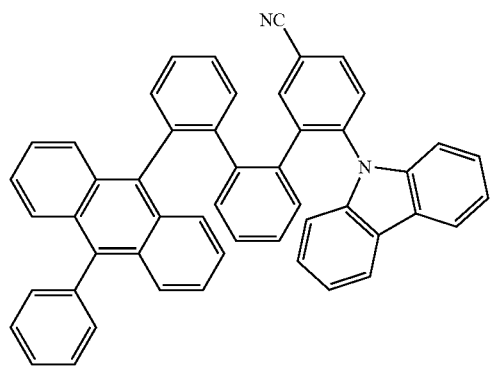
483
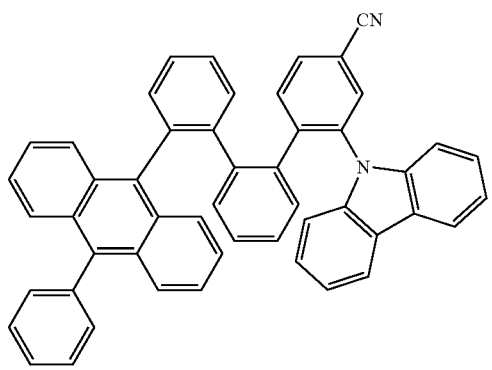
484
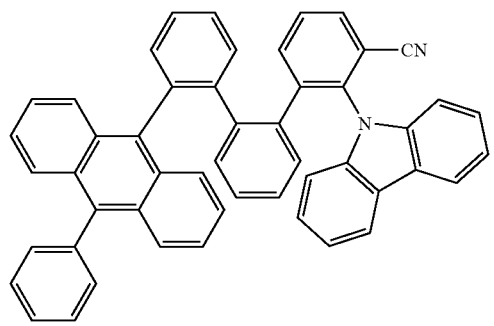
485
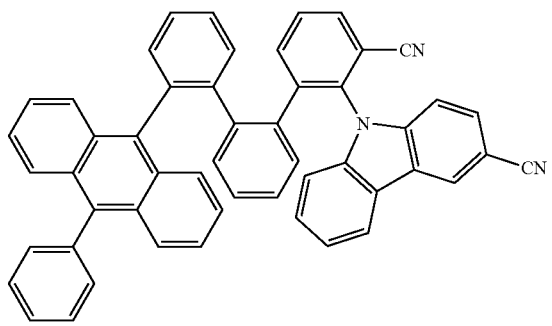
486
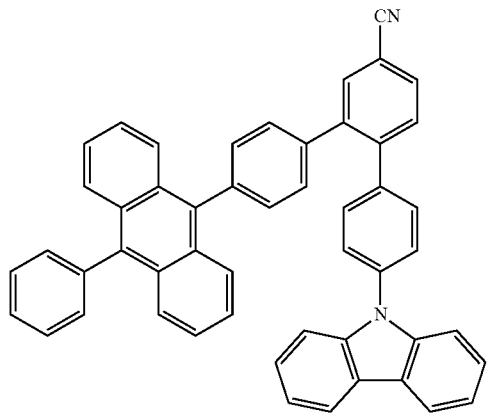
487
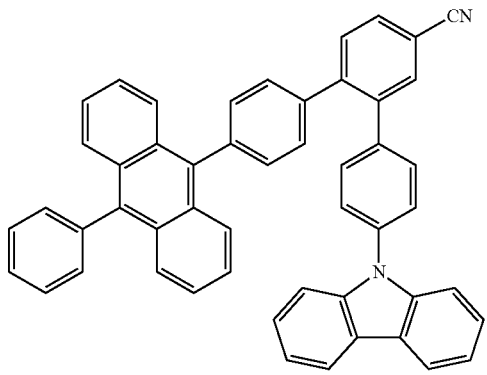

-continued
488
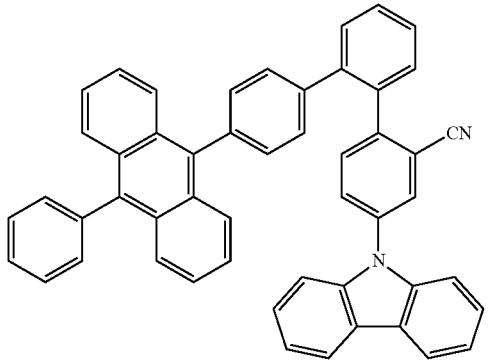
489
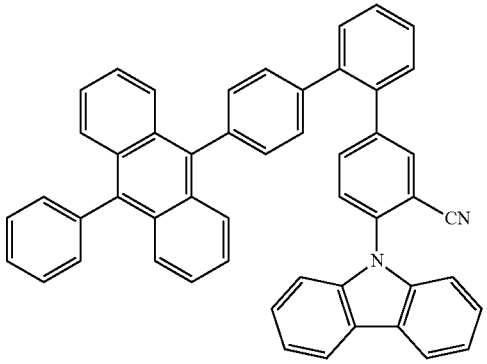
490
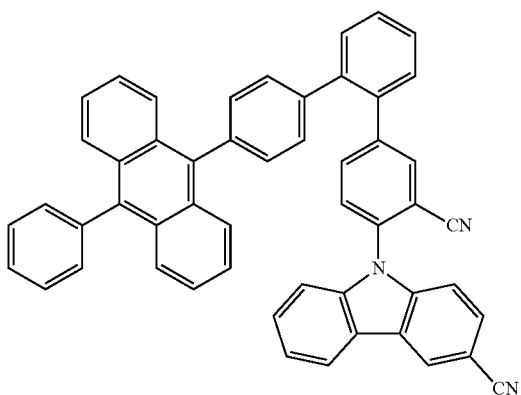
491
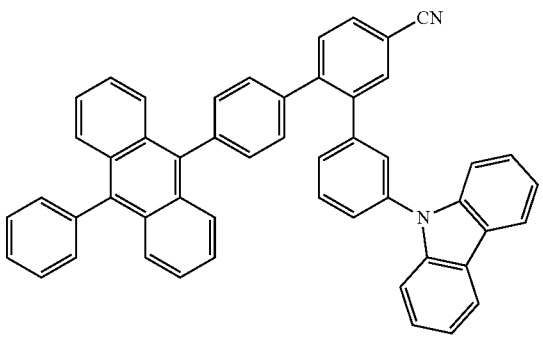
492
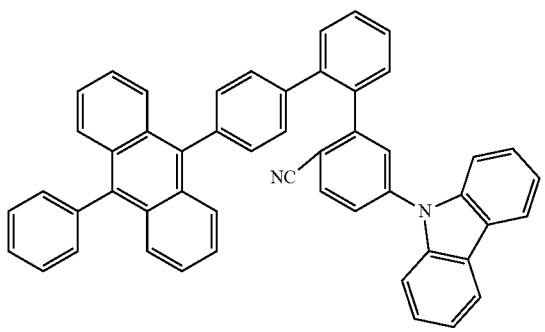
493
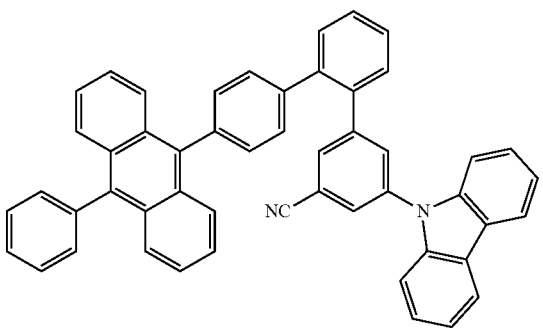
494
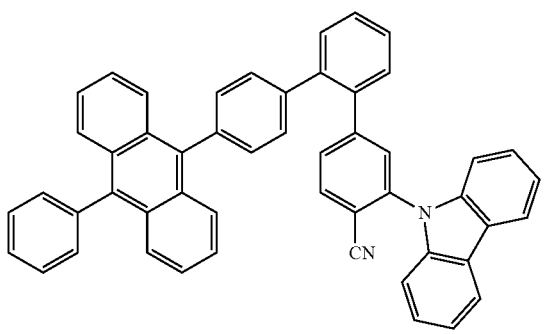
495
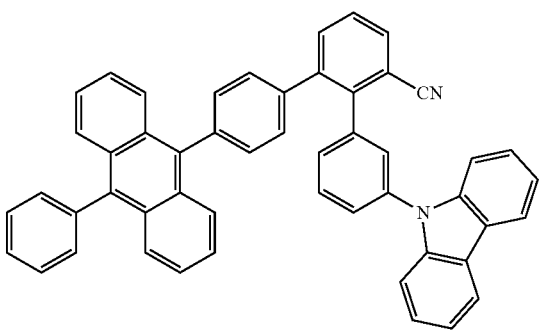

-continued
496
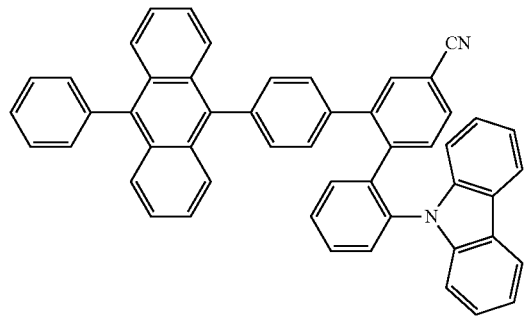
497
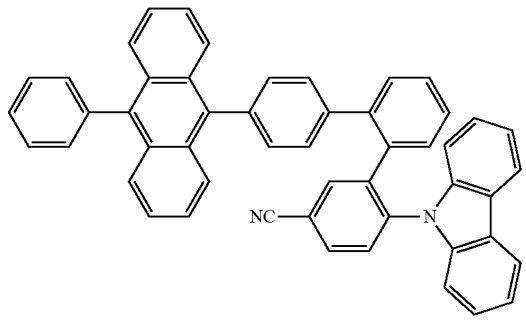
498
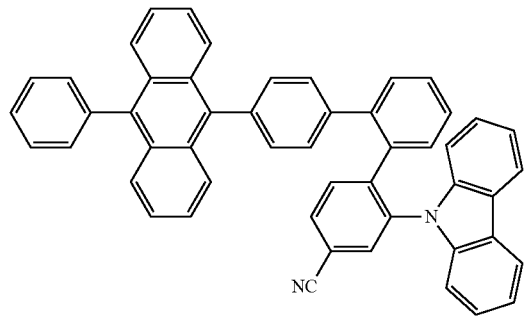
499
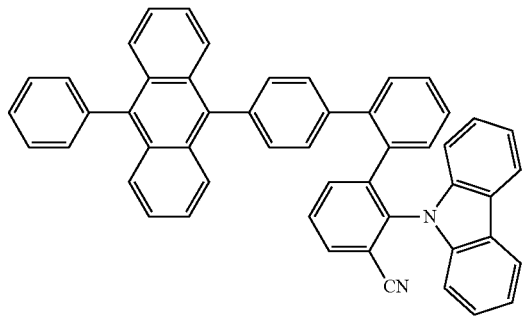
500
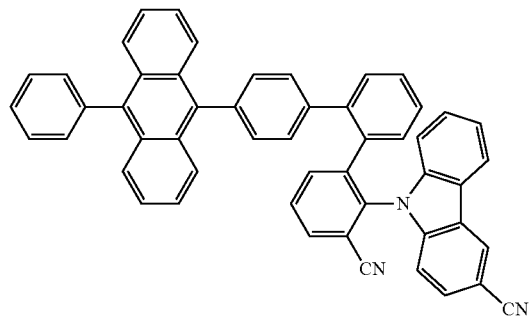
501
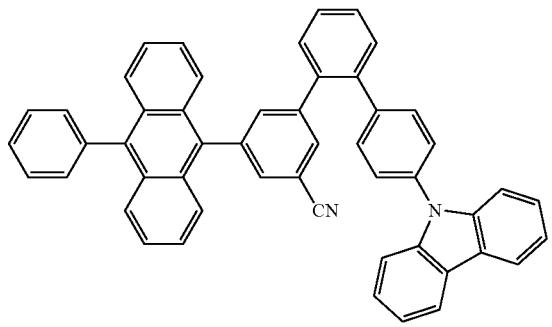
502
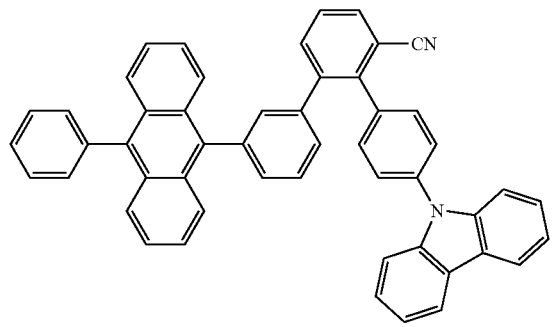
503
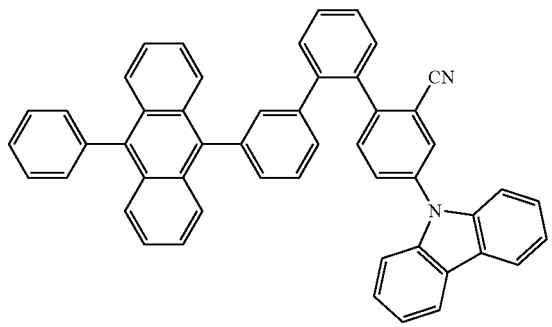

-continued
504
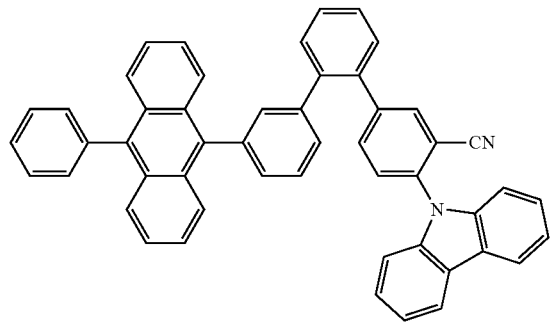
505
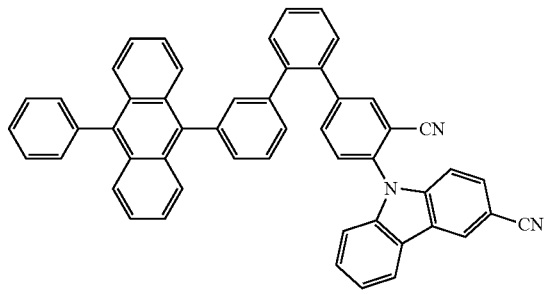
506
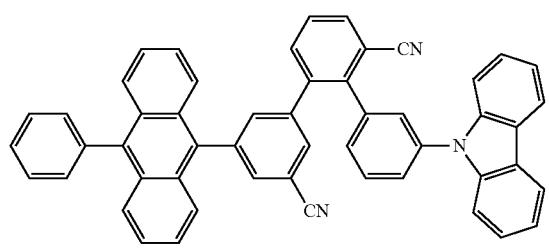
507
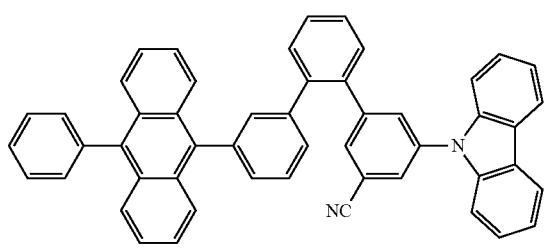
508
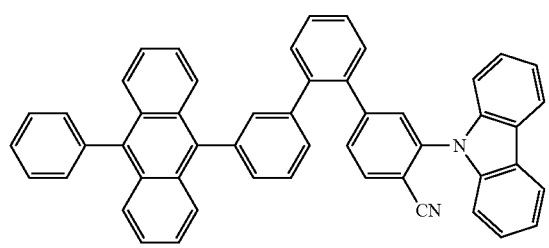
509
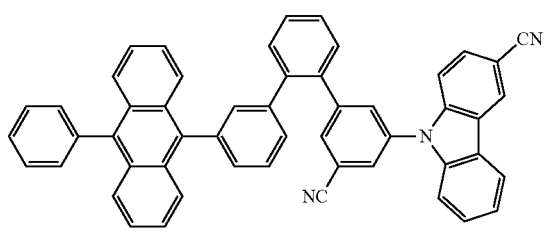
510
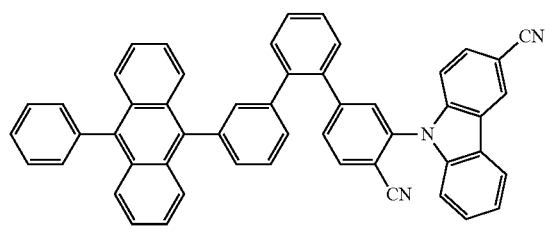
511
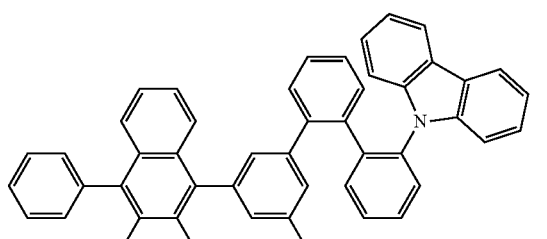
512
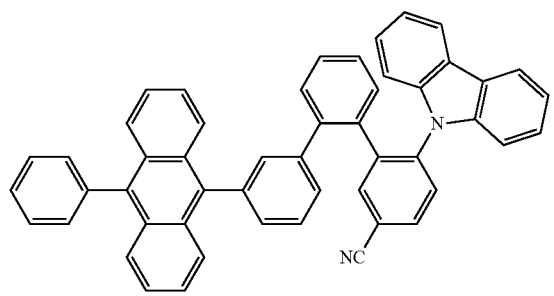
513
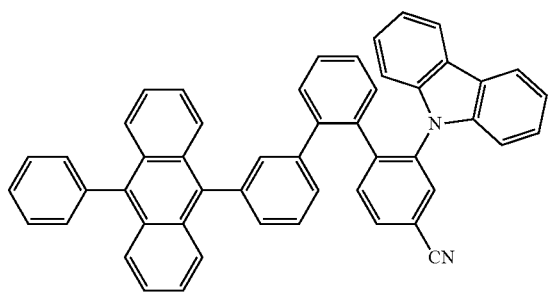

-continued
514
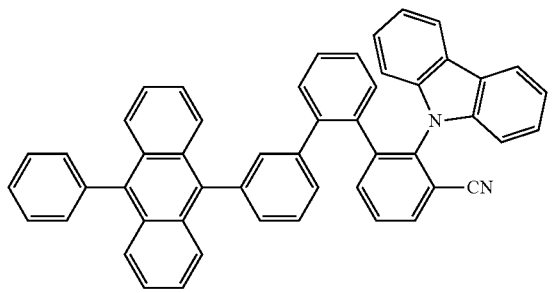
515
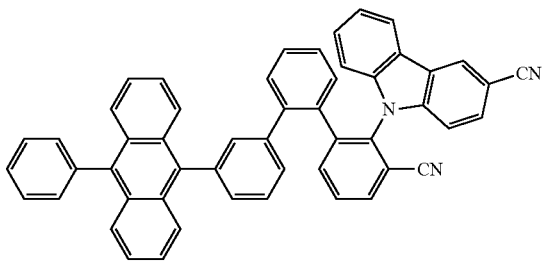
516
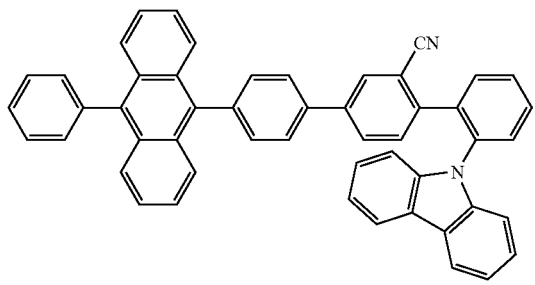
517
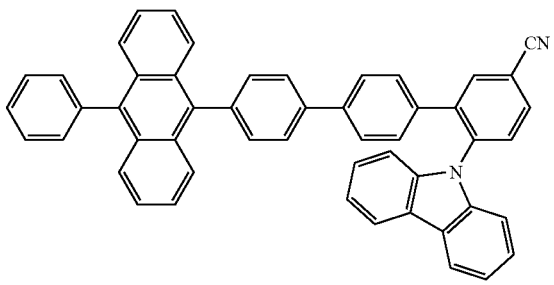
518
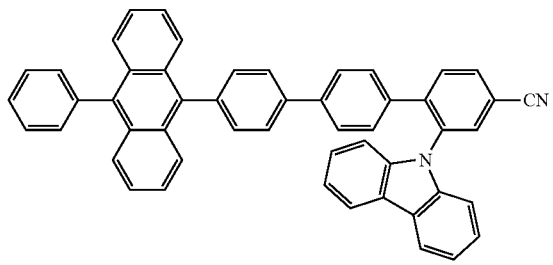
519
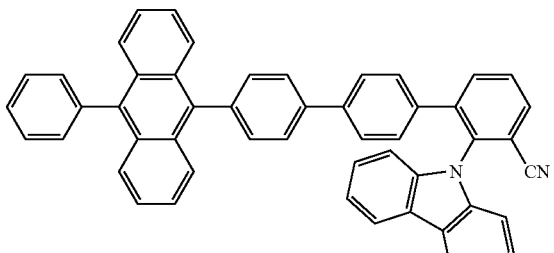
520
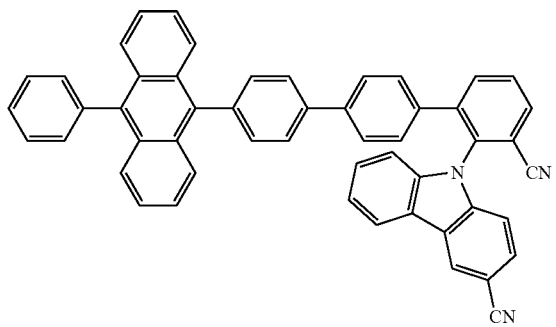
521
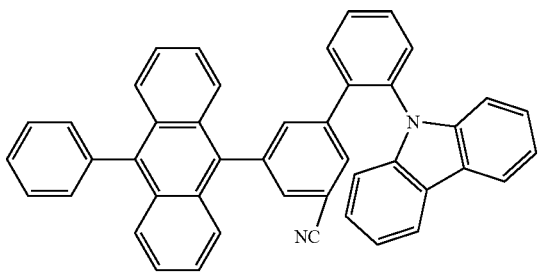
522
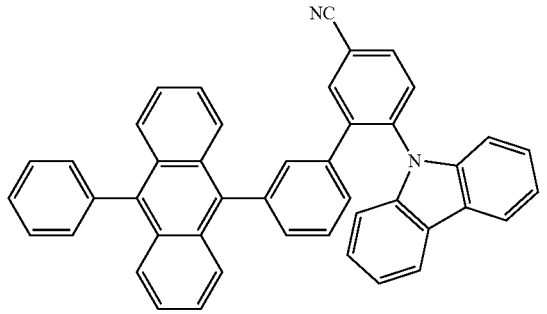
523
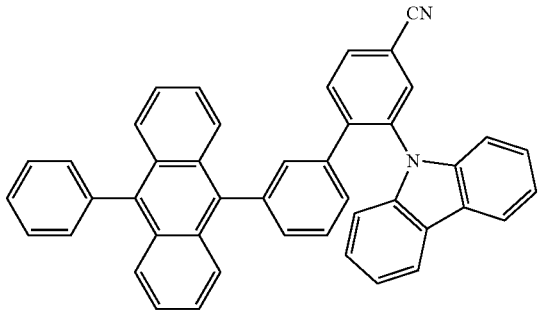

-continued
522
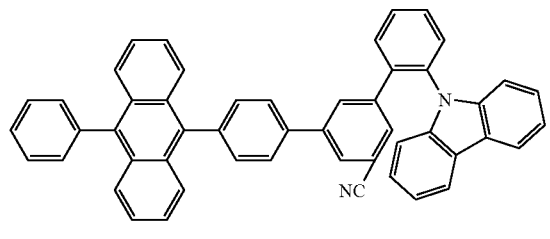
521
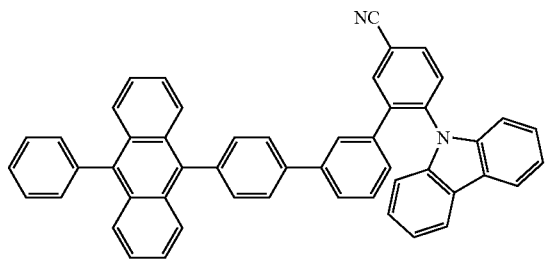
523
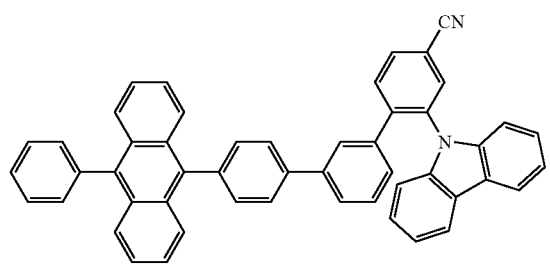
524
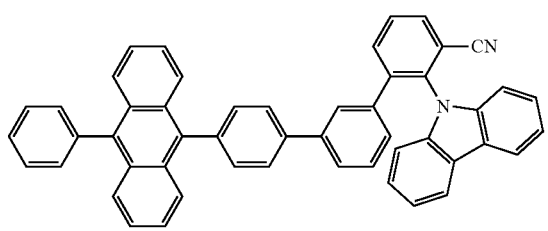
525
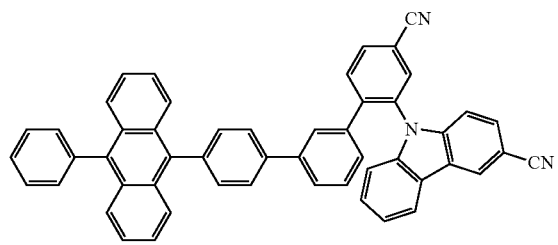
526
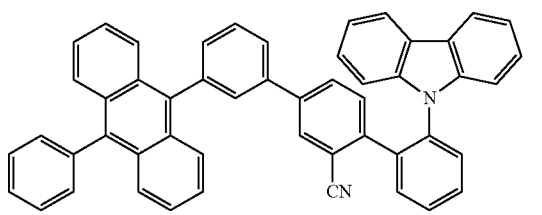
527
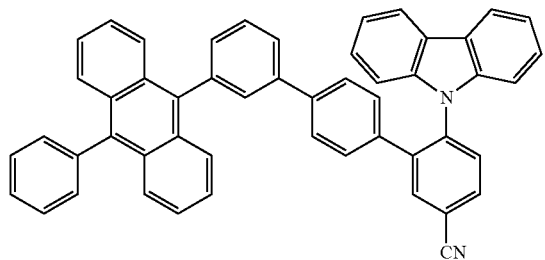
528
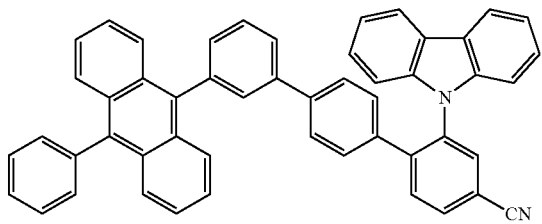
529
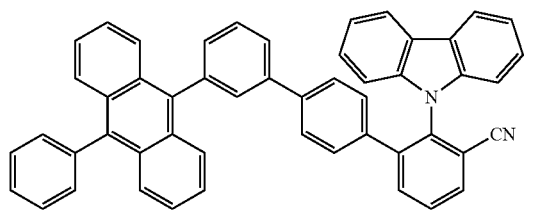
530
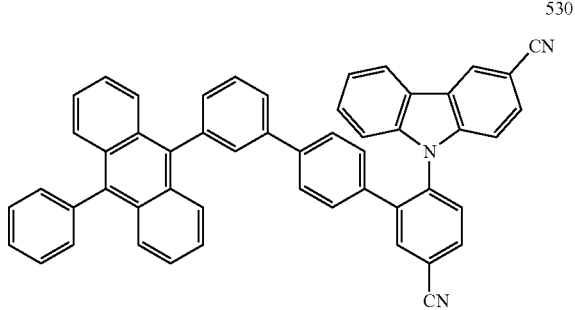

-continued
531
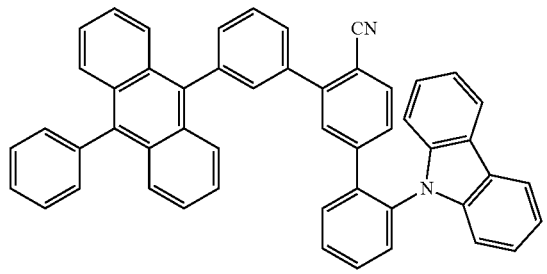
532
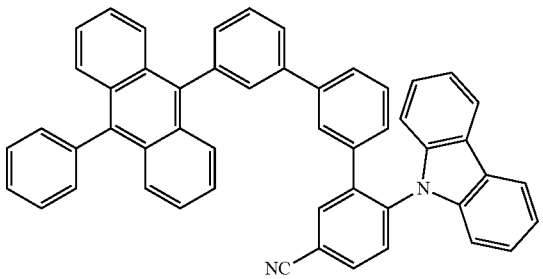
533
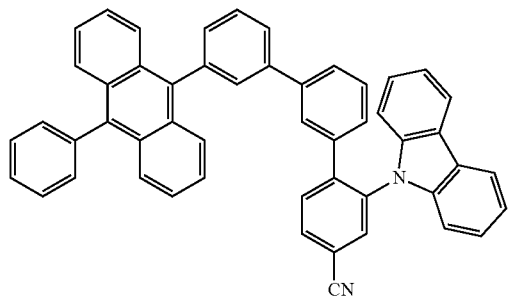
534
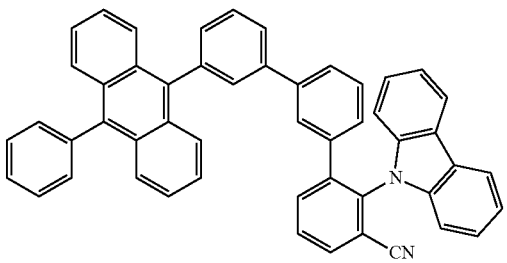
535
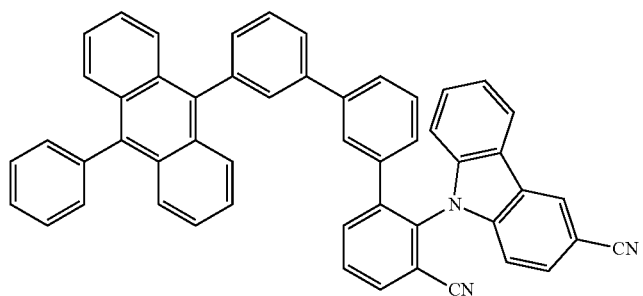
536
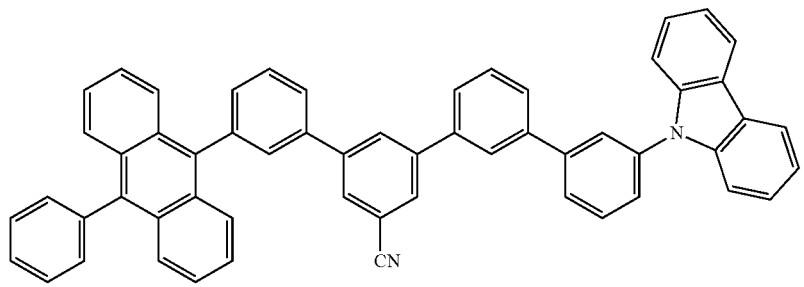
537
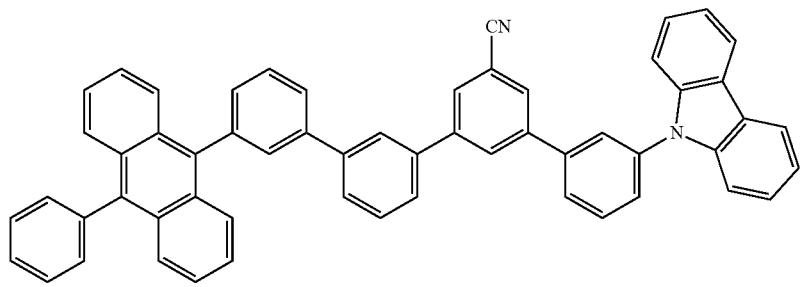

538
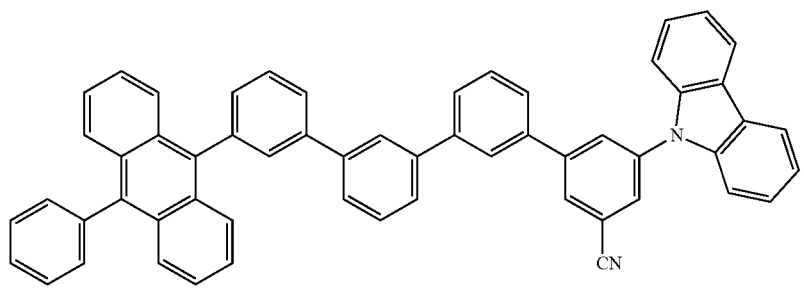
539
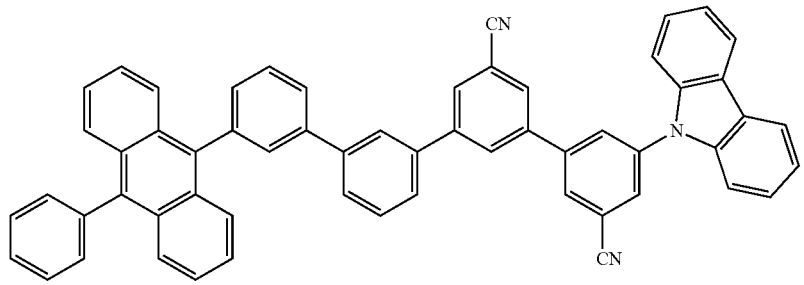
540
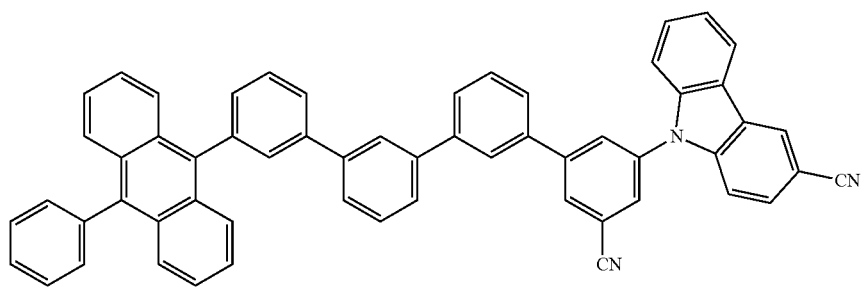
541
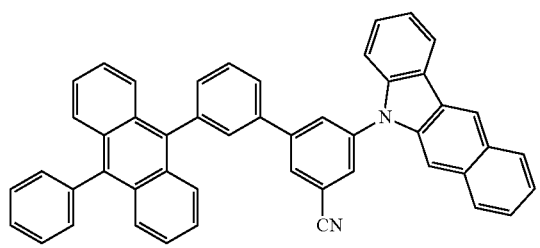
542
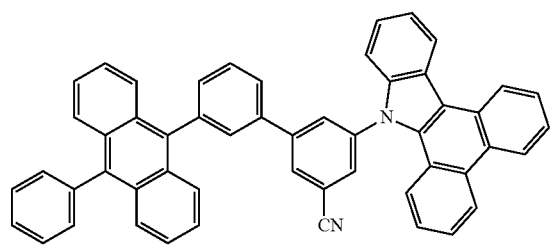
543
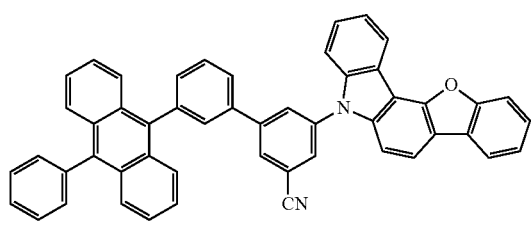
544
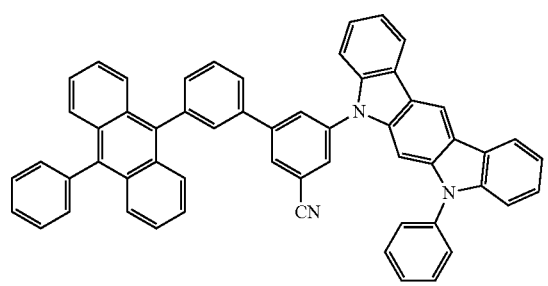

-continued
545
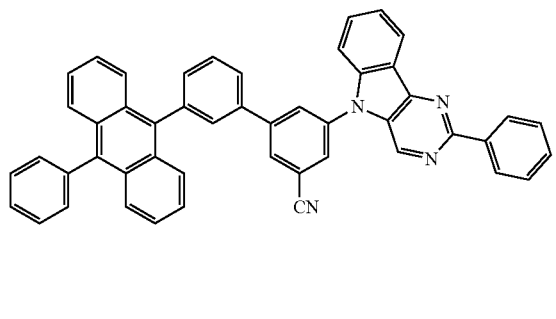
546
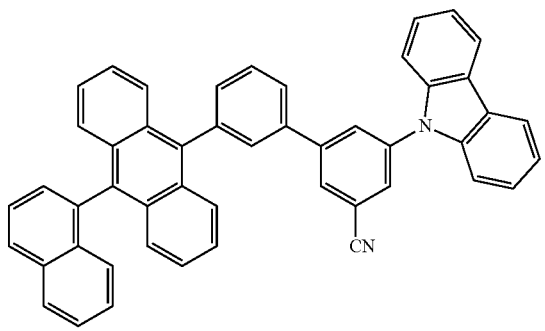
547
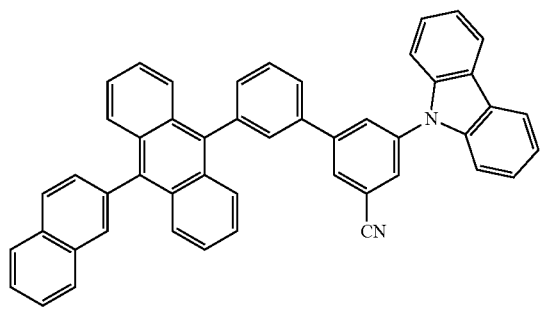
548
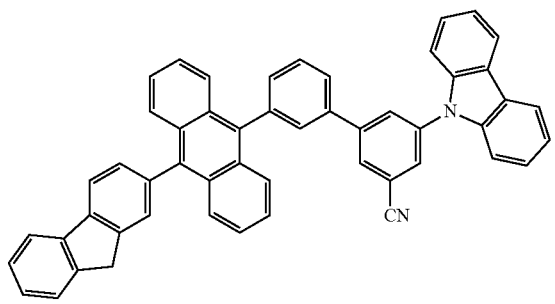
549
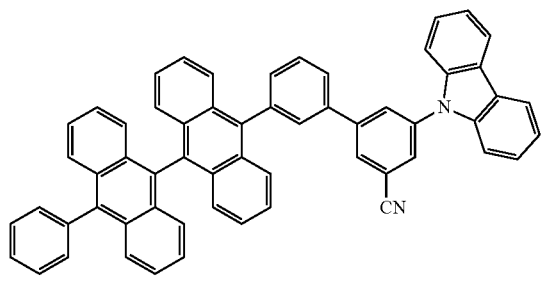
550
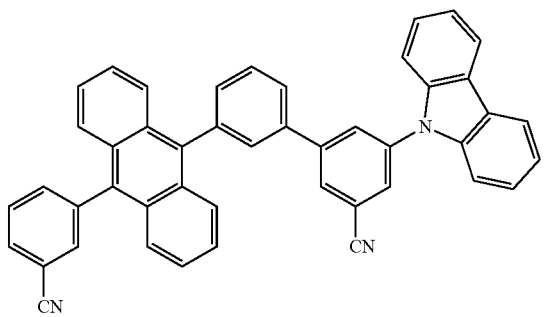
551
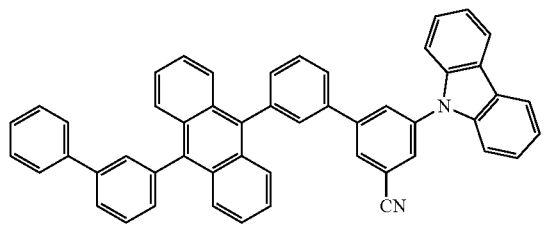
552
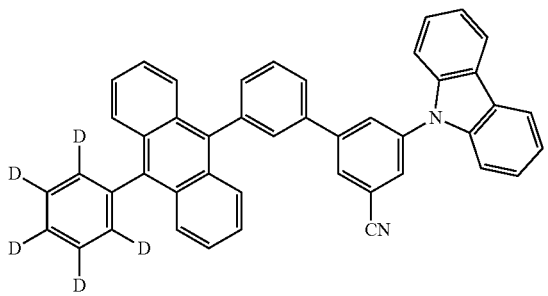

553
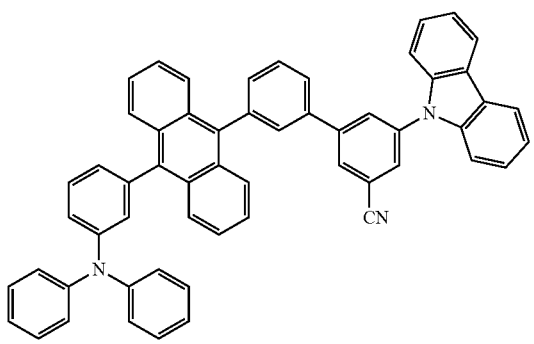

554
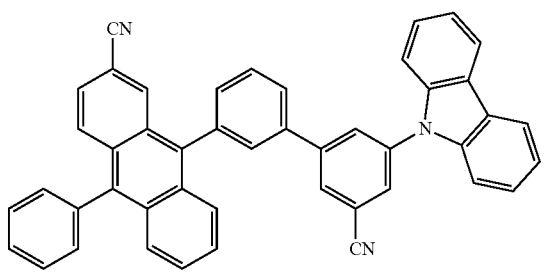

555
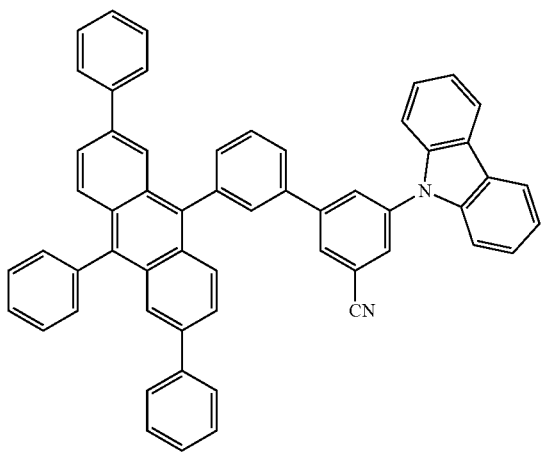

556
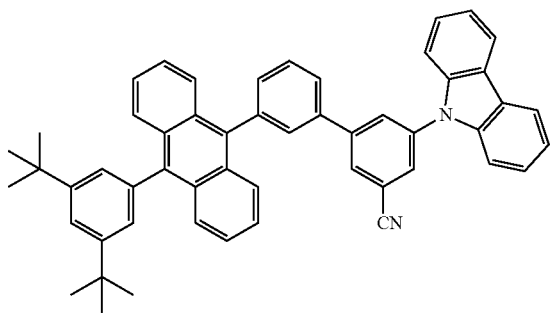

557
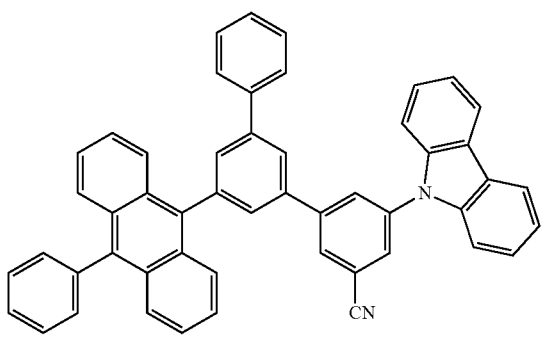

558
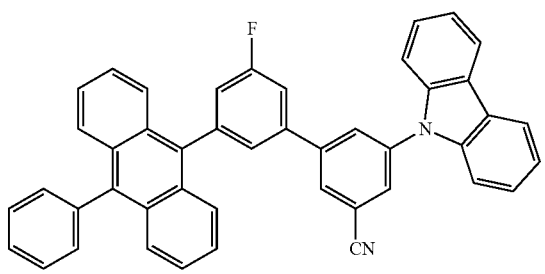

559
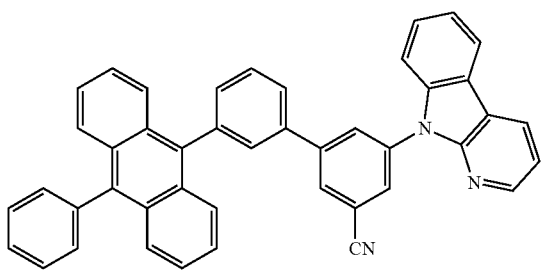

560
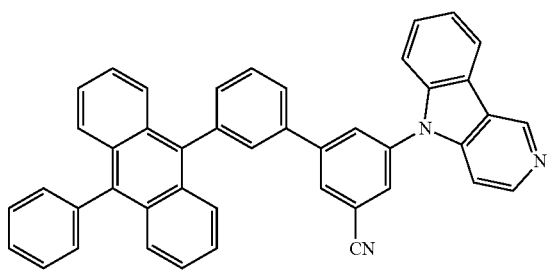

The heterocyclic compound represented by Formula 1 satisfies the structure of Formula 1, and has an asymmetric structure in which an anthracene group and an N-containing hetero-ring are linked via two or more phenylene linkers. In this regard, the heterocyclic compound represented by Formula 1 may have an effect of securing relatively excellent amorphous thin film characteristics.

In addition, the heterocyclic compound represented by Formula 1 has a structure in which the two or more phenylene group linkers are substituted with at least one cyano group, so that the charge mobility is increased and the efficiency and driving characteristics of an organic light-emitting device may be improved.

As described above, the heterocyclic compound represented by Formula 1 may have such electrical characteristics suitable for use as a material for an organic light-emitting device, for example, a host material in the emission layer, a hole transport material, an electron transport material, and the like. Accordingly, an organic light-emitting device using the heterocyclic compound may have high efficiency and/or a long lifespan.

In an embodiment, the heterocyclic compound represented by Formula 1 may satisfy Equation 1:

$$E(T1) < E(S1) < 2 \times E(T1) \quad \text{Equation 1}$$

wherein, in Equation 1,

E(T1) indicates a lowest excitation triplet energy level of the heterocyclic compound, and E(S1) indicates a lowest excitation singlet energy level of the heterocyclic compound.

In one or more embodiments, the heterocyclic compound represented by Formula 1 may satisfy Equation 2:

$$[2 \times E(T1)] - E(S1) < 1 \text{ electron volts} \quad \text{Equation 2}$$

wherein, in Condition 2,

E(T1) indicates a lowest excitation triplet energy level of the heterocyclic compound, and E(S1) indicates a lowest excitation singlet energy level of the heterocyclic compound.

Since the heterocyclic compound represented by Formula 1 satisfies Condition 1, Condition 2, or both Conditions 1 and 2, the triplet-triplet fusion (TTF) phenomenon in which triplet excitons are fused to generate singlet excitons may be highly likely to occur. The TTF phenomenon is a method of recycling the triplet excitons, which are lost through a non-luminescence transition path, as singlet excitons that are capable of emitting light. Accordingly, when the heterocyclic compound is applied to an organic light-emitting device, fluorescence emission may occur from singlet excitons generated by the TTF phenomenon, thereby improving the luminescence efficiency of the organic light-emitting device.

In an embodiment, the heterocyclic compound represented by Formula 1 may satisfy Equation 2-1:

$$[2 \times E(T1)] - E(S1) < 0.5 \text{ electron volts} \quad \text{Equation 2-1}$$

wherein, in Condition 2-1,

E(T1) indicates a lowest excitation triplet energy level of the heterocyclic compound, and E(S1) indicates a lowest excitation singlet energy level of the heterocyclic compound.

For example, a highest occupied molecular orbital (HOMO), a lowest unoccupied molecular orbital (LUMO), a triplet energy level (E(T1)), and a singlet energy level (E(S1)) of Compounds 1, 21, 66, 141, 144, 162, 166, 384, 428, and 430 were measured using the DFT method of the Gaussian program (B3LYP, structurally optimized at the level of 6-31G (d, p)). The evaluation results are shown in Table 1.

TABLE 1

| Compound No. | HOMO (eV) | LUMO (eV) | E(S1) (eV) | E(T1) (eV) | 2E(T1) − E(S1) (eV) |
|---|---|---|---|---|---|
| Compound 1 | −5.30 | −1.81 | 3.11 | 1.74 | 0.37 |
| Compound 21 | −5.38 | −1.89 | 3.02 | 1.73 | 0.44 |
| Compound 66 | −5.39 | −1.98 | 3.02 | 1.74 | 0.46 |
| Compound 141 | −5.39 | −1.89 | 3.02 | 1.74 | 0.46 |

TABLE 1-continued

| Compound No. | HOMO (eV) | LUMO (eV) | E(S1) (eV) | E(T1) (eV) | 2E(T1) − E(S1) (eV) |
|---|---|---|---|---|---|
| Compound 144 | −5.35 | −1.97 | 3.01 | 1.73 | 0.45 |
| Compound 162 | −5.37 | −1.88 | 3.16 | 1.74 | 0.32 |
| Compound 166 | −5.27 | −1.78 | 3.15 | 1.74 | 0.33 |
| Compound 186 | −5.36 | −1.94 | 3.02 | 1.74 | 0.46 |
| Compound 384 | −5.18 | −1.72 | 3.14 | 1.73 | 0.32 |
| Compound 428 | −5.30 | −2.01 | 3.01 | 1.73 | 0.45 |
| Compound 430 | −5.26 | −1.95 | 3.05 | 1.73 | 0.41 |

Referring to Table 1, it is confirmed that the heterocyclic compound represented by Formula 1 has electric characteristics suitable for use in an electronic device, for example, as a material for forming an emission layer of an organic light-emitting device.

A suitable synthesis method of the heterocyclic compound represented by Formula 1 may be recognized by those skilled in the art with reference to the following Synthesis Examples.

The heterocyclic compound represented by Formula 1 may be suitable for use in an organic layer, for example, in an emission layer, as a hole transport region material, and/or as an electron transport region material of an organic layer. Thus, according to one or more embodiments, an organic light-emitting device includes: a first electrode; a second electrode; and an organic layer located between the first electrode and the second electrode and including an emission layer, wherein the organic layer includes at least one of the heterocyclic compound represented by Formula 1.

The organic light-emitting device may have a low driving voltage, high efficiency, high luminance, high quantum emission efficiency, and long lifespan, due to the inclusion of an organic layer including the heterocyclic compound represented by Formula 1 as described above.

In an embodiment, in the organic light-emitting device, the first electrode may be an anode and the second electrode may be a cathode, the organic layer may include a hole transport region located between the first electrode and the emission layer and an electron transport region located between the emission layer and the second electrode, the hole transport region may include a hole injection layer, a hole transport layer, an electron blocking layer, or any combination thereof, and the electron transport region may include a hole blocking layer, an electron transport layer, an electron injection layer, or any combination thereof, but embodiments of the present disclosure are not limited thereto.

For example, the emission layer of the organic light-emitting device may include at least one of the heterocyclic compounds represented by Formula 1.

In an embodiment, the emission layer in the organic light-emitting device may include a host and a dopant, and the host may include at least one of the heterocyclic compound represented by Formula 1, and the dopant may include a phosphorescent dopant or a fluorescent dopant.

The host may further include another host, in addition to the heterocyclic compound represented by Formula 1, that is different from the heterocyclic compound represented by Formula 1.

The emission layer may emit red light, green light, or blue light.

In an embodiment, the emission layer may emit blue light. For example, the emission layer may emit blue light having a maximum luminescence wavelength of about 410 nm to about 490 nm.

In an embodiment, the emission layer may include a fluorescent dopant, but embodiments of the present disclosure are not limited thereto.

In an embodiment, the heterocyclic compound represented by Formula 1 may be included in the hole transport region of the organic light-emitting device.

For example, the hole transport region of the organic light-emitting device may include at least one of a hole injection layer, a hole transport layer and an electron blocking layer, and at least one of the hole injection layer, the hole transport layer, and the electron blocking layer may include the heterocyclic compound represented by Formula 1.

In one or more embodiments, the heterocyclic compound represented by Formula 1 may be included in the electron transport region of the organic light-emitting device.

For example, the electron transport region of the organic light-emitting device may include at least one of a hole blocking layer, an electron transport layer, and an electron injection layer, and at least one of the hole blocking layer, the electron transport layer, and the electron injection layer may include the heterocyclic compound represented by Formula 1.

In an embodiment, the hole transport region of the organic light-emitting device may include an electron blocking layer, and the heterocyclic compound represented by Formula 1 may be included in the electron blocking layer. The electron blocking layer may be in direct contact with the emission layer.

In an embodiment, the electron transport region of the organic light-emitting device may include a hole blocking layer, and the heterocyclic compound represented by Formula 1 may be included in the hole blocking layer. The hole blocking layer may be in direct contact with the emission layer.

In an embodiment, the organic layer of the organic light-emitting device may further include a fluorescent dopant in addition to the heterocyclic compound represented by Formula 1.

In an embodiment, the fluorescent dopant may be a condensation polycyclic compound or a styryl compound.

In one or more embodiments, the fluorescent dopant may include one of a naphthalene-containing core, a fluorene-containing core, a spiro-bifluorene-containing core, a benzofluorene-containing core, a dibenzofluorene-containing core, a phenanthrene-containing core, an anthracene-containing core, a fluoranthene-containing core, a triphenylene-containing core, a pyrene-containing core, a chrysene-containing core, a naphthacene-containing core, a picene-containing core, a perylene-containing core, a pentaphene-containing core, an indenoanthracene-containing core, a tetracene-containing core, a bisanthracene-containing core, or a core represented by one of Formulae 501-1 to 501-18, but embodiments of the present disclosure are not limited thereto:

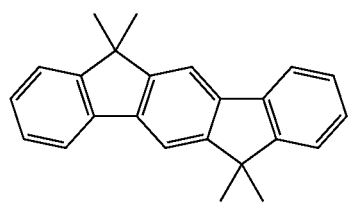

501-1

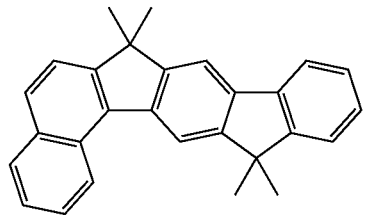

501-2

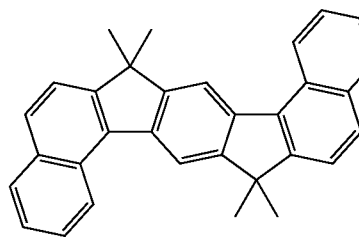

501-3

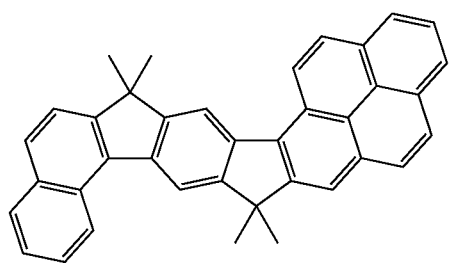

501-4

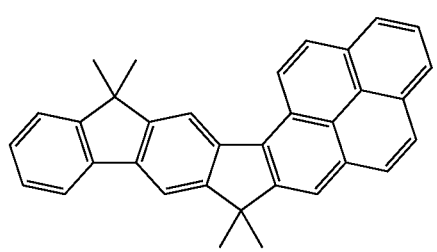

501-5

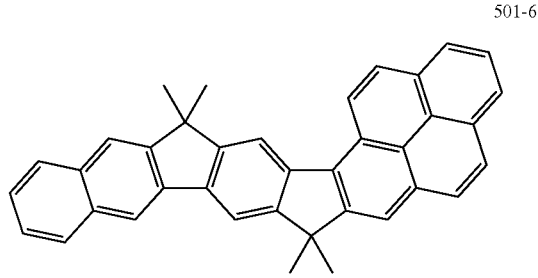

501-6

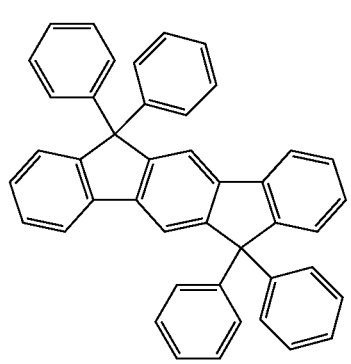

501-7

-continued
501-8
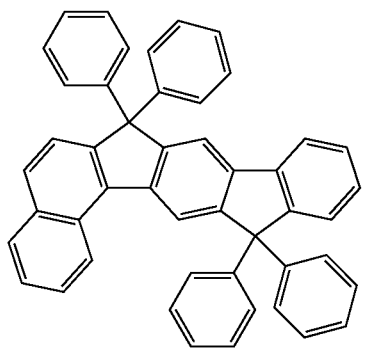
501-9
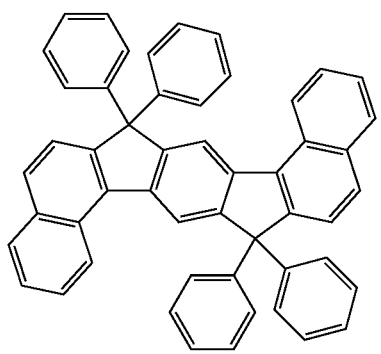
501-10
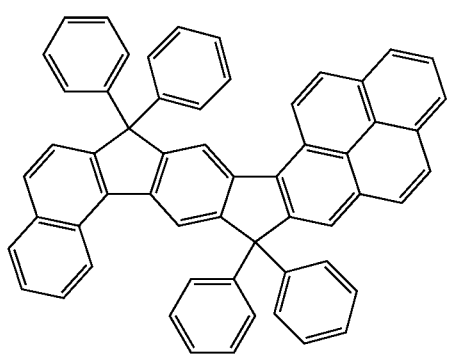
501-11
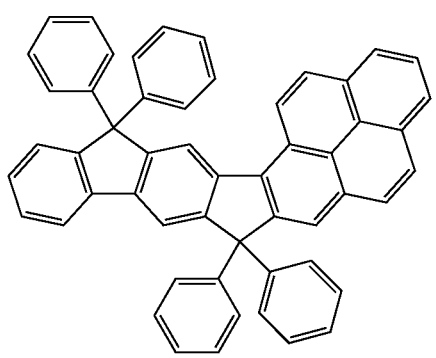
-continued
501-12
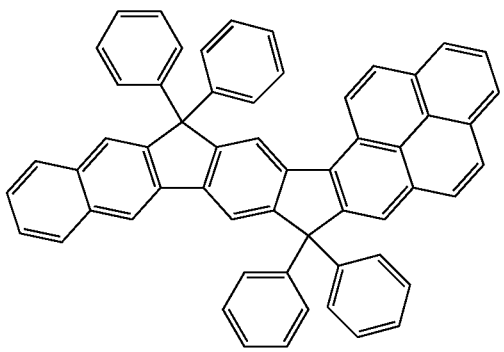
501-13
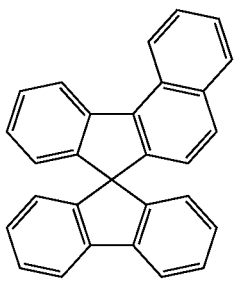
501-14
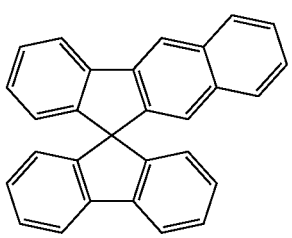
501-15
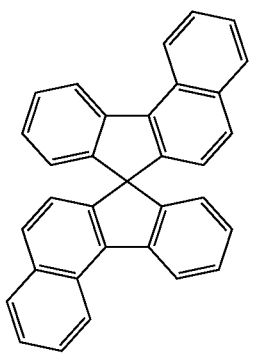
501-16
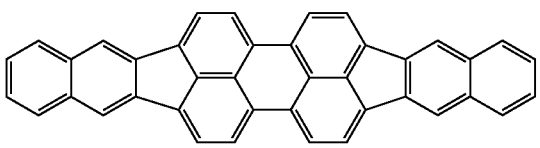
501-17
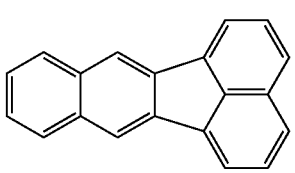

-continued 501-18

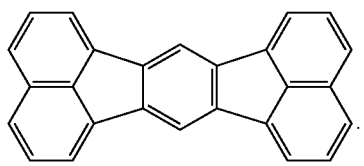

In one or more embodiments, the fluorescent dopant may be a styryl-amine-based compound or a styryl-carbazole-based compound, but embodiments of the present disclosure are not limited thereto.

In an embodiment, the fluorescent dopant may be a compound represented by Formula 501:

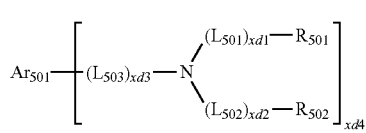

Formula 501 wherein, in Formula 501,
$Ar_{501}$ may be:
a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, or a group represented by one of Formulae 501-1 to 501-18; or
a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, or a group represented by one of Formulae 501-1 to 501-18, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_6$-$C_{60}$ heteroarylthio group, a monovalent non-aromatic condensed polycyclic group, a monovalent non-aromatic condensed heteropolycyclic group or —Si($Q_{501}$)($Q_{502}$) ($Q_{503}$),
wherein $Q_{501}$ to $Q_{503}$ may each independently be hydrogen, $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group, $L_{501}$ to $L_{503}$ may each independently be a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_6$-$C_{60}$ heteroarylene group, a substituted or unsubstituted divalent non-aromatic condensed polycyclic group, or a substituted or unsubstituted divalent non-aromatic condensed heteropolycyclic group,
$R_{501}$ to $R_{508}$ may each independently be:
a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, or a dibenzothiophenyl group; and
a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group, each substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group,
xd1 to xd3 may each independently be 0, 1, 2, or 3, and xd4 may be 0, 1, 2, 3, 4, 5, or 6.
For example, in Formula 501,
$Ar_{501}$ may be:
a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, or a group represented by one Formulae 501-1 to 501-18; or
a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, or a group represented by one of Formula 501-1 to 501-18, each substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a dibenzofuranyl group, a dibenzothiophenyl group, a carbazolyl group, a pyridinyl group, a pyrimidinyl group, a triazinyl group, a quinolinyl group, an isoquinolinyl group, or —Si($Q_{501}$)($Q_{502}$)($Q_{503}$), wherein $Q_{501}$ to $Q_{503}$ may each independently be hydrogen, a $C_1$-$C_{20}$ alkyl group, a $C_1$-$C_{20}$ alkoxy group, a phenyl group, a biphenyl group, a terphenyl group, or a naphthyl group, $L_{501}$ to $L_{503}$ may each be the same as described in connection with $L_{21}$, xd1 to xd3 may each independently be 0, 1, or 2, and xd4 may be 0, 1, 2, or 3, but embodiments of the present disclosure are not limited thereto.

In one or more embodiments, the fluorescent dopant may include a compound represented by one of Formulae 502-1 to 502-5:

$L_{501}$ to $L_{508}$ may each be the same as described in connection with $L_{501}$ in Formula 501, xd1 to xd8 may each be the same as described in connection with xd1 in Formula 501, $R_{501}$ to $R_{508}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, or a $C_1$-$C_{20}$ alkoxy group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, or a dibenzothiophenyl group; or a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a Formula 502-1

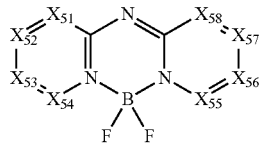

Formula 502-2

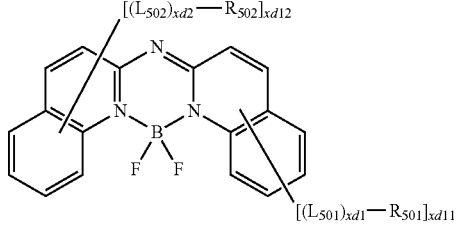

Formula 502-3

Formula 502-4

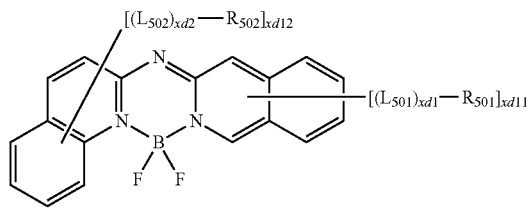

Formula 502-5

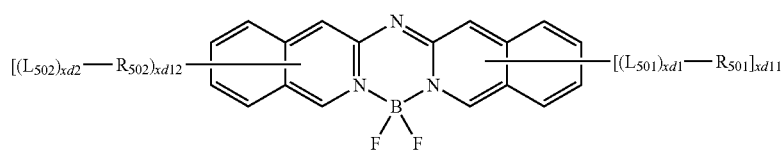

wherein, in Formulae 502-1 to 502-5, $X_{51}$ may be N or C-[($L_{501}$)$_{xd1}$-$R_{501}$], $X_{52}$ may be N or C-[($L_{502}$)$_{xd2}$-$R_{502}$], $X_{53}$ may be N or C-[($L_{503}$)$_{xd3}$-$R_{503}$], $X_{54}$ may be N or C-[($L_{504}$)$_{xd4}$-$R_{504}$], $X_{55}$ may be N or C-[($L_{505}$)$_{xd5}$-$R_{505}$], $X_{56}$ may be N or C-[($L_{506}$)$_{xd6}$-$R_{506}$], $X_{57}$ may be N or C-[($L_{507}$)$_{xd7}$-$R_{507}$], and $X_{58}$ may be N or C-[($L_{508}$)$_{xd8}$-$R_{508}$], quinoxalinyl group, a quinazolinyl group, a carbazolyl group, a triazinyl group, a dibenzofuranyl group, or a dibenzothiophenyl group, each substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, a C$_1$-C$_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group, xd11 and xd12 may each independently be an integer from 0 to 5, two of R$_{501}$ to R$_{504}$ may optionally be linked to each other to form a saturated or unsaturated ring, and two of R$_{505}$ to R$_{508}$ may optionally be linked to each other to form a saturated or unsaturated ring.

The fluorescent dopant may include, for example, at least one of Compounds FD(1) to FD(16) and FD1 to FD14:

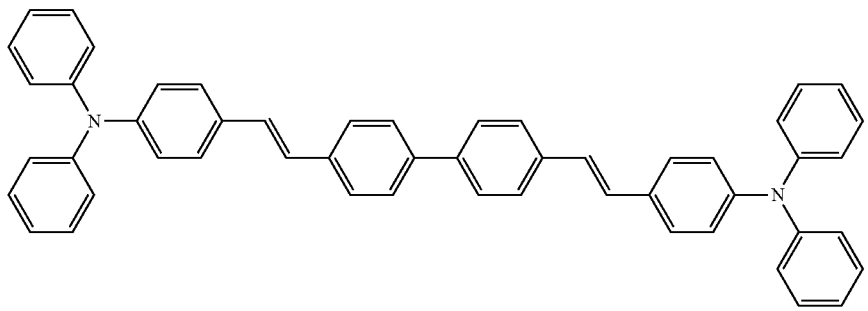

FD(1)

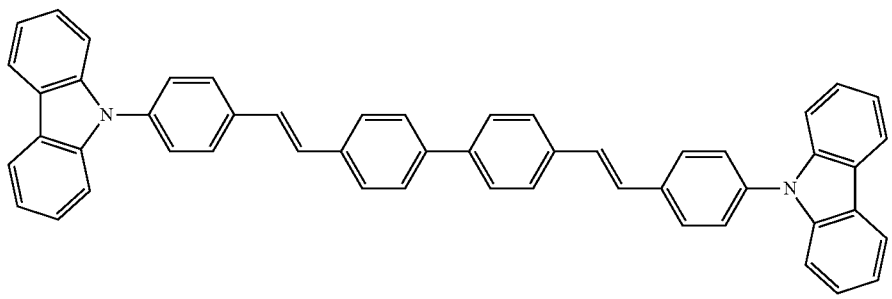

FD(2)

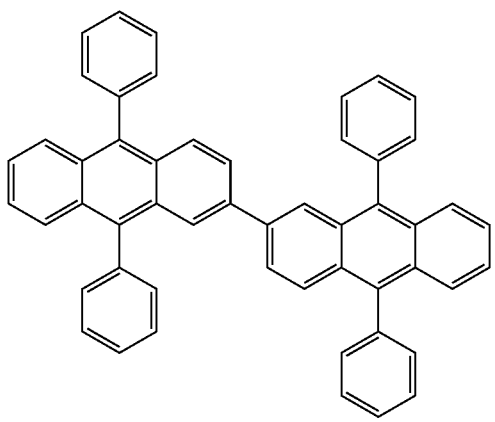

FD(3)

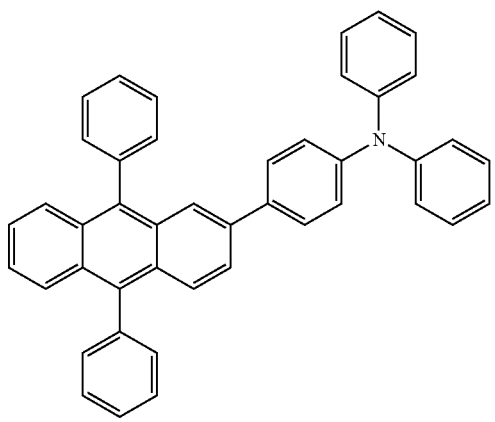

FD(4)

-continued
FD(5)
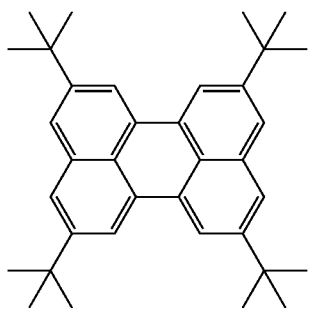
FD(6)
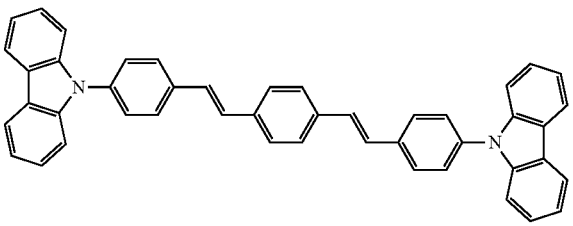
FD(7)
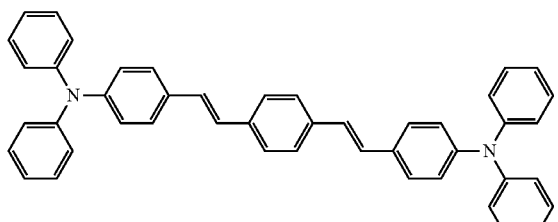
FD(8)
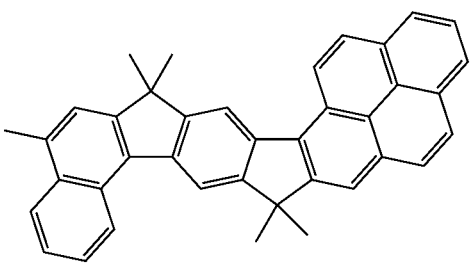
FD(9)
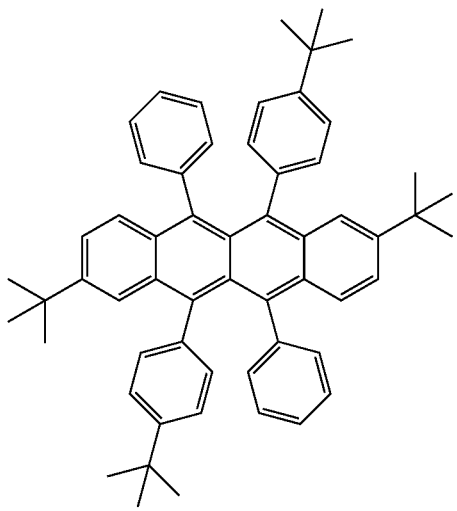
FD(10)
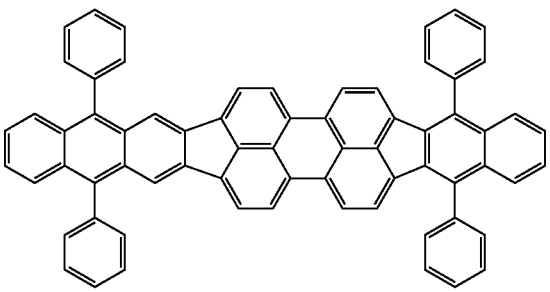
FD(11)
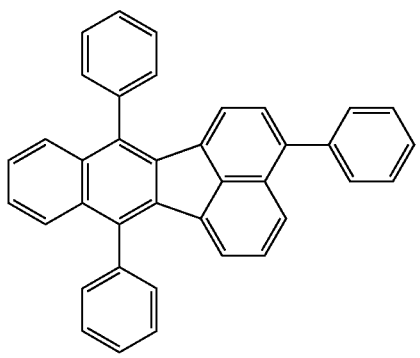
FD(12)
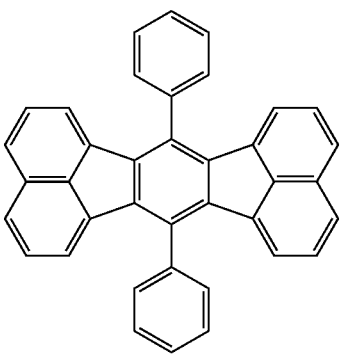

-continued
FD(13)
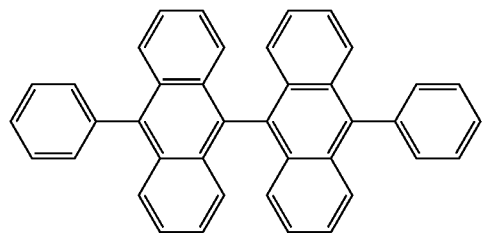
FD(14)
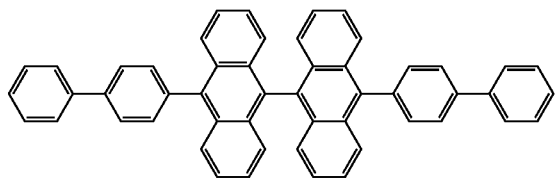
FD(15)
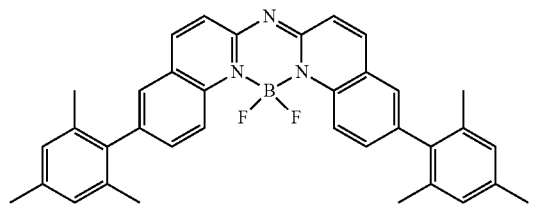
FD(16)
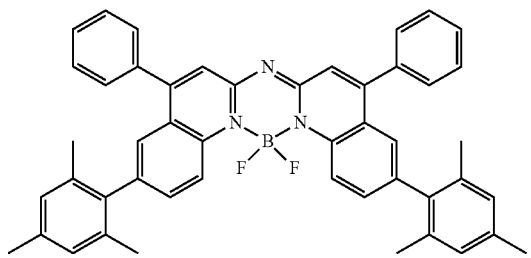
FD1
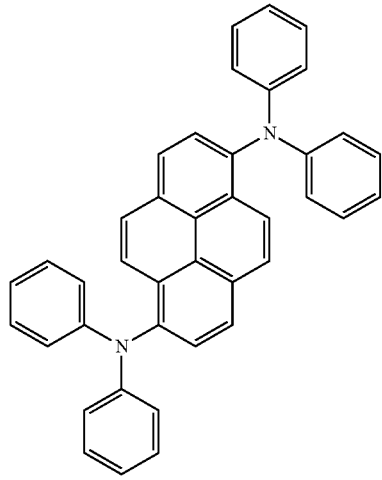
FD2
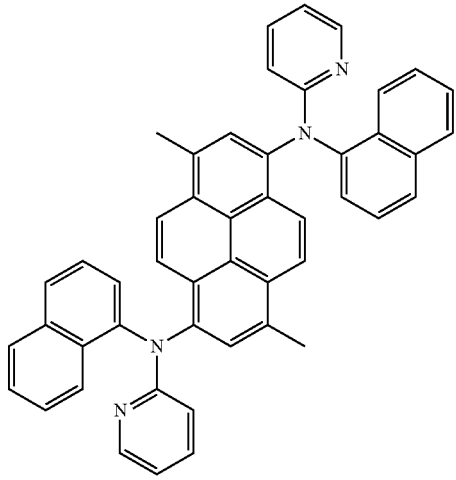
FD3
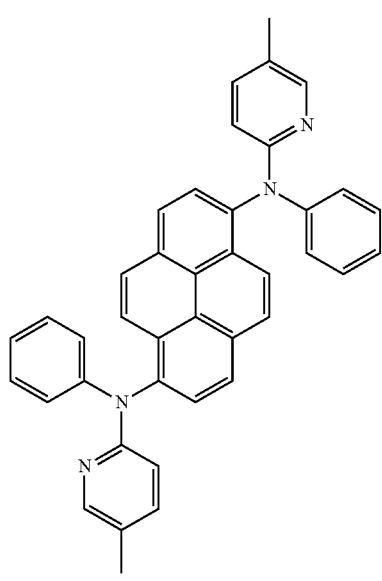
FD4
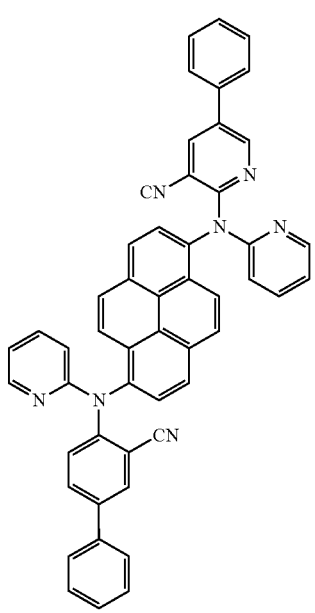

-continued
FD5
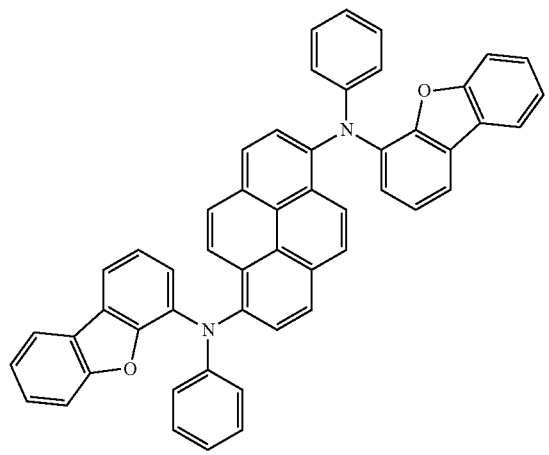
FD6
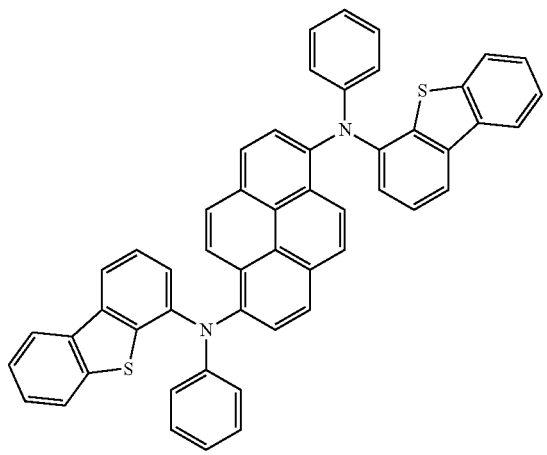
FD7
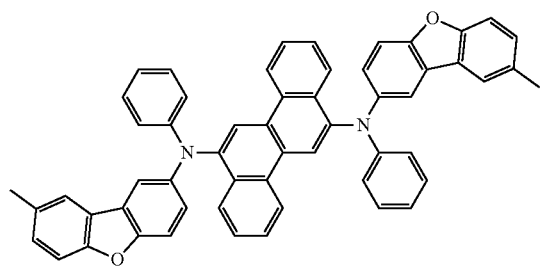
FD8
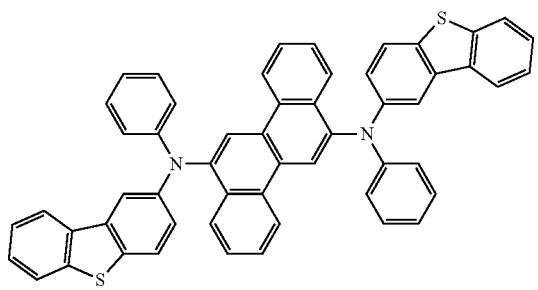
FD9
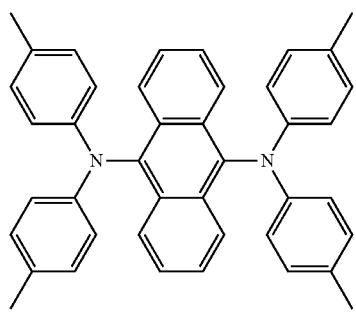
FD10
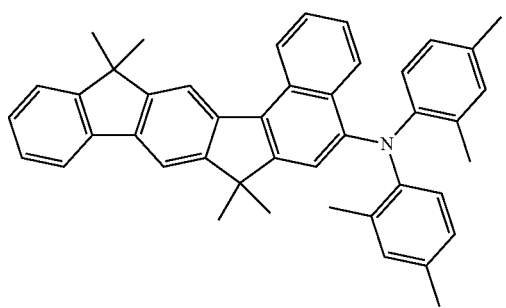
FD11
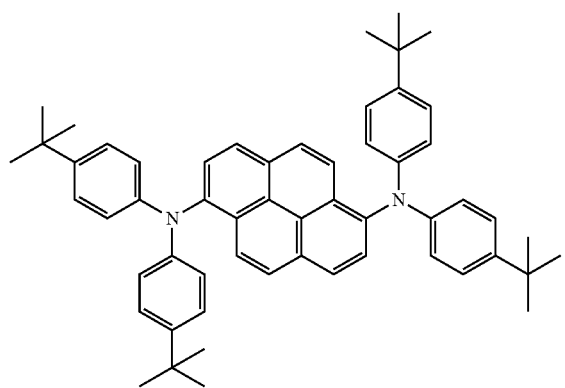
FD12
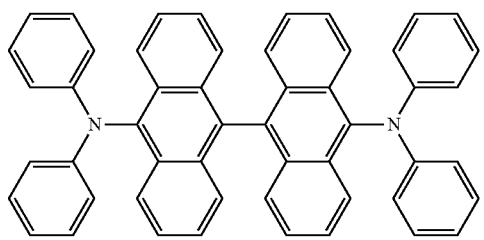

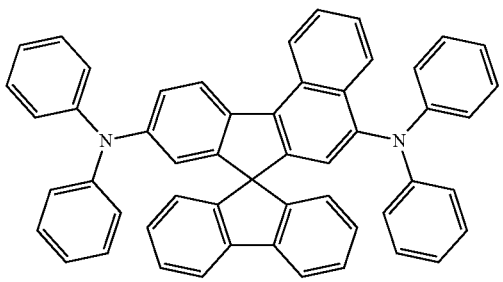

FD13

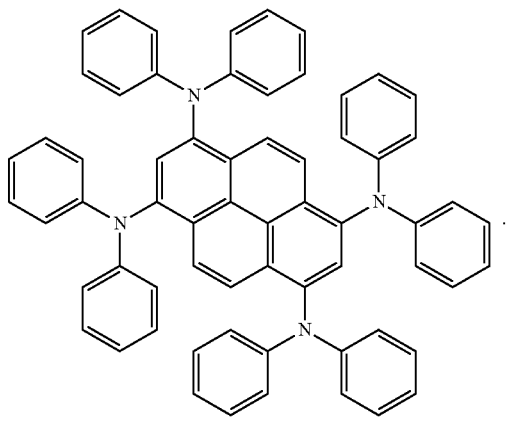

FD14

In one or more embodiments, the organic layer of the organic light-emitting device may further include a phosphorescent dopant in addition to the heterocyclic compound represented by Formula 1.

For example, the phosphorescent dopant may further include an organometallic compound represented by Formula 81:

$$M(L_{81})_{n81}(L_{82})_{n82}$$ Formula 81

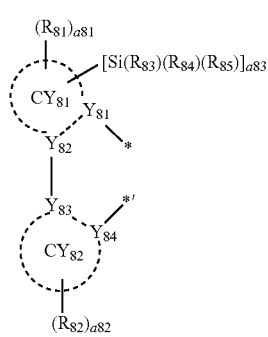

Formula 81A wherein, in Formulae 81 and 81A,
M may be iridium (Ir), platinum (Pt), osmium (Os), titanium (Ti), zirconium (Zr), hafnium (Hf), europium (Eu), terbium (Tb), thulium (Tm), or rhodium (Rh),
$L_{81}$ may be a ligand represented by Formula 81A, and n81 may be an integer from 1 to 3, wherein, when n81 is 2 or more, two or more $L_{81}$(s) may be identical to or different from each other,
$L_{82}$ may be an organic ligand, and n82 may be an integer from 0 to 4, wherein, when n82 is 2 or more, two or more $L_{82}$(s) may be identical to or different from each other,
$Y_{81}$ to $Y_{84}$ may each independently be carbon (C) or nitrogen (N),
$Y_{81}$ and $Y_{82}$ may be linked to each other via a single bond or a double bond, and $Y_{83}$ and $Y_{84}$ may be linked to each other via a single bond or a double bond,
$CY_{81}$ and $CY_{82}$ may each independently be a $C_5$-$C_{30}$ carbocyclic group or a $C_2$-$C_{30}$ heterocarbocyclic group,
$CY_{81}$ and $CY_{82}$ optionally may be linked to each other via an organic linking group, $R_{81}$ to $R_{85}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ heteroaryl group, a substituted or unsubstituted $C_6$-$C_{60}$ heteroaryloxy group, a substituted or unsubstituted $C_6$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_{81}$)($Q_{82}$)($Q_{83}$), —N($Q_{84}$)($Q_{85}$), —B($Q_{86}$)($Q_{87}$), or —P(=O)($Q_{88}$)($Q_{89}$),
a81 to a83 may each independently be an integer from 0 to 5,
wherein, when a81 is 2 or more, two or more $R_{81}$(s) may be identical to or different from each other,
wherein, when a82 is 2 or more, two or more $R_{82}$(s) may be identical to or different from each other,
when a81 is 2 or more, two neighboring $R_{81}$(s) may optionally be linked to each other form a saturated or unsaturated $C_2$-$C_{30}$ ring such as a benzene ring, a cyclopentane ring, a cyclohexane ring, a cyclopentene ring, a cyclohexene ring, a norbornane ring, a bicyclo[2.2.1]heptane ring, a naphthalene ring, a benzoindene ring, a benzoindole ring, a benzofuran ring, a benzothiophene ring, a pyridine ring, a pyrimidine ring, or a pyrazine ring; or a saturated or unsaturated $C_2$-$C_{30}$ ring substituted with at least one $R_{88}$ (for example, a benzene ring, cyclopentane ring, a cyclohexane ring, cyclopentene ring, a cyclohexene ring, norbornane ring, a bicyclo[2.2.1]heptane ring, a naphthalene ring, benzoindene ring, benzoindole ring, a benzofuran ring, a benzothiophene ring, a pyridine ring, a pyrimidine ring, or a pyrazine ring, each substituted with at least one $R_{88}$), when a82 is 2 or more, two neighboring $R_{82}$(s) may optionally be linked to each other to form a saturated or unsaturated $C_2$-$C_{30}$ ring (for example, a benzene ring, a cyclopentane ring, a cyclohexane ring, a cyclopentene ring, a cyclohexene ring, a norbornane ring, a bicyclo[2.2.1]heptane ring, a naphthalene ring, a benzoindene ring, a benzoindole ring, a benzofuran ring, a benzothiophene ring, a pyridine ring, a pyrimidine ring, or a pyrazine ring) or a saturated or unsaturated $C_2$-$C_{30}$ ring substituted with at least one $R_{89}$ (for example, a benzene ring, cyclopentane ring, a cyclohexane ring, cyclopentene ring, a cyclohexene ring, norbornane ring, a bicyclo[2.2.1]heptane ring, a naphthalene ring, benzoindene ring, benzoindole ring, a benzofuran ring, a benzothiophene ring, a pyridine ring, a pyrimidine ring, or a pyrazine ring, each substituted with at least one $R_{89}$), $R_{88}$ may be the same as described in connection with $R_{81}$,
$R_{89}$ may be the same as described in connection with $R_{82}$,
and *' in Formula 81A each indicate a binding site to M
in Formula 81, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroaryloxy group, the substituted $C_1$-$C_{60}$ heteroarylthio group, the substituted monovalent non-aromatic condensed polycyclic group, and the substituted monovalent non-aromatic condensed heteropolycyclic group may be deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_6$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, or —Si($Q_{91}$)($Q_{92}$)($Q_{93}$), and $Q_{81}$ to $Q_{89}$ and $Q_{91}$ to $Q_{93}$ may each independently be hydrogen, deuterium, a $C_1$-$C_{60}$ alkyl group, a $C_6$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

In an embodiment, in Formula 81A,
a83 may be 1 or 2,
$R_{83}$ to $R_{85}$ may each independently be:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CH_3$, —$CD_2CD_3$, —$CD_2CD_2H$, or —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group, each substituted with at least one of deuterium, a $C_1$-$C_{10}$ alkyl group, or a phenyl group, but embodiments of the present disclosure are not limited thereto.

In one or more embodiments, in Formula 81A,
$Y_{81}$ may be nitrogen, $Y_{82}$ and $Y_{83}$ may each be carbon, $Y_{84}$ may be nitrogen or carbon, and $CY_{81}$ and $CY_{82}$ may each independently be a cyclopentadiene group, a benzene group, a heptalene group, an indene group, a naphthalene group, an azulene group, a heptalene group, an indacene group, acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coronene group, an ovalene group, a pyrrole group, an isoindole group, an indole group, an indazole group, a pyrazole group, an imidazole group, a triazole group, an oxazole group, an isoxazole group, an oxadiazole group, a thiazole group, an isothiazole group, a thiadiazole group, a purine group, a furan group, a thiophene group, a pyridine group, a pyrimidine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, a benzofuran group, a benzothiophene group, an isobenzothiazole group, a benzoxazole group, an isobenzoxazole group, a benzocarbazole group, a dibenzocarbazole group, an imidazopyridine group, an imidazopyrimidine group, a dibenzofuran group, a dibenzothiophene group, a dibenzothiophene sulfone group, a carbazole group, a dibenzosilole group, or a 2,3-dihydro-1H-imidazole group.

In one or more embodiments, in Formula 81A, $Y_{81}$ may be nitrogen, $Y_{82}$ to $Y_{84}$ may each be carbon, $CY_{81}$ may be a 5-membered ring in which two nitrogen atoms are ring-forming atoms, and $CY_{82}$ may be a benzene group, a naphthalene group, a fluorene group, a dibenzofuran group, or a dibenzothiophene group, but embodiments of the present disclosure are not limited thereto.

In one or more embodiments, in Formula 81A, $Y_{81}$ may be nitrogen, $Y_{82}$ to $Y_{84}$ may each be carbon, $CY_{81}$ may be an imidazole group or a 2,3-dihydro-1H-imidazole group, and $CY_{82}$ may be a benzene group, a naphthalene group, a fluorene group, a dibenzofuran group, or a dibenzothiophene group, but embodiments of the present disclosure are not limited thereto.

In one or more embodiments, in Formula 81A,
$Y_{81}$ may be nitrogen and $Y_{82}$ to $Y_{84}$ may each be carbon, CY₈₁ may be a pyrrole group, a pyrazole group, an imidazole group, a triazole group, an oxazole group, an isoxazole group, an oxadiazole group, a thiazole group, an isothiazole group, a thiadiazole group, a pyridine group, a pyrimidine group, a quinoline group, an isoquinoline group, a benzoquinoline group, a phthalazine group, a naphthyridine group, a quinoxaline group, a quinazoline group, a cinnoline group, a benzimidazole group, an isobenzothiazole group, a benzoxazole group, or an isobenzoxazole group, and CY₈₂ may be a cyclopentadiene group, a benzene group, a naphthalene group, a fluorene group, a benzofluorene group, a dibenzofluorene group, a phenanthrene group, an anthracene group, a triphenylene group, a pyrene group, a chrysene group, a perylene group, a benzofuran group, a benzothiophene group, a benzocarbazole group, a dibenzocarbazole group, a dibenzofuran group, a dibenzothiophene group, a dibenzothiophene sulfone group, a carbazole group, or a dibenzosilole group.

In one or more embodiments, in Formula 81A $R_{81}$ and $R_{82}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF₅, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one of deuterium, —F, —Cl, —Br, —I, —CD₃, —CD₂H, —CDH₂, —CF₃, —CF₂H, —CFH₂, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, or a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one of deuterium, —F, —Cl, —Br, —I, —CD₃, —CD₂H, —CDH₂, —CF₃, —CF₂H, —CFH₂, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group; or —B($Q_{86}$)($Q_{87}$) and —P(=O)($Q_{88}$)($Q_{89}$), Wherein $Q_{86}$ to $Q_{89}$ may each independently be:
—CH₃, —CD₃, —CD₂H, —CDH₂, —CH₂CHS, —CH₂CD₃, —CH₂CD₂H, —CH₂CDH₂, —CHDCH₃, —CHDCD₂H, —CHDCDH₂, —CHDCD₃, —CD₂CH₃, —CD₂CD₃, —CD₂CD₂H, or —CD₂CDH₂;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group, each substituted with at least one of deuterium, a $C_1$ to $C_{10}$ alkyl group, or a phenyl group.

In one or more embodiments, in Formula 81A, at least one selected from $R_{81}$(s) in the number of a81 and $R_{82}$(s) in the number of a82 may be a cyano group.

In one or more embodiments, in Formula 81A, at least one group $R_{82}$ in the number of a82 may be a cyano group.

In one or more embodiments, in Formula 81A, at least one group $R_{81}$ in the number of a81 and at least one group $R_{82}$ in the number of a82 may be deuterium.

In one or more embodiments, $L_{82}$ in Formula 81 may be a ligand represented by one of Formulae 3-1(1) to 3-1(60), 3-1(61) to 3-1(69), 3-1(71) to 3-1(79), 3-1(81) to 3-1 (88), 3-1 (91) to 3-1 (98), or 3-1 (101) to 3-1 (114):

3-1(1)

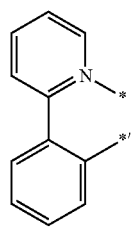

3-1(2)

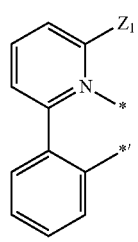

3-1(3)

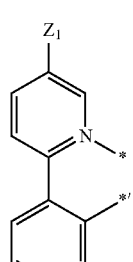

3-1(4)

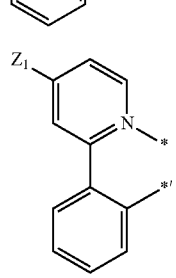

3-1(5)

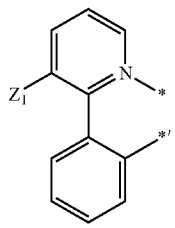

3-1(6)

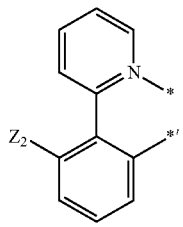

3-1(7)

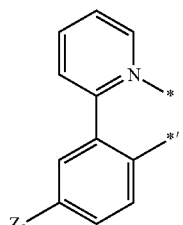

3-1(8)

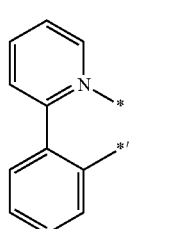

3-1(9)

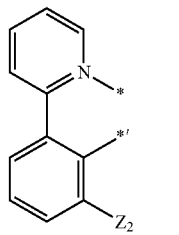

3-1(10)

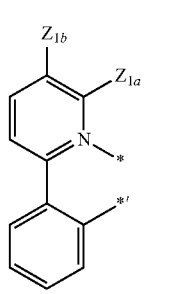

3-1(11)
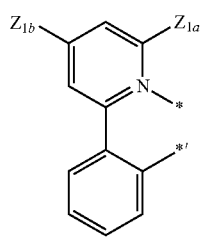
3-1(17)
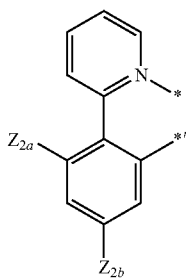
3-1(12)
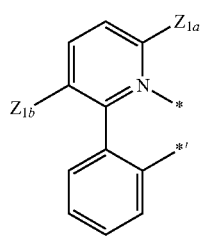
3-1(18)
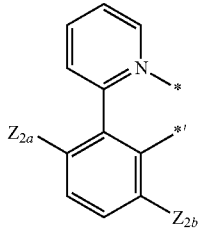
3-1(13)
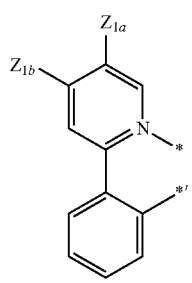
3-1(19)
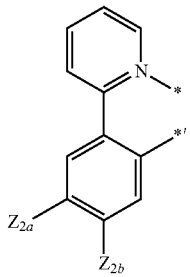
3-1(14)
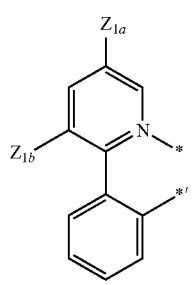
3-1(20)
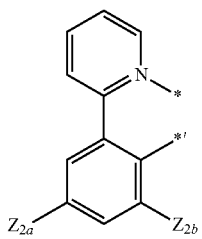
3-1(15)
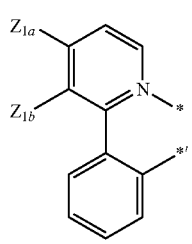
3-1(21)
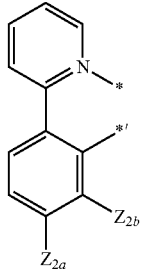
3-1(16)
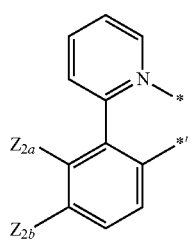
3-1(22)
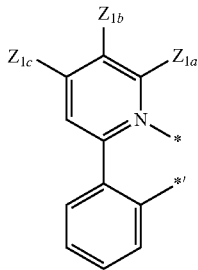

3-1(23)
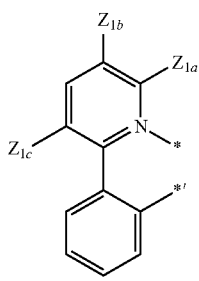
3-1(24)
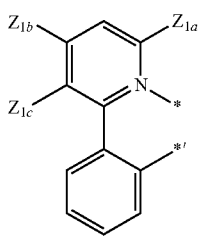
3-1(25)
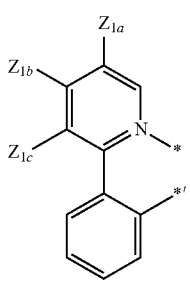
3-1(26)
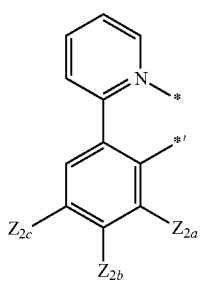
3-1(27)
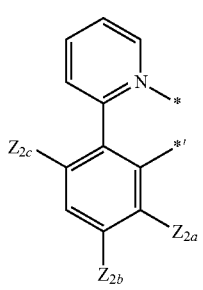
3-1(28)
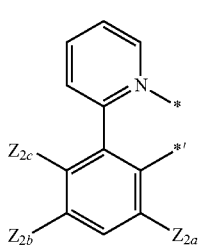
3-1(29)
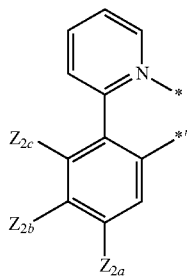
3-1(30)
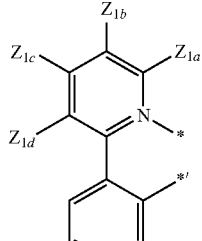
3-1(31)
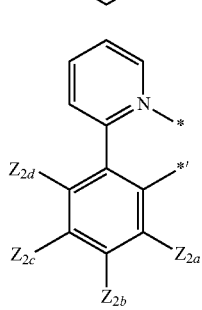
3-1(32)
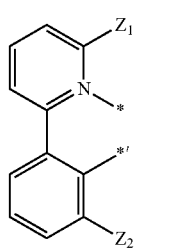
3-1(33)
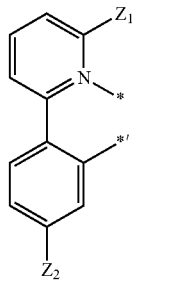
3-1(34)
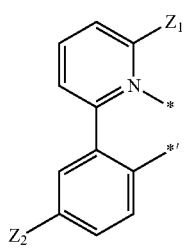

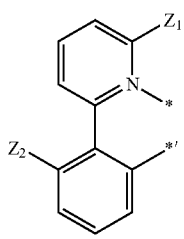 3-1(35)
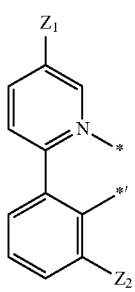 3-1(36)
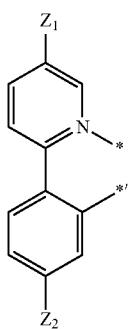 3-1(37)
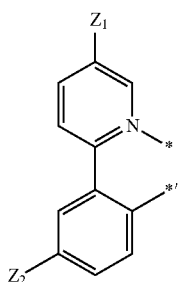 3-1(38)
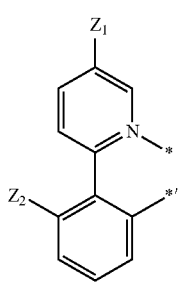 3-1(39)
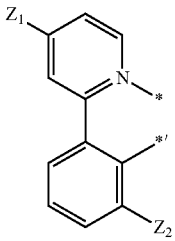 3-1(40)
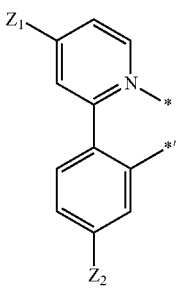 3-1(41)
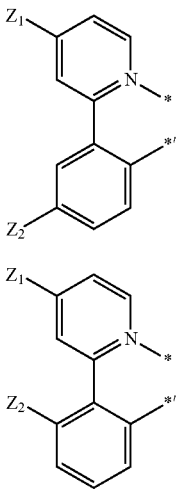 3-1(42)
3-1(43)
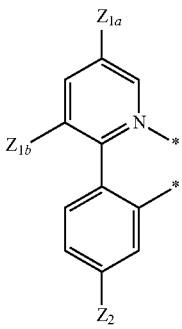 3-1(44)
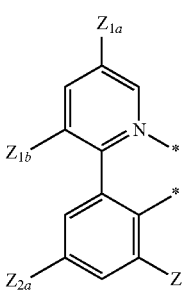 3-1(45)

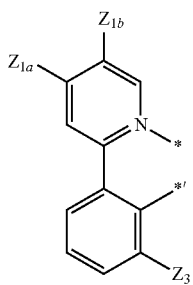
3-1(46)
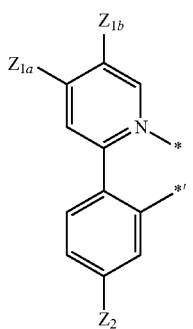
3-1(47)
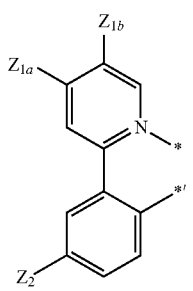
3-1(48)
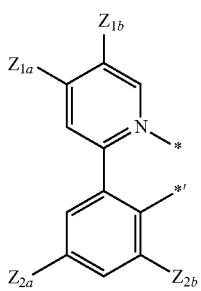
3-1(49)
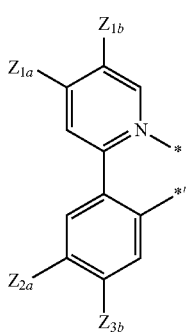
3-1(50)
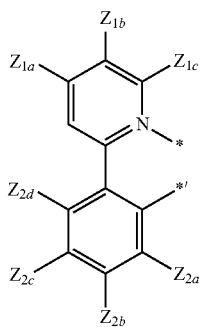
3-1(51)
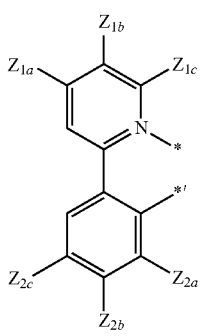
3-1(52)
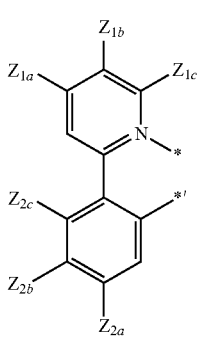
3-1(53)
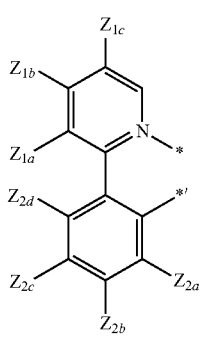
3-1(54)
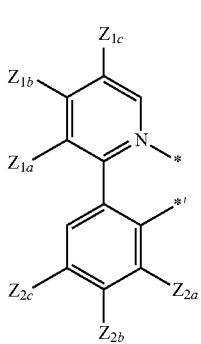
3-1(55)

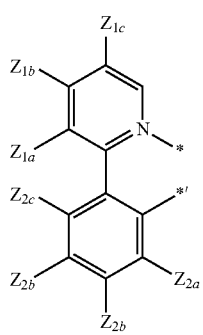 3-1(56)
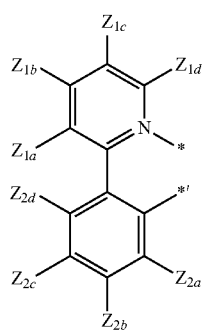 3-1(57)
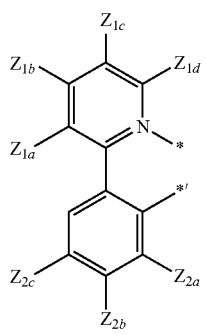 3-1(58)
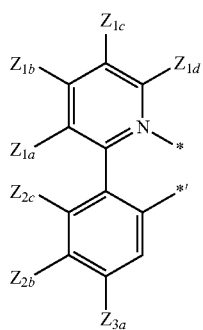 3-1(59)
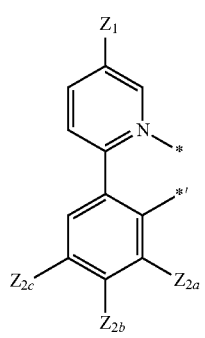 3-1(60)
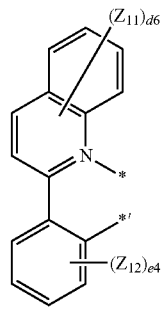 3-1(61)
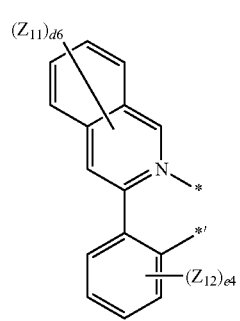 3-1(62)
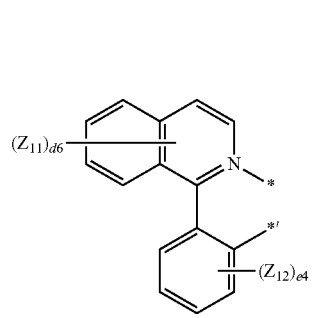 3-1(63)
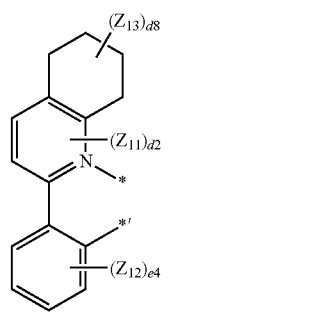 3-1(64)
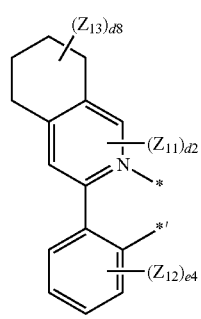 3-1(65)

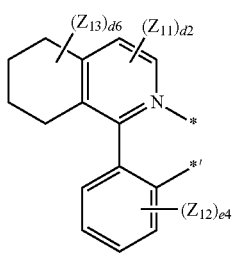
3-1(66)
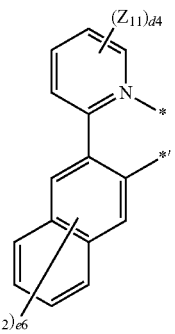
3-1(72)
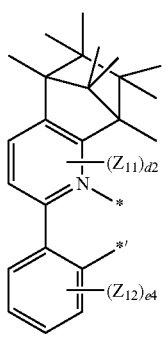
3-1(67)
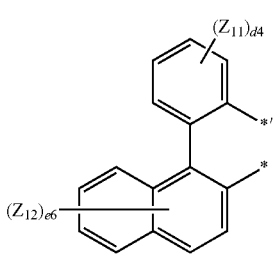
3-1(73)
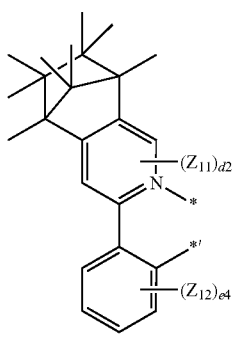
3-1(68)
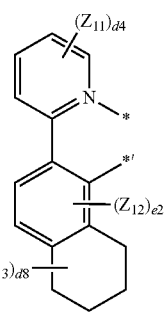
3-1(74)
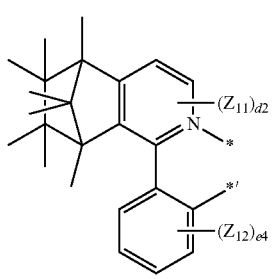
3-1(69)
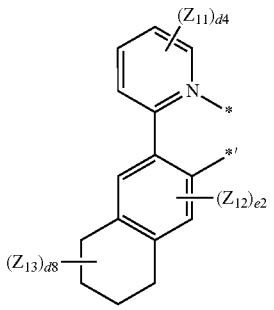
3-1(75)
3-1(71)
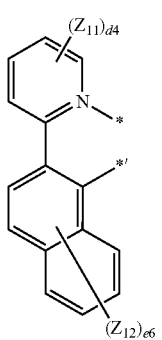
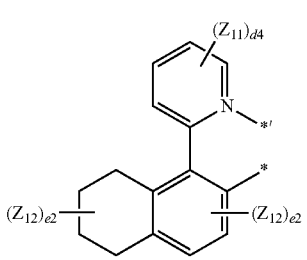
3-1(76)

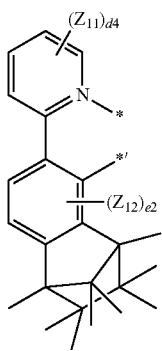 3-1(77)
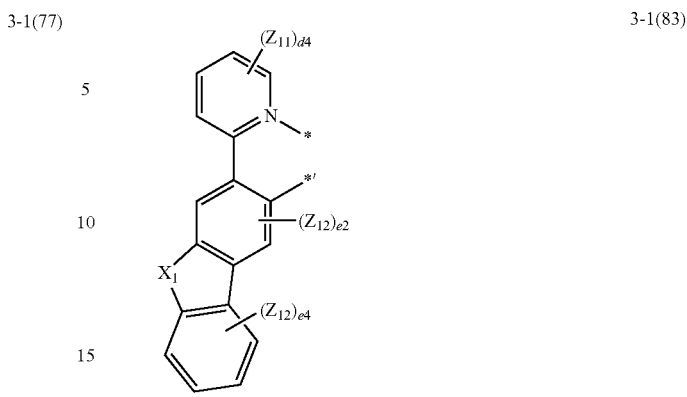 3-1(83)
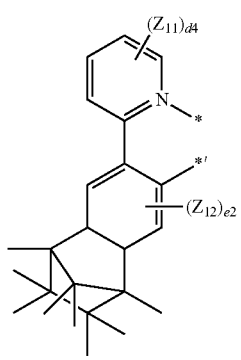 3-1(78)
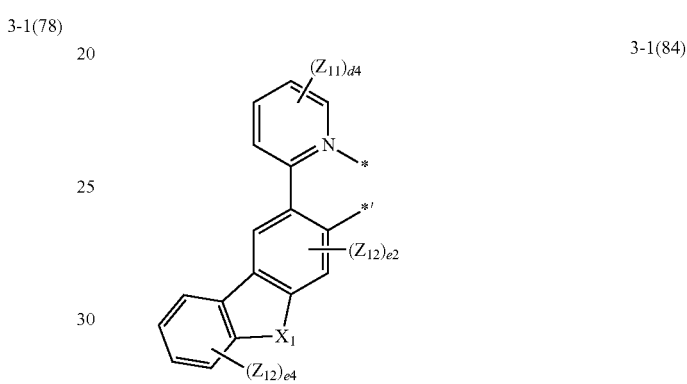 3-1(84)
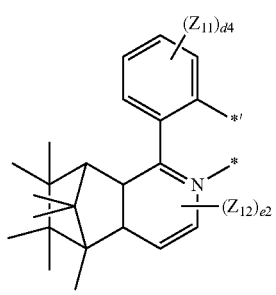 3-1(79)
3-1(81)
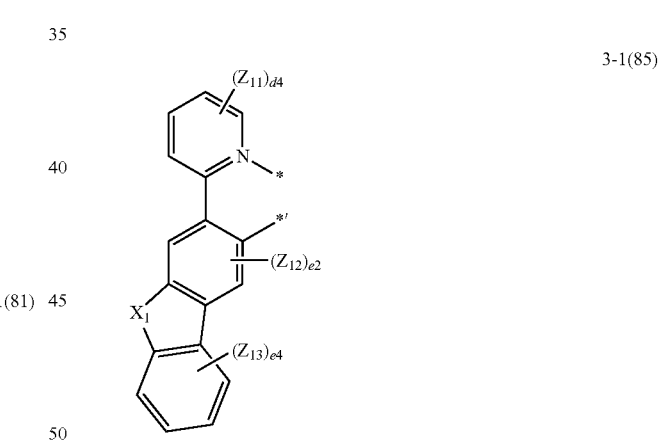 3-1(85)
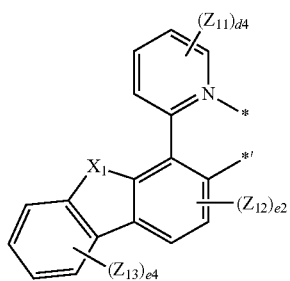 3-1(82)
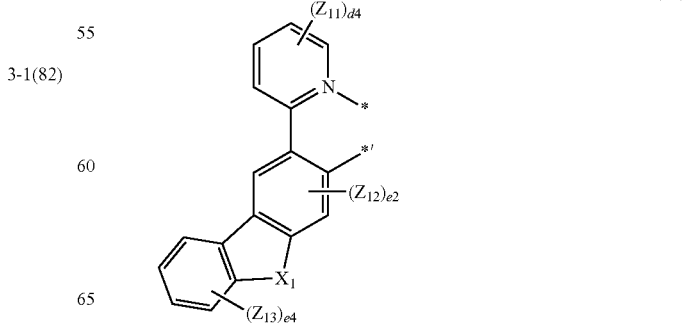 3-1(86)
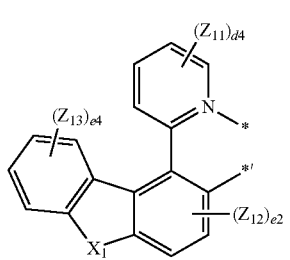

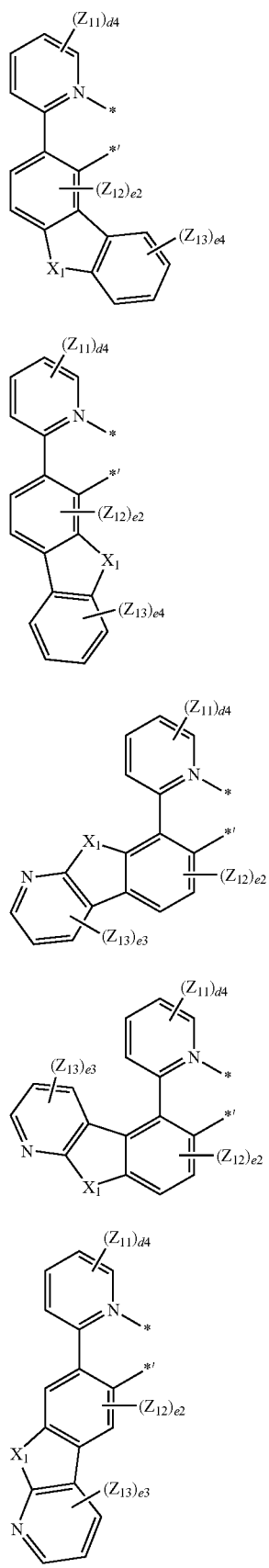
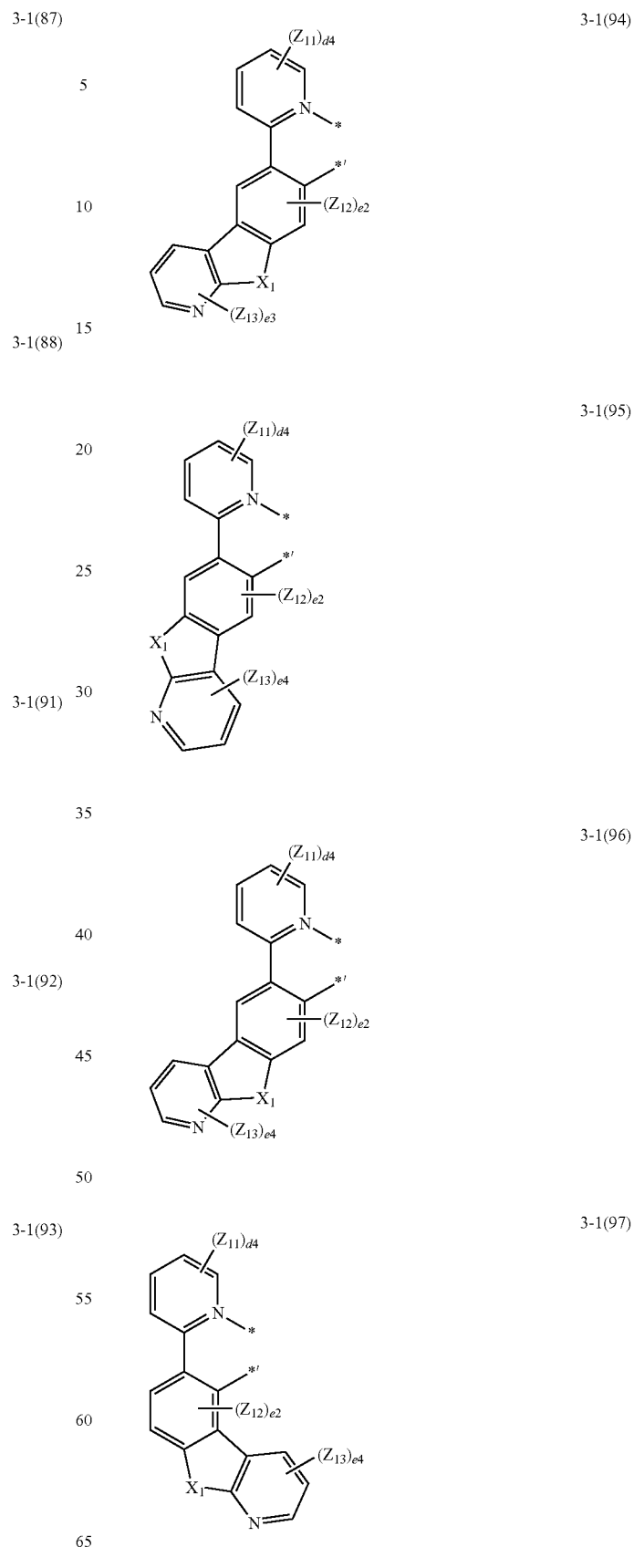

-continued
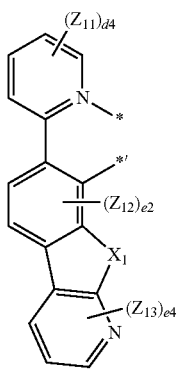
3-1(98)
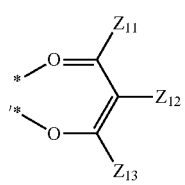
3-1(101)
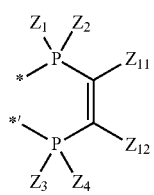
3-1(102)
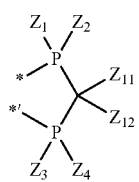
3-1(103)
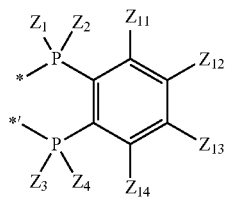
3-1(104)
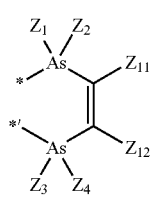
3-1(105)
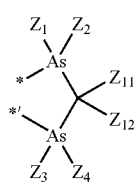
3-1(106)
-continued
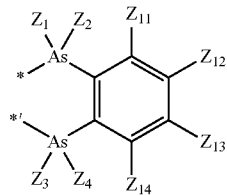
3-1(107)
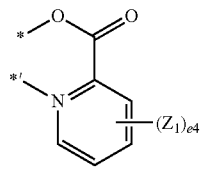
3-1(108)
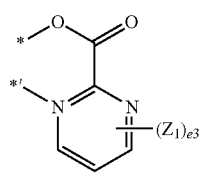
3-1(109)
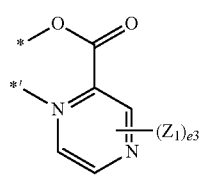
3-1(110)
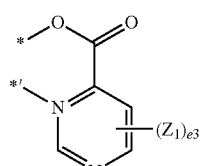
3-1(111)
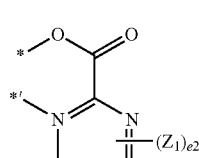
3-1(112)
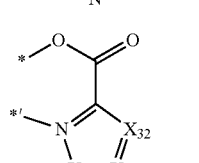
3-1(113)
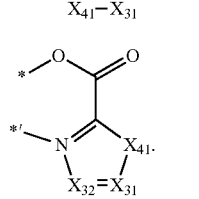
3-1(114)
In Formulae 3-1(1) to 3-1(60), 3-1 (61) to 3-1(69), 3-1 (71) to 3-1(79), 3-1 (81) to 3-1(88), 3-1(91) to 3-1(98), and 3-1(101) to 3-1(114),
$X_1$ may be O, S, $C(Z_{21})(Z_{22})$, or $N(Z_{23})$,
$X_{31}$ may be N or $C(Z_{1a})$ and $X_{32}$ may be N or $C(Z_{1b})$,
$X_{41}$ may be O, S, $N(Z_{1a})$, or $C(Z_{1a})(Z_{1b})$,
$Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$ and $Z_{21}$ to $Z_{23}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a C$_1$-C$_{20}$ alkyl group, or a C$_1$-C$_{20}$ alkoxy group;

a C$_1$-C$_{20}$ alkyl group or a C$_1$-C$_{20}$ alkoxy group, each substituted with at least one of deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, or a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one of deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group; or —B(Q$_{86}$)(Q$_{87}$) and —P(=O)(Q$_{88}$)(Q$_{89}$), wherein Q$_{86}$ to Q$_{89}$ may each independently be:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CH$_3$, —CD$_2$CD$_3$, —CD$_2$CD$_2$H, or —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group, each substituted with at least one of deuterium, a C$_1$ to C$_{10}$ alkyl group, or a phenyl group, d2 and e2 may each independently be 0 or 2, e3 may be an integer from 0 to 3, d4 and e4 may each independently be an integer from 0 to 4, d6 and e6 may each independently be an integer from 0 to 6, d8 and e8 may each independently be an integer from 0 to 8, and and *' each indicate a binding site to M in Formula 1.

In one or more embodiments, in Formula 81, M may be Ir and the sum of n81 and n82 may be 3; or M may be Pt and the sum of n81 and n82 may be 2. In one or more embodiments, the organometallic compound represented by Formula 81 may be electrically neutral rather than a salt consisting of the pair of a cation and an anion.
In one or more embodiments, the organometallic compound represented by Formula 81 may include at least one of compounds PD1 to PD78 and $Flr_6$, but embodiments of the present disclosure are not limited thereto.
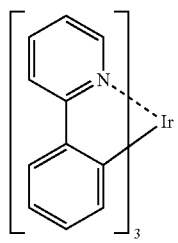
PD1
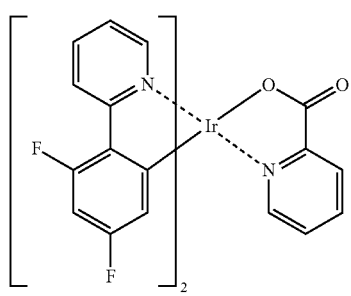
PD2
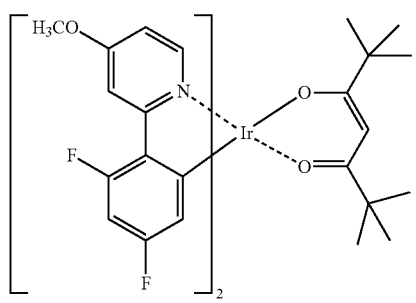
PD3
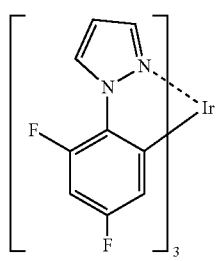
PD4
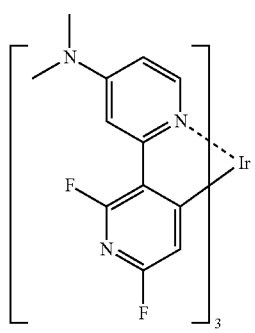
PD5
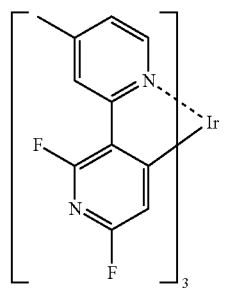
PD6
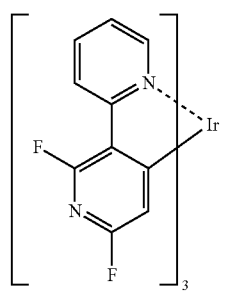
PD7
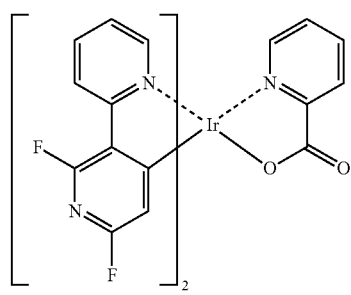
PD8
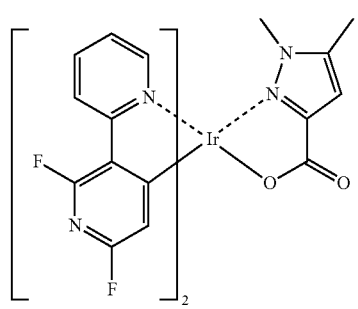
PD9
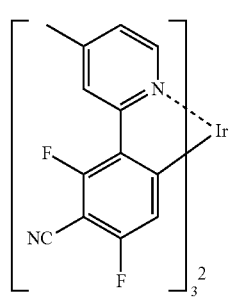
PD10

PD11 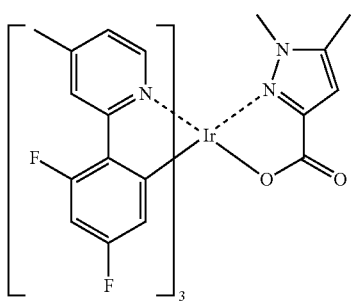
PD12 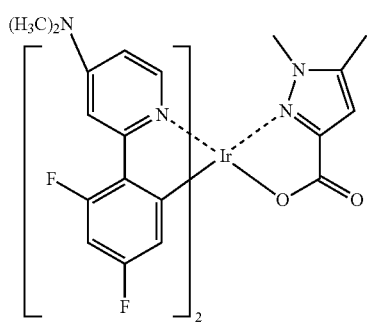
PD13 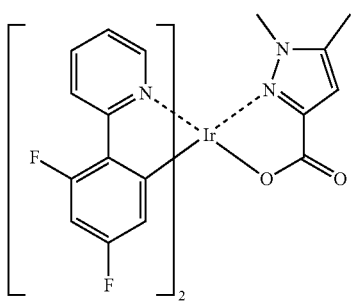
PD14 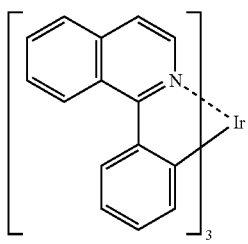
PD15 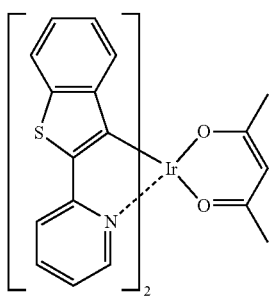
PD16 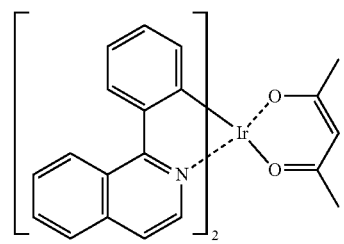
PD17 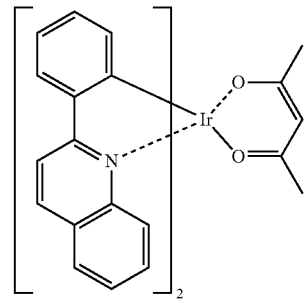
PD18 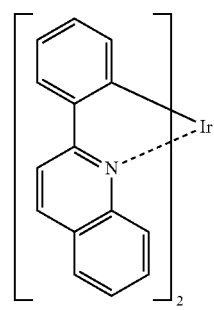
PD19 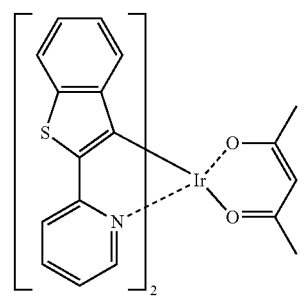
PD20 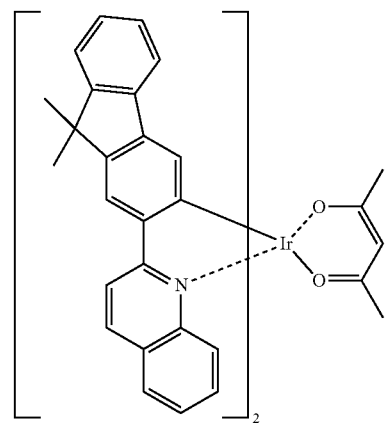

-continued
PD21
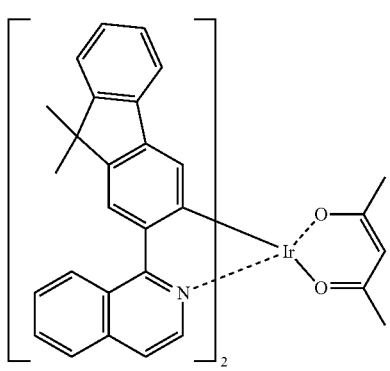
PD22
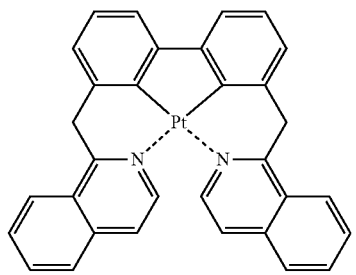
PD23

PD24

PD25
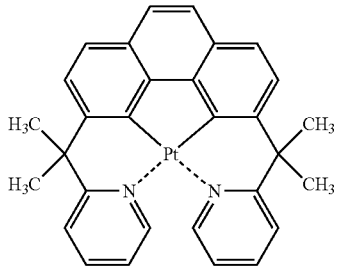
PD26
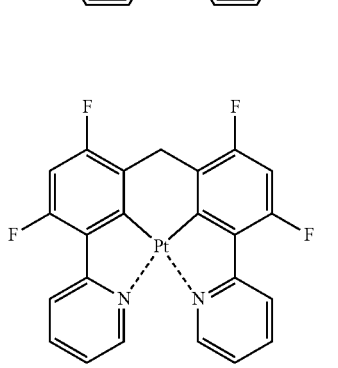
PD27
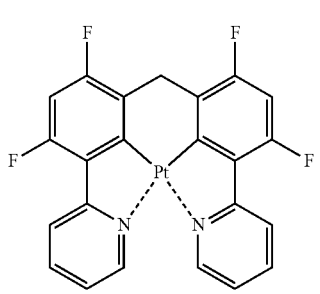
PD28
PD29
PD30
PD31
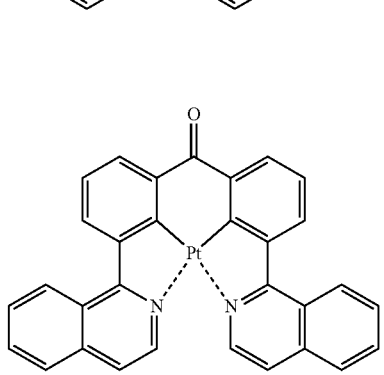

-continued
PD32 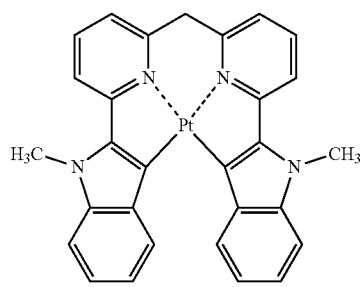
PD33 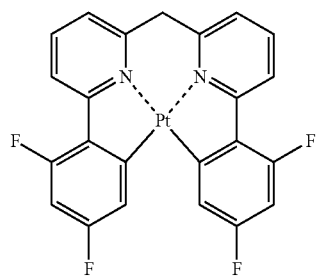
PD35
PD36
PD37 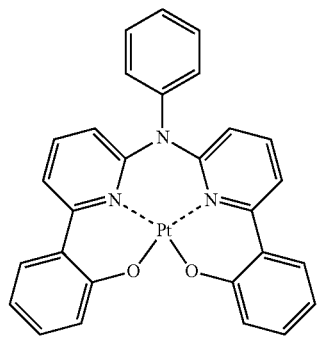
PD38 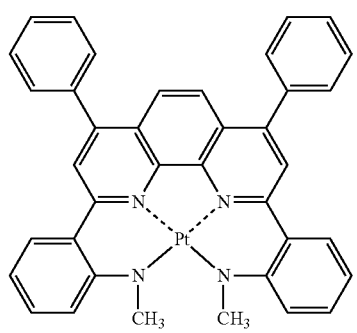
PD39 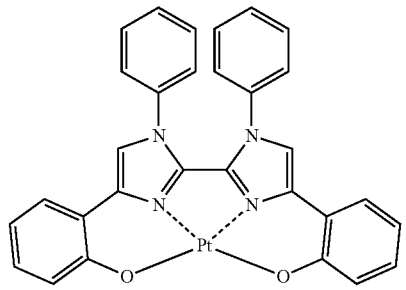
PD40 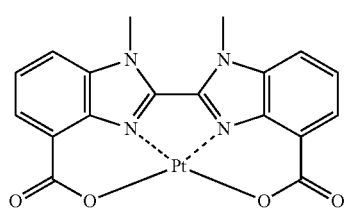
PD41 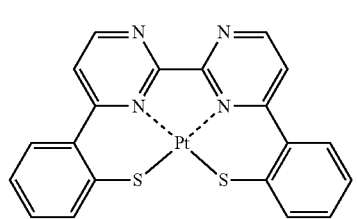

-continued
PD42
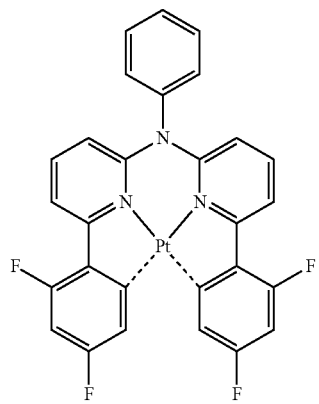
PD43
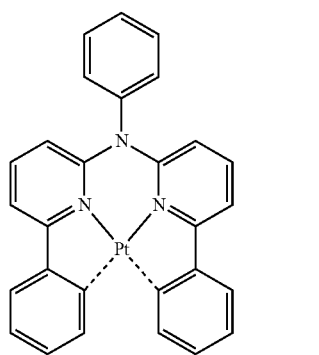
PD44
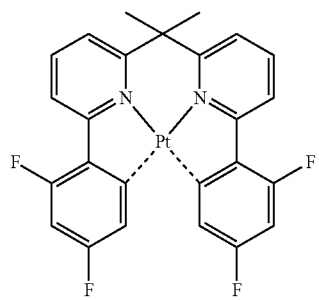
PD45
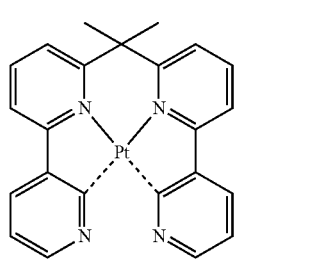
PD46
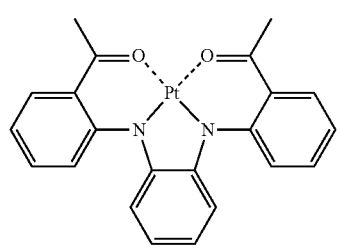
-continued
PD47
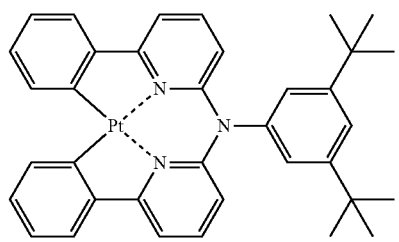
PD48
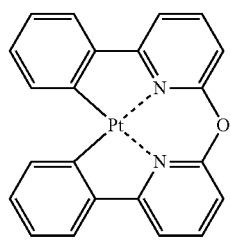
PD49
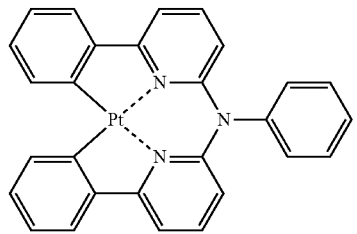
PD50
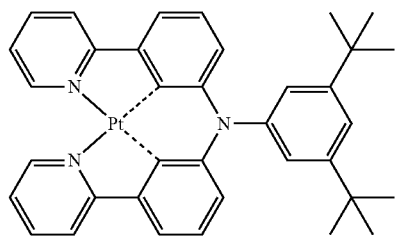
PD51
PD52
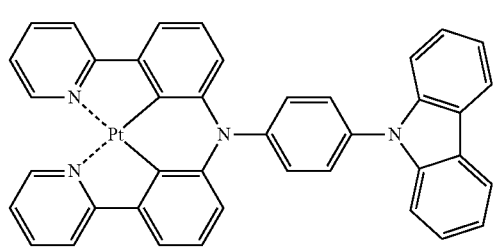

-continued
PD53
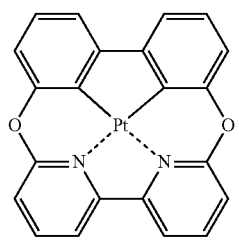
PD54
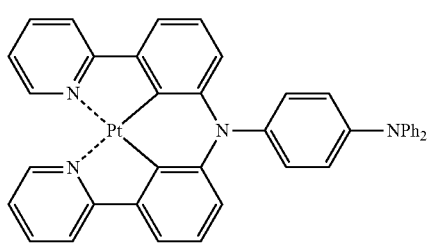
PD55
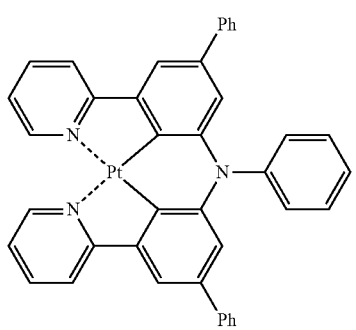
PD56
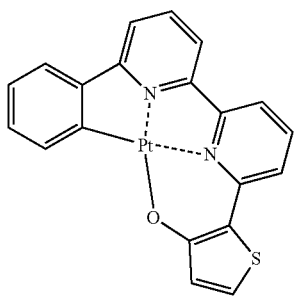
PD57
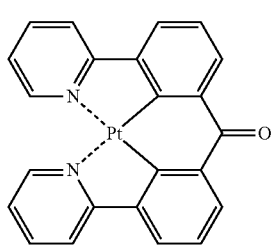
-continued
PD58
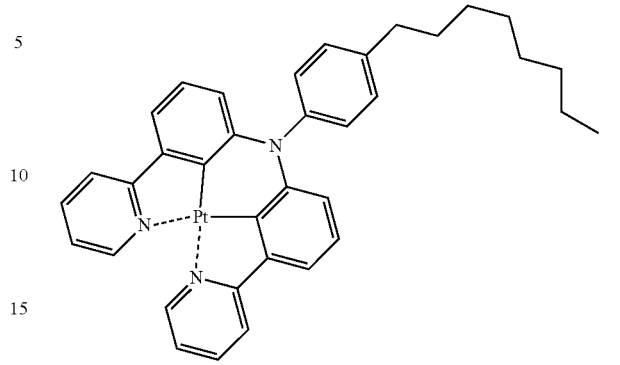
PD59
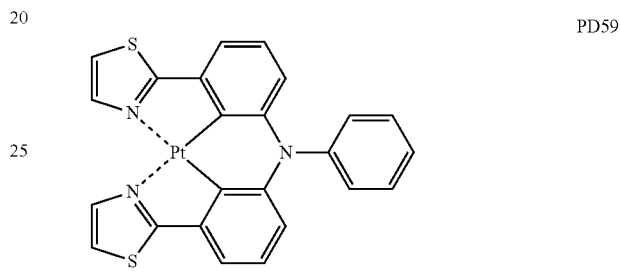
PD60
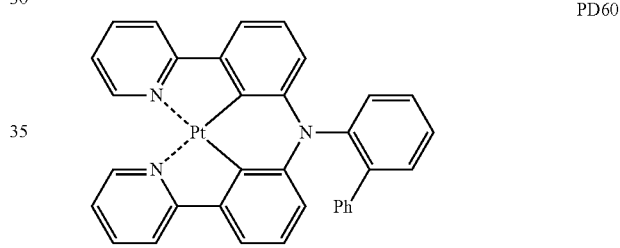
PD61
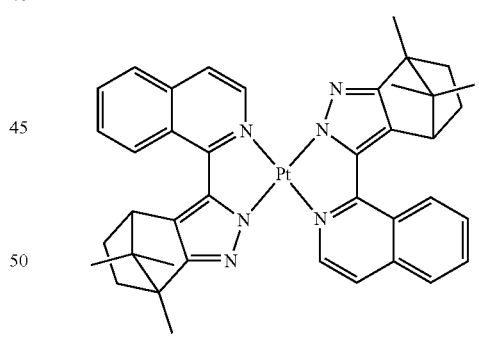
PD62
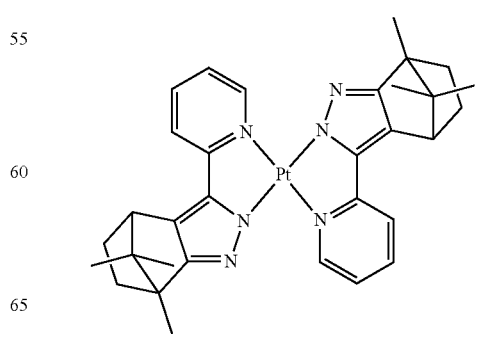

PD63 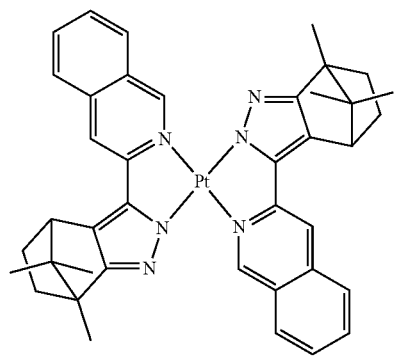
PD64 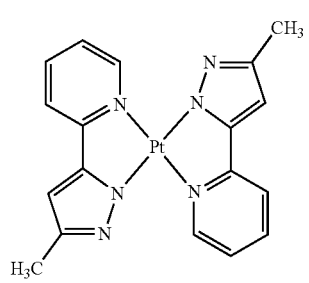
PD65 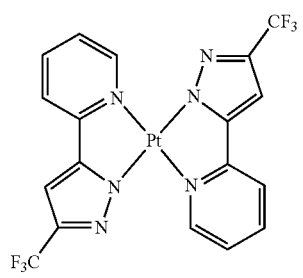
PD66 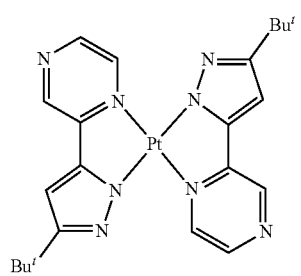
PD67 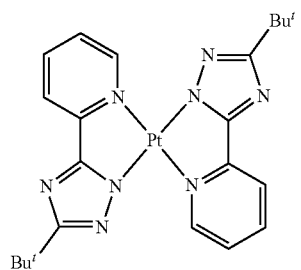
PD68 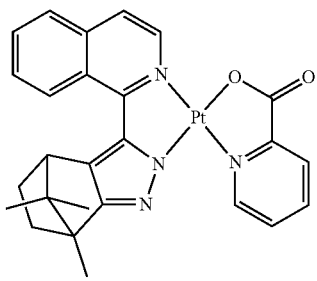
PD69 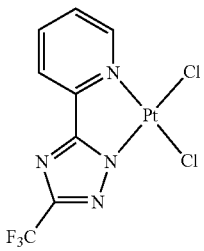
PD70 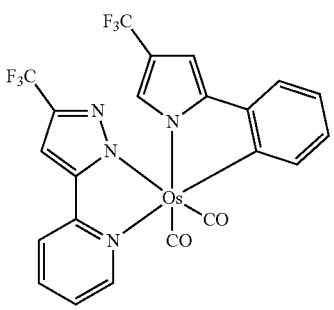
PD71 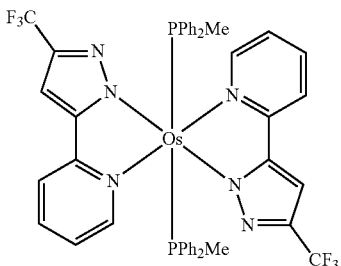
PD72 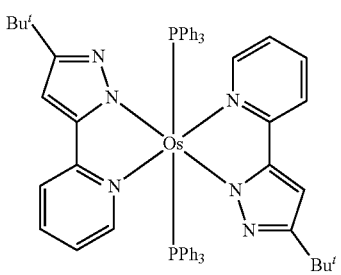

-continued

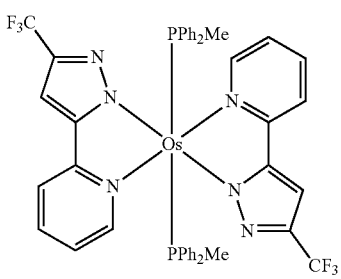
PD73

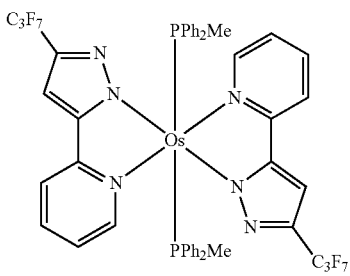
PD74

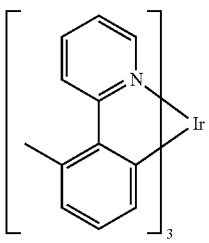
PD75

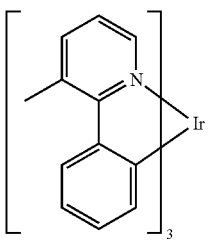
PD76

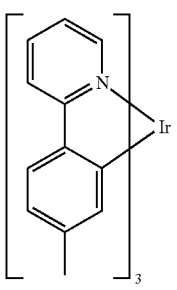
PD77

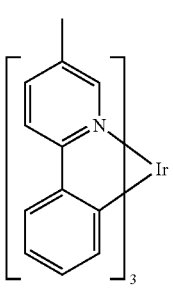
PD78

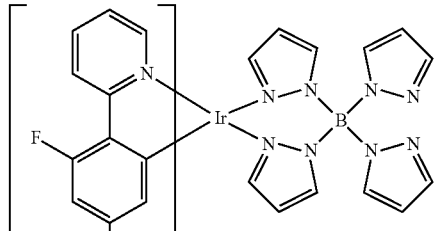
Flr6

The expression "(an organic layer) includes at least one heterocyclic compound" as used herein may include a case in which "(an organic layer) includes identical heterocyclic compounds represented by Formula 1" and a case in which "(an organic layer) includes two or more different heterocyclic compounds represented by Formula 1".

For example, the organic layer may include, as the heterocyclic compound, only Compound 1. Here, Compound 1 may be included in the emission layer of the organic light-emitting device. In one or more embodiments, the organic layer may include, as the heterocyclic compound, Compound 1 and Compound 2. Here, Compound 1 and Compound 2 may be present in an identical layer (for example, Compound 1 and Compound 2 may all be present in an emission layer), or different layers (for example, Compound 1 may be present in an emission layer and Compound 2 may be present in a hole blocking layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

The term "organic layer" as used herein refers to a single layer and/or a plurality of layers between the first electrode and the second electrode of the organic light-emitting device. The "organic layer" may include, in addition to an organic compound, an organometallic complex including metal.

FIG. 1s a schematic cross-sectional view of an organic light-emitting device 10 according to an embodiment. Hereinafter, the structure of an organic light-emitting device according to an embodiment of the present disclosure and a method of manufacturing an organic light-emitting device according to an embodiment of the present disclosure will be described in connection with the FIGURE. The organic light-emitting device 10 includes a first electrode 11, an organic layer 15, and a second electrode 19, which are sequentially stacked.

A substrate may be additionally located under the first electrode 11 or above the second electrode 19. For use as the substrate, any substrate that is used in organic light-emitting devices available in the art may be used, and the substrate may be a glass substrate or a transparent plastic substrate, each having excellent mechanical strength, thermal stability, transparency, surface smoothness, ease of handling, and water resistance.

The first electrode 11 may be, for example, formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. In an embodiment, the material for forming the first electrode 11 may be indium tin oxide (ITO), indium zinc oxide (IZO), tin oxide (SnO$_2$), or zinc oxide (ZnO). In one or more embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 11 is not limited thereto.

The organic layer 15 is located on the first electrode 11.

The organic layer 15 may include a hole transport region, an emission layer, and an electron transport region.

The hole transport region may be between the first electrode 11 and the emission layer.

The hole transport region may include at least one of a hole injection layer, a hole transport layer, an electron blocking layer, and a buffer layer.

The hole transport region may include only either a hole injection layer or a hole transport layer. In one or more embodiments, the hole transport region may have a hole injection layer/hole transport layer structure or a hole injection layer/hole transport layer/electron blocking layer structure, wherein, for each structure, each layer is sequentially stacked on the first electrode 11.

When the hole transport region includes a hole injection layer (HIL), the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100° C. to about 500° C., a vacuum pressure of about 10$^{-8}$ torr to about 10$^{-3}$ torr, and a deposition rate of about 0.01 Å/sec to about 100 Å/sec. However, the deposition conditions are not limited thereto.

When the hole injection layer is formed using spin coating, the coating conditions may vary according to the material used to form the hole injection layer, and the structure and thermal properties of the hole injection layer. For example, a coating speed may be from about 2,000 rpm to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one of m-MTDATA, TDATA, 2-TNATA, NPB, β-NPB, TPD, Spiro-TPD, Spiro-NPB, methylated-NPB, TAPC, HMTPD, 4,4',4''-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, or a compound represented by Formula 202:

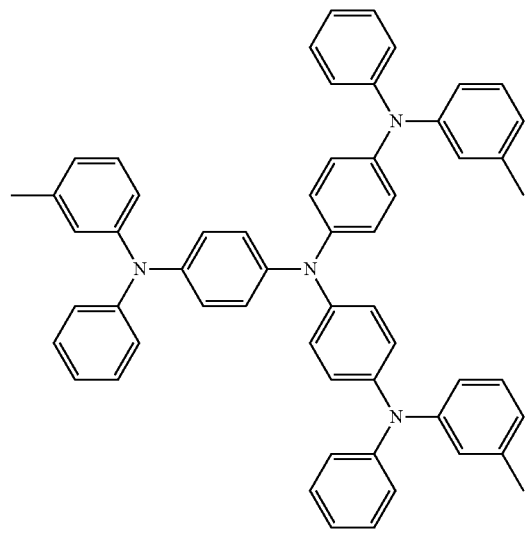

m-MTDATA

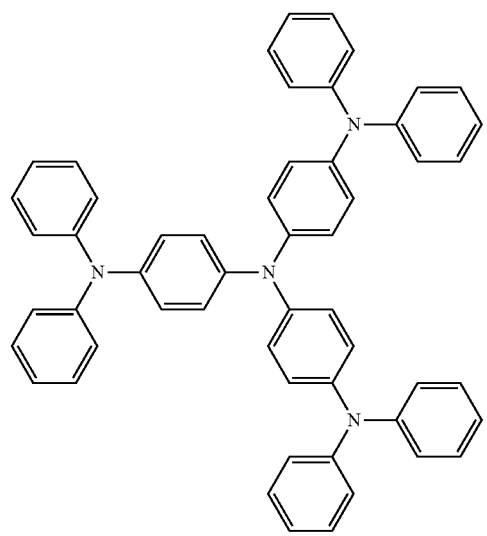

TDATA

-continued
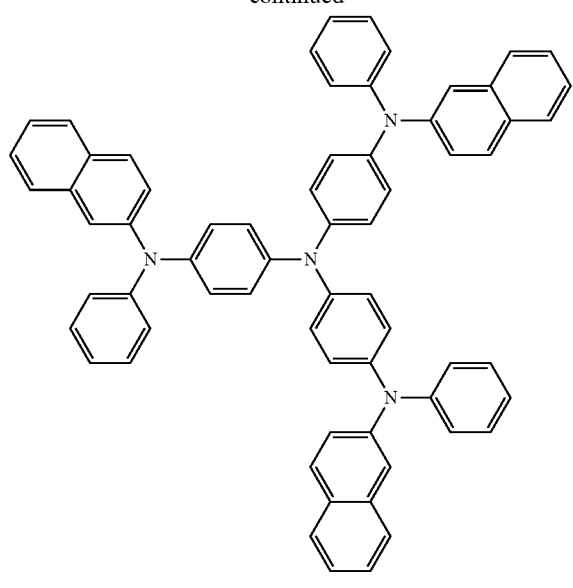
2-TNATA
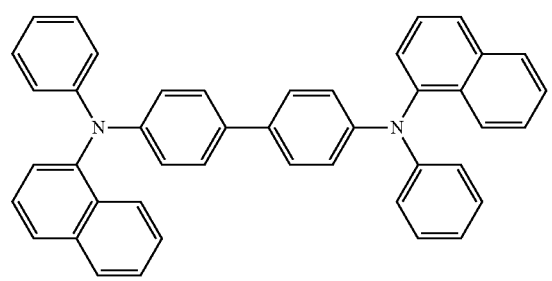
NPB
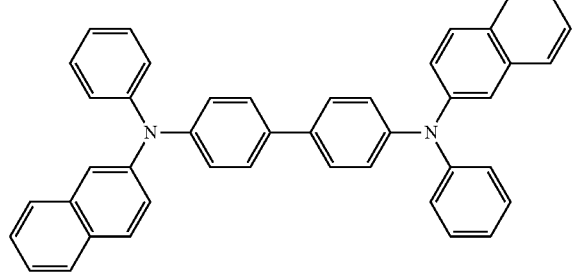
β-NPB
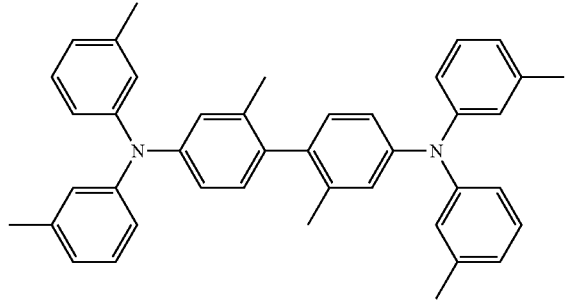
TPD
-continued
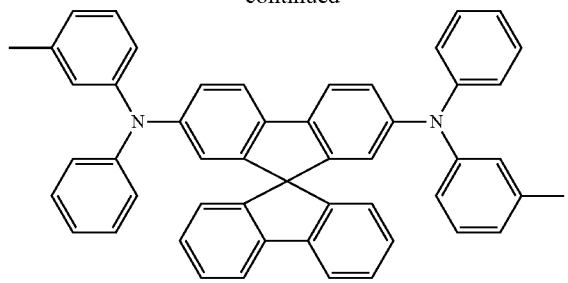
Spiro-TPD
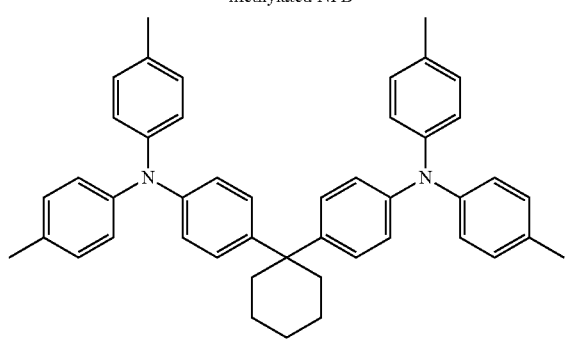
Spiro-NPB
methylated NPB
TAPC
HMTPD Formula 201

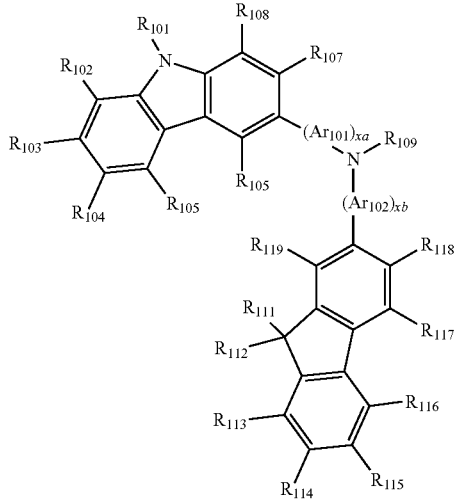

Formula 202

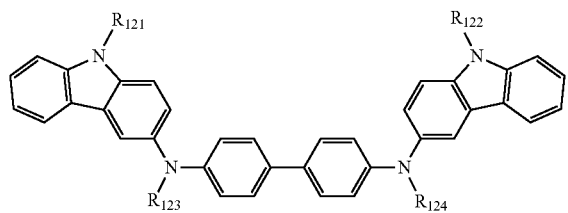

wherein $Ar_{101}$ to $Ar_{102}$ in Formula 201 may each independently be:
a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group; or a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_6$-$C_{60}$ heteroaryl group, a $C_1$-$C_{60}$ heteroaryloxy group, a $C_1$-$C_{60}$ heteroarylthio group, a monovalent non-aromatic condensed polycyclic group, or a monovalent non-aromatic condensed heteropolycyclic group.

In Formula 201, xa and xb may each independently be an integer from 0 to 5, or 0, 1, or 2. For example, xa may be 1 and xb may be 0, but embodiments of the present disclosure are not limited thereto.

In Formulae 201 and 202, $R_{101}$ to $R_{108}$, $R_{111}$ to $R_{119}$, and $R_{121}$ to $R_{124}$ may each independently be:
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, a hexyl group, etc.), or a $C_1$-$C_{10}$ alkoxy group (for example, a methoxy group, an ethoxy group, a propoxy group, a butoxy group, a pentoxy group, etc.);

a $C_1$-$C_{10}$ alkyl group or a $C_1$-$C_{10}$ alkoxy group, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, or a phosphoric acid group or a salt thereof;

a phenyl group, a naphthyl group, an anthracenyl group, a fluorenyl group, or a pyrenyl group; or a phenyl group, a naphthyl group, an anthracenyl group, a fluorenyl group, or a pyrenyl group, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, or a $C_1$-$C_{10}$ alkoxy group, but embodiments of the present disclosure are not limited thereto.

In Formula 201, $R_{109}$ may be:
a phenyl group, a naphthyl group, an anthracenyl group, or a pyridinyl group; or a phenyl group, a naphthyl group, an anthracenyl group, or a pyridinyl group, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, or a pyridinyl group.

In an embodiment, the compound represented by Formula 201 may be represented by Formula 201A, but embodiments of the present disclosure are not limited thereto:

Formula 201A
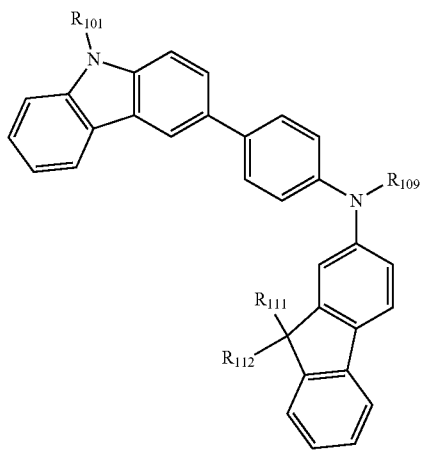
wherein $R_{101}$, $R_{111}$, $R_{112}$, and $R_{109}$ in Formula 201A may each be the same as described in the present specification.
For example, the compound represented by Formula 201 and the compound represented by Formula 202 may include Compounds HT1 to HT20, but are not limited thereto:
HT1
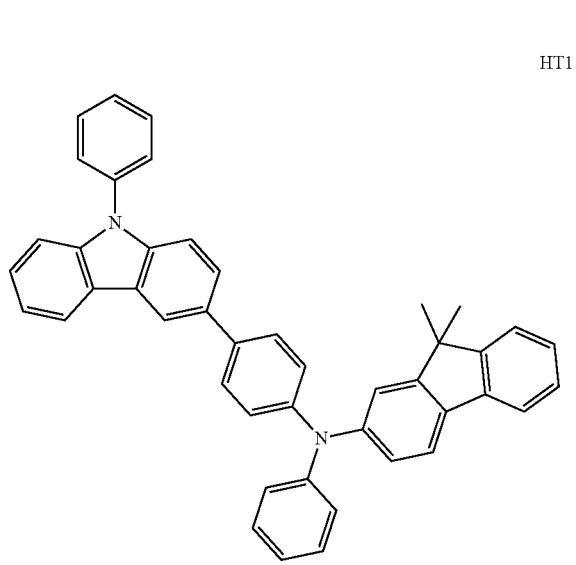
HT2
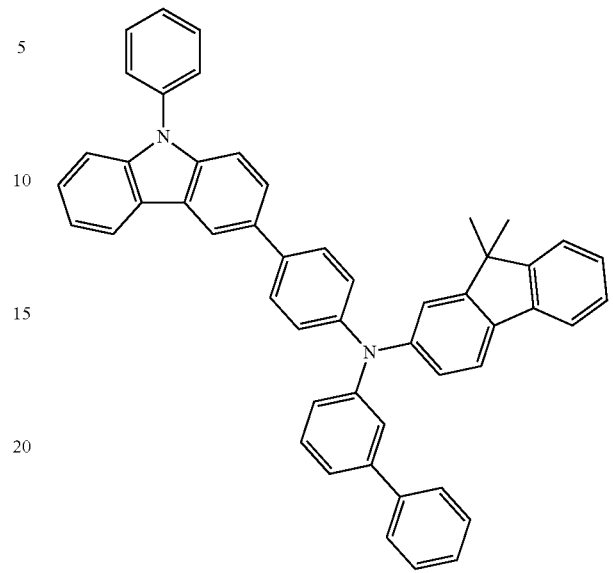
HT3
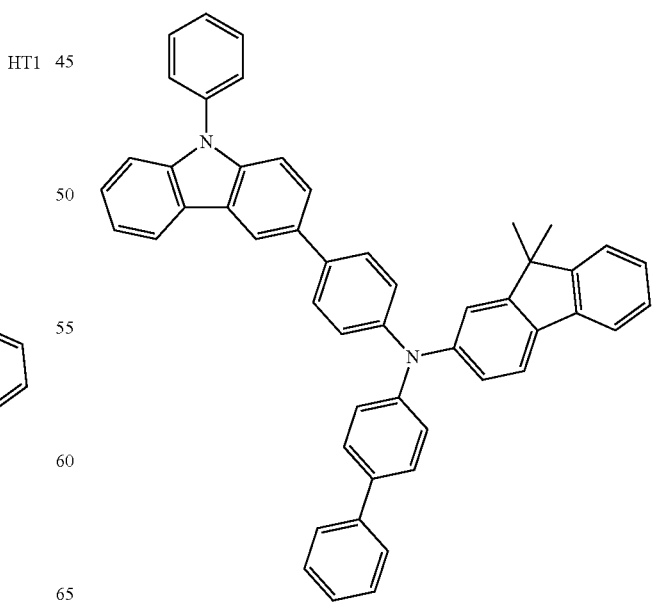

267
-continued
HT4
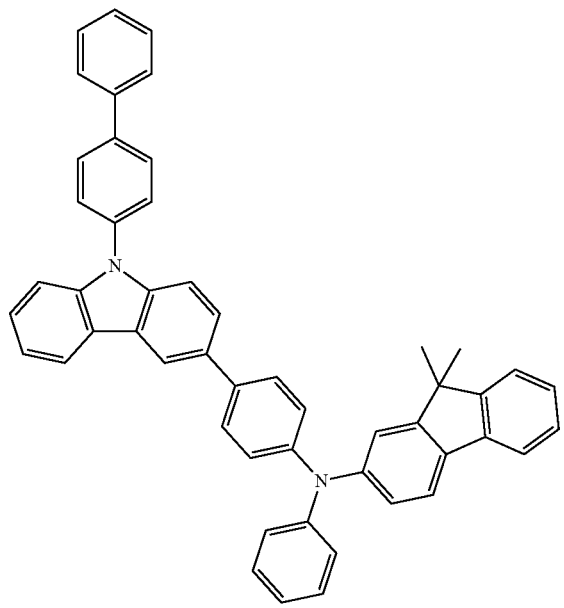
HT5
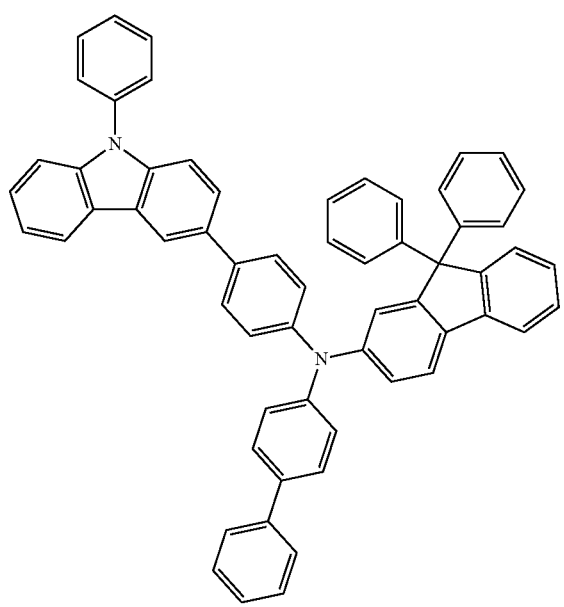
268
-continued
HT6
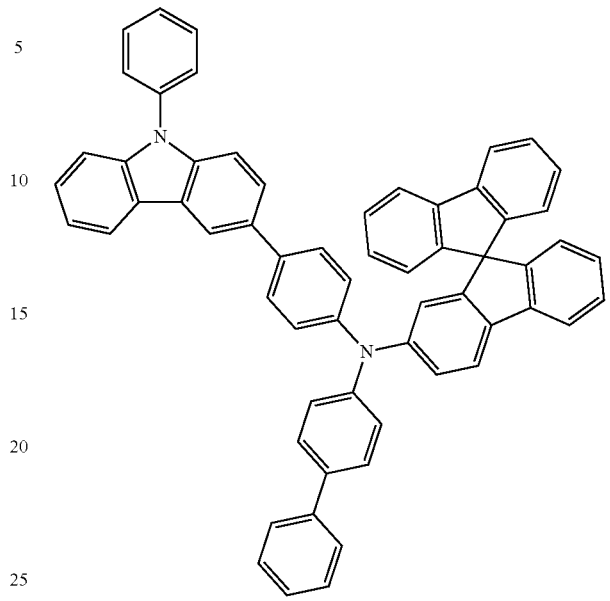
HT7
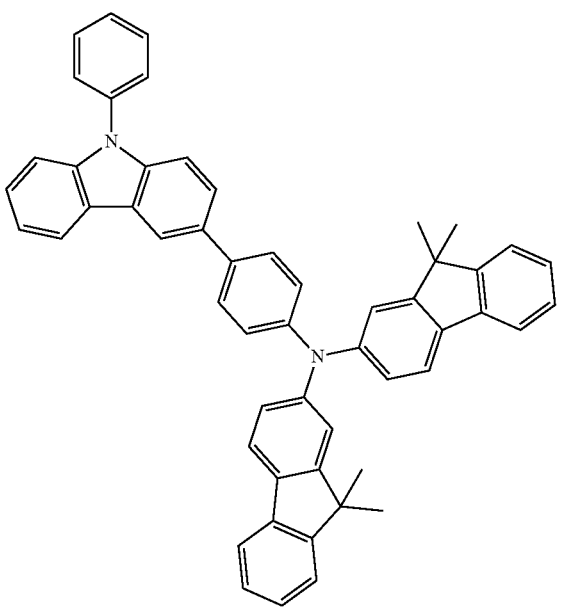

HT8
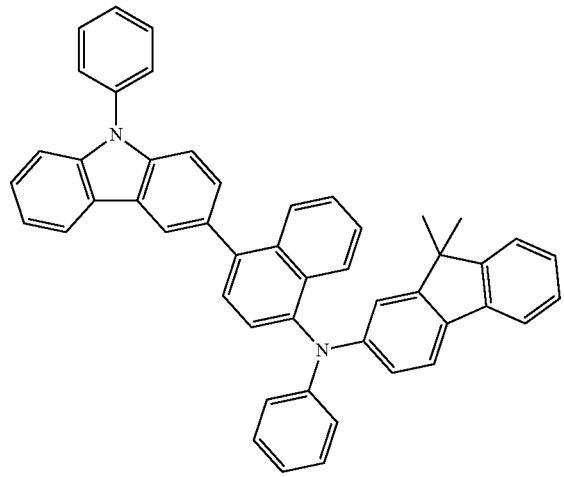
HT9
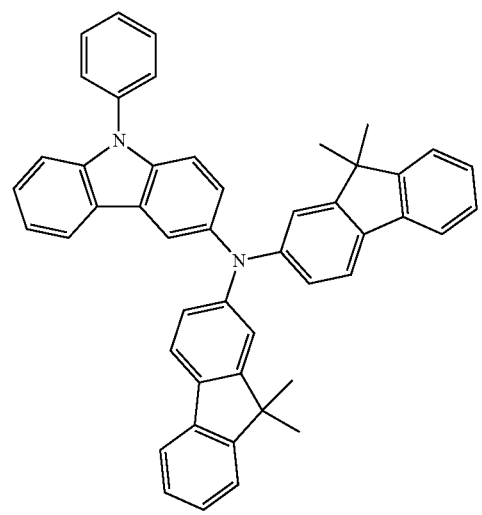
HT10
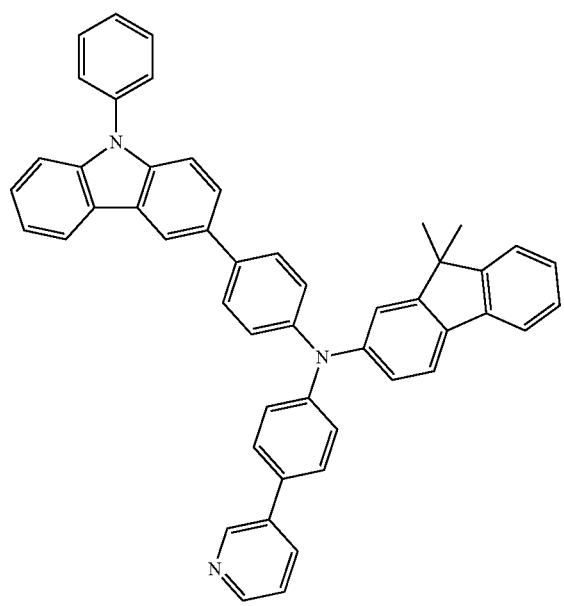
HT11
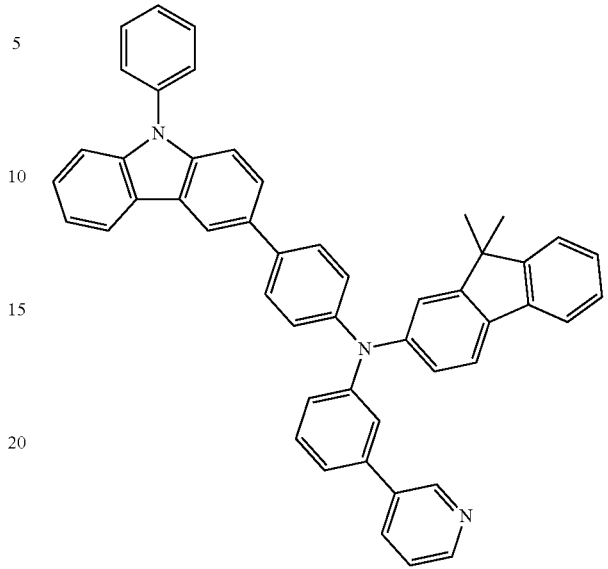
HT12
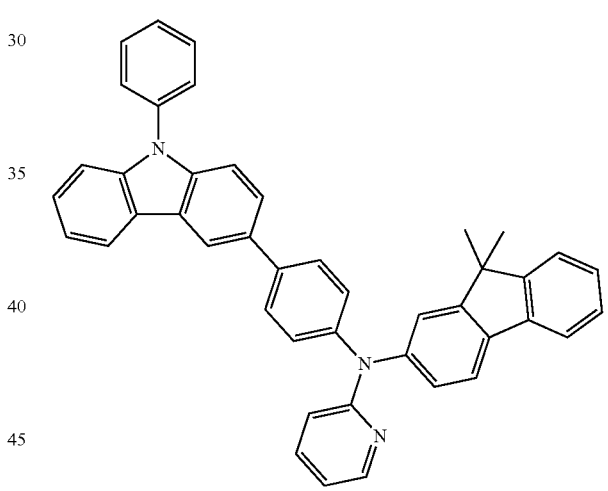
HT13
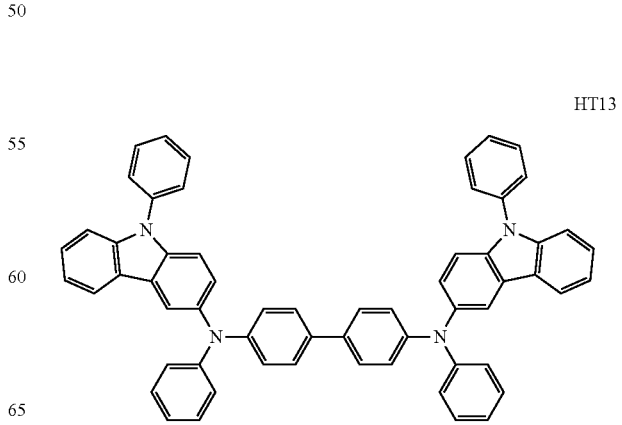

HT14
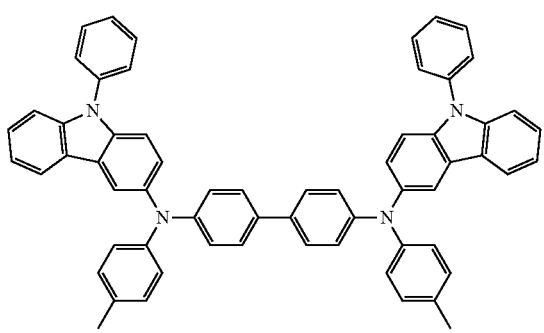

HT15
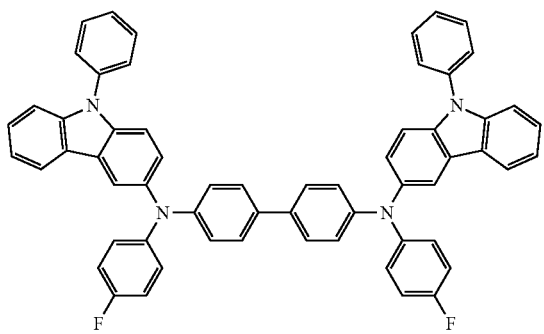

HT16
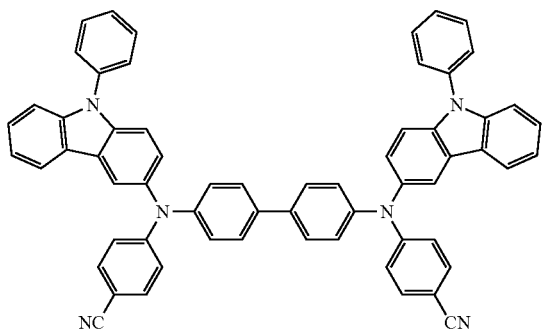

HT17
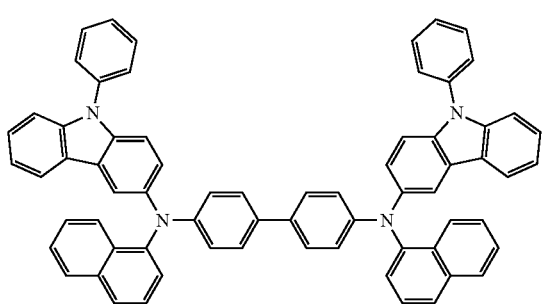

HT18

HT19
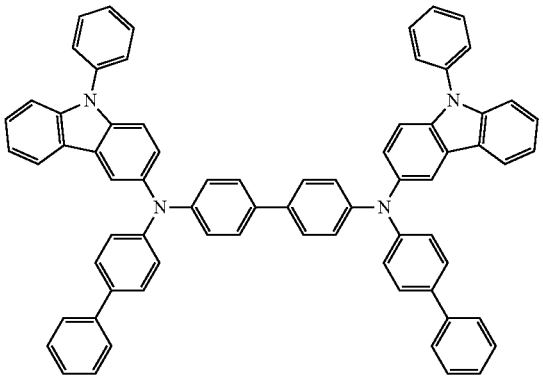

HT20
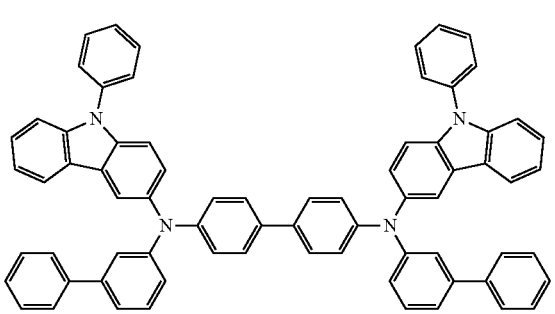

A thickness of the hole transport region may be in the range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be a quinone derivative, a metal oxide, a cyano group-containing compound, or a combination thereof, but embodiments of the present disclosure are not limited thereto. Non-limiting examples of the p-dopant are a quinone derivative, such as tetracyanoquinodimethane (TCNQ) or 2,3,5,6-tetrafluoro-tetracyano-1,4-benzoquinodimethane (F4-TCNQ); a metal oxide, such as a tungsten oxide or a molybdenum oxide; and a cyano group-containing compound, such as Compound HT-D1 or Compound HT-D2, but are not limited thereto:

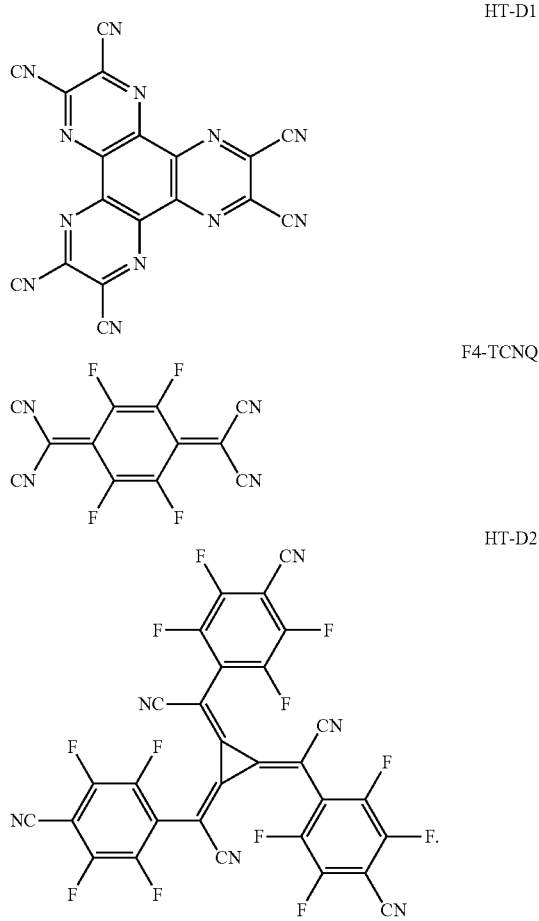

The hole transport region may include a buffer layer.

Also, the buffer layer may compensate for an optical resonance distance according to a wavelength of light emitted from the emission layer, and thus, efficiency of a formed organic light-emitting device may be improved.

The hole transport region may further include an electron blocking layer. The electron blocking layer may include a material available in the art, for example, mCP, but embodiments of the present disclosure are not limited.

The thickness of the electron blocking layer may be about 50 Å to about 1,000 Å, for example about 70 Å to about 500 Å. When the thickness of the electron blocking layer is within these ranges, satisfactory electron blocking characteristics may be obtained without a substantial increase in driving voltage.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a material that is used to form the emission layer.

When the organic light-emitting device 10 is a full-color organic light-emitting device, the emission layer may be patterned into a red emission layer, a green emission layer, and a blue emission layer. For example, due to a stacked structure including a red emission layer, a green emission layer, and/or a blue emission layer, the emission layer may emit white light.

The emission layer may include the heterocyclic compound represented by Formula 1.

In an embodiment, the emission layer may include the heterocyclic compound represented by Formula 1 alone.

In one or more embodiments, the emission layer may include a host and a dopant, wherein the host may include the heterocyclic compound represented by Formula 1, and the dopant may be a fluorescent dopant.

When the emission layer includes a host and a dopant, an amount of the dopant may be in a range of about 0.01 parts by weight to about 20 parts by weight based on 100 parts by weight of the emission layer. However, embodiments of the present disclosure are not limited thereto. When the amount of the dopant is satisfied with this range, luminescence without extinction phenomenon may be implemented.

When the emission layer includes the heterocyclic compound represented by Formula 1 and a second compound different from the heterocyclic compound represented by Formula 1, the weight ratio of the heterocyclic compound represented by formula 1 to the second compound may be in a range of about 1:99 to about 99:1, for example, about 70:30 to about 30:70. For example, the weight ratio of the heterocyclic compound represented by Formula 1 to the second compound may be in a range of about 60:40 to about 40:60. When the weight ratio of the heterocyclic compound represented by formula 1 to the second compound in the emission layer is within this range, the charge transport balance in the emission layer may be effectively performed.

A thickness of the emission layer may be in the range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be located on the emission layer.

The electron transport region may include at least one of a hole blocking layer, an electron transport layer, or an electron injection layer.

For example, the electron transport region may have a hole blocking layer/electron transport layer/electron injection layer structure or an electron transport layer/electron injection layer structure, and the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and Bphen, but embodiments of the present disclosure are not limited thereto.

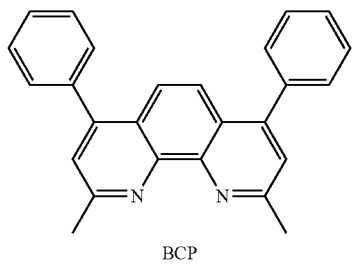

BCP

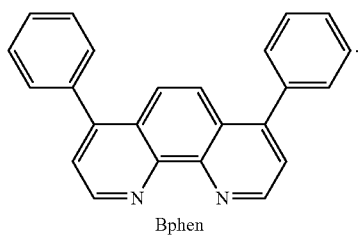

Bphen

In one or more embodiments, the hole blocking layer may include the heterocyclic compound represented by Formula 1.

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include at least one of BCP, Bphen, $Alq_3$, BAlq, TAZ, or NTAZ.

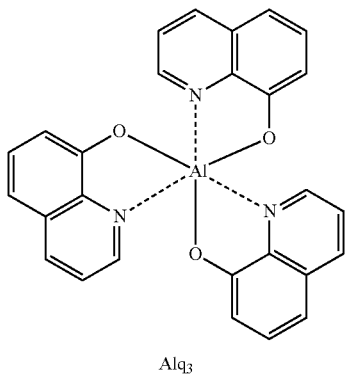

$Alq_3$

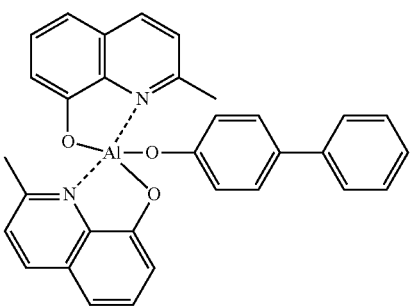

BAlq

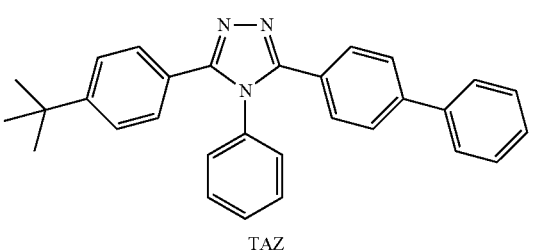

TAZ

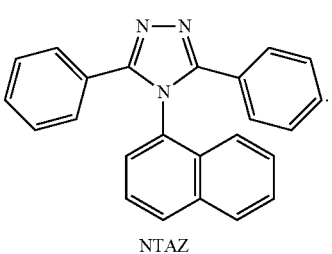

NTAZ

In one or more embodiments, the electron transport layer may include at least one of ET1, ET2, or ET3, but are not limited thereto:

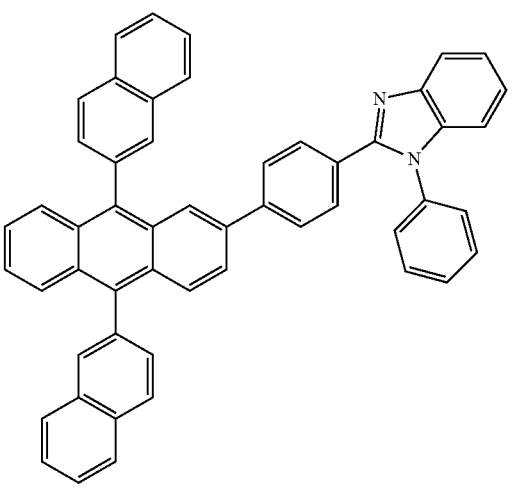

ET1

ET2

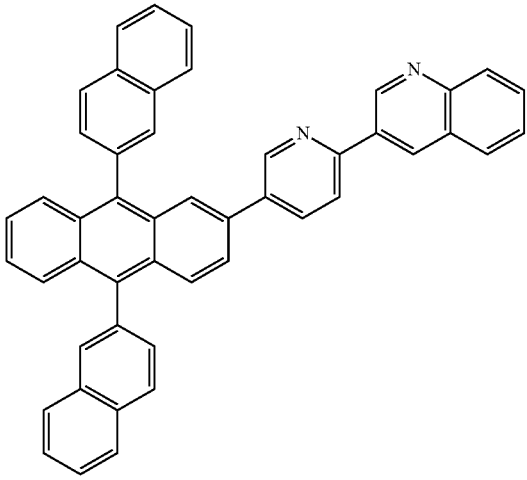

ET3

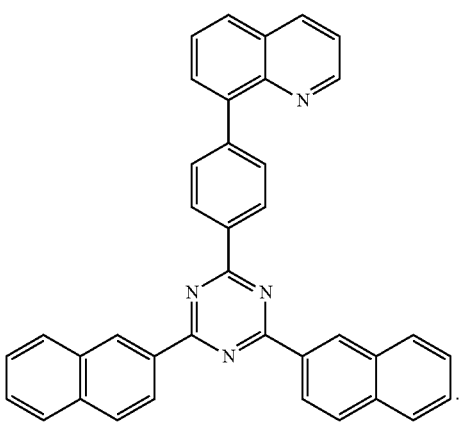

A thickness of the electron transport layer may be in the range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a L1 complex. The L1 complex may include, for example, Compound ET-D1 (lithium 8-hydroxyquinolate, LiQ) or ET-D2:

ET-D1

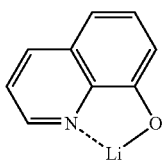

ET-D2

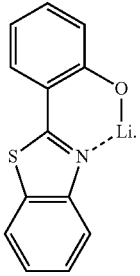

The electron transport region may include an electron injection layer that promotes the flow of electrons from the second electrode 19 thereinto.

The electron injection layer may include at least one of LiQ, LiF, NaCl, CsF, $Li_2O$, or BaO.

A thickness of the electron injection layer may be in a range of about 1 Å to about 100 Å, and, for example, about 3 Å to about 90 Å. When the thickness of the electron injection layer is within the range described above, the electron injection layer may have satisfactory electron injection characteristics without a substantial increase in driving voltage.

The second electrode 19 is located on the organic layer 15. The second electrode 19 may be a cathode. A material for forming the second electrode 19 may be metal, an alloy, an electrically conductive compound, or a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as the material for forming the second electrode 19. In one or more embodiments, to manufacture a top-emission type light-emitting device, a transmissive electrode formed using ITO or IZO may be used as the second electrode 19.

Hereinbefore, the organic light-emitting device has been described with reference to FIGURE, but embodiments of the present disclosure are not limited thereto.

The term "$C_1$-$C_{60}$ alkyl group" as used herein refers to a linear or branched saturated aliphatic hydrocarbon monovalent group having 1 to 60 carbon atoms, and non-limiting examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_2$-$C_{60}$ alkenyl group" as used herein refers to a hydrocarbon group formed by substituting at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by substituting at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si, B, Se, Ge, Te, and S as a ring-forming atom and 1 to 10 carbon atoms, and non-limiting examples thereof include a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, B, Se, Ge, Te, and S as a ring-forming atom, 1 to 10 carbon atoms, and at least one carbon-carbon double bond in its ring. Examples of the $C_1$-$C_{10}$ heterocycloalkenyl group are a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other. The $C_7$-$C_{60}$ alkylaryl group refers to a $C_6$-$C_{60}$ aryl group substituted with at least one $C_1$-$C_{60}$ alkyl group.

The term "$C_1$-$C_{60}$ heteroaryl group" as used herein refers to a monovalent group having a heterocyclic aromatic system that has at least one heteroatom selected from N, O, P, Si, B, Se, Ge, Te, and S as a ring-forming atom, and 1 to 60 carbon atoms. The term "$C_1$-$C_{60}$ heteroarylene group" as used herein refers to a divalent group having a heterocyclic aromatic system that has at least one heteroatom selected from N, O, P, Si, B, Se, Ge, Te, and S as a ring-forming atom, and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_6$-$C_{60}$ heteroaryl group and the $C_6$-$C_{60}$ heteroarylene group each include two or more rings, the rings may be fused to each other. The $C_2$-$C_{60}$ alkylheteroaryl group refers to a $C_6$-$C_{60}$ heteroaryl group substituted with at least one $C_1$-$C_{60}$ alkyl group.

The term "$C_6$-$C_{60}$ aryloxy group" as used herein indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "$C_1$-$C_{60}$ heteroaryloxy group" as used herein indicates —$OA_{104}$ (wherein $A_{104}$ is the $C_1$-$C_{60}$ heteroaryl group), and the term "$C_1$-$C_{60}$ heteroarylthio group" as used herein indicates —$SA_{105}$ (wherein $A_{105}$ is the $C_1$-$C_{60}$ heteroaryl group).

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, at least one heteroatom selected from N, O, P, Si, B, Se, Ge, Te, and S, other than carbon atoms, as a ring-forming atom, and no aromaticity in its entire molecular structure. Examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{30}$ carbocyclic group" as used herein refers to a saturated or unsaturated cyclic group having, as a ring-forming atom, 5 to 30 carbon atoms only. The $C_5$-$C_{30}$ carbocyclic group may be a monocyclic group or a polycyclic group.

The term "$C_1$-$C_{30}$ heterocyclic group" as used herein refers to a saturated or unsaturated cyclic group having, as a ring-forming atom, at least one heteroatom selected from N, O, Si, P, B, Se, Ge, Te, and S other than 1 to 30 carbon atoms. The $C_1$-$C_{30}$ heterocyclic group may be a monocyclic group or a polycyclic group.

At least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_7$-$C_{60}$ alkylaryl group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroaryloxy group, the substituted $C_6$-$C_{60}$ heteroarylthio group, the substituted $C_2$-$C_{60}$ alkylheteroaryl group, the substituted monovalent non-aromatic condensed polycyclic group, and the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a $C_2$-$C_{60}$ alkylheteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), or —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_6$-$C_{60}$ heteroaryl group, a $C_6$-$C_{60}$ heteroaryloxy group, a $C_6$-$C_{60}$ heteroarylthio group, a $C_2$-$C_{60}$ alkylheteroaryl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a $C_2$-$C_{60}$ alkylheteroaryl group, a monovalent non-aromatic condensed polycyclic group, or a monovalent non-aromatic condensed heteropolycyclic group, each substituted with at least one of deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_6$-$C_{60}$ heteroaryl group, a $C_1$-$C_{60}$ heteroaryloxy group, a $C_1$-$C_{60}$ heteroarylthio group, a $C_2$-$C_{60}$ alkylheteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), or —P(=O)($Q_{28}$)($Q_{29}$); or —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), wherein $Q_1$ to $Q_9$, $Q_{11}$ to $Q_{19}$, to $Q_{29}$, and to $Q_{39}$ may each independently be hydrogen; deuterium; —F; —Cl; —Br; —I; a hydroxyl group; a cyano group; a nitro group; an amidino group; a hydrazine group; a hydrazone group; a carboxylic acid group or a salt thereof; a sulfonic acid group or a salt thereof; a phosphoric acid group or a salt thereof; a $C_6$-$C_{60}$ alkyl group; a $C_6$-$C_{60}$ alkyl group substituted with at least one of deuterium, a $C_1$-$C_{60}$ alkyl group, or a $C_6$-$C_{60}$ aryl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_6$-$C_{60}$ aryl group substituted with at least one of deuterium, a $C_6$-$C_{60}$ alkyl group, or a $C_6$-$C_{60}$ aryl group; a $C_6$-$C_{60}$ aryloxy group; a $C_6$-$C_{60}$ arylthio group; a $C_6$-$C_{60}$ heteroaryl group; a $C_6$-$C_{60}$ heteroaryloxy group; a $C_6$-$C_{60}$ heteroarylthio group; a $C_2$-$C_{60}$ alkylheteroaryl group; a monovalent non-aromatic condensed polycyclic group; or a monovalent non-aromatic condensed heteropolycyclic group.

Hereinafter, a compound and an organic light-emitting device according to embodiments are described in detail with reference to Synthesis Example and Examples. However, the organic light-emitting device is not limited thereto. The wording "'B' was used instead of 'A'" used in describing Synthesis Examples means that an amount of 'A' used was identical to an amount of 'B' used, in terms of a molar equivalent.

EXAMPLES

Synthesis Example 1: Synthesis of Compound 1

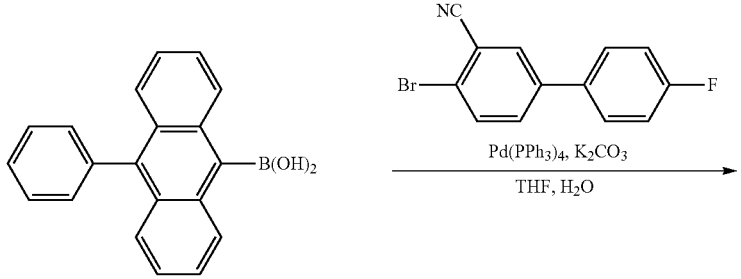

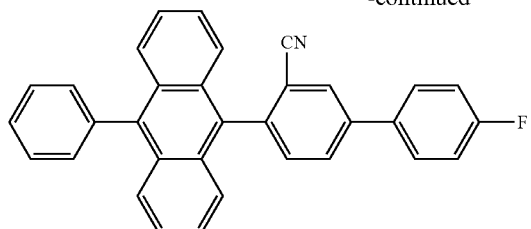

(A)

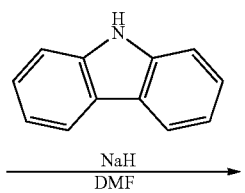

NaH / DMF

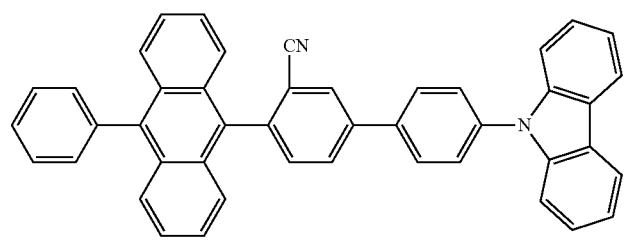

1

(1) Synthesis of Intermediate (A)

5.00 grams (g) (16.8 millimoles (mmol)) of (10-phenylanthracene-9-yl)boronic acid), 5.09 g (18.4 mmol) of 4-bromo-4'-fluoro-[1,1'-biphenyl]-3-carbonitrile, 0.969 g (0.839 mmol) of tetrakis-triphenylphosphine palladium(O) (Pd (PPh$_3$)$_4$), and 5.79 g (41.9 mmol) of potassium carbonate were added to a mixture of 60 mL of THF and 30 mL of water, and stirred under reflux for 18 hours. After completion of the reaction, the reaction mixture was cooled to room temperature and the aqueous layer was removed therefrom through extraction. The remaining product was filtered under reduced pressure through a silica gel, and the filtrate was concentrated under reduced pressure. The product was filtered by silica gel column chromatography, so as to obtain Intermediate (A) (3.07 g, yield of 54%).

LC-Mass (calculated: 449.16 grams per mole (g/mol), found: M+1=450 g/mol)

(2) Synthesis of Compound 1

1.00 g (5.98 mmol) of carbazole was dissolved in 20 mL of DMF, and the mixed solution was cooled to a temperature of 0° C. 0.251 g (6.28 mmol) of sodium hydride (NaH, 60% dispersion in mineral oil) was slowly added thereto, and stirred at a temperature of 0° C. for 30 minutes. To the resulting product, a solution obtained by diluting 2.96 g (6.28 mmol) of Intermediate (A) in 5 mL of DMF was slowly added for 10 minutes. Then, the reaction temperature was raised to 150° C., and the reaction solution was additionally stirred for 18 hours. After completion of the reaction, the reaction mixture was cooled to room temperature, a saturated ammonium chloride (NH$_4$Cl) aqueous solution was added thereto, and an organic layer was extracted with dichloromethane (DCM) for separation. Water was removed from the resultant product using anhydrous magnesium sulfate magnesium (MgSO$_4$). The remaining product obtained by filtration and concentration under reduced pressure was separated by silica gel column chromatography, so as to obtain a target compound, Compound 1 (2.68 g, yield of 75%).

LC-Mass (calculated: 596.23 g/mol, found: M+1=597 g/mol)

Synthesis Example 2: Synthesis of Compound 21

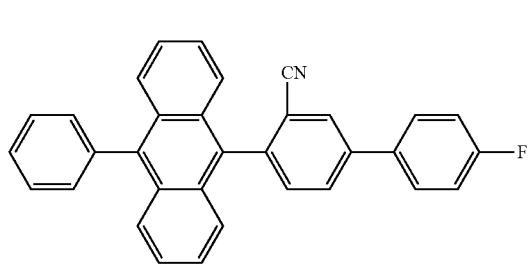

(A)

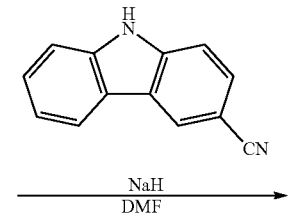

NaH / DMF

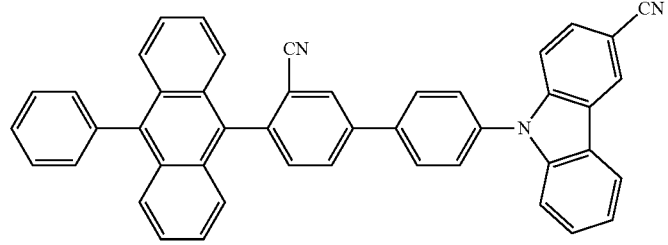
21
(2) Synthesis of Compound 21
Compound 21 (1.36 g, yield of 42%) was obtained in the same manner as used to synthesize Compound 1 of Synthesis Example 1, except that 1.00 g (5.20 mmol) of 9H-carbazole-3-carbonitrile was used instead of carbazole.
LC-Mass (calculated: 621.22 g/mol, found: M+1=622 g/mol)
Synthesis Example 3: Synthesis of Compound 66
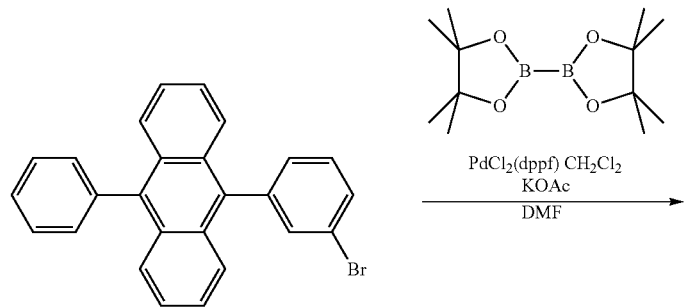
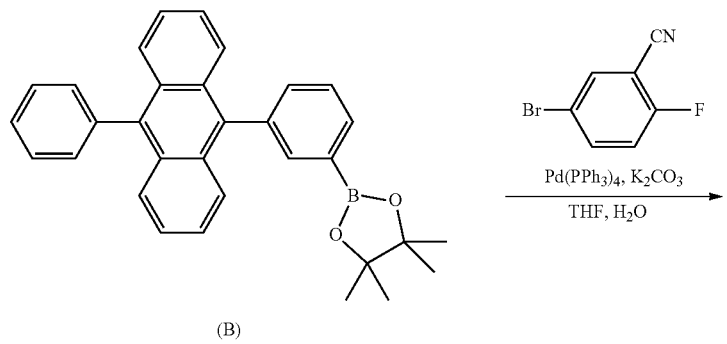
(B)
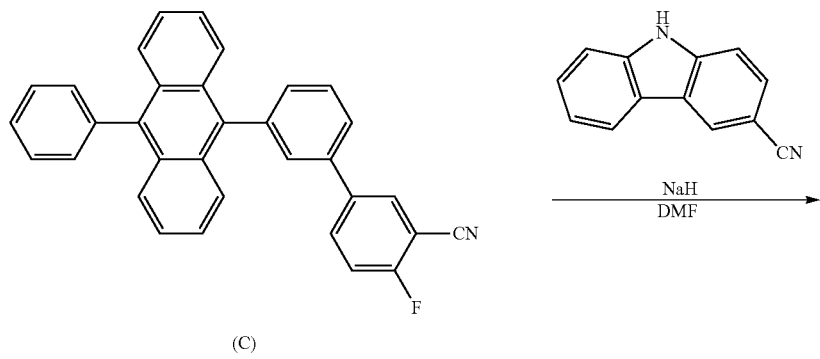
(C)

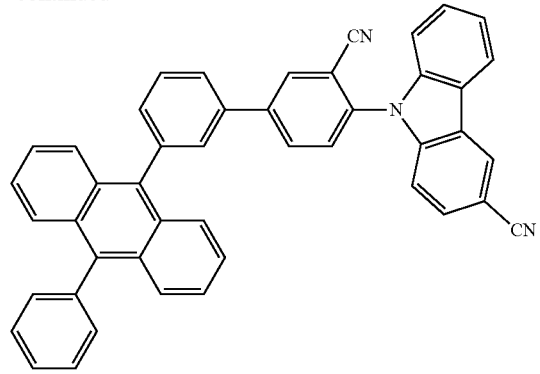

66

(1) Synthesis of Intermediate (B)

15.0 g (36.6 mmol) of 9-(3-bromophenyl)-10-phenylanthracene, 11.2 g (44.0 mmol) of bis(pinacolato)diboron, 1.50 g (1.83 mmol) of PdCl$_2$(dppf), and 10.8 g (110 mmol) of potassium acetate were mixed with 120 mL of DMF, and stirred at a temperature of 100° C. for 24 hours. After completion of the reaction, the reaction mixture was cooled to room temperature and filtered through silica gel under reduced pressure, and the filtrate was concentrated under reduced pressure. The product was filtered by silica gel column chromatography. The resulting product was recrystallized under the condition of dichloromethane (DCM)/n-hexane, so as to obtain Intermediate (B) (14.9 g, yield of 89%).

LC-Mass (calculated: 456.23 g/mol, found: M+1=457 g/mol)

(2) Synthesis of Intermediate (C)

Intermediate (C) (3.99 g, yield of 81%) was obtained in the same manner as used to obtain Intermediate (A) of Synthesis Example 1, except that 5.00 g (11.0 mmol) of Intermediate (B) was used instead of (10-phenylanthracene-9-yl)boronic acid and 2.41 g (12.1 mmol) of 5-bromo-2-fluorobenzonitrile was used instead of instead of 4-bromo-4'-fluoro-[1,1'-biphenyl]-3-carbonitrile.

LC-Mass (calculated: 449.16 g/mol, found: M+1=450 g/mol)

(3) Synthesis of Compound 66

Compound 66 (1.16 g, yield of 36%) was obtained in the same manner as used to obtain Compound 21 of Synthesis Example 2, except that 2.57 g (5.72 mmol) of Intermediate (C) was used instead of Intermediate (A).

LC-Mass (calculated: 621.22 g/mol, found: M+1=622 g/mol)

Synthesis Example 4: Synthesis of Compound 141

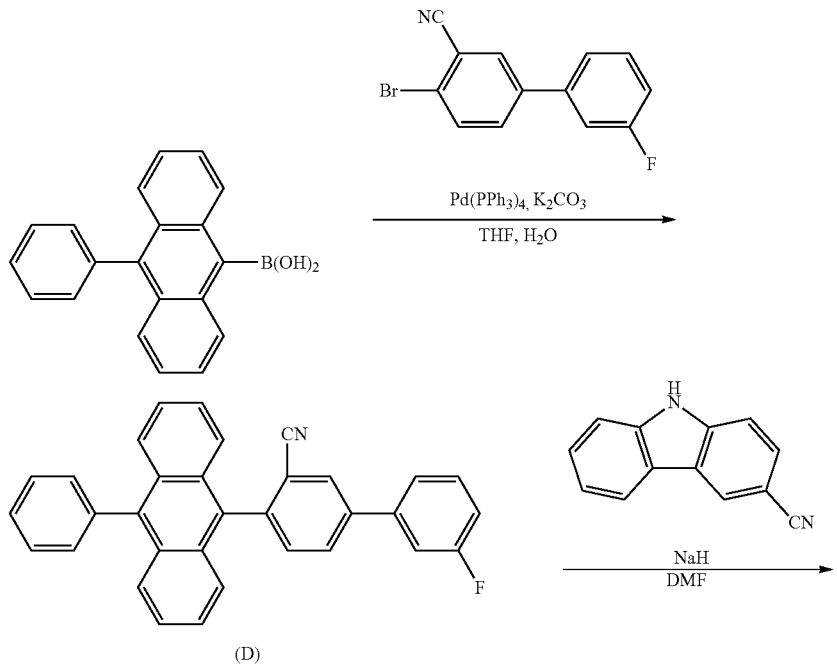

(D)

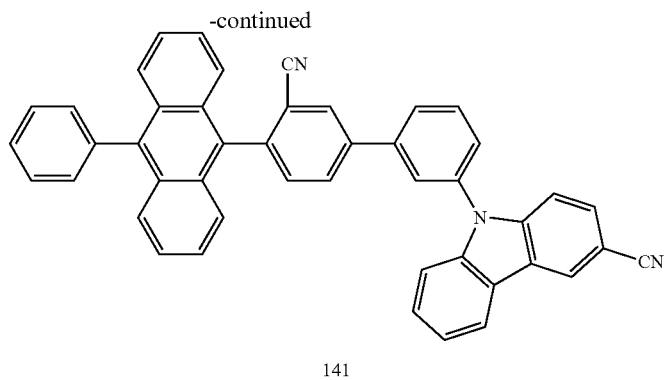

141

(1) Synthesis of Intermediate (D)

Intermediate (D) (3.52 g, yield of 62%) of Intermediate (D) was obtained in the same manner as used to obtain Intermediate (A) of Synthesis Example 1, except that 5.09 g (18.4 mmol) of 4-bromo-3'-fluoro-[1,1'-biphenyl]-3-carbonitrile was used Instead of 4-bromo-4'-fluoro-[1,1'-biphenyl]-3-carbonitrile.

LC-Mass (calculated: 449.16 g/mol, found: M+1=450 g/mol)

(2) Synthesis of Compound 141

Compound 141 (2.54 g, yield of 79%) was obtained in the same manner as used to obtain Compound 21 of Synthesis Example 2, except that 2.57 g (5.72 mmol) of Intermediate (D) was used instead of Intermediate (A).

LC-Mass (calculated: 621.22 g/mol, found: M+1=622 g/mol)

Synthesis Example 5: Synthesis of Compound 144

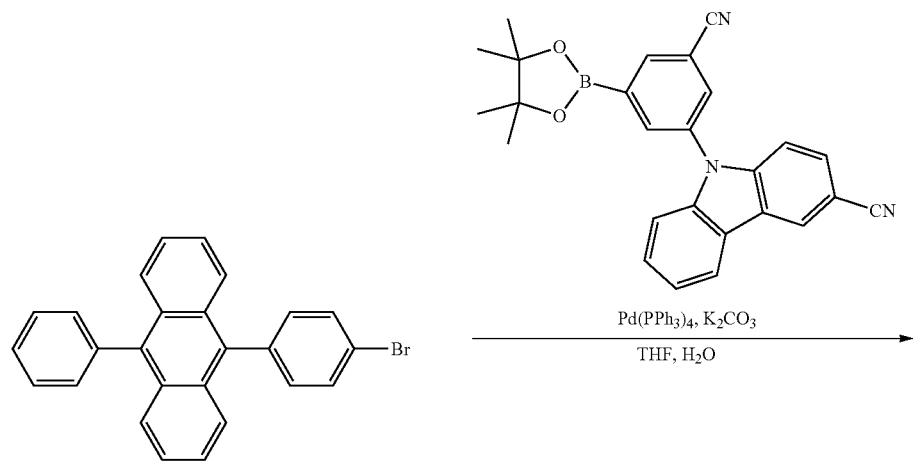

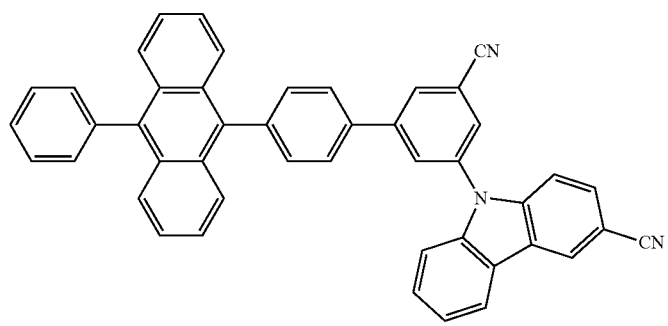

144

3.00 g (7.33 mmol) of 9-(4-bromophenyl)-10-phenylanthracene, 3.38 g (8.06 mmol) of 9-(3-cyano-5-(4,4,5,5-tetramethyl-1,3,2-dioxaborolan-2-yl)phenyl)-9H-carbazole-3-carbonitrile, 0.423 g (0.366 mmol) of Pd(PPh$_3$)$_4$, and 2.53 g (18.3 mmol) of potassium carbonate were added to a mixture of 30 mL of THF and 15 mL of water, and stirred under reflux for 18 hours. After completion of the reaction, the reaction mixture was cooled to room temperature and the aqueous layer was removed therefrom through extraction. The remaining was filtered under reduced pressure through a silica gel, and the filtrate was concentrated under reduced pressure. The product was filtered by silica gel column chromatography, so as to obtain Compound 144 (4.01 g, yield of 88%).

LC-Mass (calculated: 621.22 g/mol, found: M+1=622 g/mol)

Synthesis Example 6: Synthesis of Compound 162

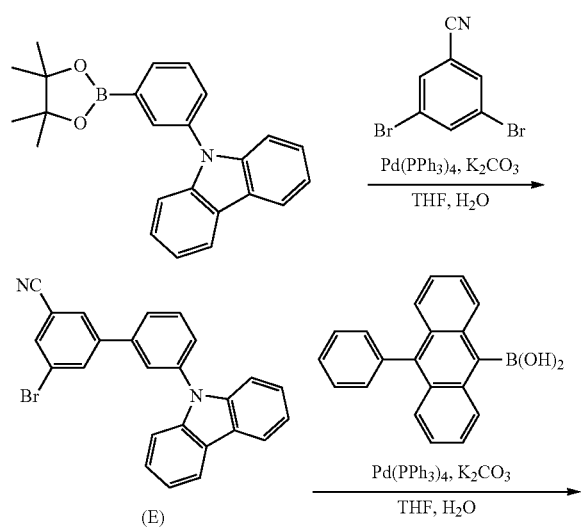

(E)

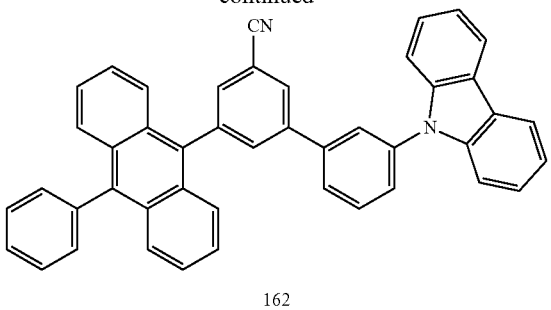

162

(1) Synthesis of Intermediate (E)

5.00 g (13.5 mmol) of 9-(3-(4,4,5,5-tetramethyl-1,3,2-dioxaborolan-2-yl)phenyl)-9H-carbazole, 5.30 g (20.3 mmol) of 3,5-dibromobenzonitrile, 0.782 g (0.677 mmol) of Pd(PPh$_3$)$_4$, and 4.68 g (33.9 mmol) of potassium carbonate added to a mixture of 50 mL of THF and 25 mL of water, and stirred under reflux for 18 hours. After completion of the reaction, the reaction mixture was cooled to room temperature and the aqueous layer was removed therefrom through extraction. The remaining was filtered under reduced pressure through a silica gel, and the filtrate was concentrated under reduced pressure. The product was filtered by silica gel column chromatography, so as to obtain Intermediate (E) (4.36 g, yield of 76%).

LC-Mass (calculated: 422.04 g/mol, found: M$^{+1}$=423 g/mol)

(2) Synthesis of Compound 162

Compound 162 (3.38 g, yield of 80%) was obtained in the same manner as used to obtain Compound 144 of Synthesis Example 5, except that 3.00 g (7.09 mmol) of Intermediate (E) was used instead of 9-(4-bromophenyl)-10-phenylanthracene) and 2.32 g (7.80 mmol) of (10-phenylanthracene-9-yl)boronic acid was used instead of 9-(3-cyano-5-(4,4,5,5-tetramethyl-1,3,2-dioxaborolan-2-yl)phenyl)-9H-carbazole-3-carbonitrile.

LC-Mass (calculated: 596.23 g/mol, found: M+1=597 g/mol)

Synthesis Example 7: Synthesis of Compound 166

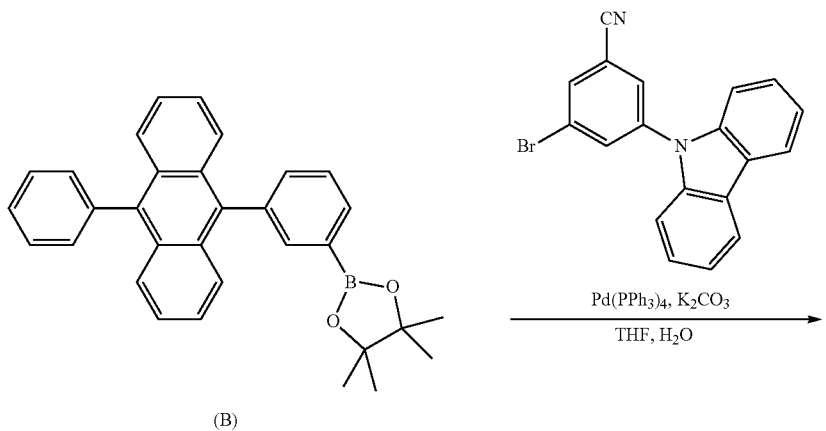

(B)

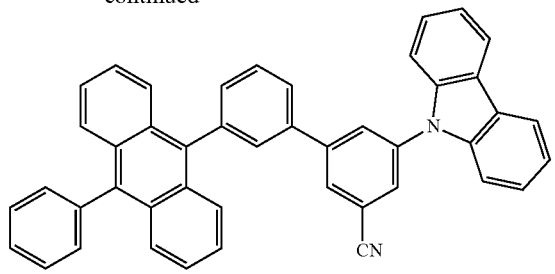

166

Compound 166 (4.33 g, yield of 84%) was obtained in the same manner as used to obtain Compound 144 of Synthesis Example 5, except that 3.00 g (8.64 mmol) of 3-bromo-5-(9H-carbazol-9-yl)benzonitrile was used instead of 9-(4-bromophenyl)-10-phenylanthracene(9-(4-bromophenyl)-10-phenylanthracene) and 4.34 g (9.50 mmol) of Intermediate (B) was used instead of 9-(3-cyano-5-(4,4,5,5-tetramethyl-1,3,2-dioxaborolan-2-yl)phenyl)-9H-carbazole-3-carbonitrile.

LC-Mass (calculated: 596.23 g/mol, found: M+1=597 g/mol)

Synthesis Example 8: Synthesis of Compound 186

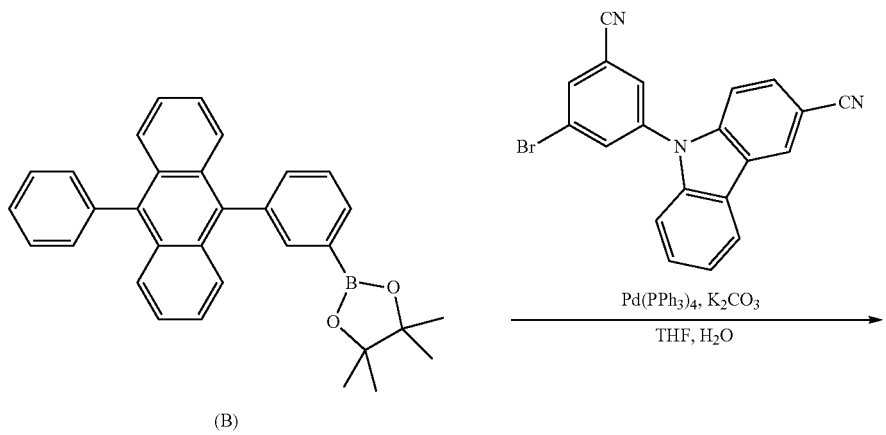

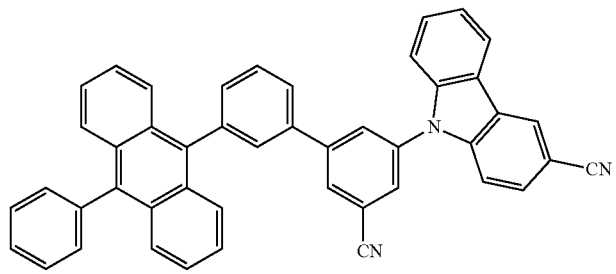

186

Compound 186 (3.46 g, yield of 69%) was obtained in the same manner as used to obtain Compound 144 of Synthesis Example 5, except that 3.00 g (8.06 mmol) of 9-(3-bromo-5-cyanophenyl)-9H-carbazole-3-carbonitrile was used instead of 9-(4-bromophenyl)-10-phenylanthracene and 4.05 g (8.87 mmol) of Intermediate (B) was used instead of 9-(3-cyano-5-(4,4,5,5-tetramethyl-1,3,2-dioxaborolan-2-yl)phenyl)-9H-carbazole-3-carbonitrile.

LC-Mass (calculated: 621.22 g/mol, found: M+1=622 g/mol)

Synthesis Example 9: Synthesis of Compound 384
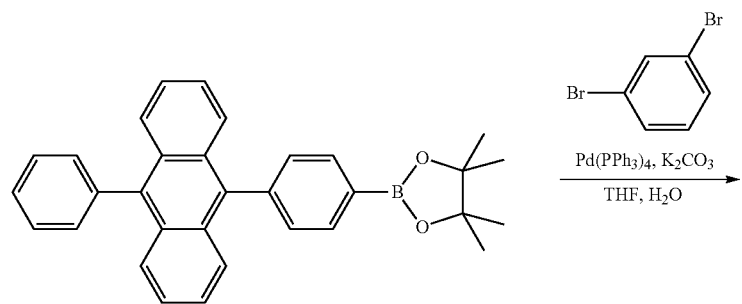
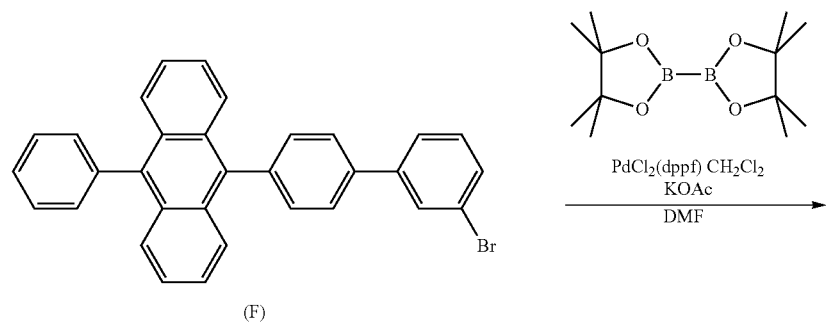
(F)
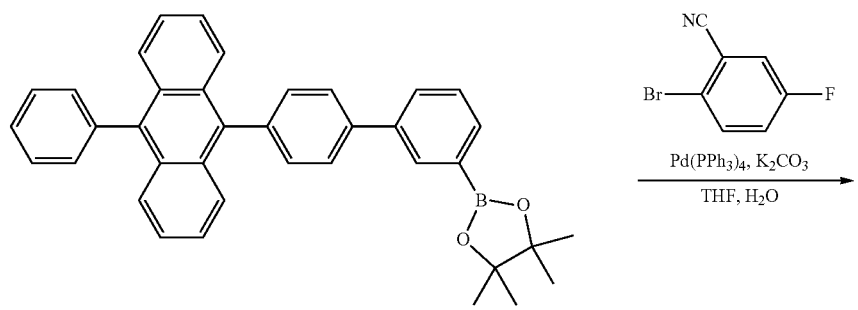
(G)
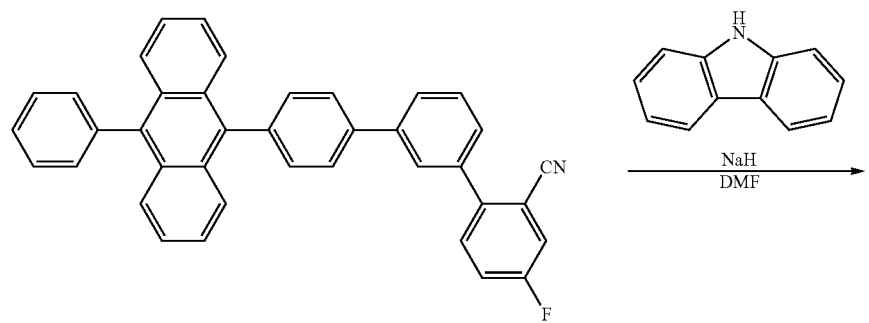
(H)

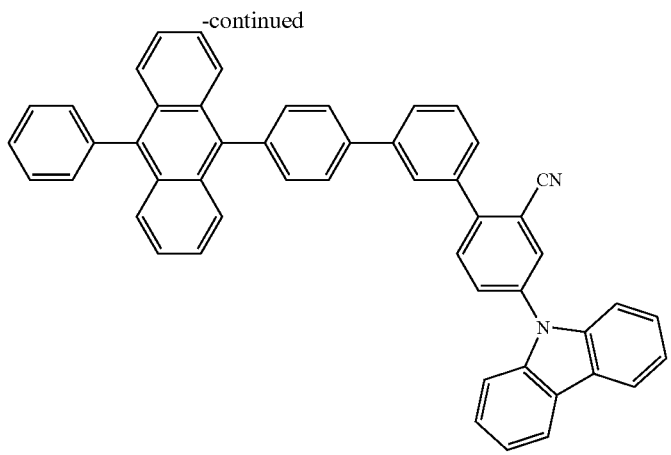

384

(1) Synthesis of Intermediate (F)

Intermediate (F) (3.51 g, 66% yield) was obtained in the same manner as used to obtain Intermediate (E) of Synthesis Example 6, except that 5.00 g (11.0 mmol) of 4,4,5,5-tetramethyl-2-(4-(10-phenylanthracene-9-yl)phenyl)-1,3,2-dioxaborolane was used instead of 9-(3-(4,4,5,5-tetramethyl-1,3,2-dioxaborolan-2-yl)phenyl)-9H-carbazole and 3.88 g (16.4 mmol) of 1,3-dibromobenzene was used instead of 3,5-dibromobenzonitrile.

LC-Mass (calculated: 484.08 g/mol, found: M+1=485 g/mol)

(2) Synthesis of Intermediate (G)

Intermediate (G) (2.73 g, yield of 71%) was obtained in the same manner as used to obtain Intermediate (B) of Synthesis Example 3, except that 3.50 g (7.21 mmol) of Intermediate (F) was used instead of 9-(3-bromophenyl)-10-phenylanthracene.

LC-Mass (calculated: 532.26 g/mol, found: M+1=533 g/mol)

(3) Synthesis of Intermediate (H)

Intermediate (H) (1.90 g, yield of 77%) was obtained in the same manner as used to obtain Intermediate (A) of Synthesis Example 1, except that 2.50 g (4.69 mmol) of Intermediate (G) was used instead of (10-phenylanthracene-9-yl)boronic acid and 1.03 g (5.16 mmol) of 2-bromo-5-fluorobenzonitrile was used instead of instead of 4-bromo-4'-fluoro-[1,1'-biphenyl]-3-carbonitrile.

LC-Mass (calculated: 521.19 g/mol, found: $M^{+1}$=522 g/mol)

(4) Synthesis of Compound 384

Compound 384 (1.63 g, yield of 75%) was obtained in the same manner as used to obtain Compound 1 of Synthesis Example 1, except that 1.70 g (3.23 mmol) of Intermediate (H) was used instead of Intermediate (A).

LC-Mass (calculated: 672.26 g/mol, found: M+1=673 g/mol)

Synthesis Example 10: Synthesis of Compound 428

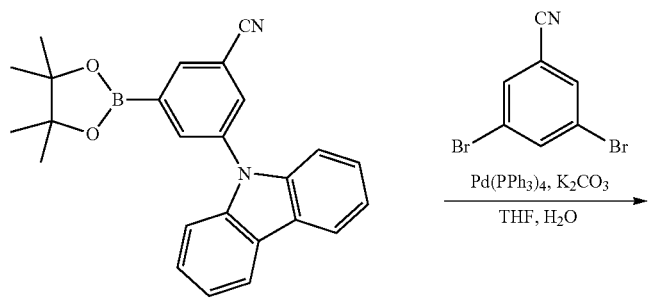

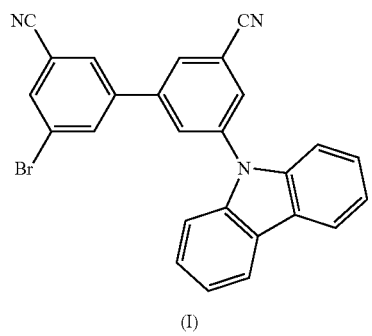 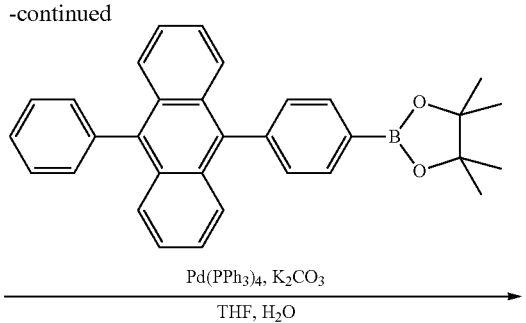

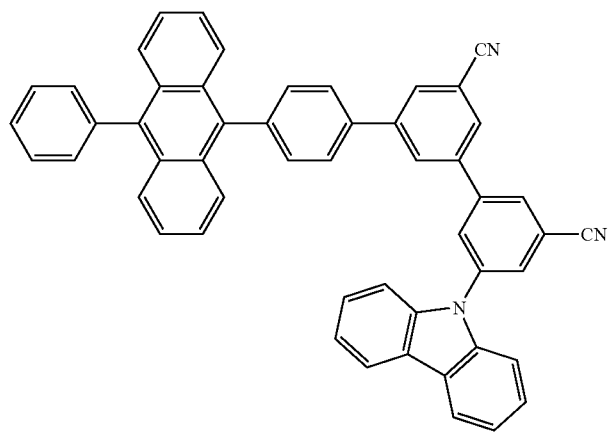

428

(1) Synthesis of Intermediate (I)

Intermediate (F) (3.12 g, yield of 74%) was obtained in the same manner as used to obtain Intermediate (E) of Synthesis Example 6, except that 5.00 g (9.39 mmol) of 3-(9H-carbazol-9-yl)-5-(4,4,5,5-tetramethyl-1,3,2-dioxaborolan-2-yl)benzonitrile was used instead of 9-(3-(4,4,5,5-tetramethyl-1,3,2-dioxaborolan-2-yl)phenyl)-9H-carbazole.

LC-Mass (calculated: 447.04 g/mol, found: M+1=448 g/mol)

(2) Synthesis of Compound 428

Compound 428 (2.71 g, yield of 58%) was obtained in the same manner as used to obtain Compound 144 of Synthesis Example 5, except that 3.00 g (7.09 mmol) of Intermediate (I) was used instead of 9-(4-bromophenyl)-10-phenylanthracene) and 3.36 g (7.36 mmol) of 4,4,5,5-tetramethyl-2-(4-(10-phenylanthracene-9-yl)phenyl)-1,3,2-dioxaborolane was used instead of 9-(3-cyano-5-(4,4,5,5-tetramethyl-1,3,2-dioxaborolan-2-yl)phenyl)-9H-carbazole-3-carbonitrile.

LC-Mass (calculated: 697.25 g/mol, found: M+1=698 g/mol)

Synthesis Example 11: Synthesis of Compound 430

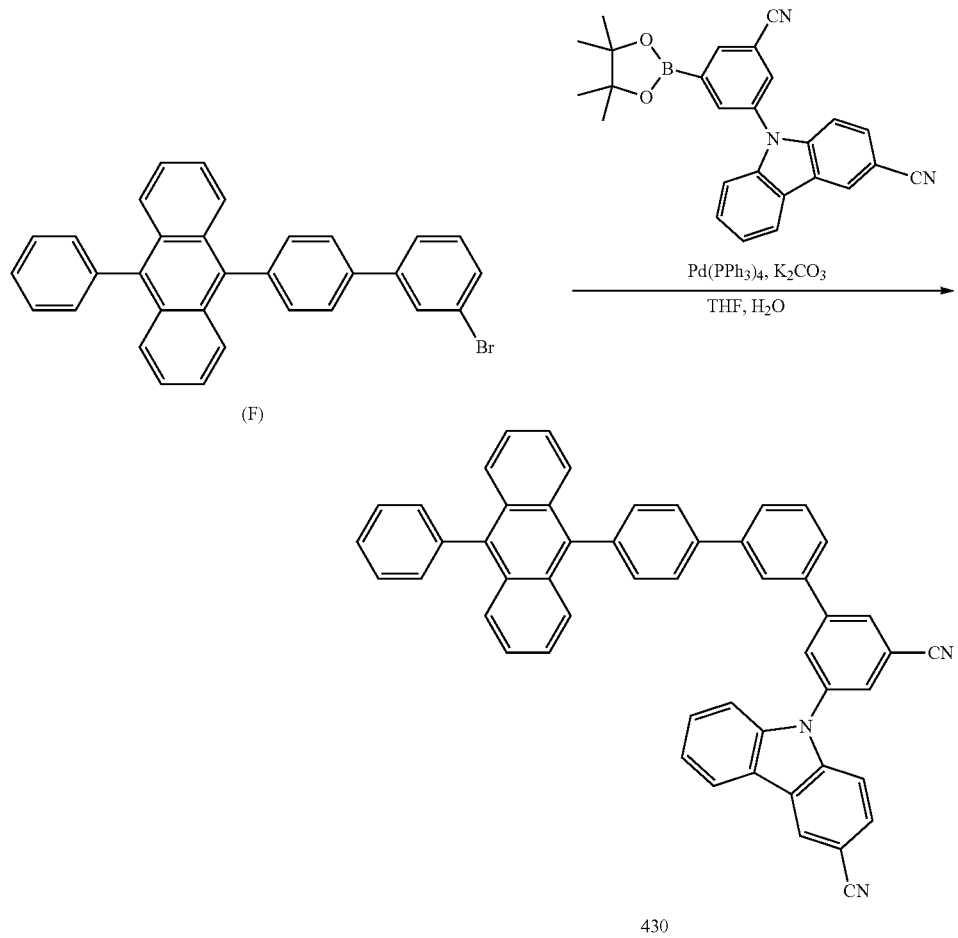

(1) Synthesis of Compound 430

Compound 430 (3.97 g, yield of 92%) was obtained in the same manner as used to obtain Compound 144 of Synthesis Example 5, except that 3.00 g (6.18 mmol) of Intermediate (F) was used instead of 9-(4-bromophenyl)-10-phenylanthracene.

LC-Mass (calculated: 697.25 g/mol, found: M+1=698 g/mol)

Example 1

An ITO-patterned glass substrate (50 mm×50 mm×0.7 mm) was ultrasonically cleaned in acetone, isopropyl alcohol, and distilled water, each for 20 minutes, and then, heat-treated at a temperature of 250° C. for 10 minutes.

Then, HATCN was deposited on the ITO electrode (anode) on the glass substrate at a deposition rate of 1 Å/sec to form a hole injection layer having a thickness of 100 Å, and NPB was deposited on the hole injection layer at a deposition rate of 1 Å/sec to form a hole transport layer having a thickness of 800 Å.

Then, mCP was deposited on the hole transport layer at a deposition rate of 1 Å/sec to form an electron blocking layer having a thickness of 50 Å.

Compound 1 (host) and Compound D1 (dopant) were co-deposited on the electron blocking layer respectively at deposition rates of 0.97 Å/sec and 0.03 Å/sec to form an emission layer having a thickness of 200 Å.

DPEPO and LiQ (at the ratio of 1:1) were co-deposited on the emission layer at the deposition rate of 0.5 Å/sec to form an electron transport layer having a thickness of 300 Å, LiQ was deposited on the electron transport layer at the deposition rate of 0.5 Å/sec to form an electron injection layer having a thickness of 10 Å, and then, Al was vacuum-deposited on the electron injection layer to form a second electrode(cathode) having a thickness of 1,000 Å, thereby completing the manufacture of an organic light-emitting device having the structure of ITO/HATCN (100 Å)/NPB (800 Å)/mCP (50 Å)/Compound 1+Compound D1 (3 volume %) (200 Å)/DPEPO:LiQ (300 Å)/LiQ (10 Å)/Al (1,000 Å).

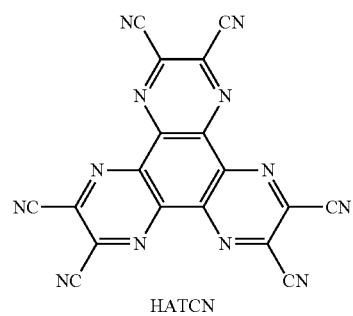

HATCN

-continued

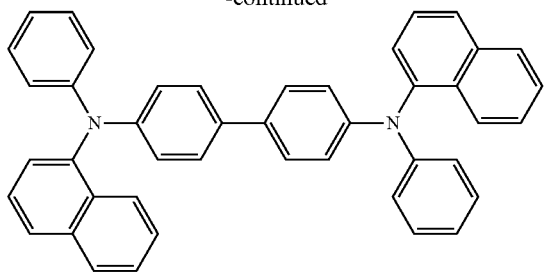

NPB

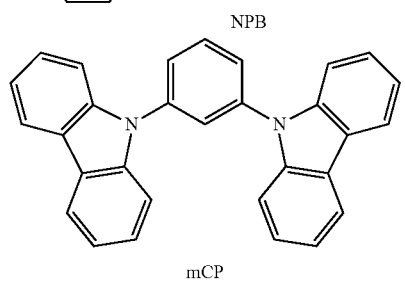

mCP

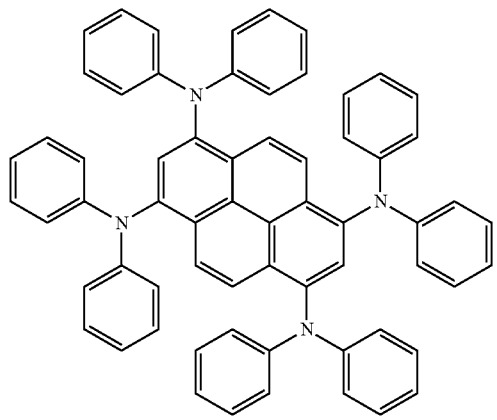

D1

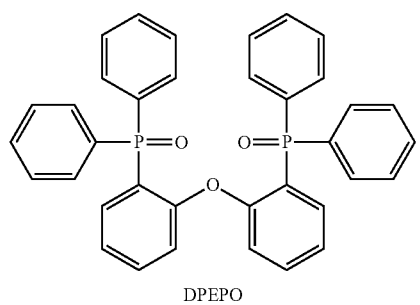

DPEPO

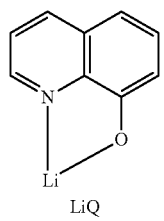

LiQ

Examples 2 to 11 and Comparative Examples 1 and 2

Organic light-emitting devices were manufactured in the same manner as in Example 1, except that Compounds shown in Table 2 were each used instead of Compound 1 as a host in forming an emission layer.

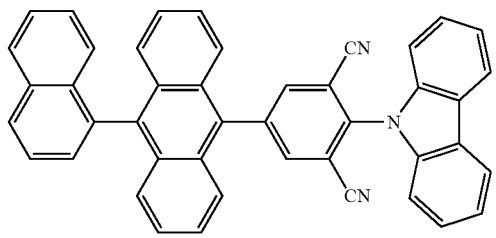

A

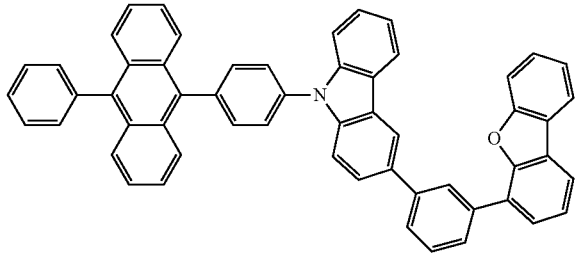

B

Evaluation Example 1: Evaluation of Characteristics of Organic Light-Emitting Device For each of the organic light-emitting devices manufactured according to Examples 1 to 11 and Comparative Examples 1 to 2, the luminescence quantum efficiency (PLQY), external quantum efficiency (EQE), TTF ratio, and lifespan (T95) were evaluated as relative values. The results are shown in Table 2. This evaluation was performed using a current-voltage meter (Keithley 2400) and a luminescence meter (Minolta Cs-1,000A), and the lifespan ($T_{95}$) (at 1,200 candela per square meter ($Cd/m^2$)) was evaluated by measuring, as a relative value, the amount of time that elapsed until luminance was reduced to 95% of the initial brightness of 100%. The TTF ratio was obtained by taking the square of the inverse of the y-intercept value in the graph of, with respect to time, the 1/square root of the TrEL (1/sqrt (TrEL)) from 500 nanoseconds (ns) to 4,000 ns after the decay of the transient electroluminescence (TrEL) was measured.

TABLE 2

| No. | Emission Layer Host | Driving voltage (relative value, %) | EQE (relative value, %) | Lifespan (T$_{95}$) (relative value, %) | TTF ratio (%) | Emission color |
|---|---|---|---|---|---|---|
| Example 1 | Compound 1 | 70 | 168 | 200 | 14.5 | Blue |
| Example 2 | Compound 21 | 81 | 134 | 171 | 9.8 | Blue |
| Example 3 | Compound 66 | 74 | 250 | 479 | 14.6 | Blue |
| Example 4 | Compound 141 | 78 | 252 | 767 | 21.7 | Blue |
| Example 5 | Compound 144 | 83 | 104 | 235 | 2.9 | Blue |
| Example 6 | Compound 162 | 71 | 235 | 276 | 7.6 | Blue |
| Example 7 | Compound 166 | 70 | 322 | 280 | 9.3 | Blue |
| Example 8 | Compound 186 | 75 | 157 | 267 | 5.7 | Blue |
| Example 9 | Compound 384 | 84 | 486 | 319 | 27.8 | Blue |
| Example 10 | Compound 428 | 75 | 226 | 257 | 7.2 | Blue |
| Example 11 | Compound 430 | 74 | 219 | 343 | 4.7 | Blue |
| Comparative Example 1 | Compound A | 100 | 100 | 100 | 2.5 | Blue |
| Comparative Example 2 | Compound B | 154 | 102 | 34 | 1.2 | Blue |

Referring to Table 2, it was confirmed that the organic light-emitting devices of Examples 1 to 11 had excellent external quantum efficiency, a long lifespan, and a high TTF ratio, compared to the organic light-emitting devices of Comparative Examples 1 and 2.

According to the one or more embodiments, a heterocyclic compound may have excellent electric characteristics and high thermal stability. Accordingly, an organic light-emitting device including the heterocyclic compound may have a low driving voltage, high efficiency, high power, high quantum efficiency, and a long lifespan. In addition, the heterocyclic compound satisfies a specific lowest excitation singlet (S1) energy level and a specific lowest excitation triplet (T1) energy level, and in this regard, an organic light-emitting device including the heterocyclic compound may efficiently undergo a triplet-triplet fusion (TTF) phenomenon, thereby having highly efficient fluorescence characteristics.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A heterocyclic compound represented by Formula 1:

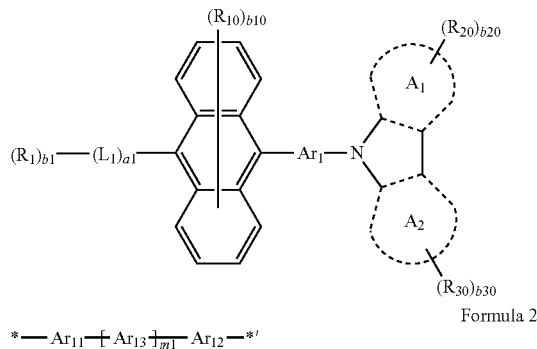

Formula 1 wherein, in Formula 1,

Ar$_1$ is a group represented by Formula 2,

Ar$_1$ comprises at least one cyano group,

A$_1$ and A$_2$ are each independently a C$_5$-C$_{30}$ carbocyclic group or a C$_1$-C$_{30}$ heterocyclic group, each L$_1$ is independently an unsubstituted or substituted C$_5$-C$_{30}$ carbocyclic group or an unsubstituted or substituted C$_1$-C$_{30}$ heterocyclic group, and a1 is 0, 1, 2, or 3, wherein, when a1 is 2 or more, two or more L$_1$(s) are identical to or different from each other, wherein, in Formula 2, Ar$_{11}$ is a group represented by Formula 4, Ar$_{12}$ is a group represented by Formula 5, and Ar$_{13}$ is a group represented by Formula 6, and m1 is 0, 1, 2, or 3,

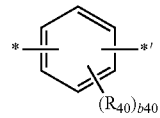

Formula 4

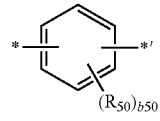

Formula 5

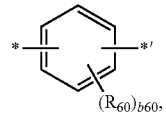

Formula 6 and wherein, in Formulae 1, 2, 4, 5, and 6,

R$_1$, R$_{10}$, R$_{20}$, R$_{30}$, R$_{40}$, R$_{50}$, and R$_{60}$ are each independently hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), or —P(=O)($Q_8$)($Q_9$), b1 is an integer from 1 to 5, wherein, when b1 is 2 or more, two or more $R_1$(s) are identical to or different from each other, b10 is an integer from 1 to 8, wherein, when b10 is 2 or more, two or more $R_{10}$(s) are identical to or different from each other, b20 and b30 are each independently an integer from 1 to 4, wherein, when b20 is 2 or more, two or more $R_{20}$(s) are identical to or different from each other, and when b30 is 2 or more, two or more $R_{30}$(s) are identical to or different from each other, b40, b50, and b60 are each independently an integer from 1 to 4, wherein, when b40 is 2 or more, two or more $R_{40}$(s) are identical to or different from each other, when b50 is 2 or more, two or more $R_{50}$(s) are identical to or different from each other, and when b60 is 2 or more, two or more $R_{60}$(s) are identical to or different from each other,

* and *' each indicate a binding site to a neighboring atom, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroaryloxy group, the substituted $C_1$-$C_{60}$ heteroarylthio group, the substituted monovalent non-aromatic condensed polycyclic group, and the substituted monovalent non-aromatic condensed heteropolycyclic group is:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), or —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, or a monovalent non-aromatic condensed heteropolycyclic group, each substituted with at least one of deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), or —B($Q_{26}$)($Q_{27}$); or —Si($Q_{31}$)($Q_{32}$)($Q_{33}$), —N($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, or a substituted or unsubstituted monovalent non-aromatic condensed heteropolycyclic group.

2. The heterocyclic compound of claim 1, wherein $Ar_1$ is represented by one of Formulae 2-1 to 2-25:

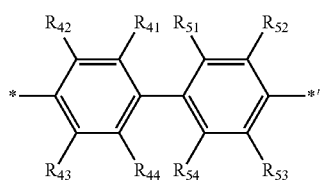
2-1

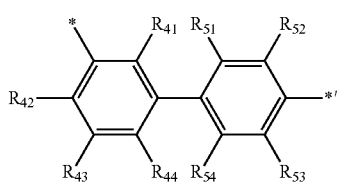
2-2

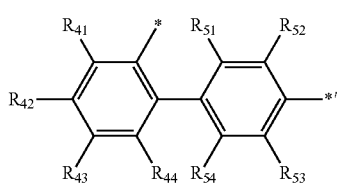
2-3

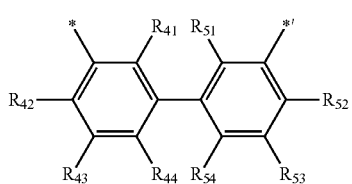
2-4

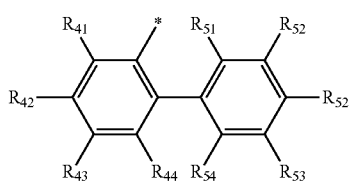
2-5

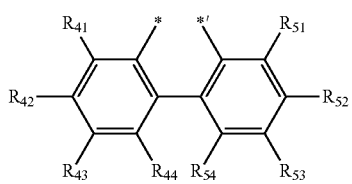
2-6

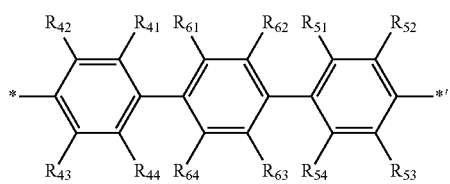
2-7

-continued

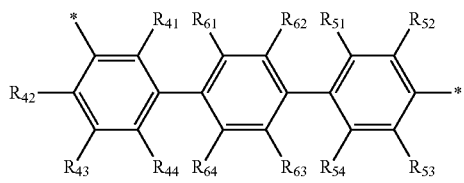
2-8

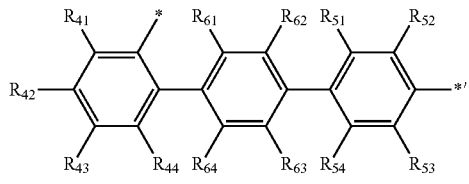
2-9

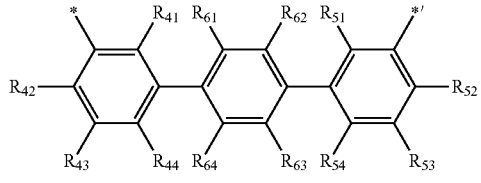
2-10

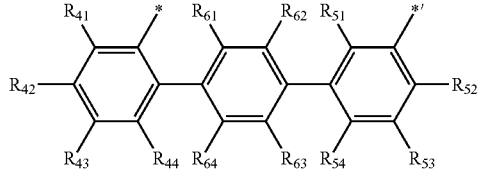
2-11

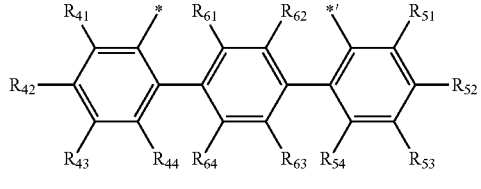
2-12

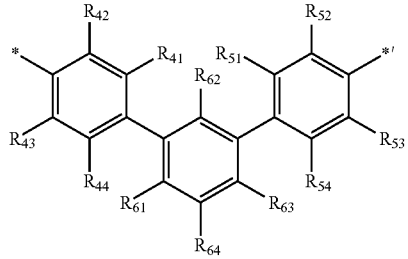
2-13

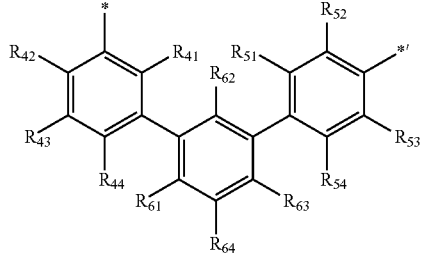
2-14

-continued
2-15
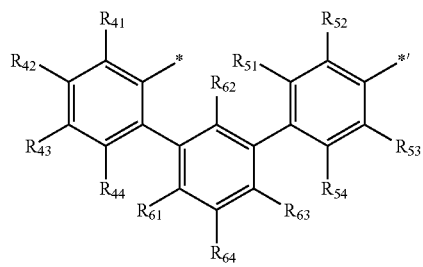
2-16
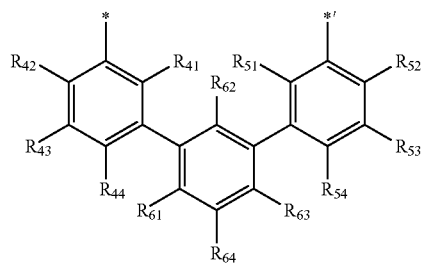
2-17
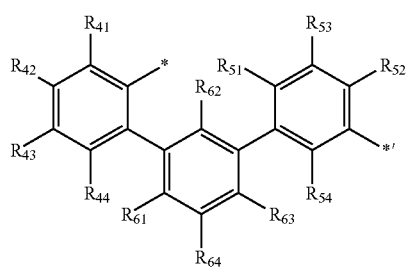
2-18
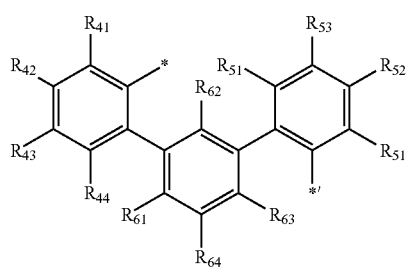
2-19
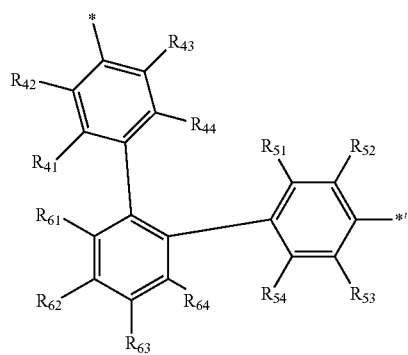
-continued
2-20
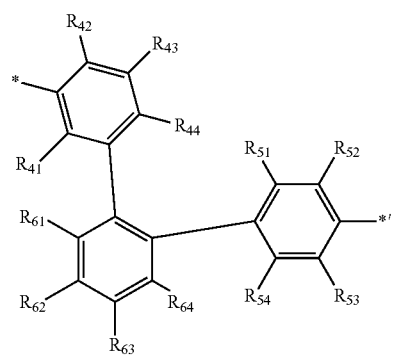
2-21
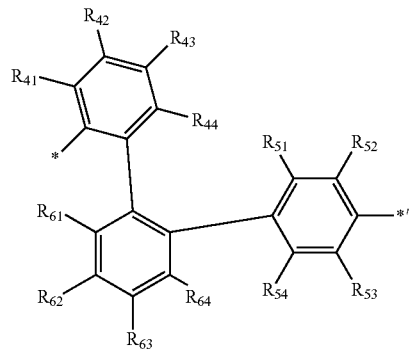
2-22
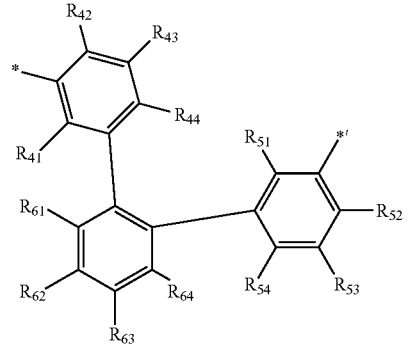
2-23
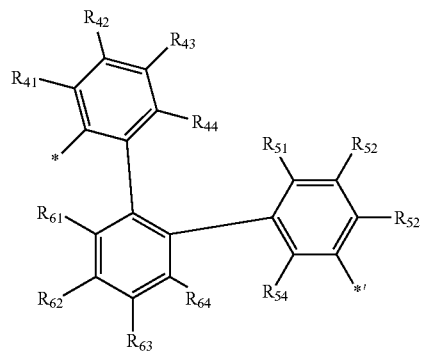

2-24

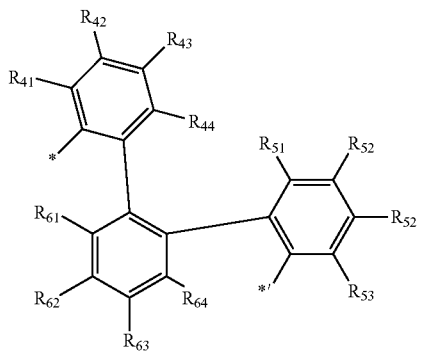

2-25

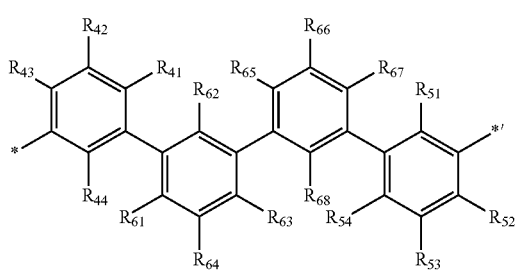

wherein, in Formulae 2-1 to 2-25, $R_{41}$ to $R_{44}$ are each independently the same as described in connection with $R_{40}$ in claim 1, $R_{51}$ to $R_{54}$ are each independently the same as described in connection with $R_{50}$ in claim 1, $R_{61}$ to $R_{68}$ are each independently the same as described in connection with $R_{60}$ in claim 1, at least one of $R_{41}$ to $R_{44}$, $R_{51}$ to $R_{54}$, and $R_{61}$ to $R_{68}$ is a cyano group, and

* and *' each indicate a binding site to a neighboring atom.

3. The heterocyclic compound of claim 1, wherein $Ar_1$ comprises 1 to 4 cyano groups.

4. The heterocyclic compound of claim 1, wherein m1 is 0, 1, or 2.

5. The heterocyclic compound of claim 1, wherein $A_1$ and $A_2$ are each independently a benzene group, a naphthalene group, an anthracene group, a phenanthrene group, a triphenylene group, a pyrene group, a 1,2,3,4-tetrahydronaphthalene group, a fluorene group, a carbazole group, a benzofuran group, a dibenzofuran group, a benzothiophene group, a dibenzothiophene group, a benzosilole group, a dibenzosilole group, an azafluorene group, an azacarbazole group, an azadibenzofuran group, an azadibenzothiophene group, an azadibenzosilole group, a pyridine group, a pyrimidine group, a pyrazine group, a pyridazine group, a triazine group, a quinoline group, an isoquinoline group, a quinoxaline group, a quinazoline group, or a phenanthroline group.

6. The heterocyclic compound of claim 1, wherein $L_1$ is:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, or a monovalent non-aromatic condensed heteropolycyclic group.

7. The heterocyclic compound of claim 1, wherein $R_1$ is a group represented by one of Formulae 9-1 to 9-19 or a group represented by one of Formulae 10-1 to 10-194:

9-1

9-2

9-3

9-4

9-5

9-6

9-7

9-8

9-9

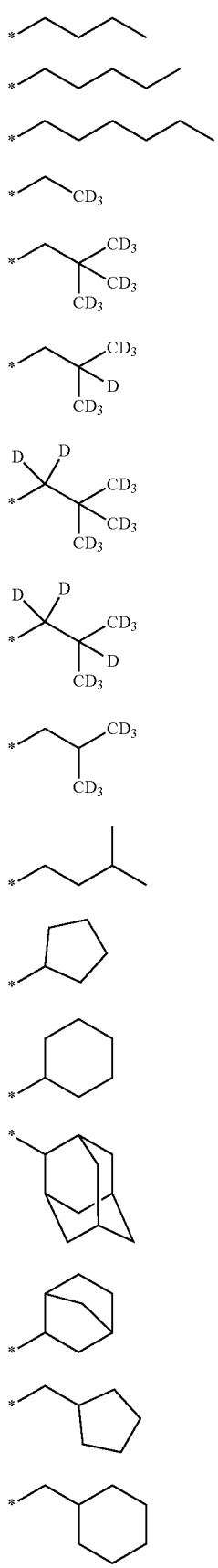
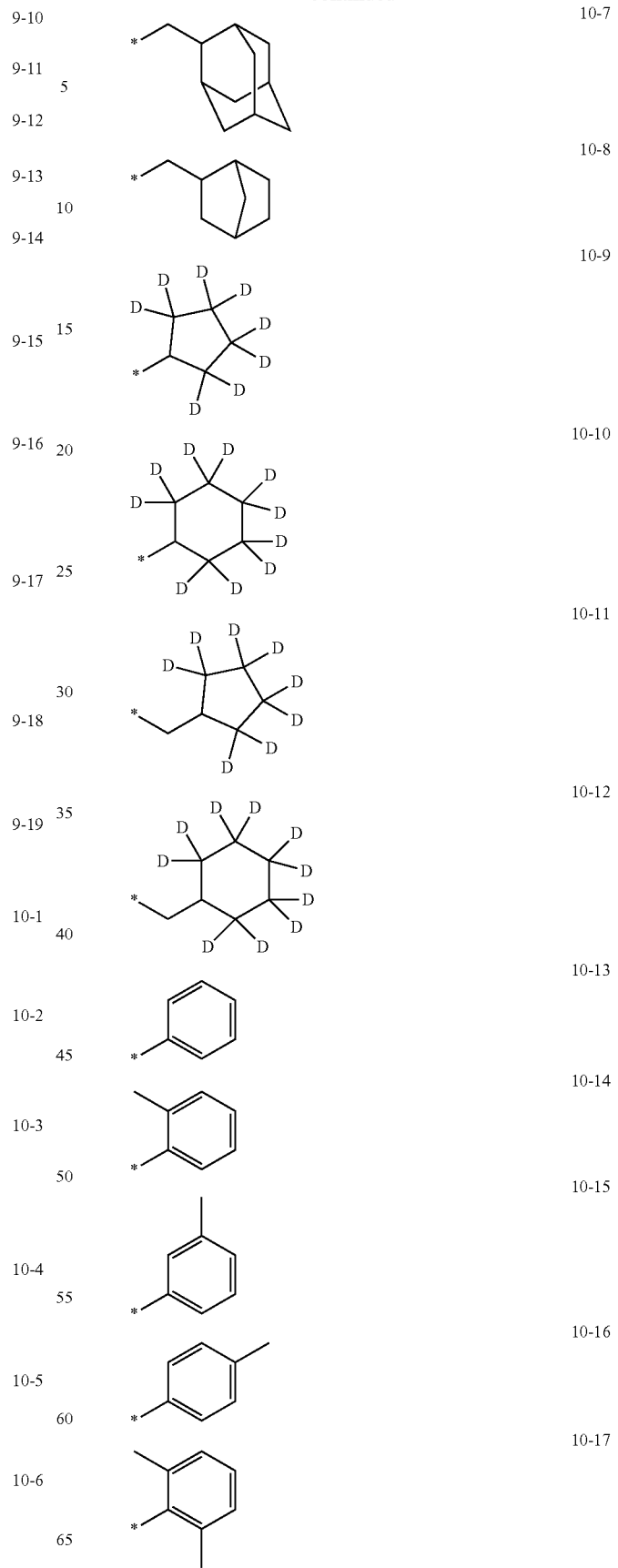

10-18 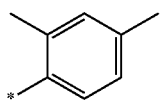
10-19 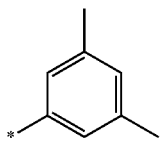
10-20 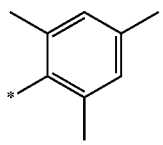
10-21 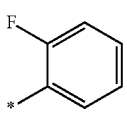
10-22 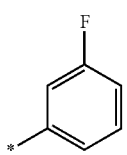
10-23 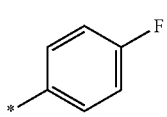
10-24 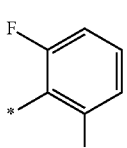
10-25 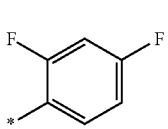
10-26 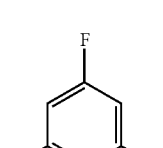
10-27 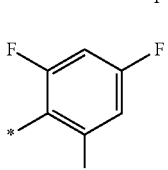
10-28 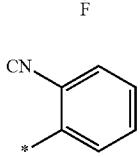
10-29 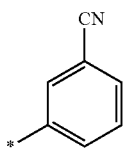
10-30 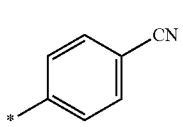
10-31 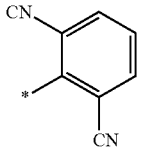
10-32 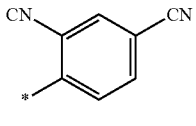
10-33 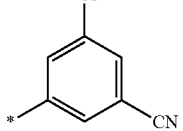
10-34 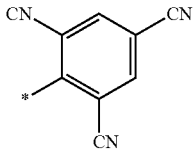
10-35 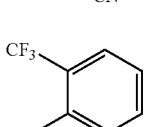
10-36 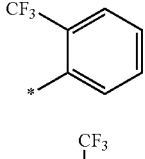
10-37 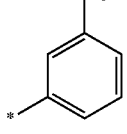
10-38 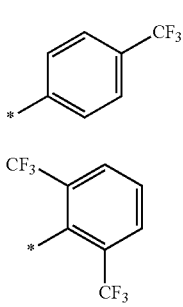
10-39 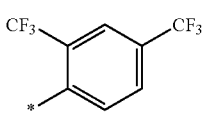

| | |
|---|---|
| 10-40 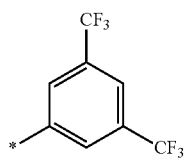 | 10-50 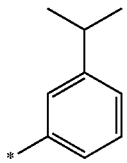 |
| 10-41 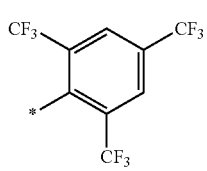 | 10-51 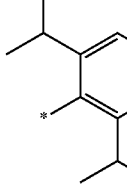 |
| 10-42 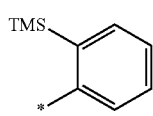 | 10-52 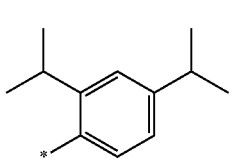 |
| 10-43 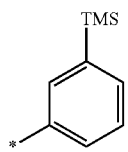 | 10-53 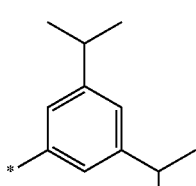 |
| 10-44 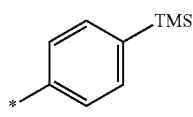 | 10-54 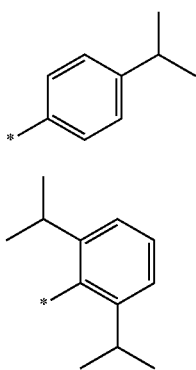 |
| 10-45 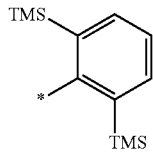 | |
| 10-46 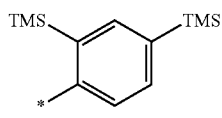 | 10-55 |
| 10-47 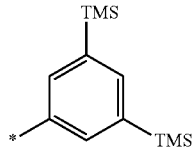 | 10-56 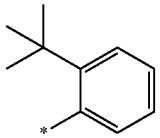 |
| 10-48 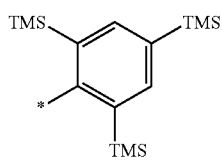 | 10-57 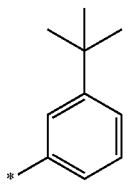 |
| 10-49 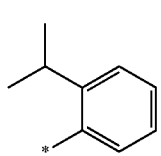 | 10-58 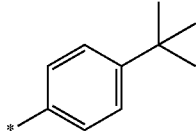 |

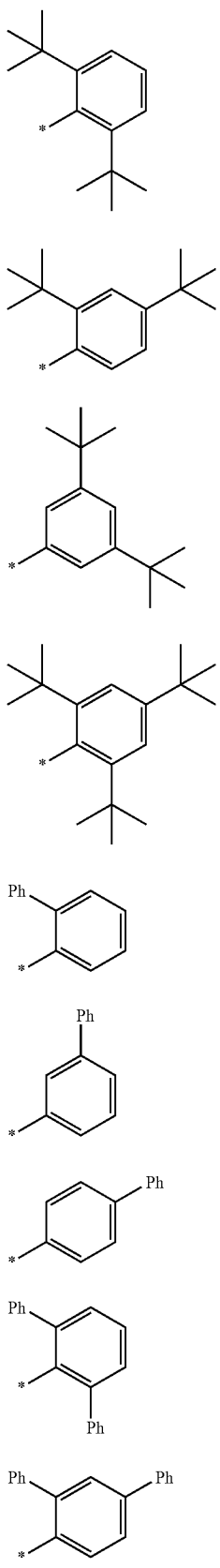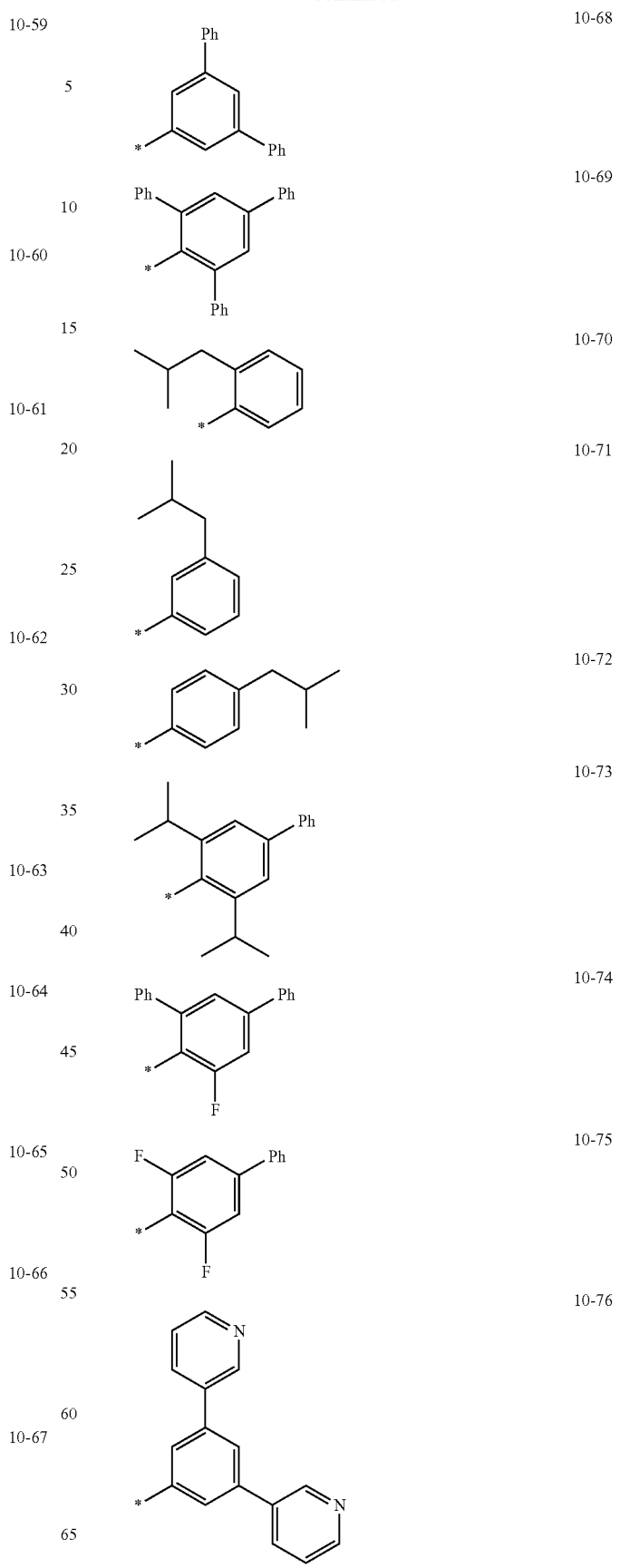

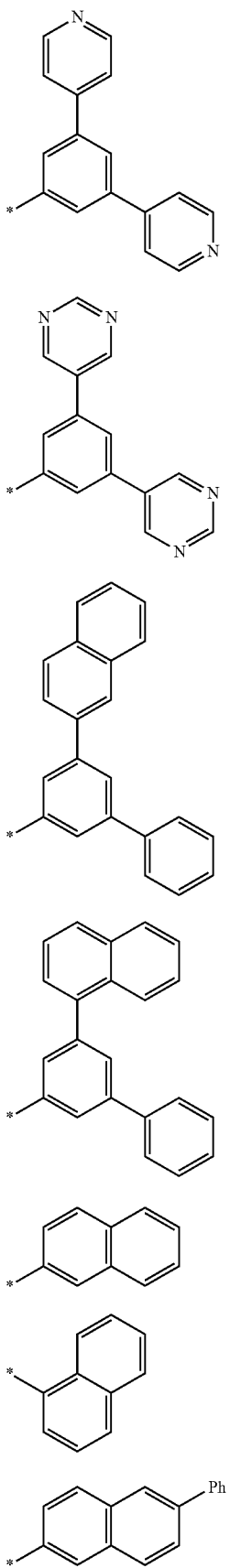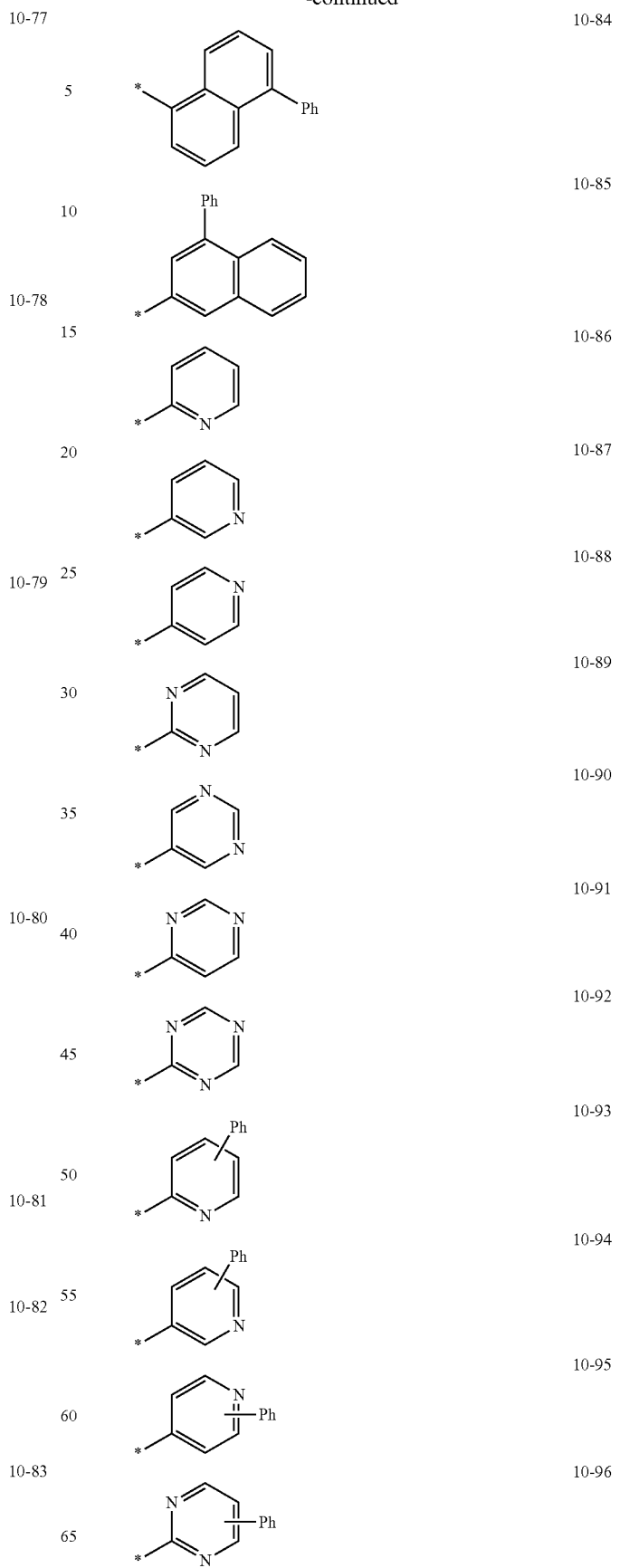

| | |
|---|---|
| 10-97 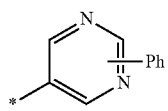 | 10-109 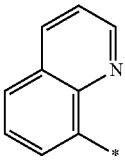 |
| 10-98 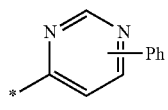 | 10-110 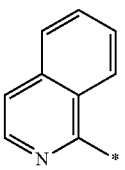 |
| 10-99 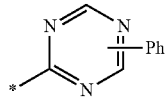 | 10-111 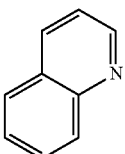 |
| 10-100 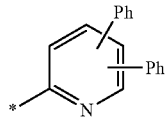 | 10-112 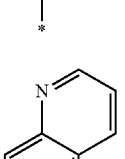 |
| 10-101 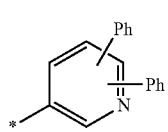 | 10-113 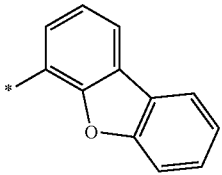 |
| 10-102 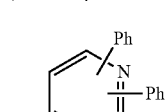 | 10-114 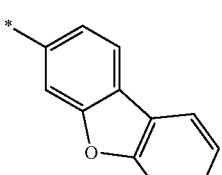 |
| 10-103 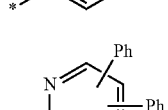 | 10-115 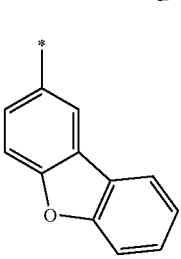 |
| 10-104 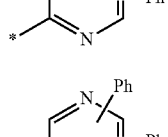 | 10-116 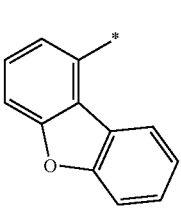 |
| 10-105 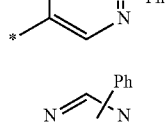 | |
| 10-106 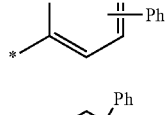 | |
| 10-107 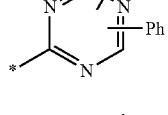 | |
| 10-108 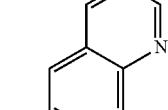 | |
| 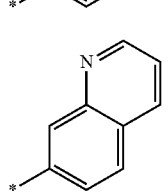 | |

| | |
|---|---|
| 10-117 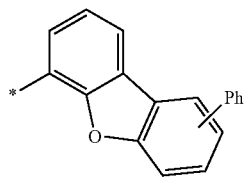 | 10-125 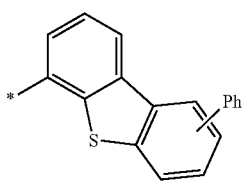 |
| 10-118 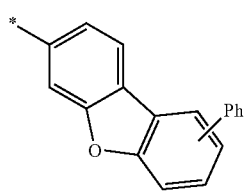 | 10-126 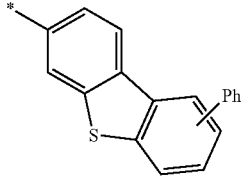 |
| 10-119 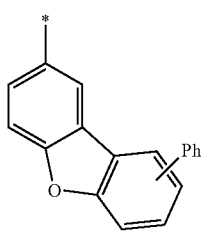 | 10-127 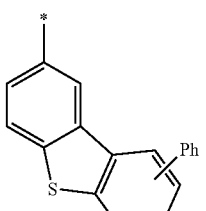 |
| 10-120 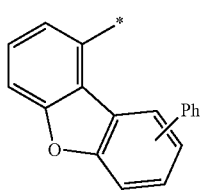 | 10-128 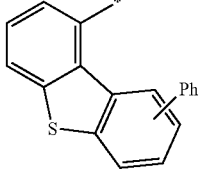 |
| 10-121 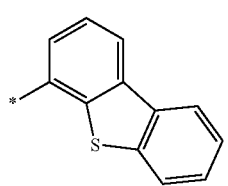 | 10-129 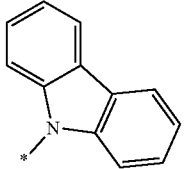 |
| 10-122 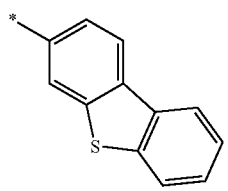 | 10-130 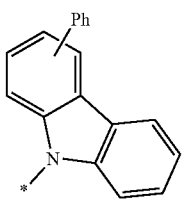 |
| 10-123 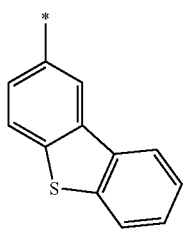 | 10-131 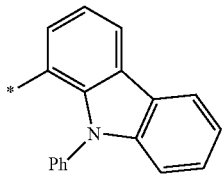 |
| 10-124 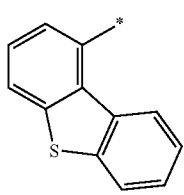 | 10-132 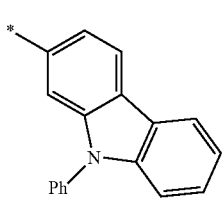 |

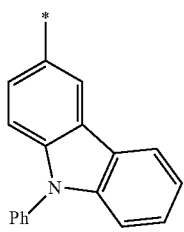
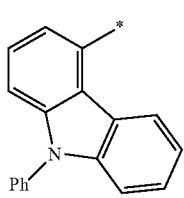
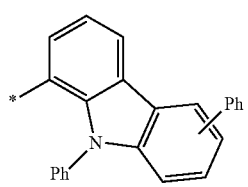
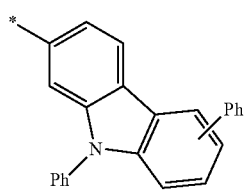
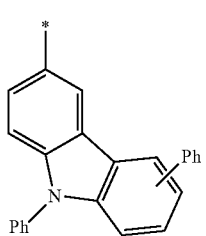
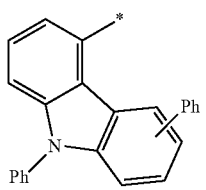
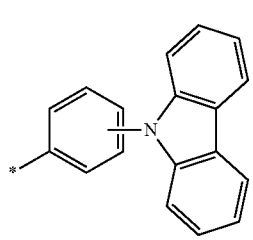
10-133
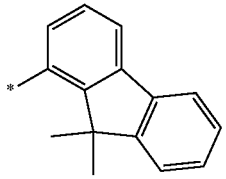
10-134
10-135
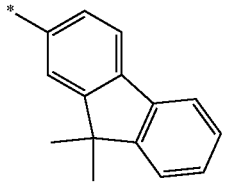
10-136
10-137
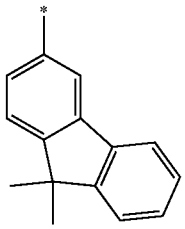
10-138
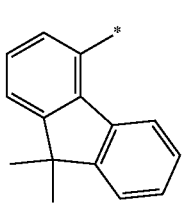
10-139
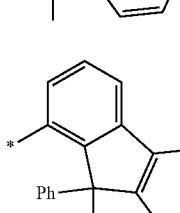
10-140
10-141
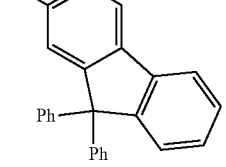
10-142
10-143
10-144
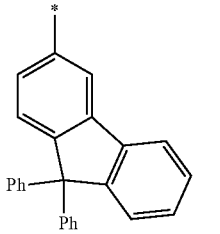
10-145
10-146

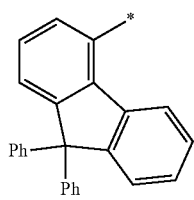
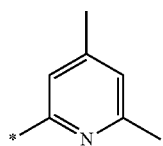
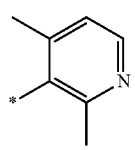
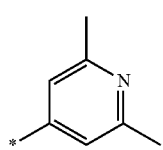
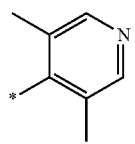
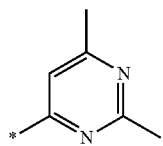
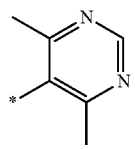
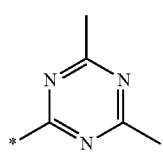
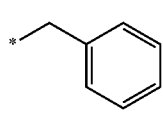
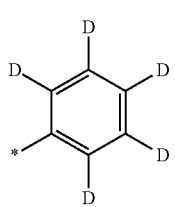
10-147
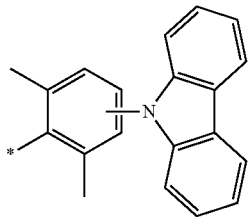
10-148
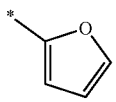
10-149
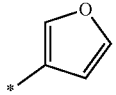
10-150
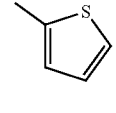
10-151
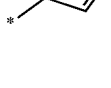
10-152
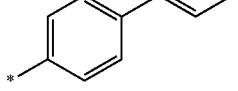
10-153
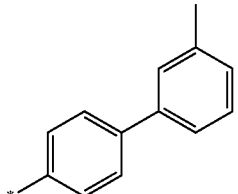
10-154
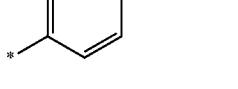
10-155
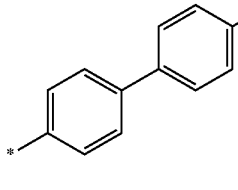
10-156
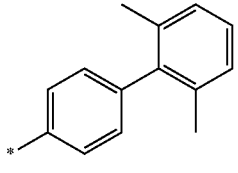
10-157
10-158
10-159
10-160
10-161
10-162
10-163
10-164
10-165
10-166
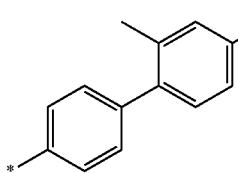

10-167
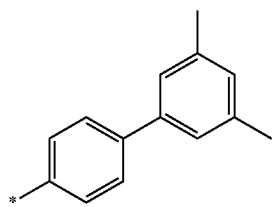
10-168
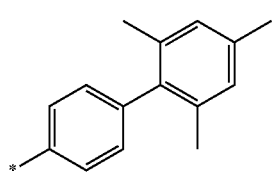
10-169
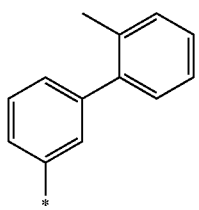
10-170
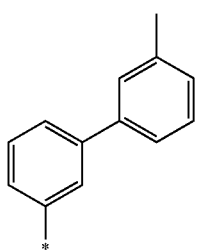
10-171
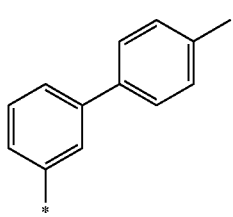
10-172
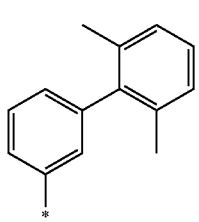
10-173
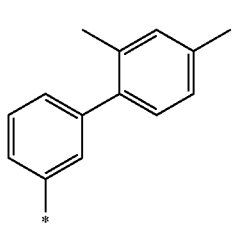
10-174
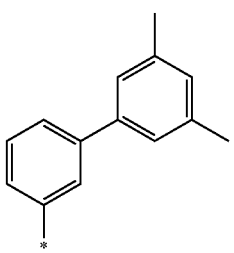
10-175
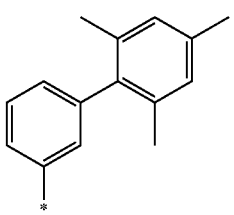
10-176
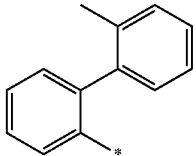
10-177
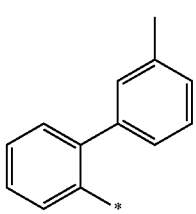
10-178
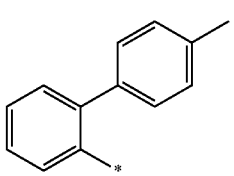
10-179
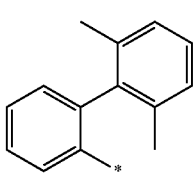
10-180
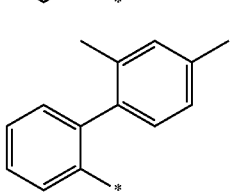
10-181
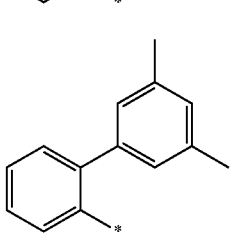

-continued 10-182 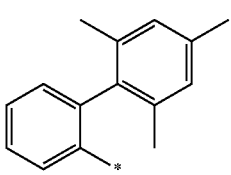

10-183 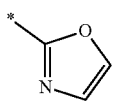

10-184 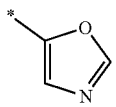

10-185 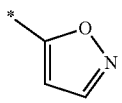

10-186 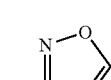

10-187 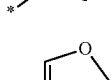

10-188 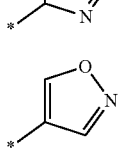

10-189 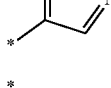

10-190 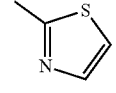

10-191 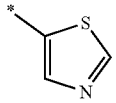

10-192 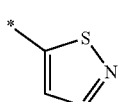

10-193 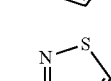

10-194 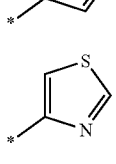

wherein, in Formulae 9-1 to 9-19 and 10-1 to 10-194, * indicates a binding site to a neighboring atom, Ph is a phenyl group, and TMS is a trimethylsilyl group.

8. The heterocyclic compound of claim 1, wherein $R_{10}$, $R_{20}$, $R_{30}$, $R_{40}$, $R_{50}$, and $R_{60}$ are each independently: hydrogen, deuterium, a cyano group, a $C_1$-$C_{20}$ alkyl group, or a $C_1$-$C_{20}$ alkoxy group;
a $C_1$-$C_{20}$ alkyl group or a $C_1$-$C_{20}$ alkoxy group, each substituted with at least one of deuterium, a cyano group, a phenyl group, a biphenyl group, a terphenyl group, or a naphthyl group;
a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, or a dibenzothiophenyl group; and
a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, or a dibenzothiophenyl group, each substituted with at least one of deuterium, a cyano group, a $C_1$-$C_{20}$ alkyl group, a $C_1$-$C_{20}$ alkoxy group, a phenyl group, a biphenyl group, a terphenyl group, or a naphthyl group.

9. The heterocyclic compound of claim 1, wherein $R_{10}$, $R_{20}$, and $R_{30}$ are each independently hydrogen or a cyano group.

10. The heterocyclic compound of claim 1, wherein the heterocyclic compound represented by Formula 1 is a compound represented by Formula 10:

Formula 10

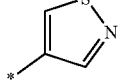

wherein, in Formula 10,
$Ar_1$, $L_1$, a1, $R_1$, and b1 are each the same as described in claim 1,
$X_{21}$ is $C(R_{21})$ or N, $X_{22}$ is $C(R_{22})$ or N, $X_{23}$ is $C(R_{23})$ or N, and $X_{24}$ is $C(R_{24})$ or N,
$X_{31}$ is $C(R_{31})$ or N, $X_{32}$ is $C(R_{32})$ or N, $X_{33}$ is $C(R_{33})$ or N, and $X_{34}$ is $C(R_{34})$ or N,
$R_{11}$ to $R_{18}$ are each independently the same as described in connection with $R_{10}$ in claim 1,
$R_{21}$ to $R_{24}$ are each independently the same as described in connection with $R_{20}$ in claim 1, and
$R_{31}$ to $R_{34}$ are each independently the same as described in connection with $R_{30}$ in claim 1.

11. The heterocyclic compound of claim 1, wherein the heterocyclic compound represented by Formula 1 satisfies Equation 1:

$$E(T1)<E(S1)<2\times E(T1) \qquad \text{Equation 1}$$

wherein, in Equation 1,
$E(T1)$ is a lowest excitation triplet energy level of the heterocyclic compound and $E(S1)$ is a lowest excitation singlet energy level of the heterocyclic compound.

12. The heterocyclic compound of claim 1, wherein the heterocyclic compound represented by Formula 1 satisfies Equation 2:

$$[2 \times E(T1)] - E(S1) < 1 \text{ electron volt} \quad \text{Equation 2}$$

wherein, in Equation 2,

E(T1) is a lowest excitation triplet energy level of the heterocyclic compound and E(S1) is a lowest excitation singlet energy level of the heterocyclic compound.

13. The heterocyclic compound of claim 1, wherein the heterocyclic compound represented by Formula 1 is represented by one of Compounds 1 to 560:

1

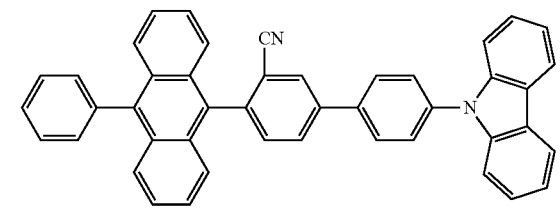

2

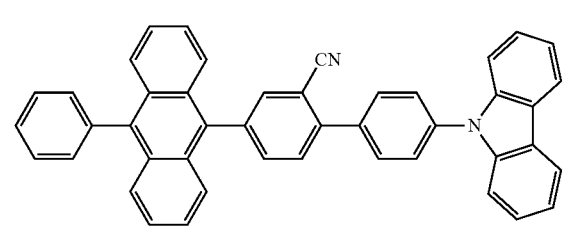

3

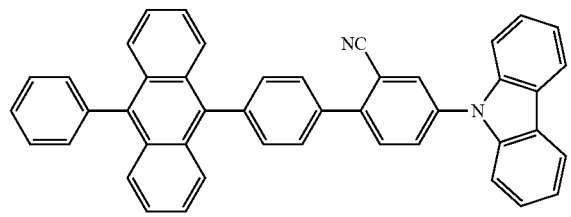

4

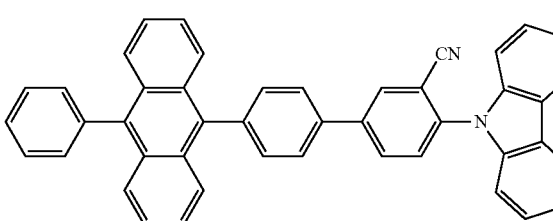

5

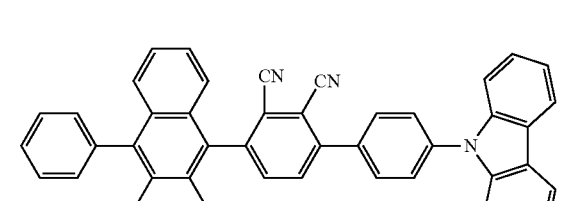

-continued

6

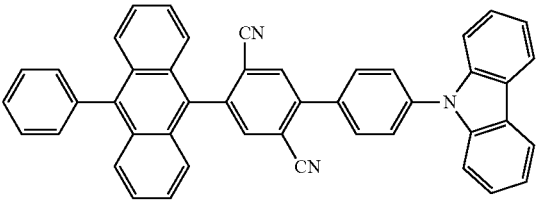

7

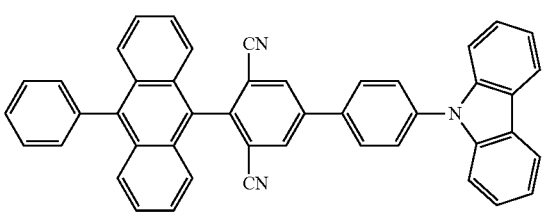

8

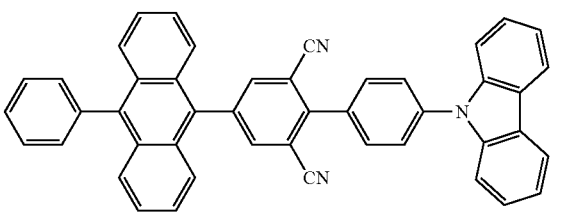

9

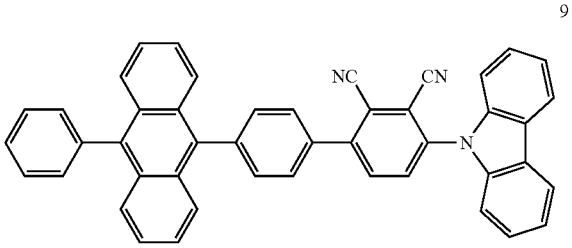

10

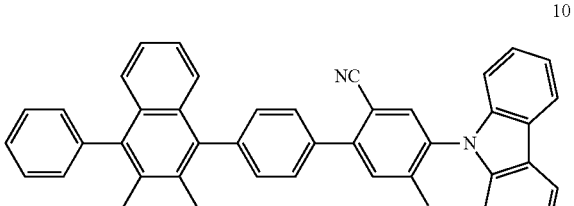

11

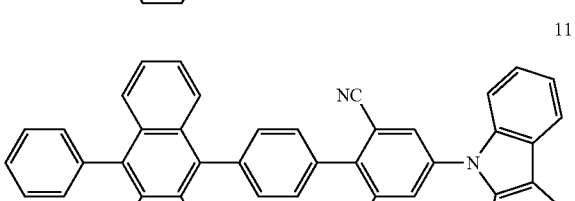

339
-continued
12
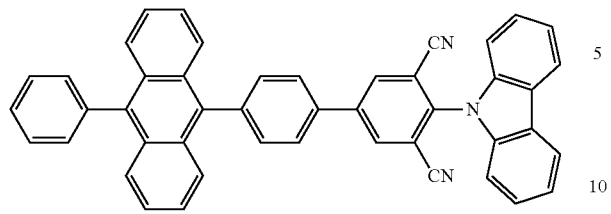
13
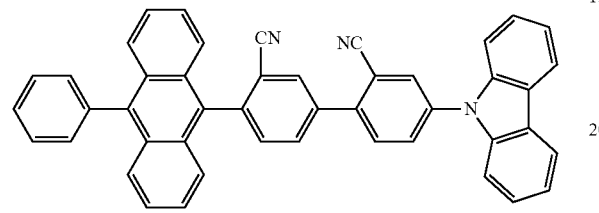
14
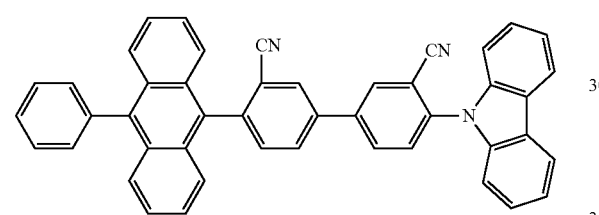
15
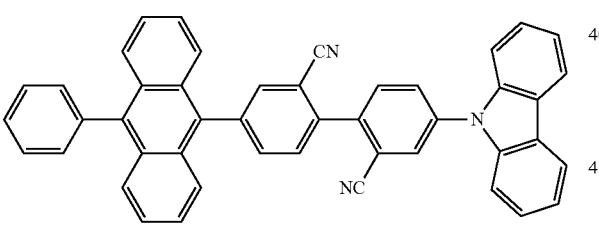
16
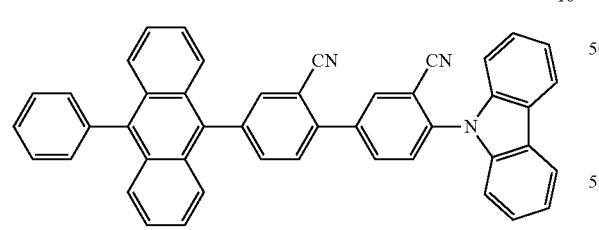
17
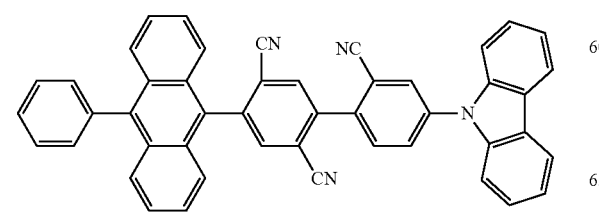
340
-continued
18
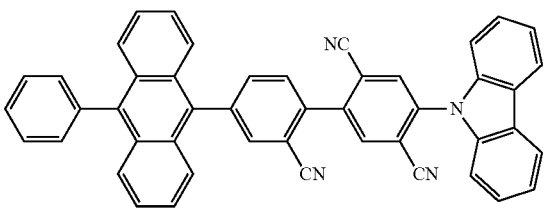
19
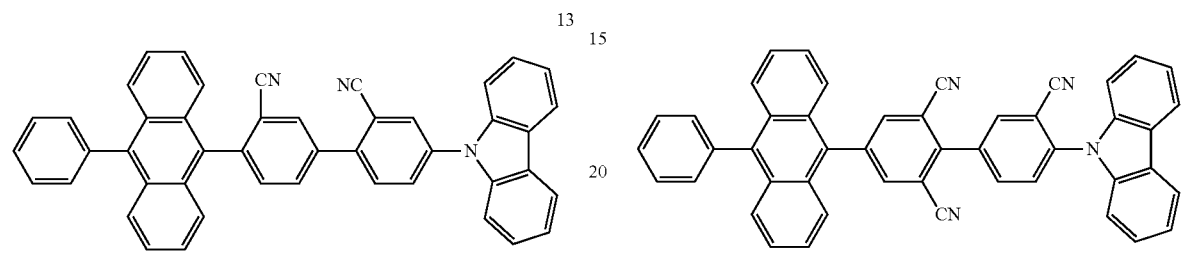
20
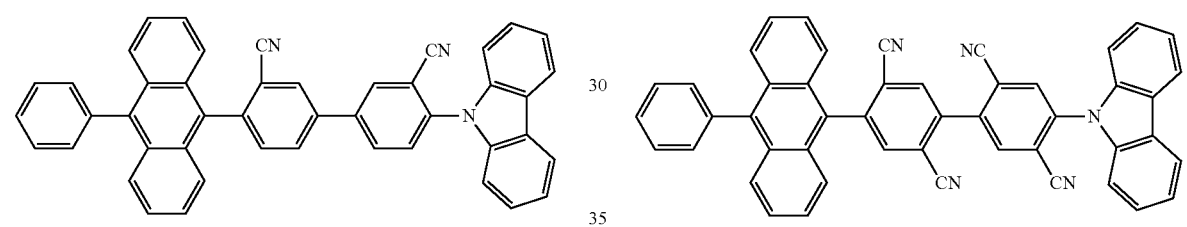
21
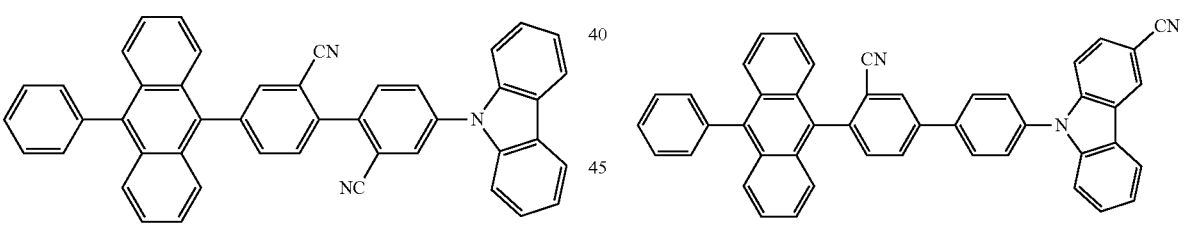
22
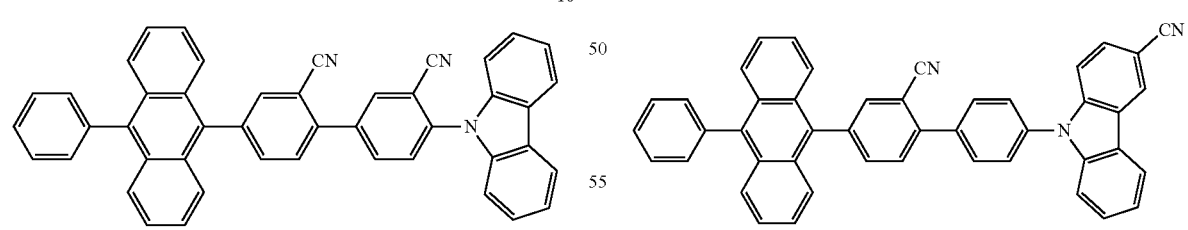
23
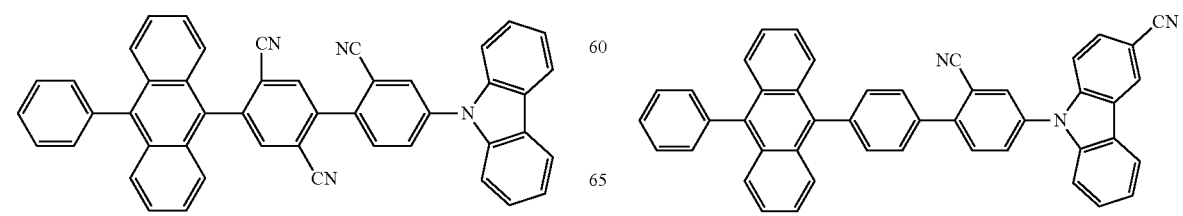

341
-continued
24
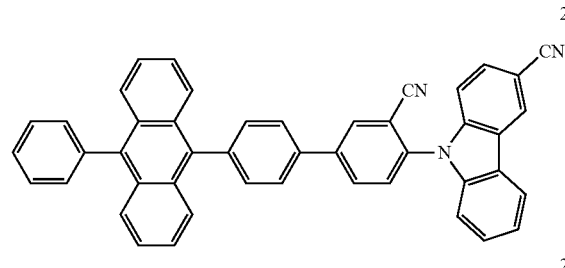
25
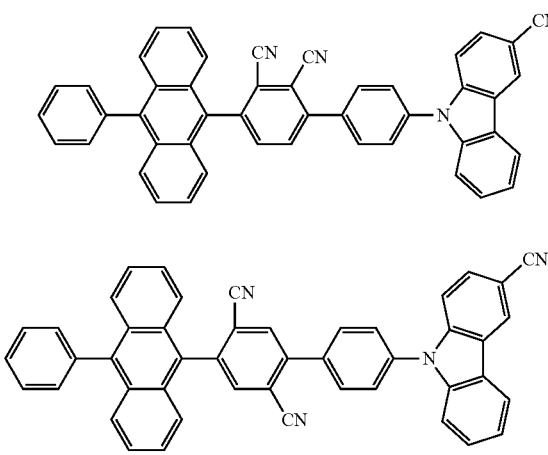
26
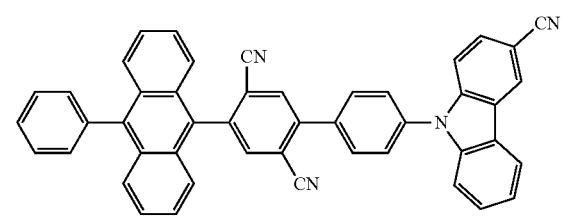
27
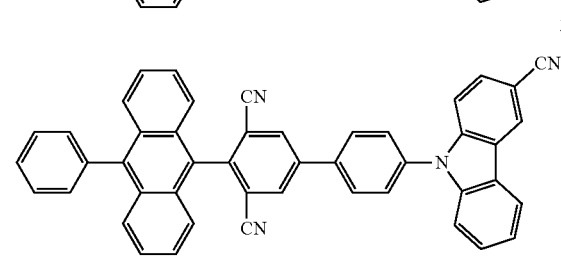
28
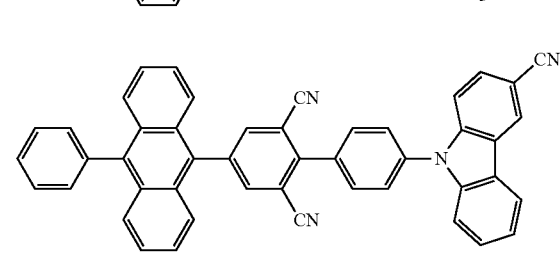
29
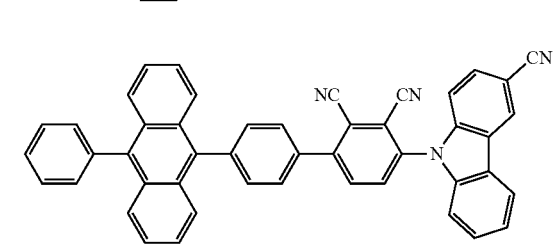
30
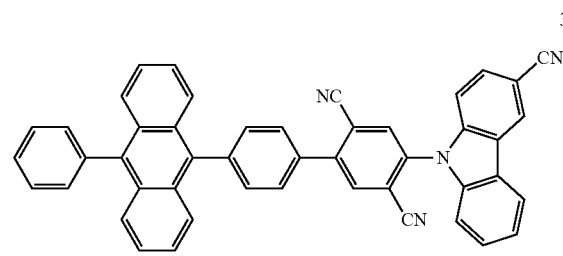
342
-continued
31
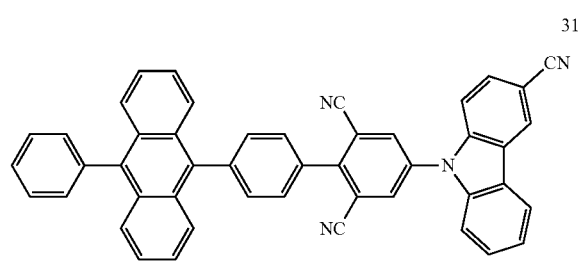
32
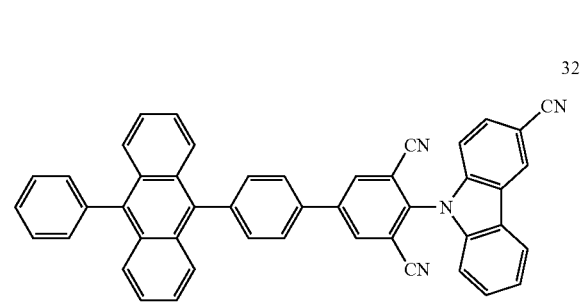
33
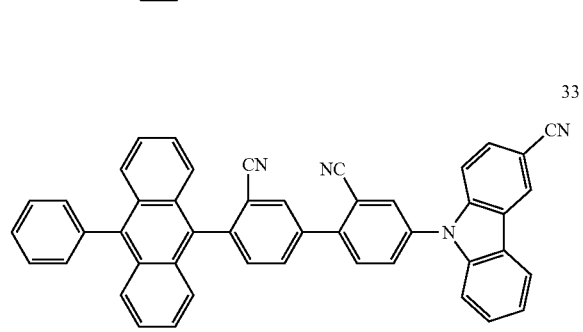
34
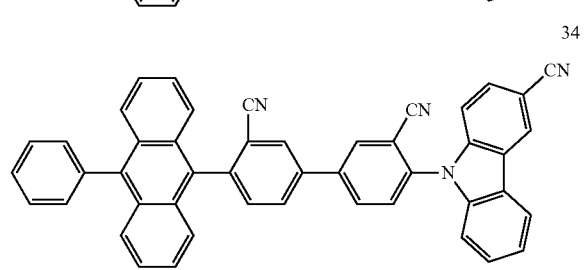
35
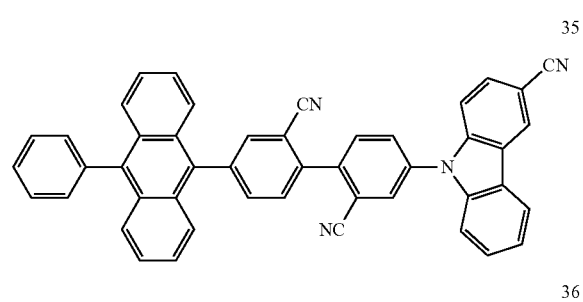
36
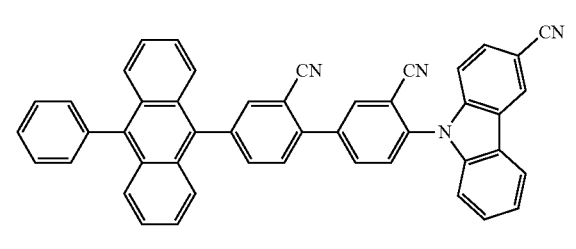

-continued
37
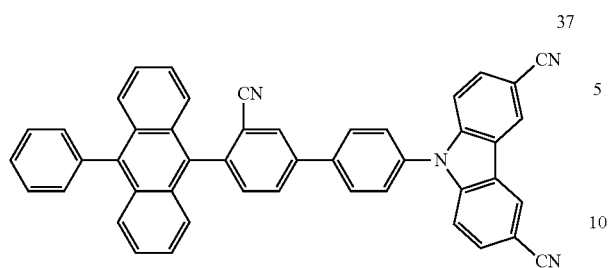
38
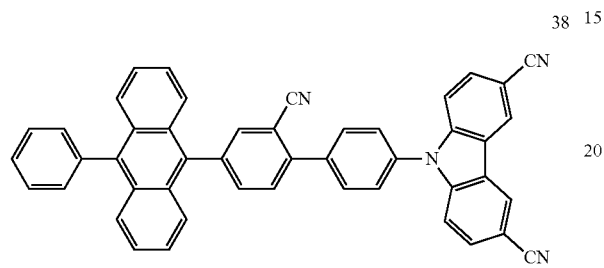
39
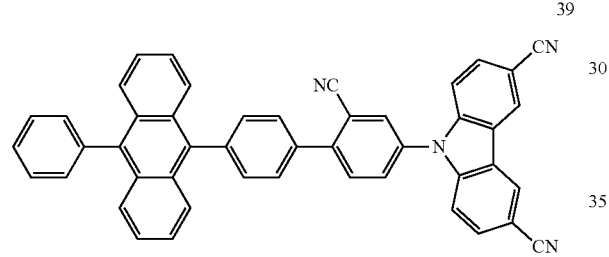
40
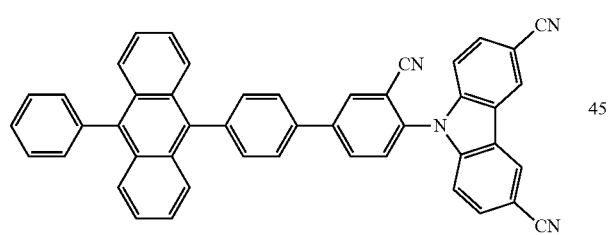
41
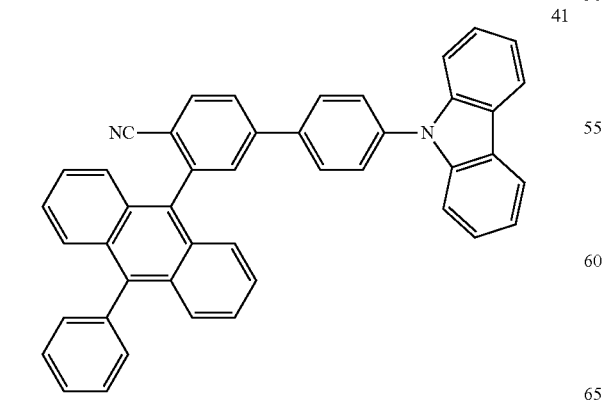
-continued
42
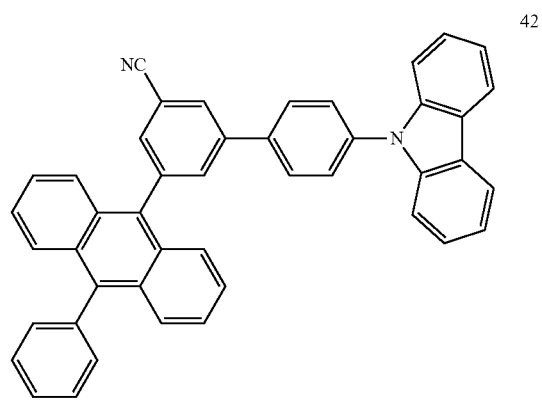
43
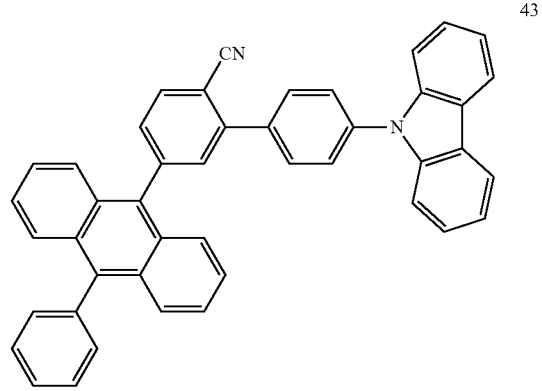
44
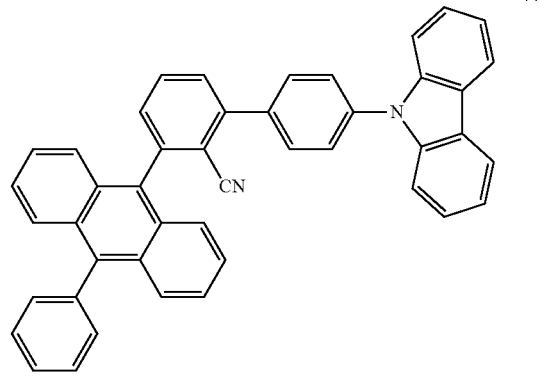
45
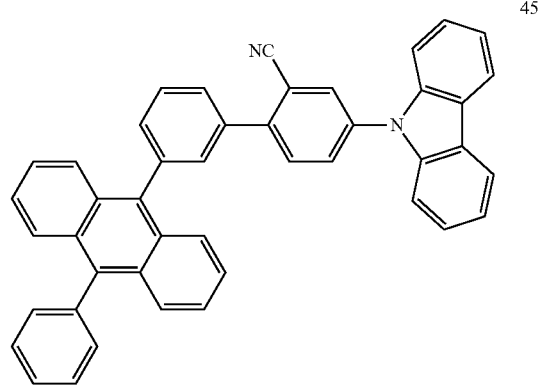

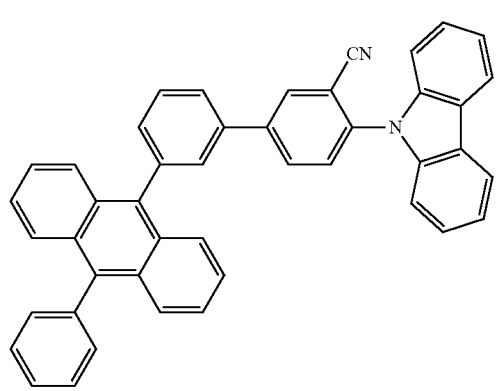
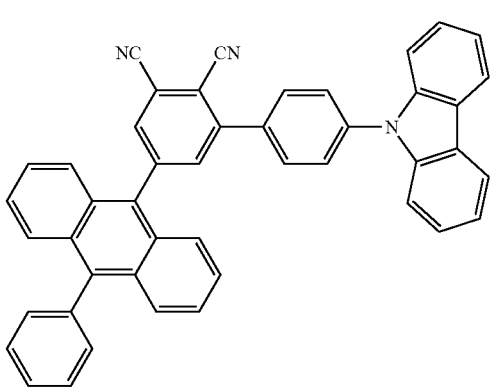
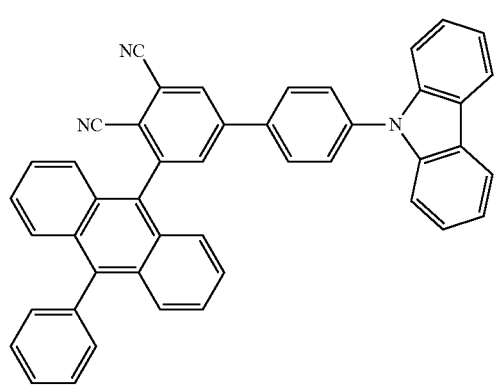

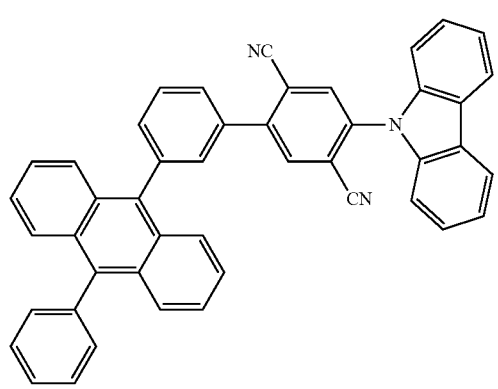
54
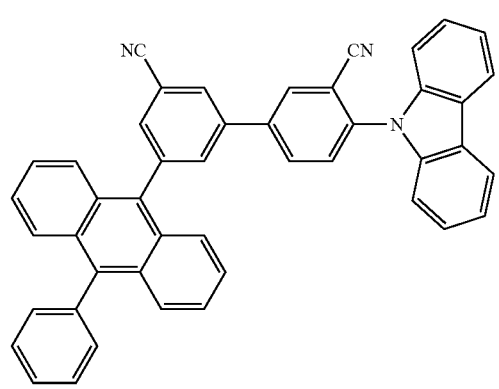
58
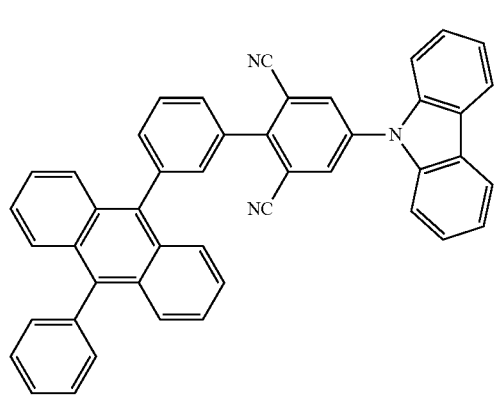
55
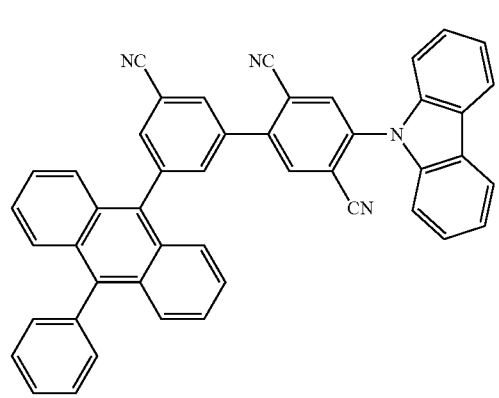
59
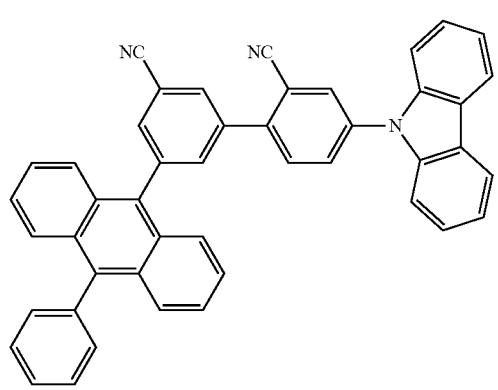
56
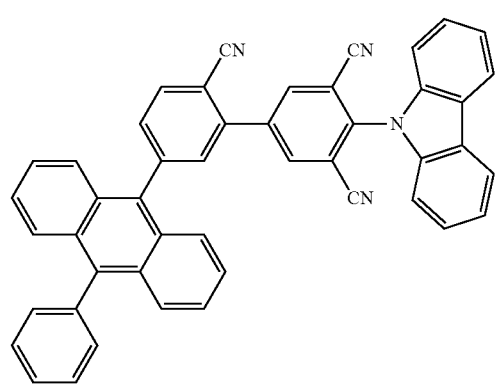
60
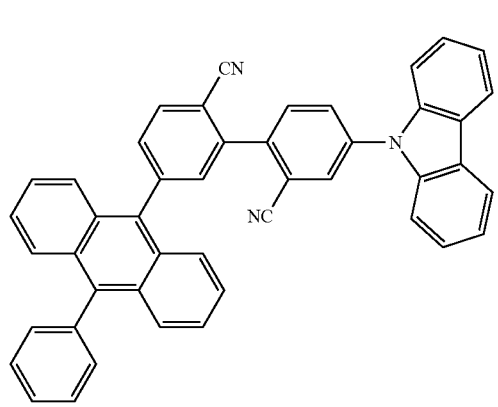
57
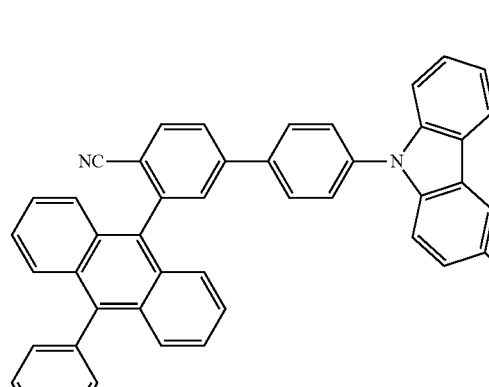
61

-continued
62
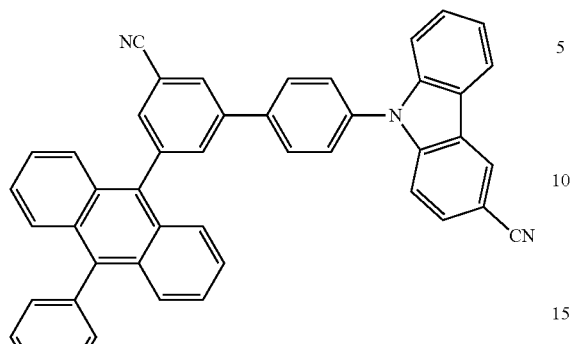
63
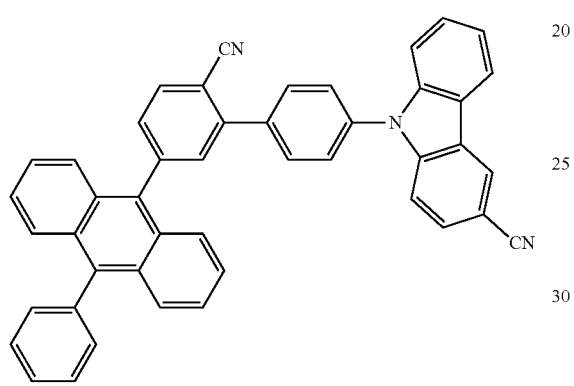
64
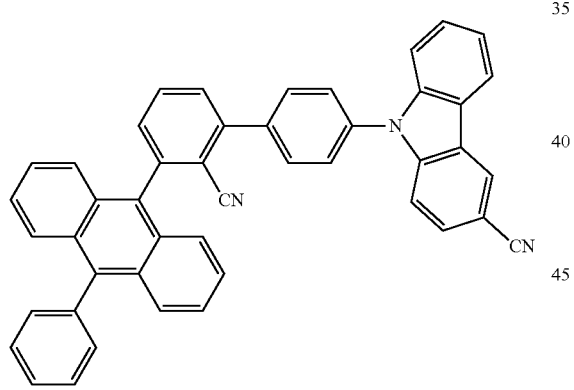
65
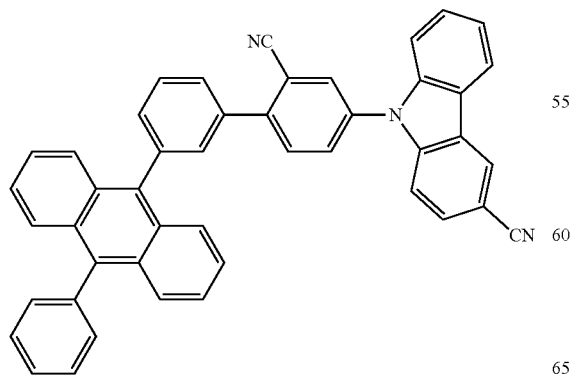
-continued
66
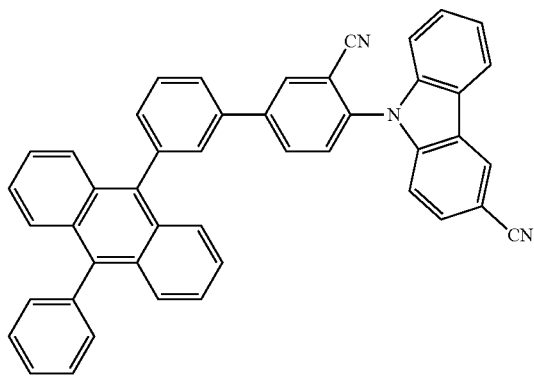
67
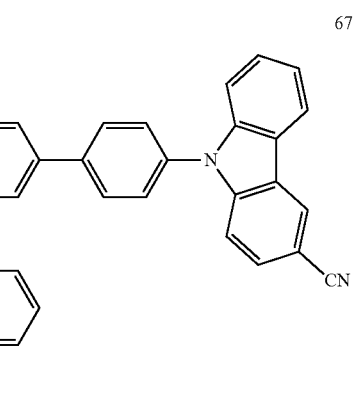
68
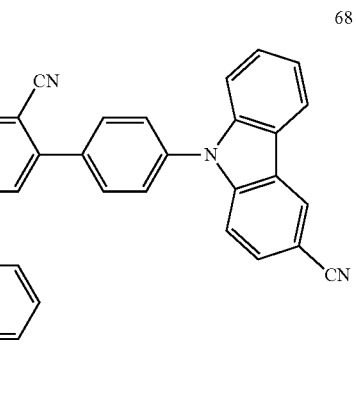
69
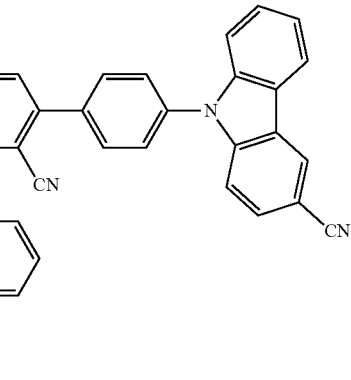

351
-continued
70
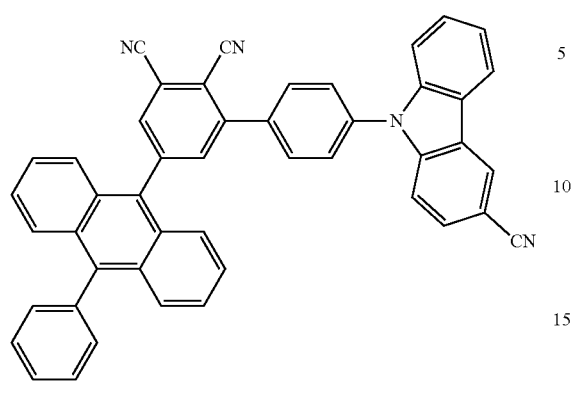
71
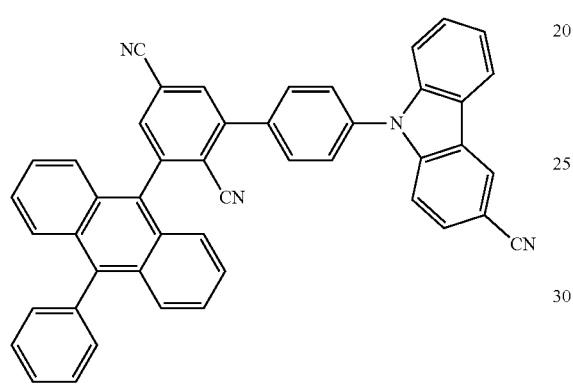
72
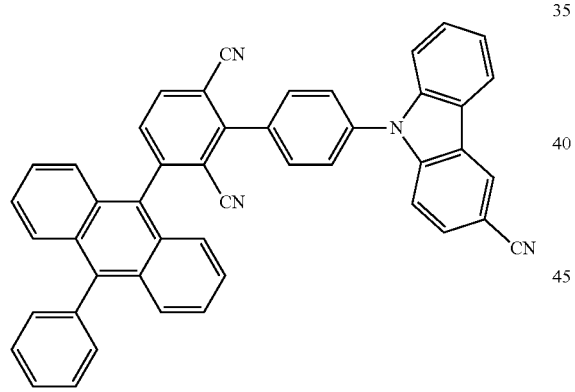
73
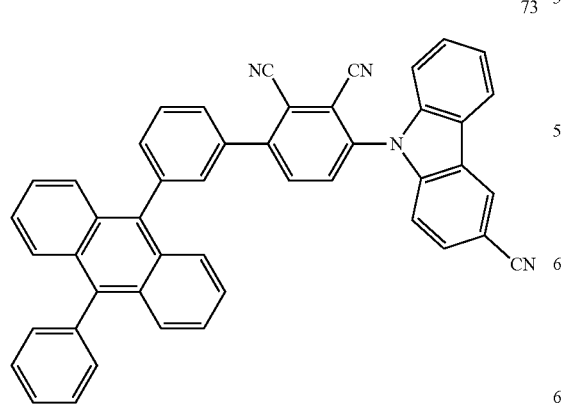
352
-continued
74
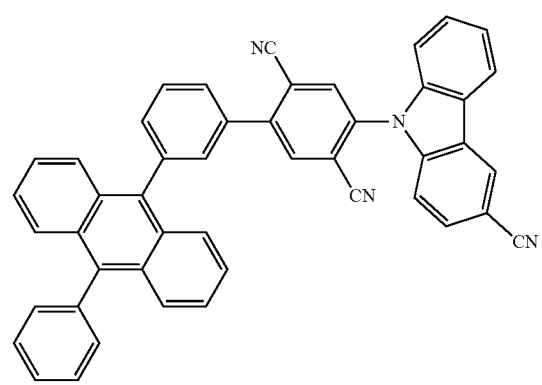
75
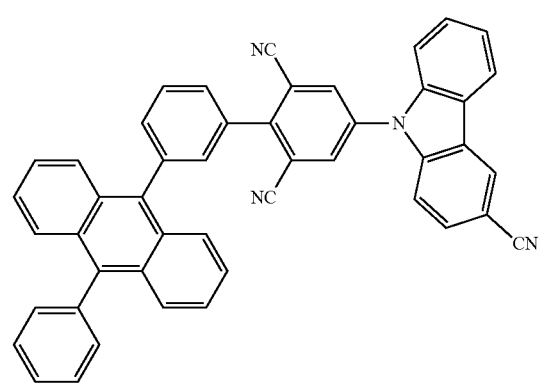
76
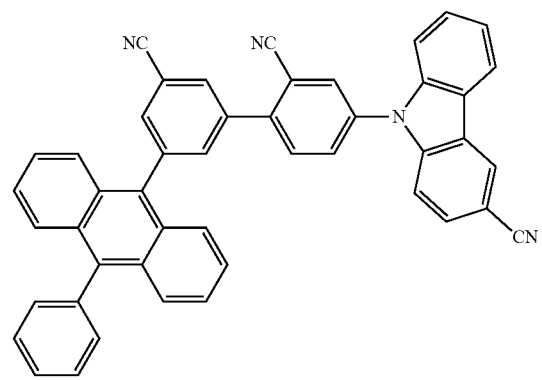
77
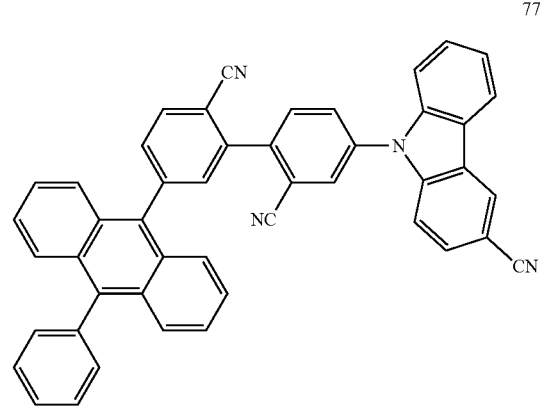

-continued
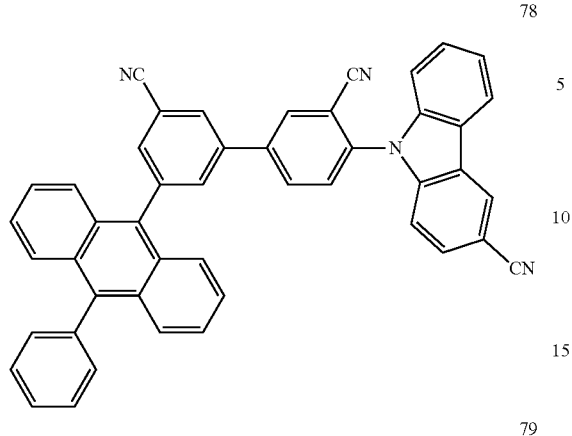
78
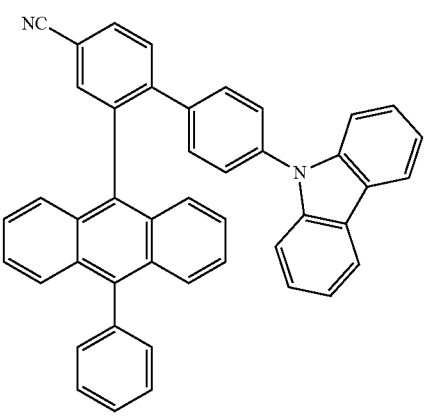
82
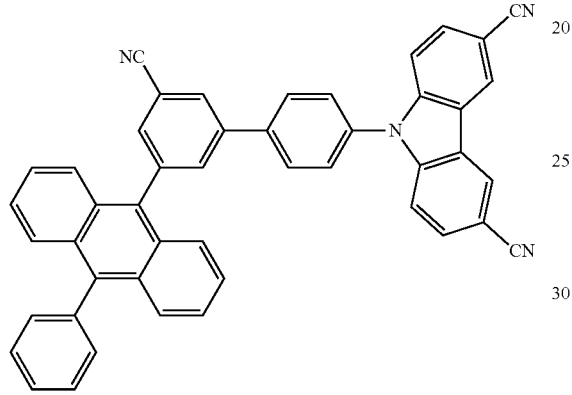
79
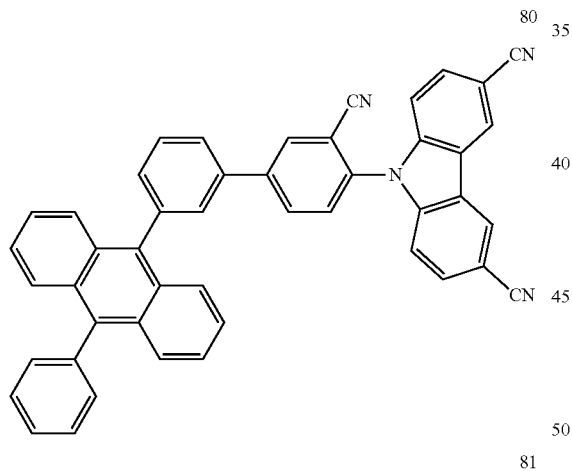
80
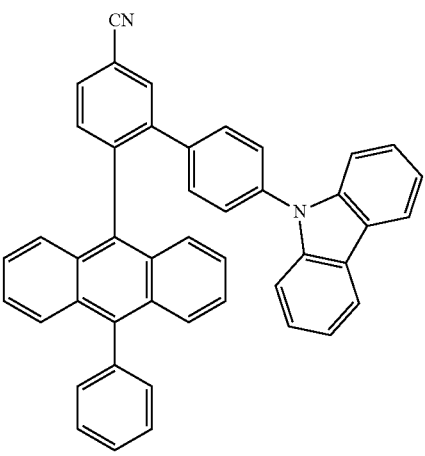
83
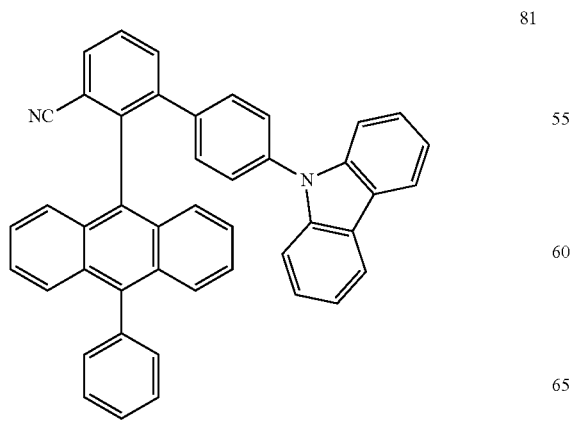
81
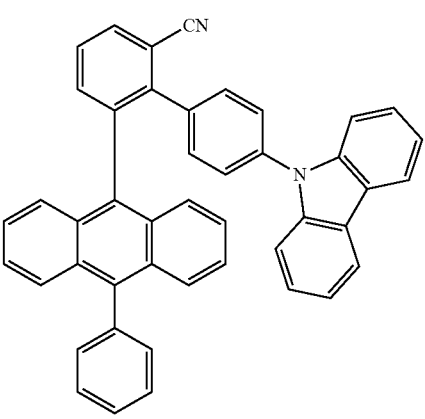
84

355
-continued
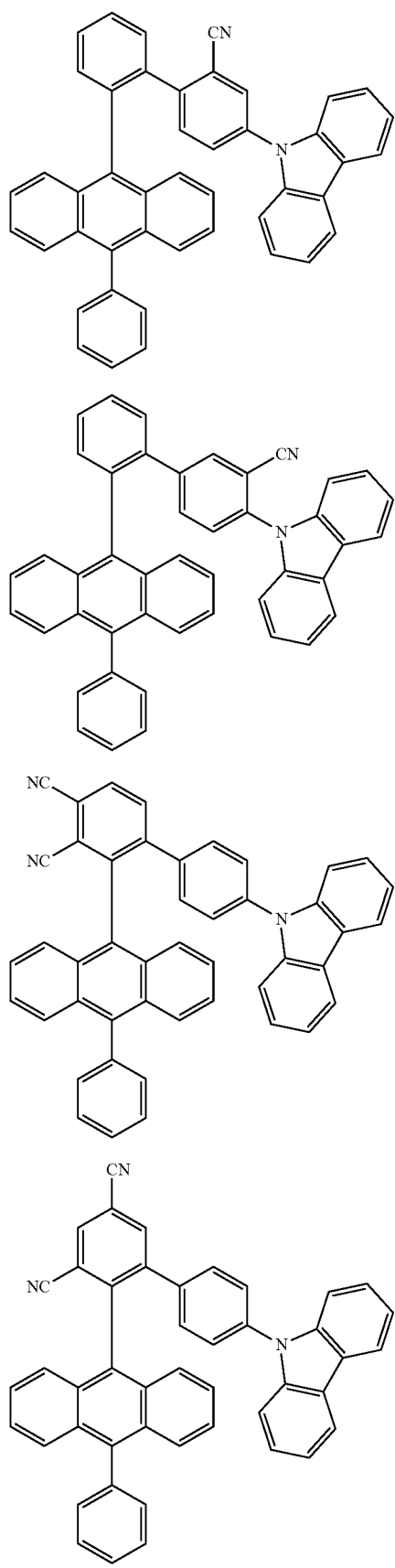
356
-continued
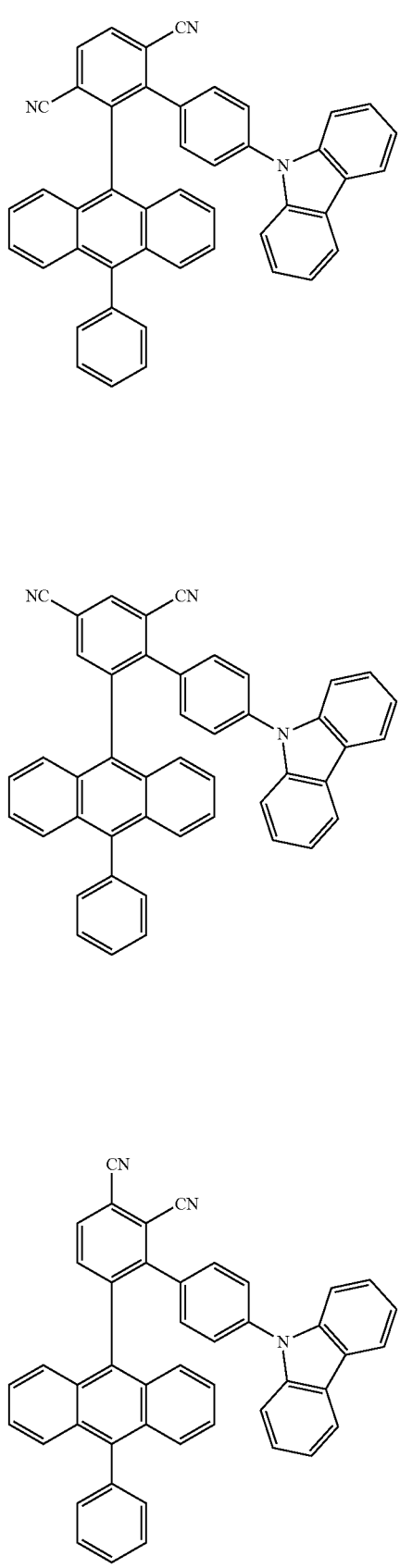

357
-continued
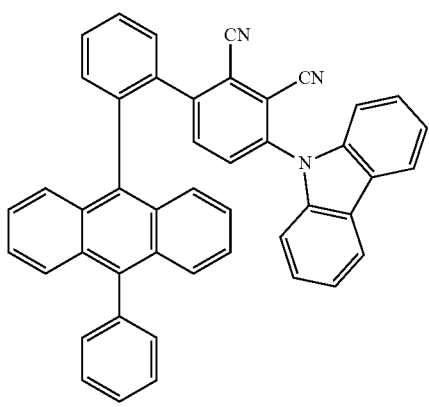
92
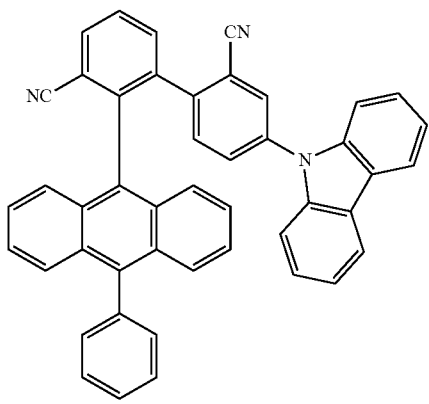
93
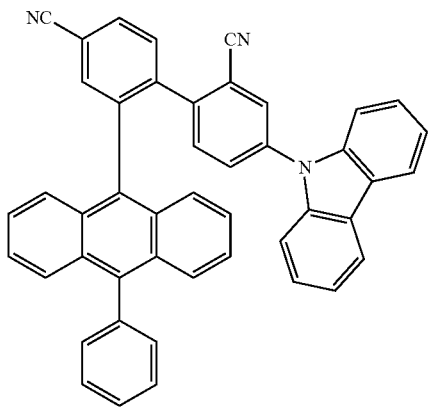
94
358
-continued
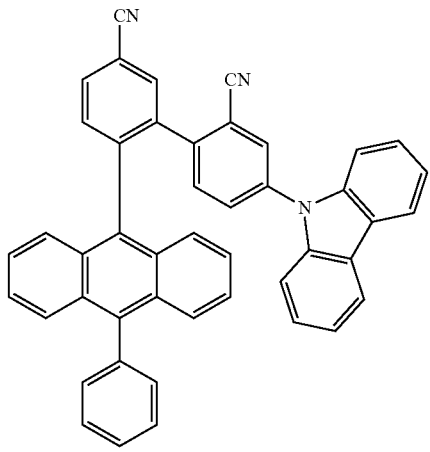
95
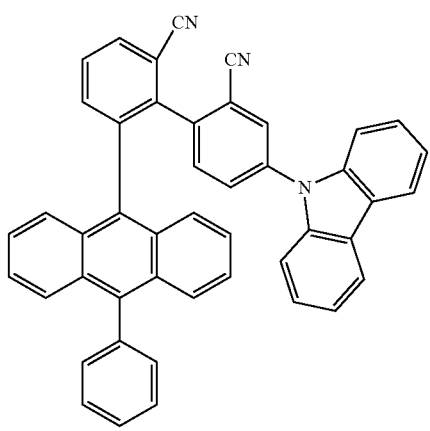
96
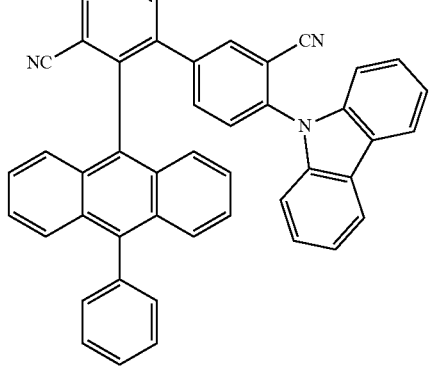
97

98
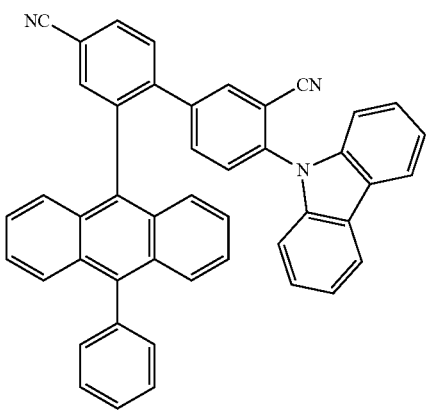
99
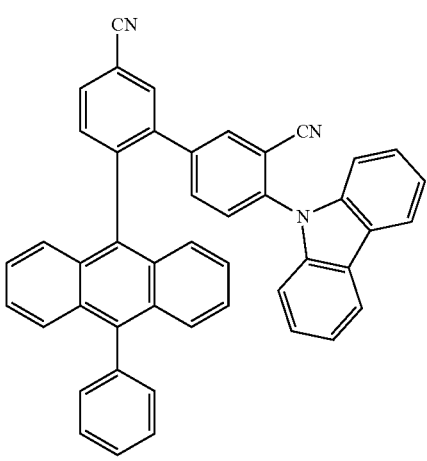
100
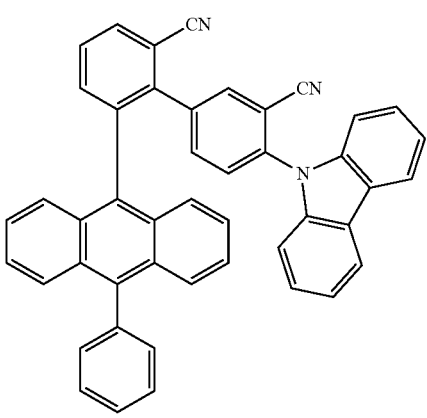
101
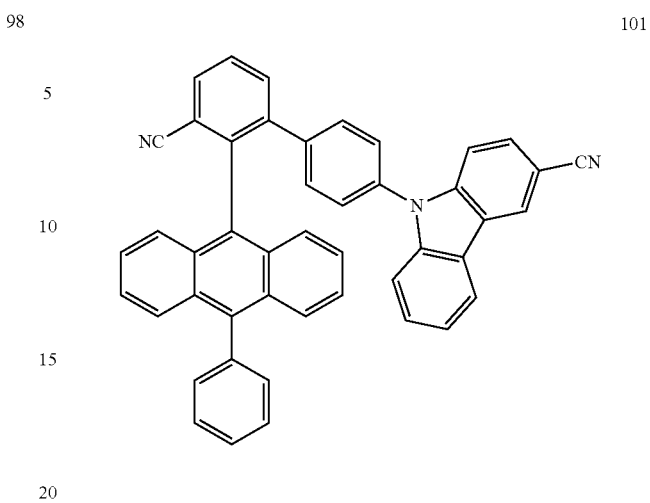
102
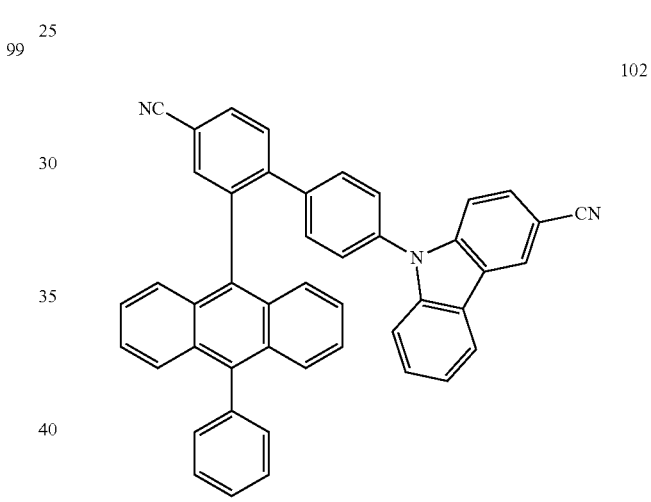
103
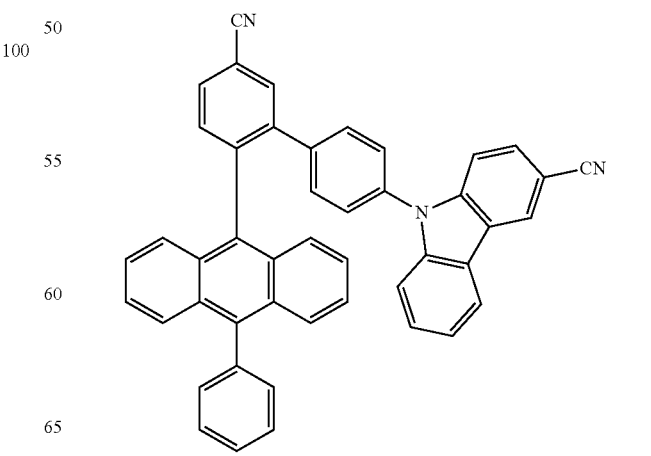

| 104 | 107 |
|---|---|
| 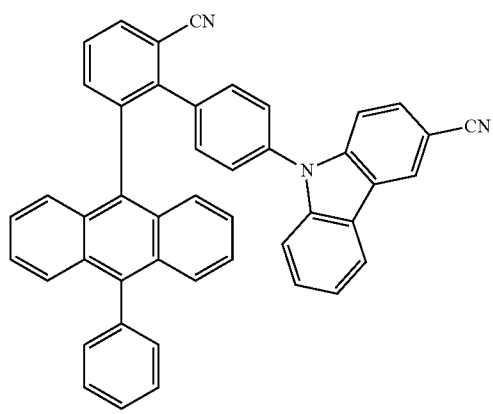 | 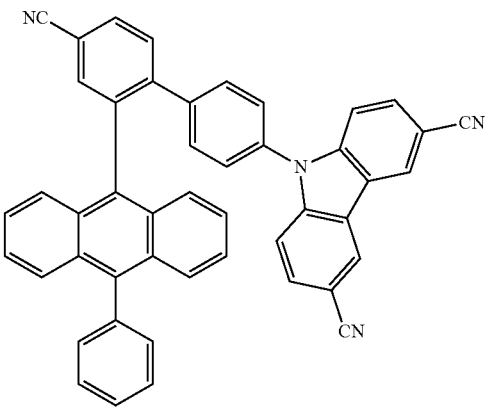 |
| 105 | 108 |
|---|---|
| 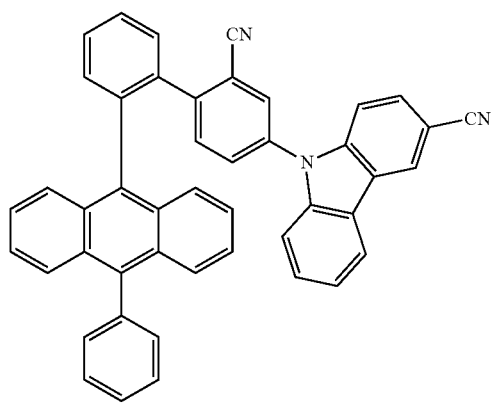 | 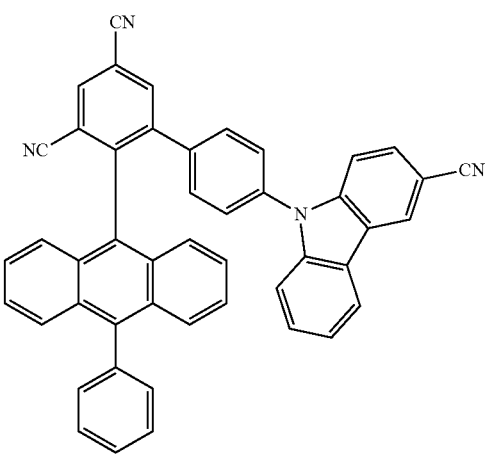 |
| 106 | 109 |
|---|---|
| 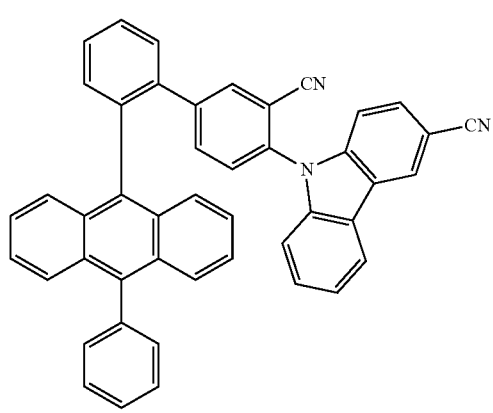 | 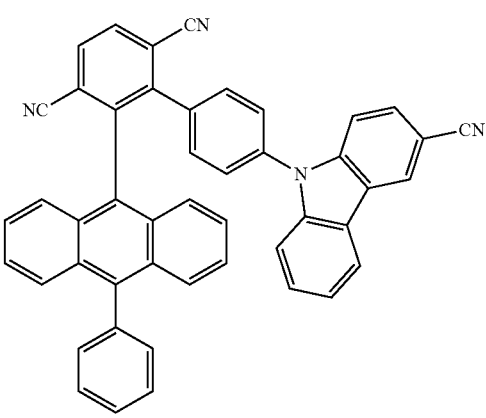 |

363
-continued
110
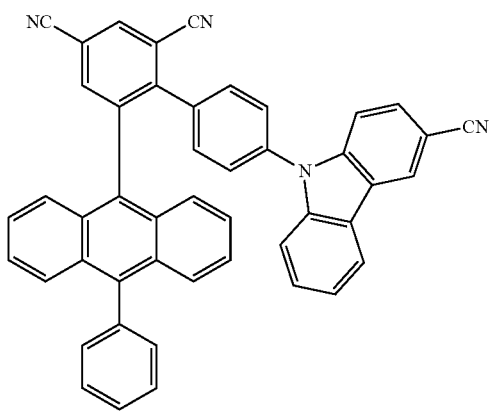
111
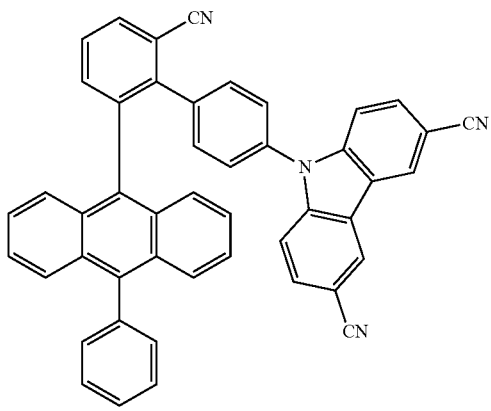
112
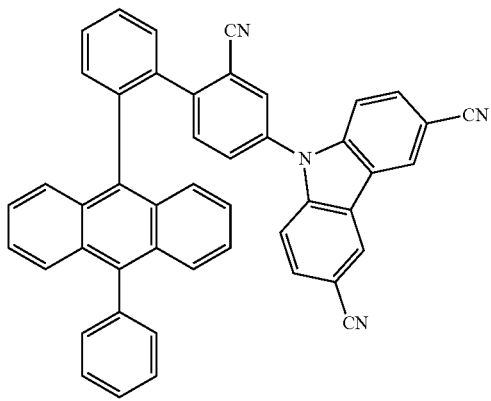
364
-continued
113
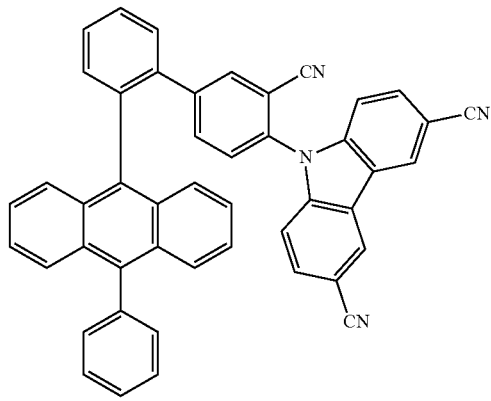
114
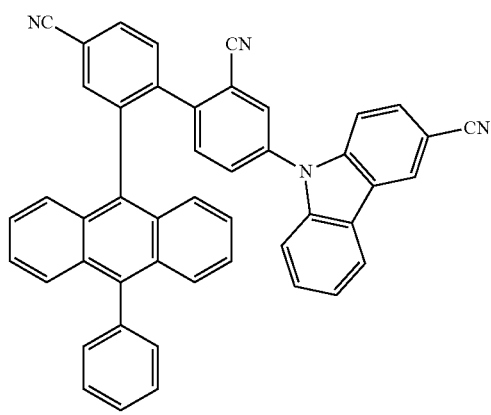
115
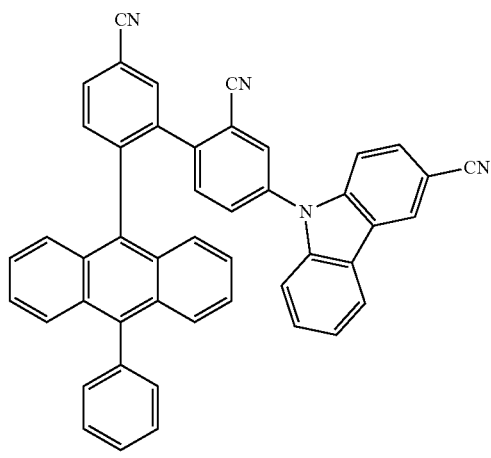

116
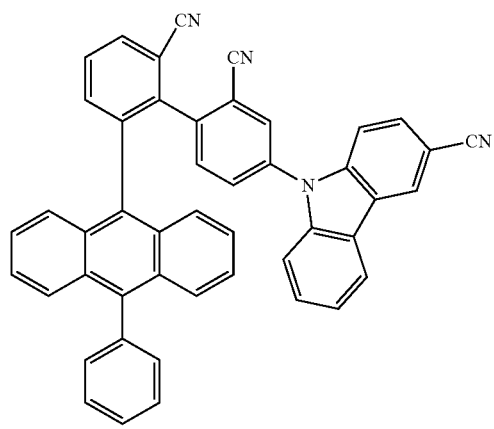
117
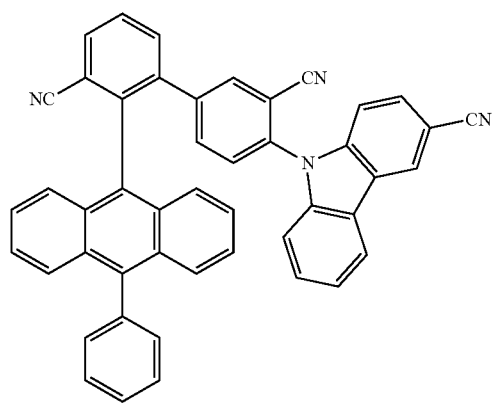
118
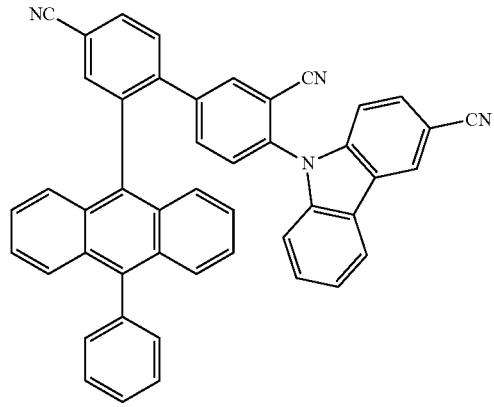
119
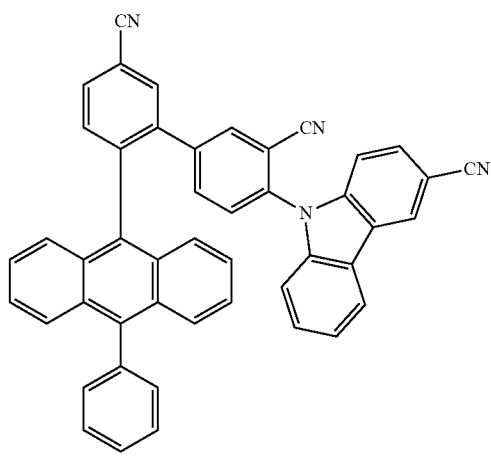
120
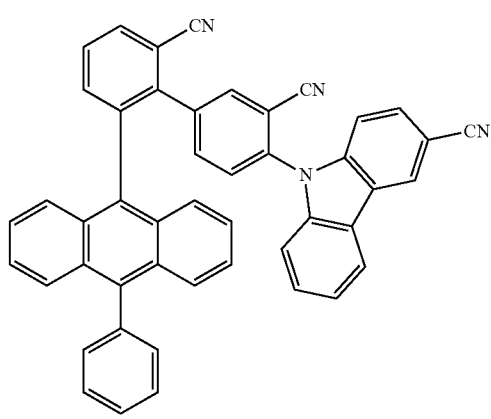
121
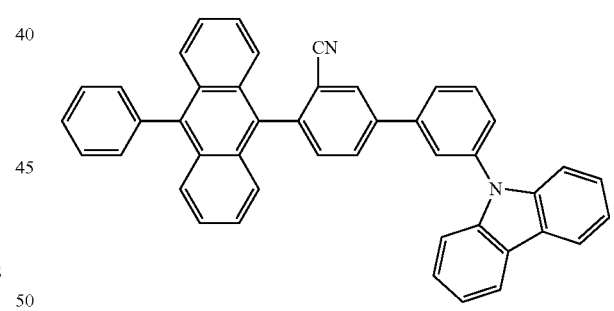
122
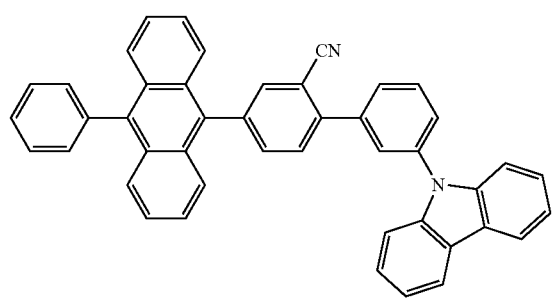

123
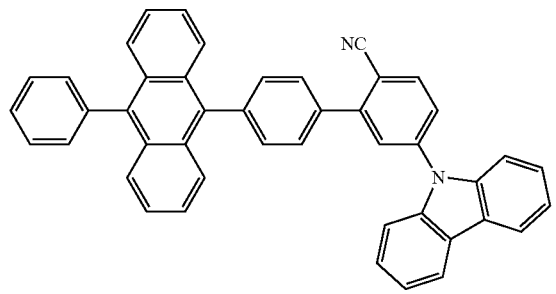
124
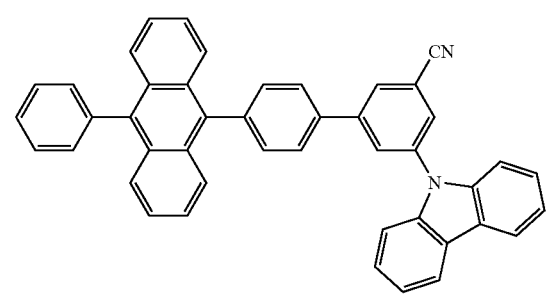
125
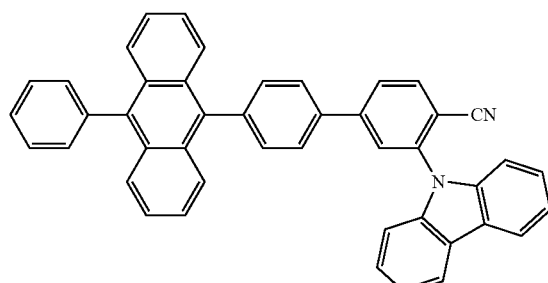
126
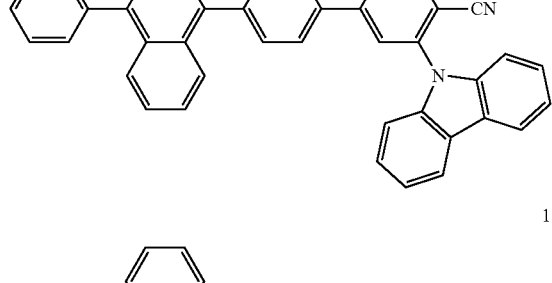
127
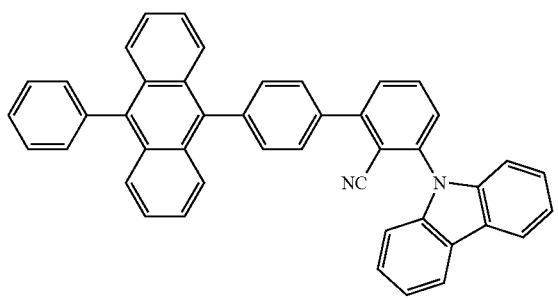
128
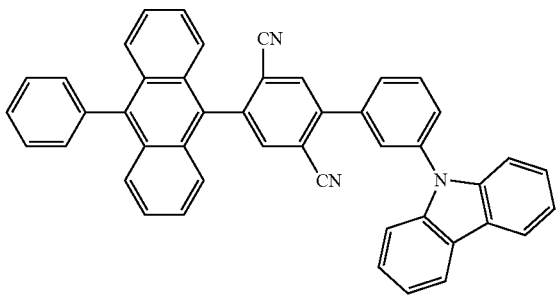
129
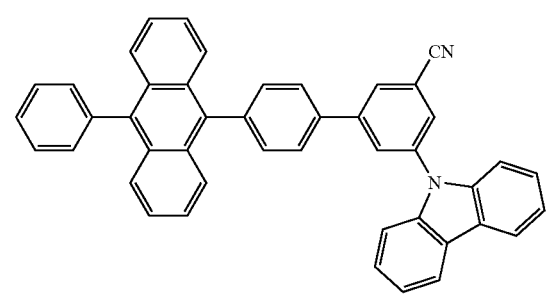
130
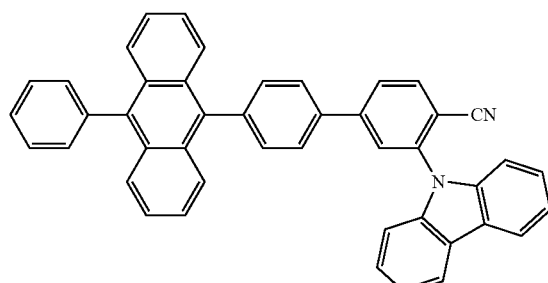
131
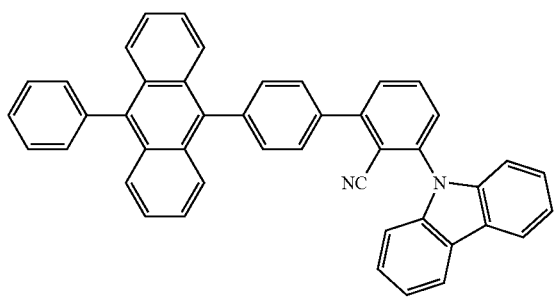
132
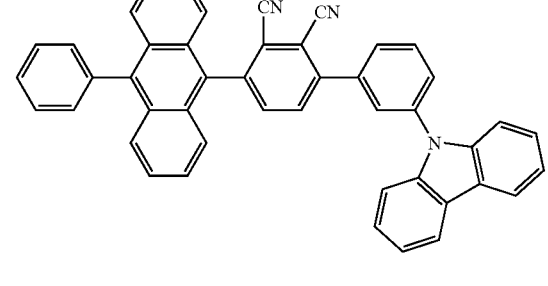

133
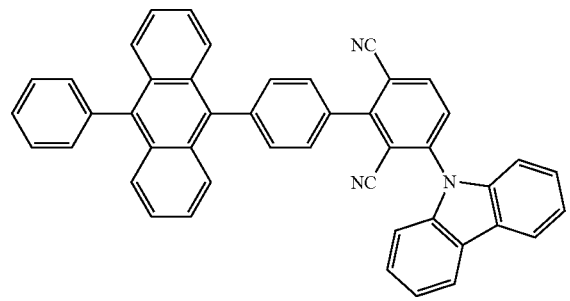
134
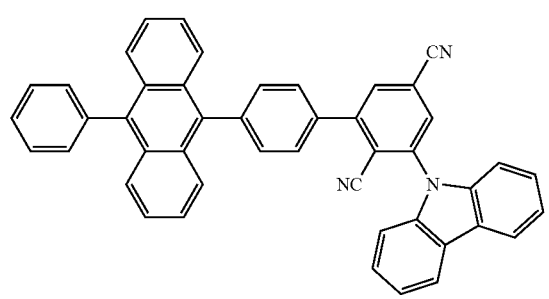
135
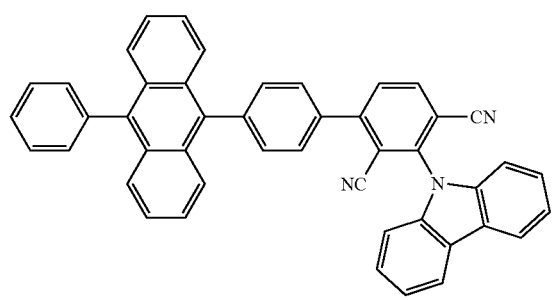
136
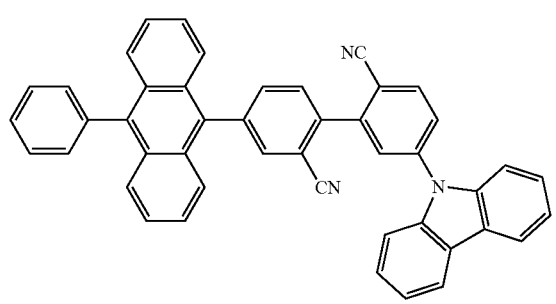
137
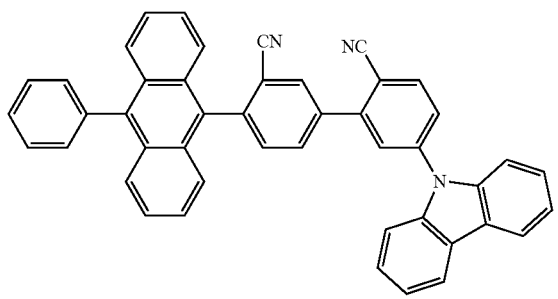
138
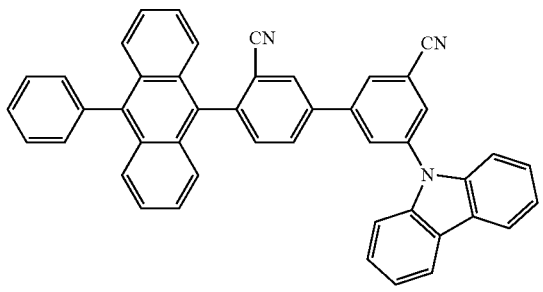
139
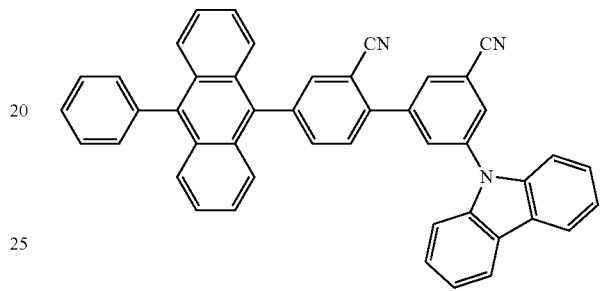
140
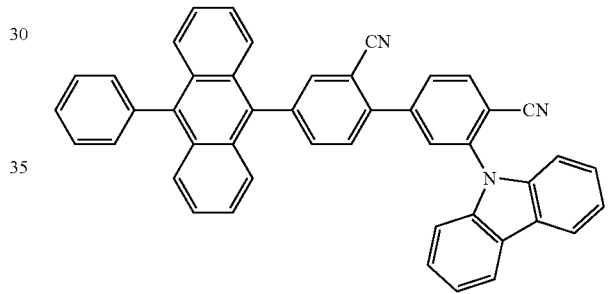
141
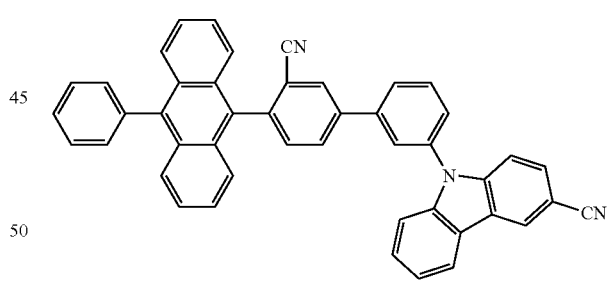
142
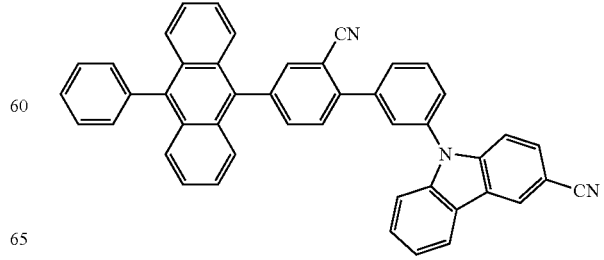

143
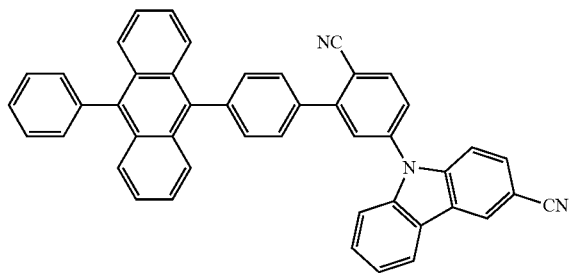
144
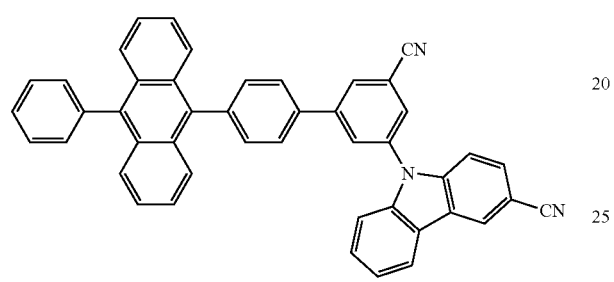
145
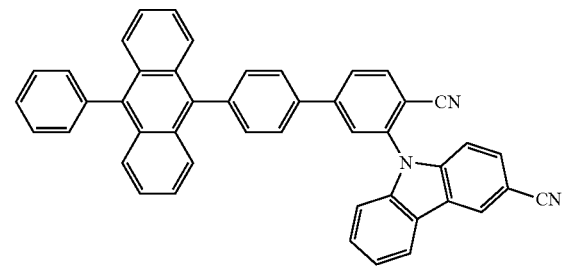
146
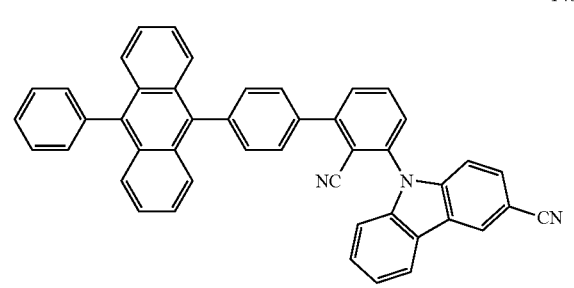
147
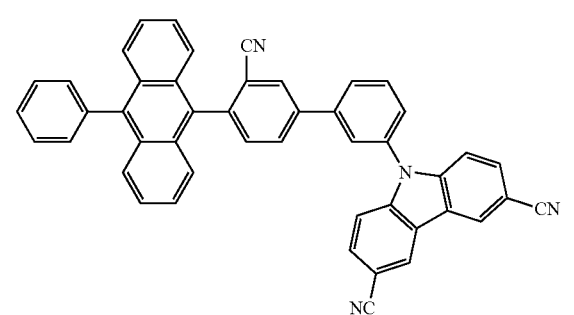
148
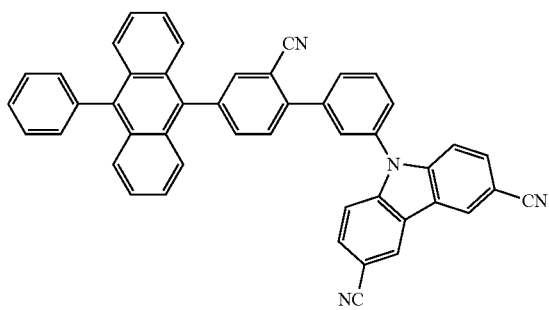
149
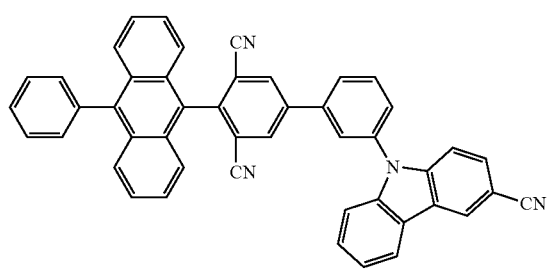
150
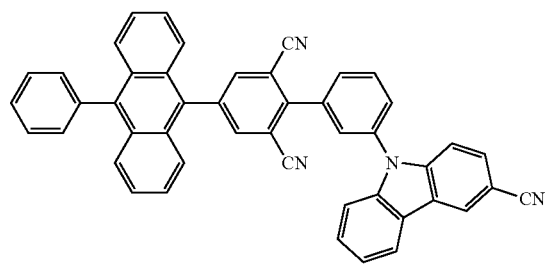
151
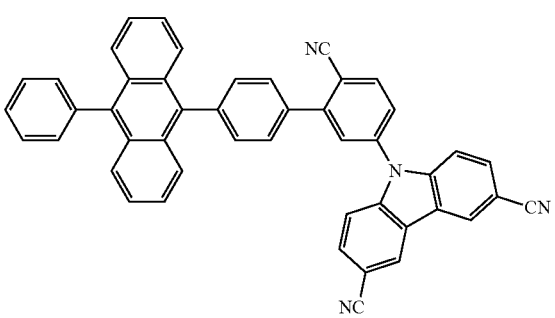
152

153
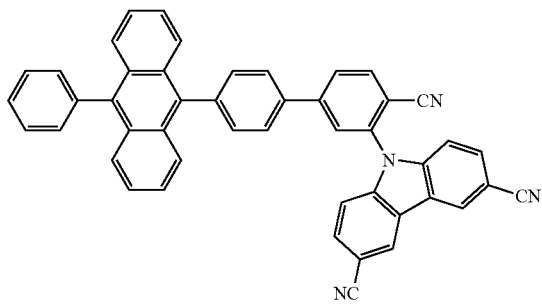
154
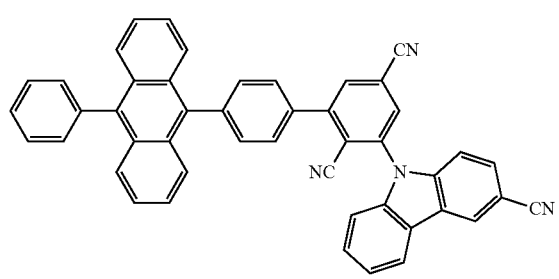
155
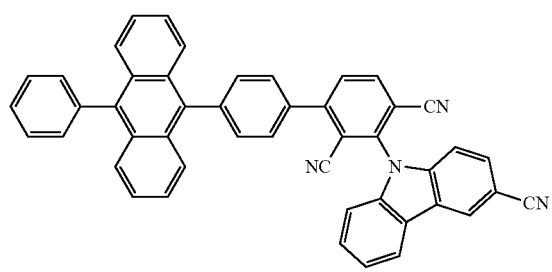
156
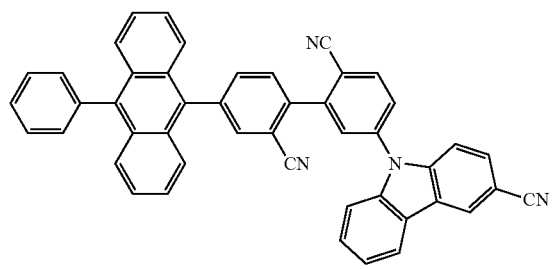
157
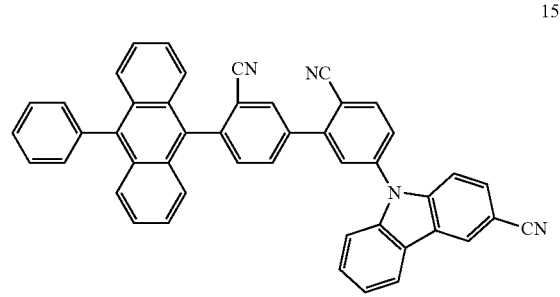
158
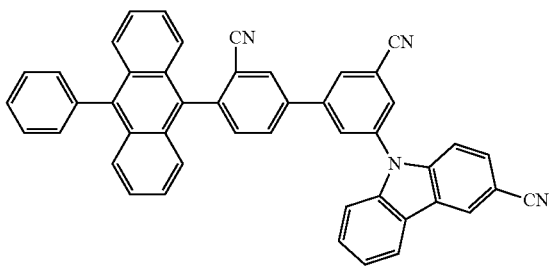
159
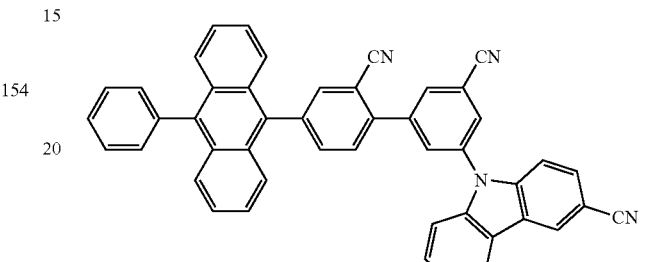
160
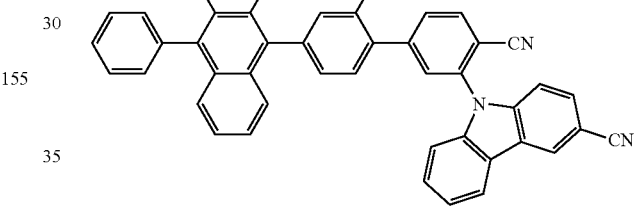
161
162
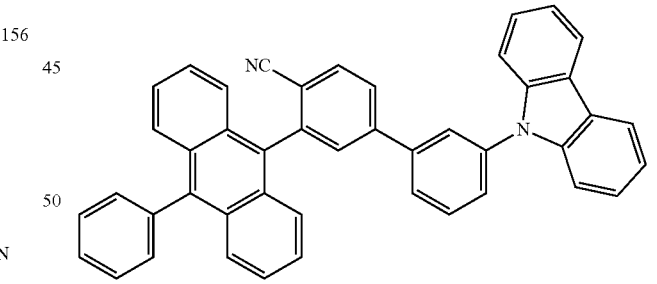

163
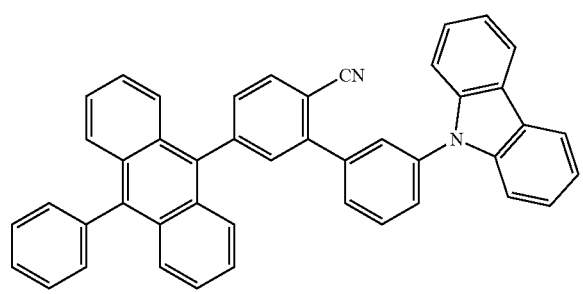
164
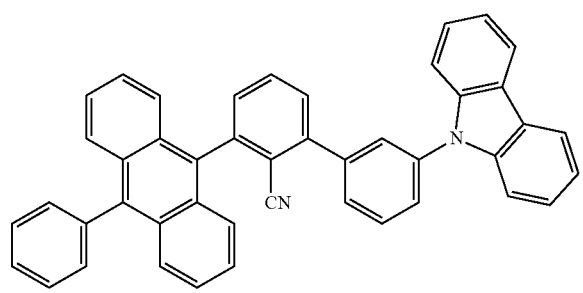
165
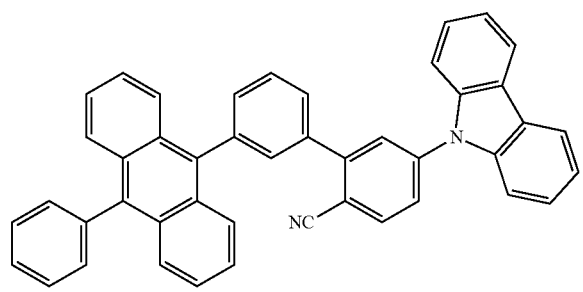
166
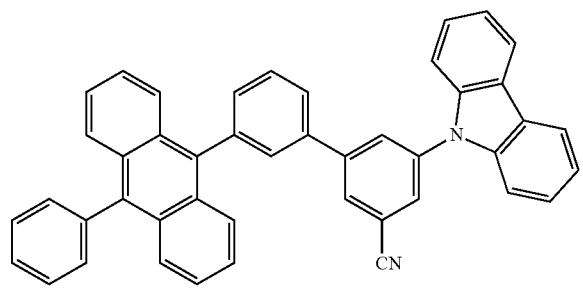
167
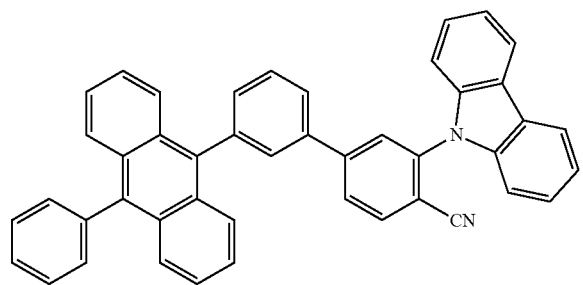
168
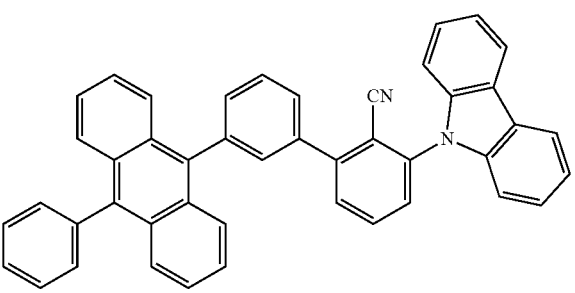
169
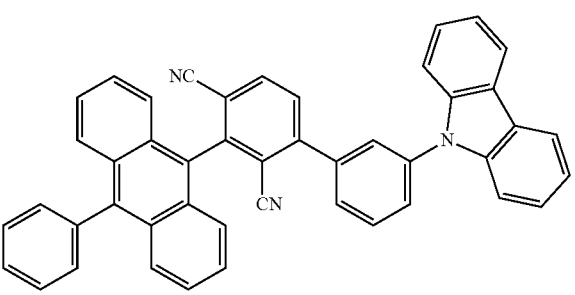
170
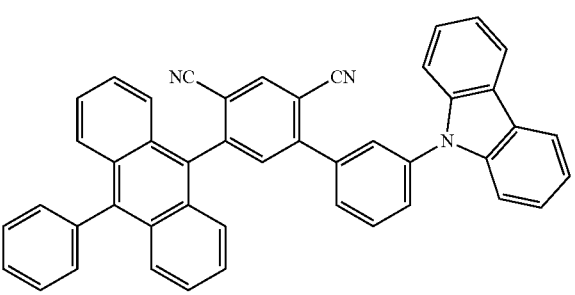
171
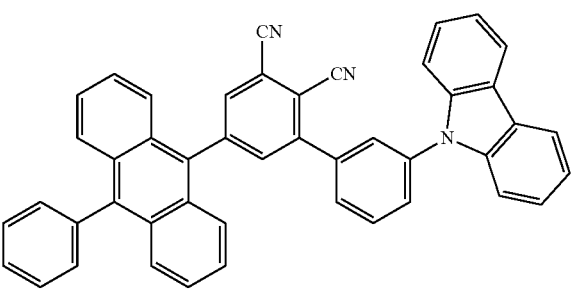
172
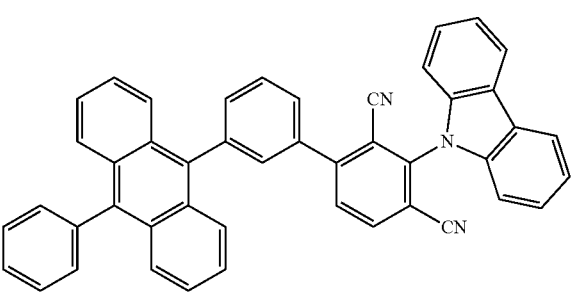

173
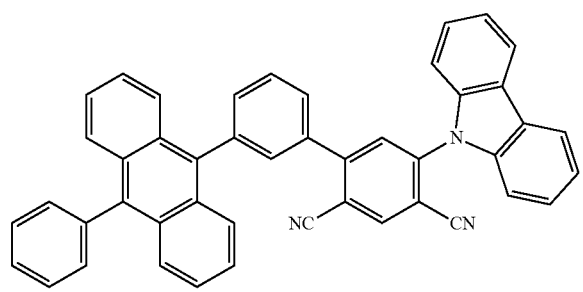
174
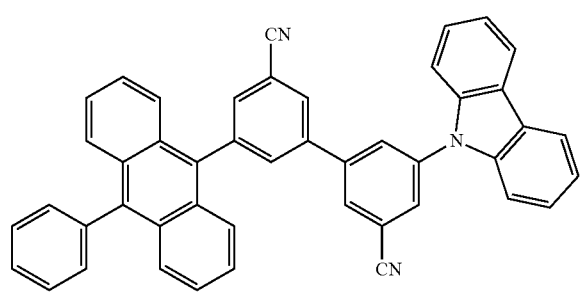
175
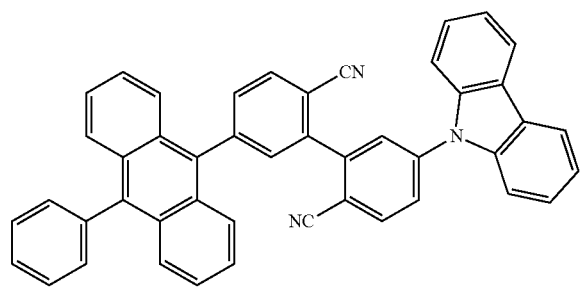
176
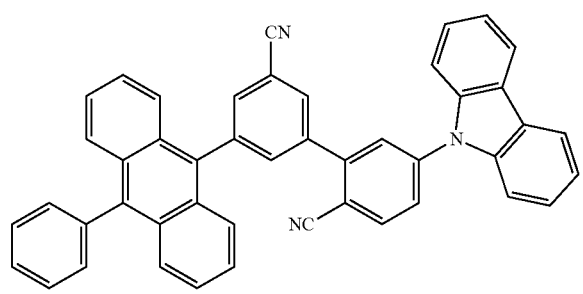
177
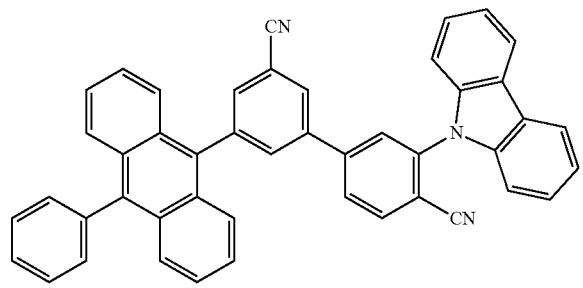
178
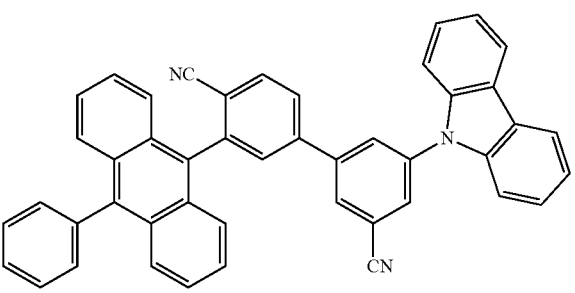
179
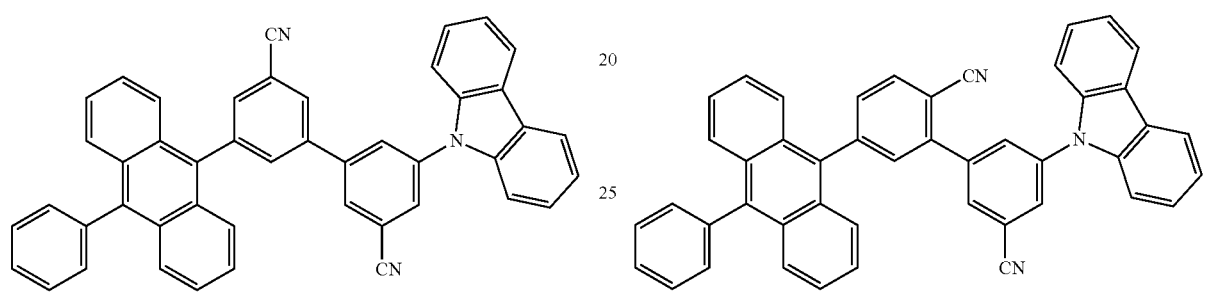
180
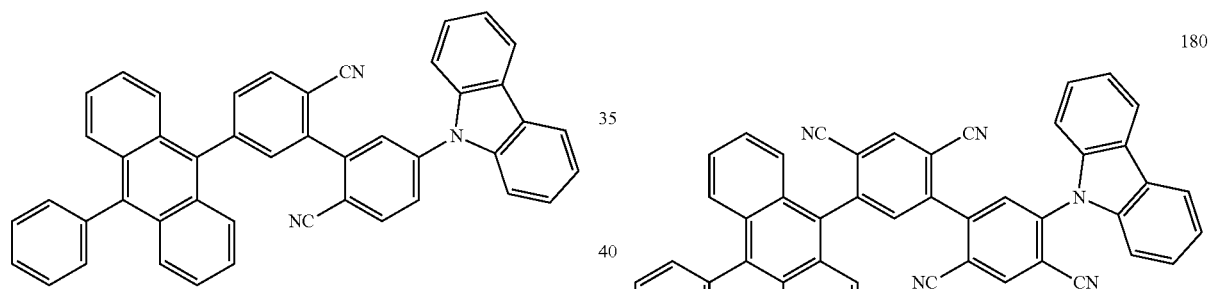
181
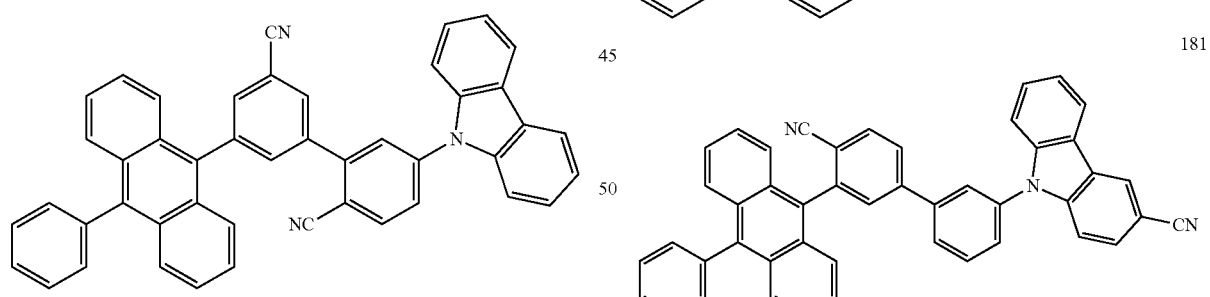
182
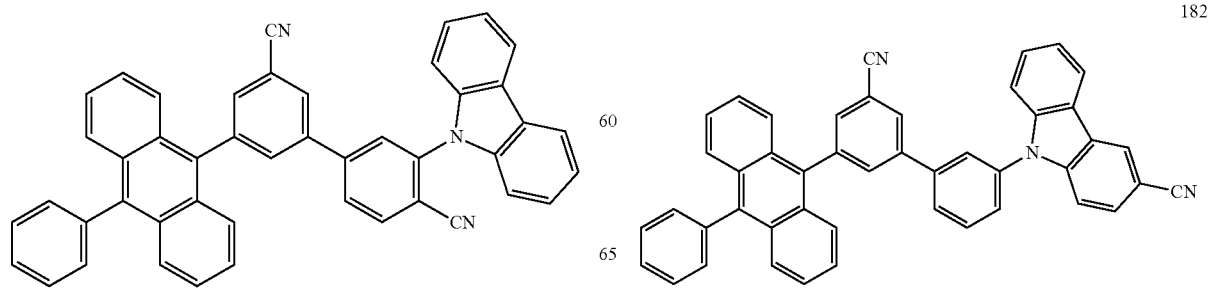

183
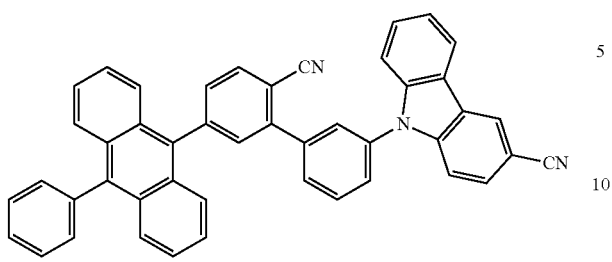
184
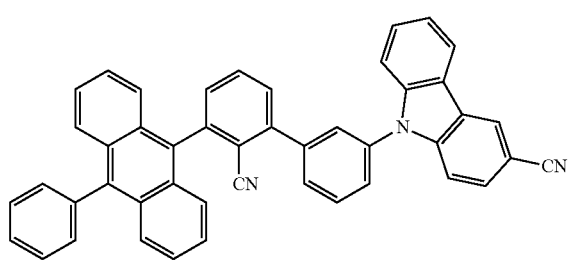
185
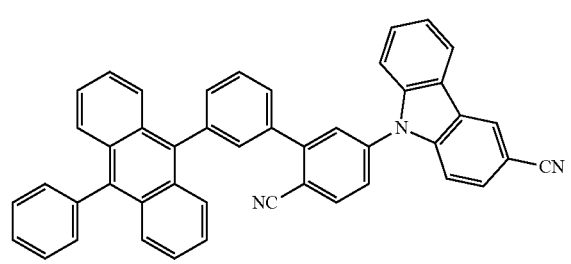
186
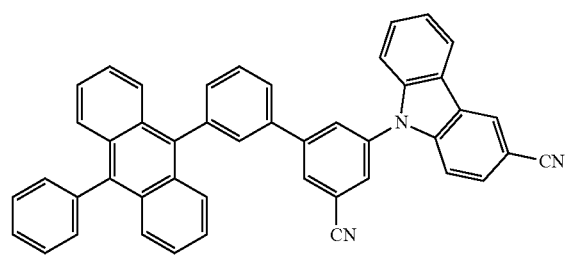
187
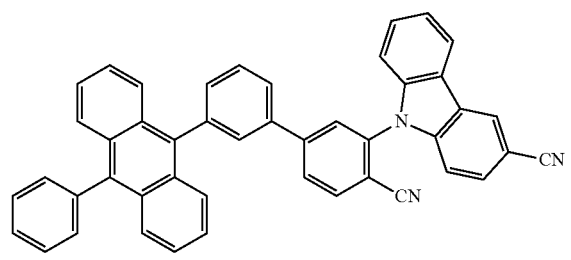
188
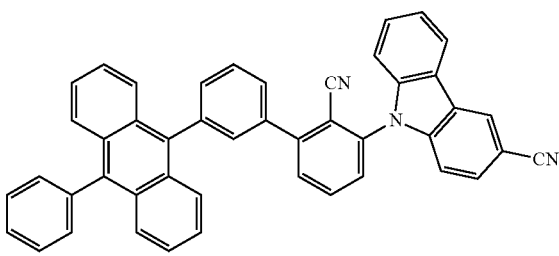
189
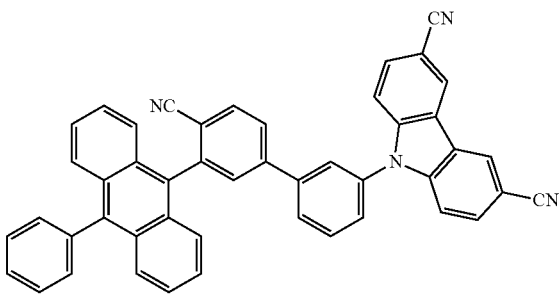
190
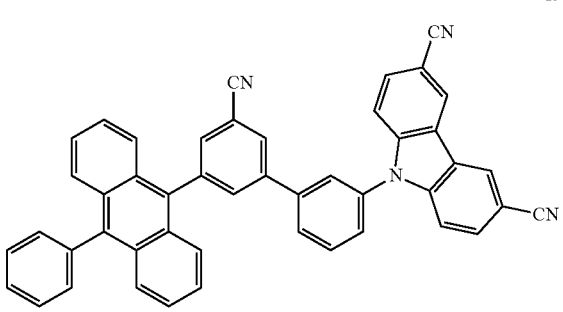
191
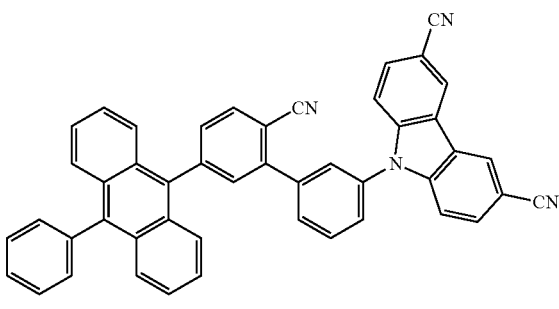
192
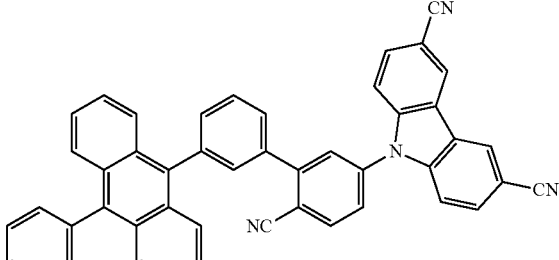

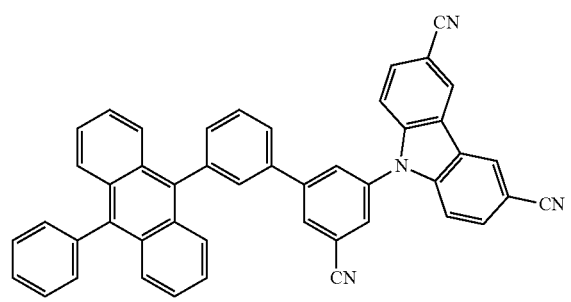
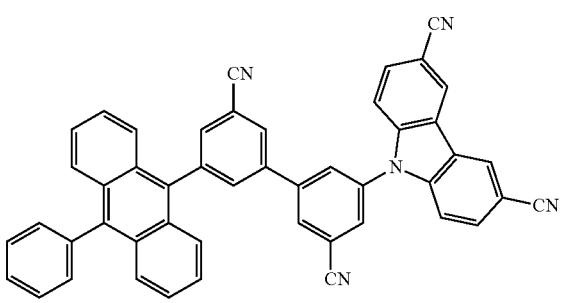
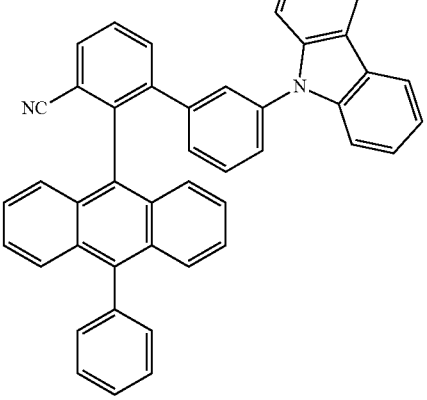

202
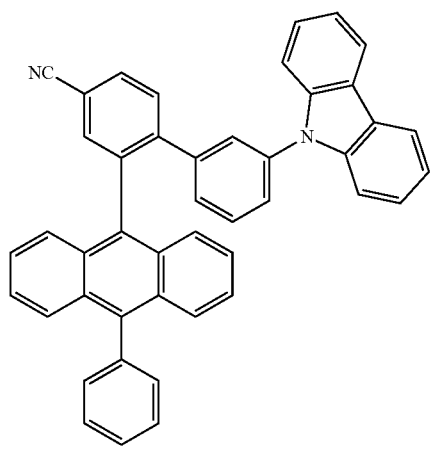
203
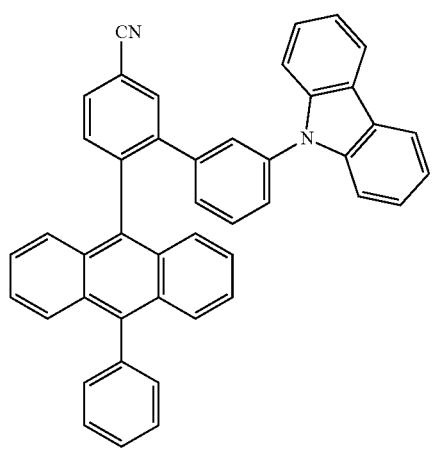
204
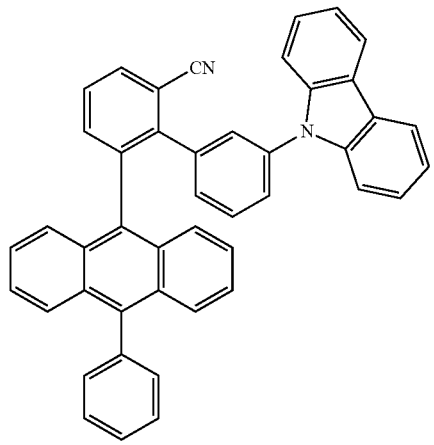
205
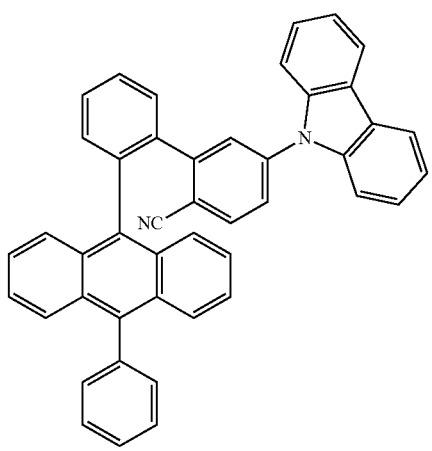
206
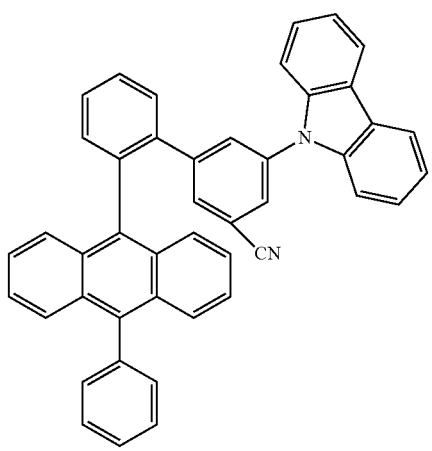
207
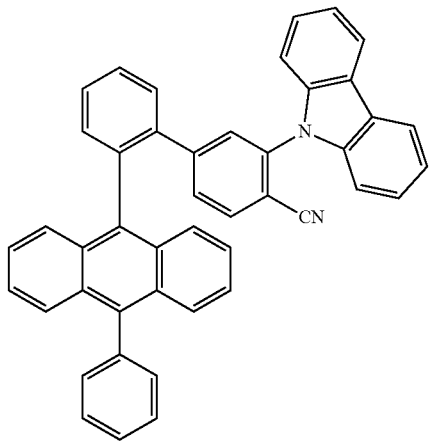

-continued
208
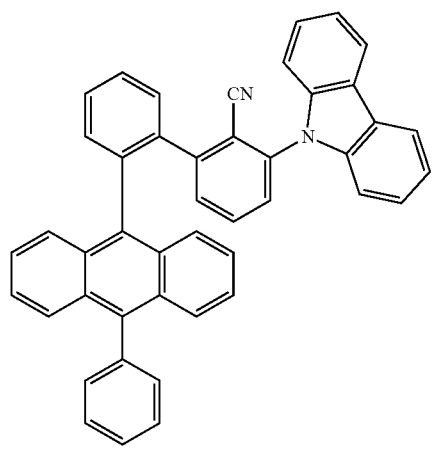
211
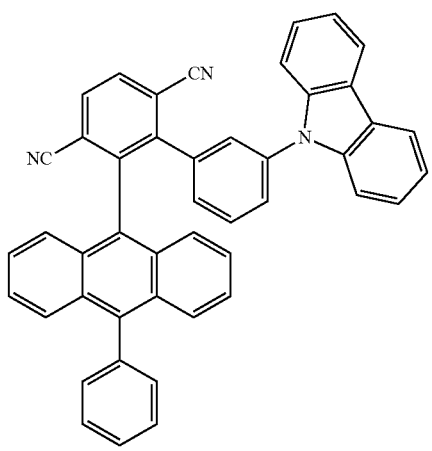
209
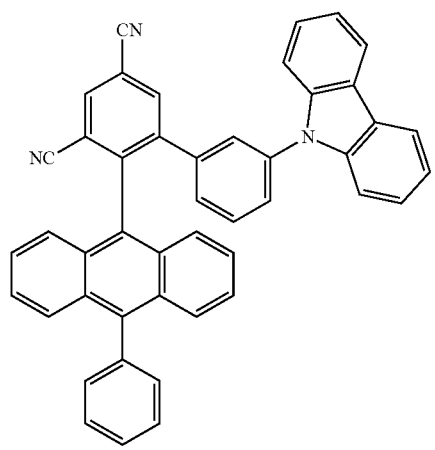
212
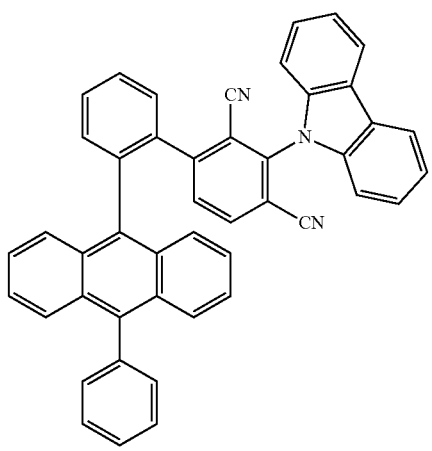
210
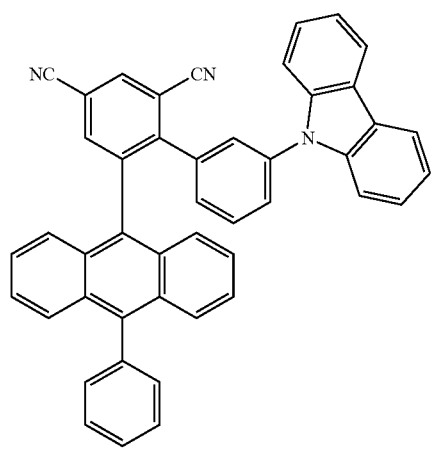
213
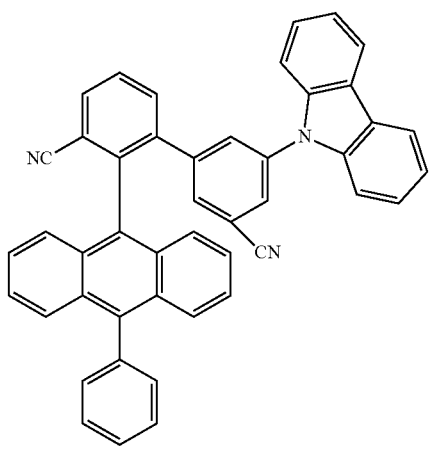

-continued
214
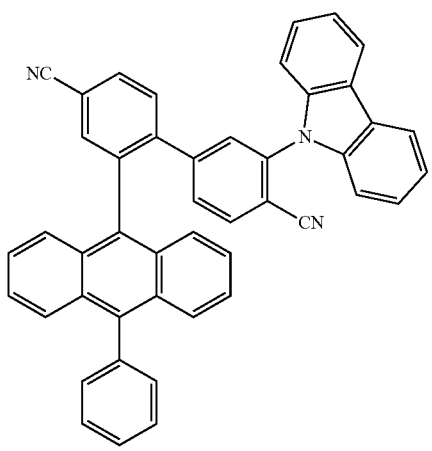
217
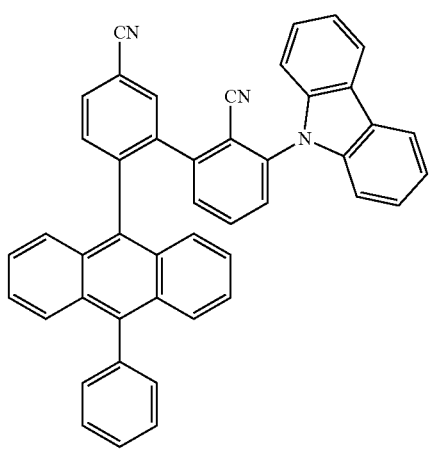
215
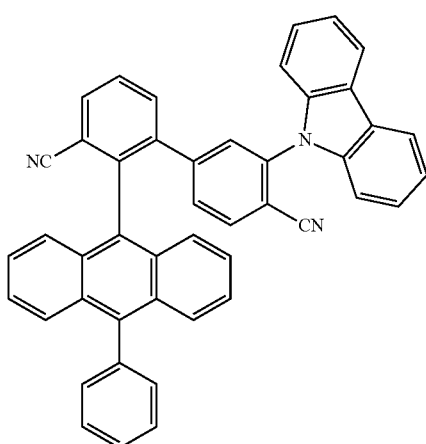
218
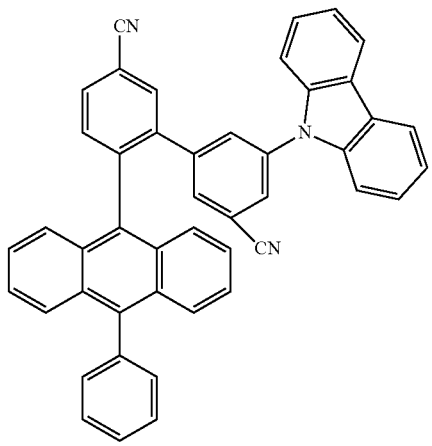
216
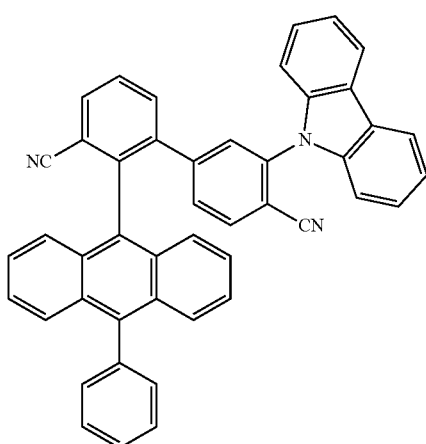
219
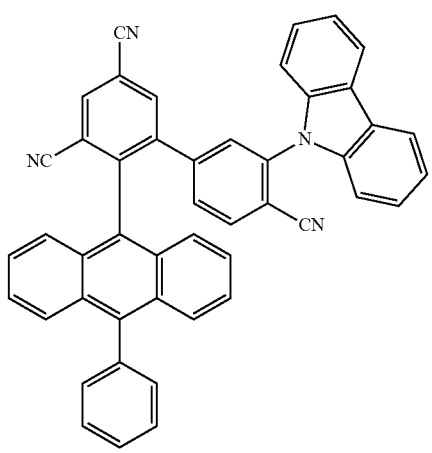

389
-continued
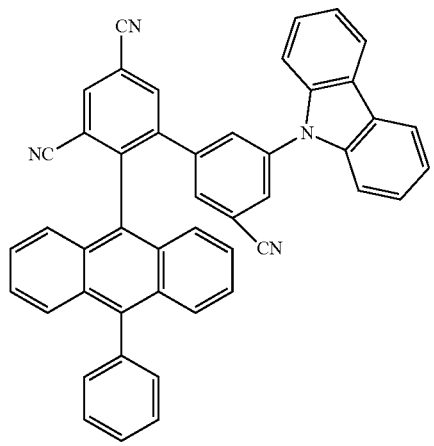
220
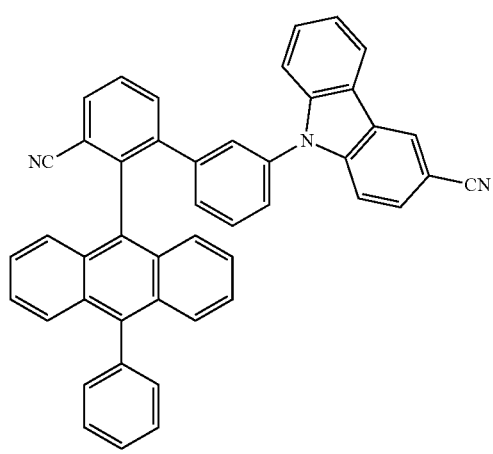
221
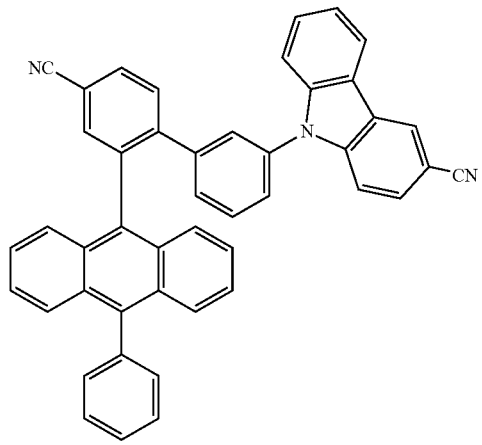
222
390
-continued
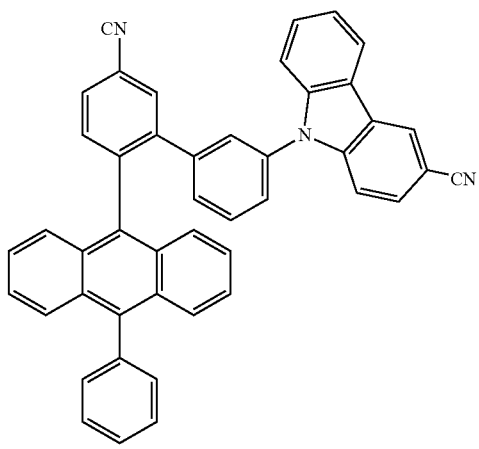
223
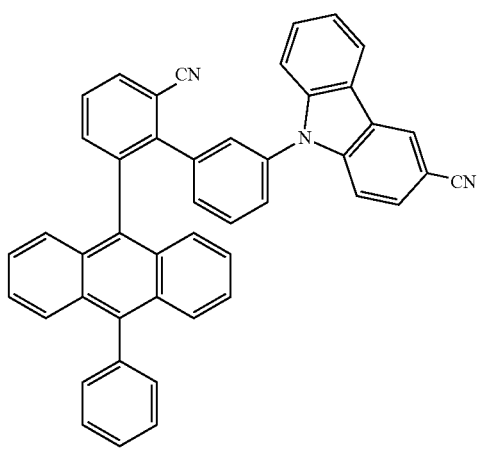
224
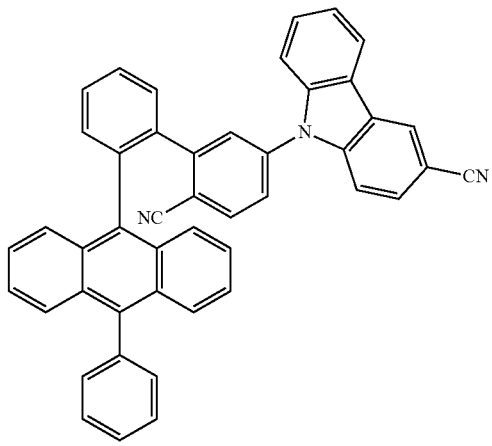
225

391
-continued
226
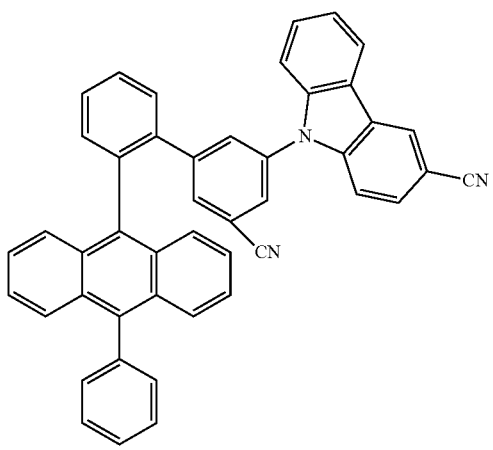
227
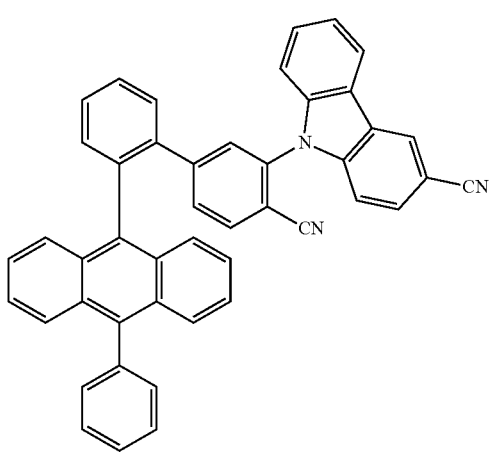
228
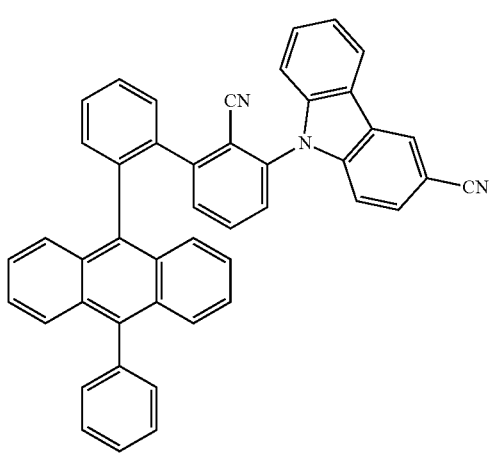
392
-continued
229
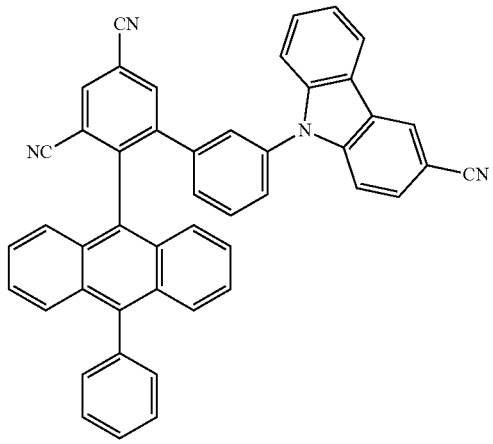
230
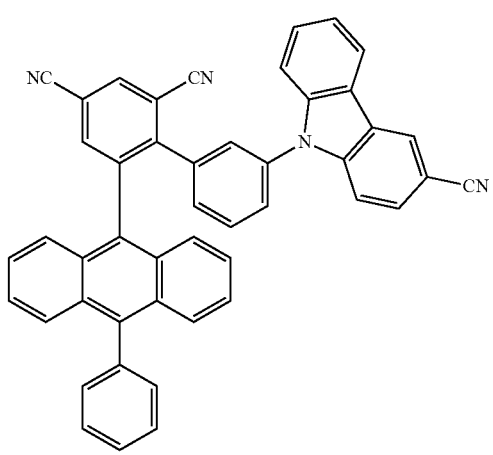
231
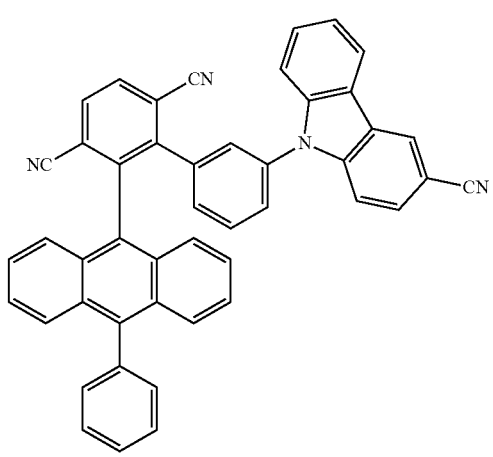

232
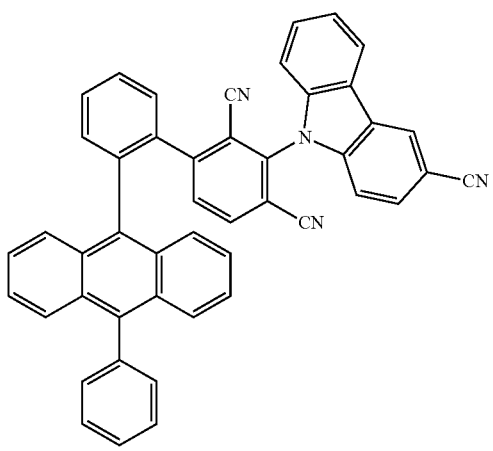
235
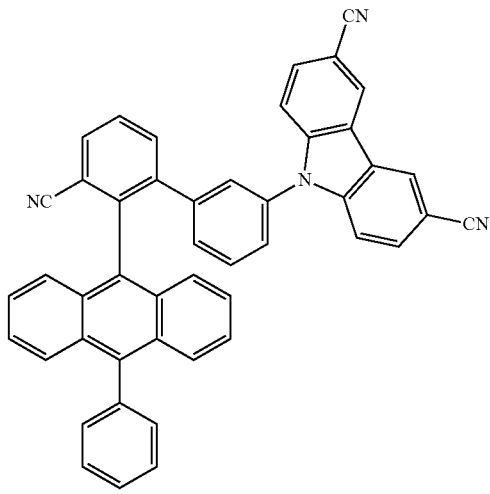
233
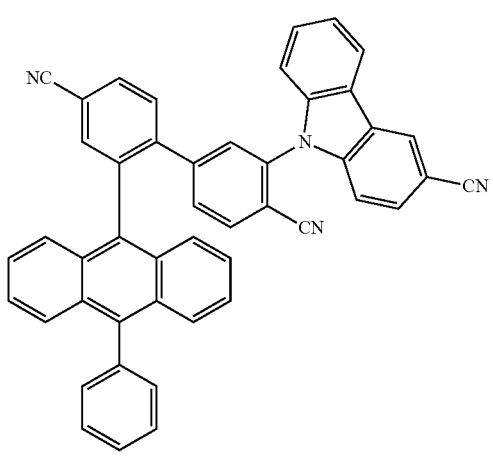
236
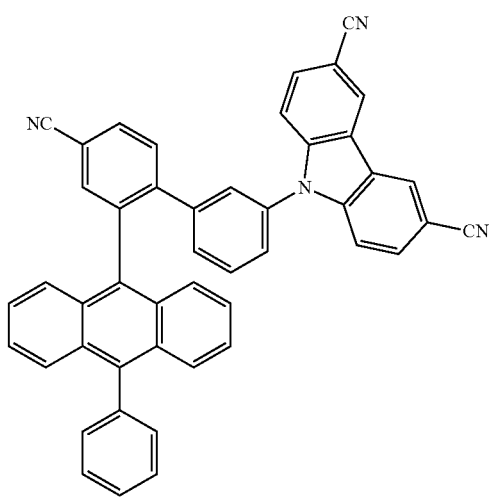
234
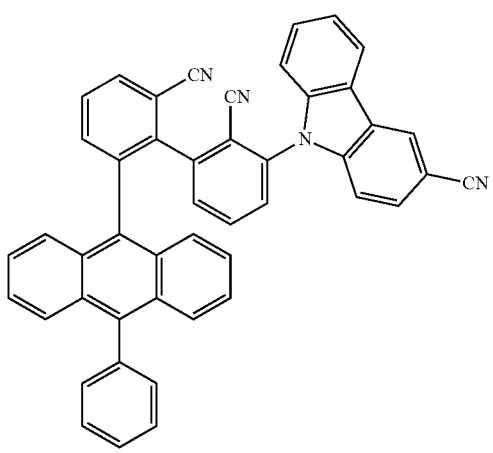
237
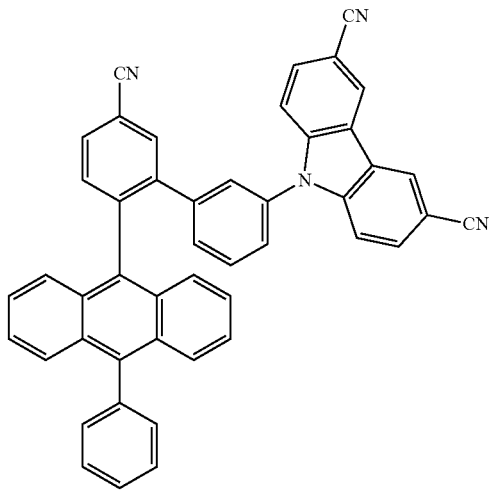

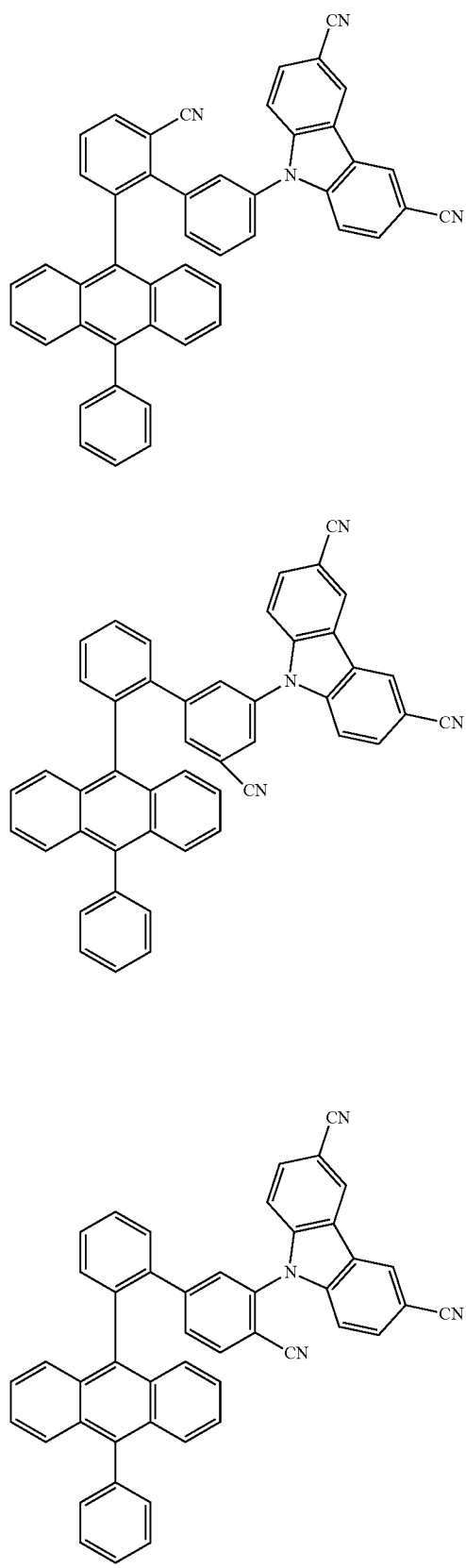
238
239
240
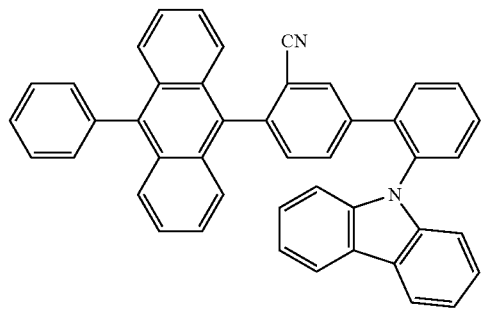
241
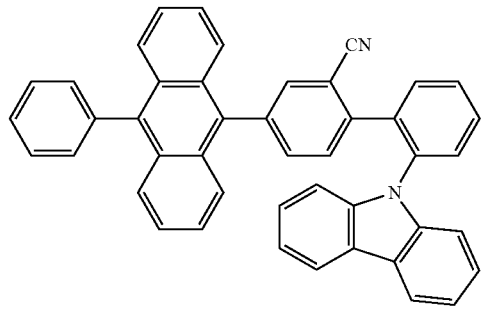
242
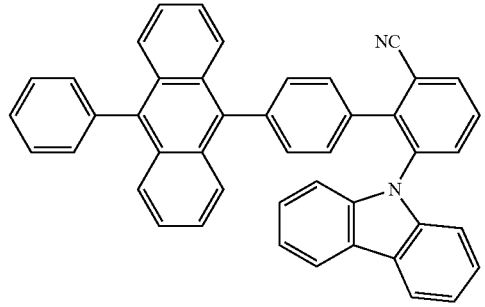
243
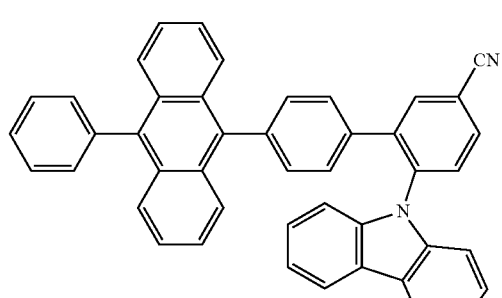
244
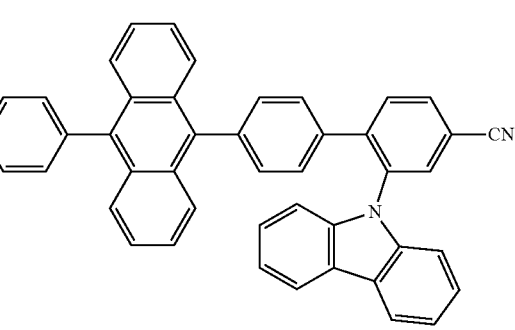
245

246
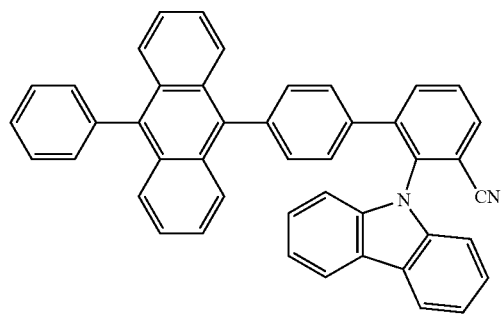
247
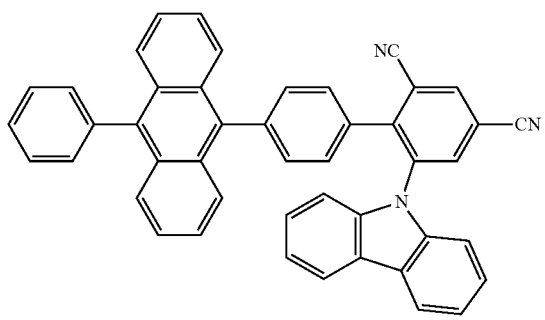
248
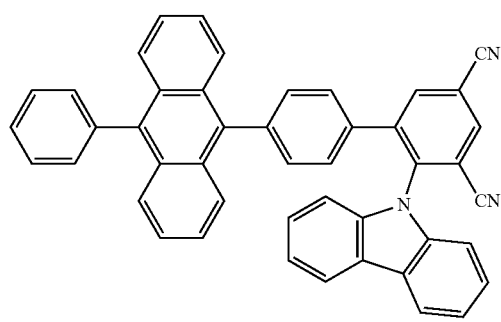
249
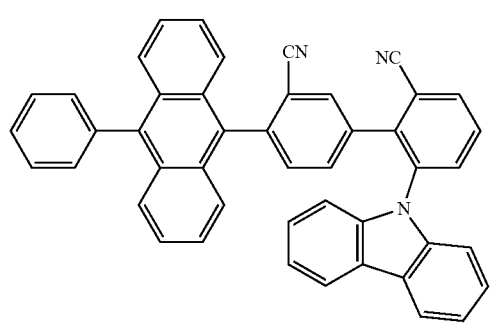
250
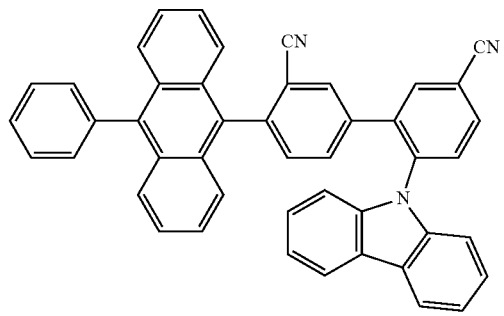
251
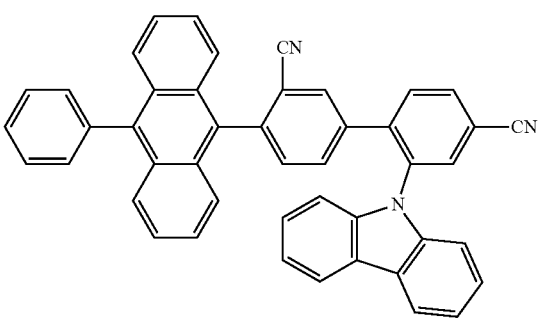
252
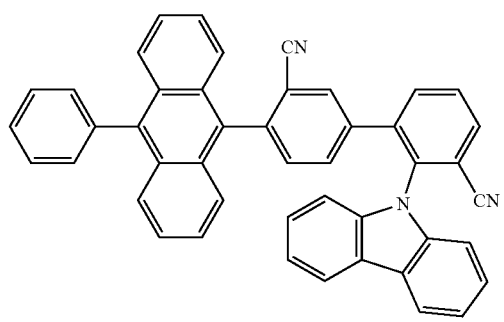
253
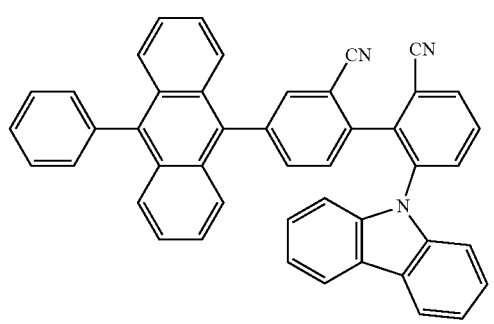

-continued
254
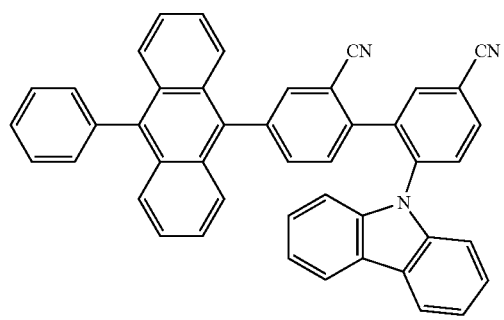
255
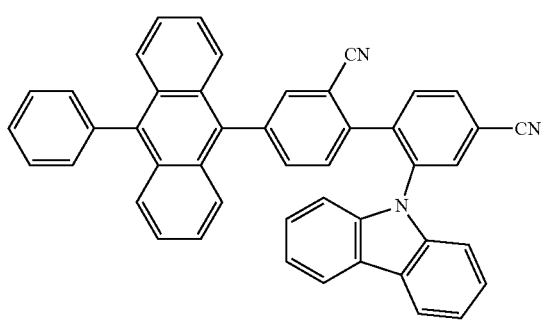
256
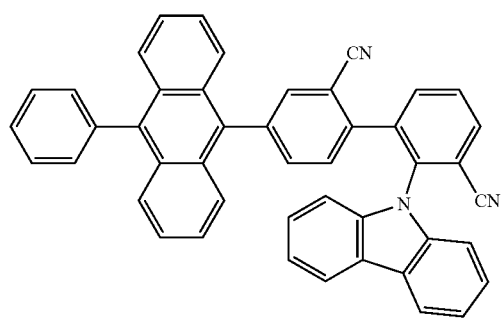
257
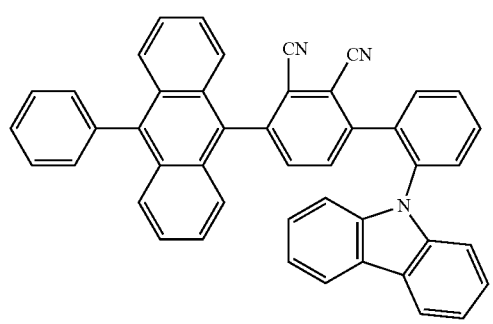
-continued
258
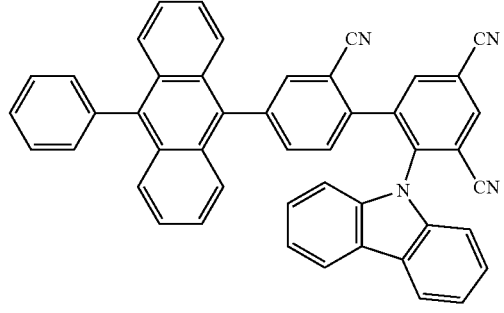
259
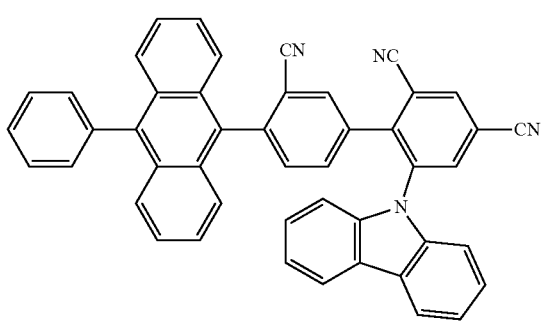
260
261
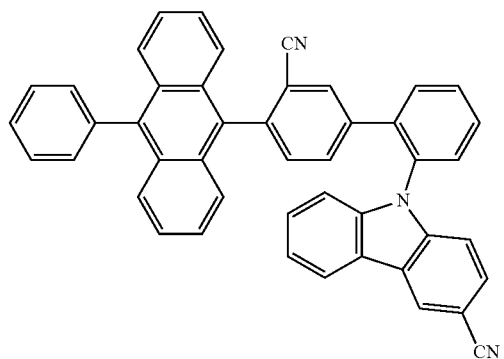

401
-continued
262
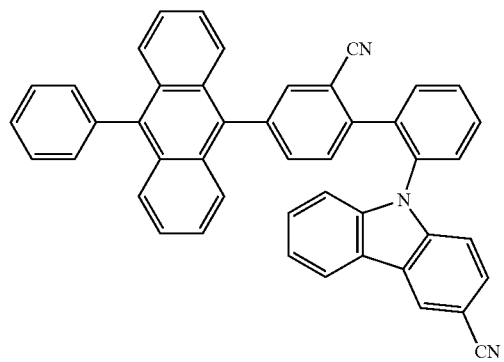
263
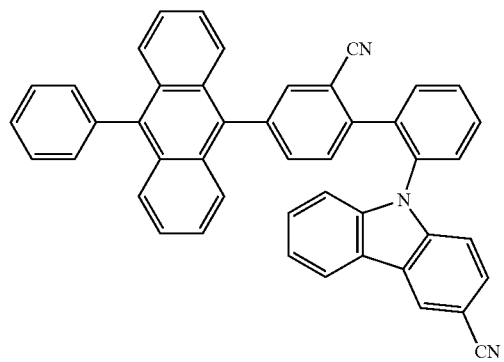
264
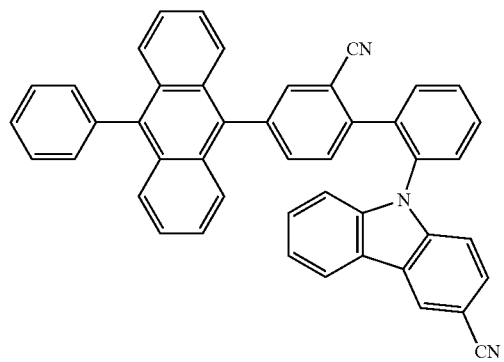
265
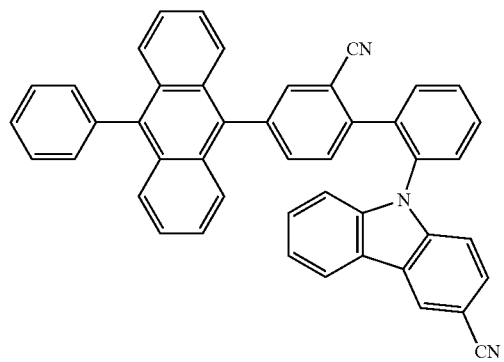
402
-continued
266
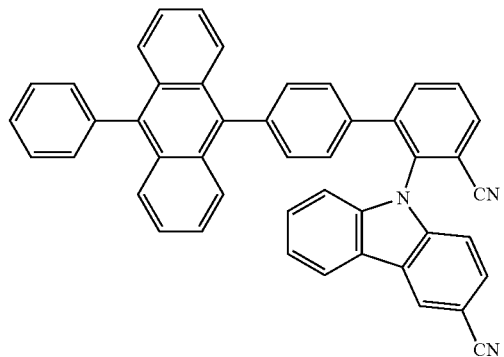
267
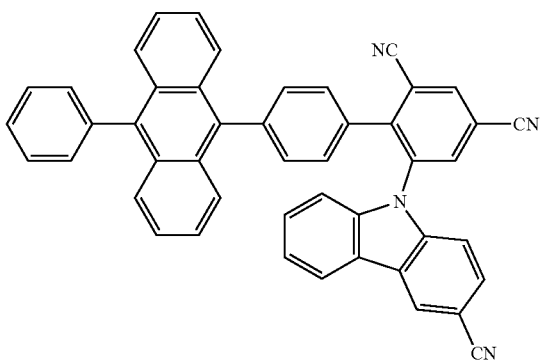
268
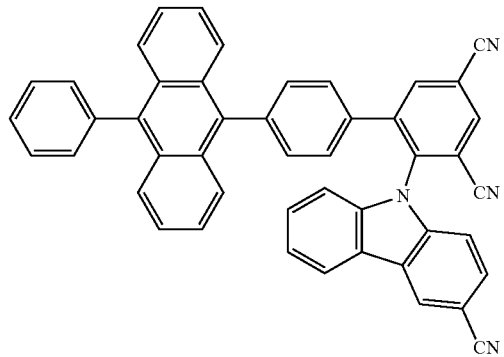
269
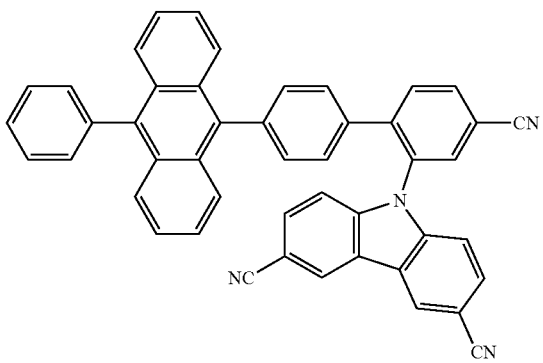

-continued
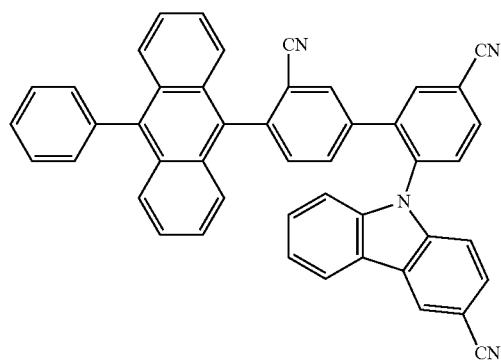
270
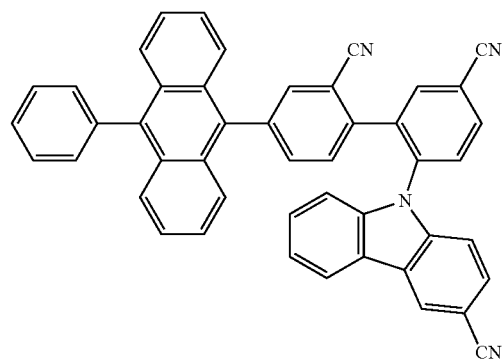
274
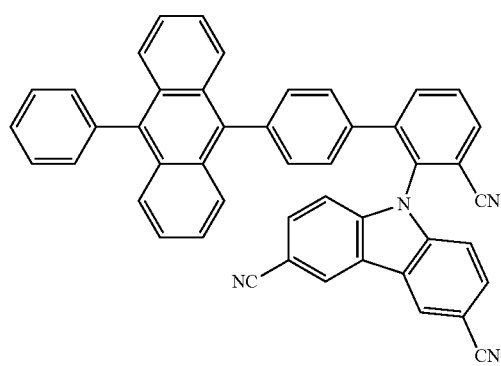
271
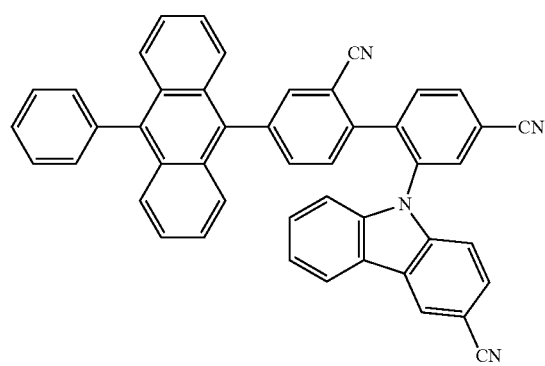
275
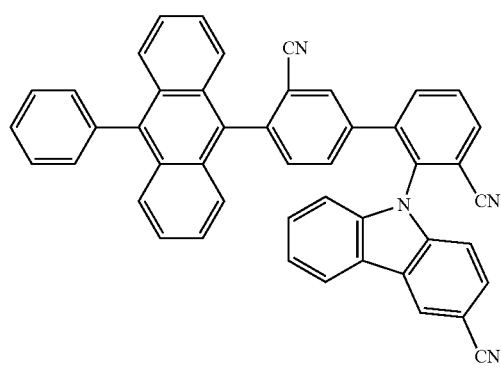
272
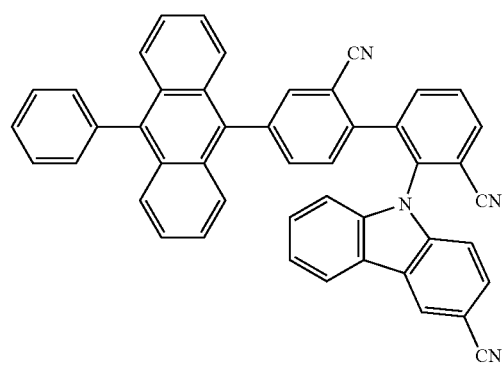
276
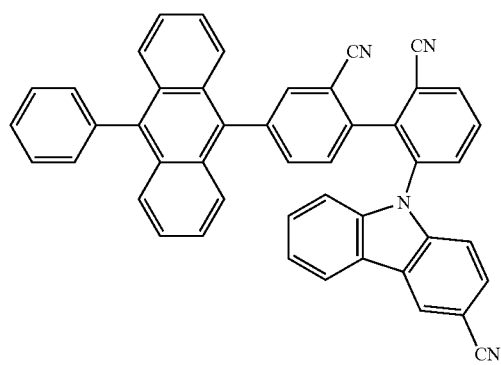
273
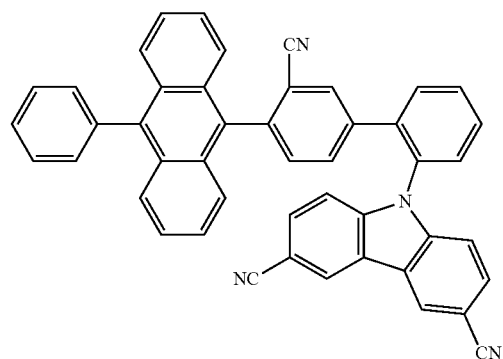
277

278
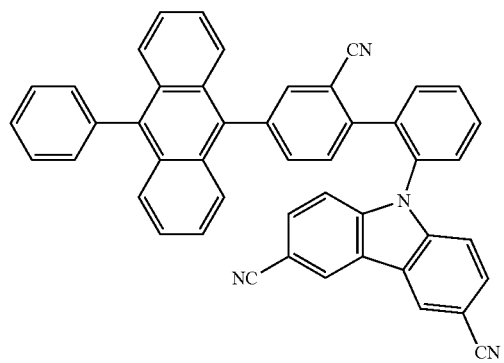
282
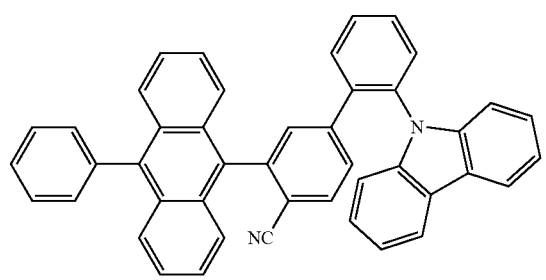
279
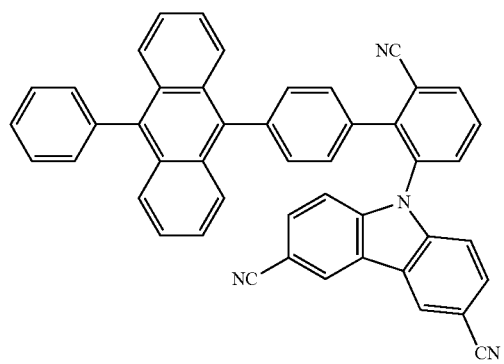
283
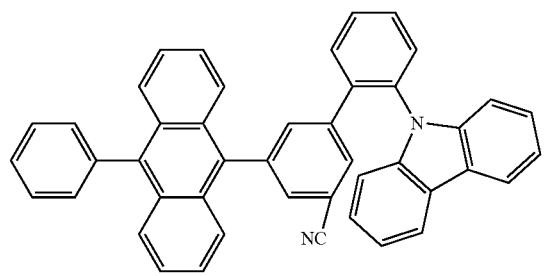
284
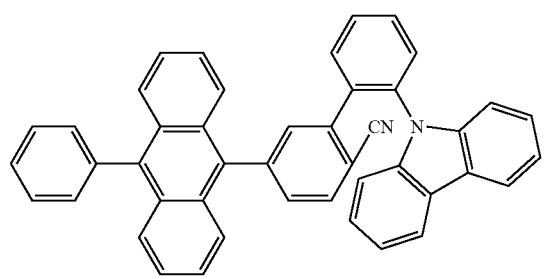
280
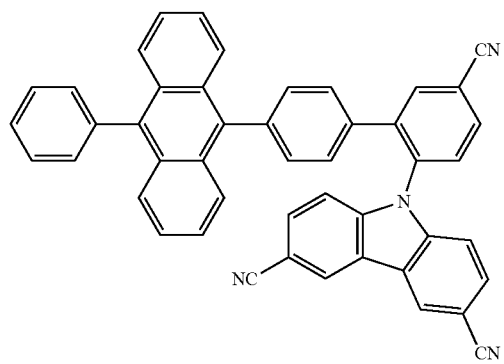
285
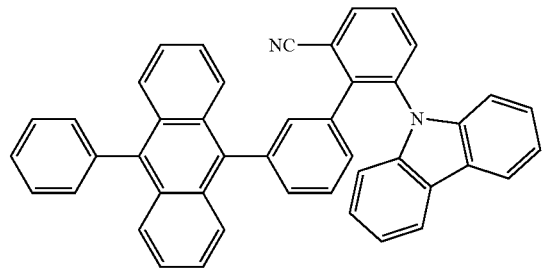
281
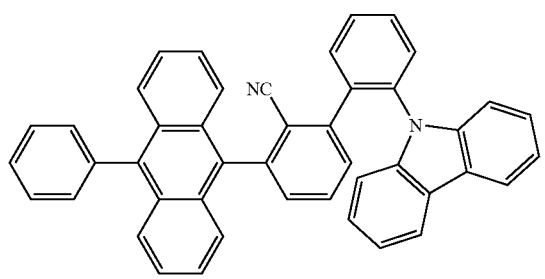
286
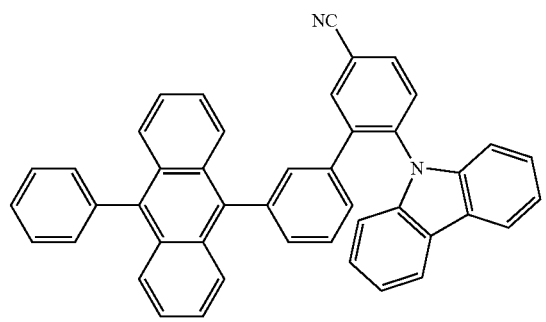

-continued
287
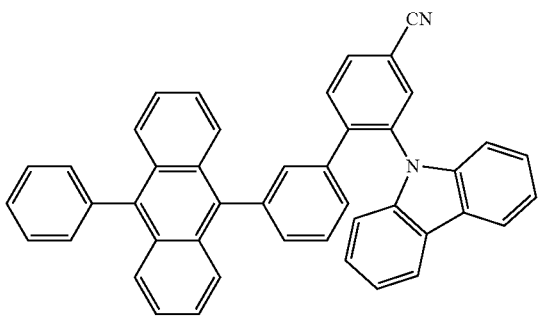
288
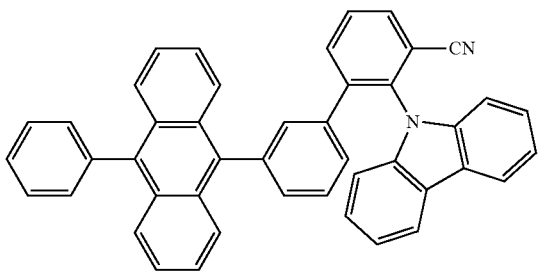
289
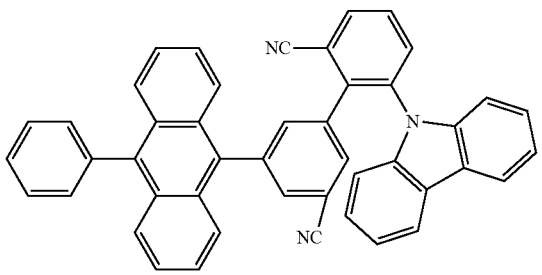
290
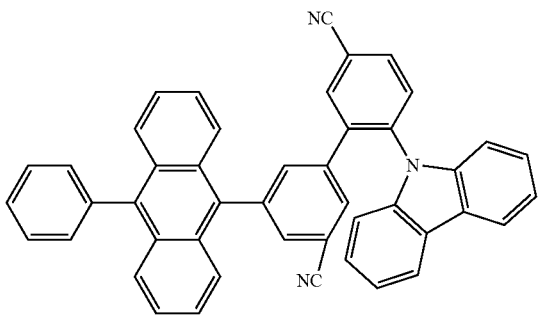
291
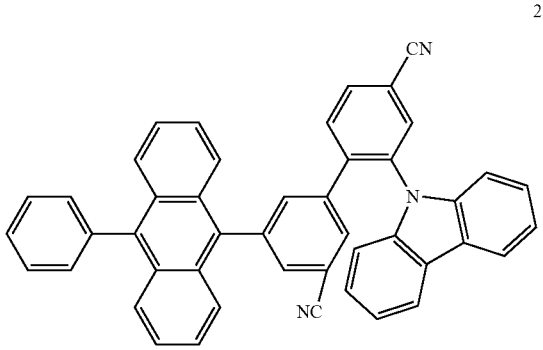
-continued
292
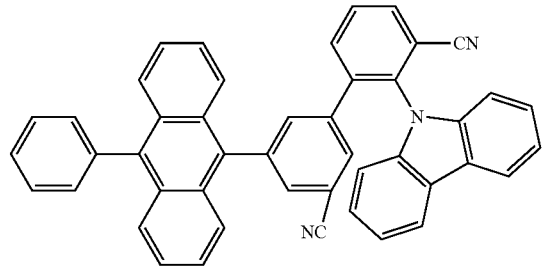
293
294
295
296

-continued
297
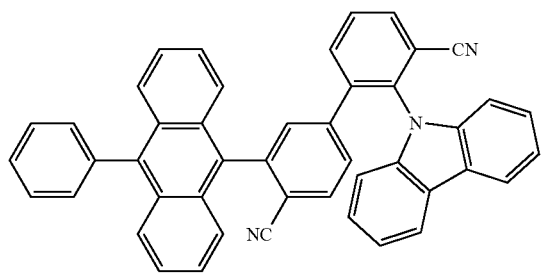
298
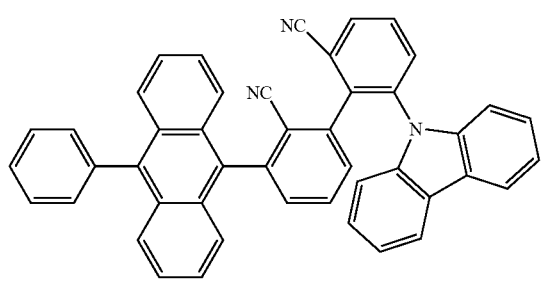
299
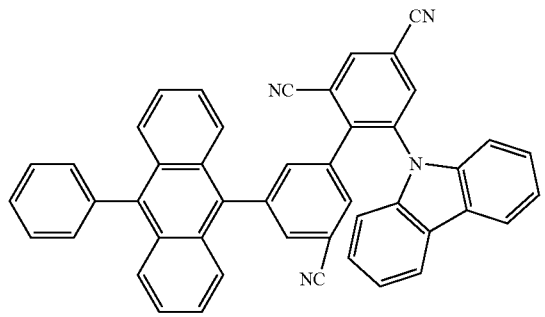
300
302
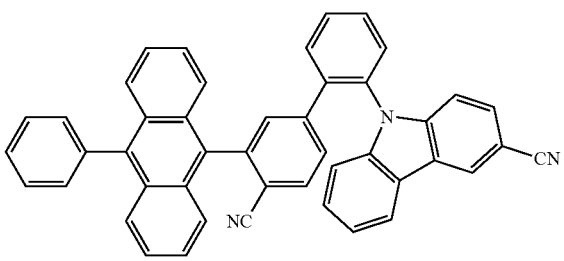
303
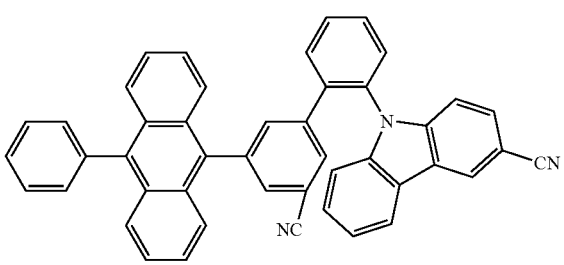
304
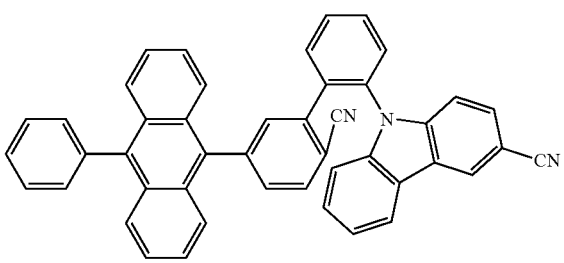
305
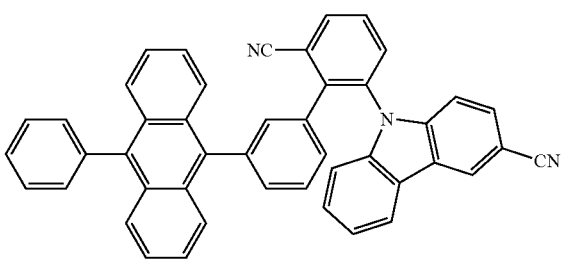
306
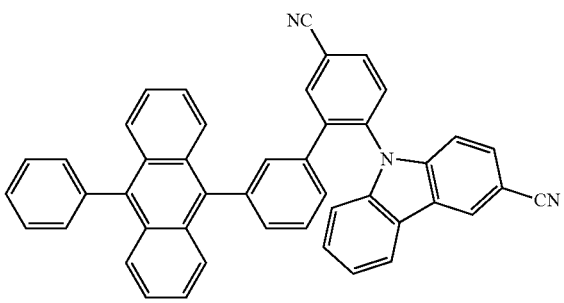
301

411
-continued
307
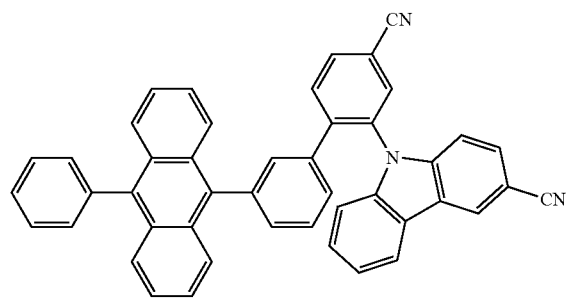
308
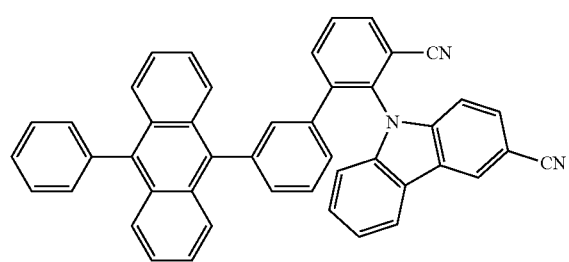
309
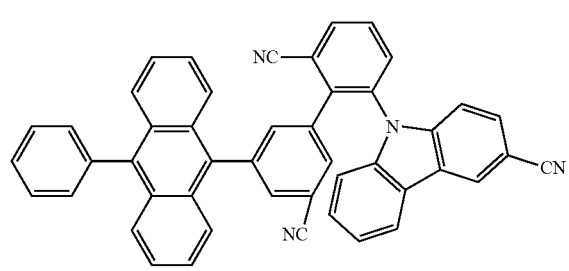
310
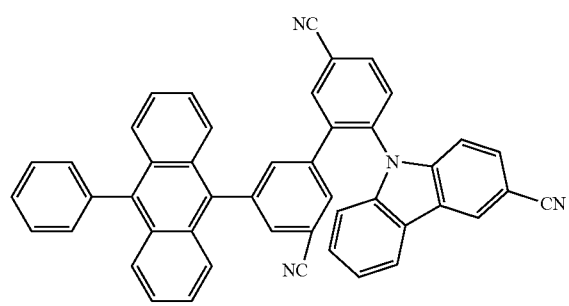
311
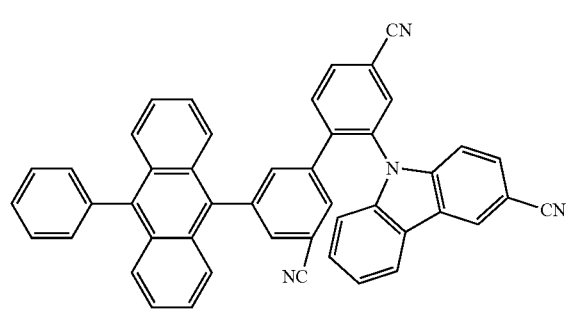
412
-continued
312
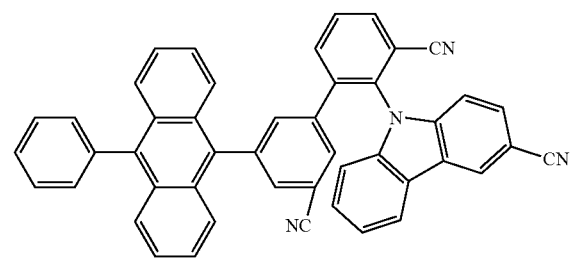
313
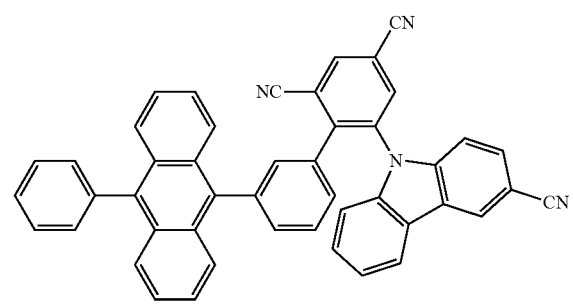
314
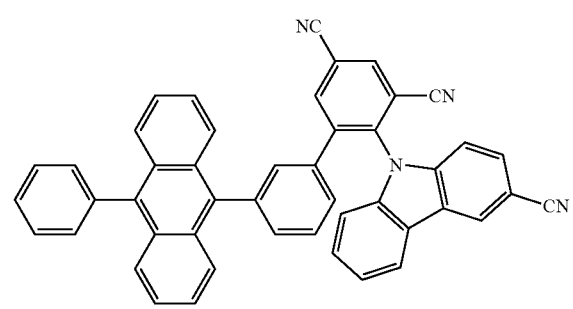
315
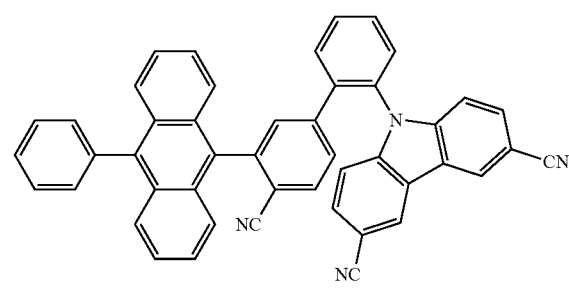
316
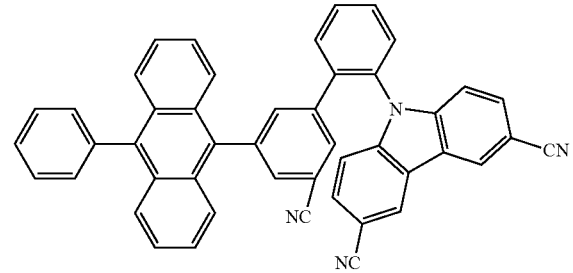

317
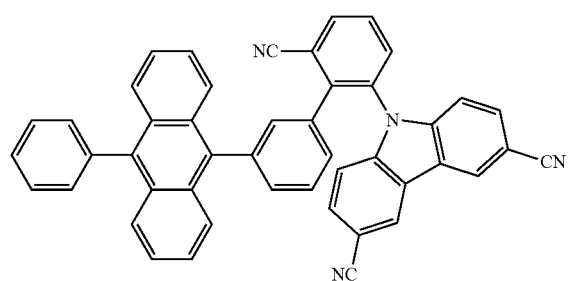
318
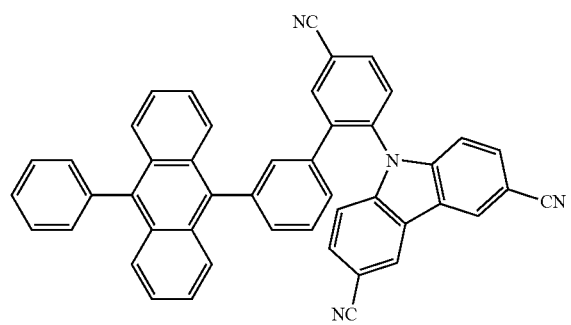
321
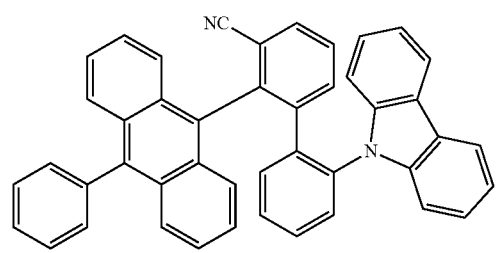
323
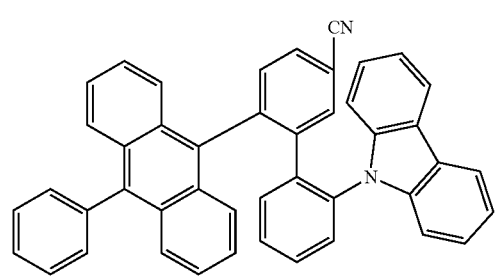
325
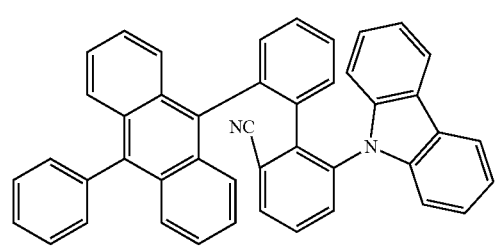
319
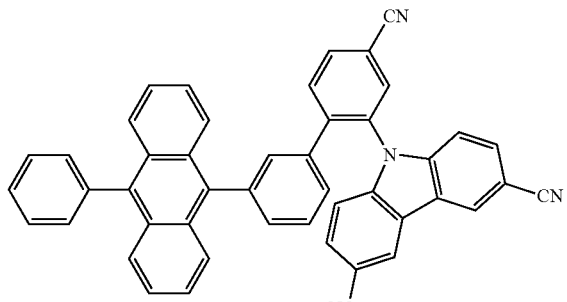
320
322
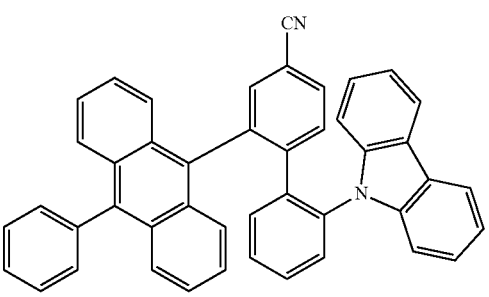
324
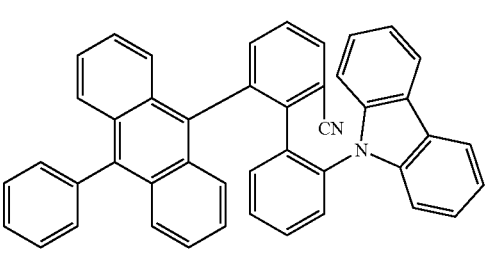
326
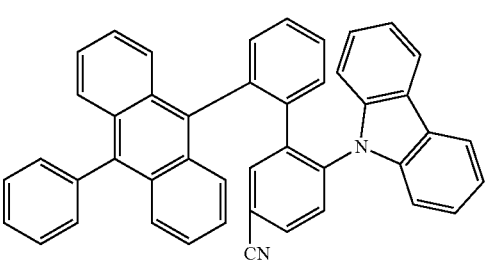

-continued
| 327 | 328 |
|---|---|
| 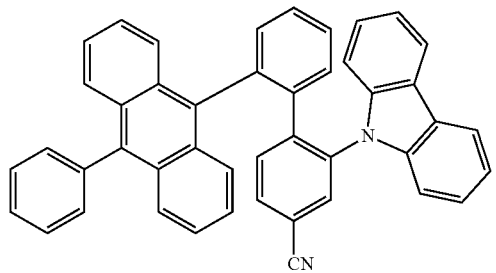 | 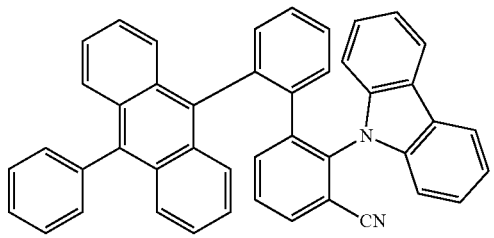 |
| 329 | 330 |
| 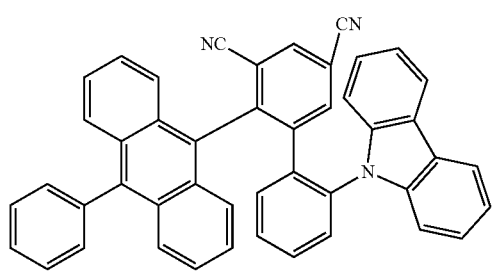 | 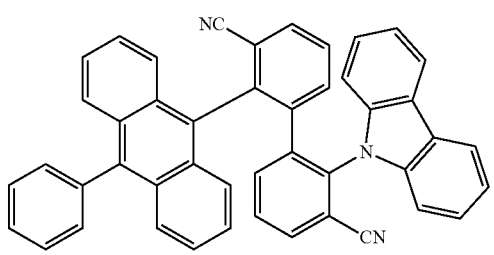 |
| 331 | 332 |
| 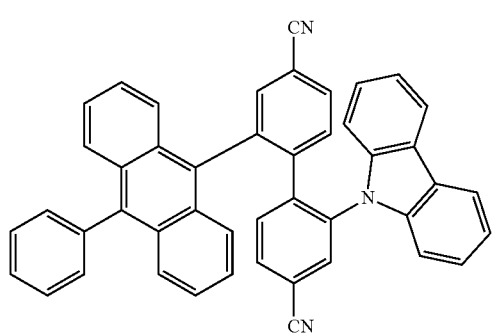 | 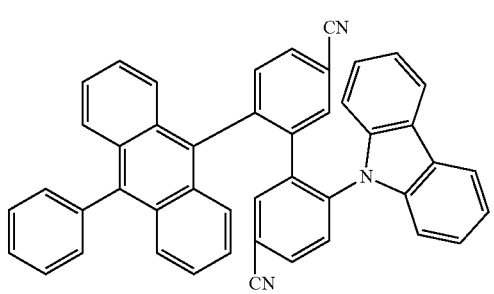 |
| 333 | 334 |
| 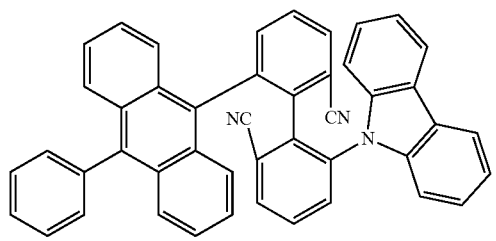 | 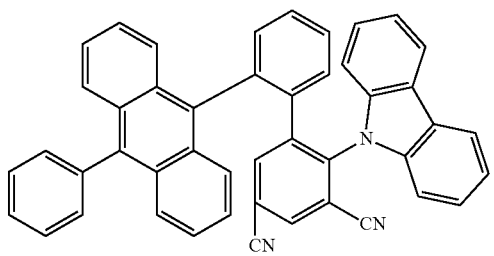 |
| 335 | 336 |
| 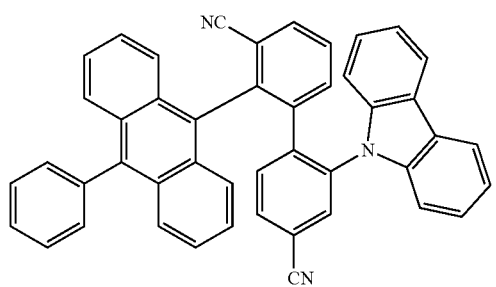 | 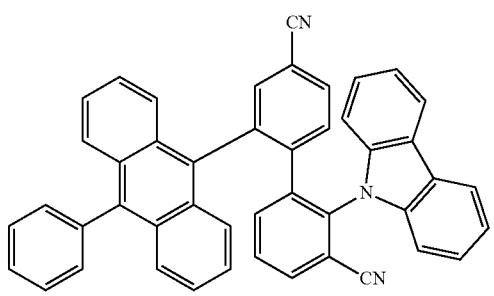 |

-continued
337
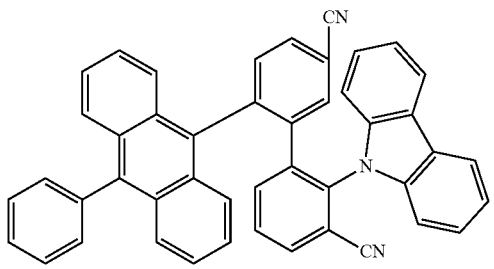
338
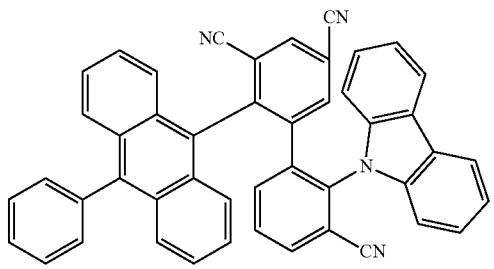
339
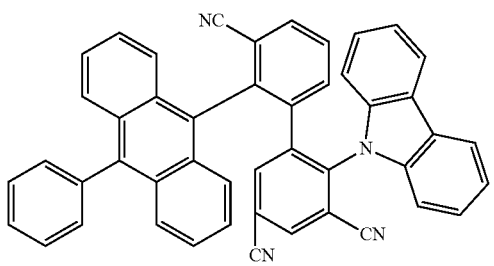
340
341
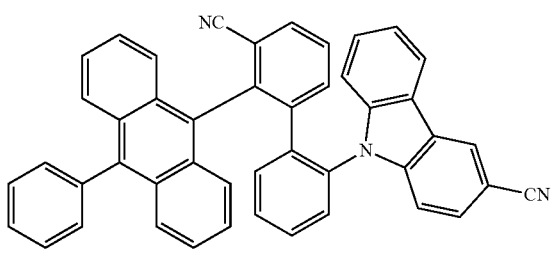
342
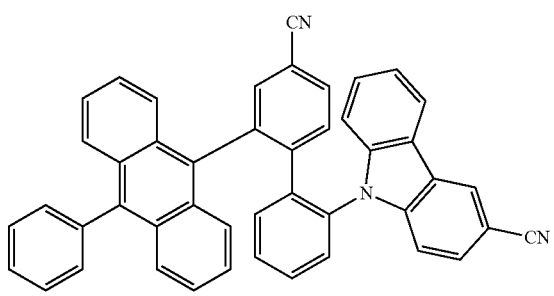
343
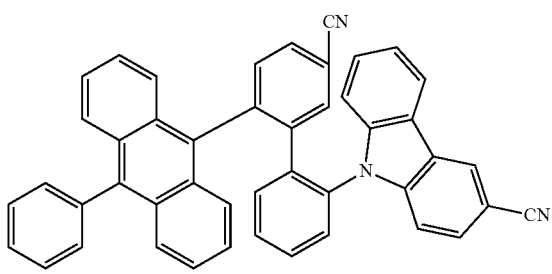
344
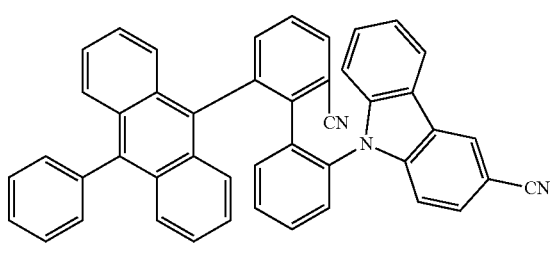
345
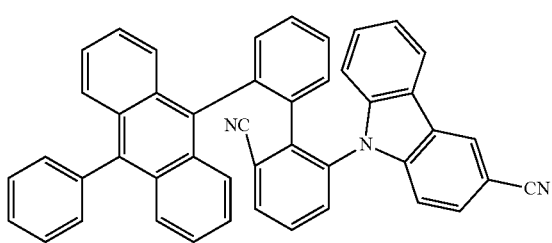
346
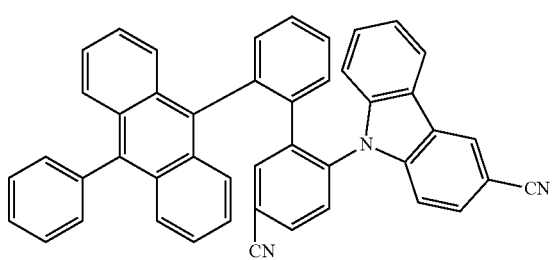

419    420
-continued
347 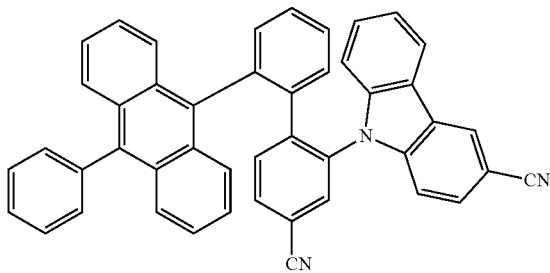　　348 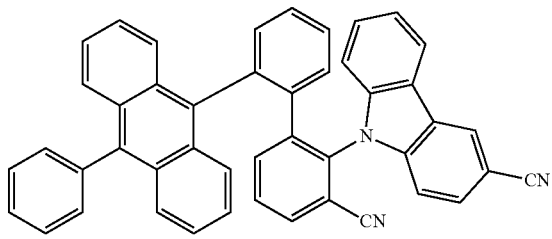
349 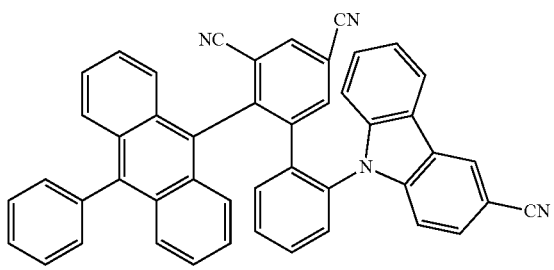　　350 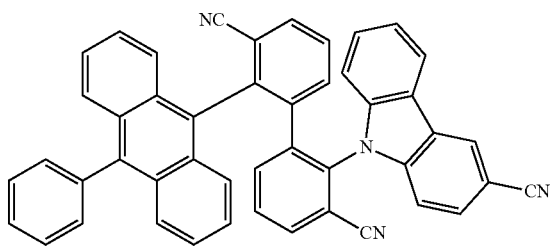
351 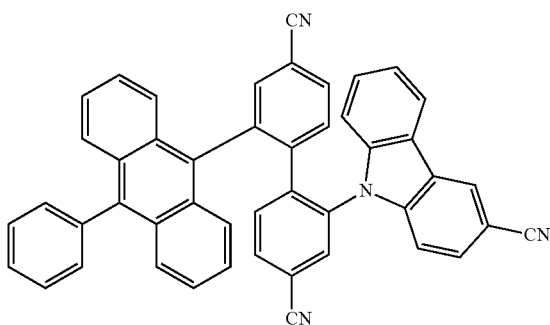　　352 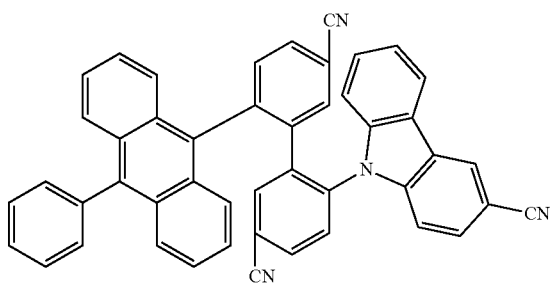
353 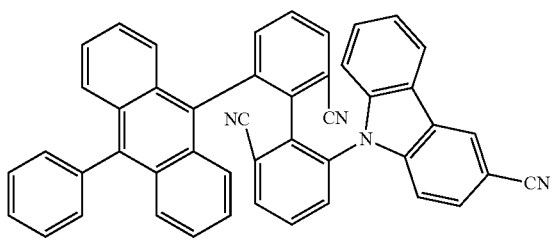　　354 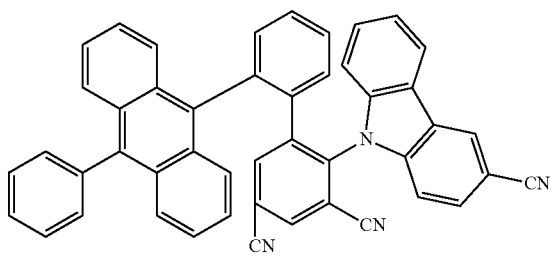
355 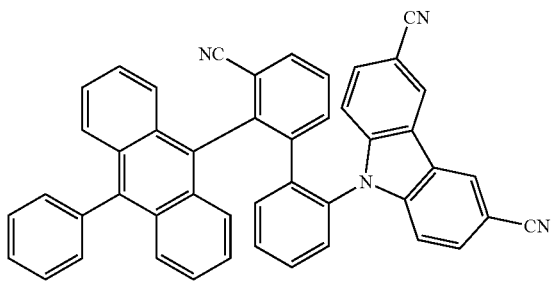　　356 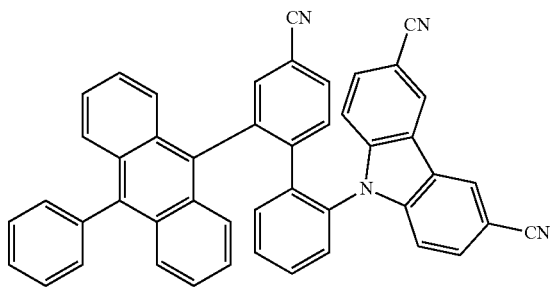

-continued
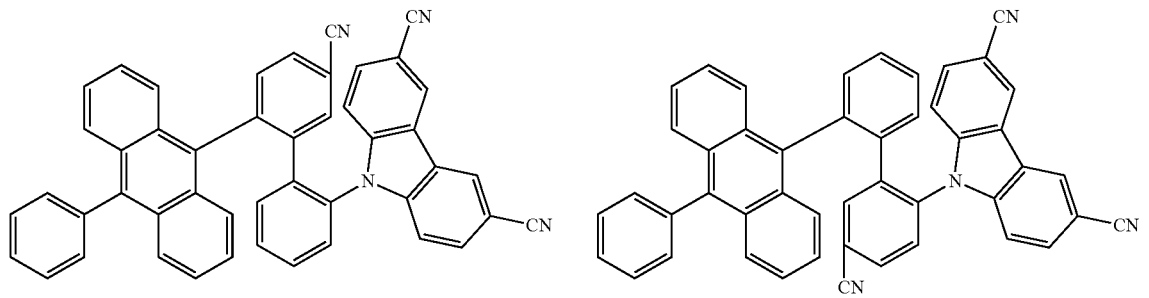
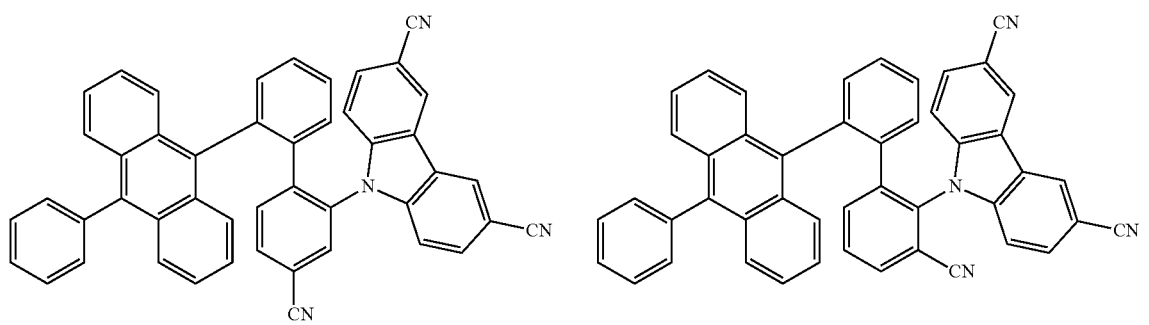
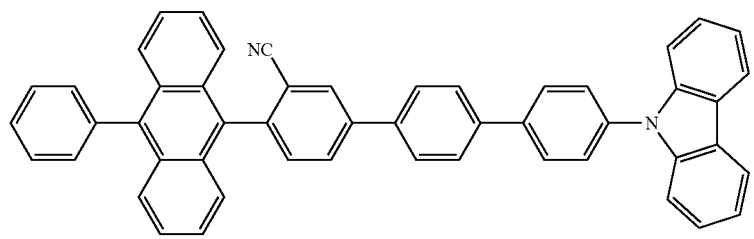
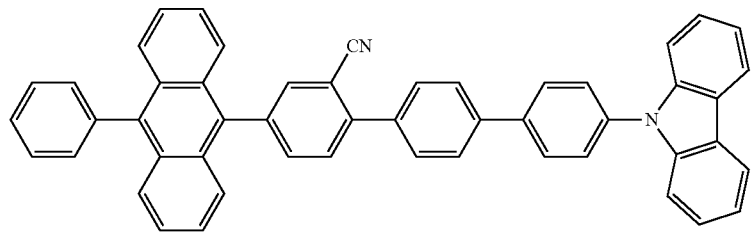
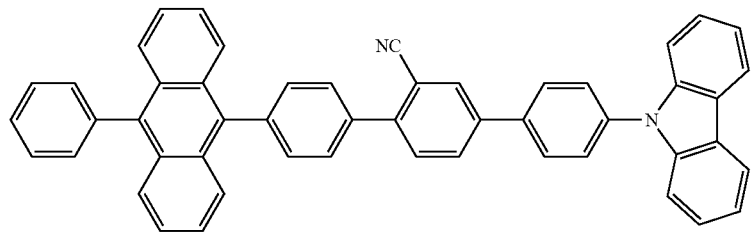
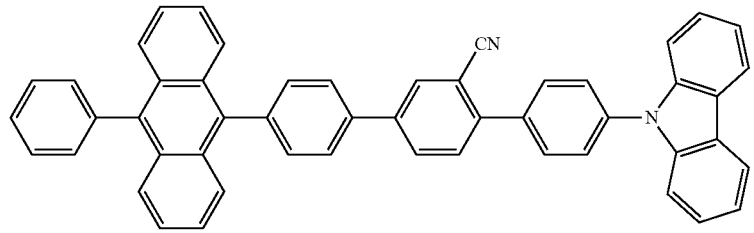

-continued
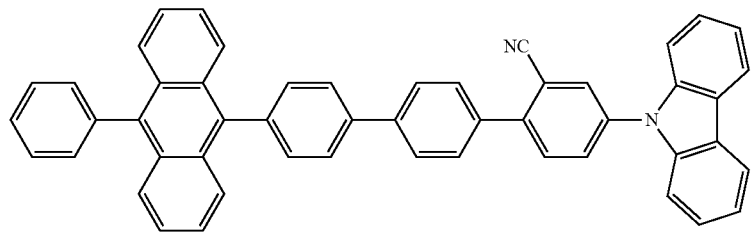
365
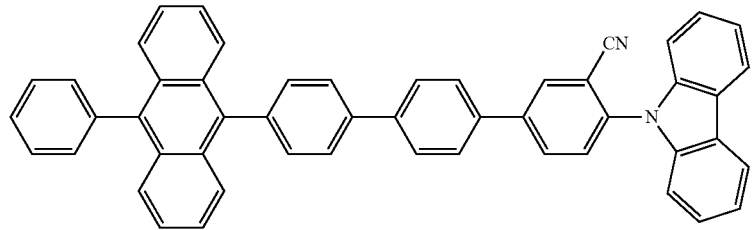
366
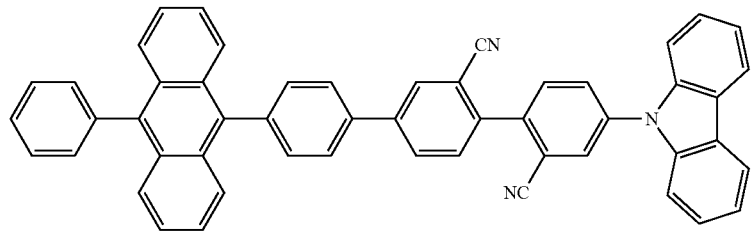
367
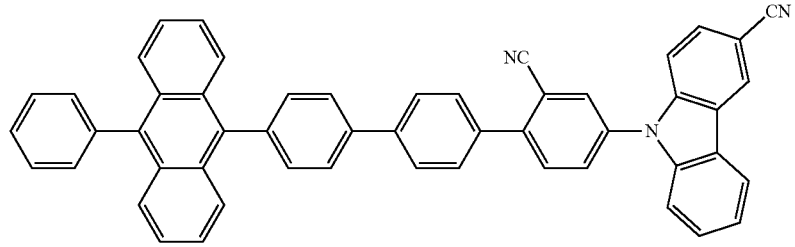
368
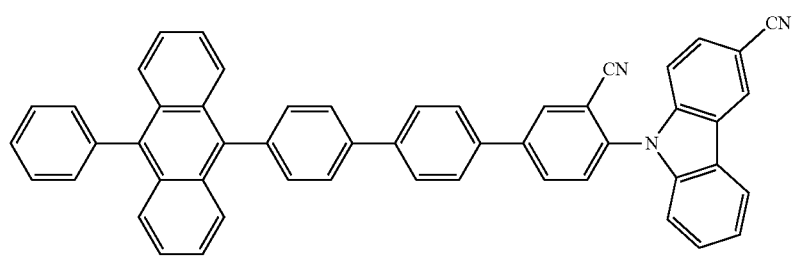
369
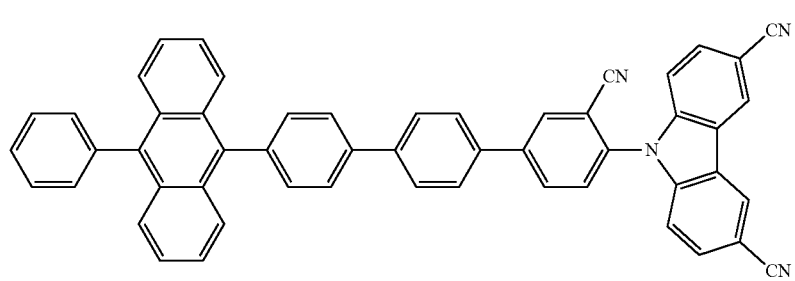
370

-continued
371
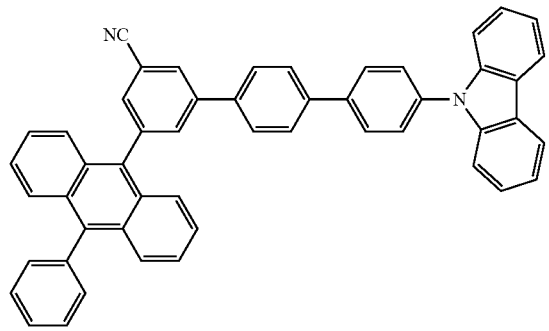
372
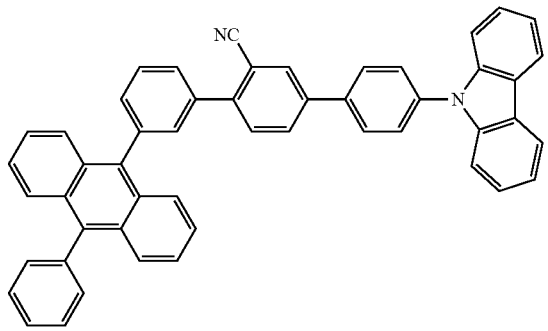
373
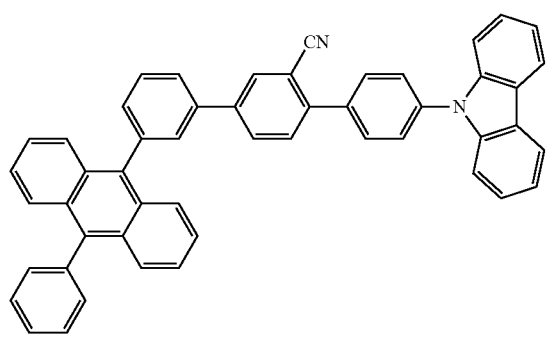
374
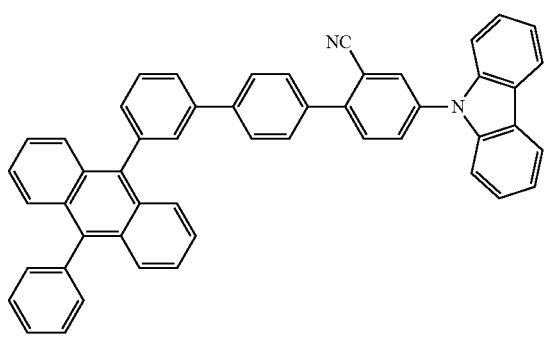
375
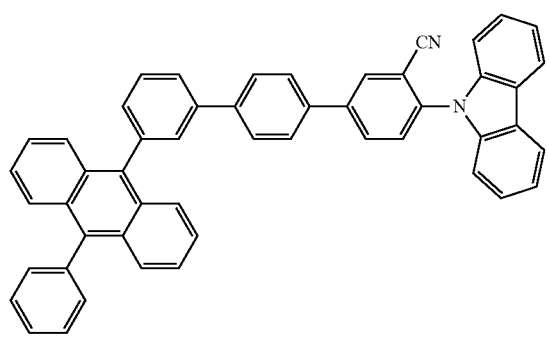
376
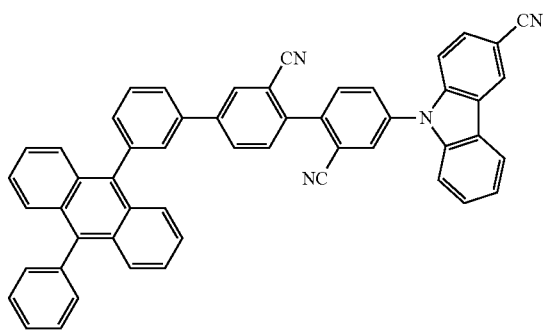
377
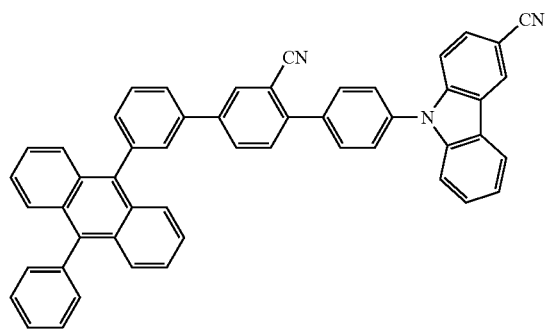
378
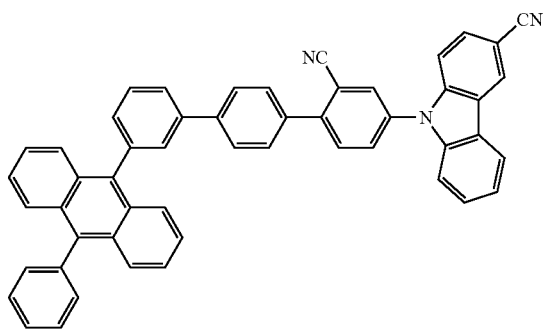

-continued
379
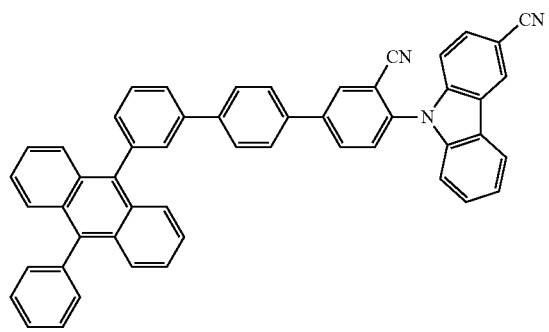
380
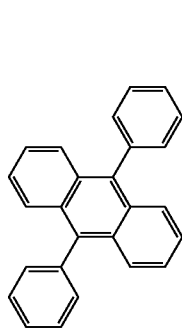
381
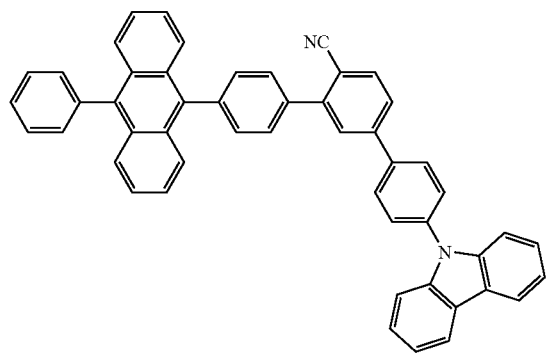
382
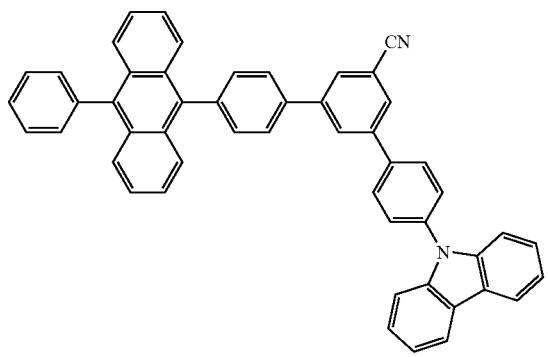
383
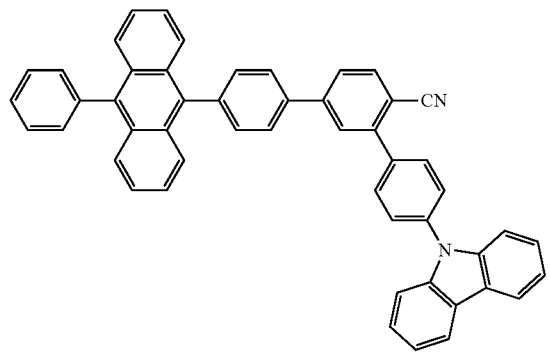
384
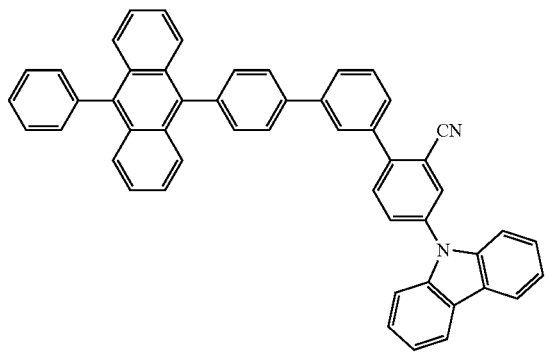
385
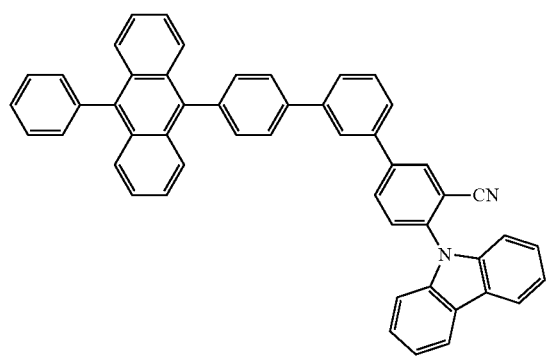
389
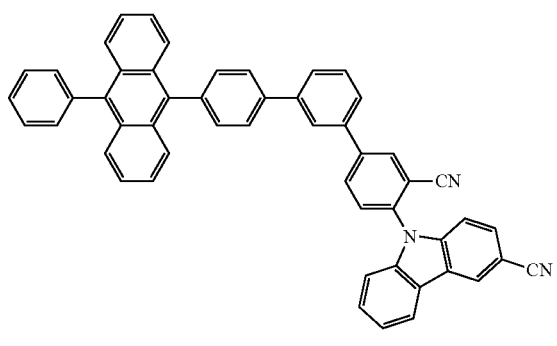

-continued
386
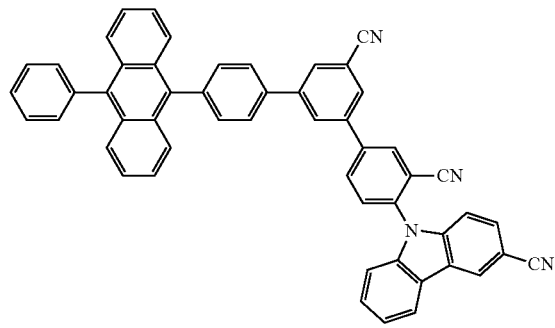
387
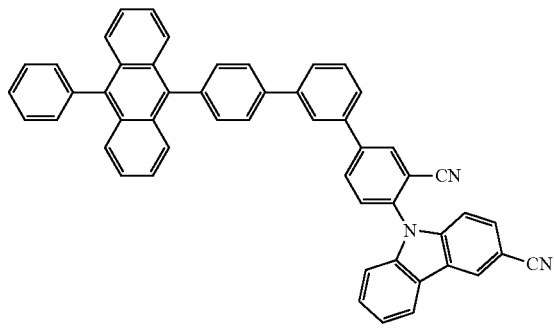
388
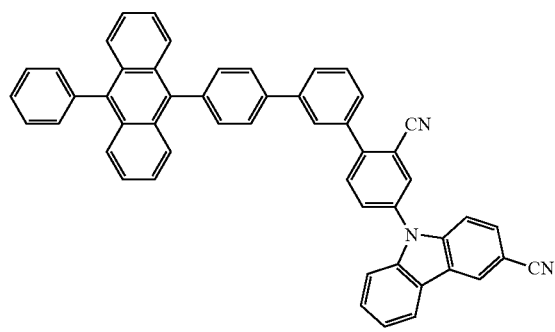
390
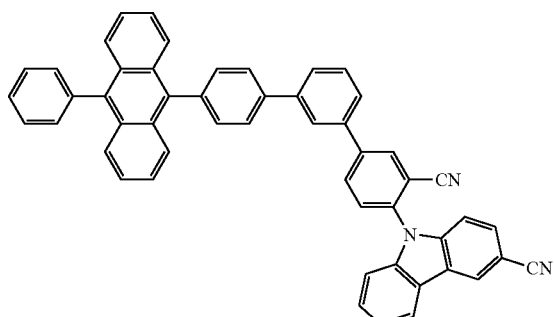
391
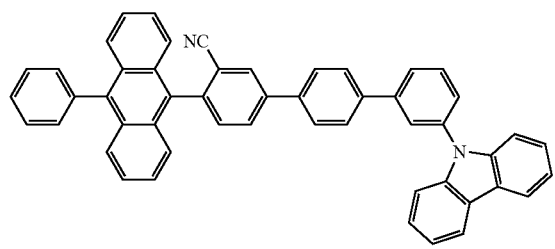
392
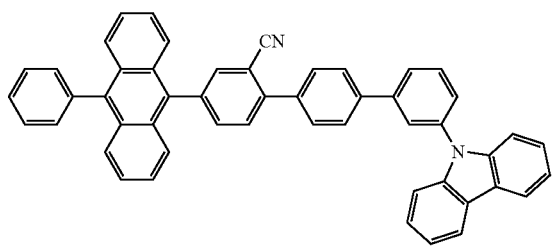
393
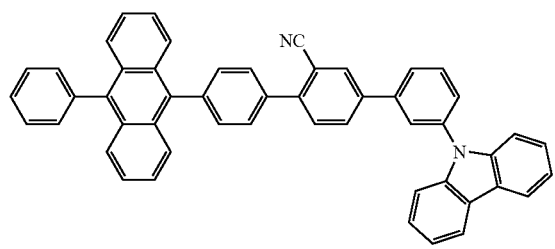
394
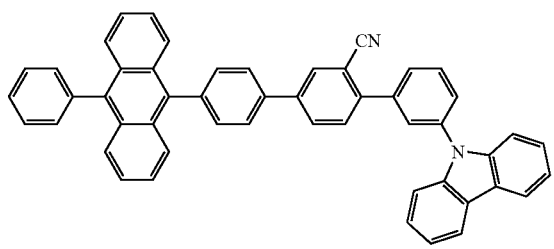
395
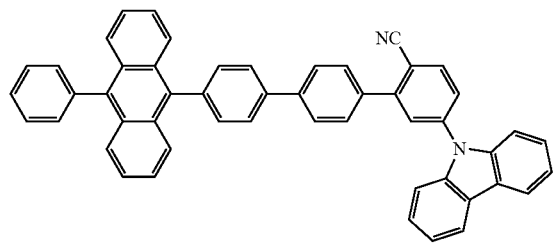
396
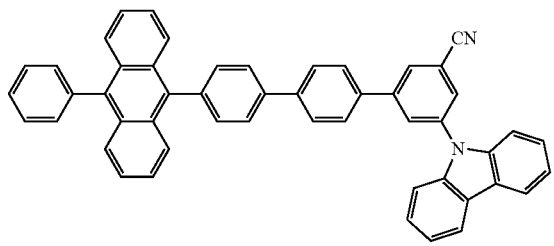

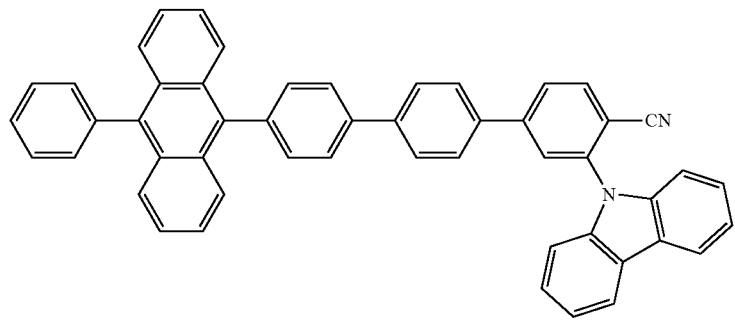
397
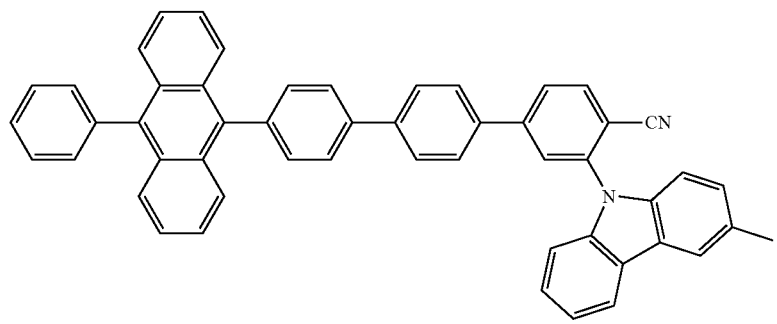
398
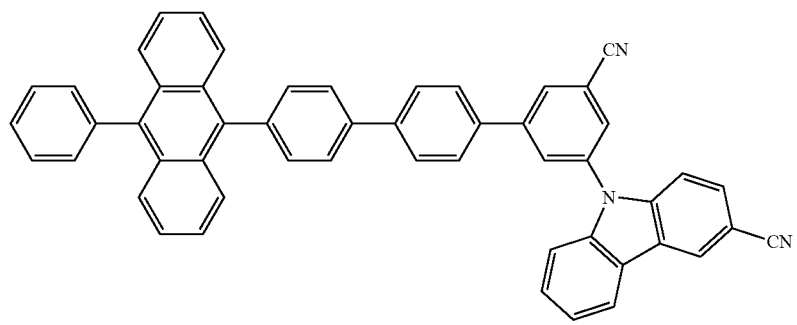
399
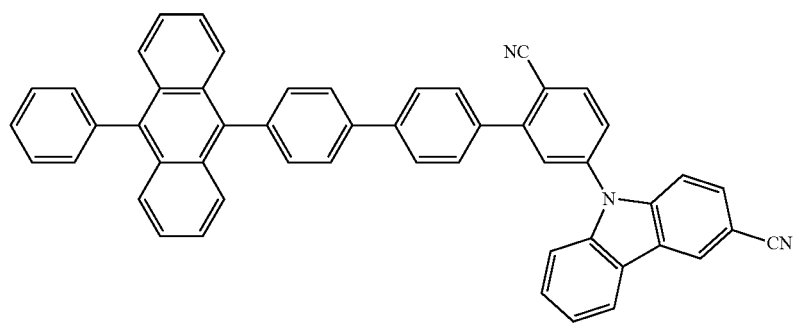
400

-continued
401
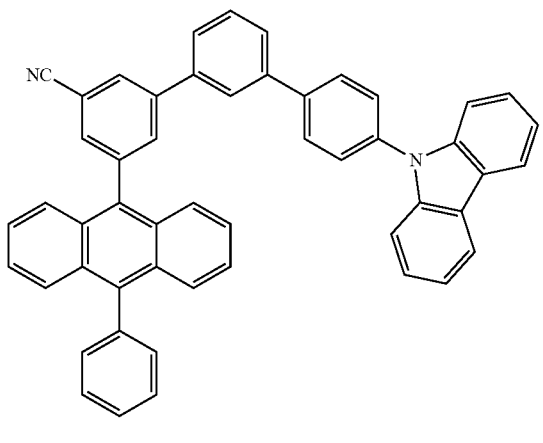
402
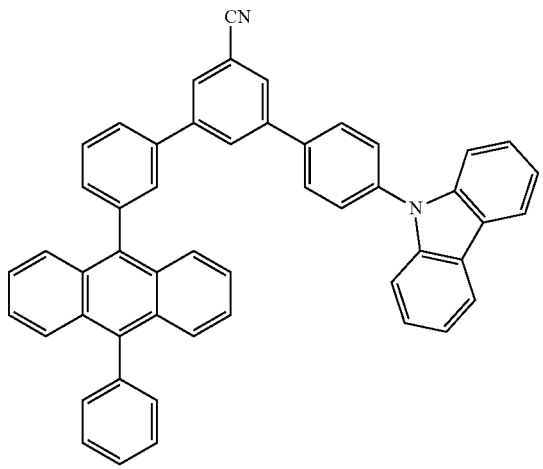
403
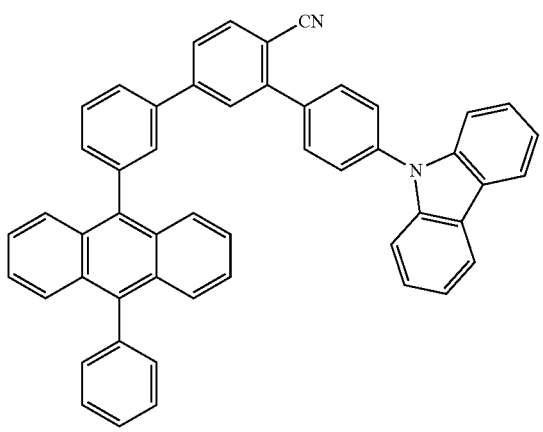
404
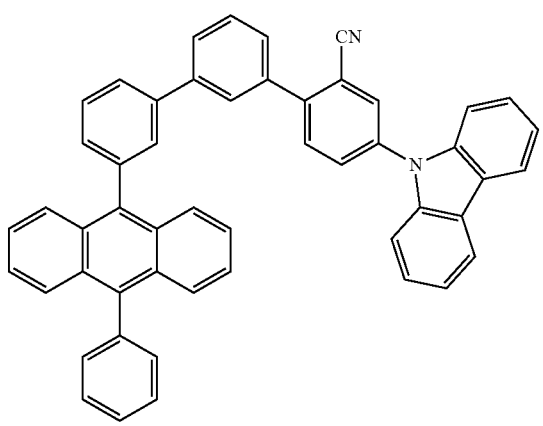
405
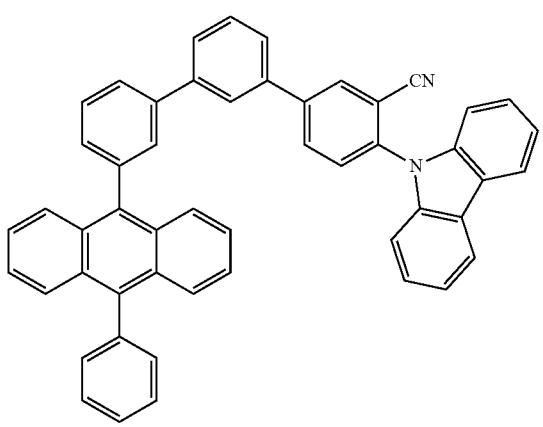
406
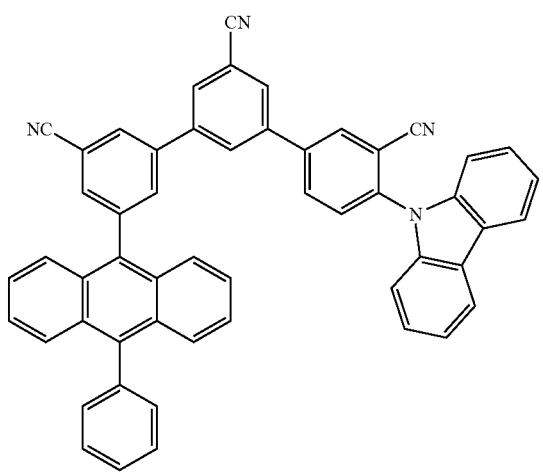

-continued
407
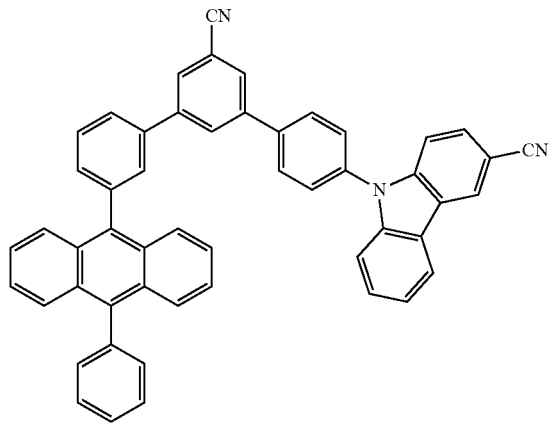
408
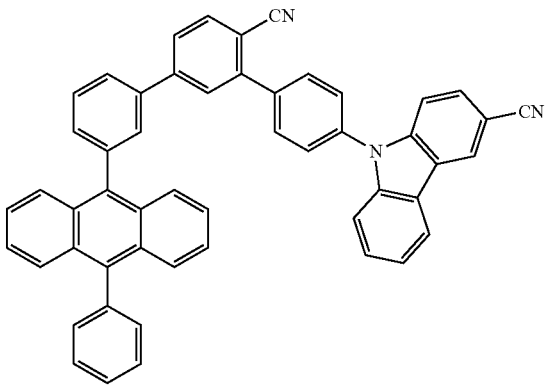
409
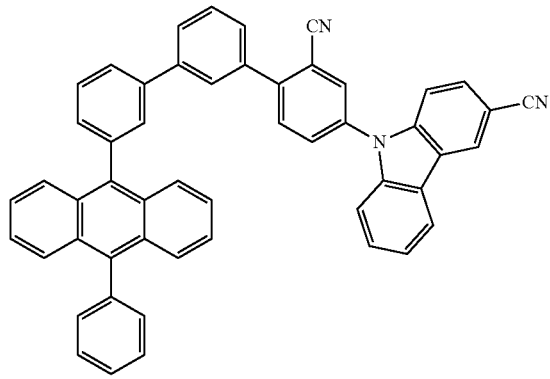
410
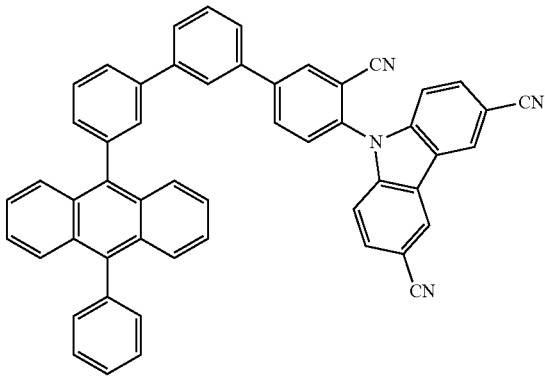
411
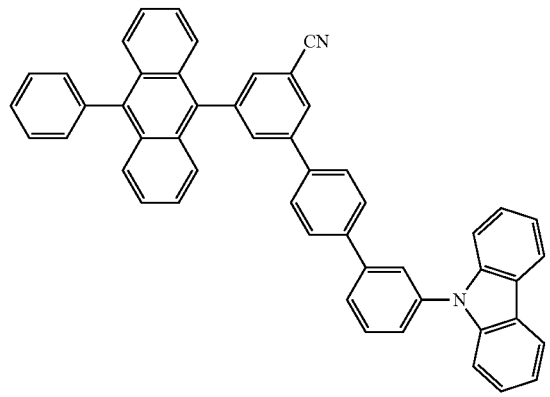
412
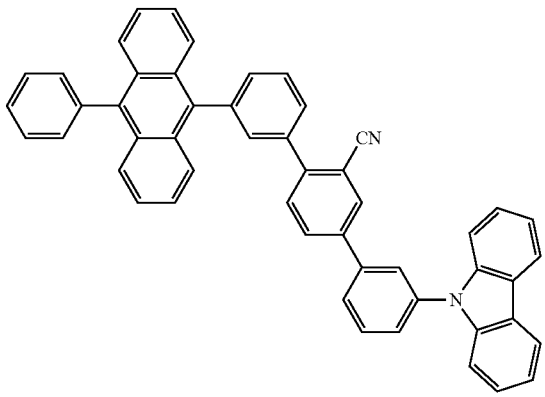

-continued
413
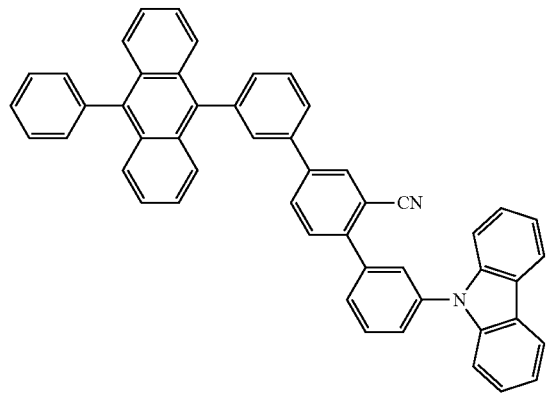
414
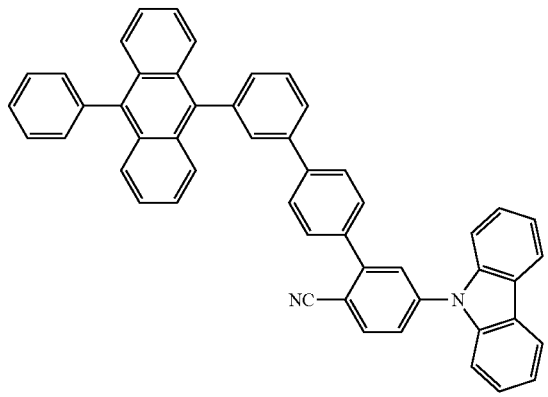
415
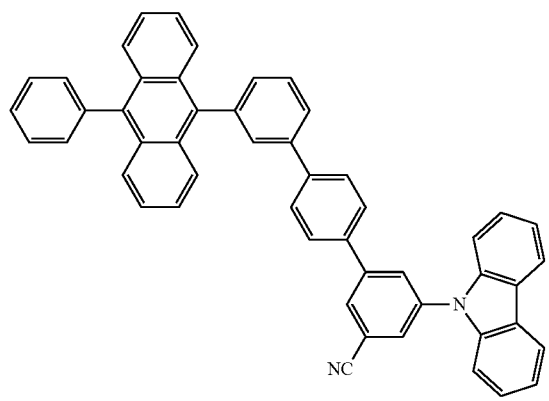
416
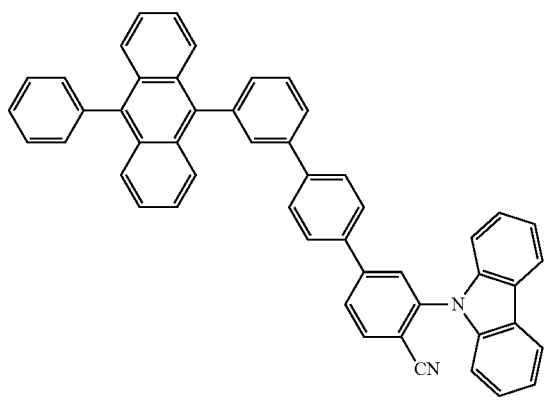
417
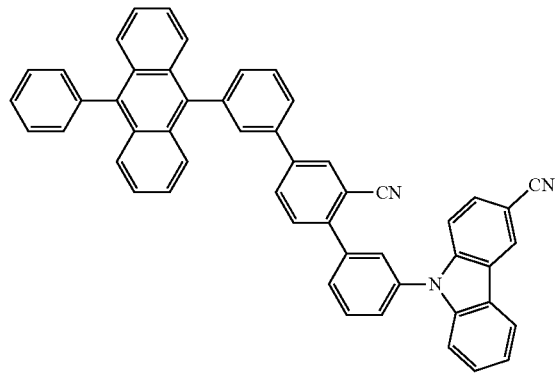
418
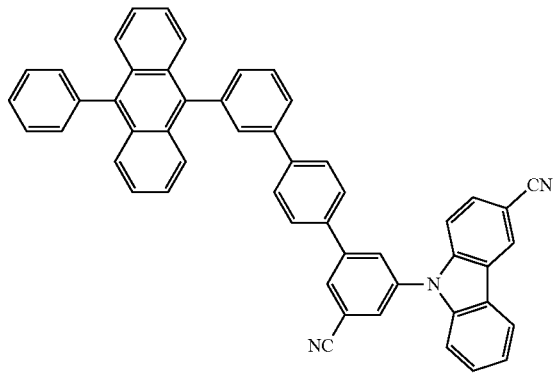
419
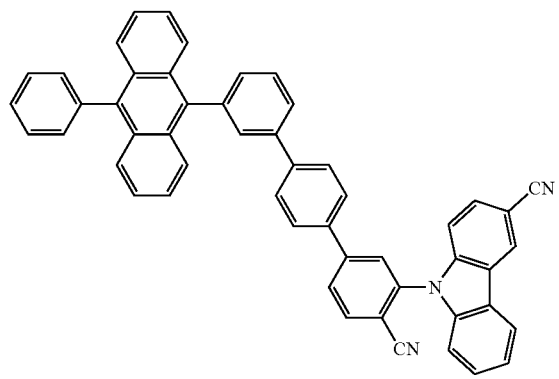
420
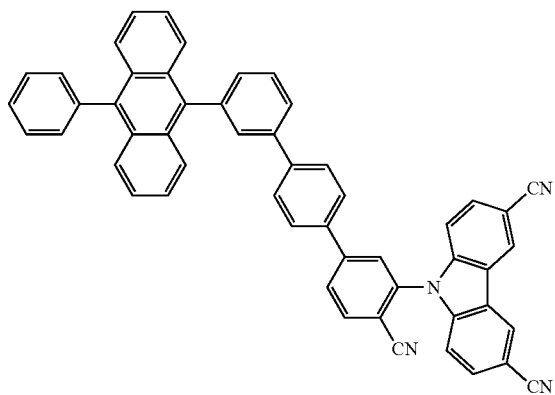

-continued
421
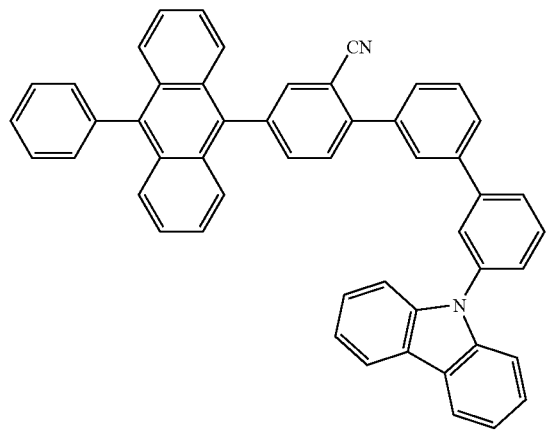
422
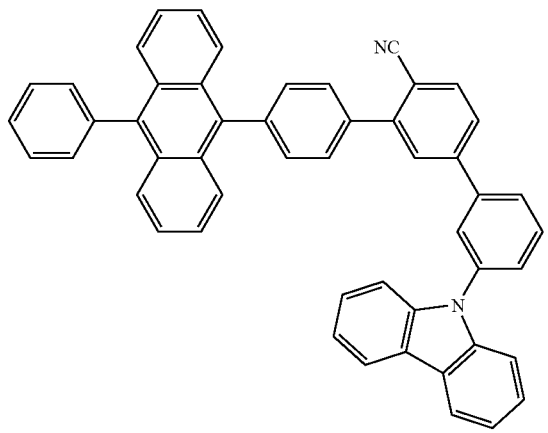
423
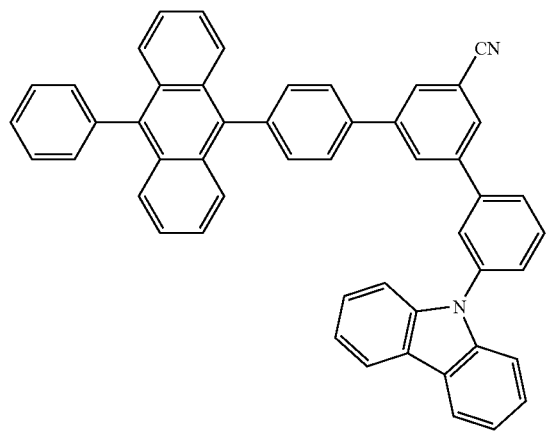
424
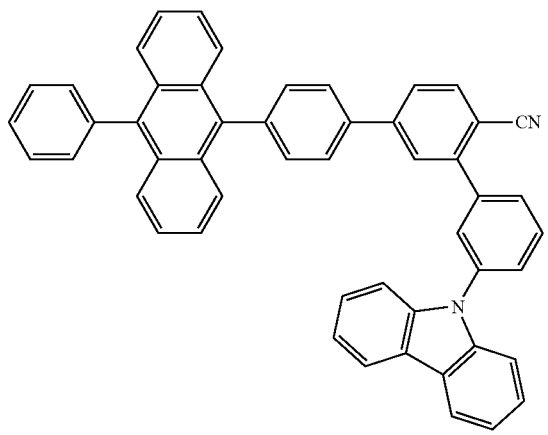
425
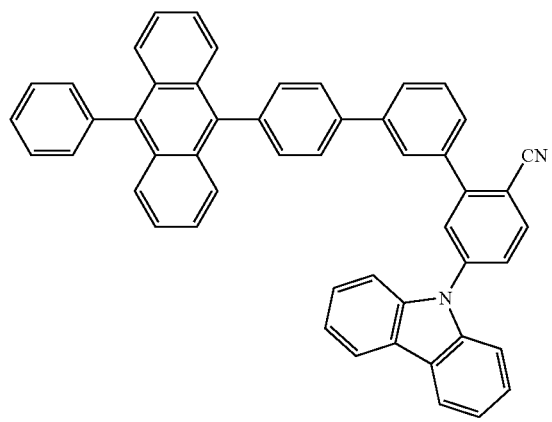
426
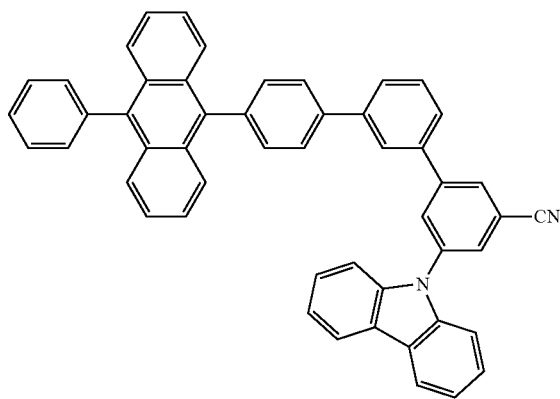

-continued
427
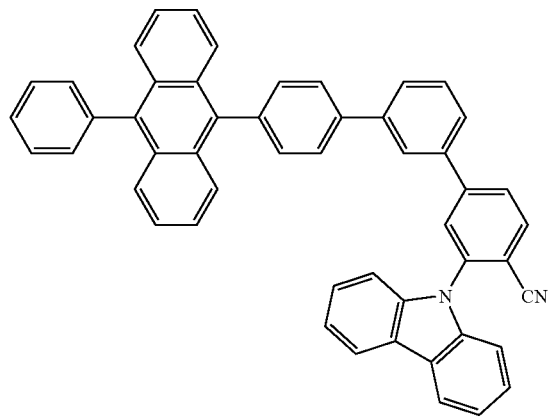
428
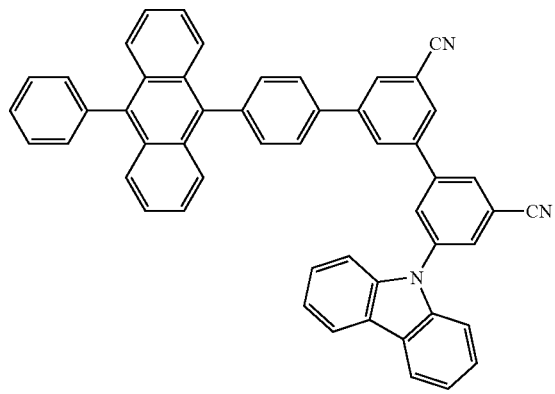
429
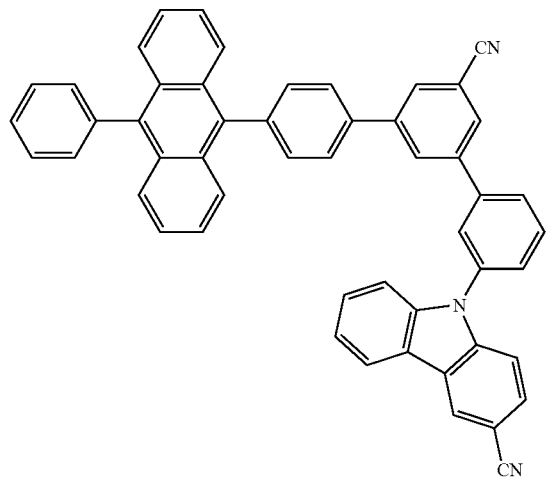
430
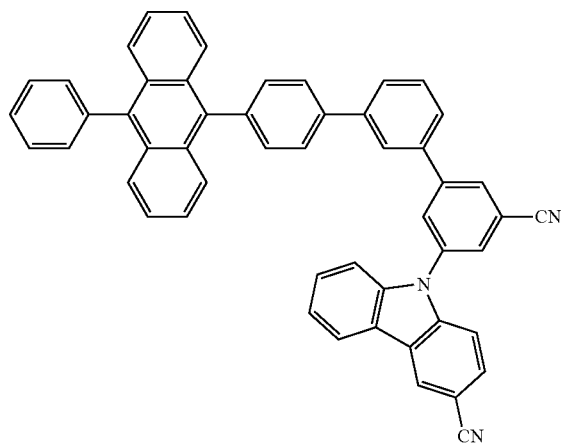
431
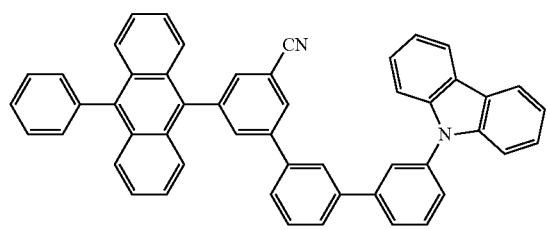
432
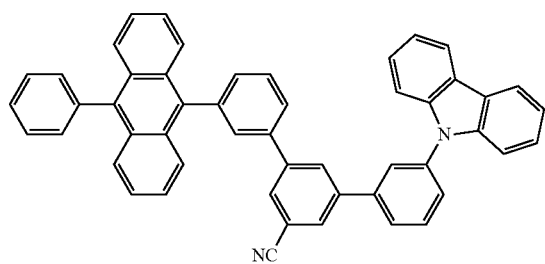
433
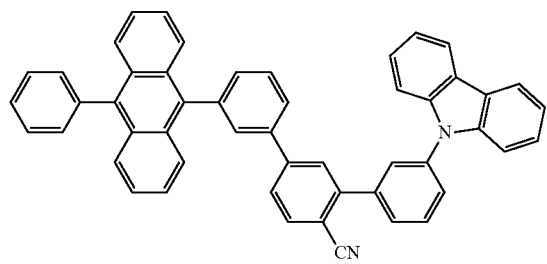
434
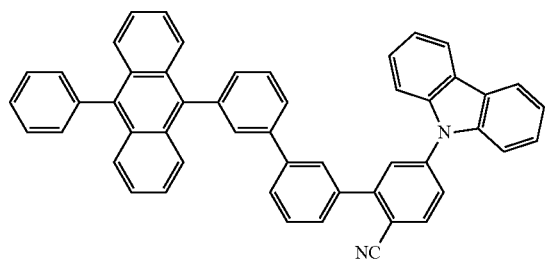

-continued
435
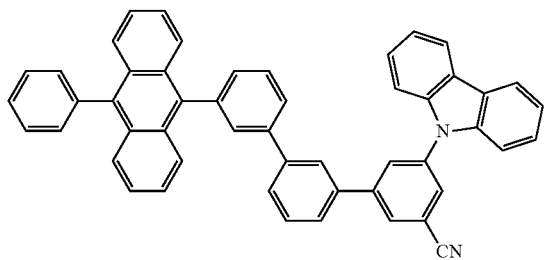
436
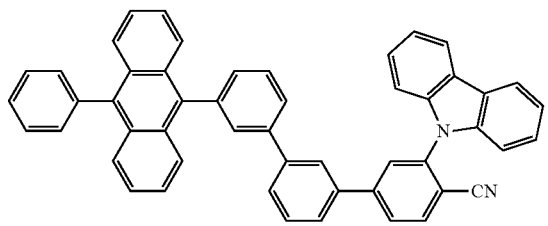
437
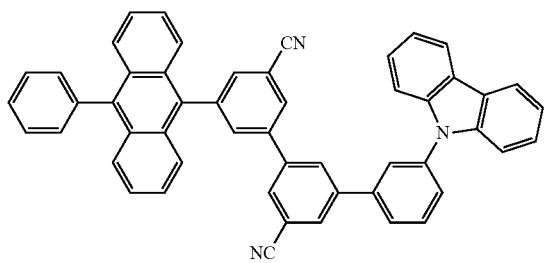
438
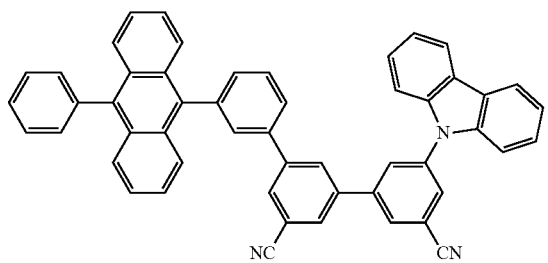
439
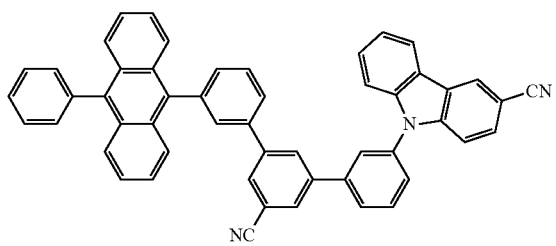
440
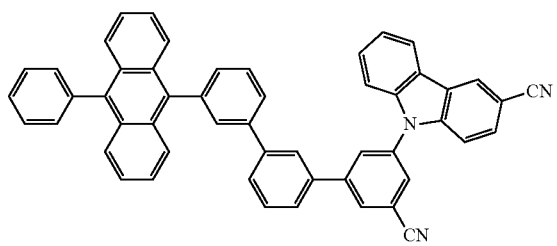
441
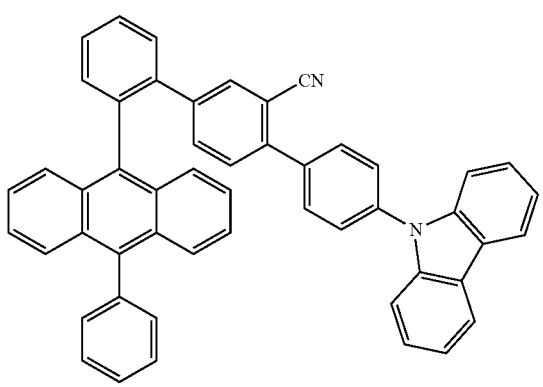
442
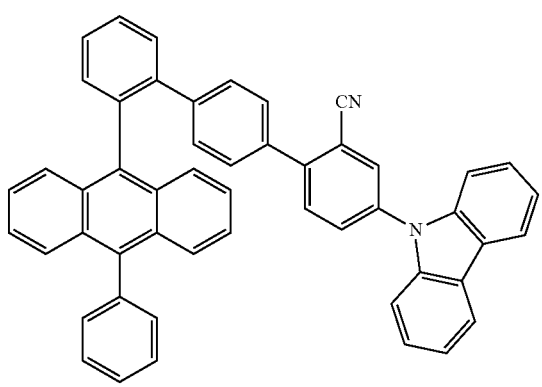
443
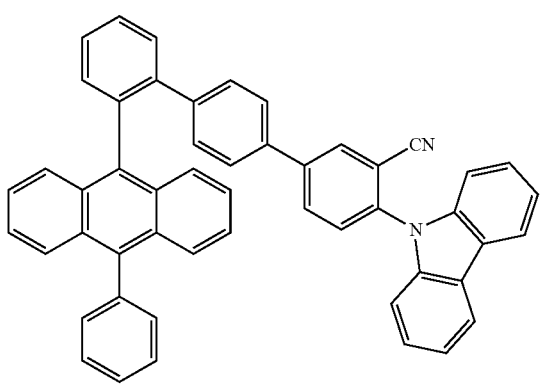
444
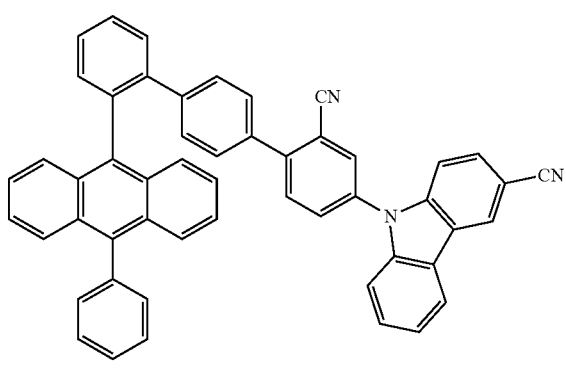

-continued
445
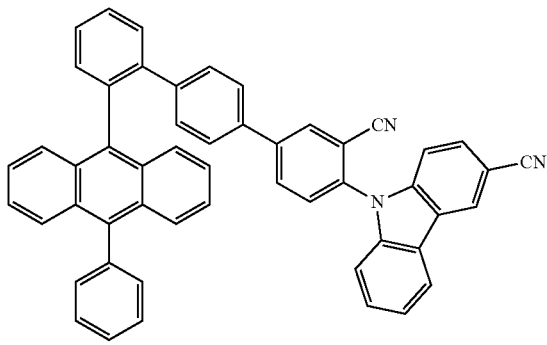
446
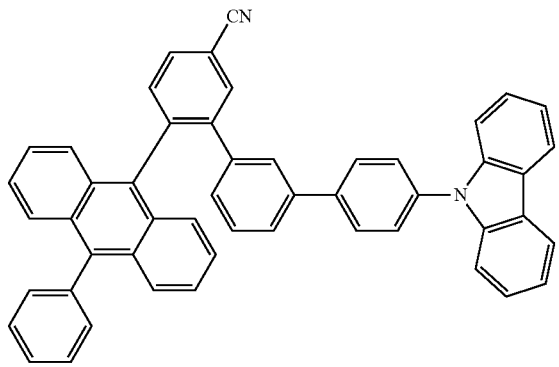
447
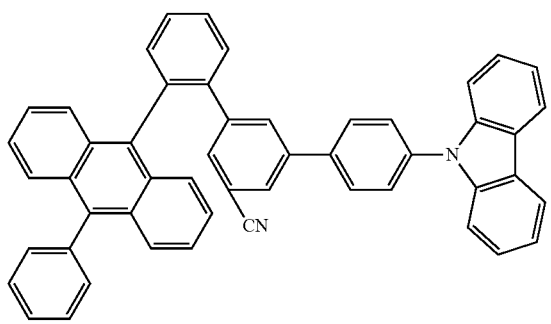
448
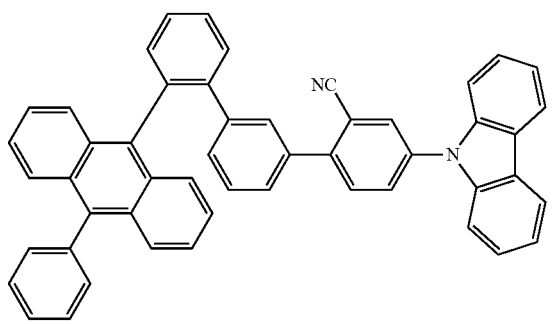
449
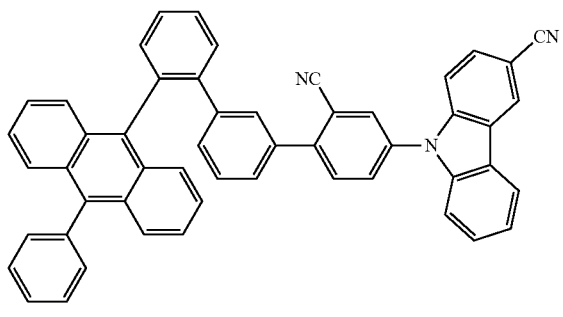
450
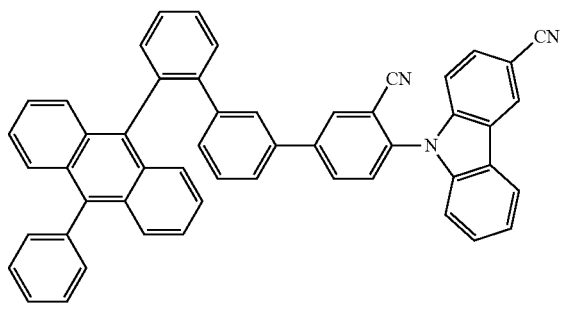
451
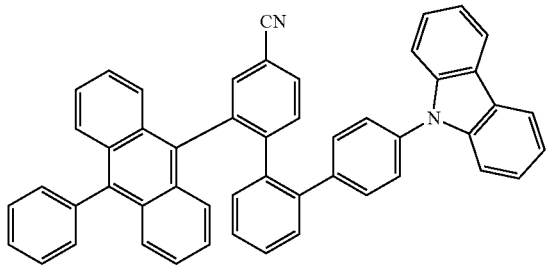
452
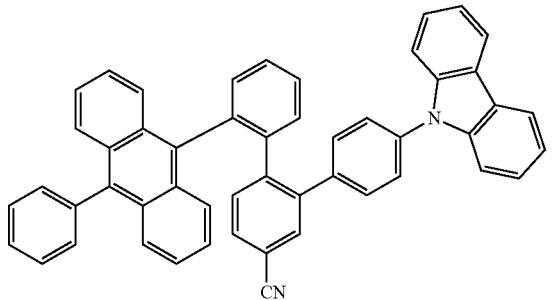

-continued
453
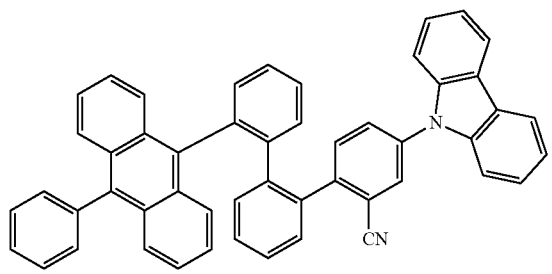
454
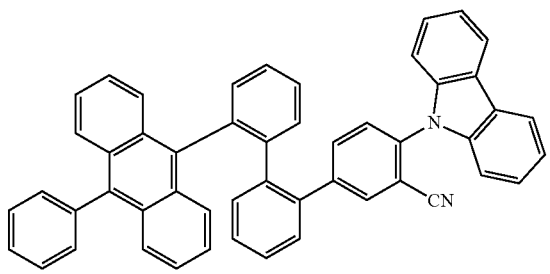
455
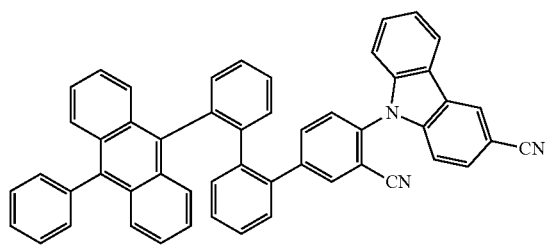
456
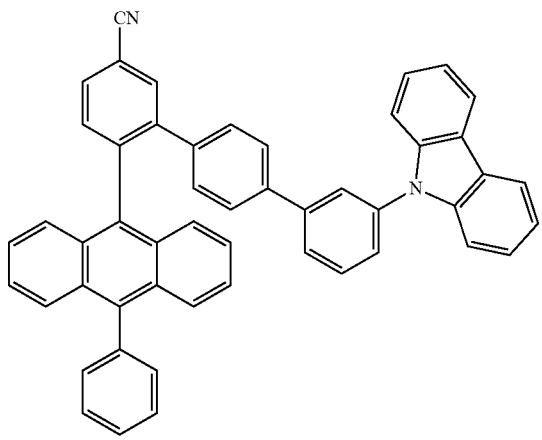
457
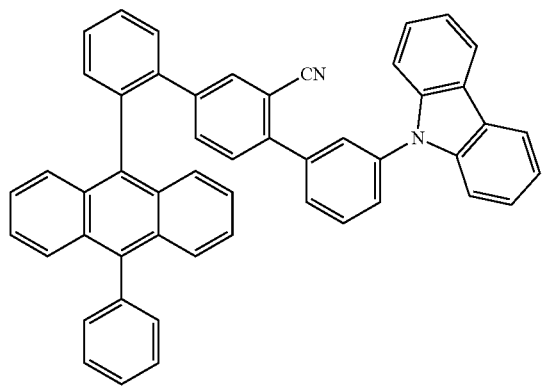
458
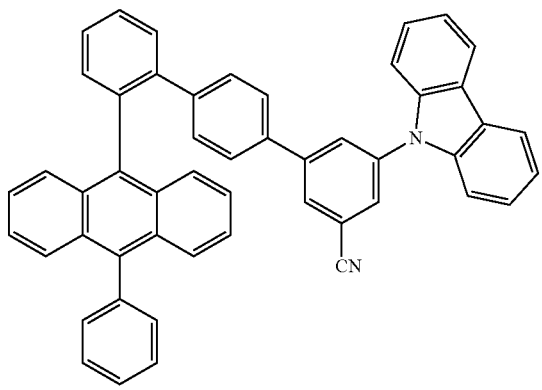
459
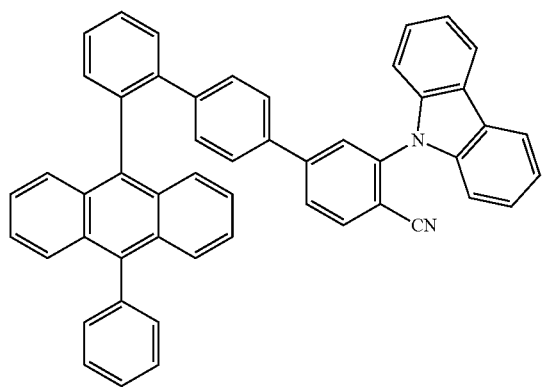
460
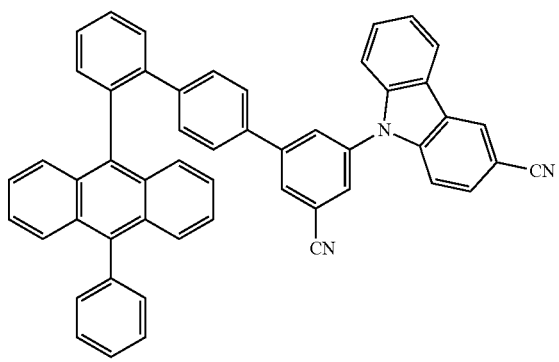

-continued
461
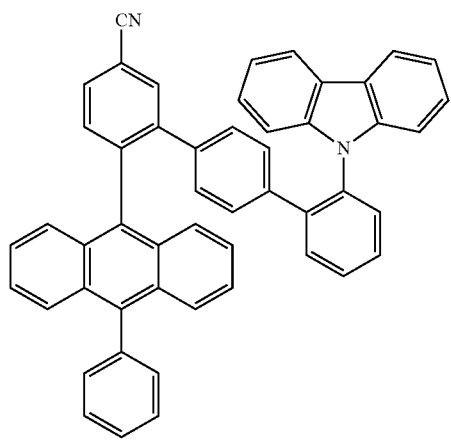
462
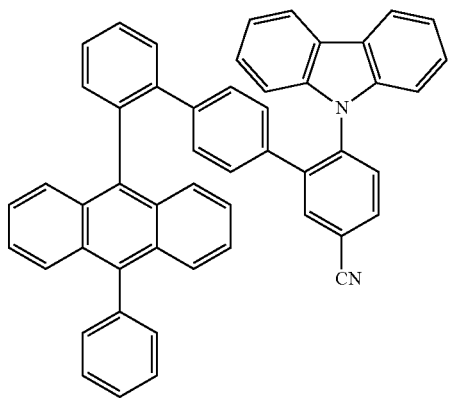
463
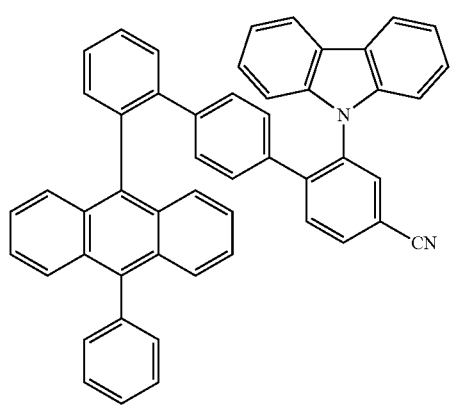
464
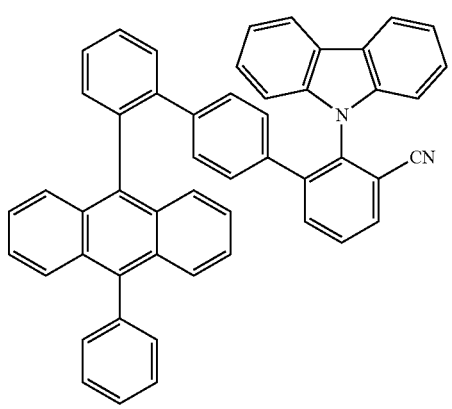
465
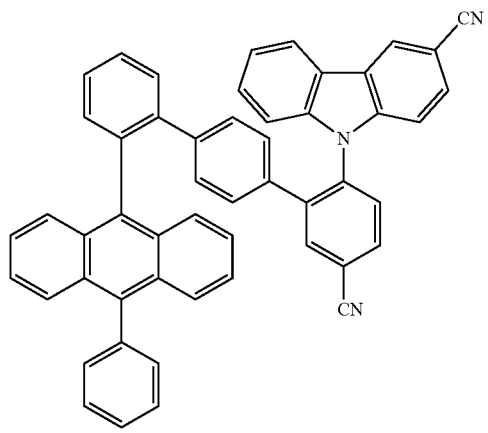
466
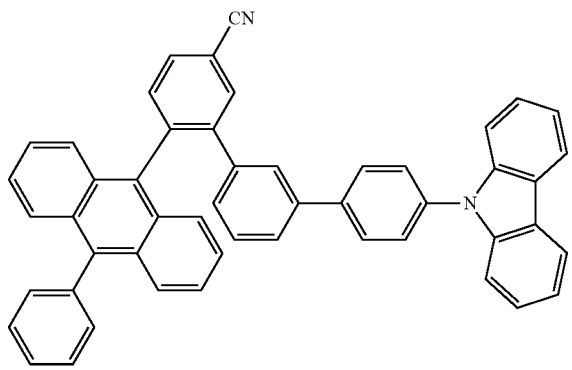
467
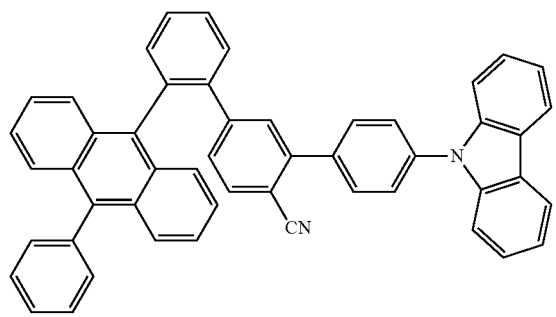
468
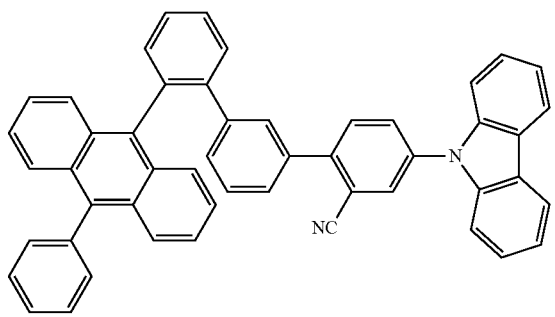

-continued
469
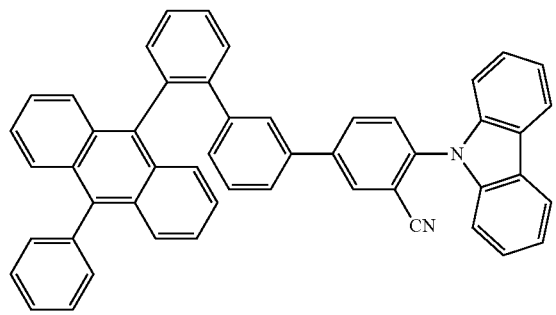
470
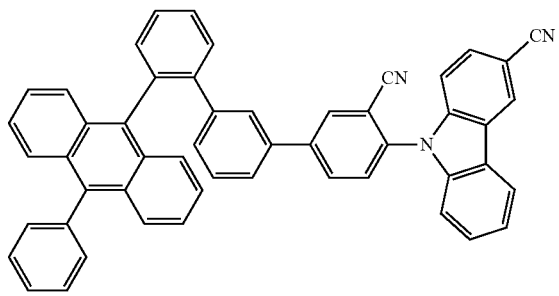
471
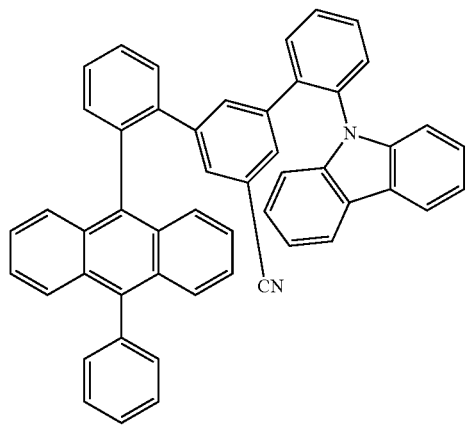
472
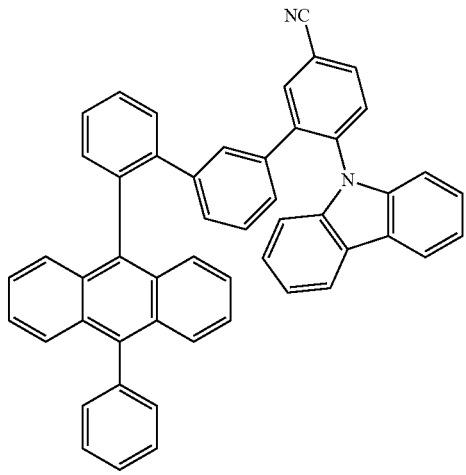
473
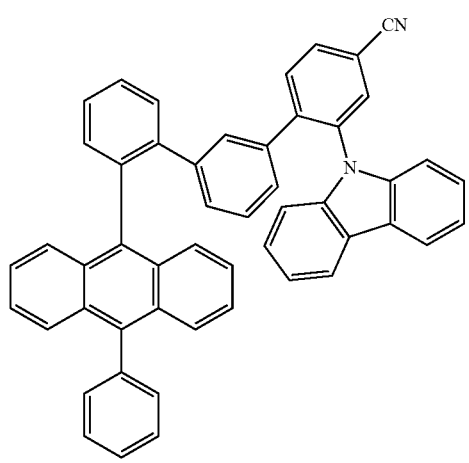
474
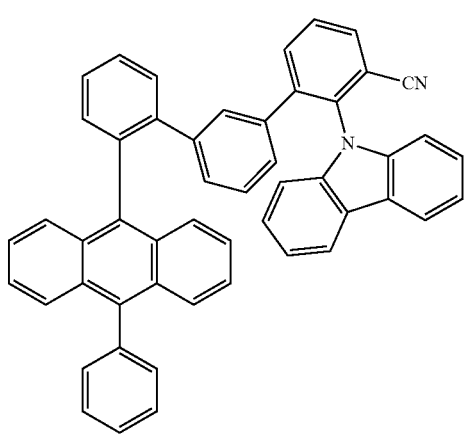

-continued
475
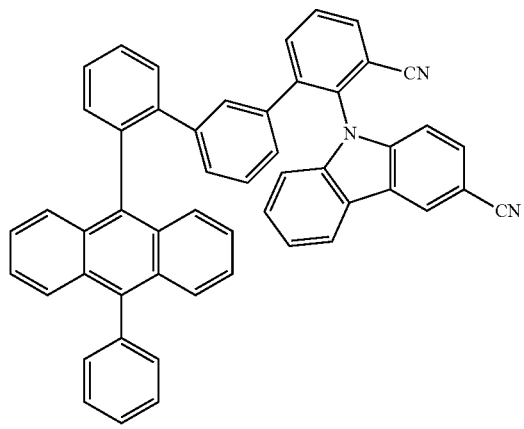
476
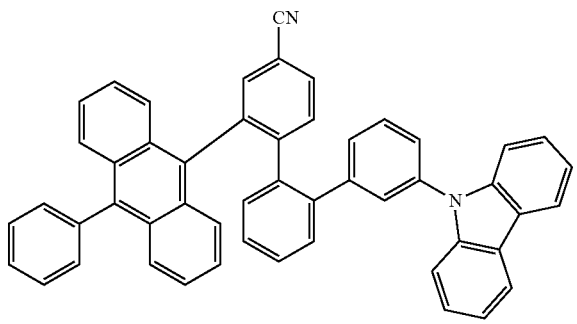
477
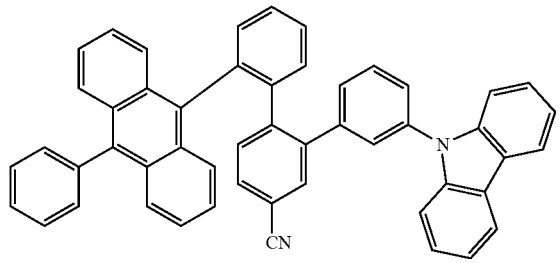
478
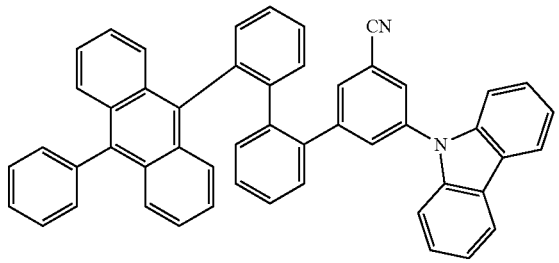
479
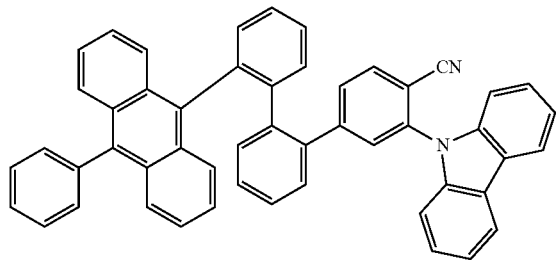
480
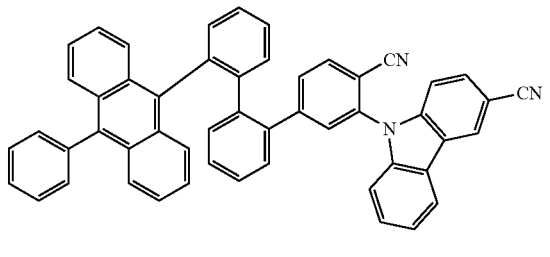
481
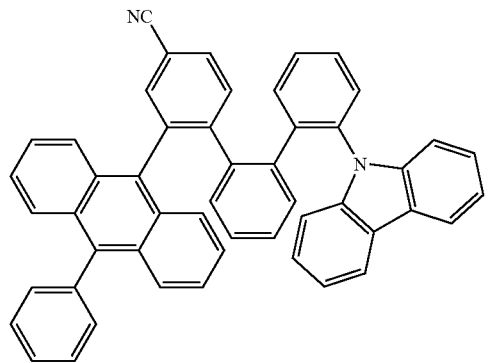
482
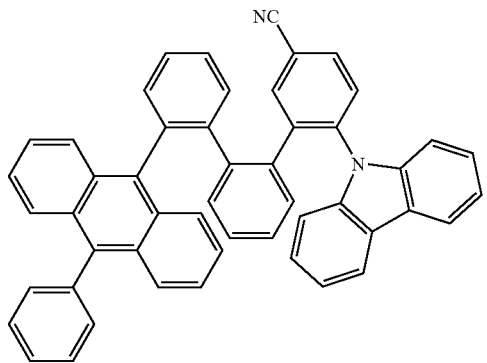

-continued
483
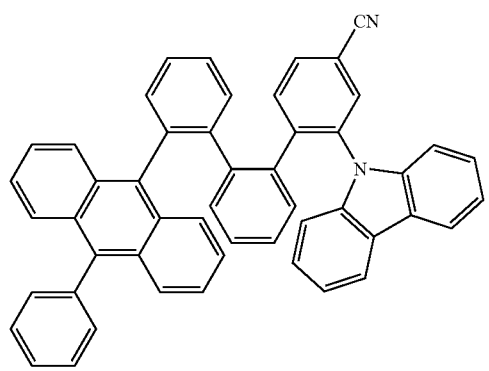
484
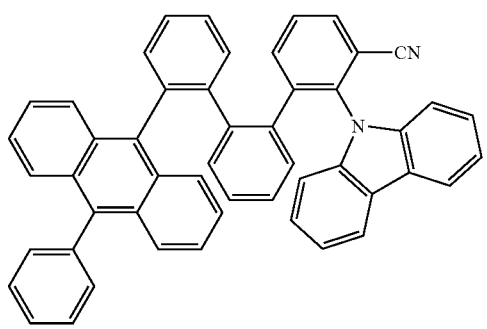
485
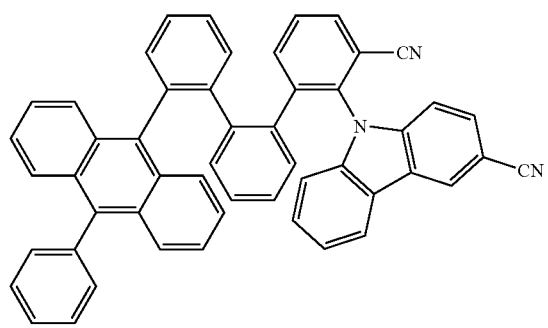
486
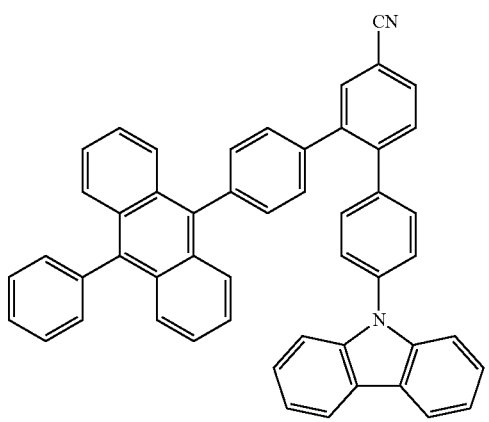
487
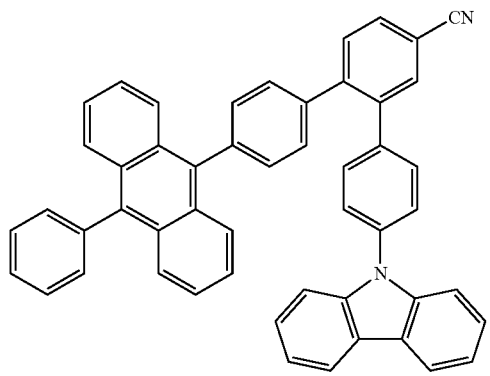
488
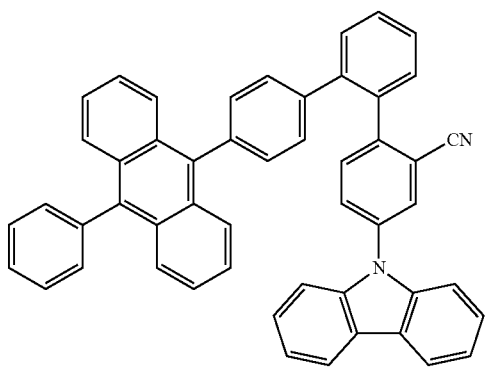
489
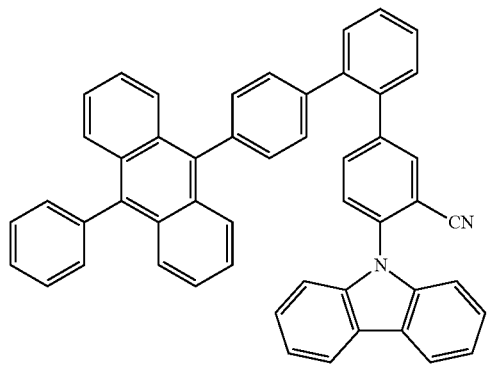
490
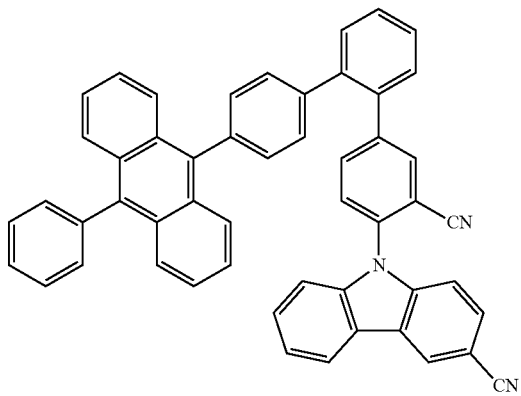

-continued
491
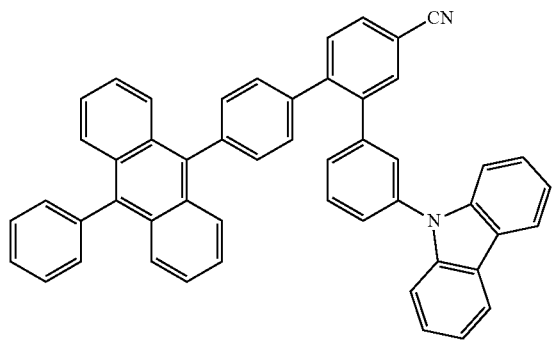
492
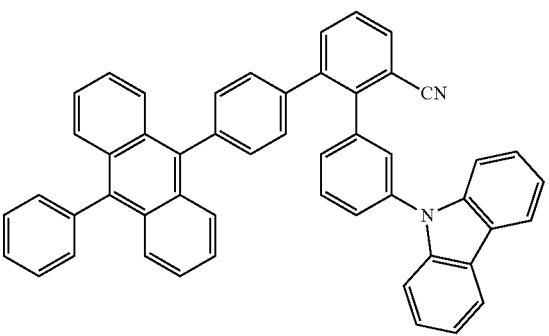
493
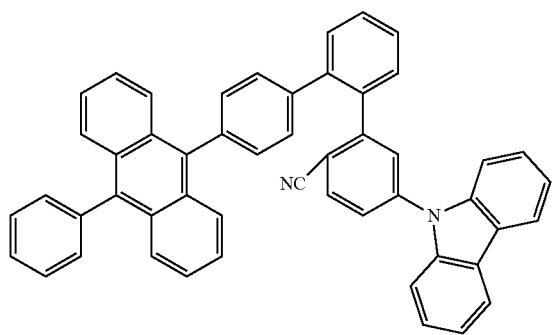
494
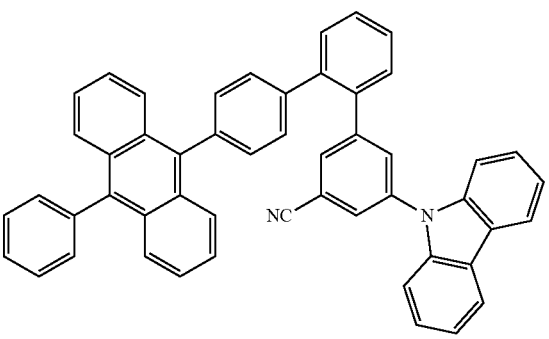
495
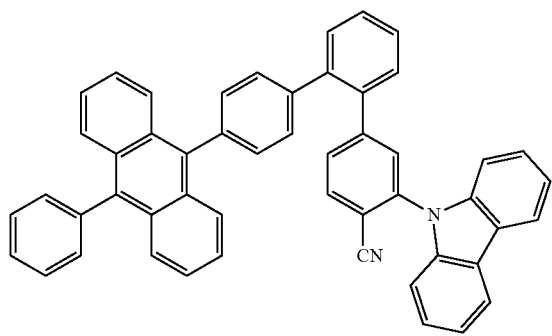
496
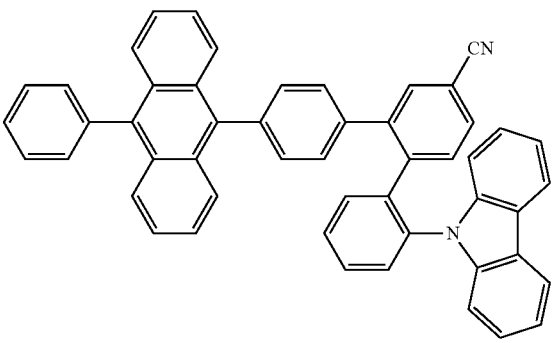
497
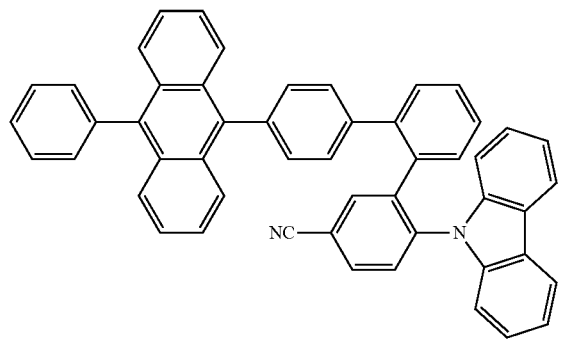
498
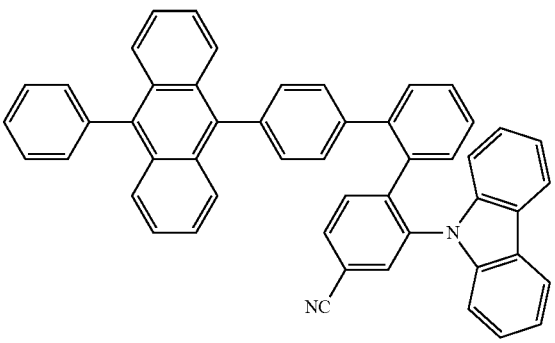

-continued
499
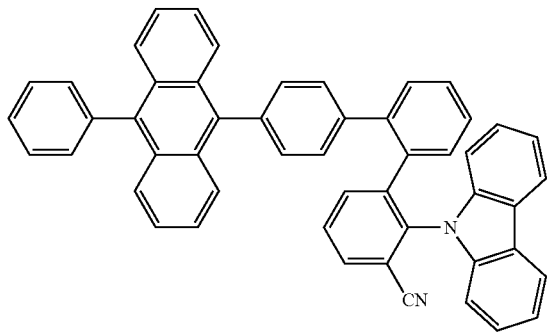
500
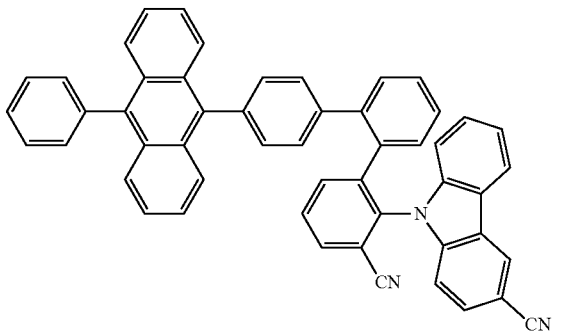
501
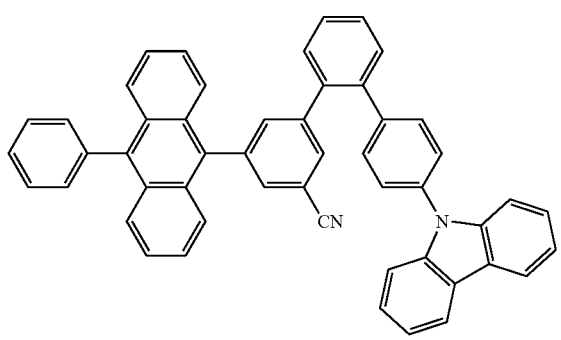
502
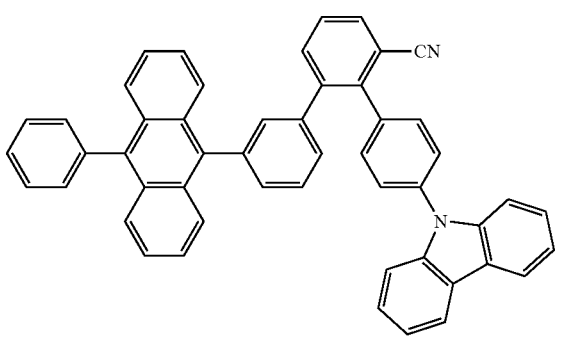
503
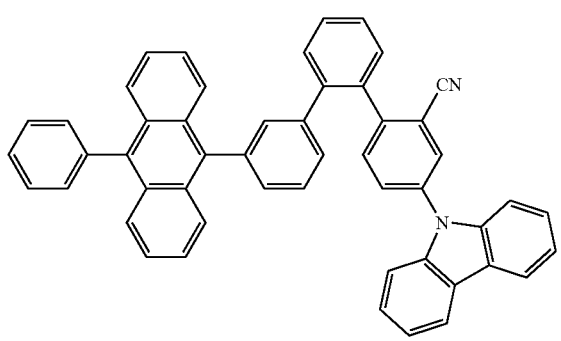
504
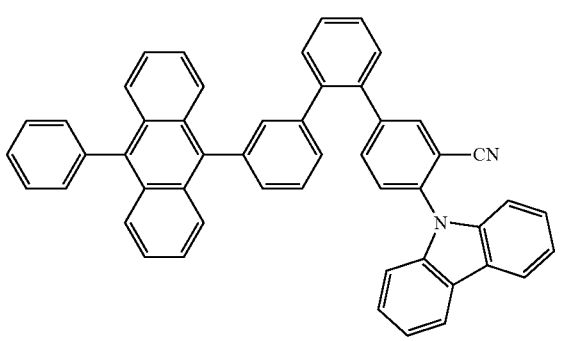
505
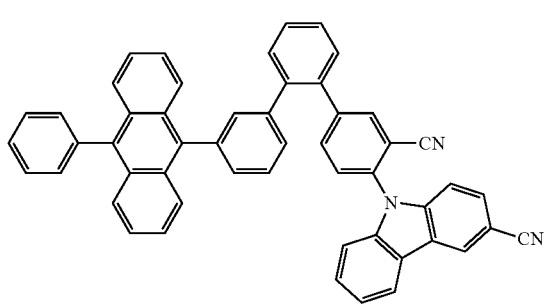
506
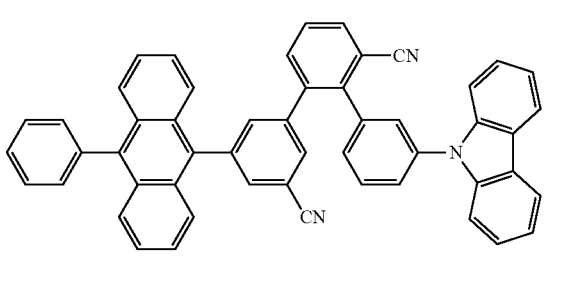
507
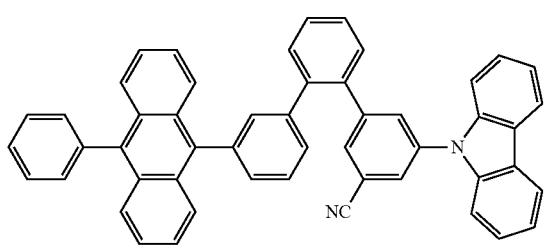
508
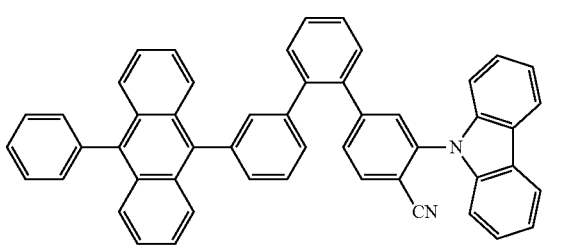

-continued
509
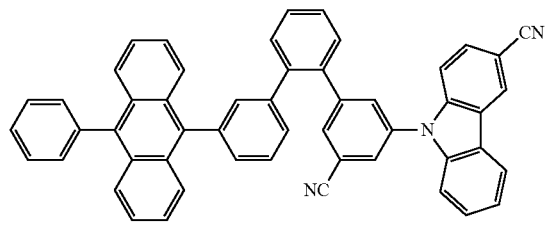
510
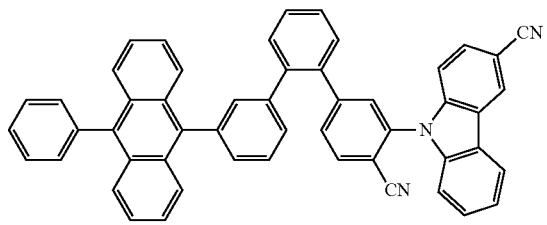
511
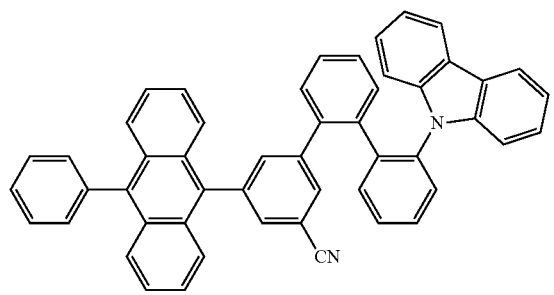
512
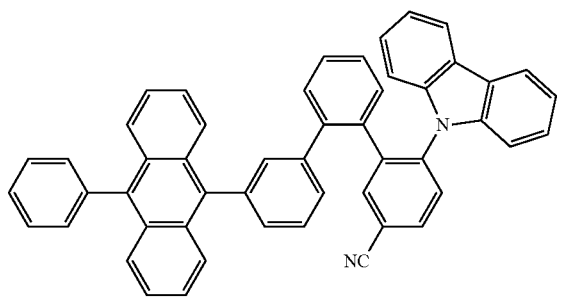
513
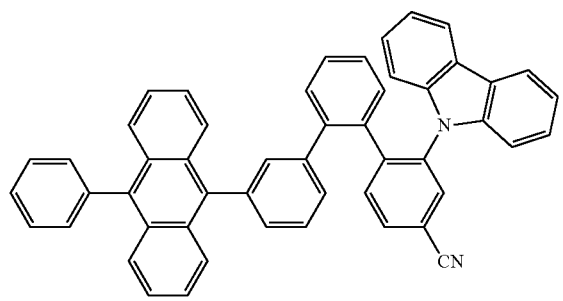
514
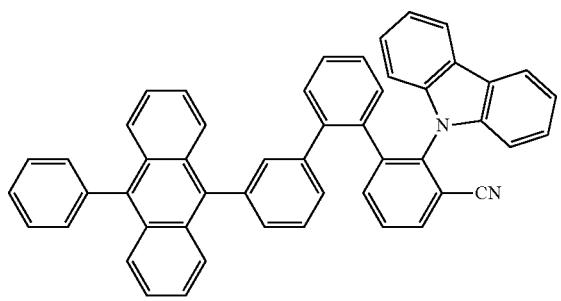
515
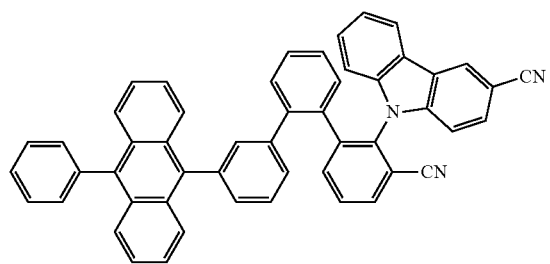
516
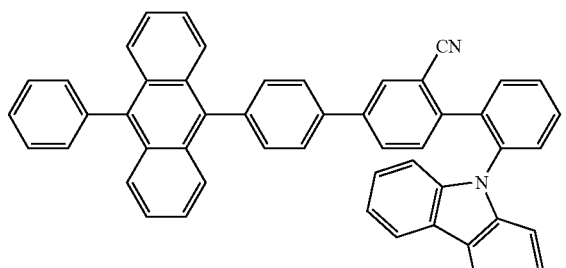
517
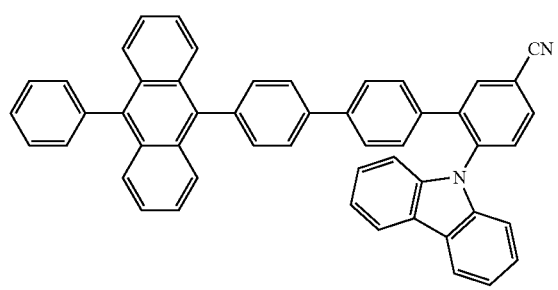
518
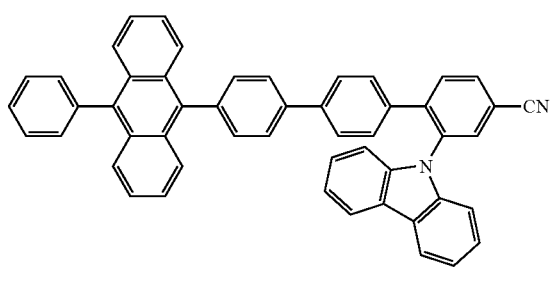

| 519 | 520 |
|---|---|
| 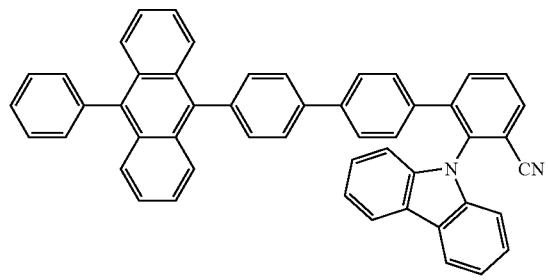 | 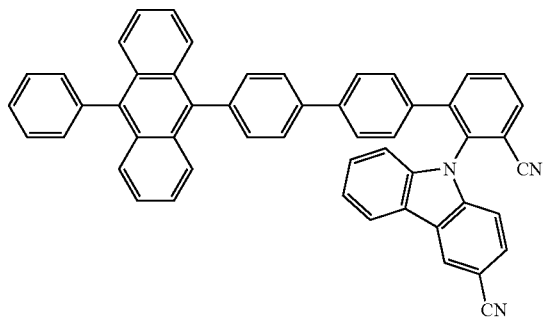 |
| 521 | 522 |
| 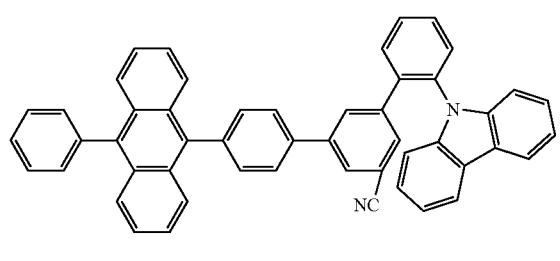 | 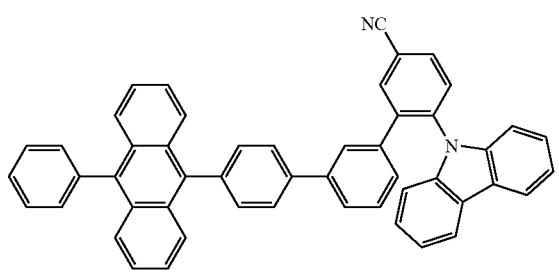 |
| 523 | 524 |
| 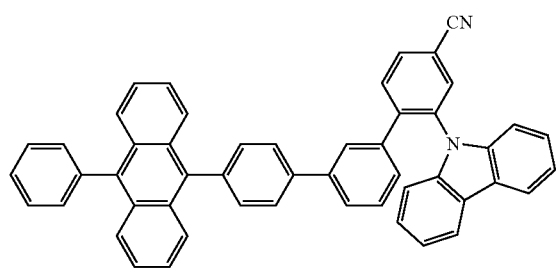 | 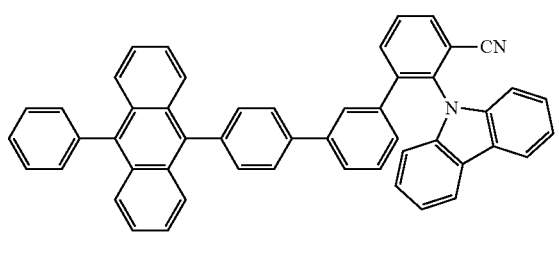 |
| 525 | 526 |
| 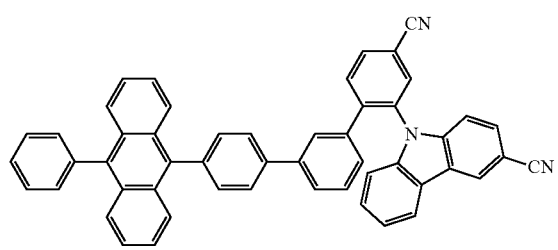 | 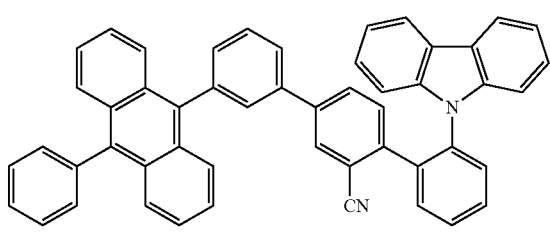 |
| 527 | 528 |
| 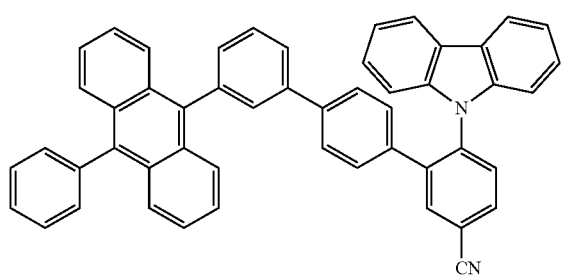 | 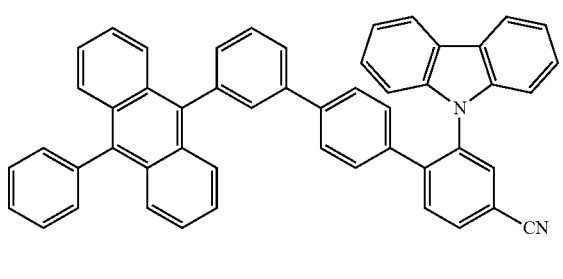 |

-continued
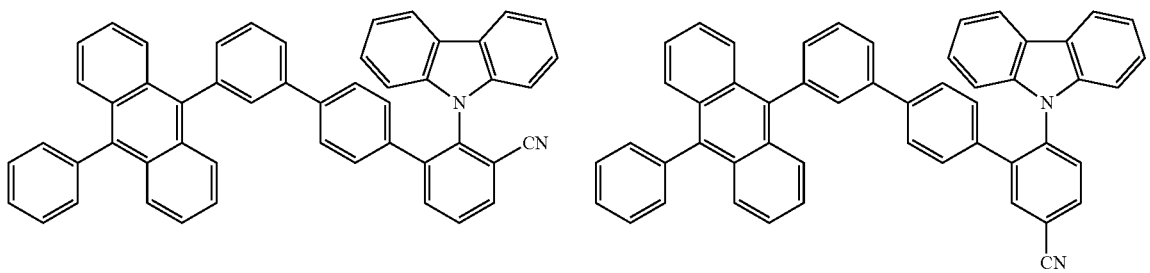
529
530
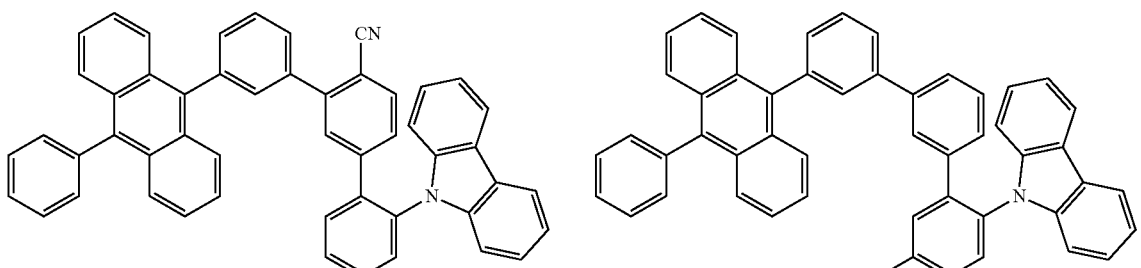
531
532
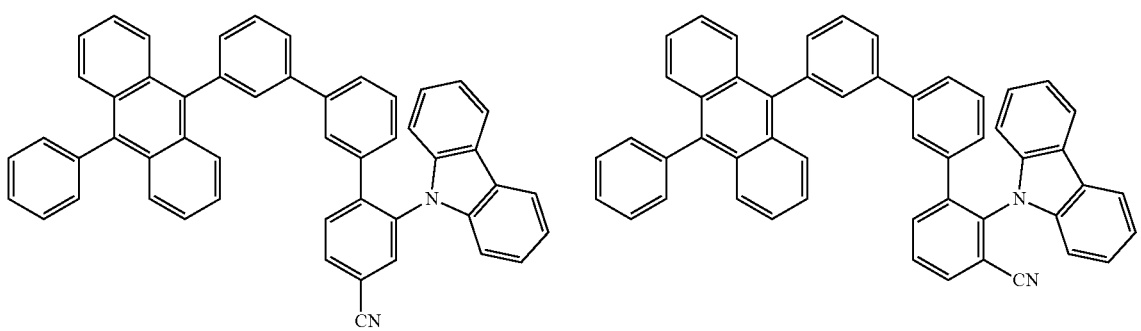
533
534
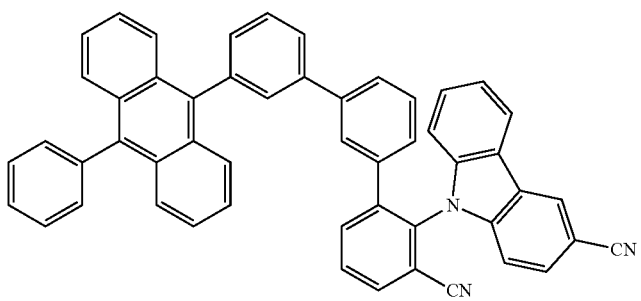
535
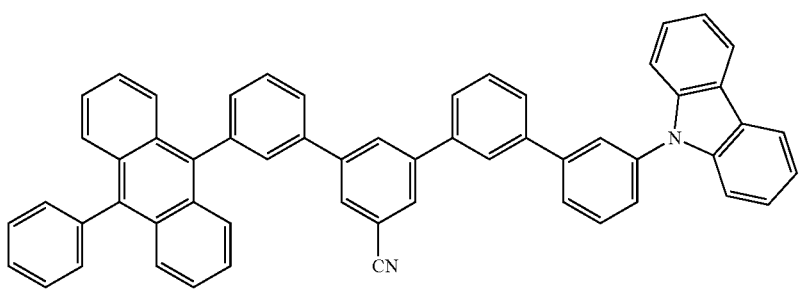
536

-continued
537
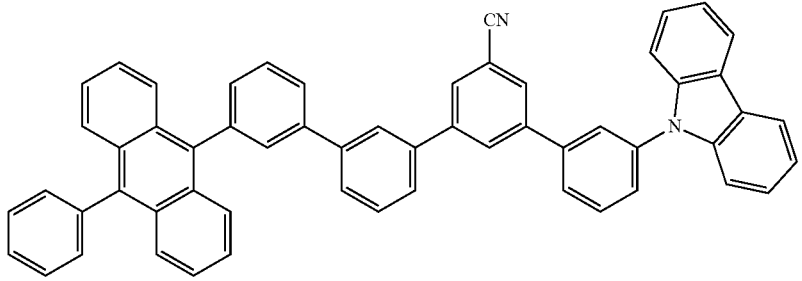
538
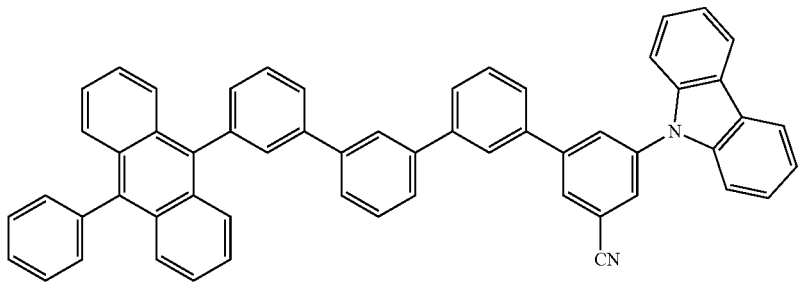
539
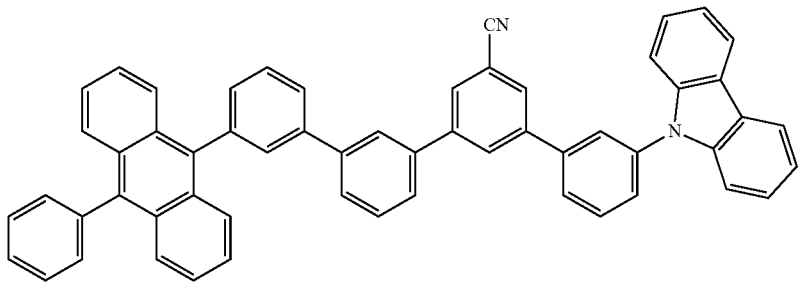
540
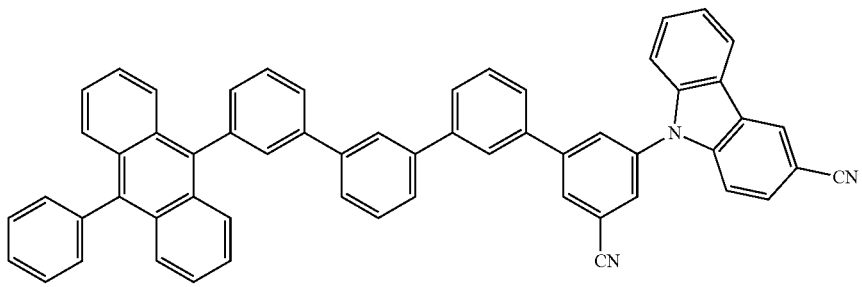
541 542
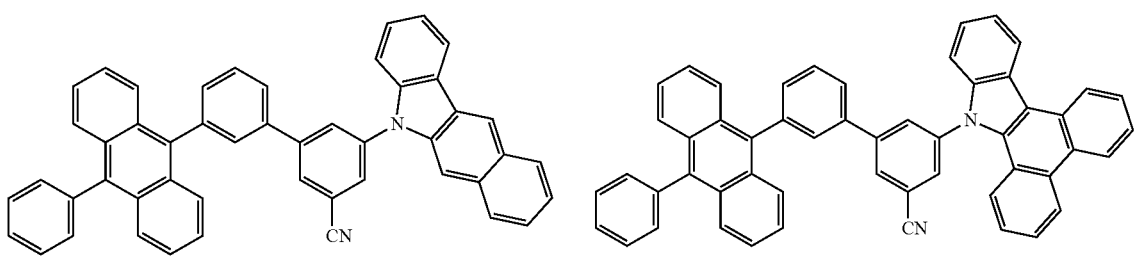

-continued
543
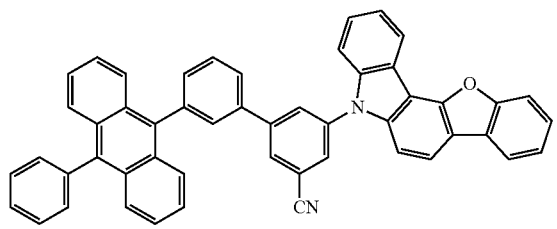
544
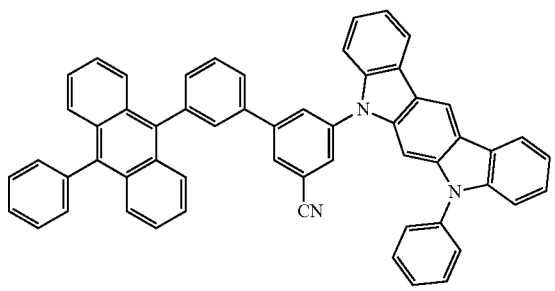
545
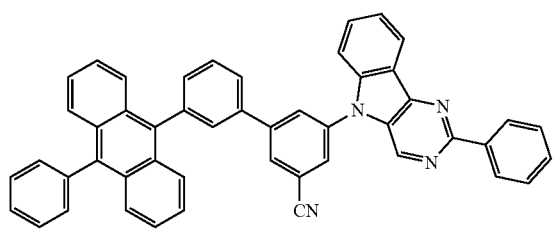
546
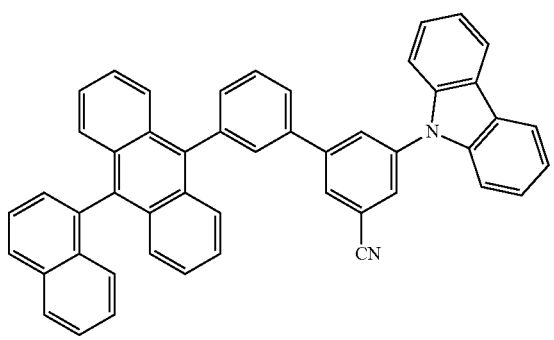
547
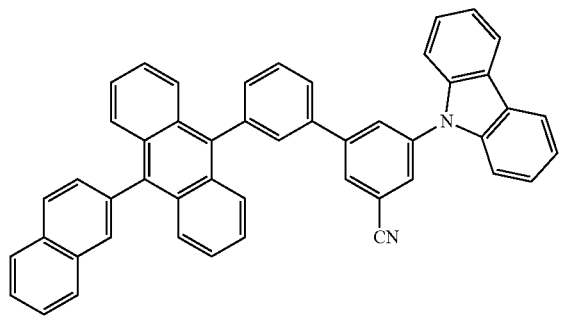
548
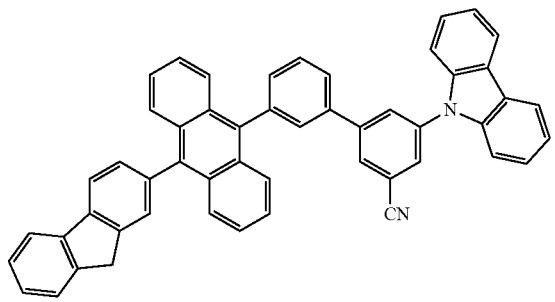
549
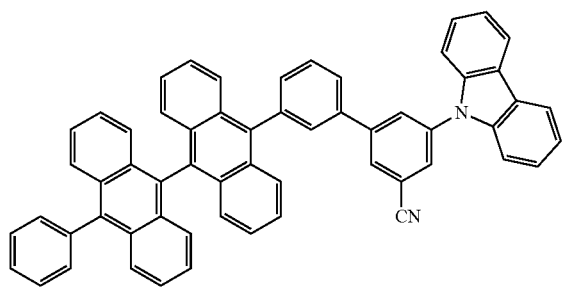
550
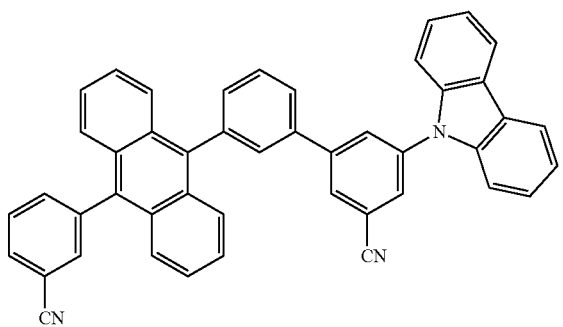

551
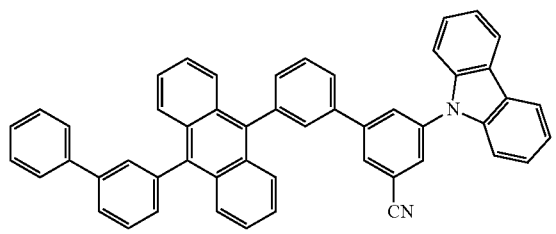
552
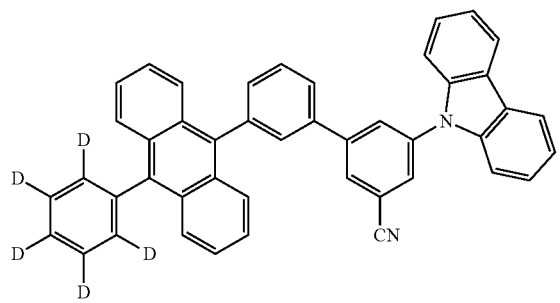
553
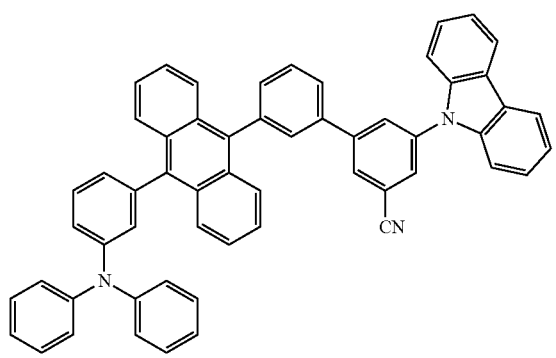
554
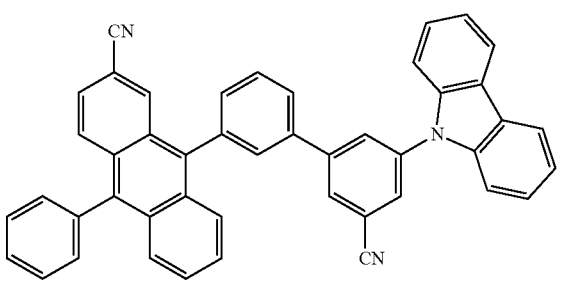
555
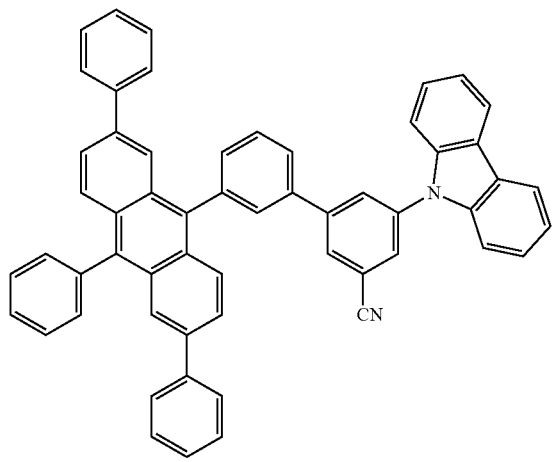
556
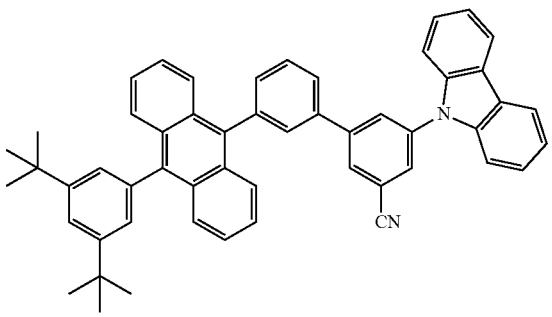
557
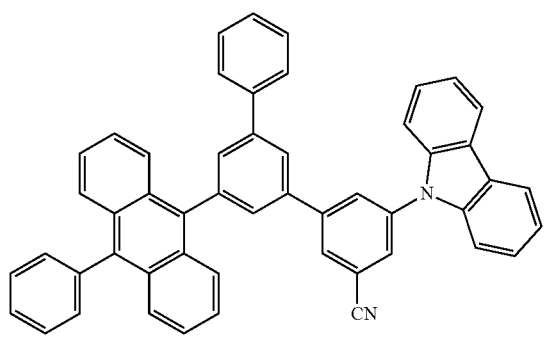
558
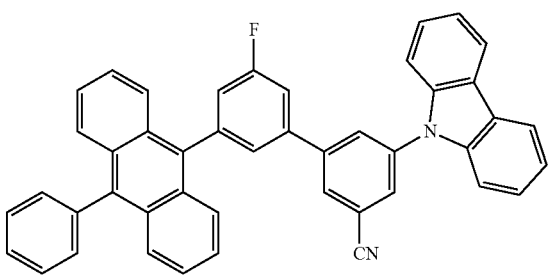

-continued

559 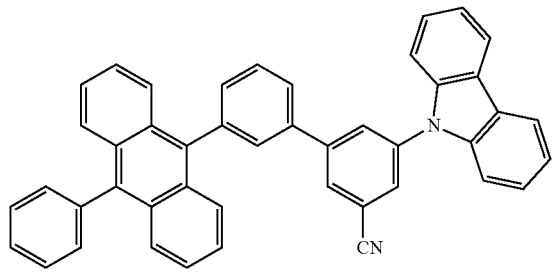

560 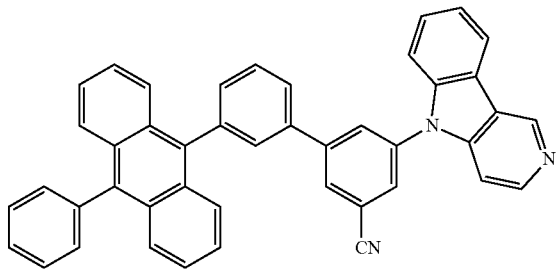

14. An organic light-emitting device comprising:
a first electrode;
a second electrode; and
an organic layer located between the first electrode and the second electrode and comprising an emission layer, wherein the organic layer comprises at least one heterocyclic compound represented by Formula 1 of claim 1.

15. The organic light-emitting device of claim 14, wherein the emission layer comprises the at least one heterocyclic compound represented by Formula 1.

16. The organic light-emitting device of claim 15, wherein the emission layer further comprises a dopant, and
the at least one of the heterocyclic compound represented by Formula 1 is a host.

17. The organic light-emitting device of claim 16, wherein the dopant is a fluorescent dopant.

18. The organic light-emitting device of claim 15, wherein a percentage of triplet-triplet fusion (TTF) components among all luminescent components emitted from the emission layer is equal to or greater than 30%.

19. The organic light-emitting device of claim 15, wherein the emission layer emits blue light having a maximum luminescence wavelength of 410 nanometers to 490 nanometers.

20. The organic light-emitting device of claim 14, wherein the first electrode is an anode, and the second electrode is a cathode,
the organic layer comprises a hole transport region located between the first electrode and the emission layer and an electron transport region located between the emission layer and the second electrode,
the hole transport region comprises at least one of a hole injection layer, a hole transport layer, or an electron blocking layer,
the electron transport region comprises at least one of a hole blocking layer, an electron transport layer, or an electron injection layer, and
at least one of the hole transport region and the electron transport region comprises the at least one heterocyclic compound represented by Formula 1.

\* \* \* \* \*